US012563969B2

(12) United States Patent
Yoon et al.

(10) Patent No.: US 12,563,969 B2
(45) Date of Patent: Feb. 24, 2026

(54) ORGANIC COMPOUND AND ORGANIC LIGHT EMITTING DIODE AND ORGANIC LIGHT EMITTING DEVICE INCLUDING THE SAME

(71) Applicant: LG DISPLAY CO., LTD., Seoul (KR)

(72) Inventors: Dae Wi Yoon, Paju-si (KR); Seon Keun Yoo, Paju-si (KR); Seong Su Jeon, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 983 days.

(21) Appl. No.: 17/636,216

(22) PCT Filed: Aug. 2, 2021

(86) PCT No.: PCT/KR2021/010054
§ 371 (c)(1),
(2) Date: Feb. 17, 2022

(87) PCT Pub. No.: WO2022/124516
PCT Pub. Date: Jun. 16, 2022

(65) Prior Publication Data

US 2022/0416176 A1 Dec. 29, 2022

(30) Foreign Application Priority Data

Dec. 8, 2020 (KR) ........................ 10-2020-0170431

(51) Int. Cl.
*C07D 471/04* (2006.01)
*C09K 11/06* (2006.01)
(Continued)

(52) U.S. Cl.
CPC ....... *H10K 85/6572* (2023.02); *C07D 471/04* (2013.01); *C09K 11/06* (2013.01);
(Continued)

(58) Field of Classification Search
CPC .............. H10K 85/6572; C07D 471/04; C09K 2211/1018
See application file for complete search history.

(56) References Cited

U.S. PATENT DOCUMENTS

2016/0043327 A1* 2/2016 Yoo ........................ H10K 50/13 257/40
2017/0155055 A1 6/2017 Joo et al.
(Continued)

FOREIGN PATENT DOCUMENTS

CN 102443003 A 5/2012
CN 105321984 A 2/2016
(Continued)

OTHER PUBLICATIONS

International Search Report dated Aug. 2, 2021, issued in International Patent Application No. PCT/KR2021/010054.
(Continued)

*Primary Examiner* — Jennifer A Boyd
*Assistant Examiner* — Rachel Simbana
(74) *Attorney, Agent, or Firm* — Morgan, Lewis & Bockius LLP

(57) ABSTRACT

The present disclosure relates to an organic compound of Formula, and an organic light emitting diode and an organic light emitting display device including the organic compound. In Formula, X is oxygen (O) or sulfur (S), and each of R1 to R4 is independently selected from the group consisting of deuterium, halogen, cyano, C1 to C10 alkyl group, C1 to C10 alkoxy group, C3 to C30 cycloalkyl group, C6 to C30 aryl group, C6 to C30 arylamino group, and C5 to C30 heteroaryl group, wherein each of L1 and L2 is independently selected from the group consisting of C6 to C30 arylene group and C5 to C30 heteroarylene group, and
(Continued)

wherein each of a and b is independently 0 or 1, each of c and f is independently an integer of 0 to 3, and each of d and e is independently an integer of 0 to 2.

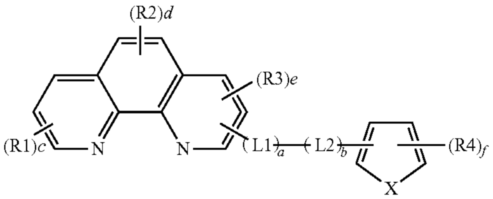

19 Claims, 3 Drawing Sheets

(51) Int. Cl.

| | |
|---|---|
| ***H10K 50/16*** | (2023.01) |
| ***H10K 50/19*** | (2023.01) |
| ***H10K 50/842*** | (2023.01) |
| ***H10K 59/35*** | (2023.01) |
| ***H10K 59/38*** | (2023.01) |
| ***H10K 85/60*** | (2023.01) |

(52) U.S. Cl.

CPC ......... *H10K 85/615* (2023.02); *H10K 85/622* (2023.02); *H10K 85/626* (2023.02); *H10K 85/653* (2023.02); *H10K 85/655* (2023.02); *C09K 2211/1018* (2013.01); *H10K 50/16* (2023.02); *H10K 50/19* (2023.02)

(56) References Cited

U.S. PATENT DOCUMENTS

| | | | | |
|---|---|---|---|---|
| 2018/0166647 | A1 * | 6/2018 | Shin | H10K 50/16 |
| 2020/0203626 | A1 | 6/2020 | Zhang et al. | |

FOREIGN PATENT DOCUMENTS

| | | | |
|---|---|---|---|
| CN | 106565705 | A | 4/2017 |
| CN | 106749411 | A | 5/2017 |
| CN | 106816450 | A | 6/2017 |
| CN | 107619468 | A | 1/2018 |
| CN | 111039882 | A | 4/2020 |
| CN | 111834537 | A | 10/2020 |
| EP | 2161272 | A1 | 3/2010 |
| KR | 10-20160018332 | A | 2/2016 |
| KR | 10-2017-0061603 | A | 6/2017 |
| KR | 10-20170062629 | A | 6/2017 |
| WO | 2018/092927 | A1 | 5/2018 |

OTHER PUBLICATIONS

Office Action issued Oct. 7, 2023 for counterpart Chinese Patent Application No. 202180005350.5 (See English Translation).

Vidal, et al., "Conjugated Polyrotaxanes Incorporating Mono- or Divalent Copper Complexes", 1999, Inorg. Chem., vol. 38, p. 4203-4210.

Peng et al., "Comparisons on isomeric 1,10-phenanthroline aromatic heterocyclic derivatives with triphenylamine and thiophene donors before and after rhenium(I) carbonyl complexation", 2016, Tetrahedron, vol. 72, p. 3443-3453.

Ammann et al., "Synthesis and electronic properties of series of oligothiophene-[1,10]phenanthrolines", 2005, Org. Biomol. Chem., vol. 3, p. 4143-4152.

Huang, et al., "Spectral, Structural, and Computational Studies of a New Family of Ruthenium(II) Complexes Containing Substituted 1,10-Phenanthroline Ligands and in situ Electropolymerization of a Phenanthrolineruthenium(II) Complex Bridging Nanogap Gold Electrodes", 2009, Eur. J. Inorg. Chem., p. 1321-1330.

Hu, et al., "Linear Heterocyclic Aromatic Fluorescence Compounds Having Various Donor-Acceptor Spacers Prepared by the Combination of Carbon-Carbon Bond and Carbon-Nitrogen Bond Cross-Coupling Reactions", 2011, J. Org. Chem., vol. 76, p. 4444-4456.

Zhang et al., "Synthesis and characterization of oligothiophene-functionalized phenanthroline chromophores with symmetrical or unsymmetrical configuration", 2013, Journal of Molecular Structure, vol. 1037, p. 122-129.

* cited by examiner

[Fig. 1]
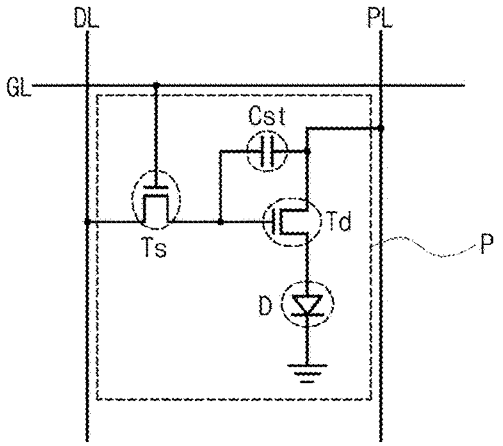
[Fig. 2]
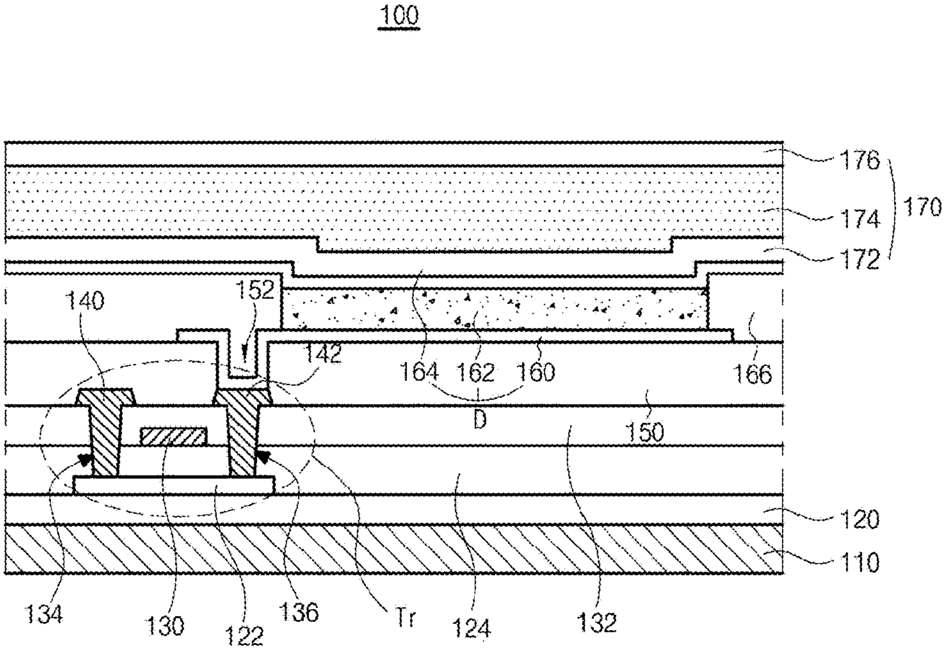
[Fig. 3]
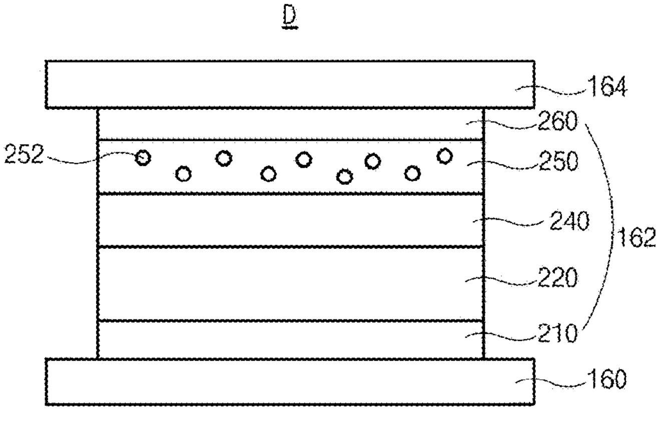

[Fig. 4]
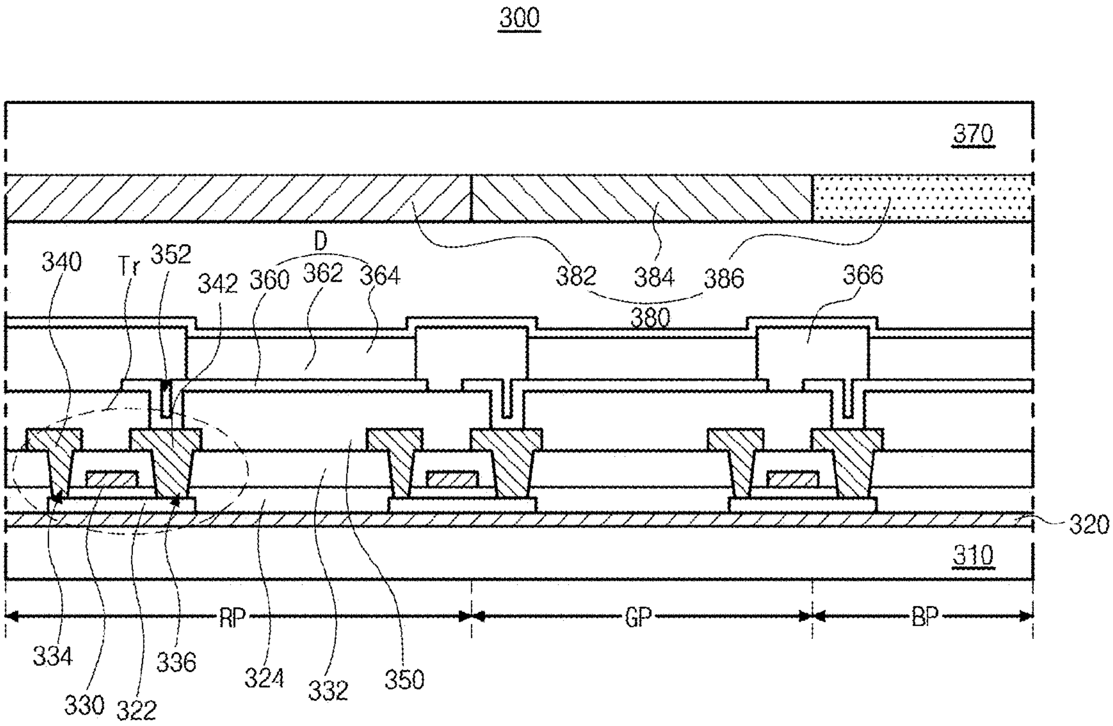
[Fig. 5]
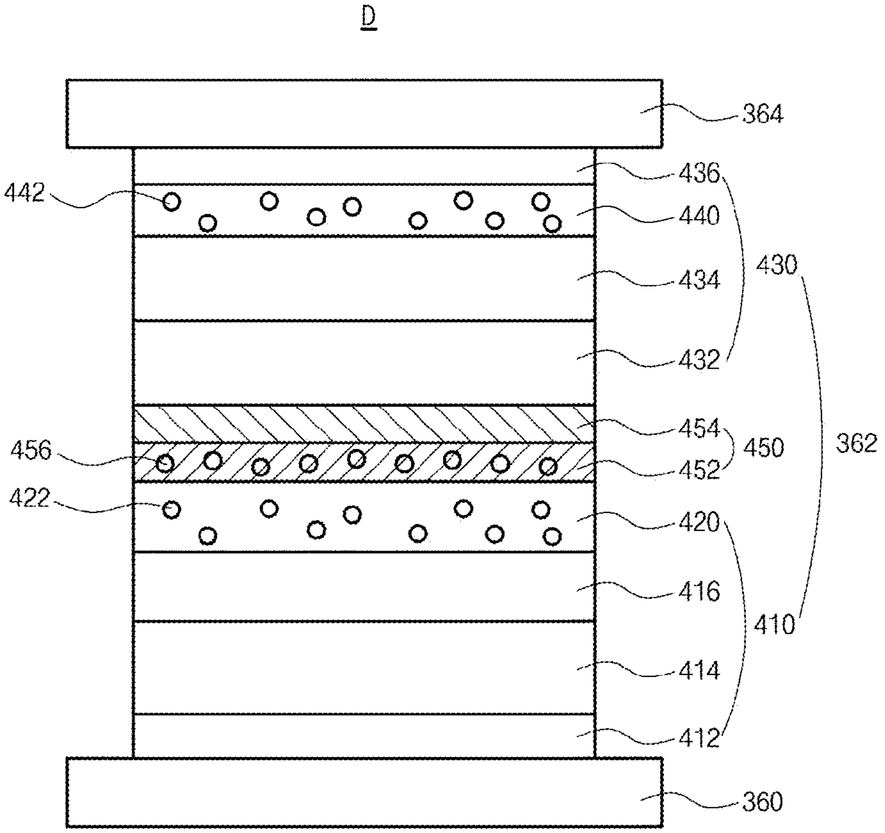

[Fig. 6]
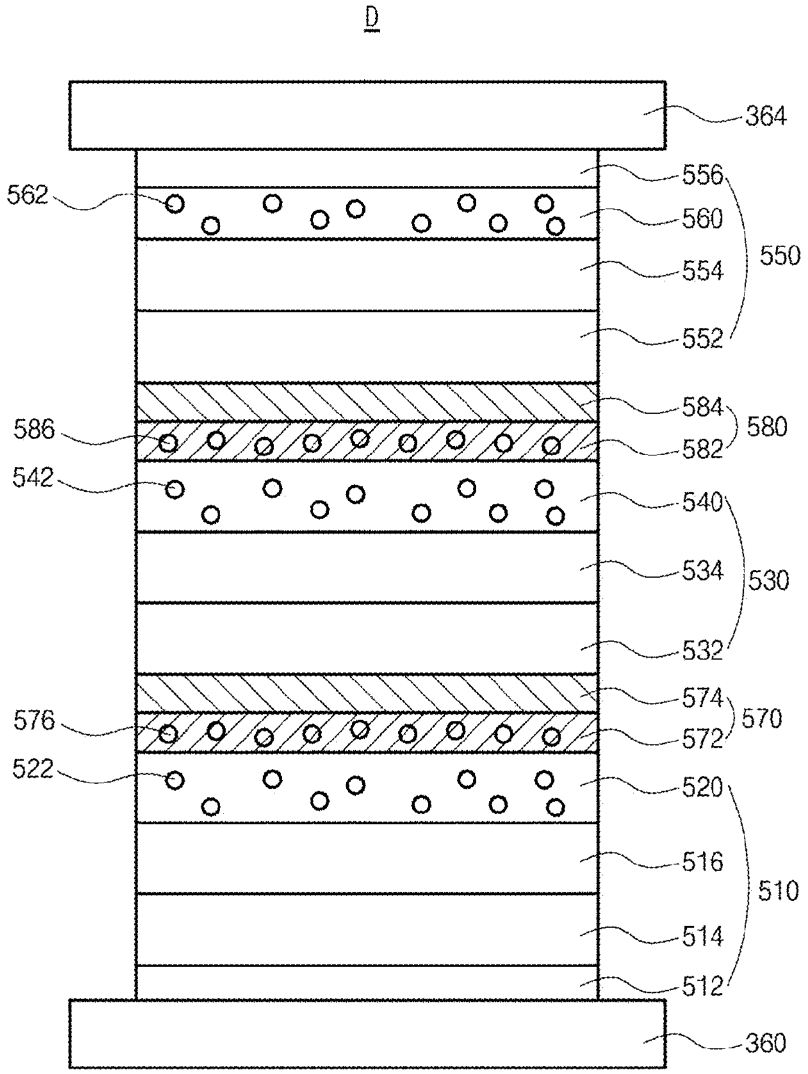

ORGANIC COMPOUND AND ORGANIC LIGHT EMITTING DIODE AND ORGANIC LIGHT EMITTING DEVICE INCLUDING THE SAME

TECHNICAL FIELD

The present disclosure relates to an organic compound, and more specifically, to an organic compound having improved electron transporting efficiency, and an organic light emitting diode and an organic light emitting display device including the same.

BACKGROUND ART

As requests for flat panel display devices having a small occupied area have been increased, an organic light emitting display device, which may be referred to as an organic electroluminescent device (OELD), including an organic light emitting diode (OLED) among the flat panel display device has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color purity.

To provide sufficient emitting efficiency and lifespan of the OLED, the development of an electron transporting material having sufficient electron transporting efficiency is required.

DISCLOSURE OF INVENTION

Technical Problem

Accordingly, the present disclosure is directed to an organic compound, an OLED and an organic light emitting device that substantially obviate one or more of the problems due to the limitations and disadvantages of the related art.

An object of the present disclosure is to provide an organic compound having improved electron transporting efficiency.

Another object of the present disclosure is to provide an OLED and an organic light emitting display device including the organic compound and having improved emitting efficiency and lifespan and lowered driving voltage.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

Solution to Problem

According to an aspect, the present disclosure provides an organic compound of Formula, wherein X is oxygen (O) or sulfur (S), and each of R1 to R4 is independently selected from the group consisting of deuterium, halogen, cyano, C1 to C10 alkyl group. C1 to C10 alkoxy group, C3 to C30 cycloalkyl group, C6 to C30 aryl group, C6 to C30 arylamino group, and C5 to C30 heteroaryl group, wherein each of L1 and L2 is independent selected from the group consisting of C6 to C30 arylene group and C5 to C30 heteroarylene group, and wherein each of a and b is independent 0 or 1, each of c and f is independently an integer of 0 to 3, and each of d and e is independently an integer of 0 to 2.

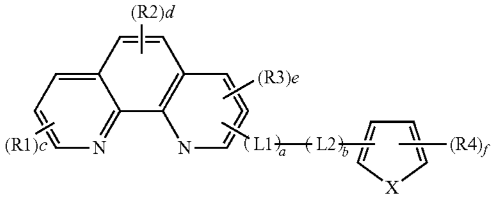

According to another aspect, the present disclosure provides an organic light emitting diode that comprises a first electrode; a second electrode facing the first electrode; and a first emitting part including a first emitting material layer and a first electron transporting layer and positioned between the first and second electrodes, wherein the first electron transporting layer includes a first electron transporting material and is positioned between the first emitting material layer and the second electrode, wherein the first electron transporting material is an organic compound of Formula, wherein X is oxygen (O) or sulfur (S), and each of R1 to R4 is independently selected from the group consisting of deuterium, halogen, cyano, C1 to C10 alkyl group. C1 to C10 alkoxy group, C3 to C30 cycloalkyl group, C6 to C30 aryl group, C6 to C30 arylamino group, and C5 to C30 heteroaryl group, wherein each of L1 and L2 is independent selected from the group consisting of C6 to C30 arylene group and C5 to C30 heteroarylene group, and wherein each of a and b is independent 0 or 1, each of c and f is independently an integer of 0 to 3, and each of d and e is independently an integer of 0 to 2.

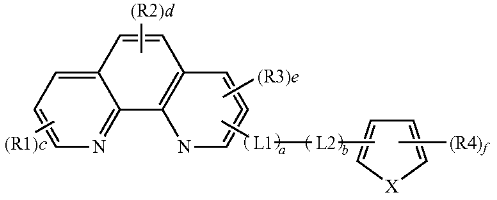

According to another aspect, the present disclosure provides an organic light emitting diode that comprises a first electrode; a second electrode facing the first electrode; a first emitting part including a first emitting material layer and positioned between the first and second electrodes; a second emitting part including a second emitting material layer and positioned between the first emitting part and the second electrode; and a first n-type charge generation layer including a first n-type charge generation material and positioned between the first and second emitting parts, wherein the first n-type charge generation material is an organic compound of Formula, wherein X is oxygen (O) or sulfur (S), and each of R1 to R4 is independently selected from the group consisting of deuterium, halogen, cyano, C1 to C10 alkyl group, C1 to C10 alkoxy group. C3 to C30 cycloalkyl group, C6 to C30 aryl group. C6 to C30 arylamino group, and C5 to C30 heteroaryl group, wherein each of L1 and L2 is independent selected from the group consisting of C6 to C30 arylene group and C5 to C30 heteroarylene group, and wherein each of a and b is independent 0 or 1, each of c and f is independently an integer of 0 to 3, and each of d and e is independently an integer of 0 to 2.

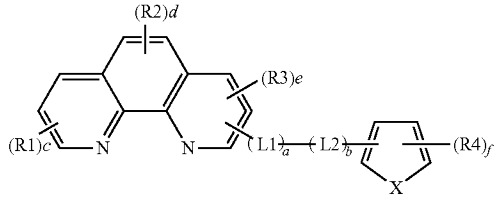

According to another aspect, the present disclosure provides an organic light emitting display device that includes a substrate; the above organic light emitting diode over the substrate; and an encapsulation film covering the organic light emitting diode.

It is to be understood that both the foregoing general description and the following detailed description are examples and are explanatory and are intended to provide further explanation of the disclosure as claimed.

Advantageous Effects of Invention

An organic compound of the present disclosure has a structure, where a thiophene moiety or a furan moiety is combined to a phenanthroline moiety directly or through a linker, to provide high electron transporting efficiency.

The organic compound of the present disclosure is included in (or used for) an electron transporting layer and/or an n-type charge generation layer of an OLED so that the OLED and an organic light emitting device have increased emitting efficiency and lifespan and decreased driving voltage.

BRIEF DESCRIPTION OF DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

FIG. 1 is a schematic circuit diagram of an organic light emitting display device of the present disclosure.

FIG. 2 is a schematic cross-sectional view of an organic light emitting display device according to a first embodiment of the present disclosure.

FIG. 3 is a schematic cross-sectional view of an OLED according to a second embodiment of the present disclosure.

FIG. 4 is a schematic cross-sectional view of an organic light emitting display device according to a third embodiment of the present disclosure.

FIG. 5 is a schematic cross-sectional view of an OLED according to a fourth embodiment of the present disclosure.

FIG. 6 is a schematic cross-sectional view of an OLED according to a fifth embodiment of the present disclosure.

MODE FOR THE INVENTION

Reference will now be made in detail to aspects of the disclosure, examples of which are illustrated in the accompanying drawings.

The present disclosure provides new organic compound, an OLED including the organic compound in an electron transporting layer and/or an n-type charge generation layer, and an organic light emitting device including the OLED. For example, the organic light emitting device may be an organic light emitting display device or an organic lightening device. As an example, an organic light emitting display device, which is a display device including the OLED of the present disclosure, will be mainly described.

FIG. 1 is a schematic circuit diagram of an organic light emitting display device of the present disclosure.

As shown in FIG. 1, an organic light emitting display device includes a gate line GL, a data line DL, a power line PL, a switching thin film transistor TFT Ts, a driving TFT Td, a storage capacitor Cst, and an OLED D. The gate line GL and the data line DL cross each other to define a pixel region P. The pixel region P may include a red pixel region, a green pixel region and a blue pixel region.

The switching TFT Ts is connected to the gate line GL and the data line DL, and the driving TFT Td and the storage capacitor Cst are connected to the switching TFT Ts and the power line PL. The OLED D is connected to the driving TFT Td.

In the organic light emitting display device, when the switching TFT Ts is turned on by a gate signal applied through the gate line GL, a data signal from the data line DL is applied to the gale electrode of the driving TFT Td and an electrode of the storage capacitor Cst.

When the driving TFT Td is turned on by the data signal, an electric current is supplied to the OLED D from the power line PL. As a result, the OLED D emits light. In this case, when the driving TFT Td is turned on, a level of an electric current applied from the power line PL to the OLED D is determined such that the OLED D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the OLED D is maintained to next frame.

As a result, the organic light emitting display device displays a desired image.

FIG. 2 is a schematic cross-sectional view of an organic light emitting display device according to a first embodiment of the present disclosure.

As shown in FIG. 2, the organic light emitting display device 100 includes a substrate 110, a TFT Tr over the substrate 110, and an OLED D on a planarization layer and connected to the TFT Tr. For example, a red pixel region, a green pixel region and a blue pixel region may be defined on the substrate 110, and the OLED D is positioned in each pixel region. Namely, the OLED D respectively emitting red, green and blue light may be disposed in the red pixel region, the green pixel region and the blue pixel region.

The substrate 110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 are formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 150 is formed on an entire surface of the substrate 110 to cover the TFT Tr. The planarization layer 150 has a drain contact hole 152 exposing the drain electrode 142 of the TFT Tr.

A first electrode 160 is disposed on the planarization layer 150 and is separately formed in each pixel region. The first electrode 160 is connected to the drain electrode 142 of the TFT Tr through the drain contact hole 152.

The first electrode 160 may be an anode and may be formed of a conductive material, e.g., a transparent conductive oxide (TCO), having a relatively high work function. For example, the first electrode 160 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 160 may have a single-layered structure of the transparent conductive material layer. When the Organic light emitting display device 100 is operated in a top-emission type, a reflection electrode or a reflection layer may be formed under the first electrode 160. For example, the reflection electrode or the reflection layer may be formed of silver (Ag) or aluminum-palladium-copper (APC) alloy. In this instance, the first electrode 160 may have a triple-layered structure of ITO/Ag/ITO or ITO/APC/ITO.

In addition, a bank layer 166 is formed on the planarization layer 150 to cover an edge of the first electrode 160. Namely, the bank layer 166 is positioned at a boundary of the pixel region and exposes a center of the first electrode 160 in the pixel region.

The organic light emitting layer 162 as an emitting unit is formed on the first electrode 160. The organic light emitting layer 162 may include an emitting material layer (EML) including an emitting material and an electron transporting layer (ETL) on or over the EML. In addition, the organic light emitting layer 162 may further include at least one of a hole injection layer (HIL), a hole transporting layer (HTL), an electron blocking layer (EBL), a hole blocking layer (HBL), and an electron injection layer (EIL). As described below, the ETL includes an organic compound having a structure, where a thiophene moiety or a furan moiety is combined to a phenanthroline moiety directly or through a linker, so that the electron is efficiently transferred into the EML by the ETL.

The second electrode 164 is formed over the substrate 110 where the organic light emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg), silver (Ag) or their alloy, e.g., Al—Mg alloy (AlMg) or Ag—Mg alloy (MgAg). In the top-emission type organic light emitting display device 100, the second electrode 164 may have a thin profile (small thickness) to provide a light transmittance property (or a semi-transmittance property).

Namely, one of the first and second electrodes 160 and 164 is a transparent (or semi-transparent) electrode, and the other one of the first and second electrodes 160 and 164 is a reflective electrode.

The first electrode 160, the organic light emitting layer 162 and the second electrode 164 constitute the OLED D.

An encapsulation film (or an encapsulation layer) 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may be omitted.

The organic light emitting display device 100 may include a color filter layer (not shown). The color filter layer may include red, green and blue color filters corresponding to the red, green and blue pixel regions, respectively. The color purity of the organic light emitting display device 100 may be improved by the color filter layer.

The organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window have a flexible property such that a flexible organic light emitting display device may be provided.

FIG. 3 is a schematic cross-sectional view of an OLED according to a second embodiment of the present disclosure.

As shown in FIG. 3, the OLED D1 includes the first and second electrodes 160 and 164, which face each other, and the organic light emitting layer 162 therebetween. The organic light emitting layer 162 includes an EML 240 between the first and second electrodes 160 and 164 and an ETL 250 between the second electrode 164 and the EML 240.

The first electrode 210 may be an anode, and the second electrode 230 may be a cathode. One of the first and second electrodes 160 and 164 is a transparent (or semi-transparent) electrode, and the other one of the first and second electrodes 160 and 164 is a reflective electrode.

The hole is provided from the first electrode 160 into or toward the EML 240, and the electron is provided from the second electrode 160 into or toward the EML 240 through the ETL 250.

The organic light emitting layer 162 may further include the HTL 220 between the first electrode 160 and the EML 240.

In addition, the organic light emitting layer 162 may further include at least one of an HIL 210 between the first electrode 160 and the HTL 220 and an EIL 260 between the second electrode 164 and the ETL 250.

Although not shown, the organic light emitting layer 162 may further include at least one of an EBL between the HTL 220 and the EML 240 and an HBL between the EML 240 and the ETL 250.

For example, the HIL 210 may include at least one compound selected from the group consisting of 4,4',4"-tris(3-methylphenylamino)triphenylamine (MTDATA), 4,4',4"-tris(N,N-diphenyl-amino)triphenylamine(NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine(2T-NATA), copper phthalocyanine (CuPc), tris(4-carbazoyl-9-yl-phenyl)amine(TCTA), N,N'-diphenyl-N,N-bis(1-naphthyl)-1,1'-biphenyl-4,4"-diamine (NPB; NPD), 1,4,5,8,9,11-hexaazatriphenylenehexacarbonitrile(dipyrazino[2,3-f:2'3'-h]quinoxaline-2,3,6,7,10,11-hexacarbonitrile; HAT-CN), 1,3,5-tris[4-(diphenylamino)phenyl]benzene(TDAPB), poly(3,4-ethylenedioxythiphene)polystyrene sulfonate(PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto.

The HTL 220 may include at least one compound selected from the group consisting of N,N'-diphenyl-N,N'-bis(3-methylphenyl)-1,1'-biphenyl-4,4'-diamine; TPD), NPB (NPD), 4,4'-bis(N-carbazolyl)-1,1'-biphenyl(CBP), poly[N,N-bis(4-butylphenyl)-N,N'-bis(phenyl)-benzidine](Poly-TPD), (poly[(9,9-dioctylfluorenyl-2,7-diyl)-co-(4,4'-(N-(4-sec-butylphenyl)diphenylamine))](TFB), di-[4-(N,N-di-p-tolyl-amino)-phenyl]cyclohexane(TAPC), 3,5-di(9H-carbazol-9-yl)-N,N-diphenylaniline(DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine, but it is not limited thereto.

The EBL may include at least one compound selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl)benzene(mCP), 3,3'-bis(N-carbazolyl)-1,1'-biphenyl(mCBP), CuPc, N,N'-bis[4-[bis(3-methylphenyl)amino]phenyl]-N,N'-diphenyl-[1,1'-biphenyl]-4,4'-dia mine(DNTPD), TDAPB, DCDPA, and 2,8-bis(9-phenyl-9H-carbazol-3-yl)dibenzo[b,d]thiophene), but it is not limited thereto.

The HBL may include at least one compound selected from the group consisting of tris-(8-hydroxyquinoline aluminum($Alq_3$), 2-biphenyl-4-yl-5-(4-t-butylphenyl)-1,3,4-oxadiazole(PBD), spiro-PBD, lithium quinolate(Liq), 1,3,5-tris(N-phenylbenzimidazol-2-yl)benzene(TPBi), bis(2-methyl-8-quinolinolato-N1,O8)-(1,1'-biphenyl-4-olato)aluminum(BAlq), 4,7-diphenyl-1,10-phenanthroline (Bphen), 2,9-bis(naphthalene-2-yl)4,7-diphenyl-1,10-phenanthroline(NBphen), 2,9-dimethyl-4,7-diphenyl-1,10-phenathroline(BCP), 3-(4-biphenyl)-4-phenyl-5-tert-butylphenyl-1,2,4-triazole(TAZ), 4-(naphthalen-1-yl)-3,5-diphenyl-4H-1,2,4-triazole(NTAZ), 1,3,5-tri(p-pyrid-3-yl-phenyl)benzene(TpPyPB), 2,4,6-tris(3'-(pyridin-3-yl)biphenyl-3-yl)1,3,5-triazine(TmPPPyTz), Poly[9,9-bis(3'-((N,N-dimethyl)-N-ethylammonium)-propyl)-2,7-fluorene]-alt-2,7-(9,9-dioctylfluorene)](PFNBr), tris(phenylquinoxaline(TPQ), and diphenyl-4-triphenylsilyl-phenylphosphine oxide(TSPO1), but it is not limited thereto.

The EIL 260 may include at least one of an alkali halide compound, such as LiF, CsF, NaF, or $BaF_2$, and an organometallic compound, such as Liq, lithium benzoate, or sodium stearate, but it is not limited thereto.

The EML 240 in the red pixel region includes a host and a red dopant, the EML 240 in the green pixel region includes a host and a green dopant, and the EML 240 in the blue pixel region includes a host and a blue dopant. Each of the red dopant, the green dopant and the blue dopant may be independently a fluorescent compound, a phosphorescent compound or a delayed fluorescent compound.

For example, in the EML 240 in the red pixel region, the host may be CBP (4,4'-bis(carbazol-9-yl)biphenyl), and the red dopant may be selected from PIQIr (acac)(bis(1-phenylisoquinoline)acetylacetonate iridium), PQIr (acac)(bis(1-phenylquinoline)acetylacetonate iridium), PQIr (tris(1-phenylquinoline)iridium), and PtOEP (octaethylporphyrin platinum). However, it is not limited thereto. The EML 240 in the red pixel region may have an emission wavelength range of about 600 to 650 nm.

In the EML 240 in the green pixel region, the host may be CBP (4,4'-bis(carbazol-9-yl)biphenyl), and the green dopant may be lr(ppy)$_3$ (fac tris(2-phenylpyridine)iridium) or Alq$_3$ (tris(8-hydroxyquinolino)aluminum). However, it is not limited thereto. The EML 240 in the green pixel region may have an emission wavelength range of about 510 to 570 nm.

In the EML 240 in the blue pixel region, the host may be an anthracene derivative, and the blue dopant may be a boron derivative. However, it is not limited thereto. For example, the host may be a compound in Formula 5, and the blue dopant may be a compound in Formula 6. In the EML 240 in the blue pixel region, the blue dopant may have a weight % of about 1 to 20, preferably about 1 to 10. The EML 240 in the blue pixel region may have an emission wavelength range of about 440 to 480 nm.

The ETL 250 includes an organic compound of the present disclosure having a structure, where a thiophene moiety or a furan moiety is combined to a phenanthroline moiety directly or through a linker, as an electron transporting material 252. The organic compound of the present disclosure is represented by Formula 1-1.

[Formula 1-1]

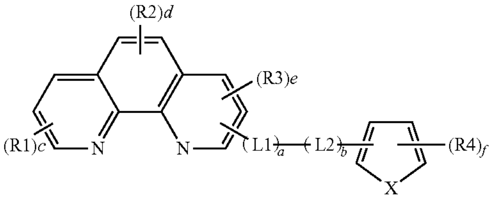

In Formula 1-1, X is oxygen (O) or sulfur (S), and each of R1 to R4 is independently selected from the group consisting of deuterium, halogen, cyano, C1 to C10 alkyl group. C1 to C10 alkoxy group. C3 to C30 cycloalkyl group, C6 to C30 aryl group, C6 to C30 arylamino group, and C5 to C30 heteroaryl group. Each of L1 and L2 is independent selected from the group consisting of C6 to C30 arylene group and C5 to C30 heteroarylene group. Each of a and b is independent 0 or 1, each of c and f is independently an integer of 0 to 3, and each of d and e is independently an integer of 0 to 2.

For example, C6 to C30 aryl group may be selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzo-phenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl and spiro-fluorenyl, and C6 to C30 arylene group may be their arylene group.

C5 to C30 heteroaryl group may be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzo-carbazolyl, dibenzocarbazolyl, indolocarbazolyl, indenocarbazolyl, benzofuro-carbazolyl, benzothienocarbazolyl, quinolinyl, isoquinolinyl, phthalazinyl, quinoxalinyl, sinolinyl, quinazolinyl, quinozolinyl, quinolinyl, purinyl, phthalazinyl, quinoxalinyl, benzoquinolinyl, benzoisoquinolinyl, benzoquinazolinyl, benzo-quinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xantenyl, chromaenyl, isochromenyl, thioazinyl, thiophenyl, benzothiophenyl, dibenzothiophenyl, difuropyrazinyl, benzo-furodibenzofuranyl, benzothienobenzothiophenyl, benzothienodibenzothiophenyl, benzothienobenzofuranyl, and benzothienodibenzofuranyl, and C5 to C30 heteroarylene group may be their heteroarylene group.

Each of C1 to C10 alkyl group, C1 to C10 alkoxy group, C3 to C30 cycloalkyl group. C6 to C30 aryl group, C6 to C30 arylamino group, C5 to C30 heteroaryl group, C6 to C30 arylene group and C5 to C30 heteroarylene group may be unsubstituted or substituted with deuterium or halogen (e.g., fluorine).

For example, each of R1 to R3 may be independently selected from the group consisting of deuterium, fluorine, cyano, methoxy, trifluoromethyl, trifluoromethoxy, methyl, phenyl, pyridyl, naphthyl, and quinolinyl. Each of R1 to R3 may be unsubstituted or substituted with deuterium.

R4 may be C6 to C30 aryl group. R4 may be selected from the group consisting of phenyl, naphthyl, phenanthrenyl, pyrenyl, anthracenyl, and phenylanthracenyl, and f may be an integer of 1 to 3. For example, f may be 2 or 3, and at least one of R4 may be a polycyclic aryl group, e.g., phenanthrenyl, pyrenyl, anthracenyl, or phenylanthracenyl. Preferably, f may be 3, two of R4 may be phenyl, and the other of R4 may be a polycyclic aryl group, e.g., phenanthrenyl, pyrenyl, anthracenyl, or phenylanthracenyl. R4 may be unsubstituted or substituted with deuterium.

Each of L1 and L2 may be C6 to C30 arylene group, e.g., phenylene or naphthylene. For example, each of L1 and L2 may be unsubstituted or substituted with deuterium, C1 to C10 alkyl or $CD_3$. At least one of a and b may be 1.

For example, each of L1 and L2 may be independently selected from the groups in Formula 1-2.

[Formula 1-2]

A-1

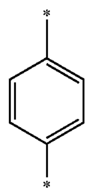

A-2

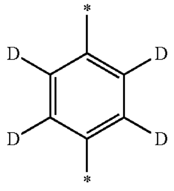

-continued
A-3
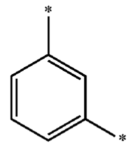
A-4
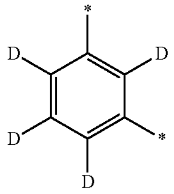
A-5
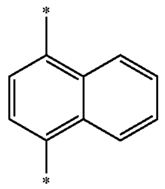
A-6
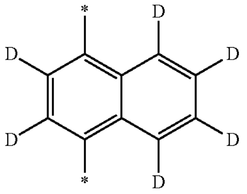
A-7
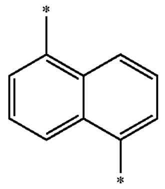
A-8
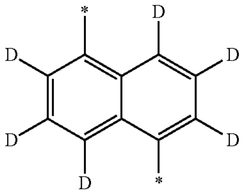
A-9
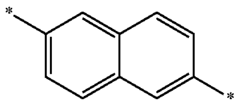
A-10
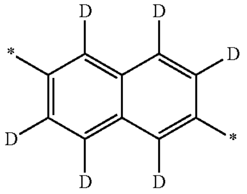
-continued
A-11
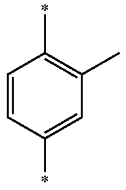
A-12
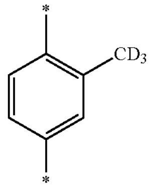
A-13
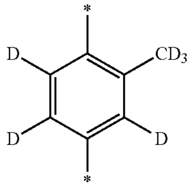
A-14
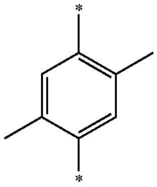
A-15
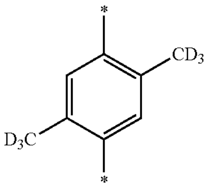
A-16
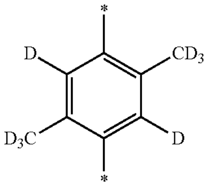
A-17
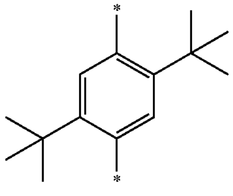
A-18
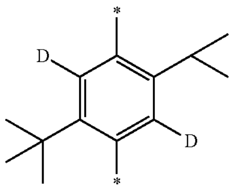
The phenanthroline moiety in Formula 1-1 may be selected from the groups in Formula 1-3.

[Formula 1-3]
A-1
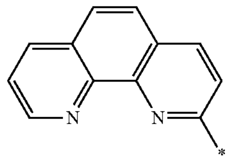
A-2
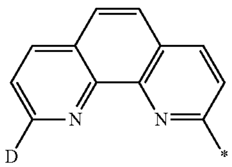
A-3
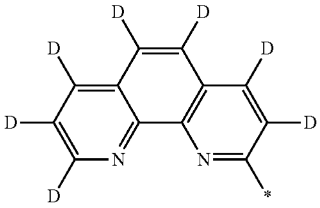
A-4
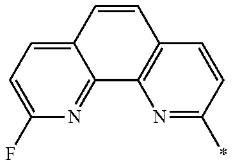
A-5
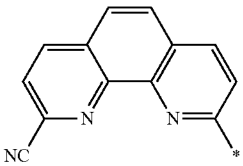
A-6
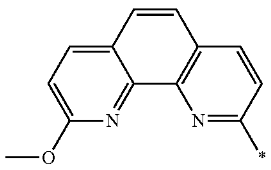
A-7
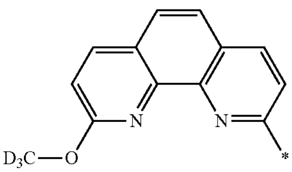
A-8
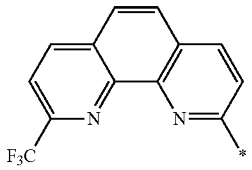
-continued
A-9
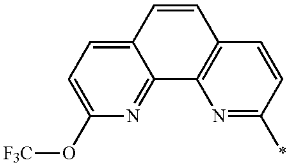
A-10
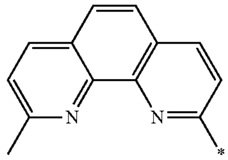
A-11
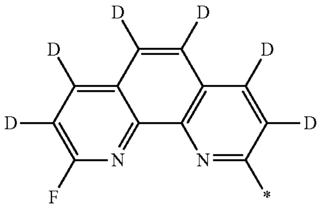
A-12
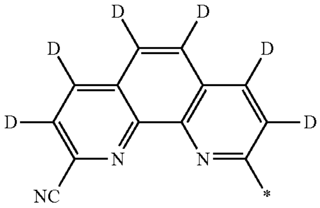
A-13
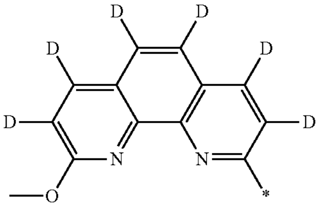
A-14
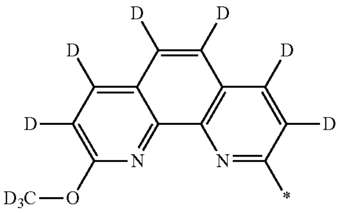
A-15
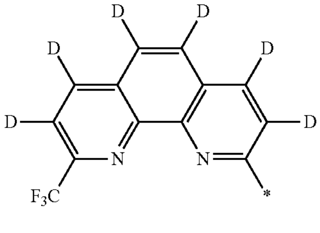

-continued
A-16
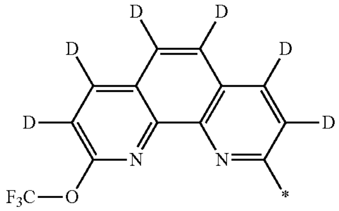
A-17
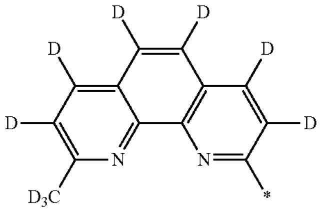
A-18
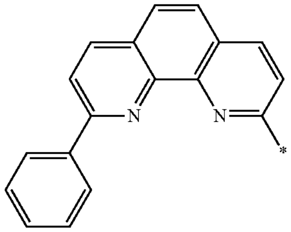
A-19
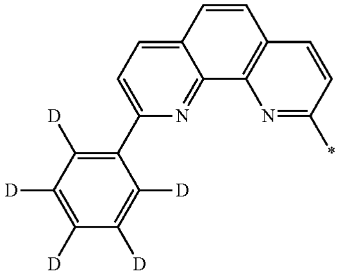
A-20
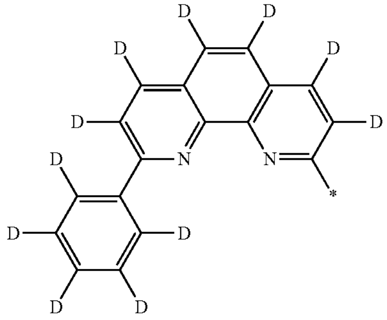
A-21
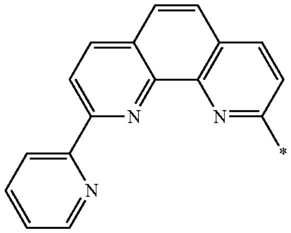
-continued
A-22
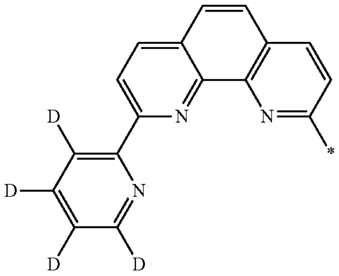
A-23
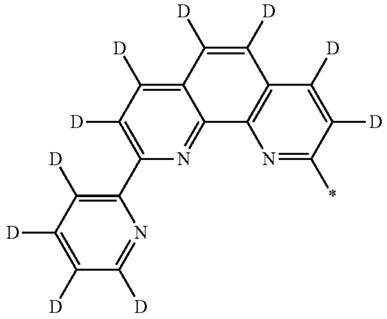
A-24
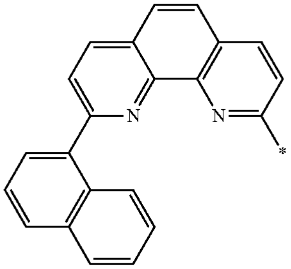
A-25
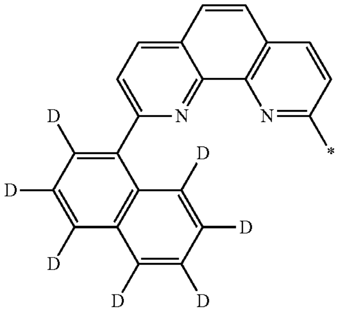
A-26
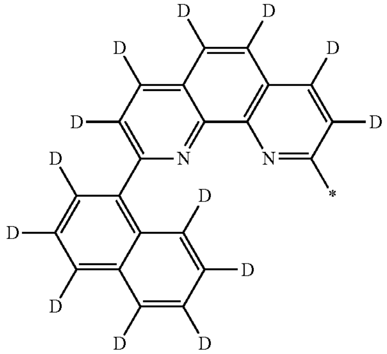

-continued
A-27
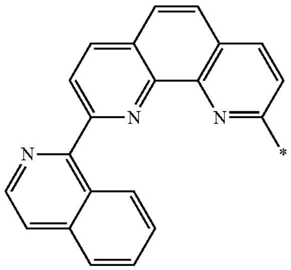
A-28
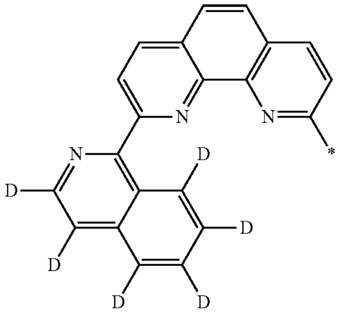
A-29
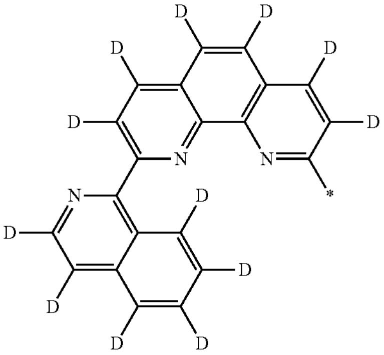
A thiophene moiety, i.e., X═S, in Formula 1-1 may be selected from the groups in Formula 1-4.
[Formula 1-4]
A-1
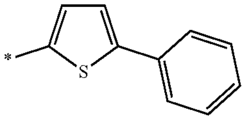
A-2
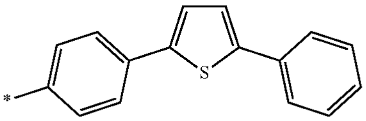
A-3
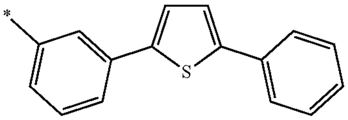
-continued
A-4
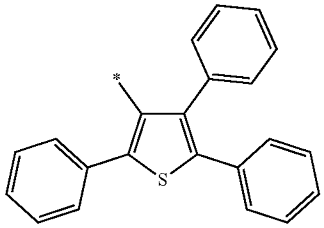
A-5
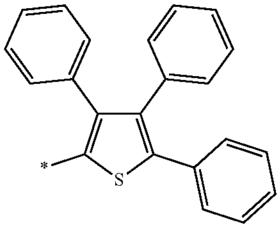
A-6
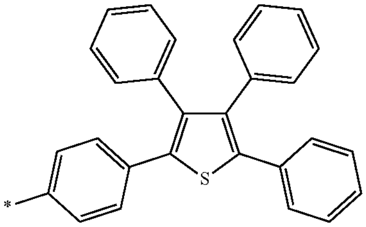
A-7
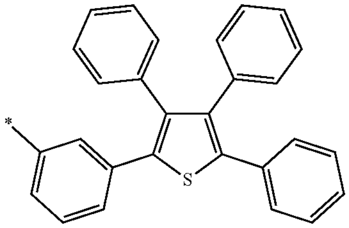
A-8
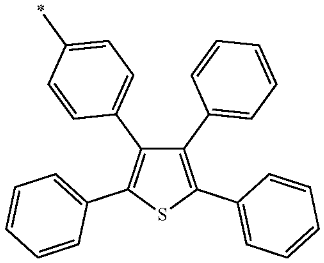
A-9
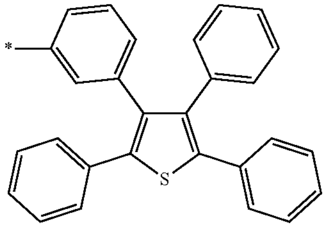

-continued
A-10
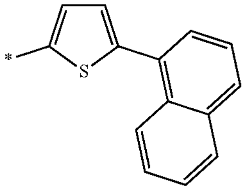
A-11
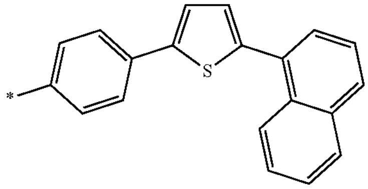
A-12
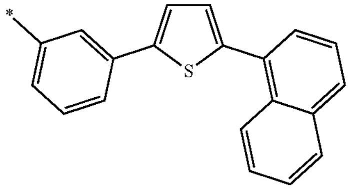
A-13
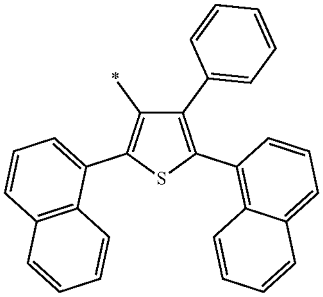
A-14
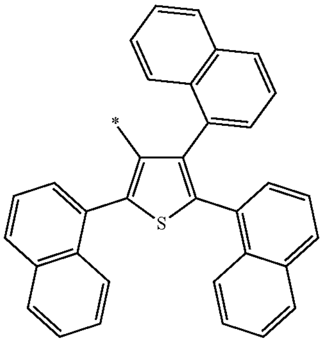
A-15
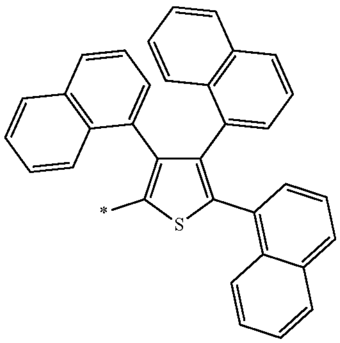
-continued
A-16
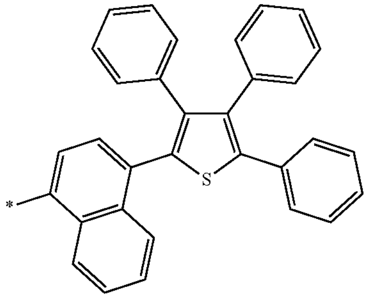
A-17
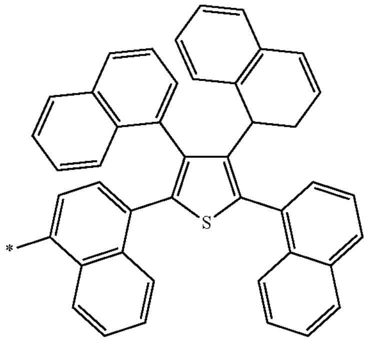
A-18
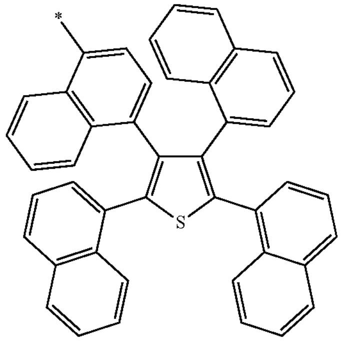
A-19
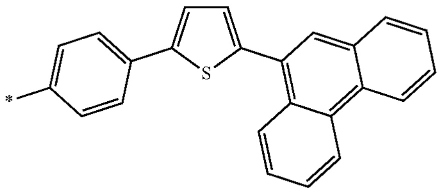
A-20
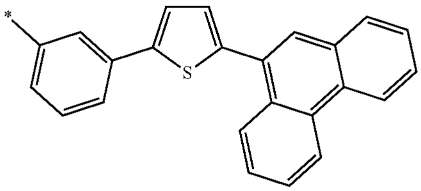

-continued
A-21
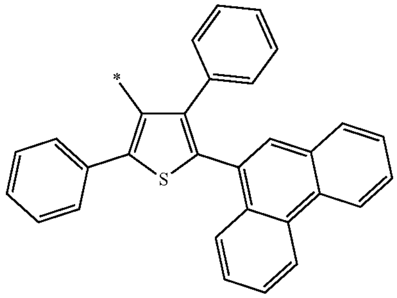
A-22
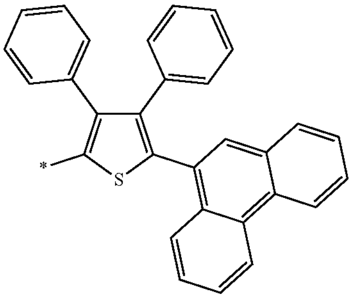
A-23
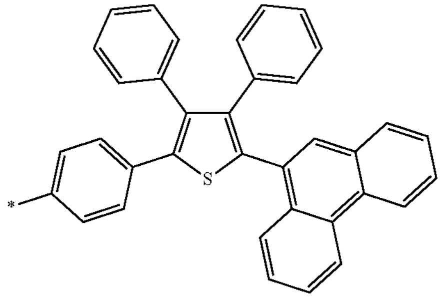
A-24
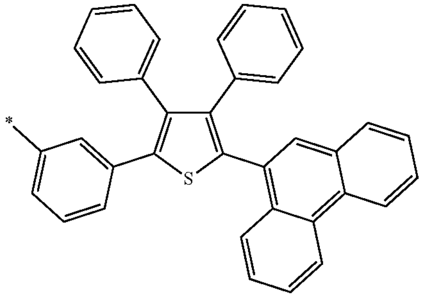
A-25
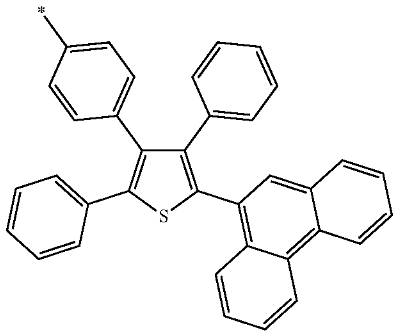
-continued
A-26
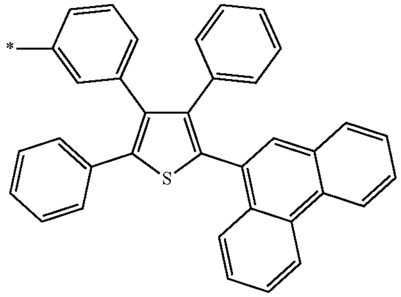
A-27
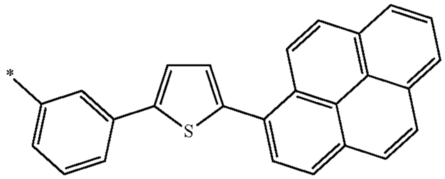
A-28
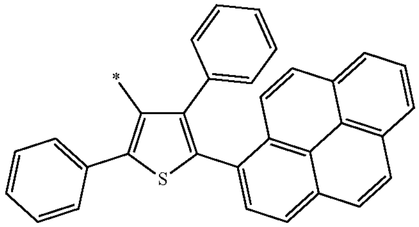
A-29
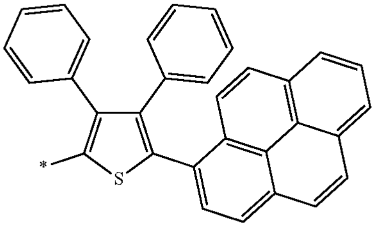
A-30
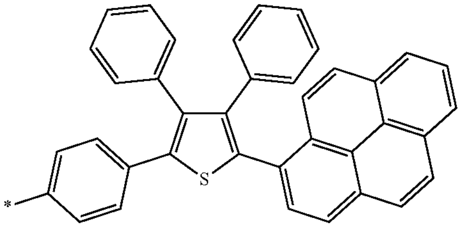
A-31
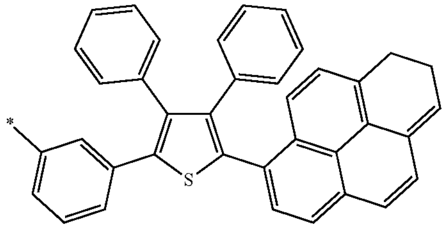

-continued
A-32
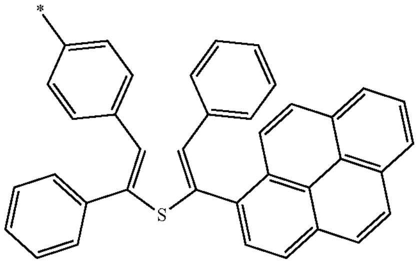
A-33
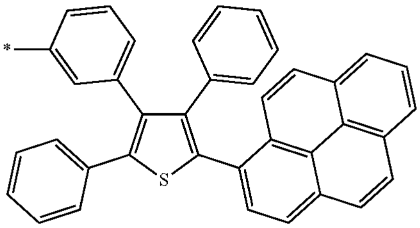
A-34
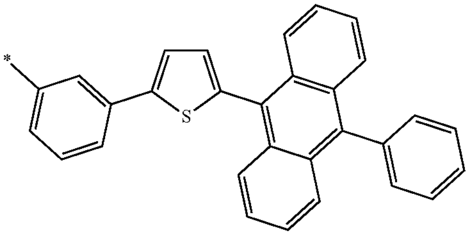
A-35
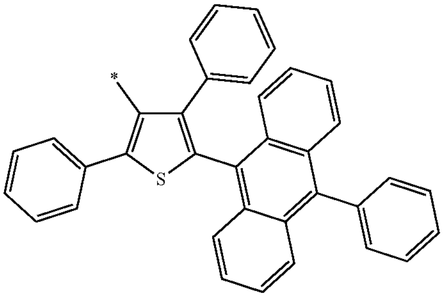
A-36
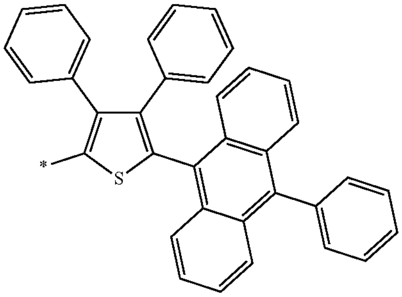
-continued
A-37
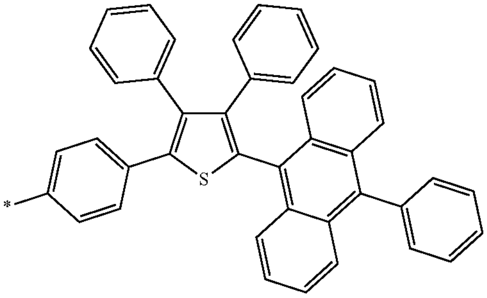
A-38
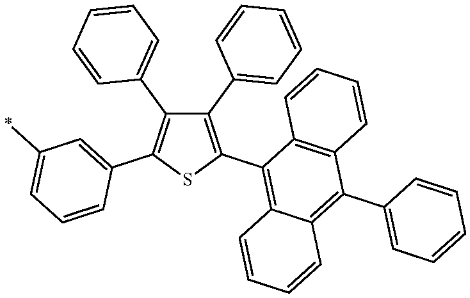
A-39
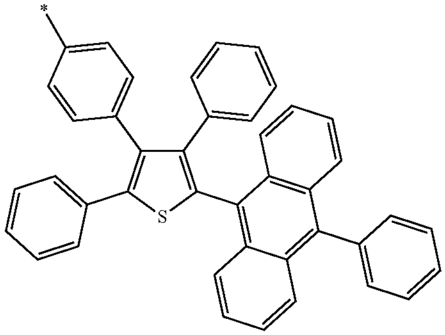
A-40
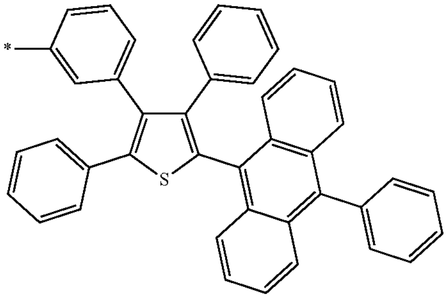
A furan moiety, i.e., X═O, in Formula 1-1 may be selected from the groups in Formula 1-5.
[Formula 1-5]
A-41
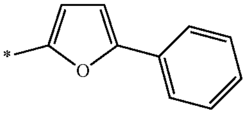

-continued
A-42
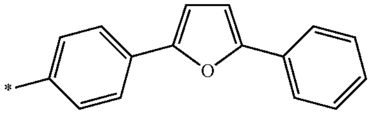
A-43
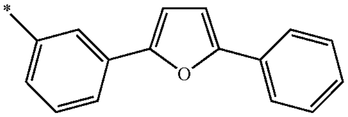
A-44
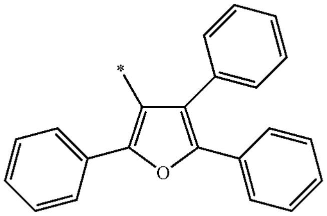
A-45
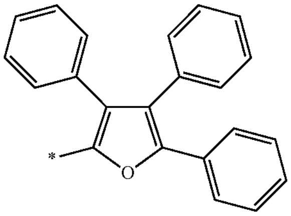
A-46
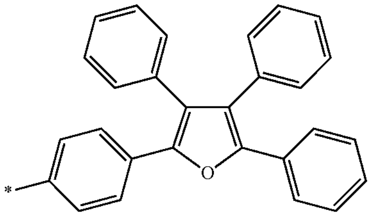
A-47
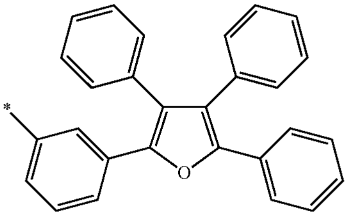
A-48
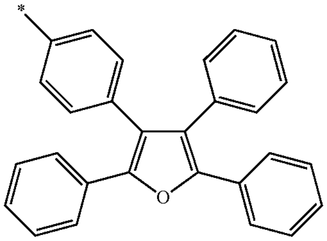
A-49
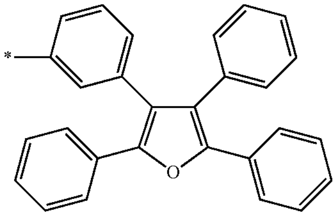
-continued
A-50
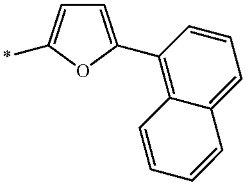
A-51
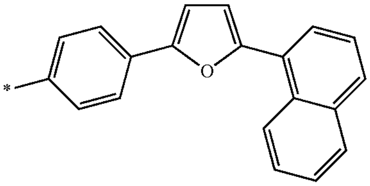
A-52
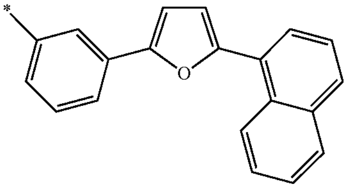
A-53
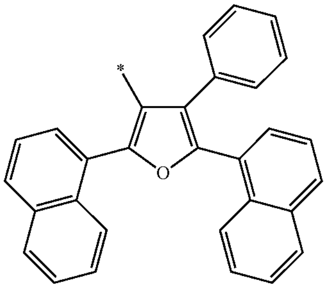
A-54
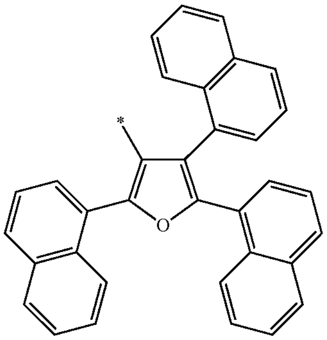
A-55
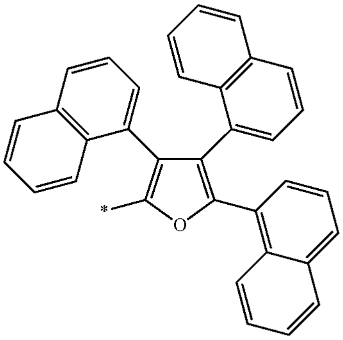

-continued
A-56
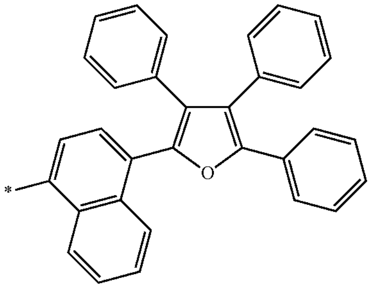
A-57
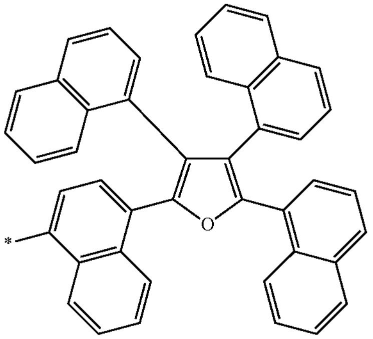
A-58
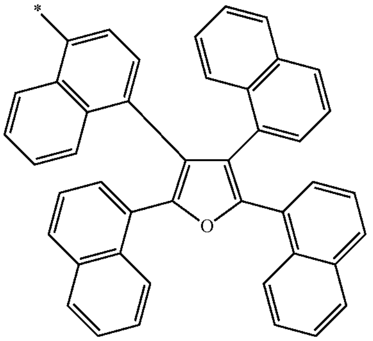
A-59
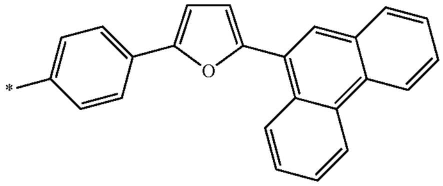
A-60
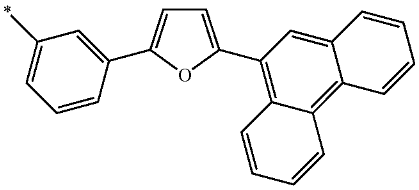
-continued
A-61
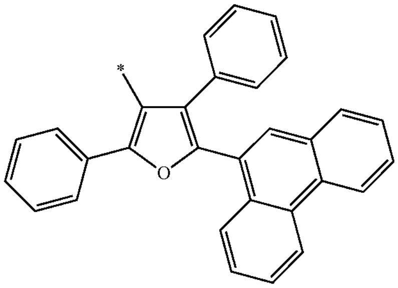
A-62
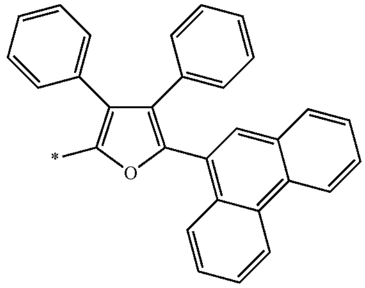
A-63
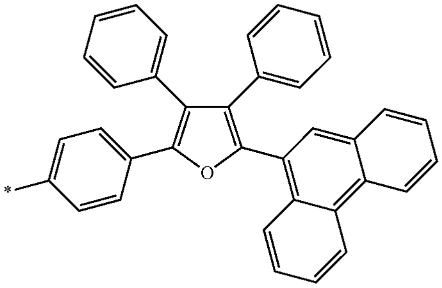
A-64
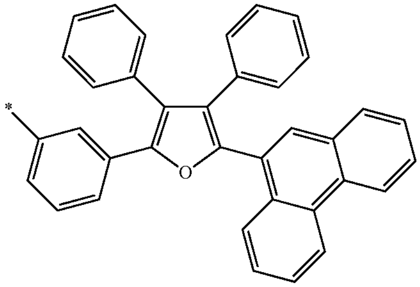
A-65
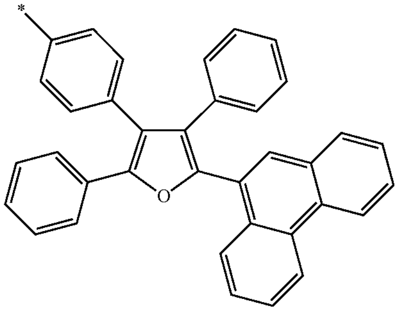

-continued
A-66
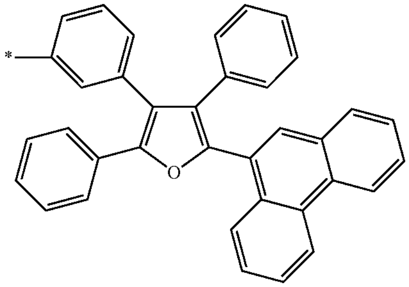
A-67
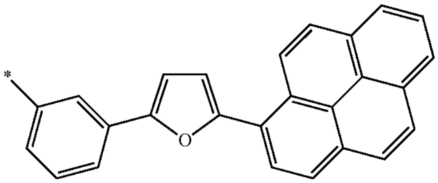
A-68
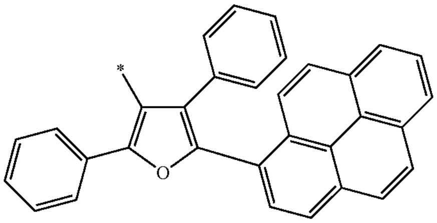
A-69
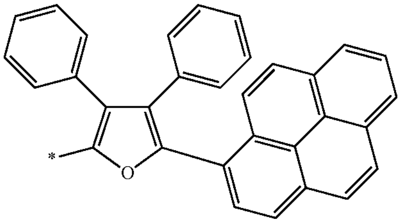
A-70
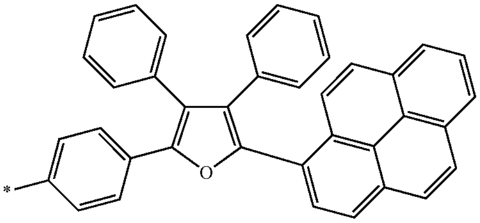
A-71
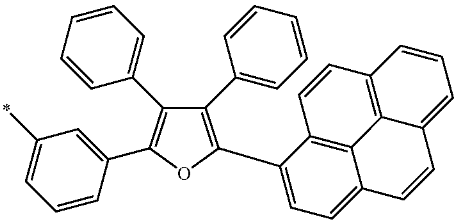
-continued
A-72
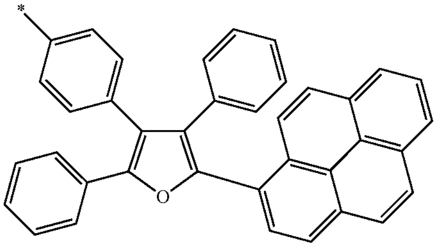
A-73
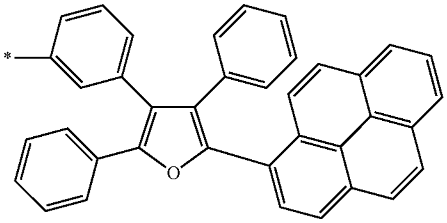
A-74
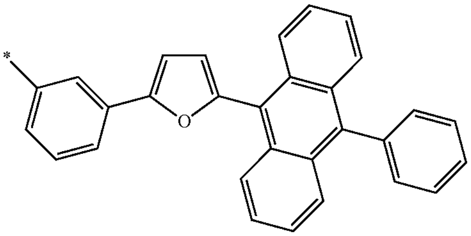
A-75
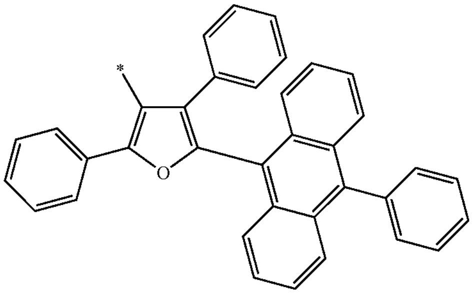
A-76
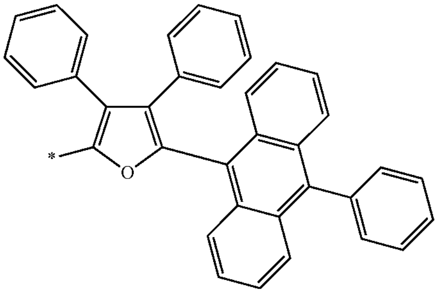
A-77
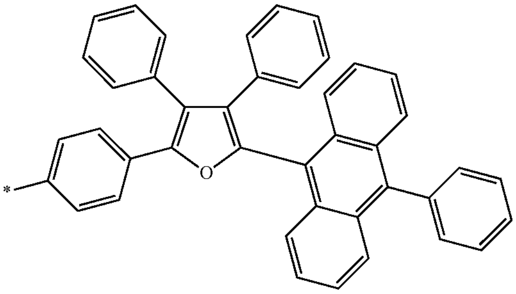

-continued

A-78

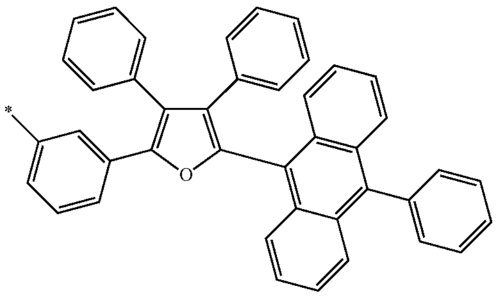

A-79

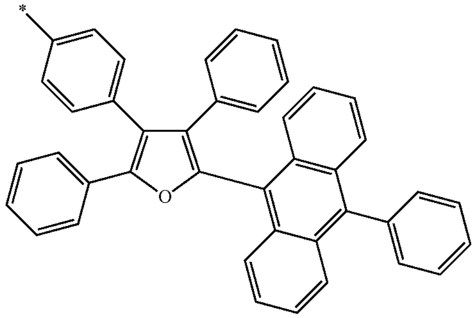

A-80

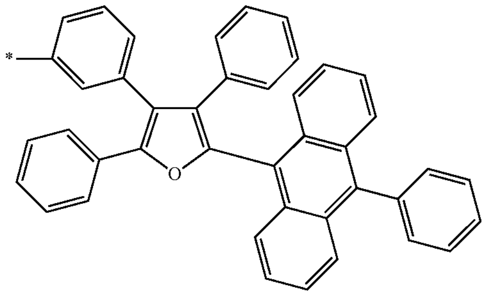

The organic compound of the present disclosure has a structure, where a thiophene moiety or a furan moiety is combined to a phenanthroline moiety directly or through a linker, to provide high electron transporting property. For example, when in Formula 1-1, a 2th-position of the thiophene moiety or the furan moiety is connected (combined or linked) to the phenanthroline moiety directly or through the linker, i.e., L1 and/or L2, and three hydrogen atoms in the thiophene moiety or the furan moiety are substituted with C6 to C30 aryl, i.e., f=3, the electron transporting property of the organic compound is further improved.

The organic compound in Formula 1-1 may be represented by Formula 1-6.

[Formula 1-6]

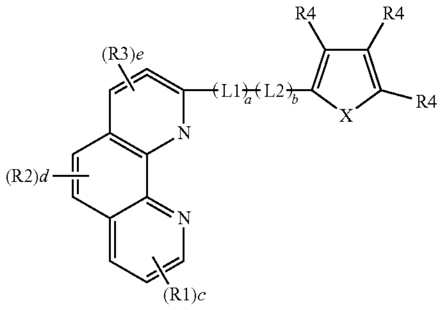

For example, the organic compound of the present disclosure may be one of the compounds in Formula 2.

[Formula 2]

D1

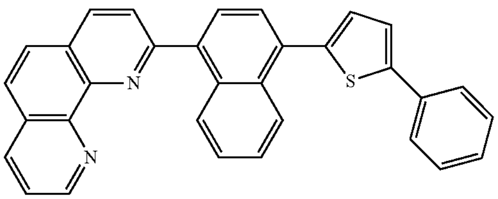

D2

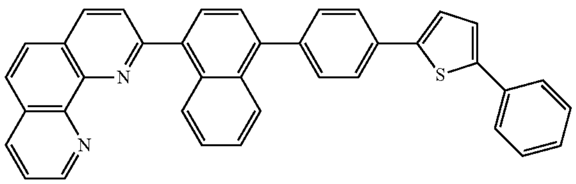

D3

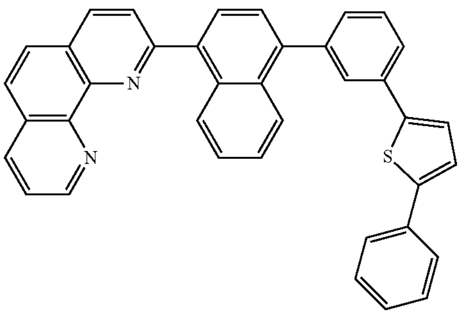

D4

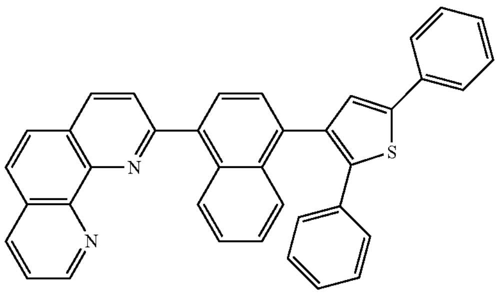

-continued
D5
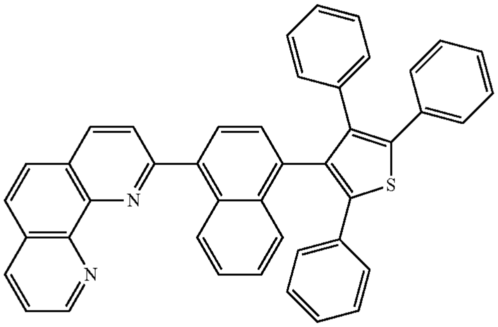
D6
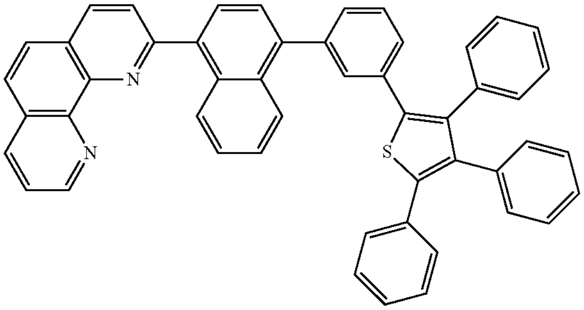
D7
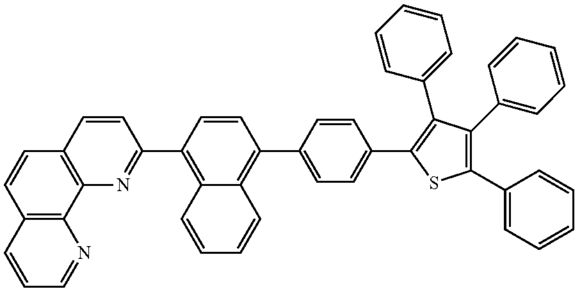
D8
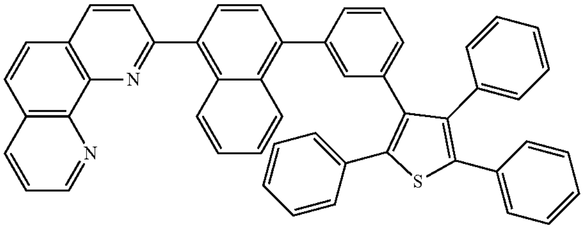
D9
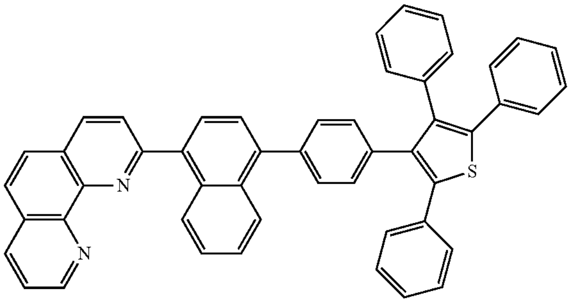
D10
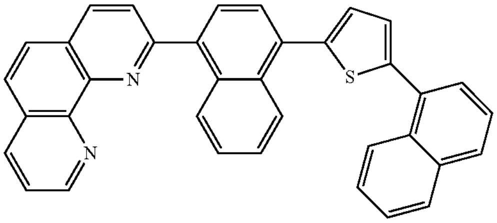
D11
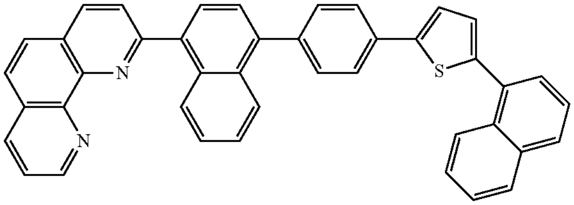
D12
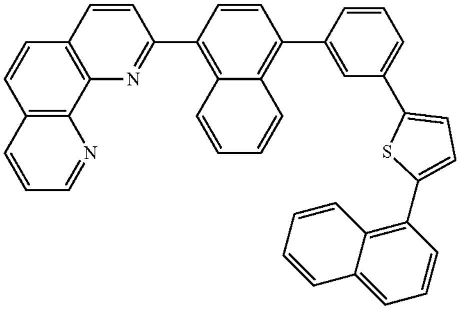

-continued
D13
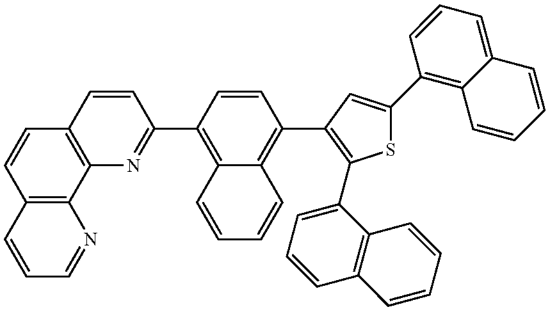
D14
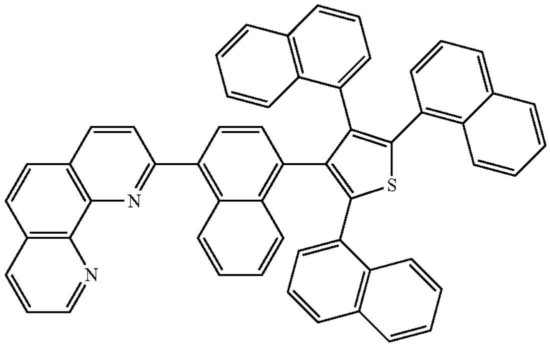
D15
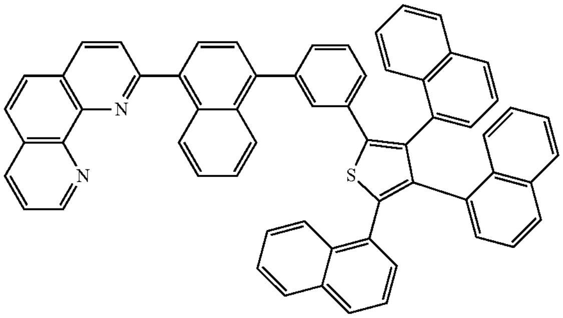
D16
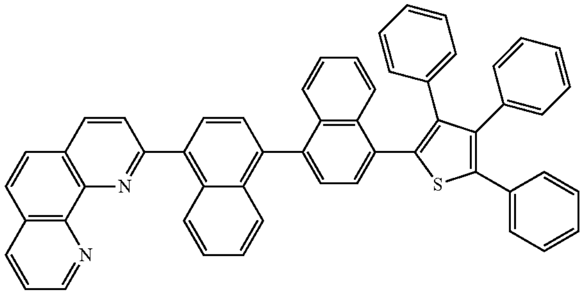
D17
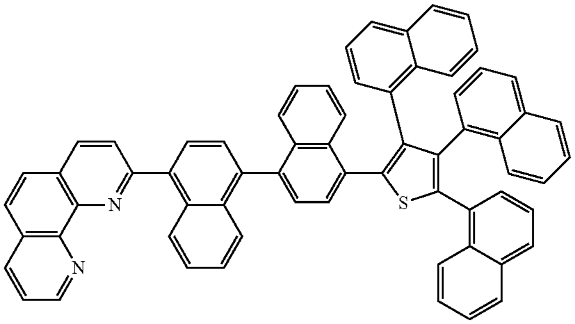
D18
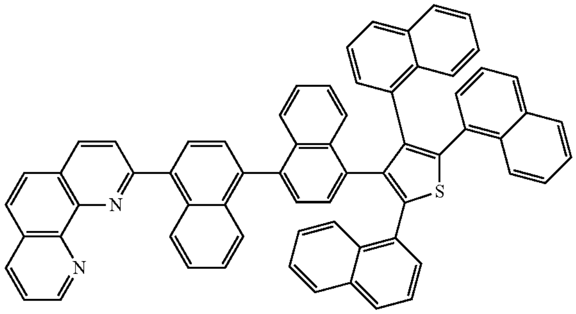
D19
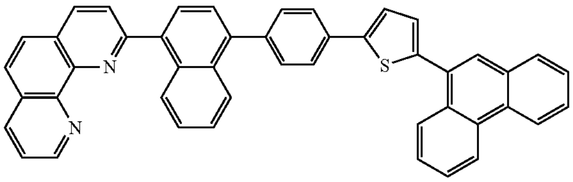
D20
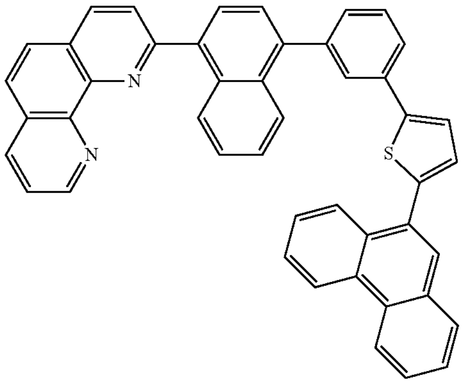

-continued
D21
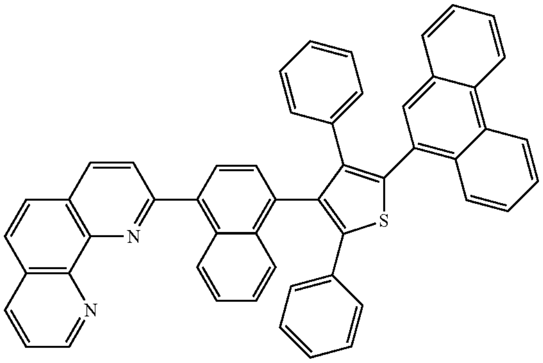
D22
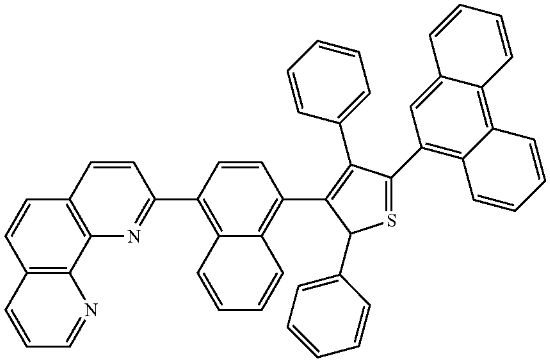
D23
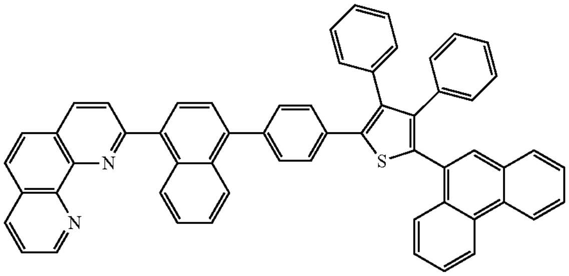
D24
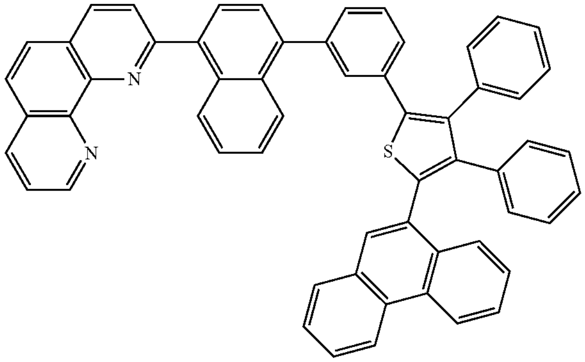
D25
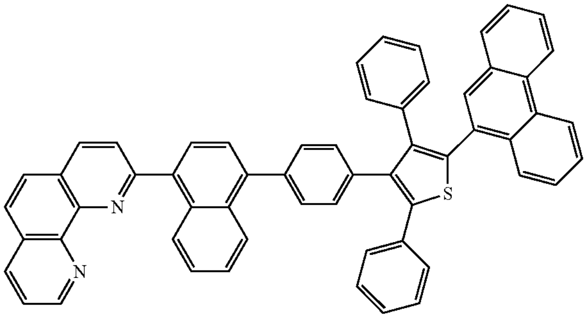
D26
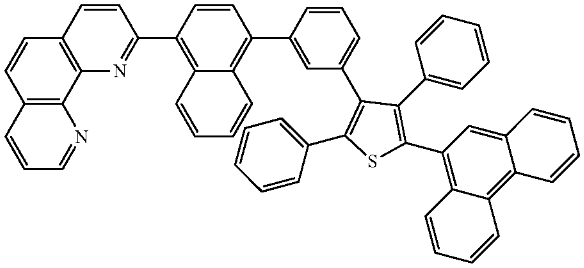
D27
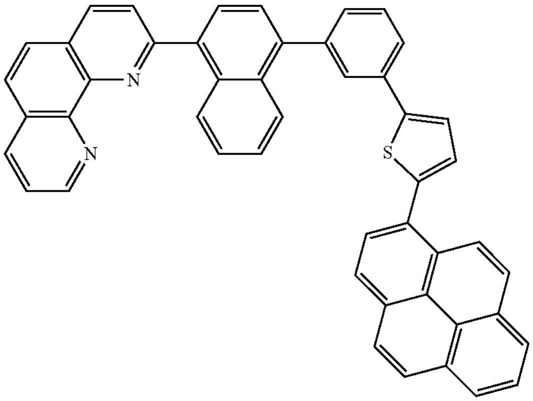
D28
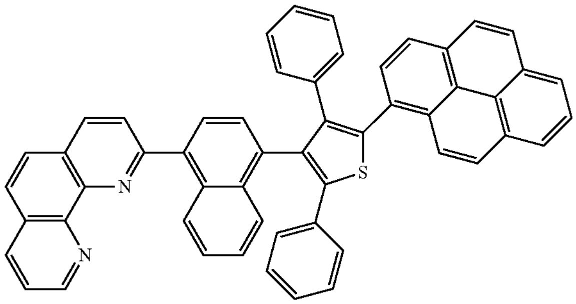

-continued
D29
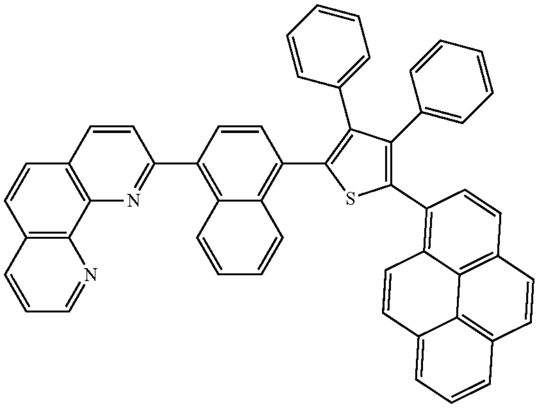
D30
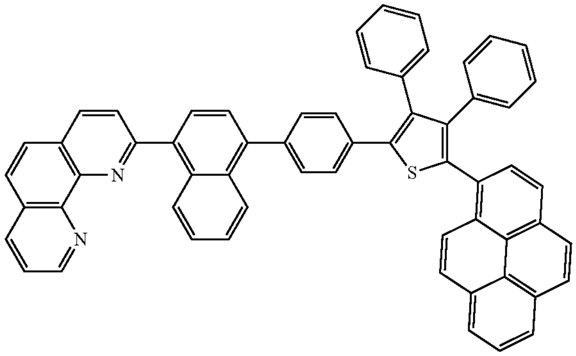
D31
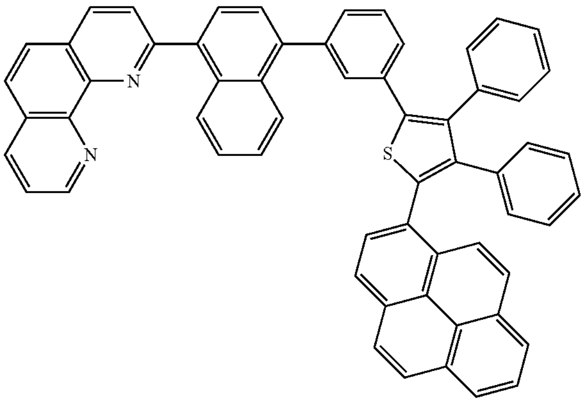
D32
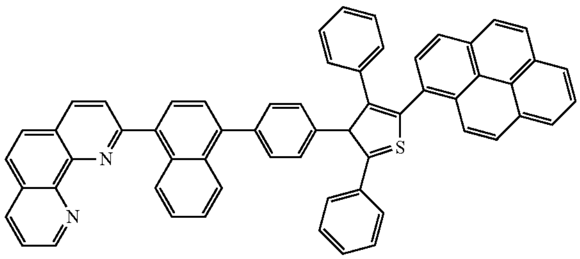
D33
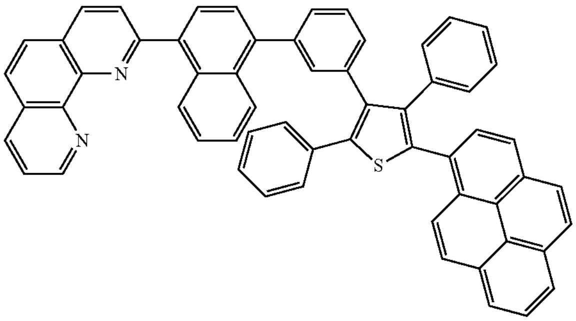
D34
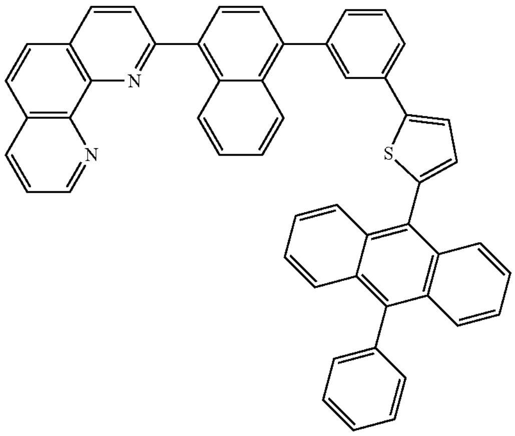

-continued
D35
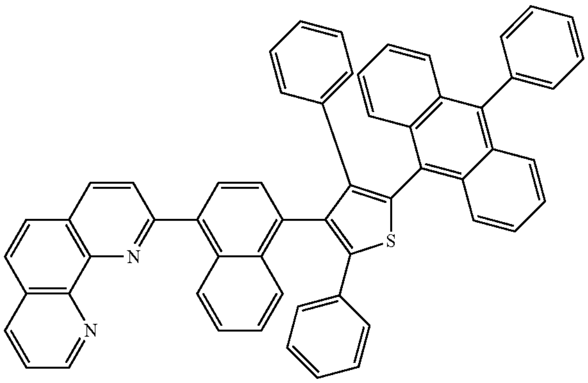
D36
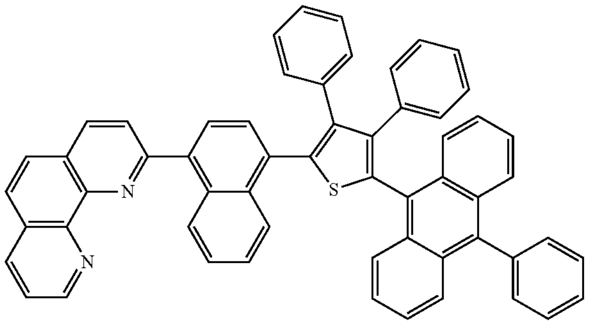
D37
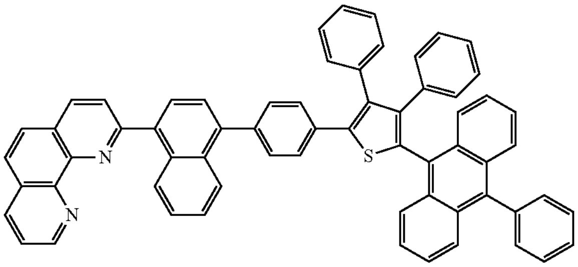
D38
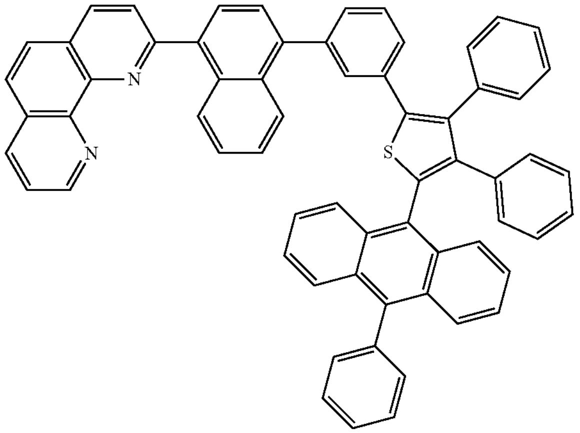
D39
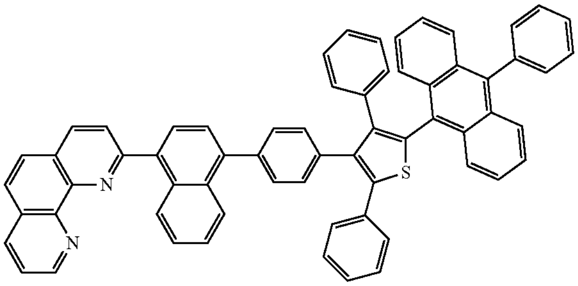
D40
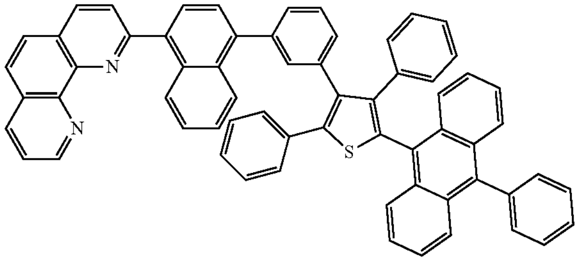
D41
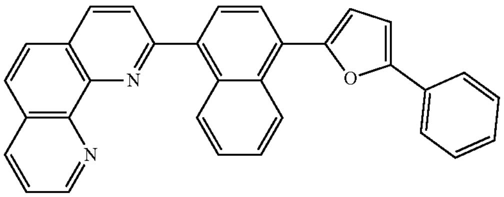
D42
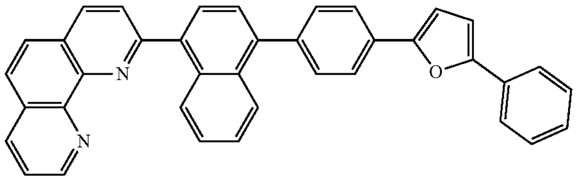

-continued
D43
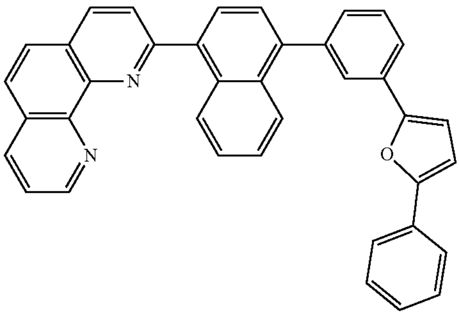
D44
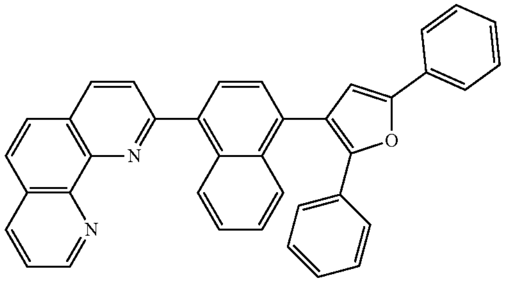
D45
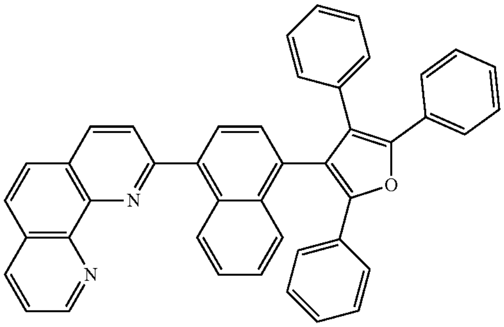
D46
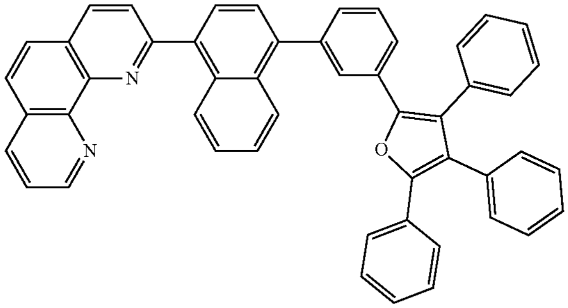
D47
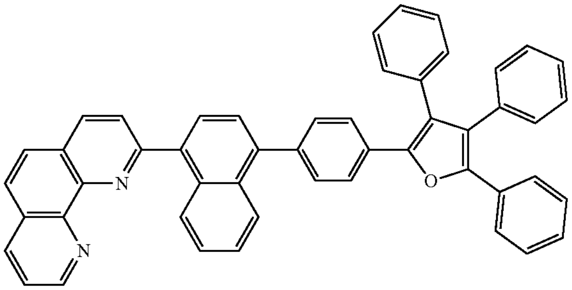
D48
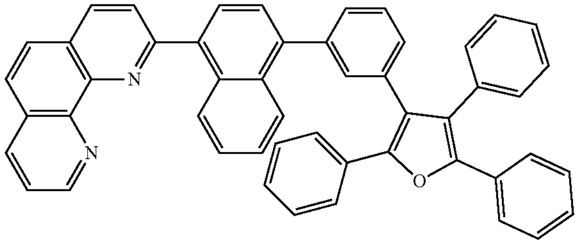
D49
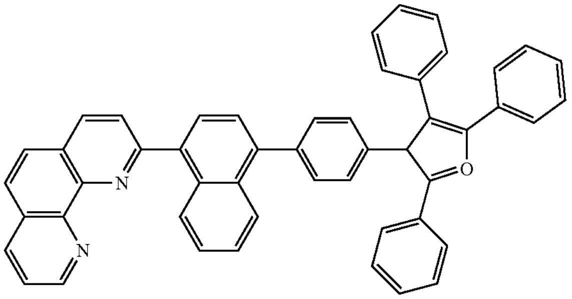
D50
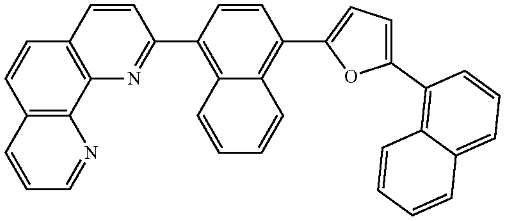
D51
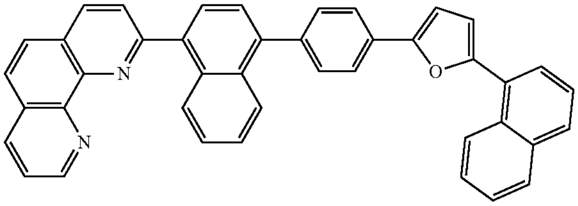
D52
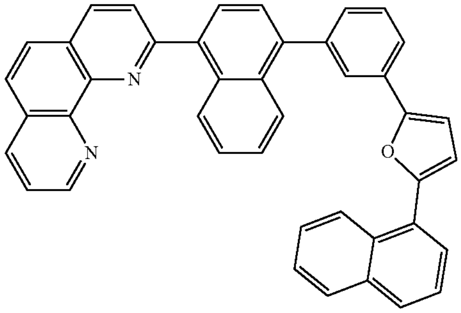

-continued
D53
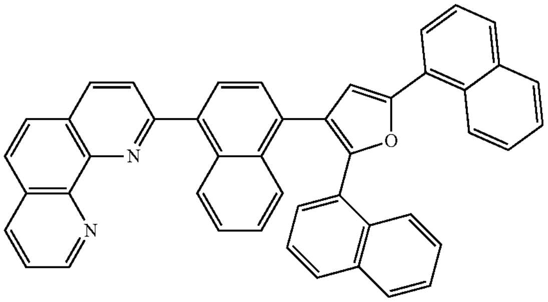
D54
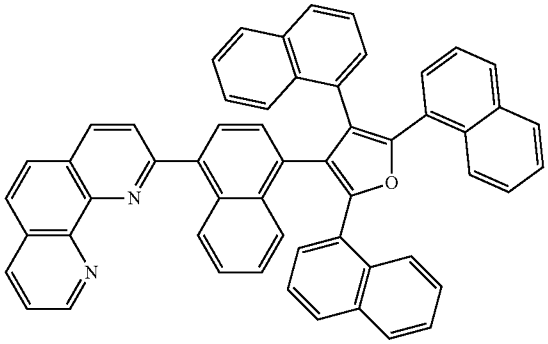
D55
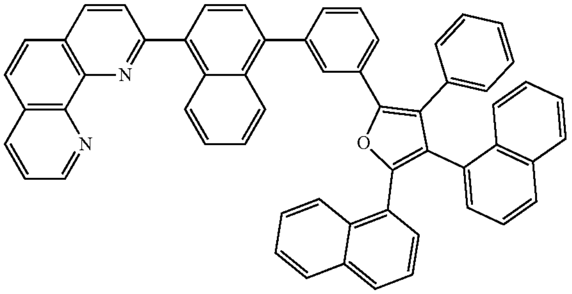
D56
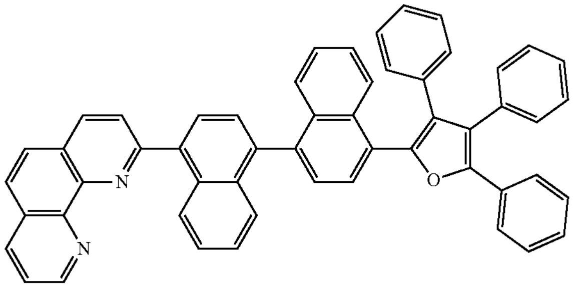
D57
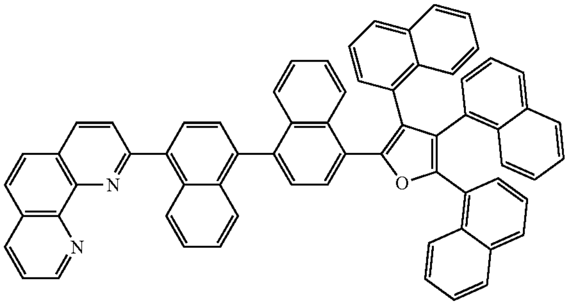
D58
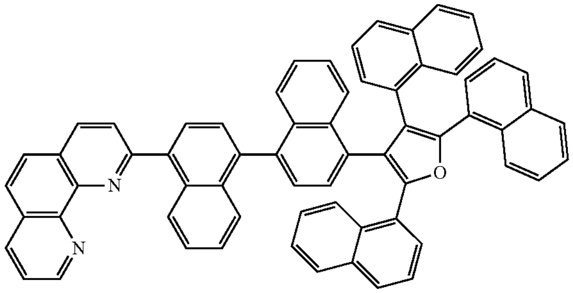
D59
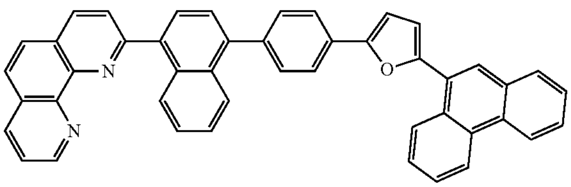
D60
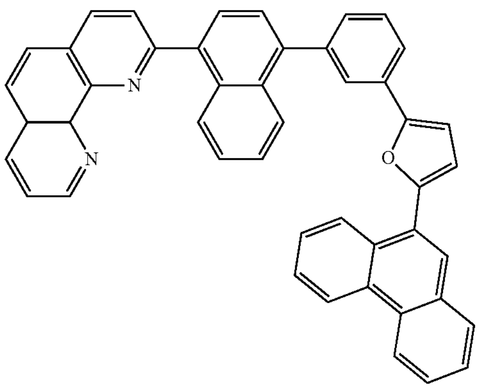

-continued
D61
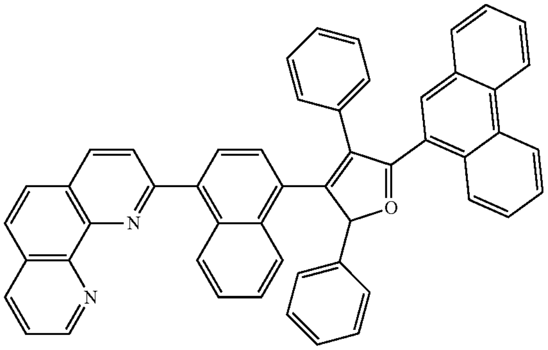
D62
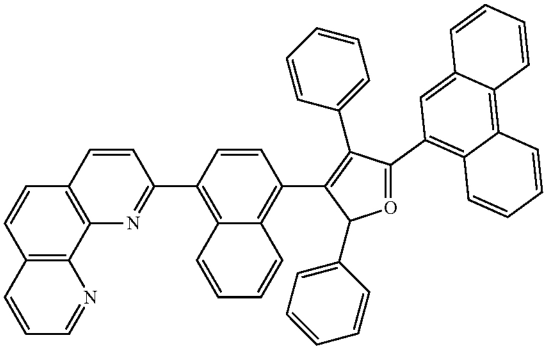
D63
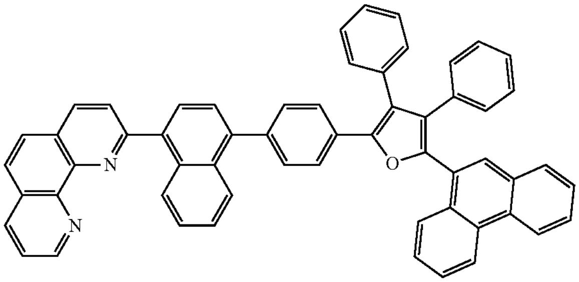
D64
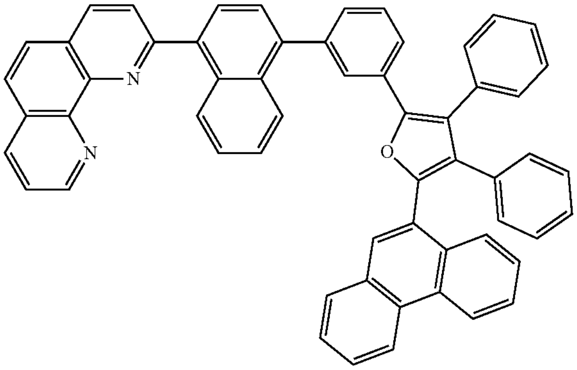
D65
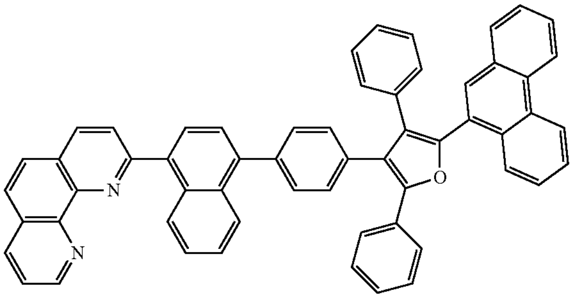
D66
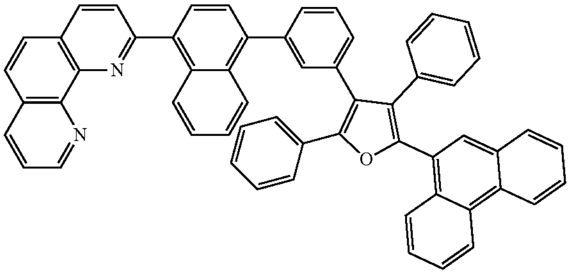
D67
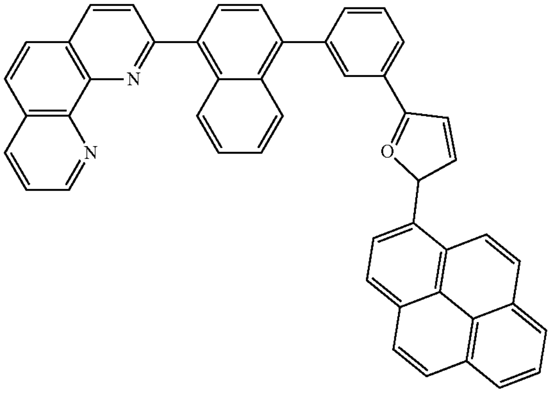
D68
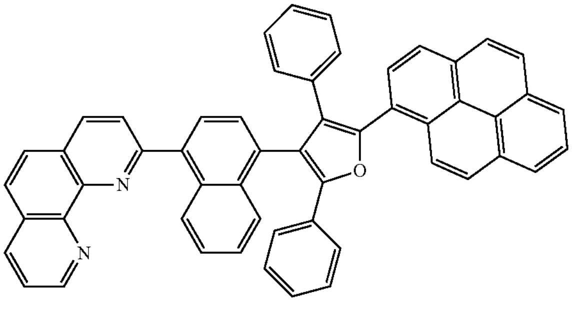

-continued
D69
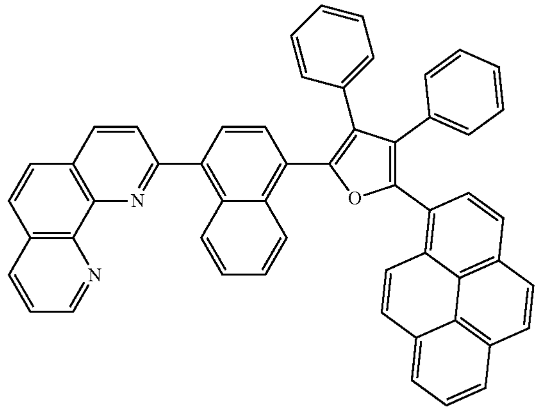
D70
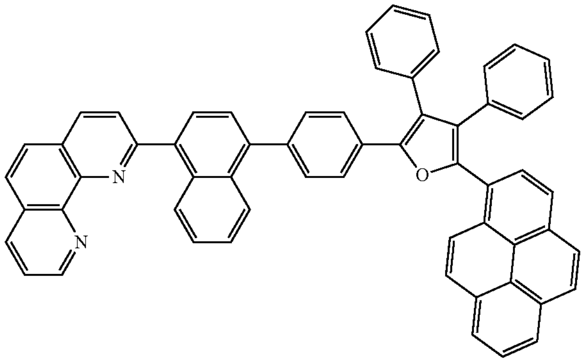
D71
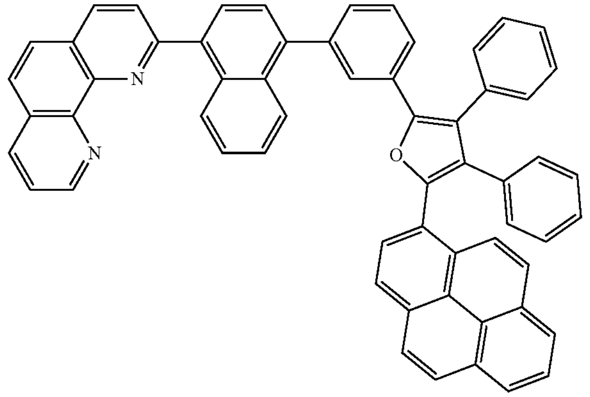
D72
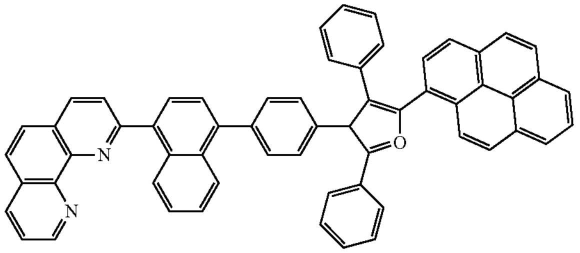
D73
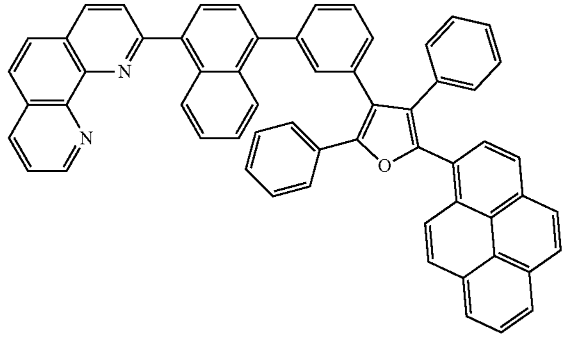
D74
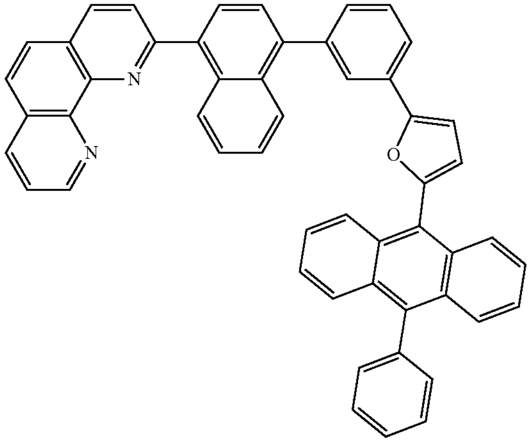

-continued
D75
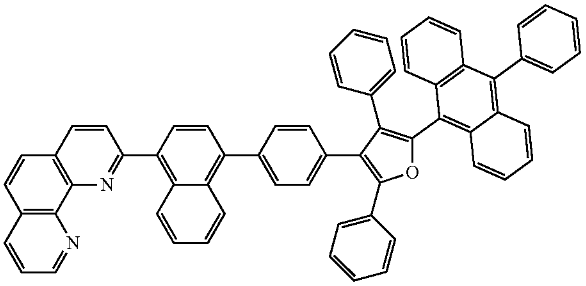
D76
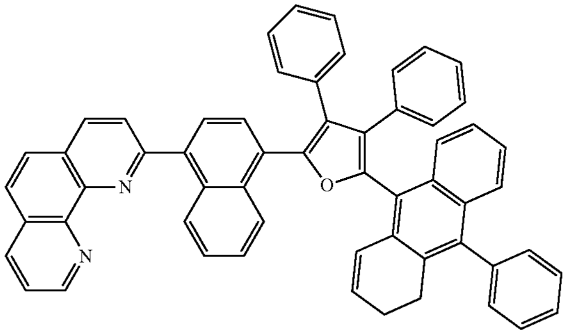
D77
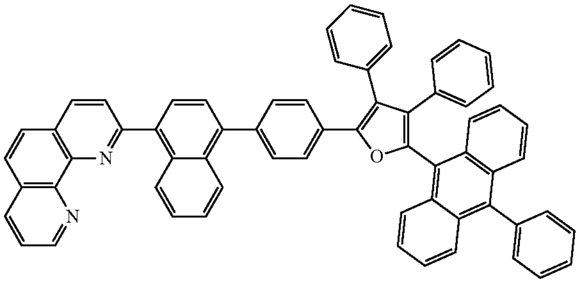
D78
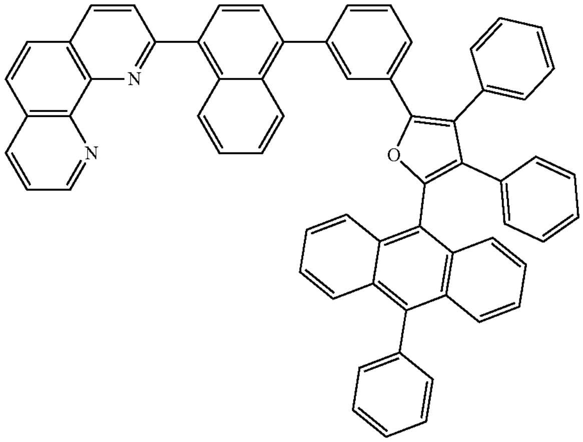
D79
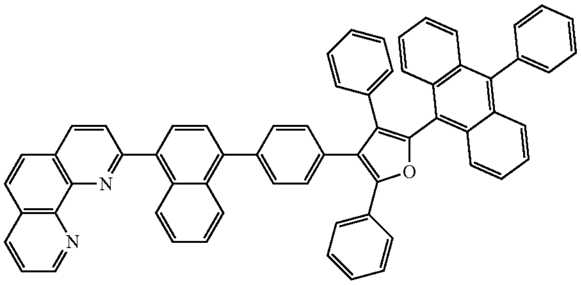
D80
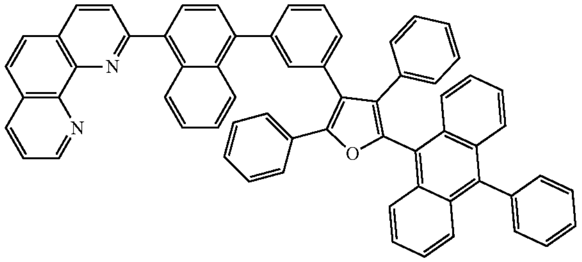
D81
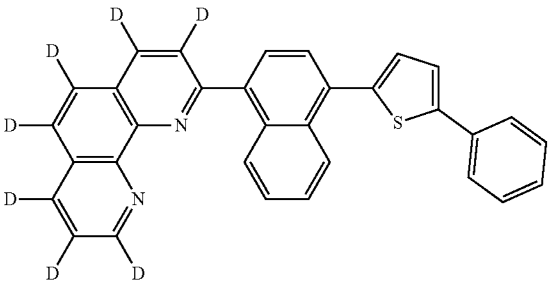
D82
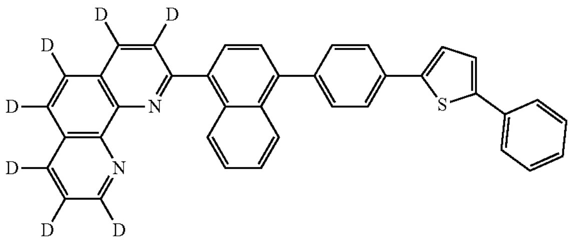

-continued
D83
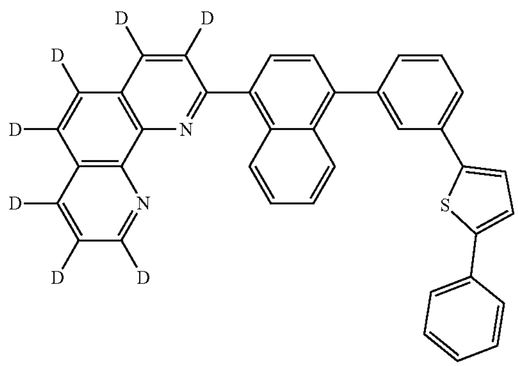
D84
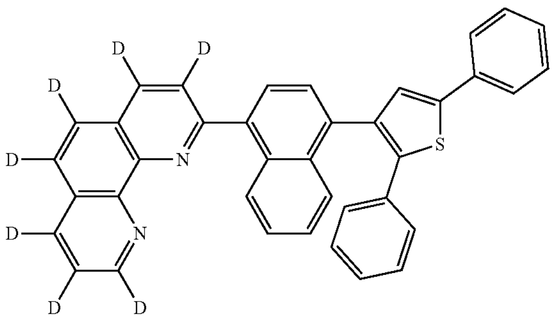
D85
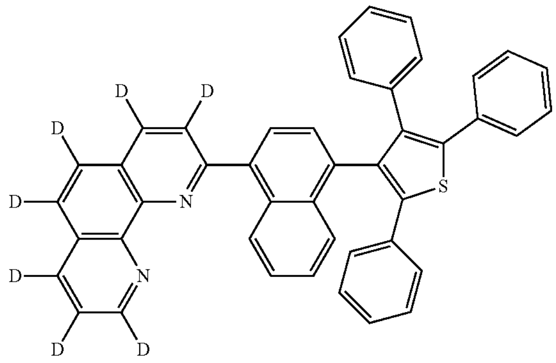
D86
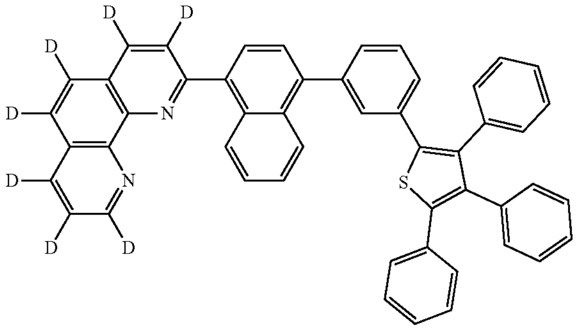
D87
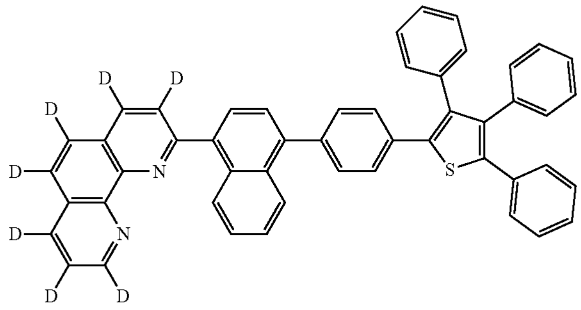
D88
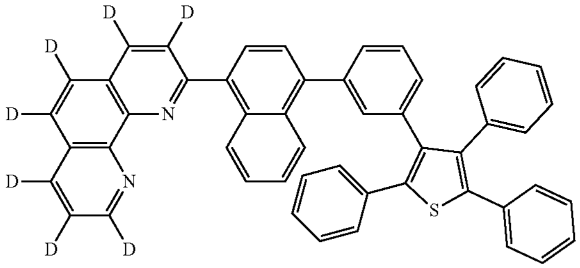
D89
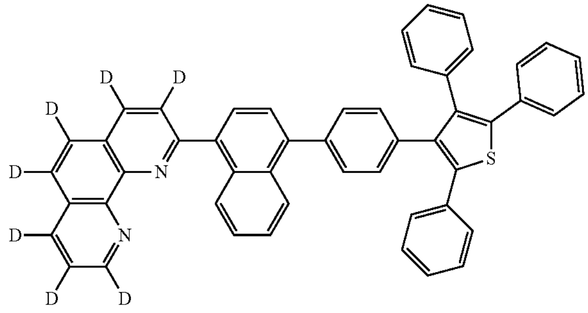
D90
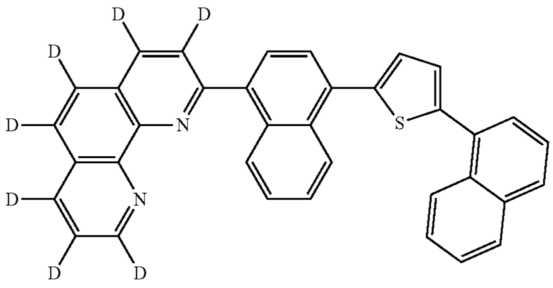

-continued
D91
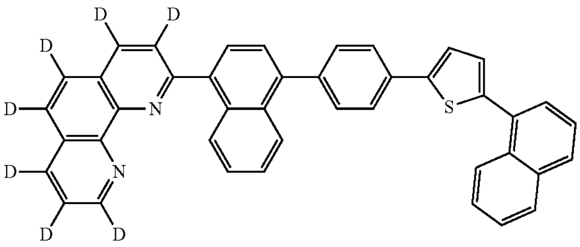
D92
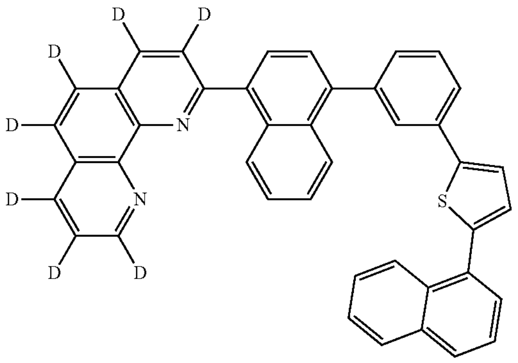
D93
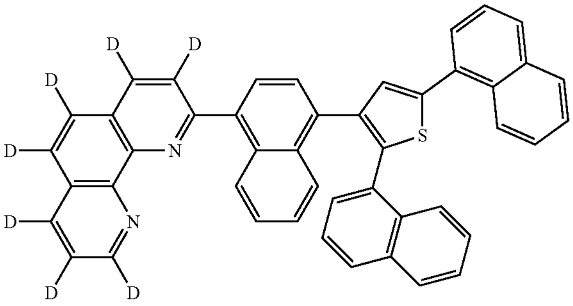
D94
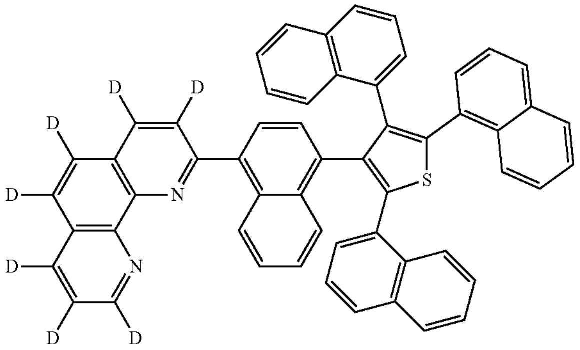
D95
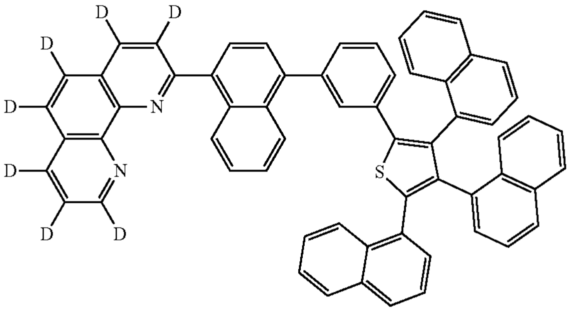
D96
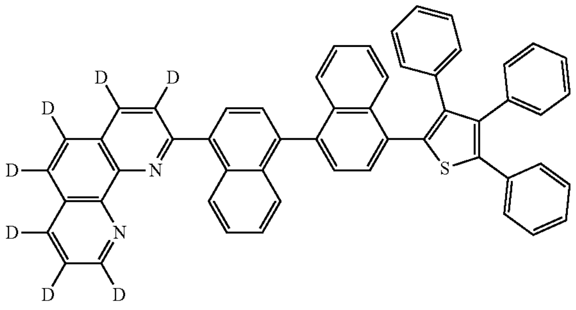
D97
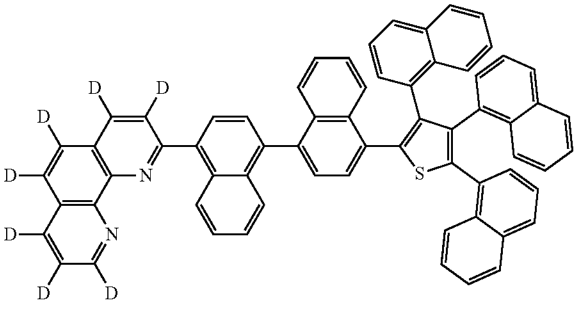
D98
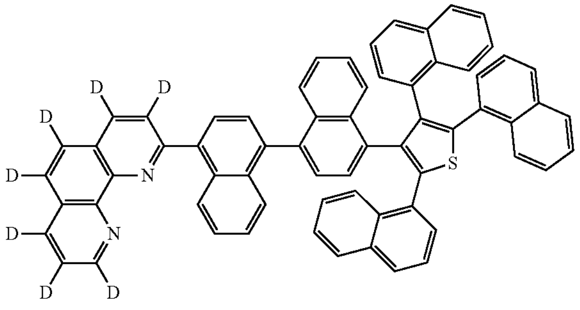

-continued
D99
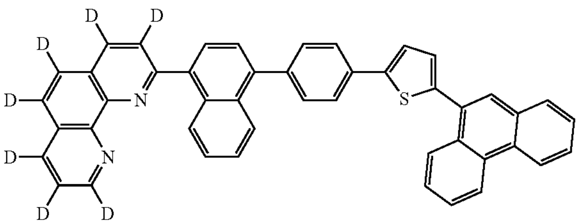
D100
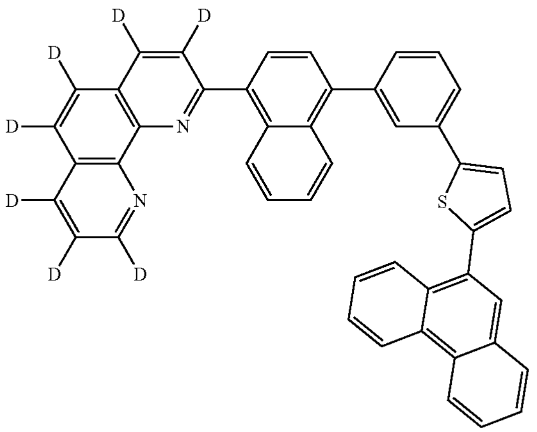
D101
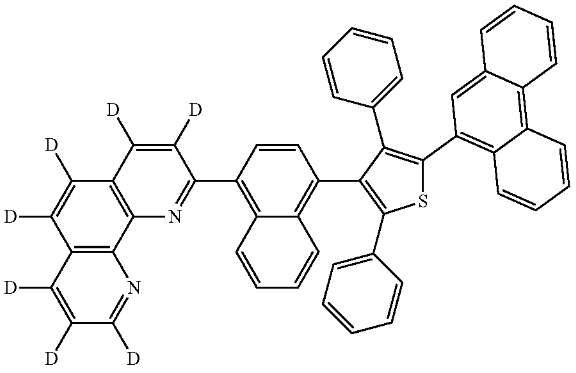
D102
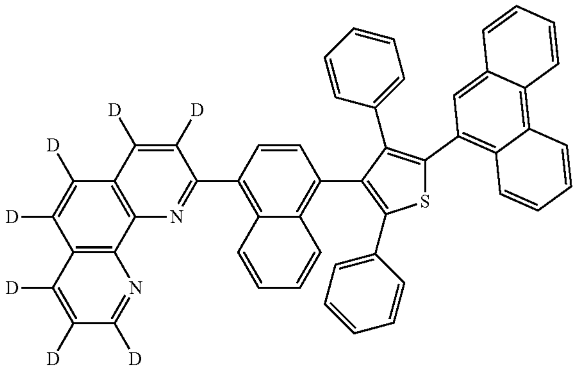
D103
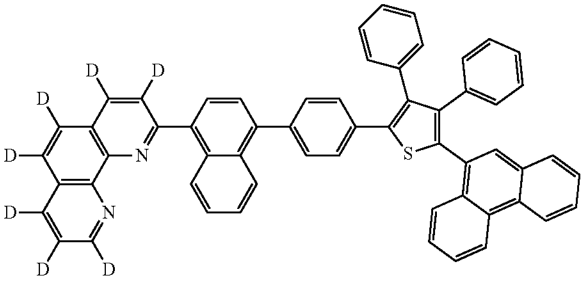
D104
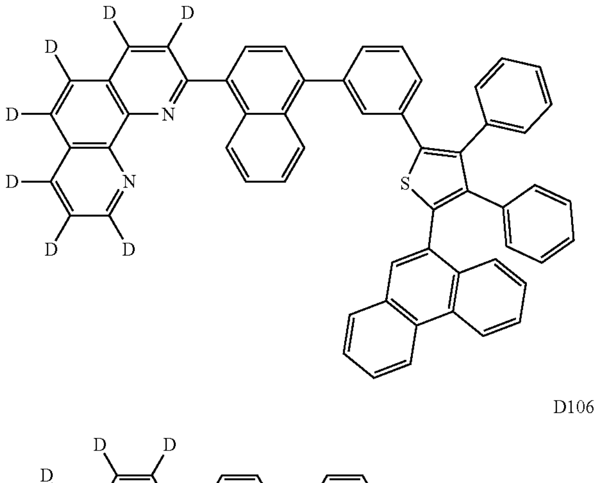
D105
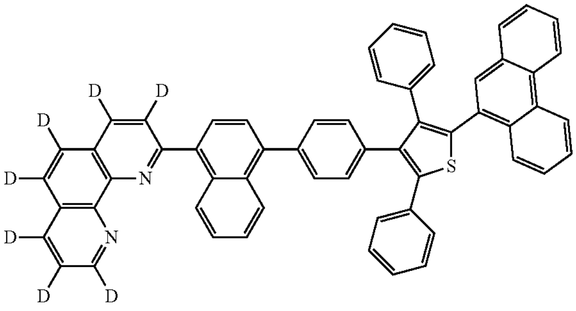
D106
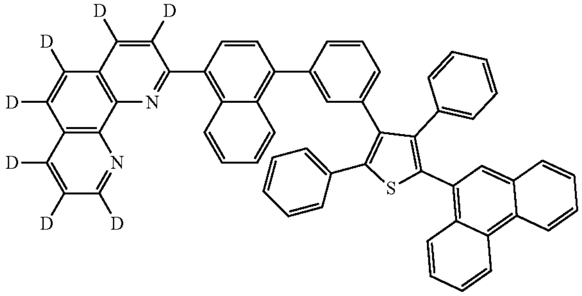

-continued
D107
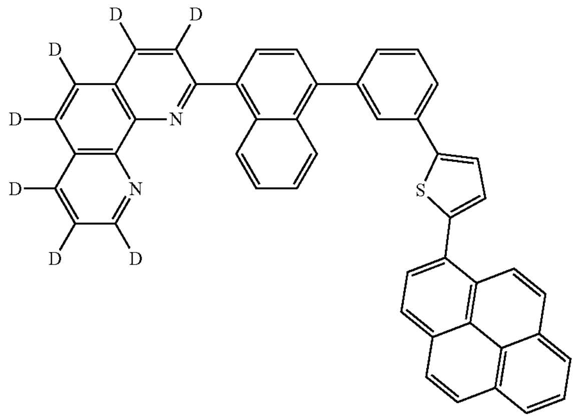
D108
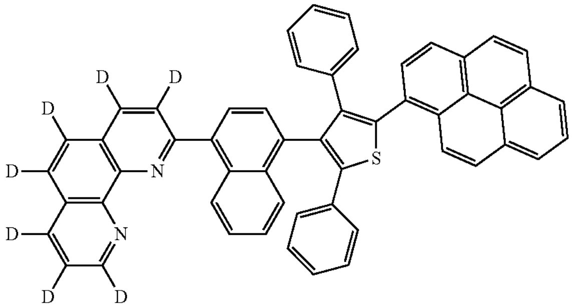
D109
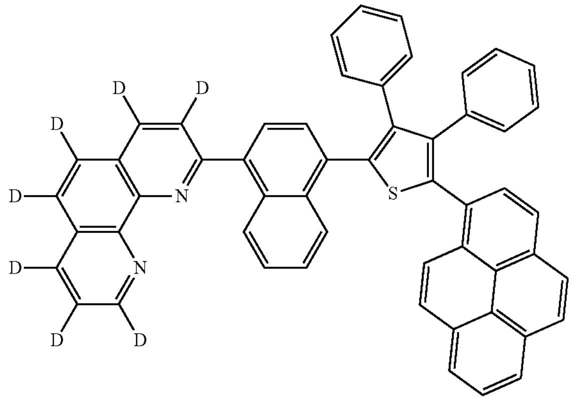
D110
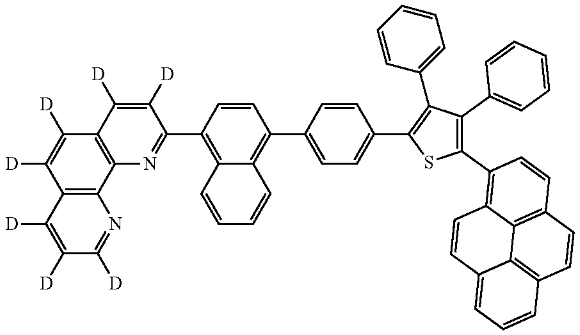
D111
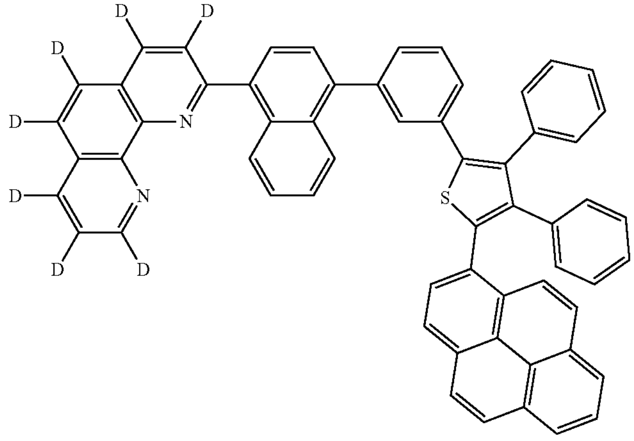

-continued
D112
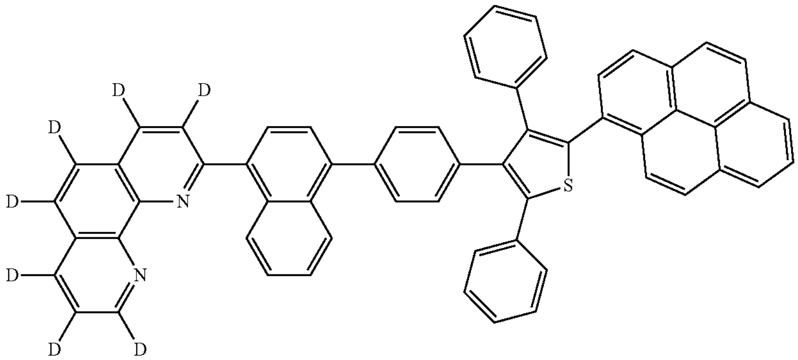
D113
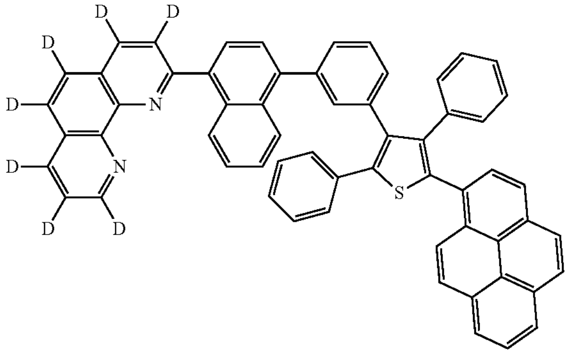
D114
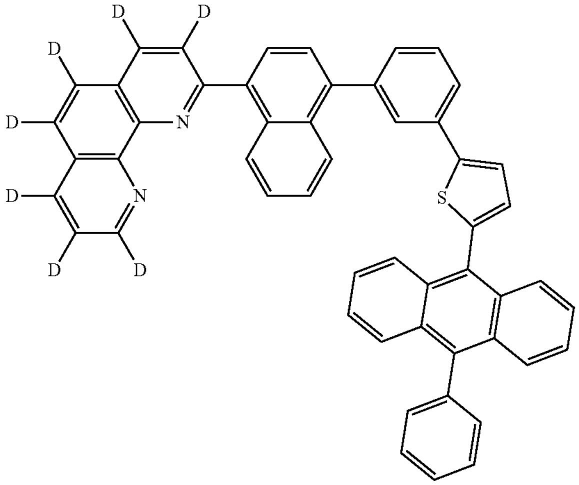
D115
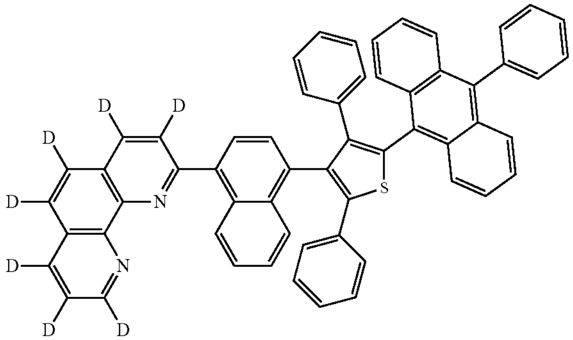
D116
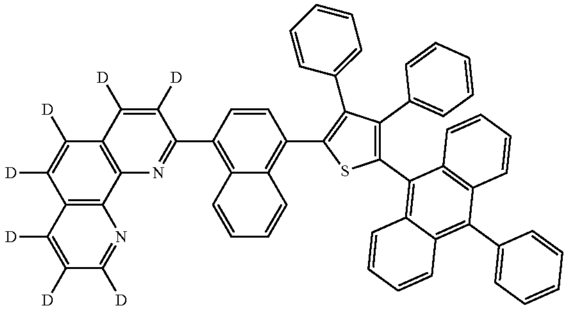
D117
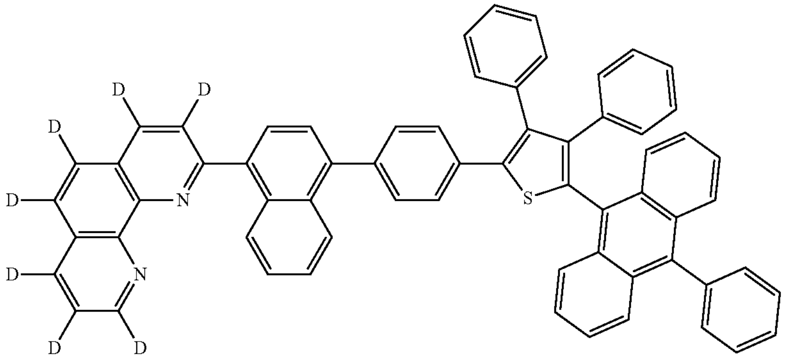

-continued
D118
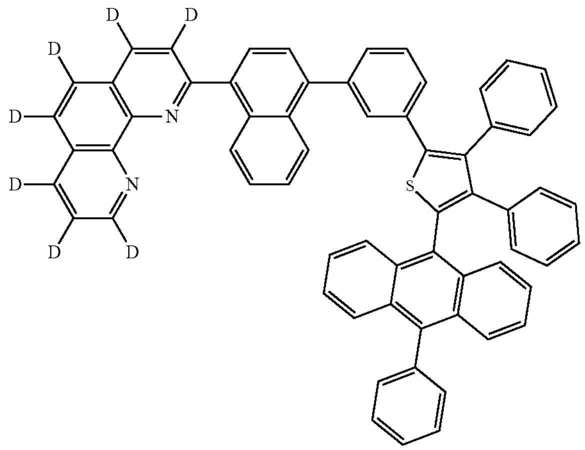
D119
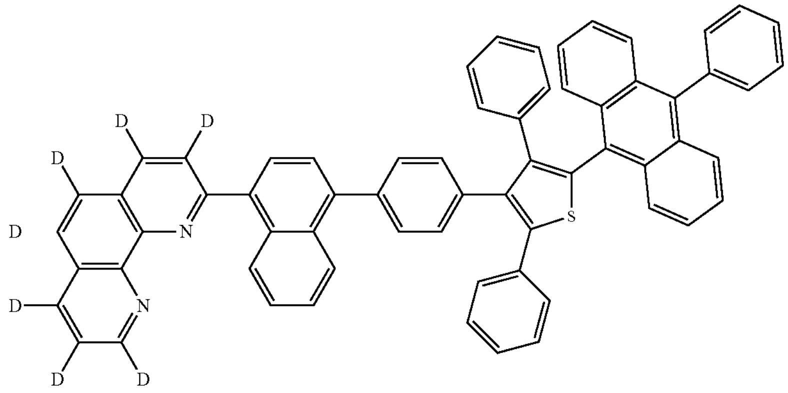
D120
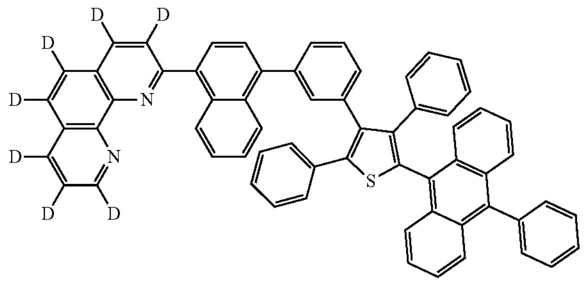
D121
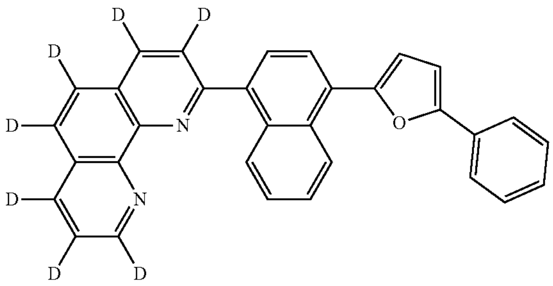
D122
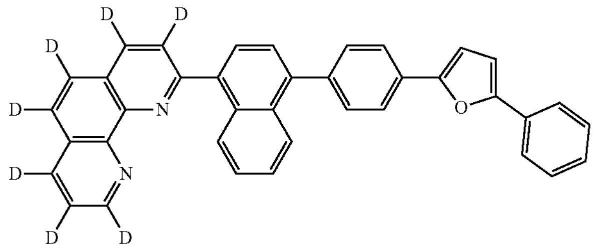
D123
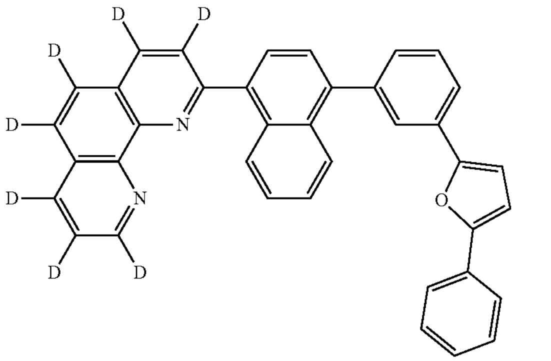

-continued
D124
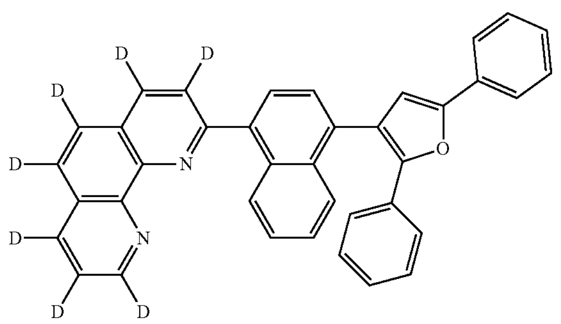
D125
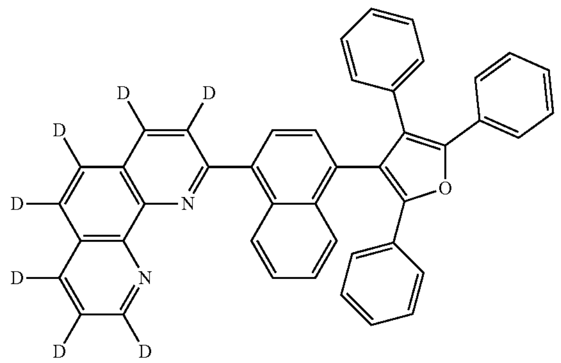
D126
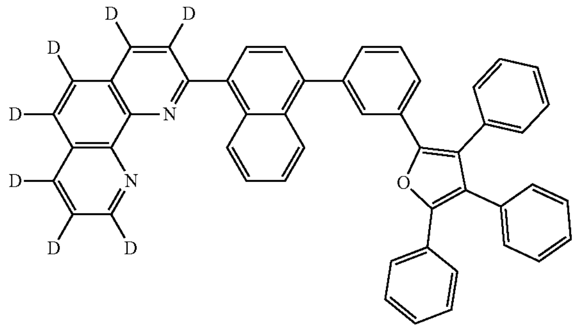
D127
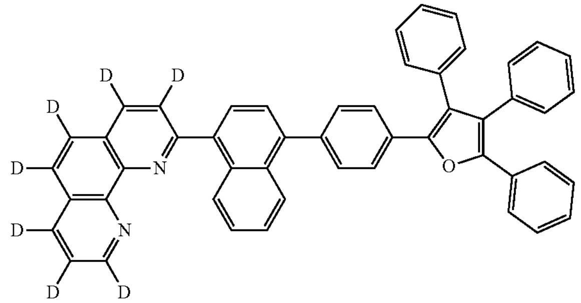
D128
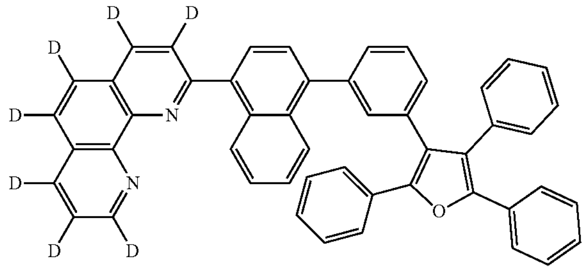
D129
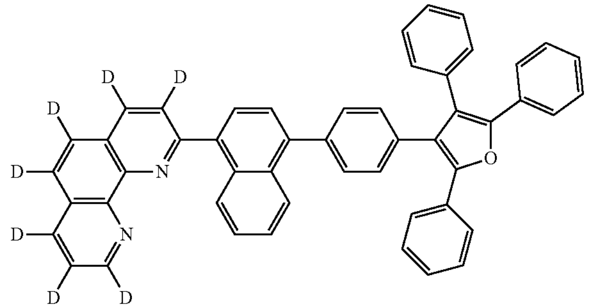
D130
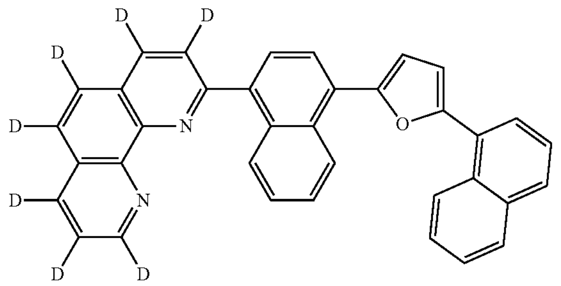
D131
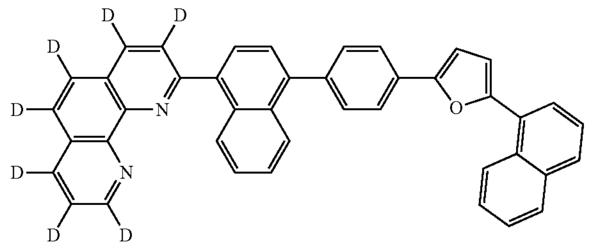

-continued
D132
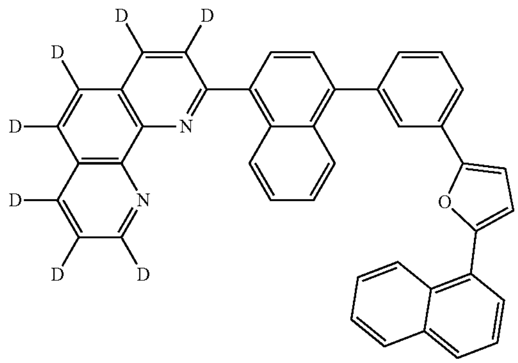
D133
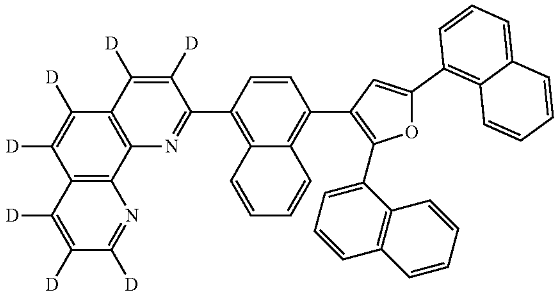
D134
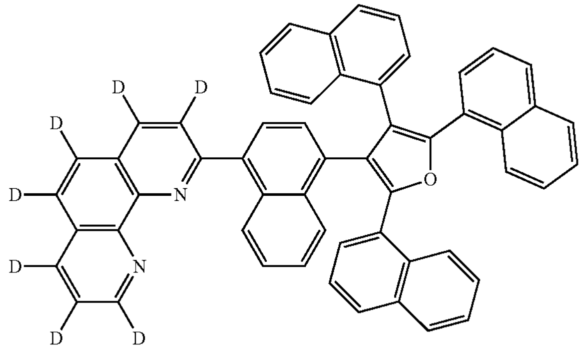
D135
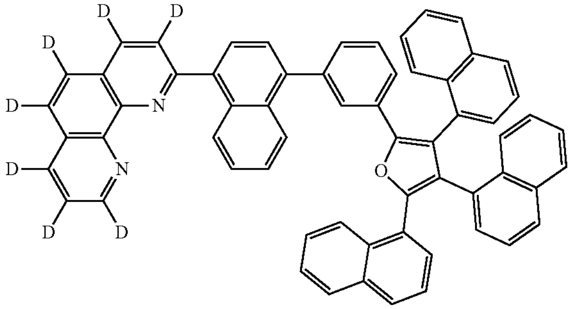
D136
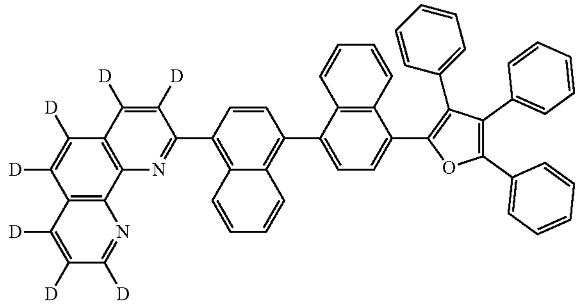
D137
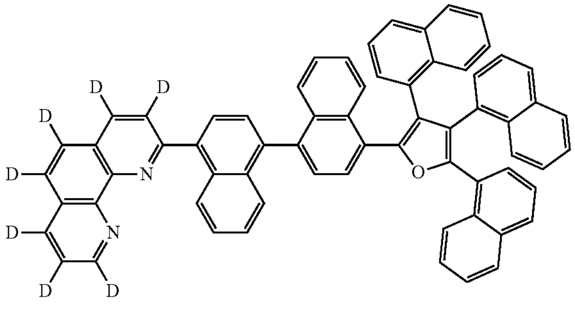
D138
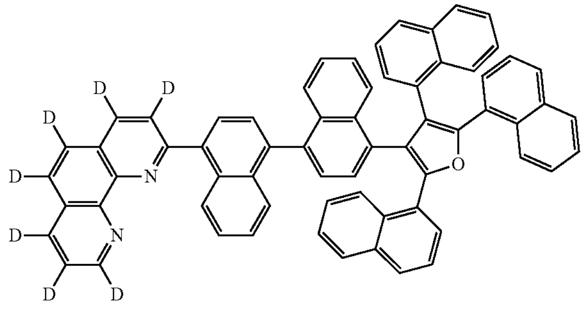
D139
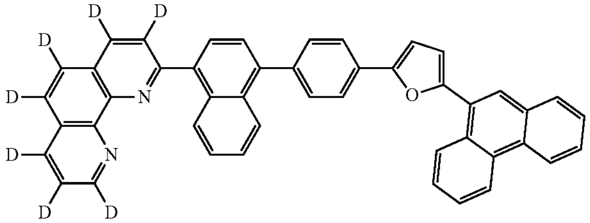

-continued
D140
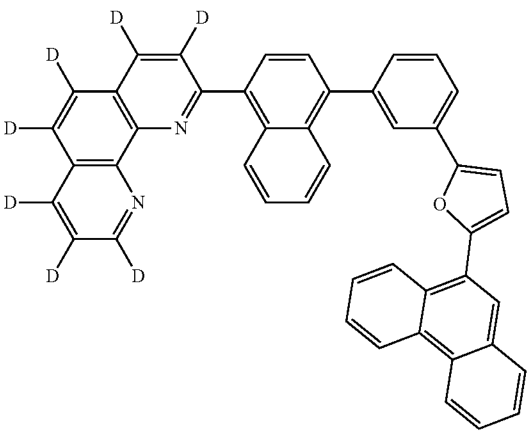
D141
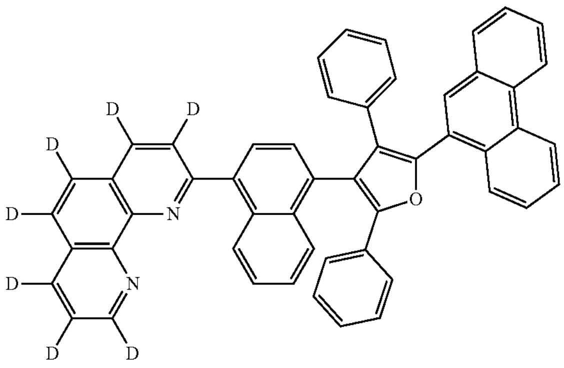
D142
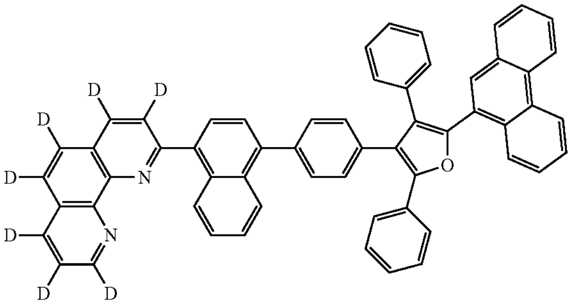
D143
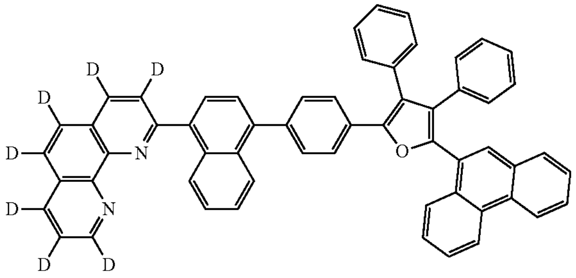
D144
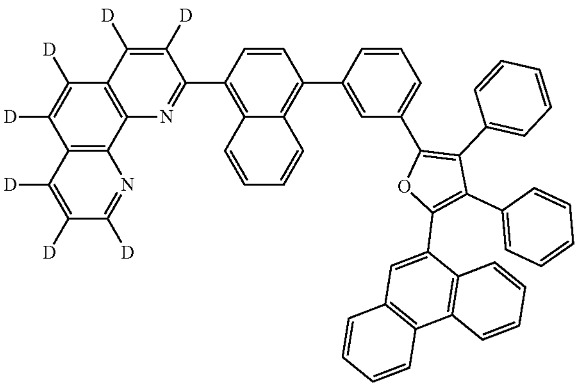
D145
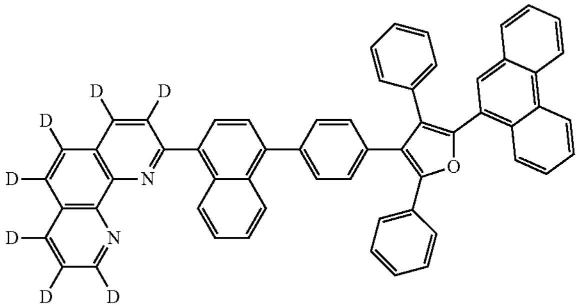
D146
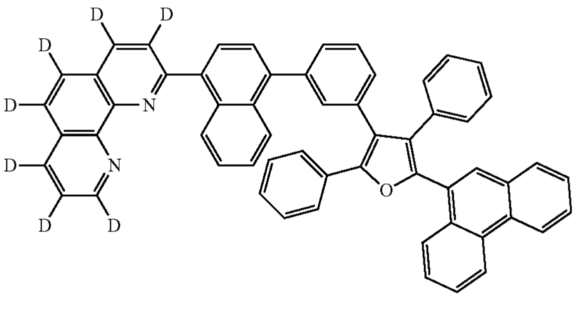
D147
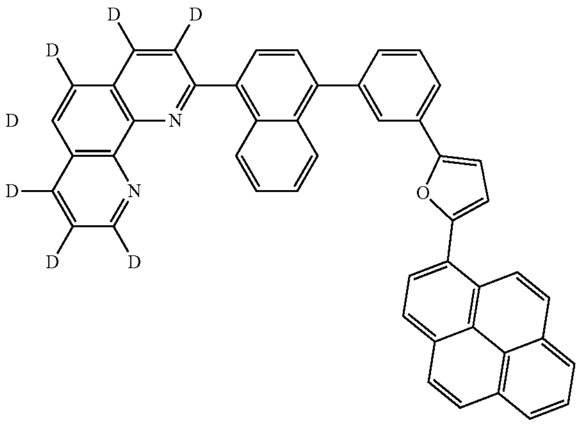

-continued
D148
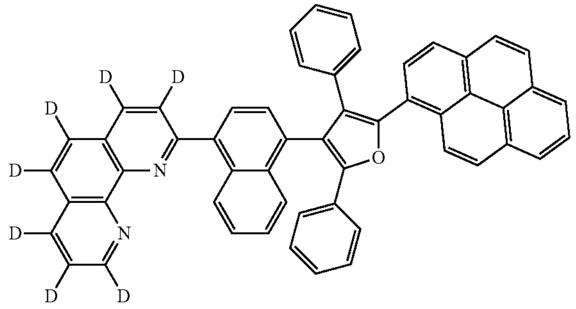
D149
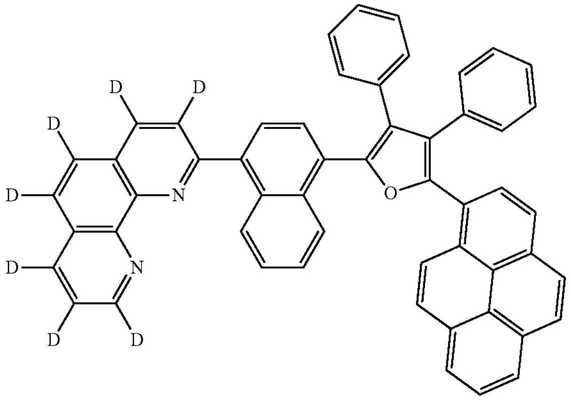
D150
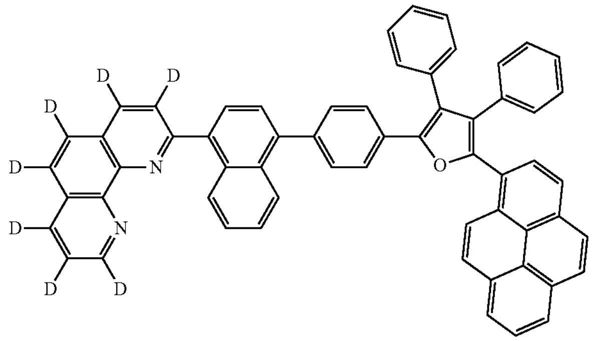
D151
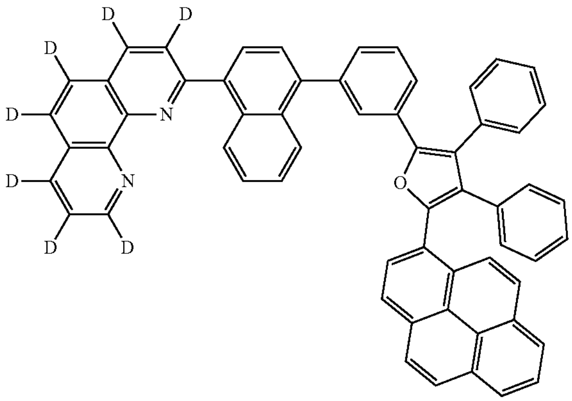
D152
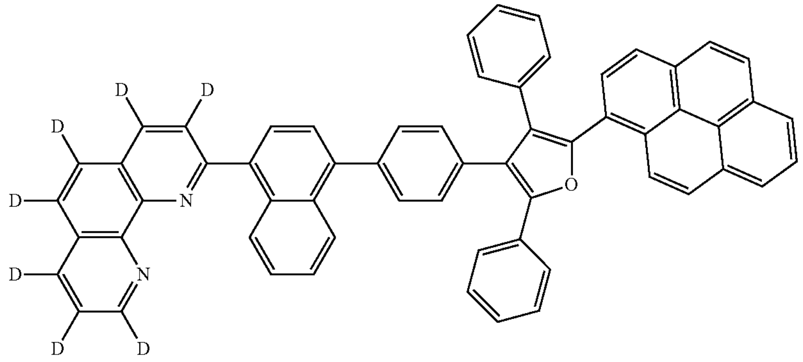

-continued
D153
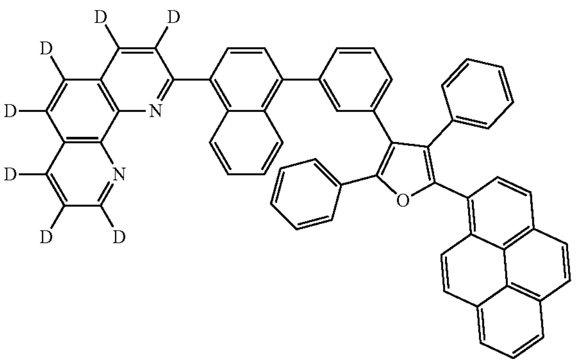
D154
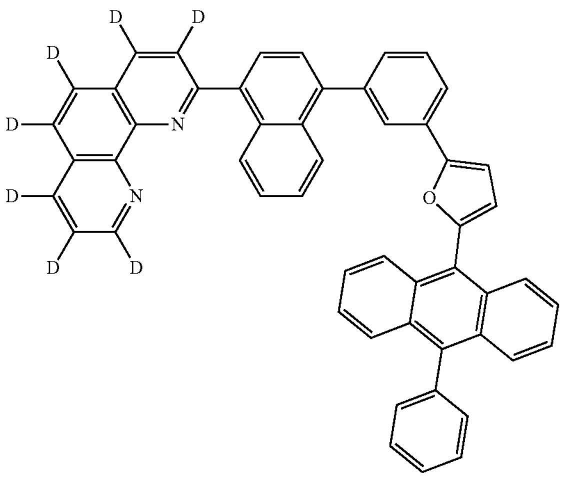
D155
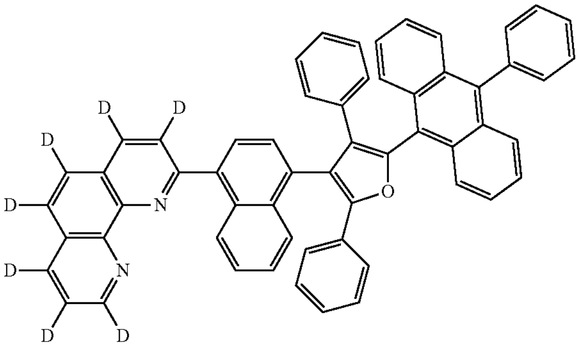
D156
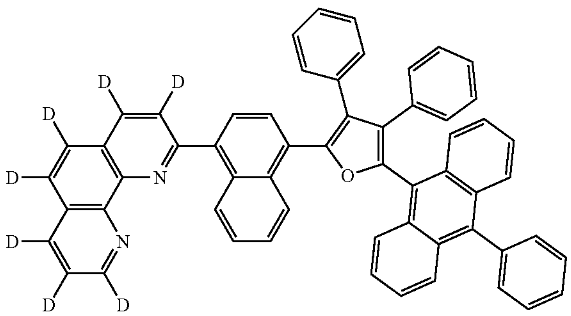
D157
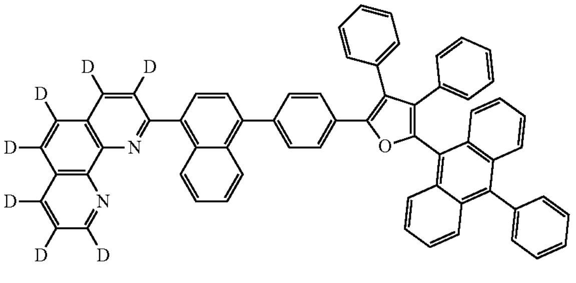
D158
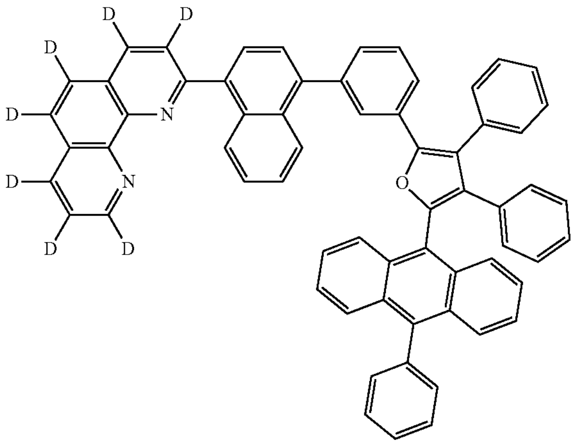

-continued
D159
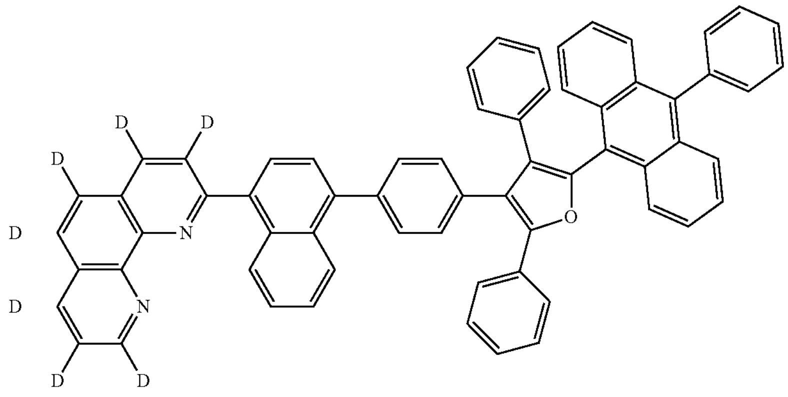
D160
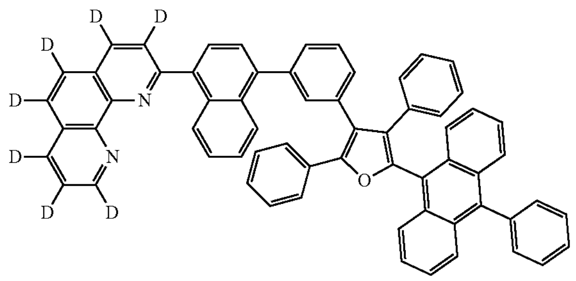
D161
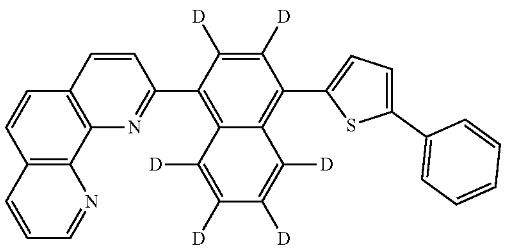
D162
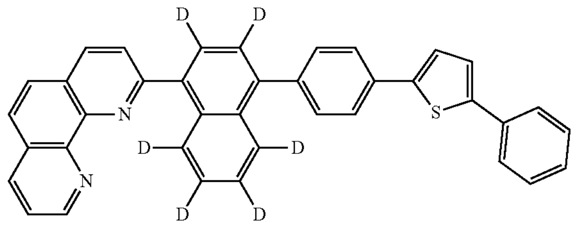
D163
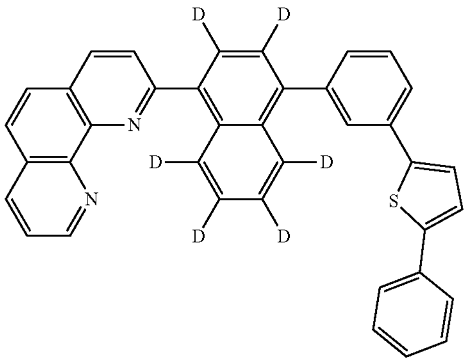
D164
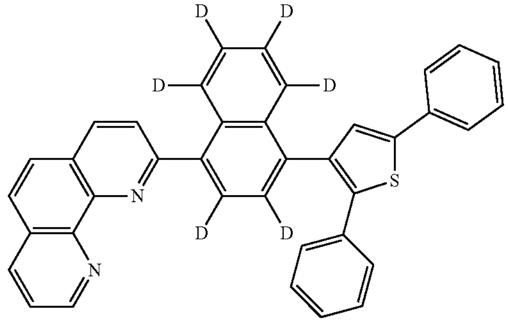
D165
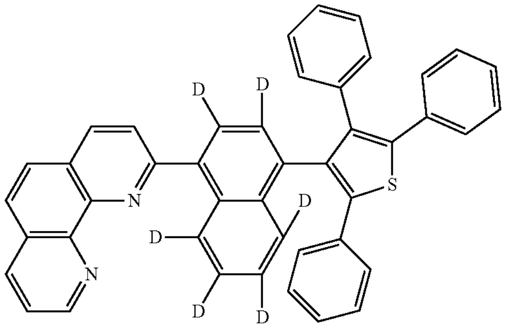

-continued
D166
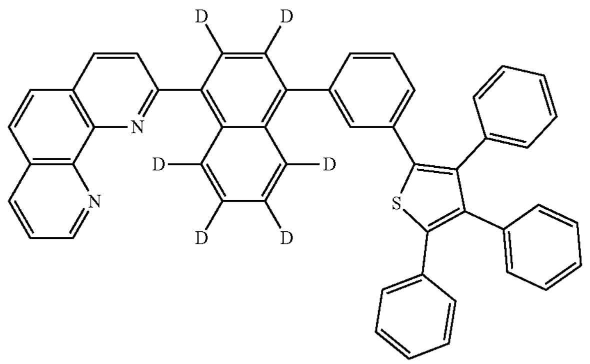
D167
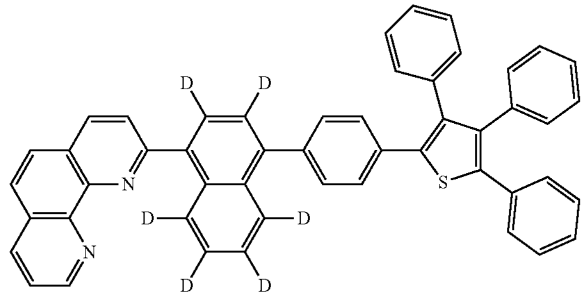
D168
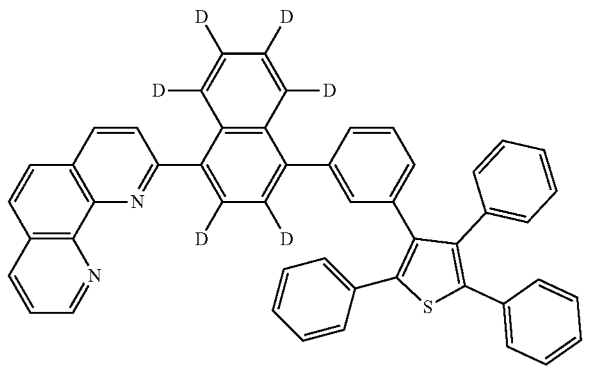
D169
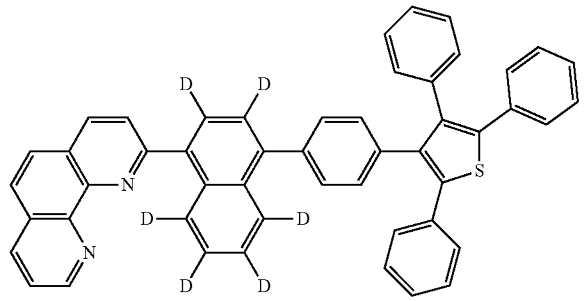
D170
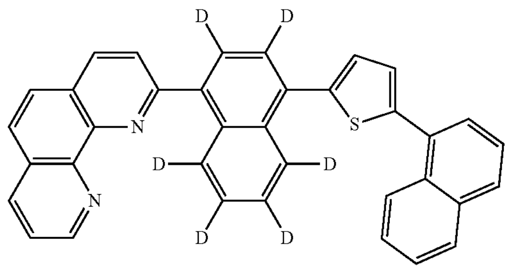
D171
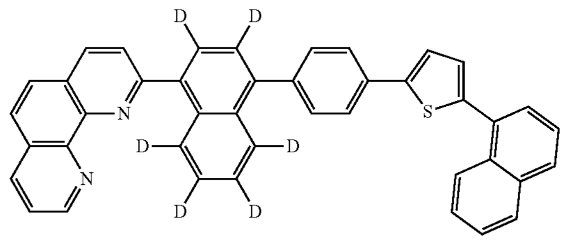
D172
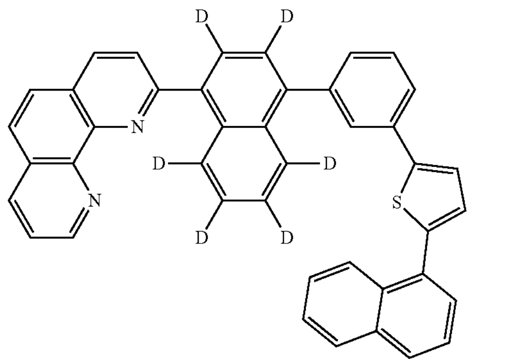
D173
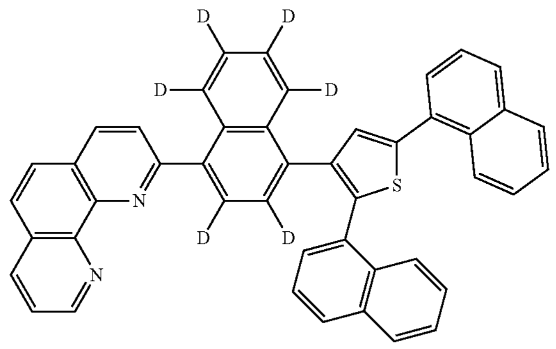

-continued
D174
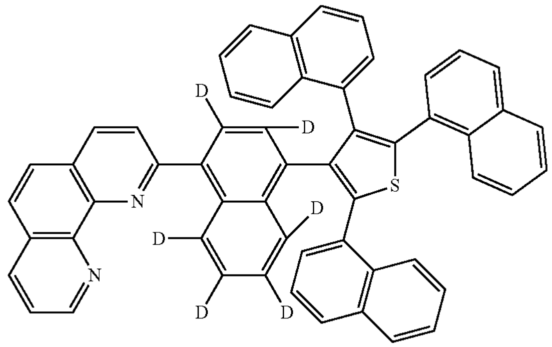
D175
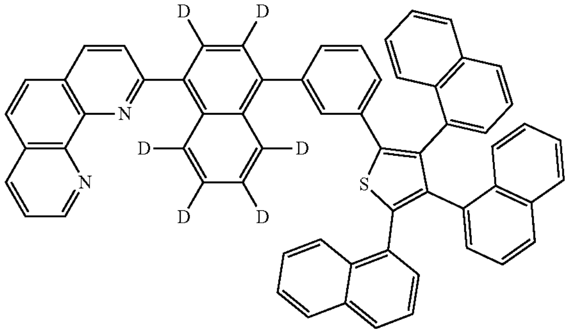
D176
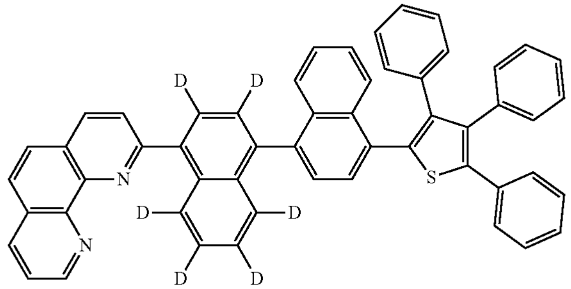
D177
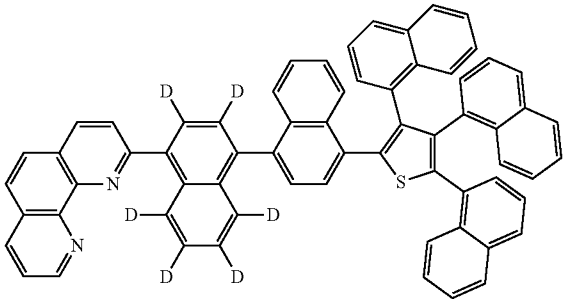
D178
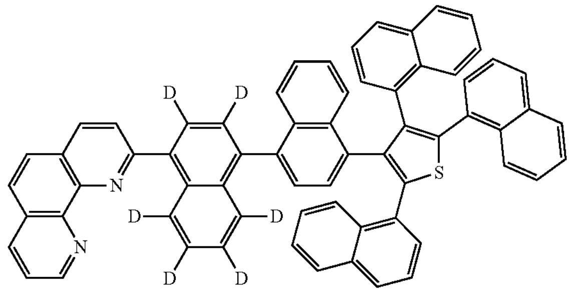
D179
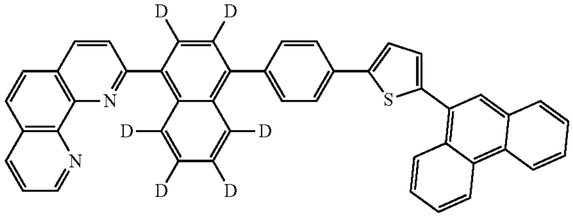
D180
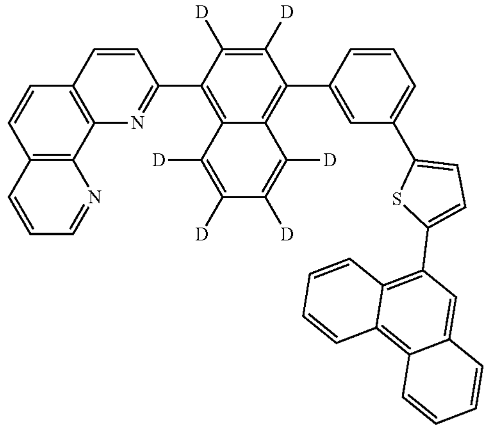
D181
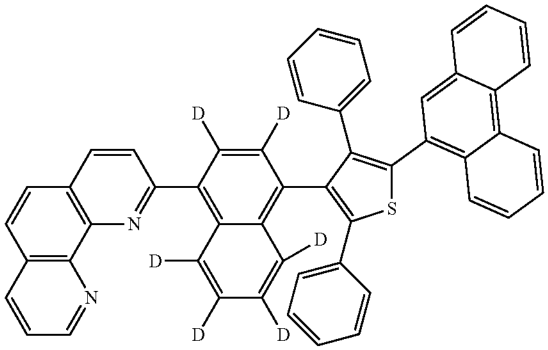

-continued
D182
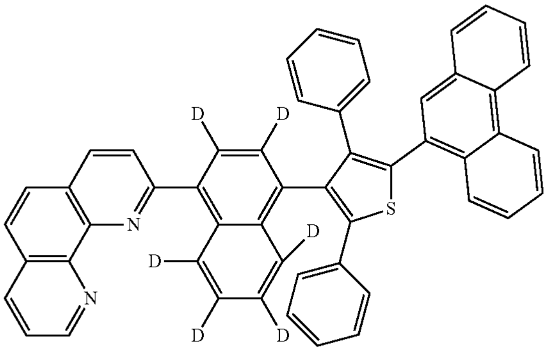
D183
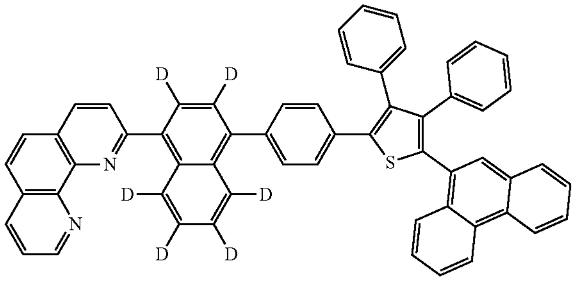
D184
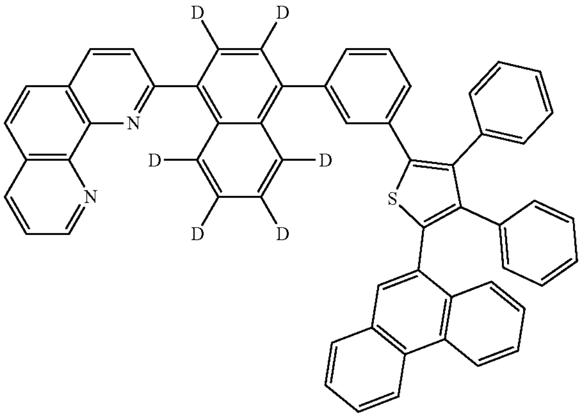
D185
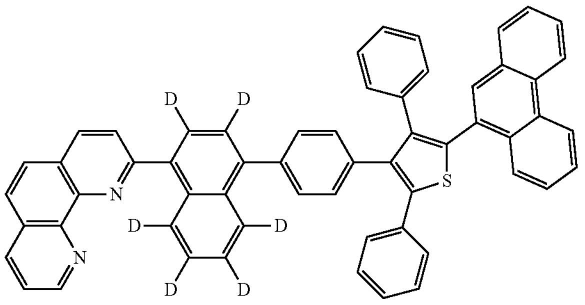
D186
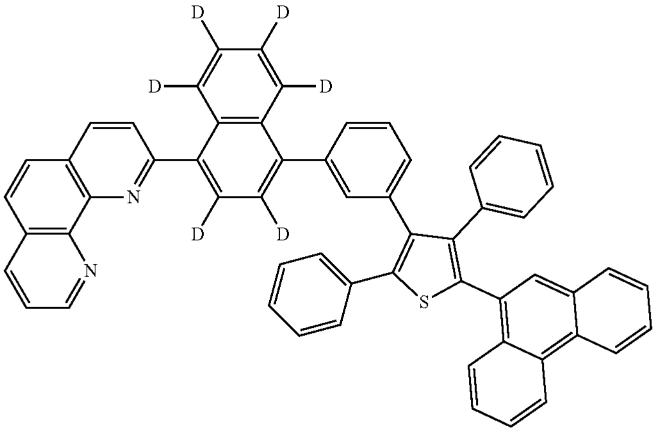

D187
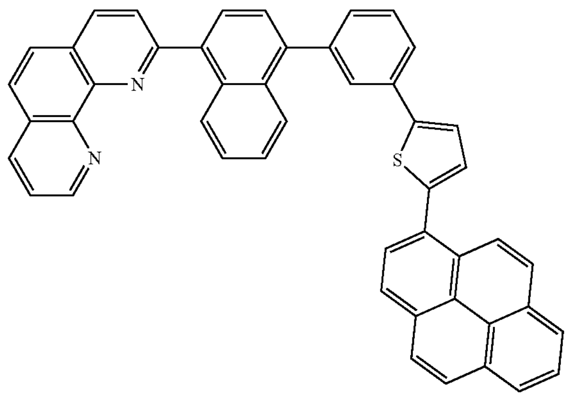
D188
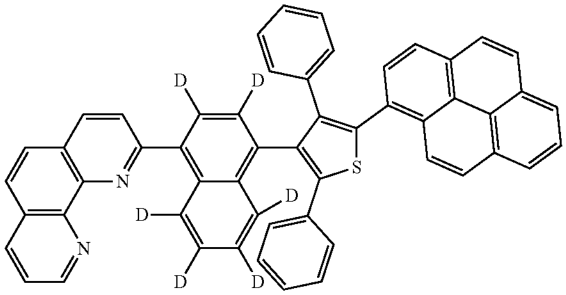
D189
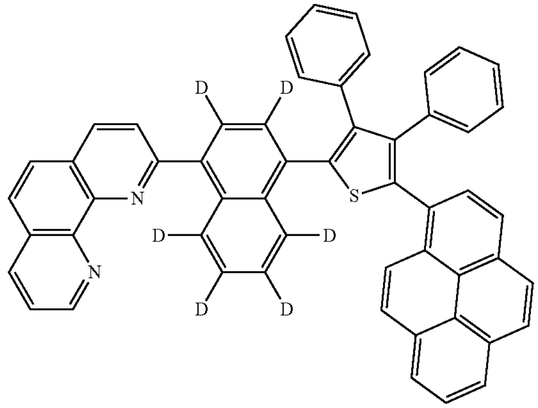
D190
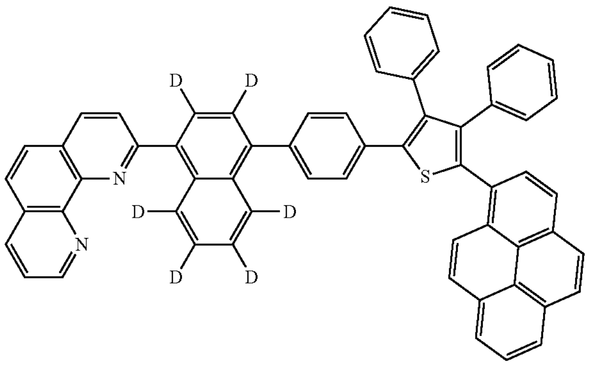
D191
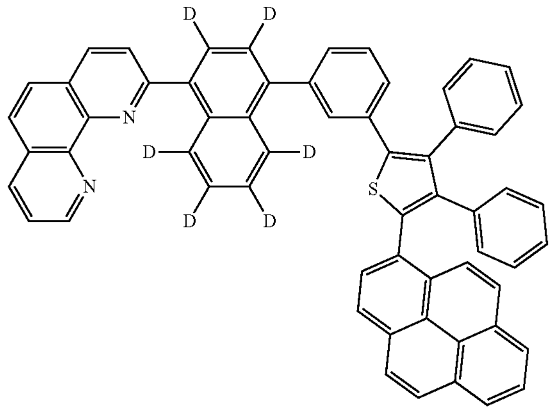
D192
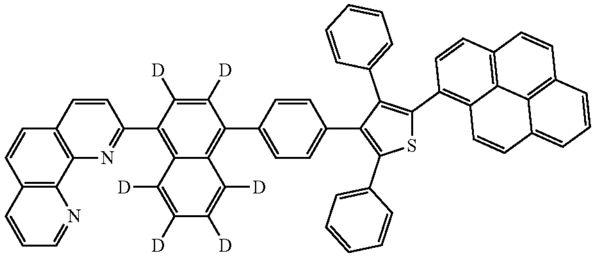

-continued
D193
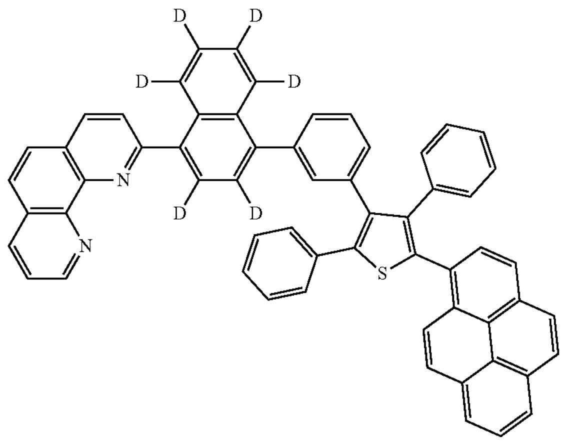
D194
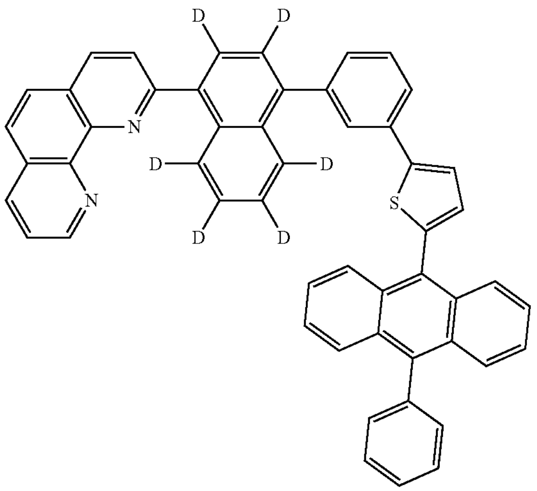
D195
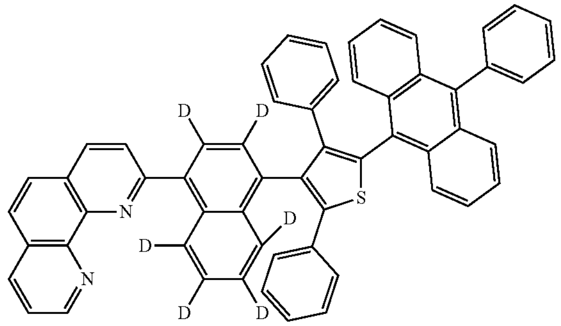
D196
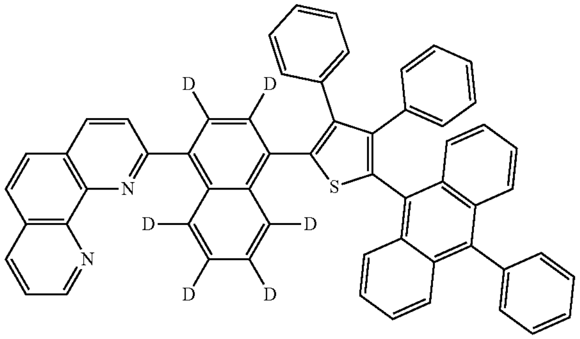
D197
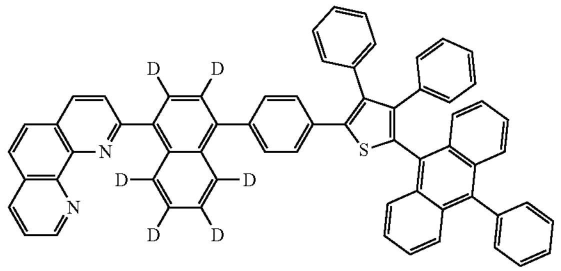
D198
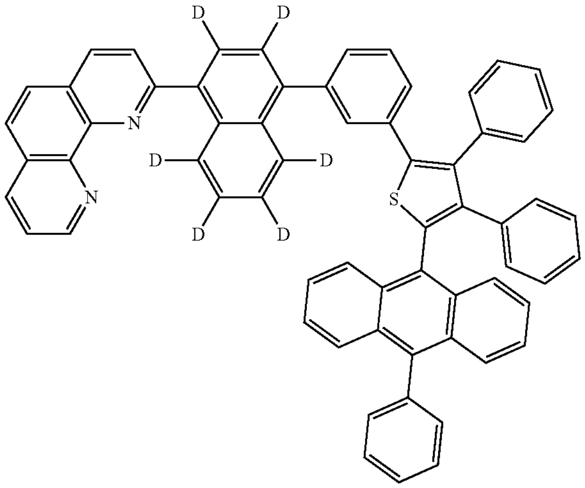

-continued
D199
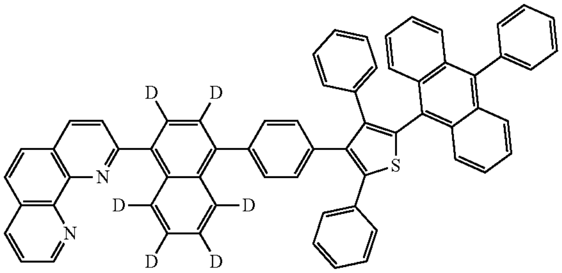
D200
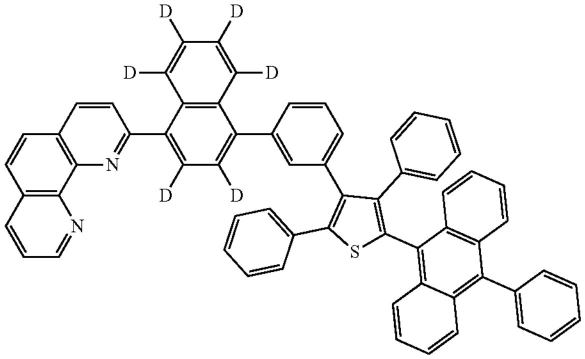
D201
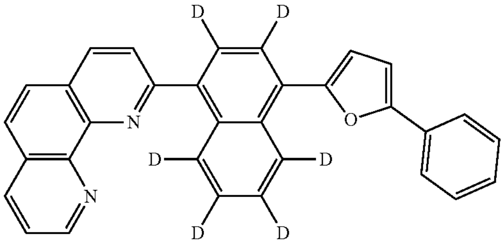
D202
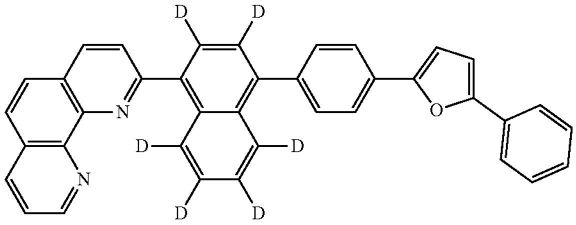
D203
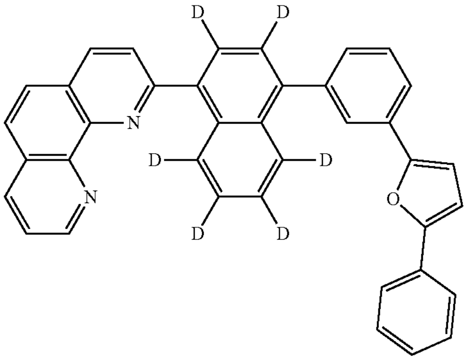
D204
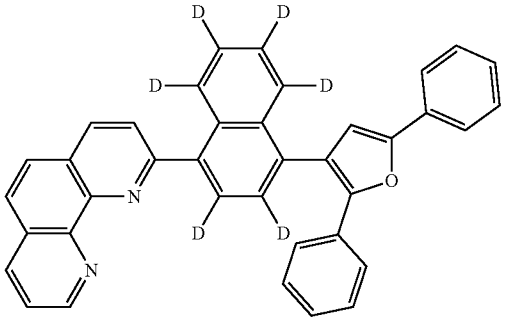
D205
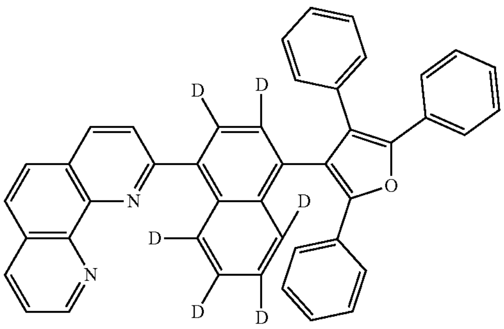
D206
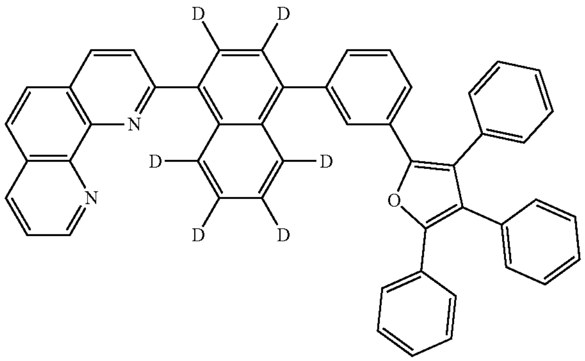

-continued
D207
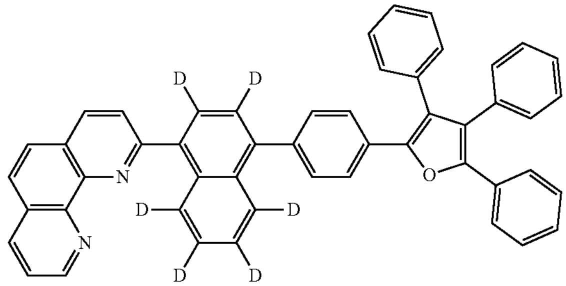
D208
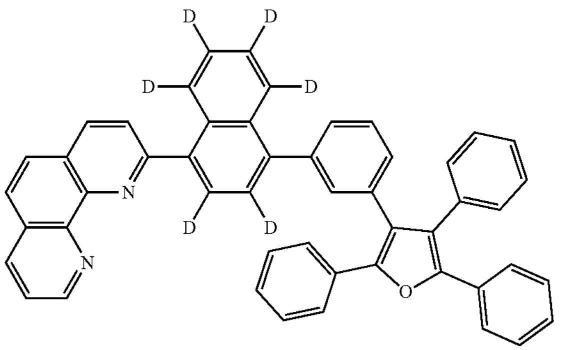
D209
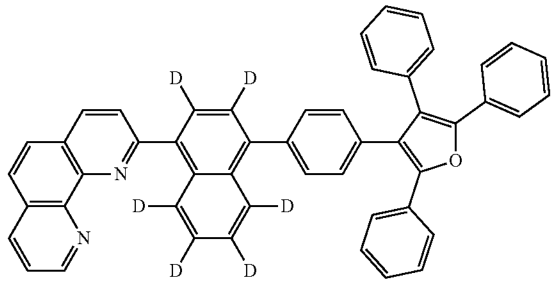
D210
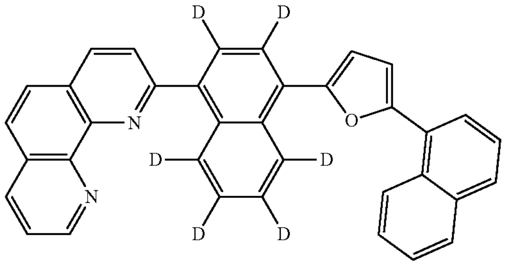
D211
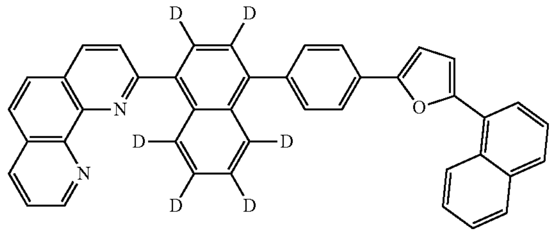
D212
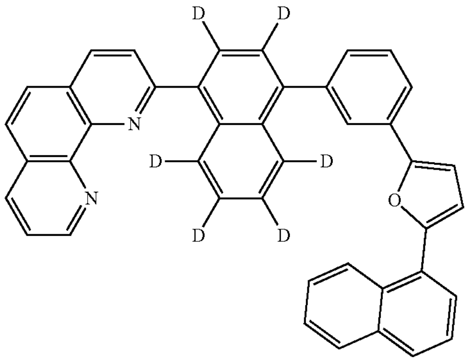
D213
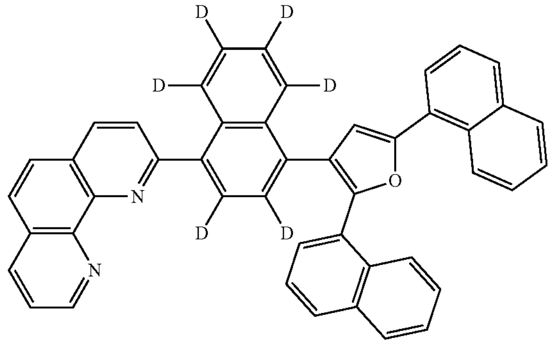
D214
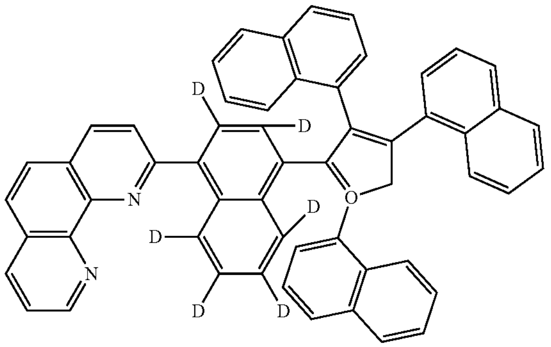

-continued
D215
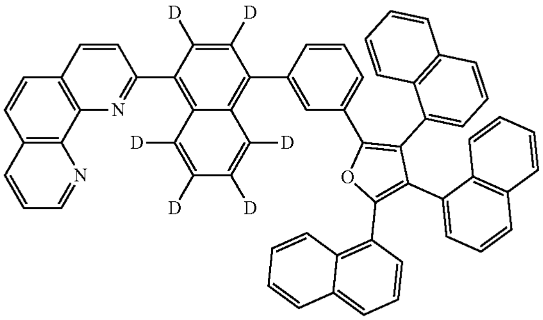
D216
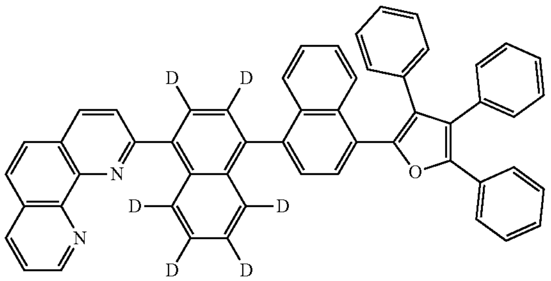
D217
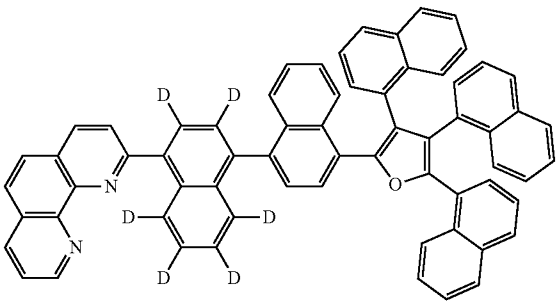
D218
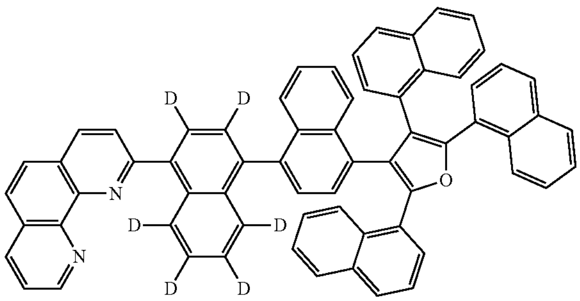
D219
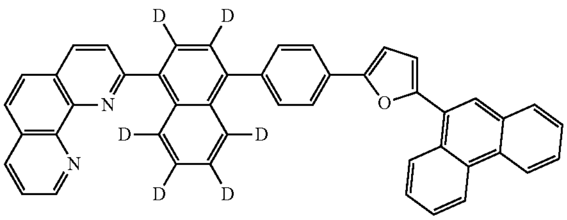
D220
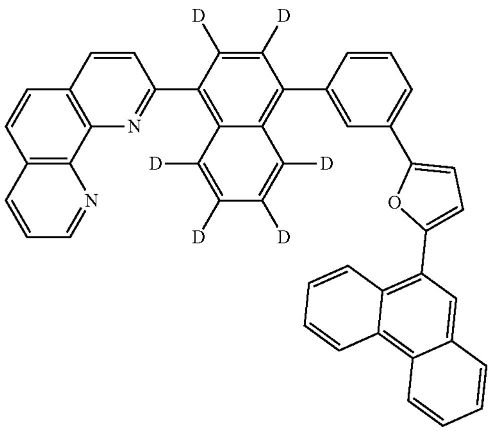
D221
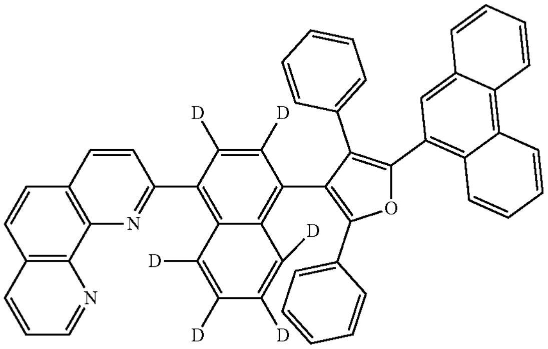
D222
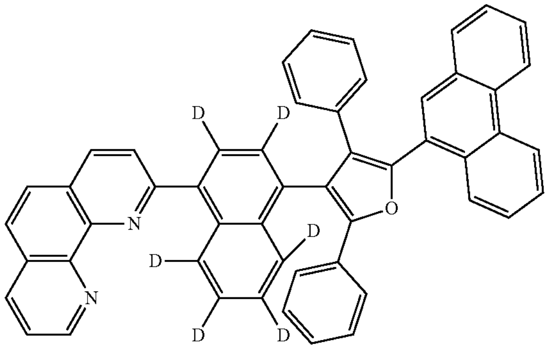

-continued
D223
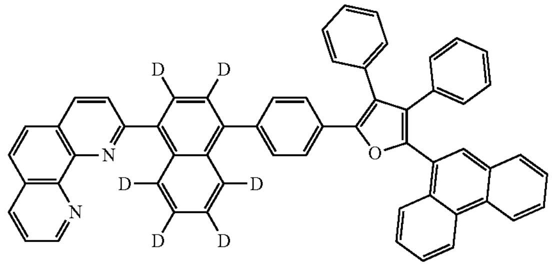
D224
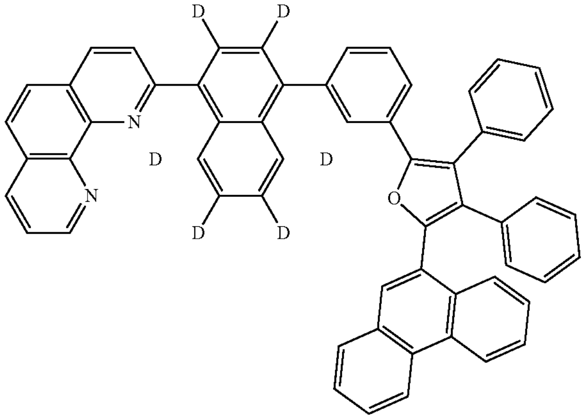
D225
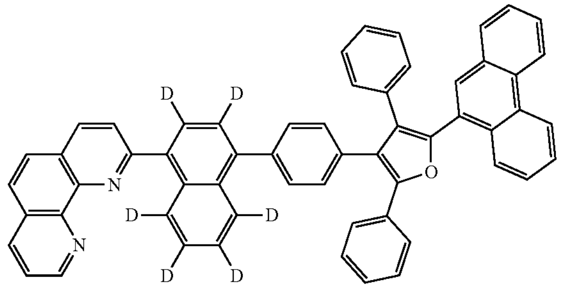
D226
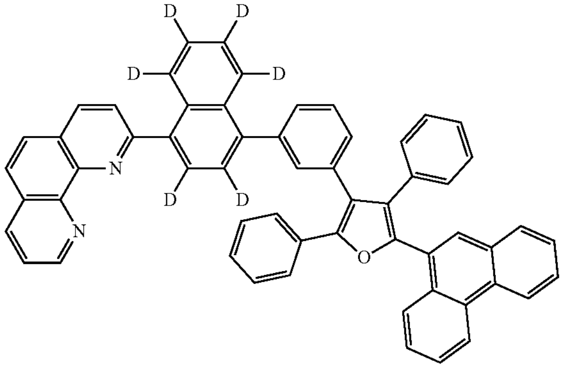
D227
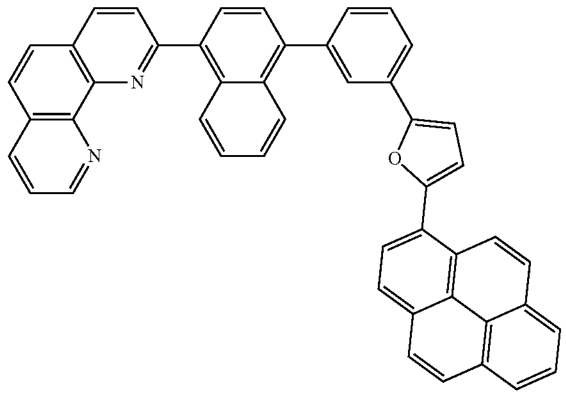
D228
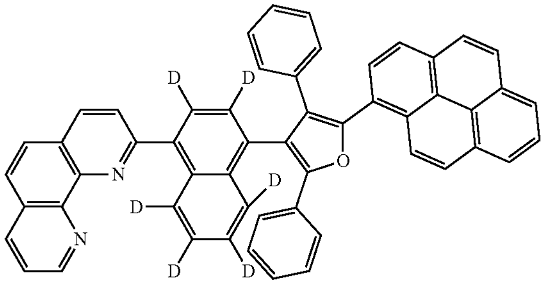

-continued
D229
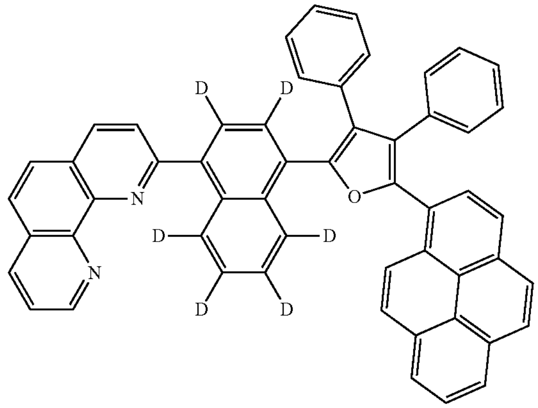
D230
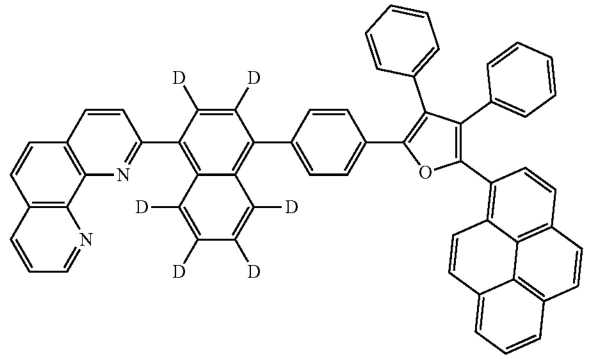
D231
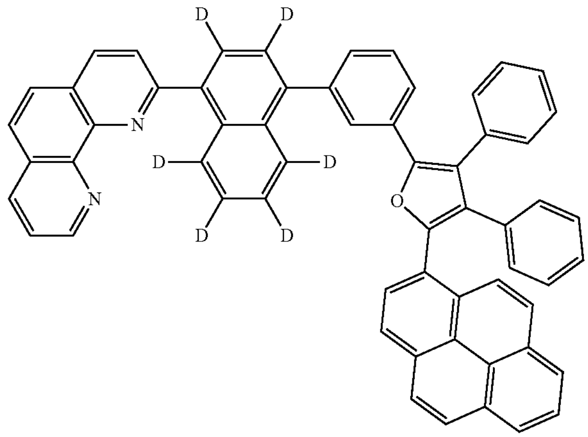
D232
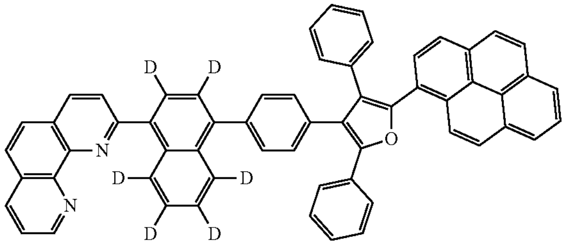
D233
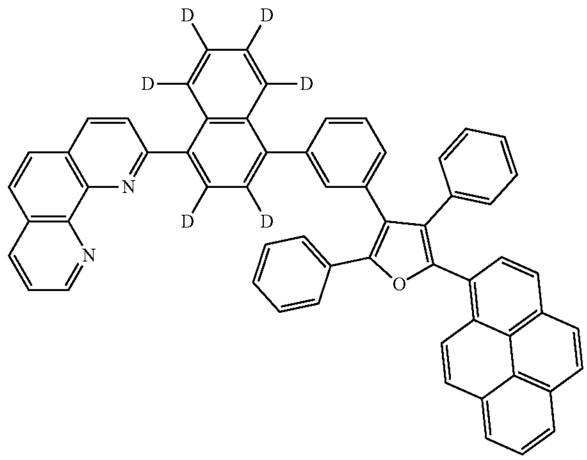
D234
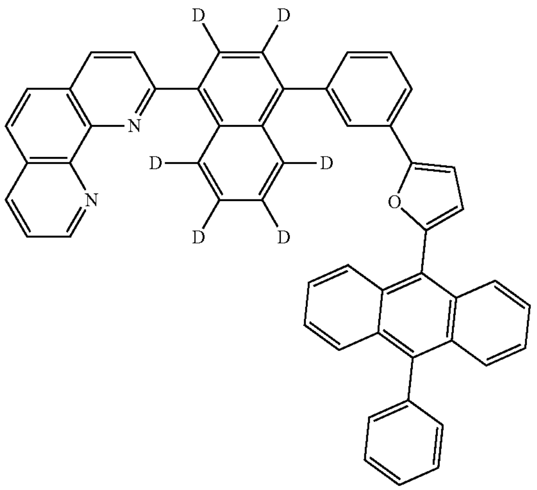

-continued
D235
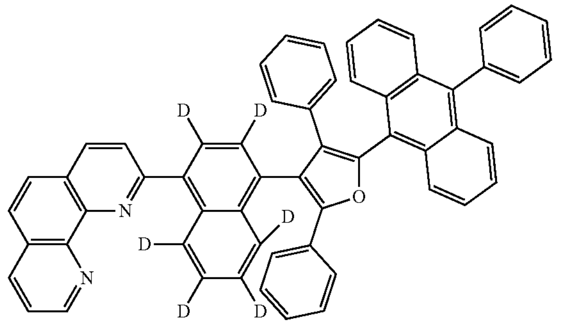
D236
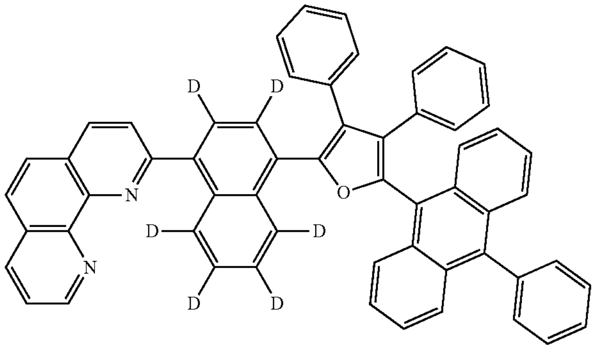
D237
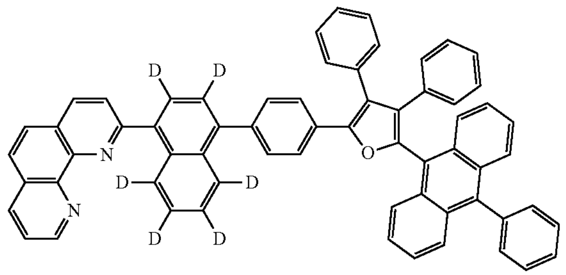
D238
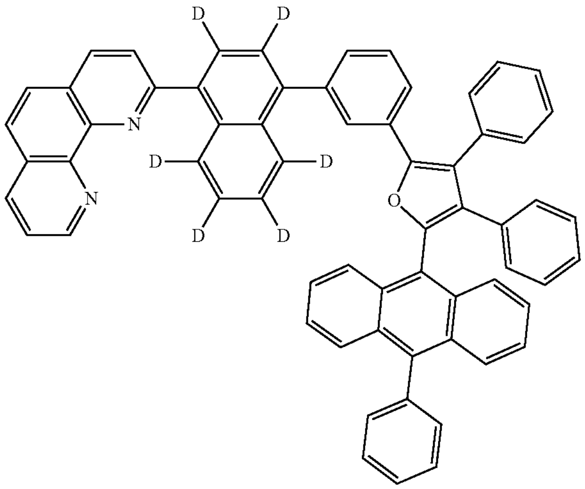
D239
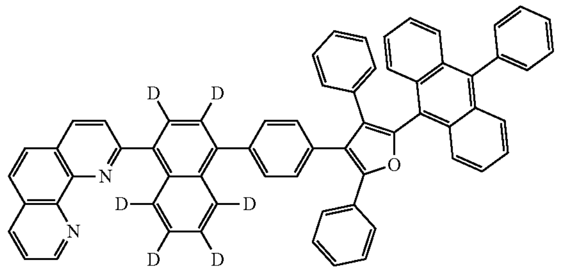
D240
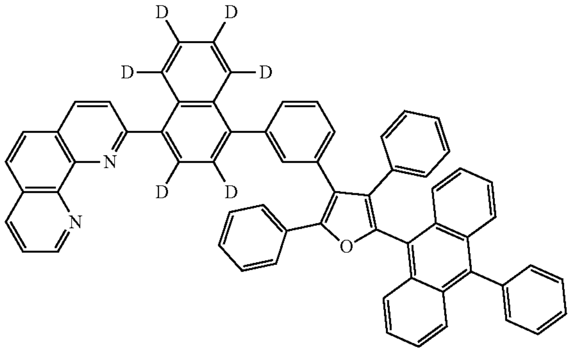
D241
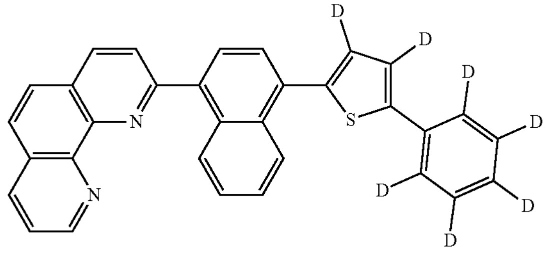
D242
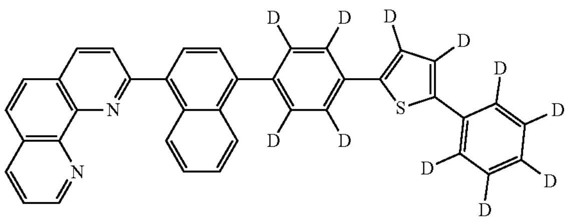

-continued
D243
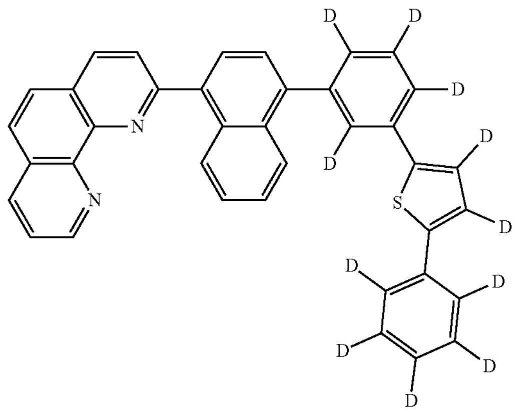
D244
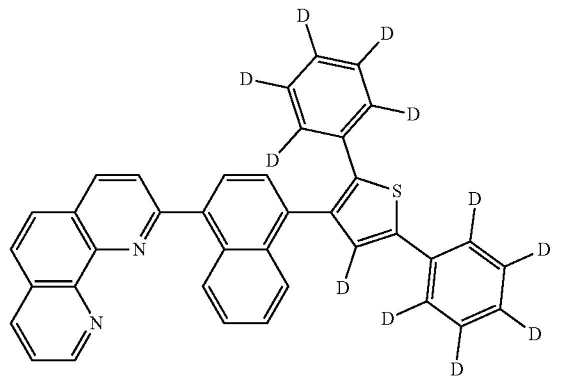
D245
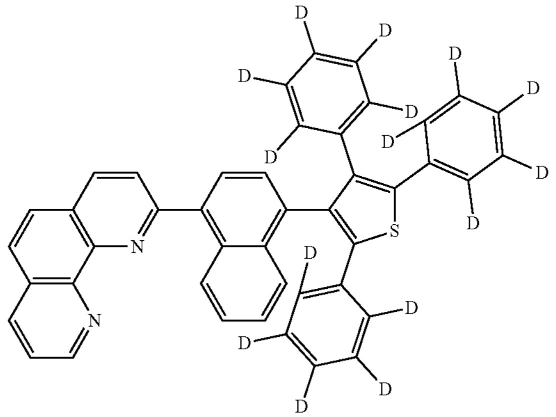
D246
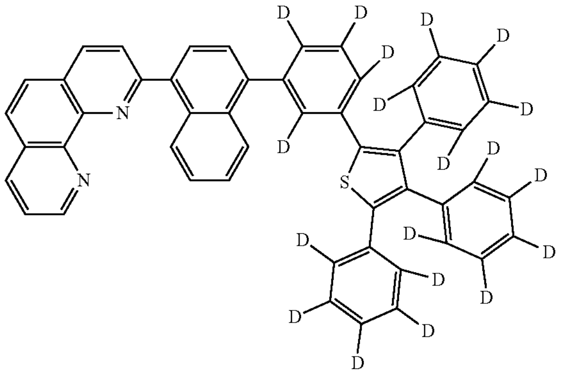
D247
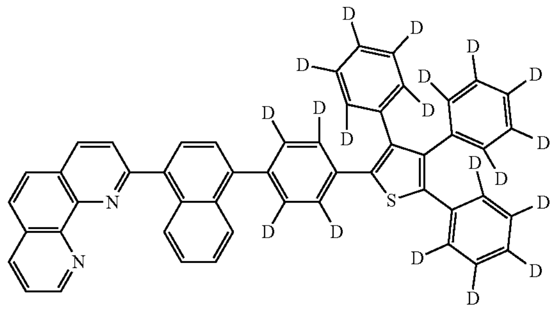
D248
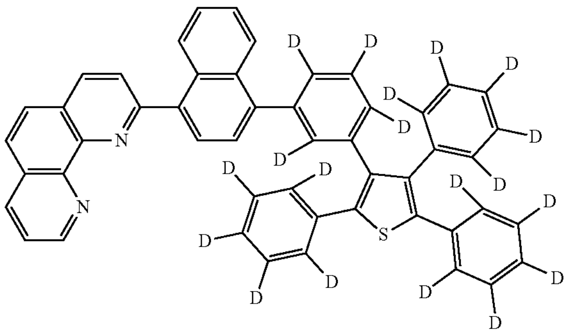
D249
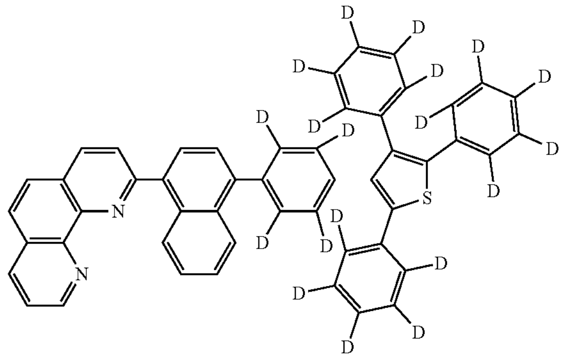
D250
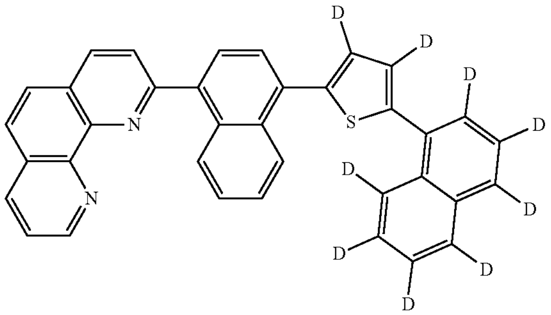

-continued
D251
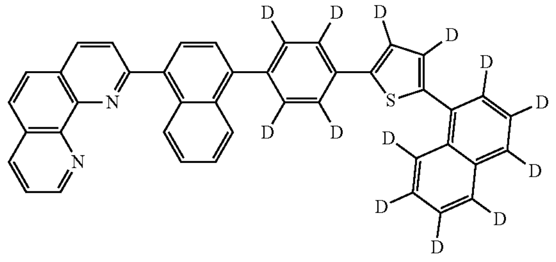
D252
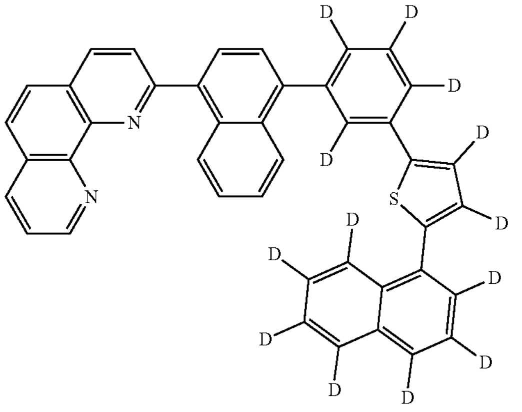
D253
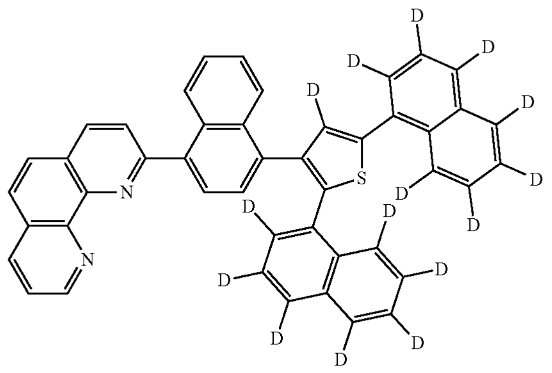
D254
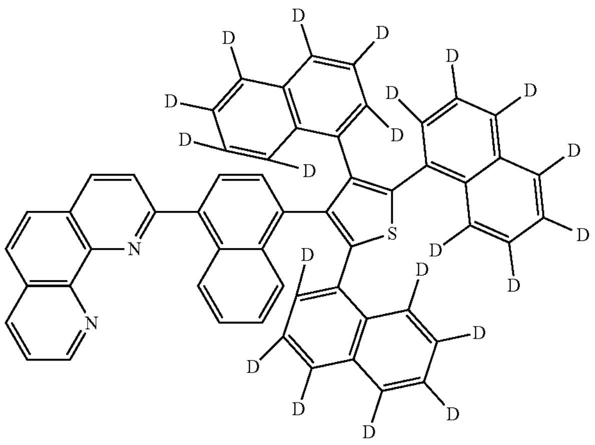
D255
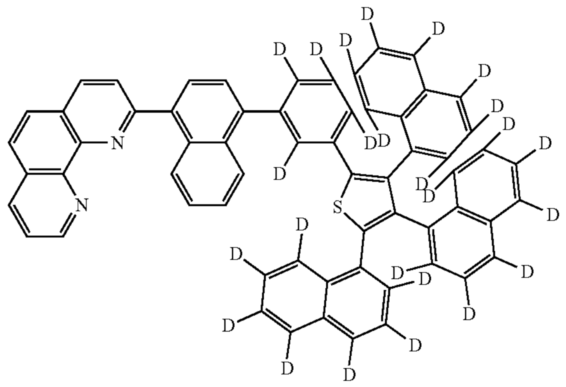
D256
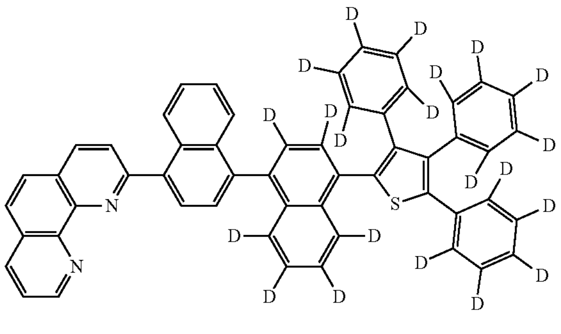

-continued
D257
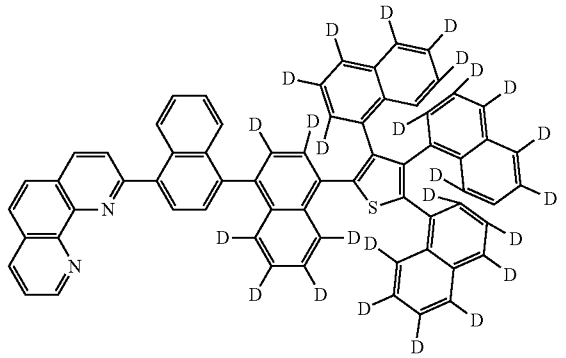
D258
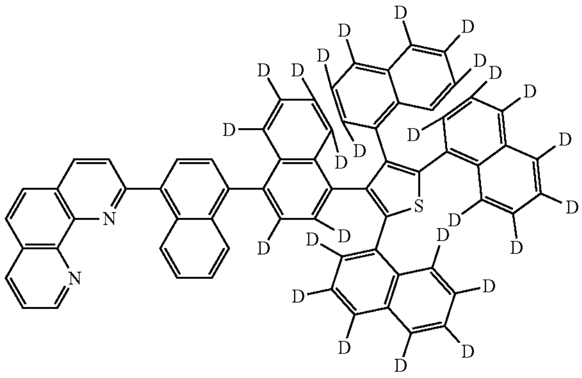
D259
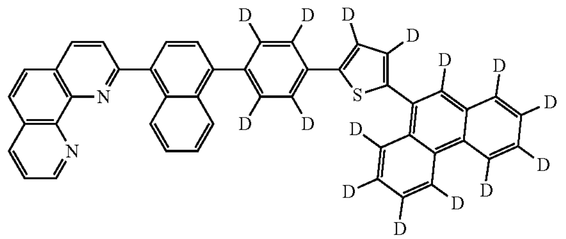
D260
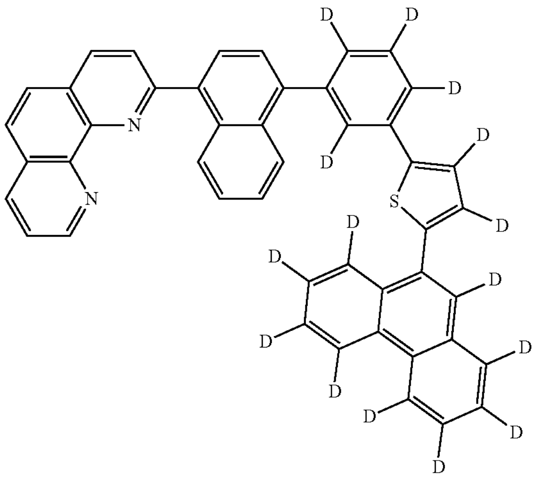
D261
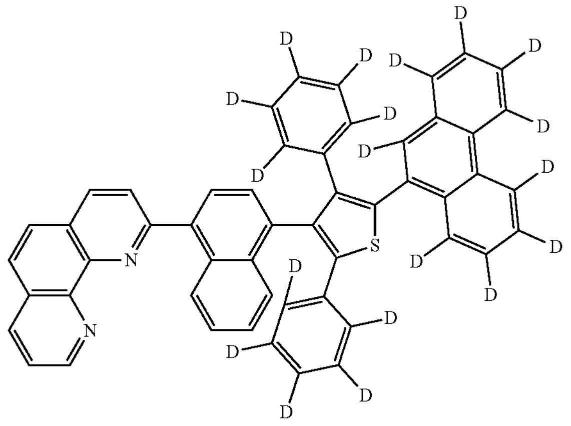
D262
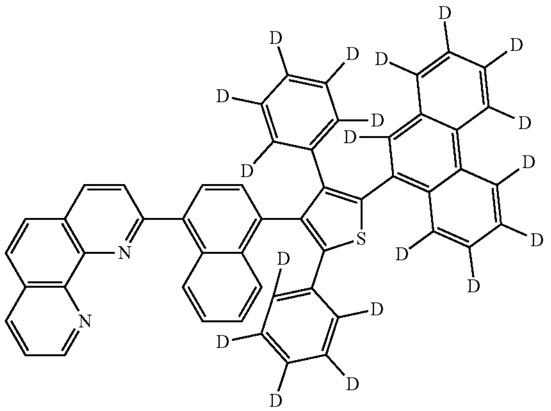

-continued
D263
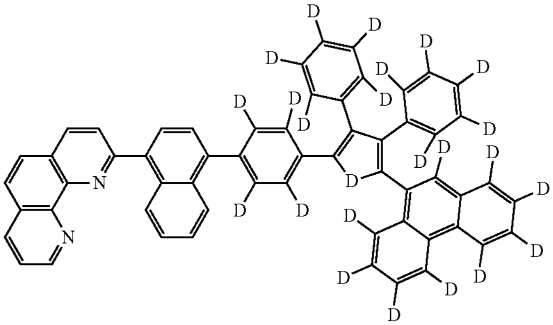
D264
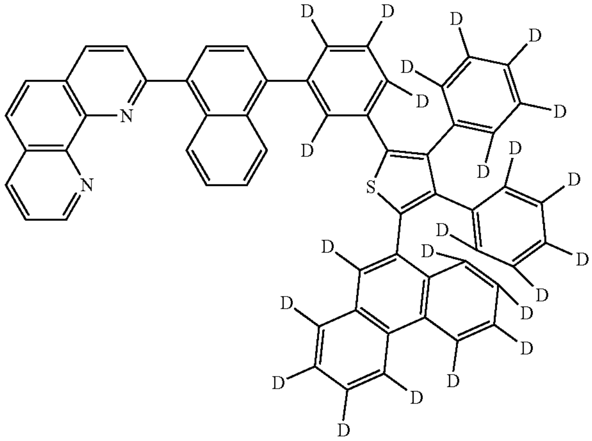
D265
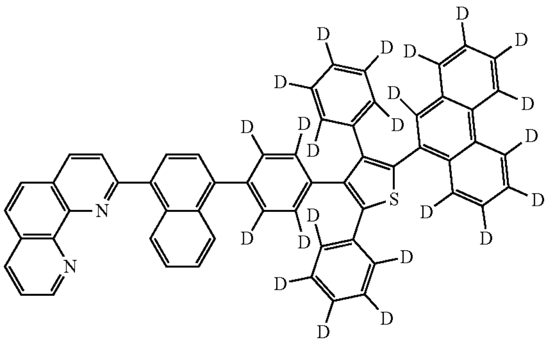
D266
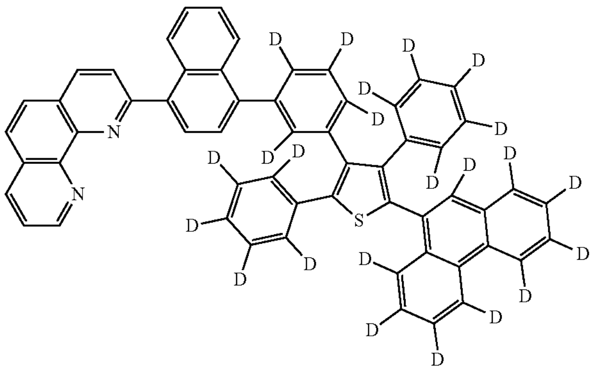
D267
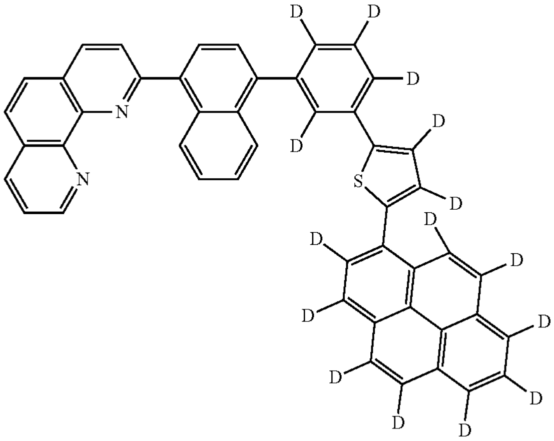
D268
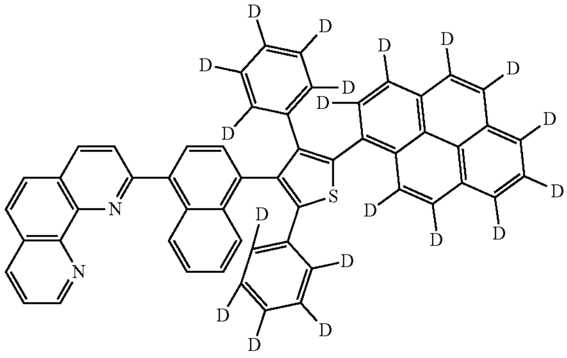

-continued
D269
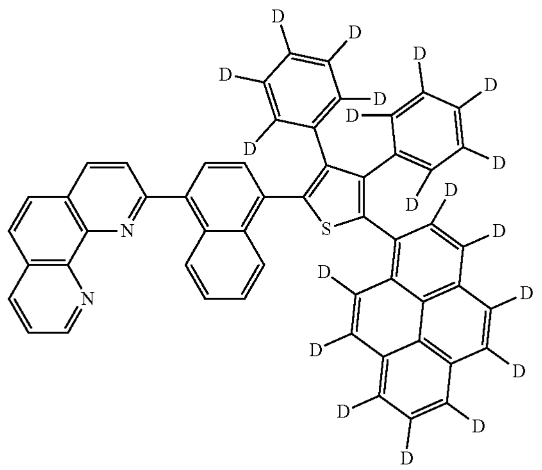
D270
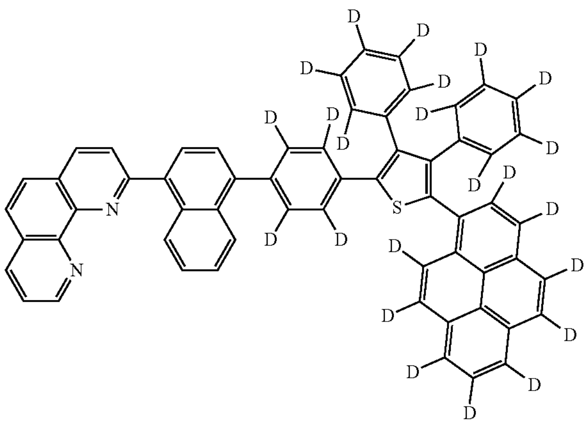
D271
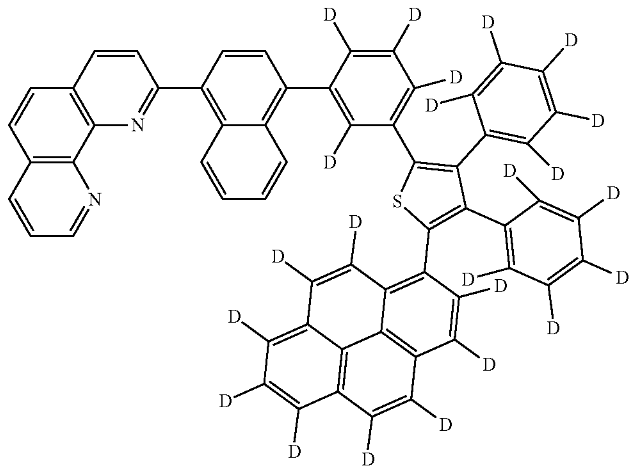
D272
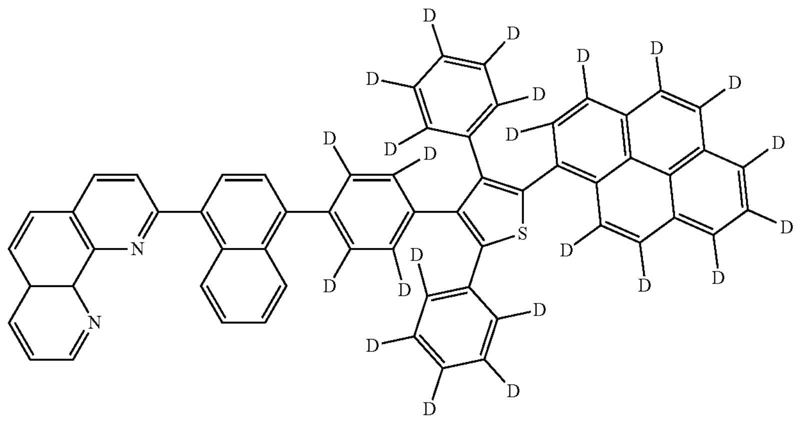

-continued
D273
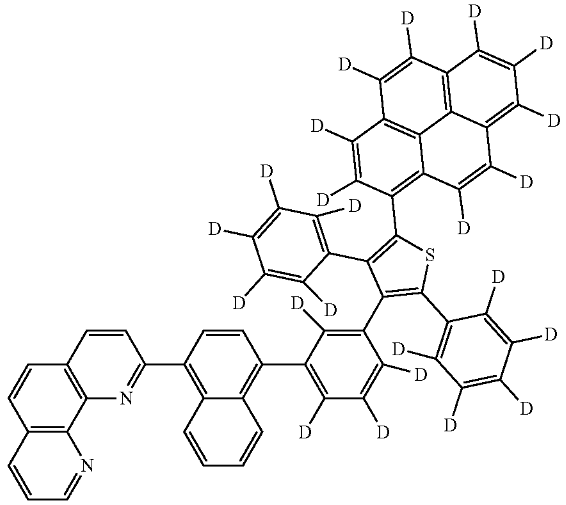
D274
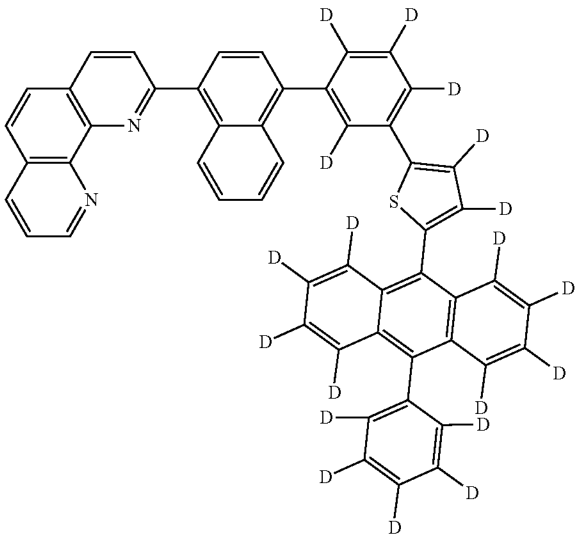
D275
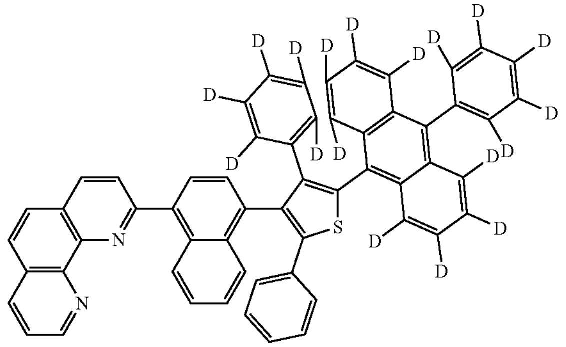
D276
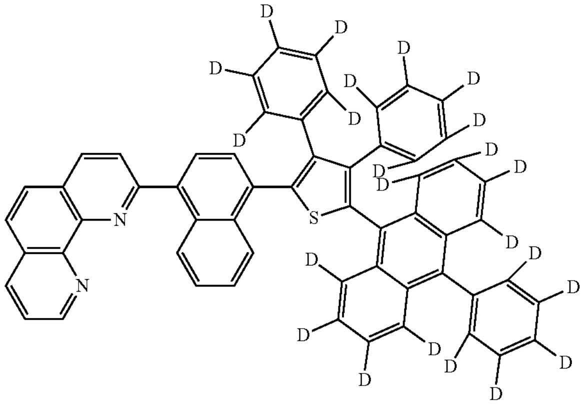
D277
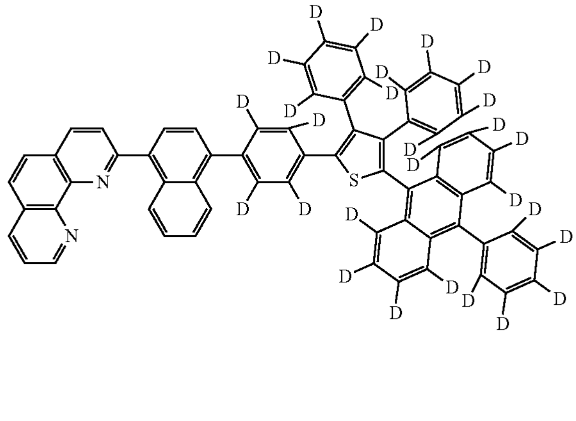
D278
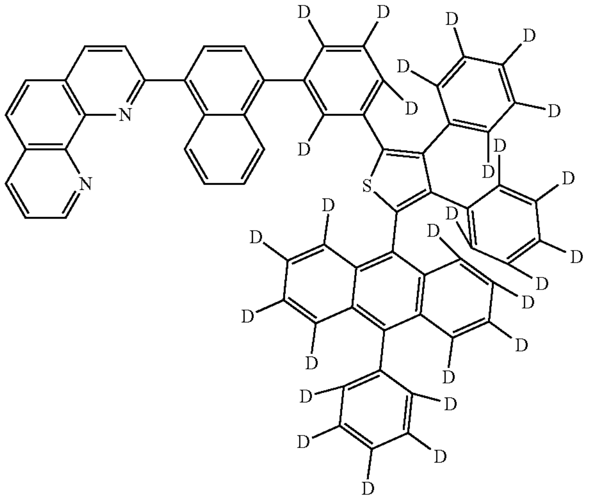

-continued
D279
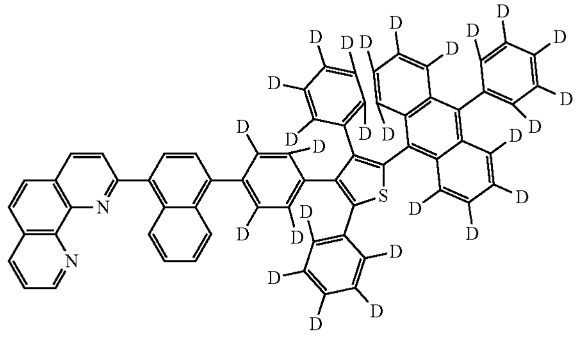
D280
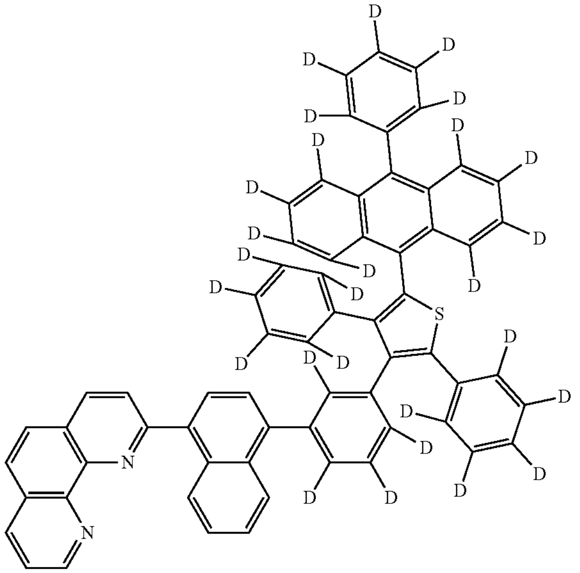
D281
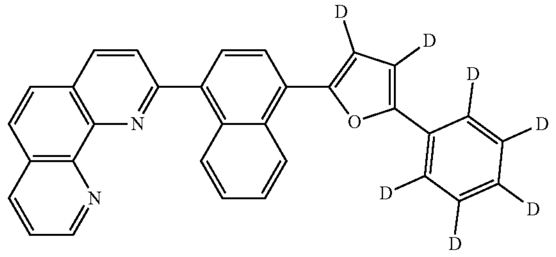
D282
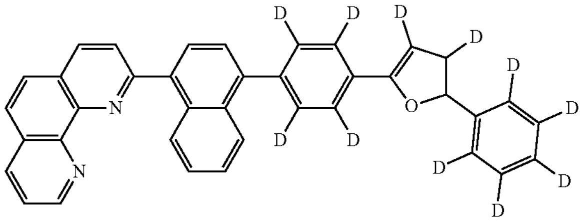
D283
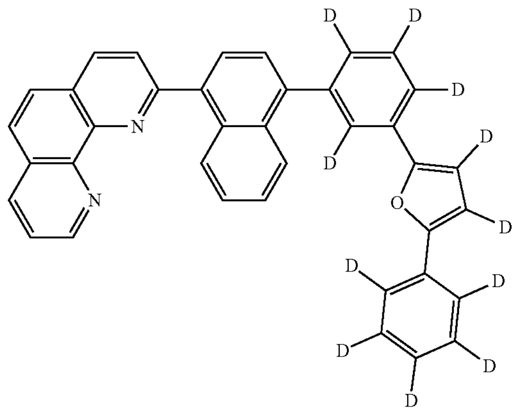
D284
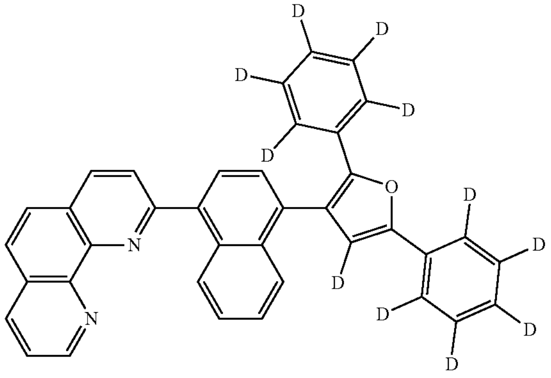

-continued
D285
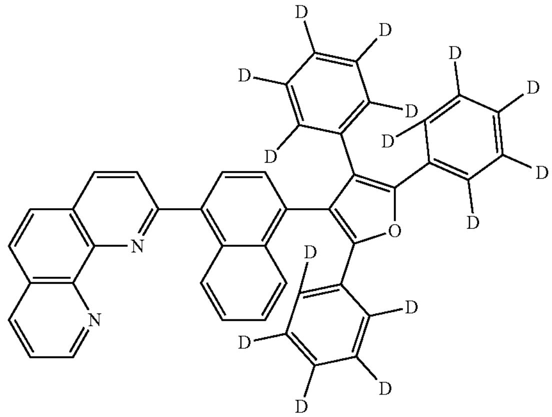
D286
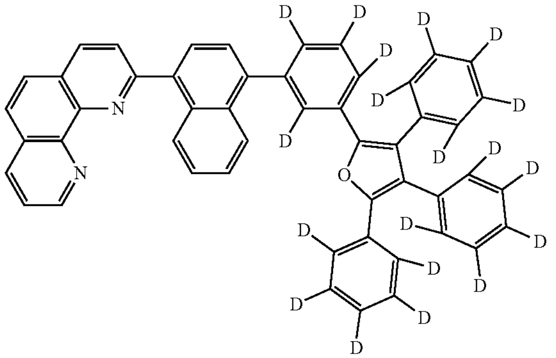
D287
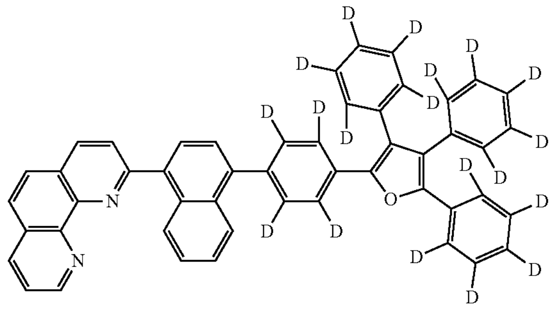
D288
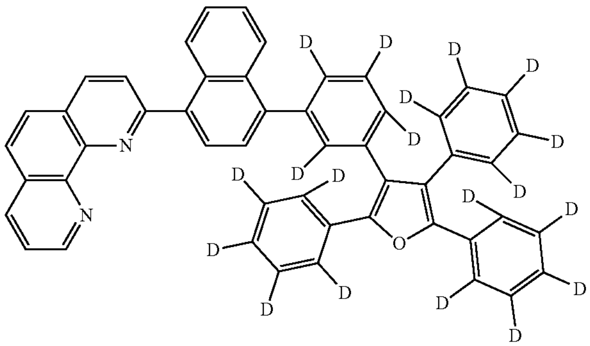
D289
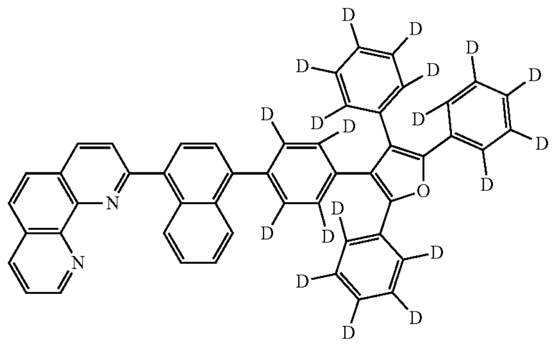
D290
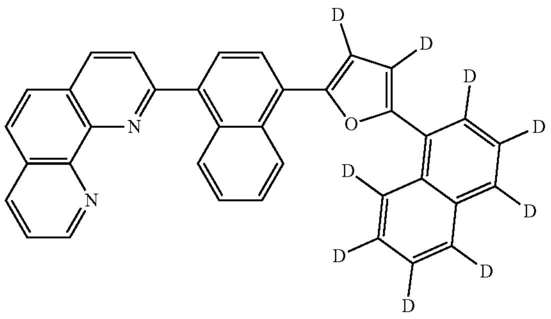
D291
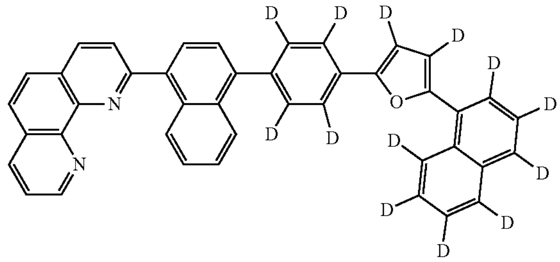
D292
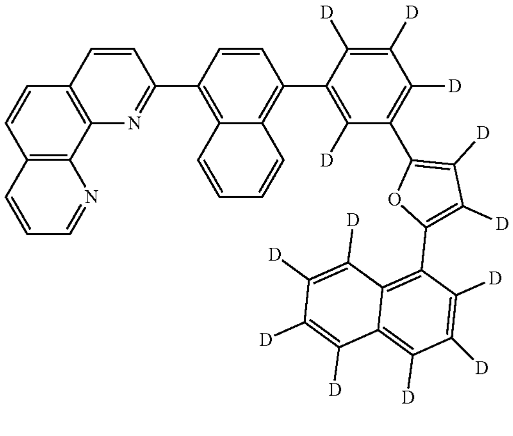

-continued
D293
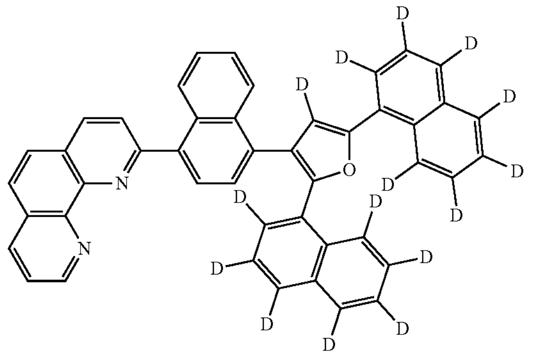
D294
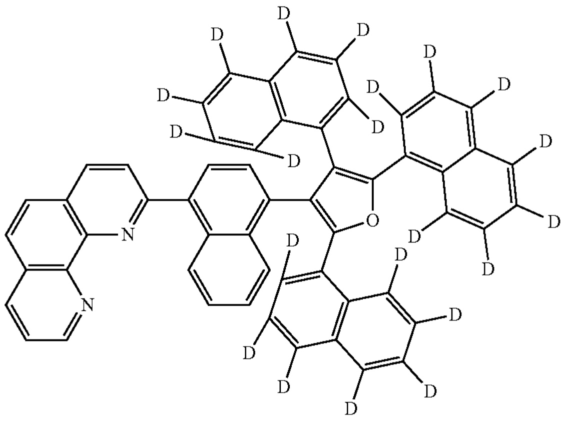
D295
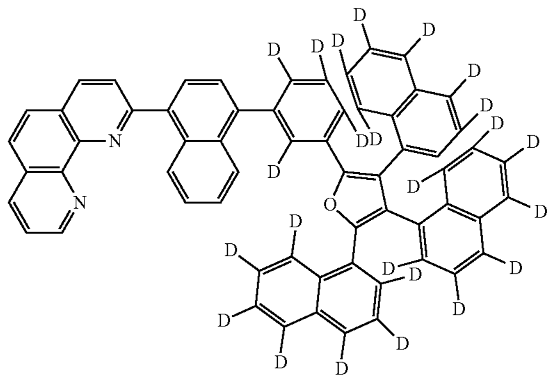
D296
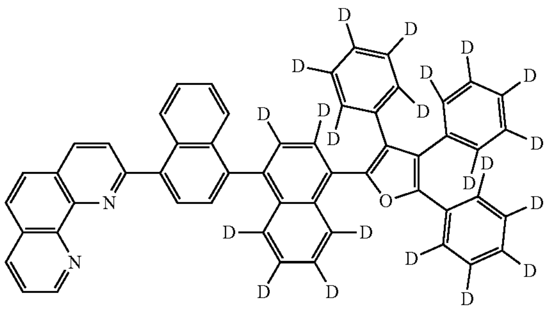
D297
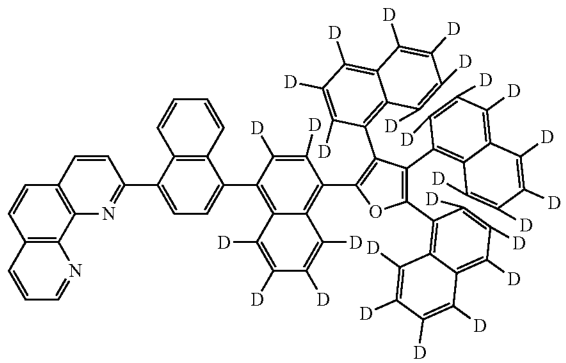
D298
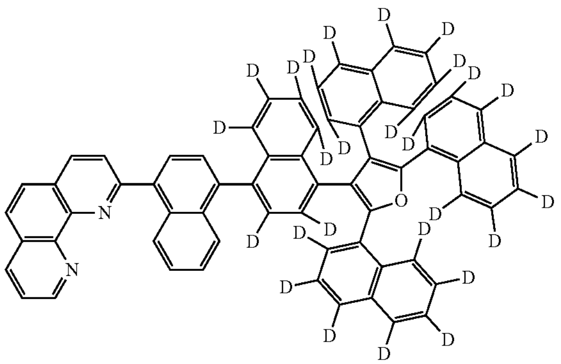

-continued
D299
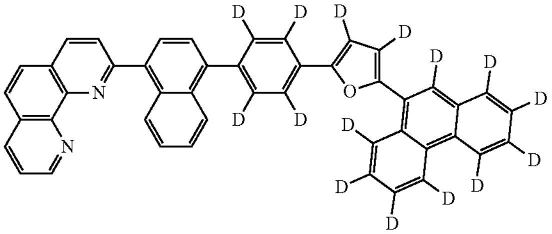
D300
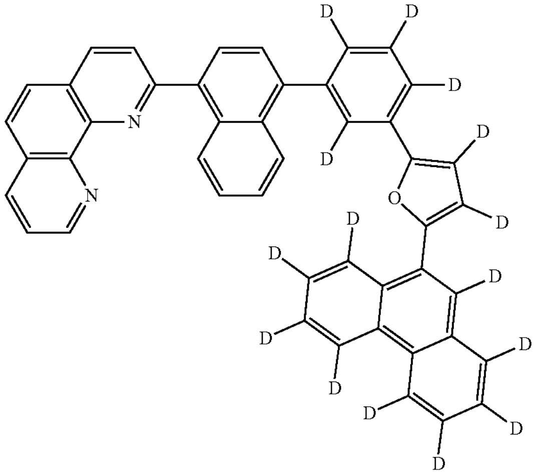
D301
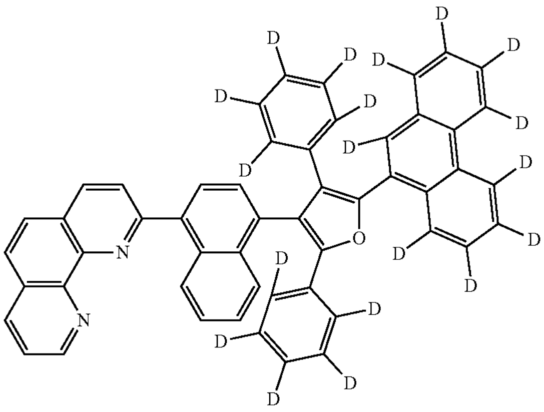
D302
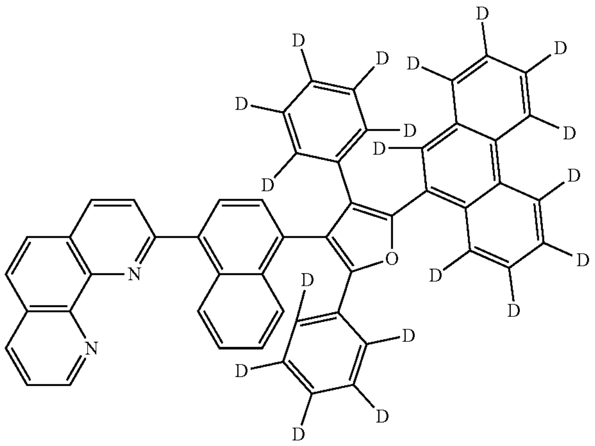
D303
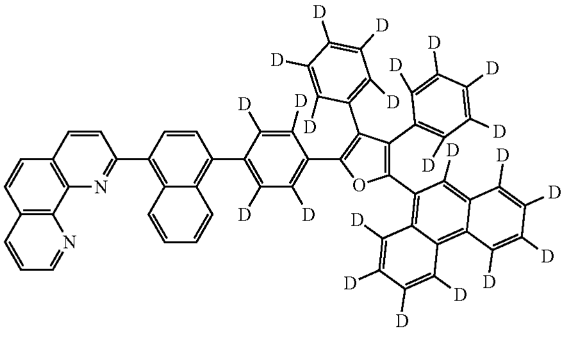
D304
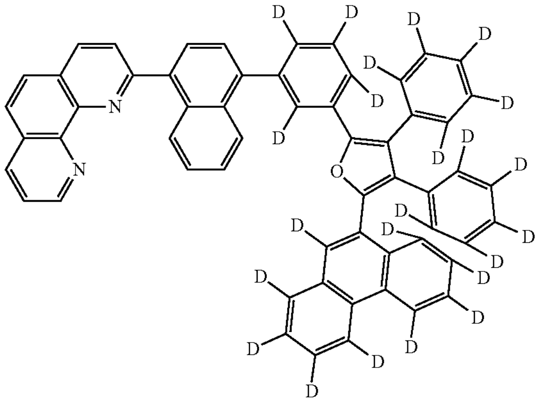

-continued
D305
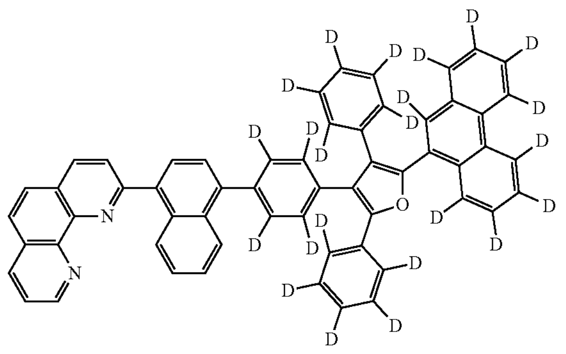
D306
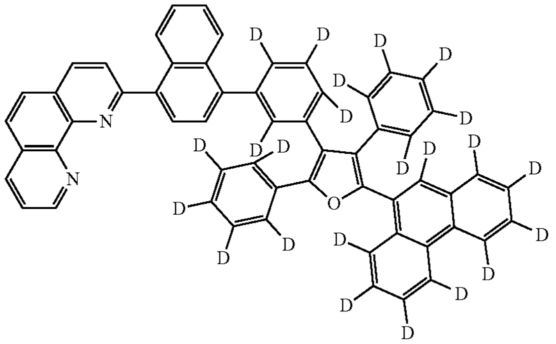
D307
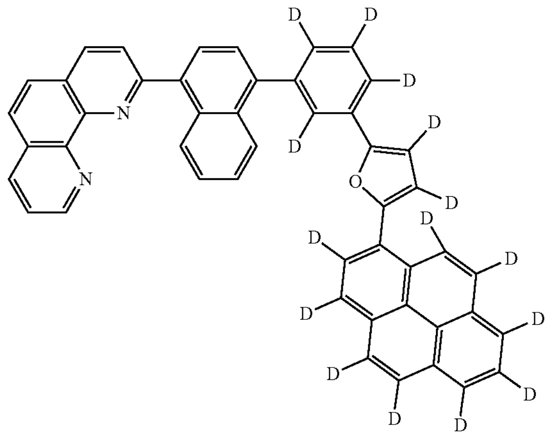
D308
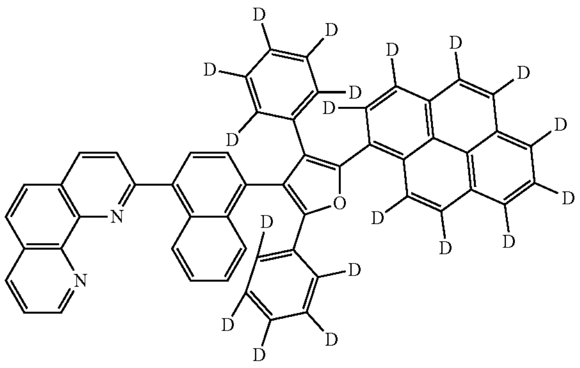
D309
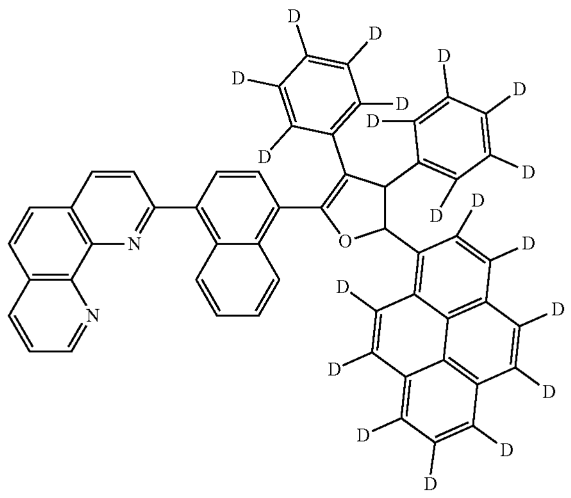
D310
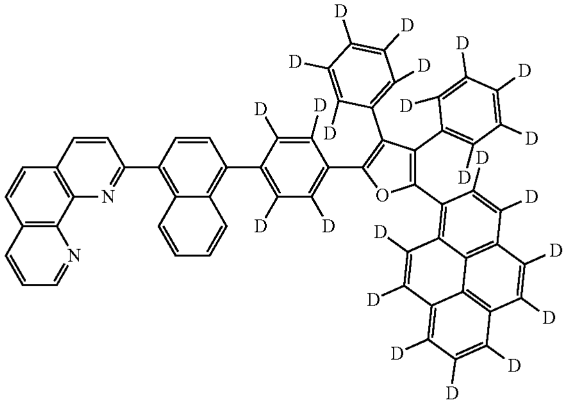

-continued
D311
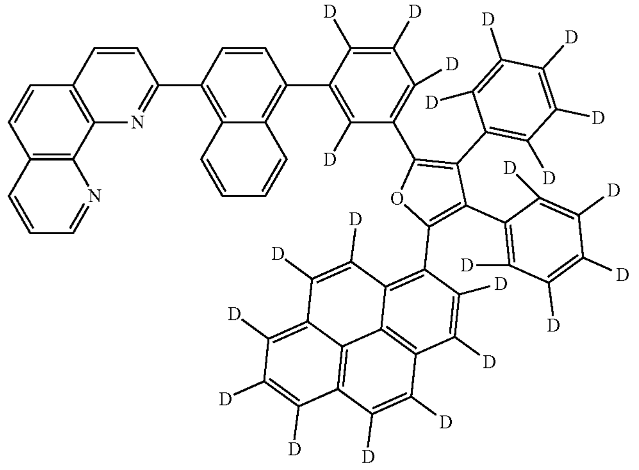
D312
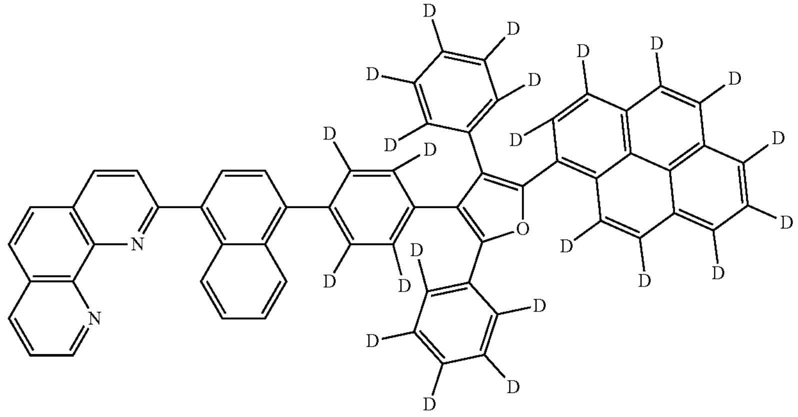
D313
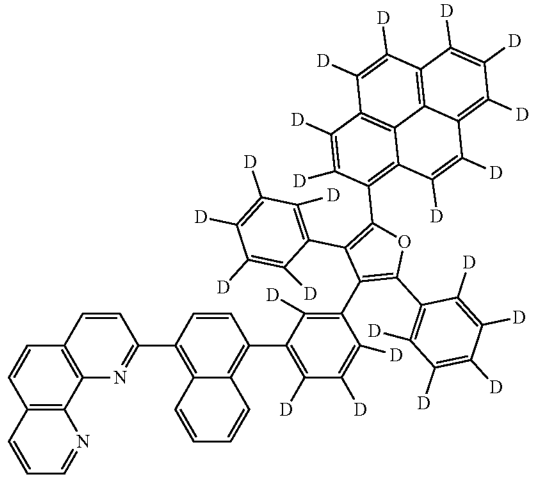
D314
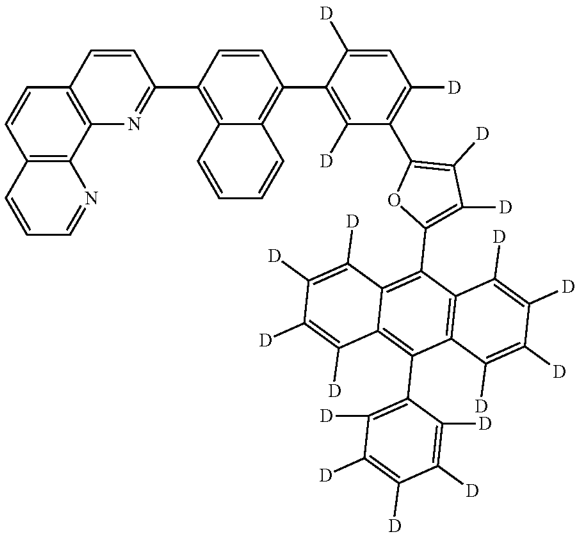

-continued
D315
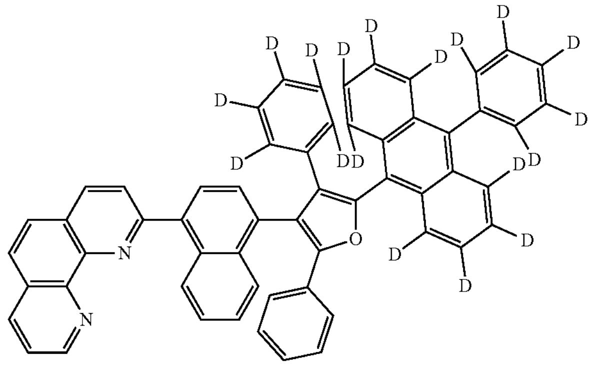
D316
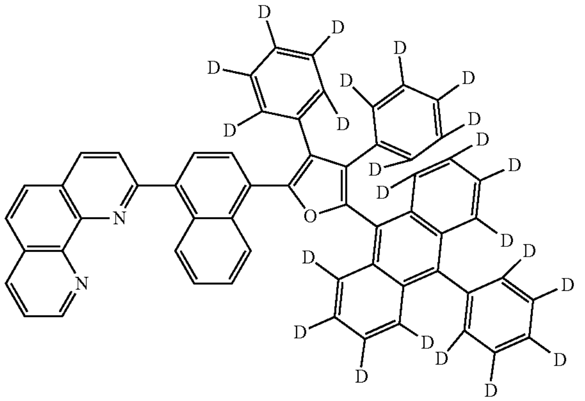
D317
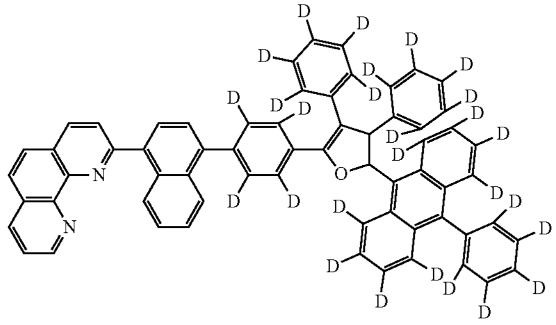
D318
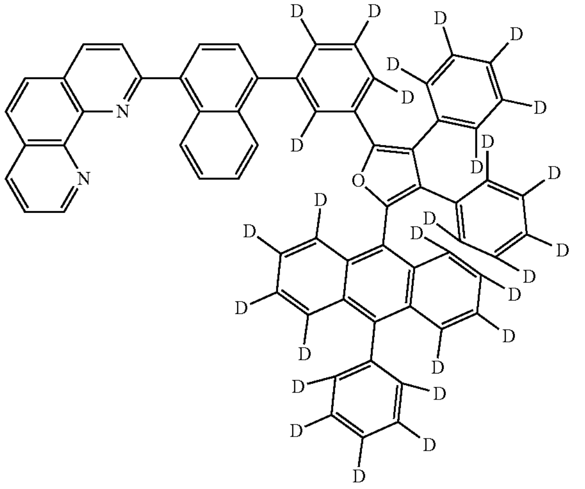
D319
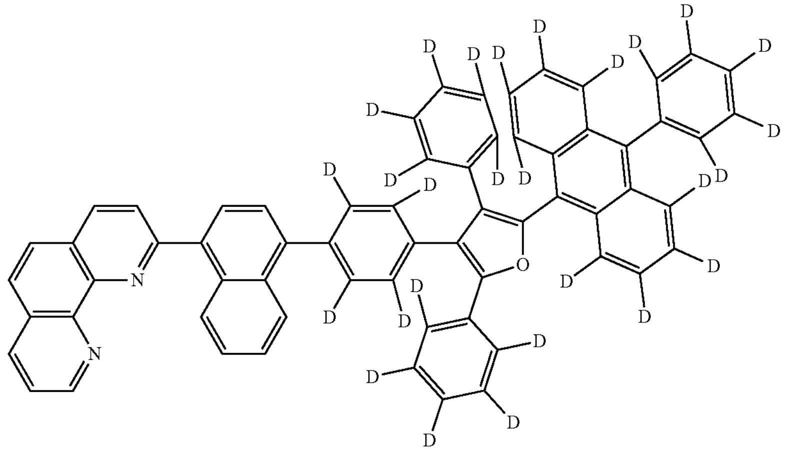

-continued
D320
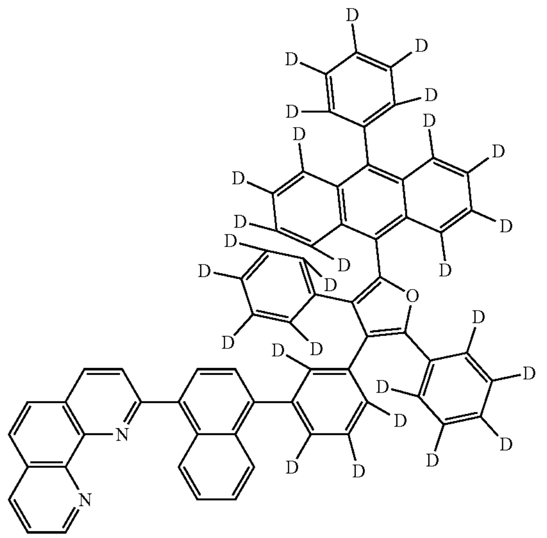
D321
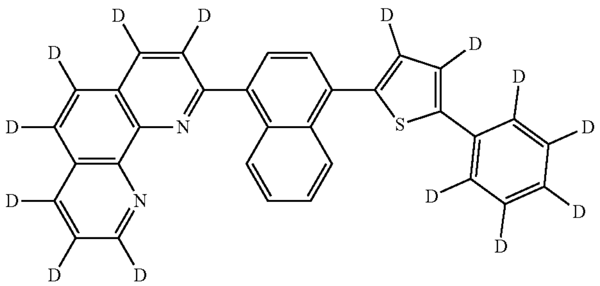
D322
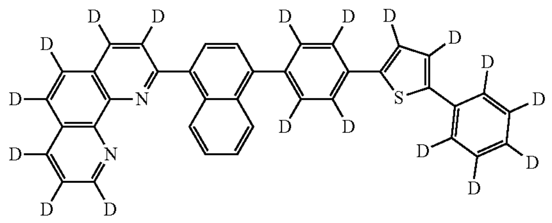
D323
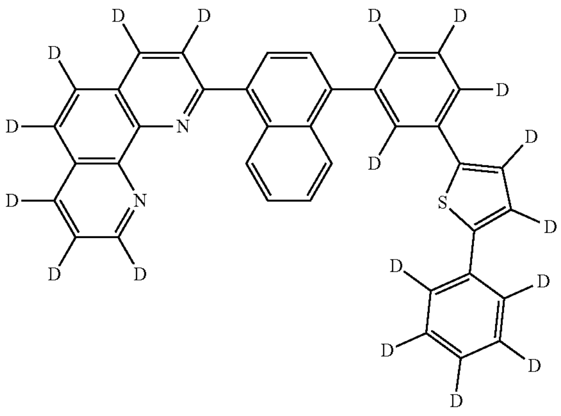
D324
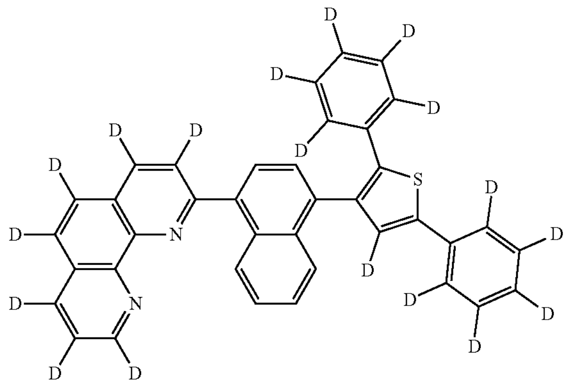
D325
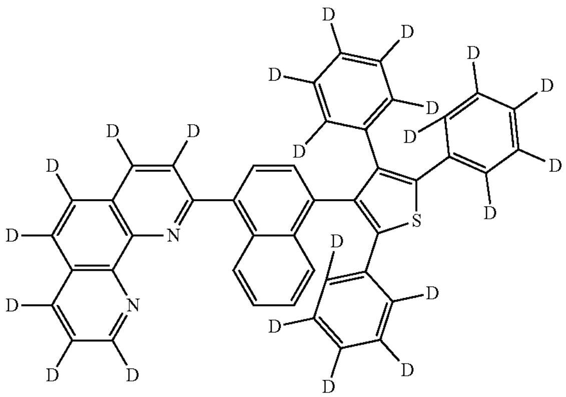

-continued
D326
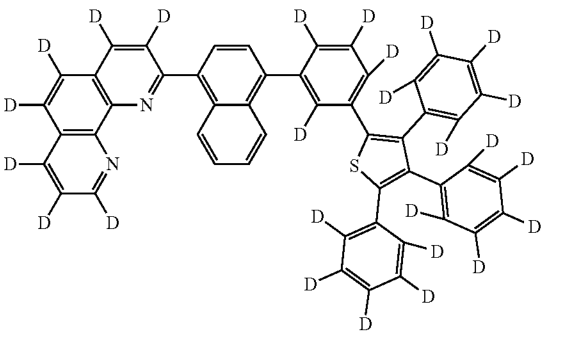
D327
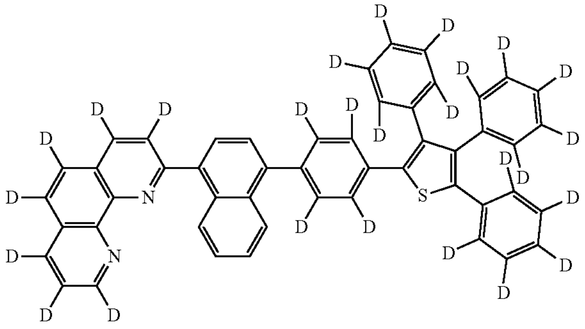
D328
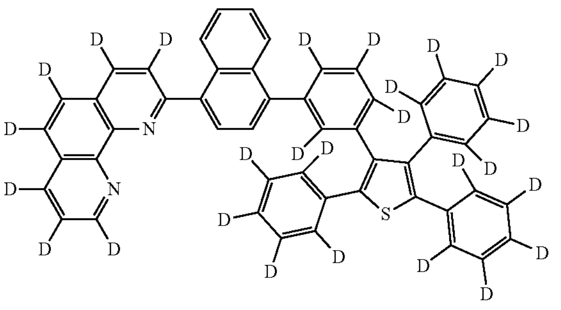
D329
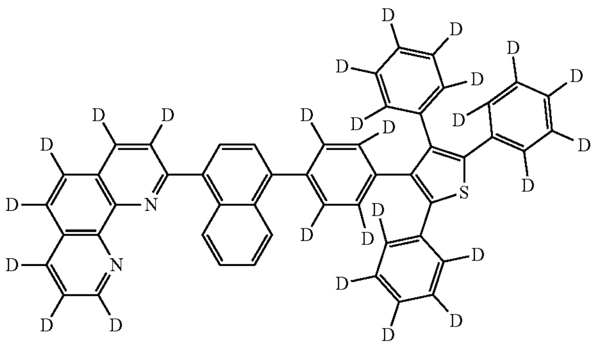
D330
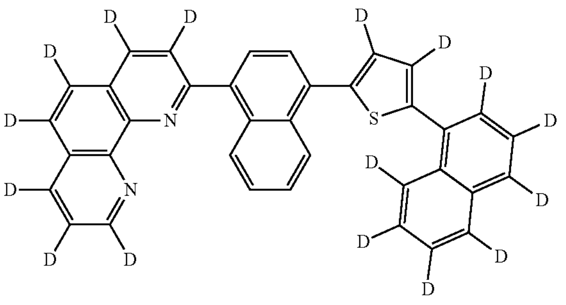
D331
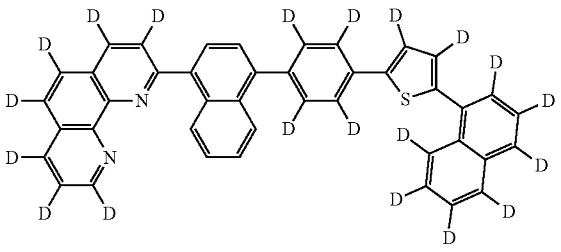
D332
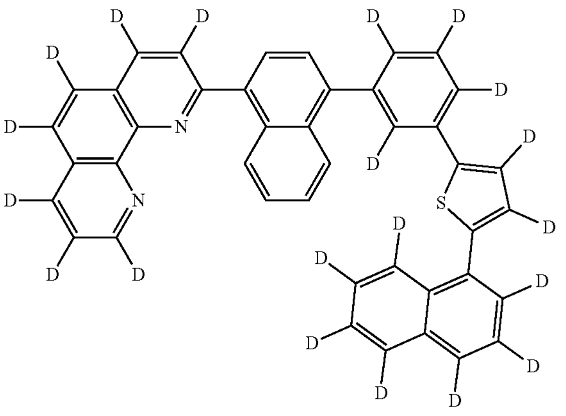
D333
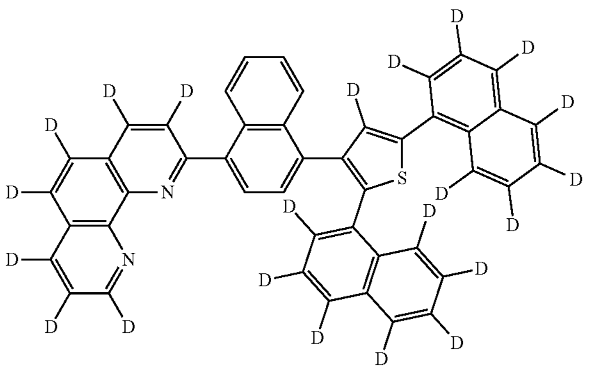

-continued
D334
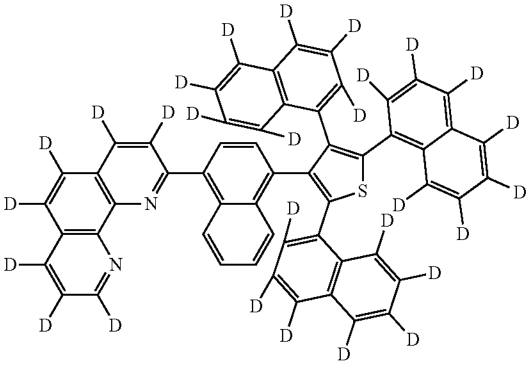
D335
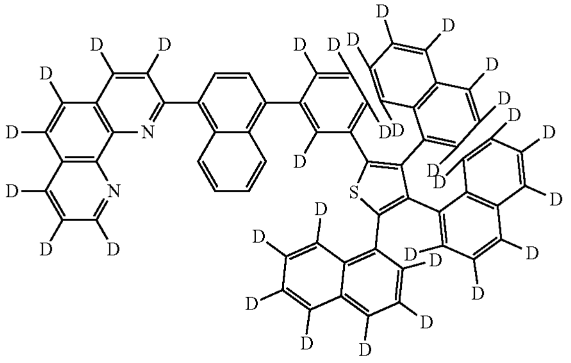
D336
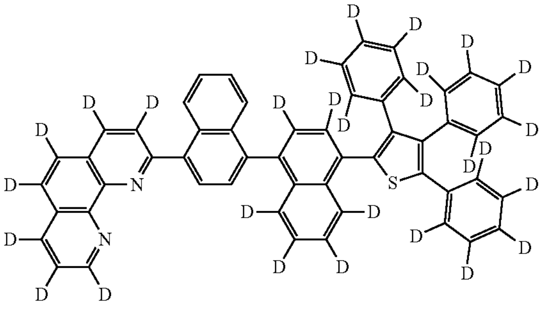
D337
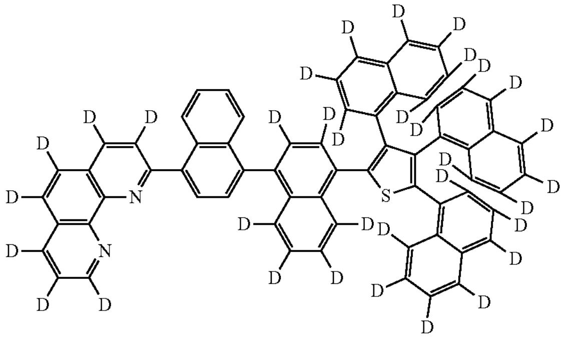
D338
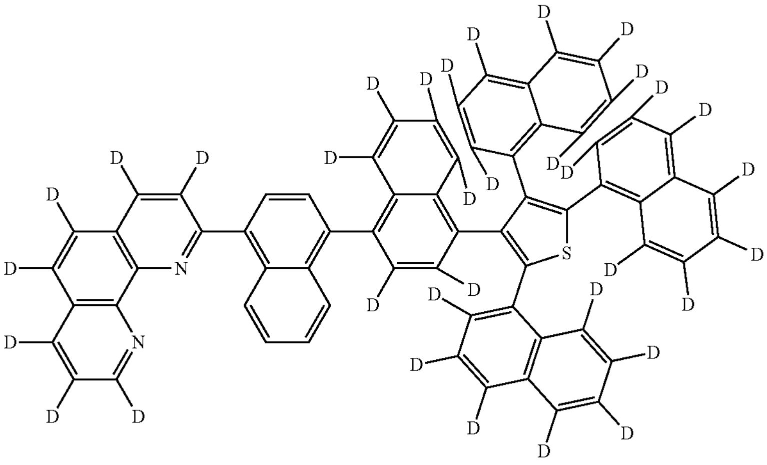
D339
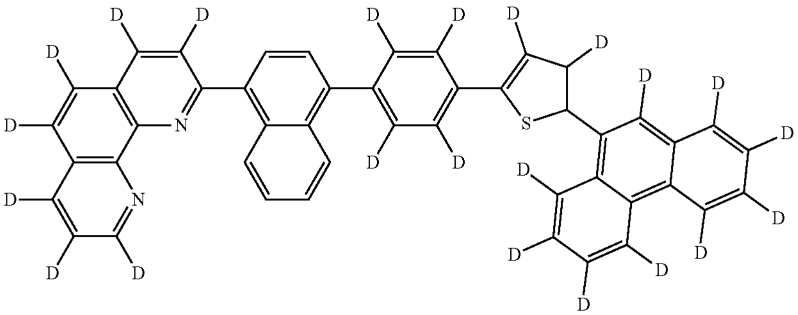

-continued
D340
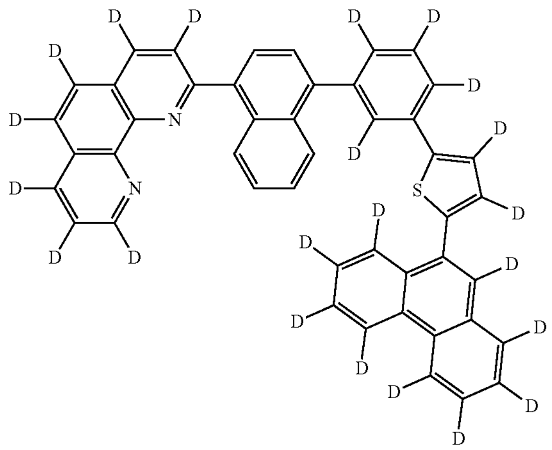
D341
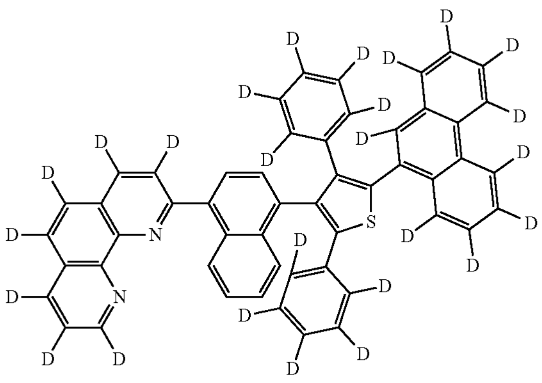
D342
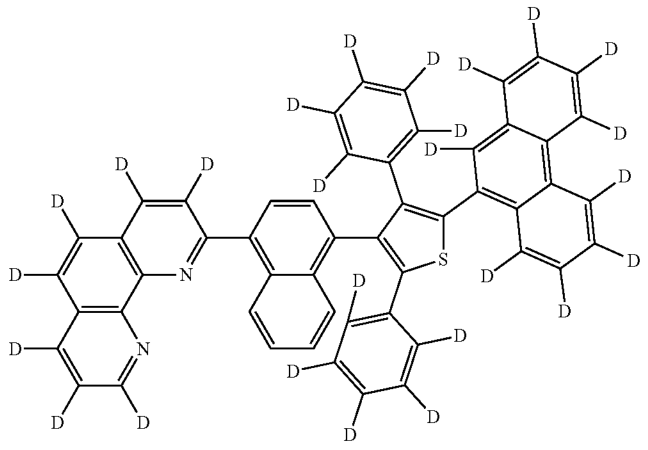
D343
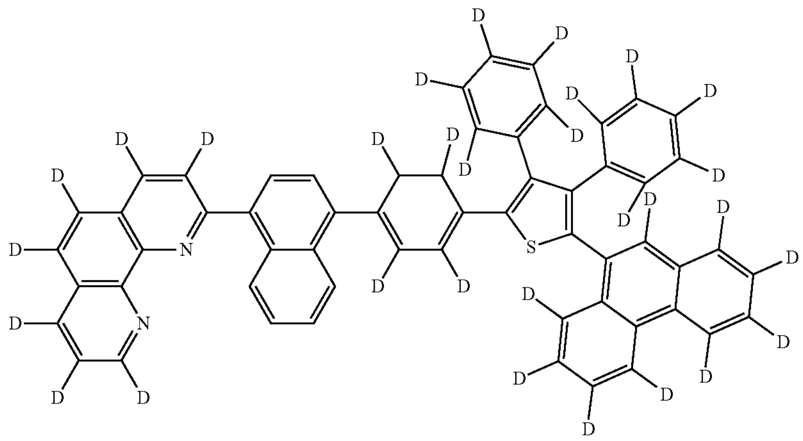

-continued
D344
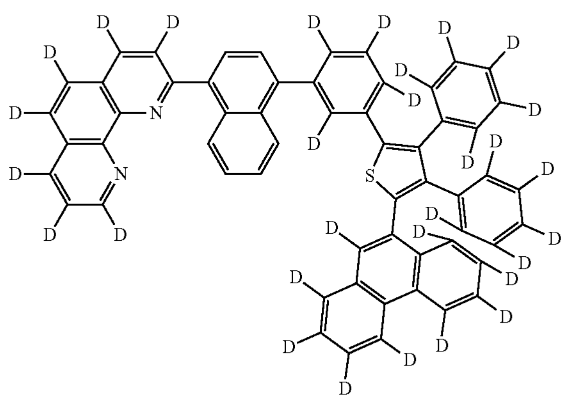
D345
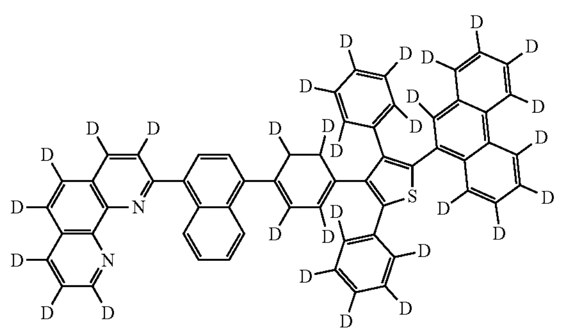
D346
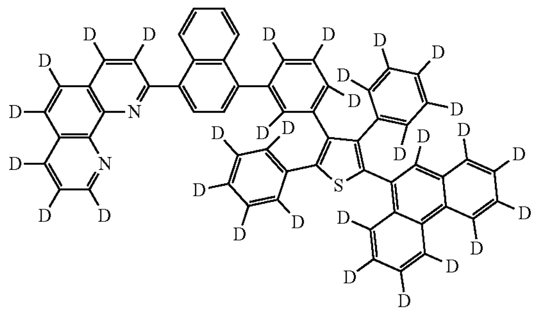
D347
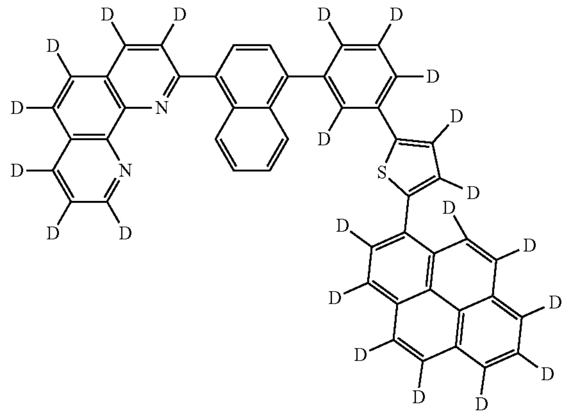
D348
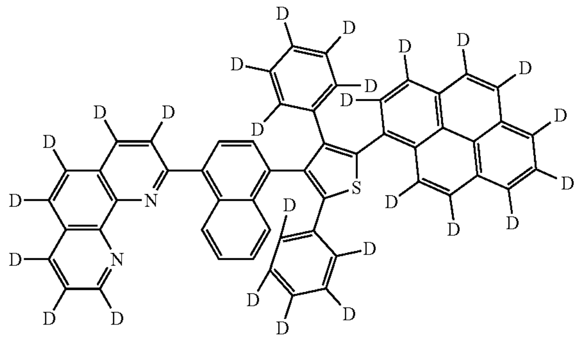
D349
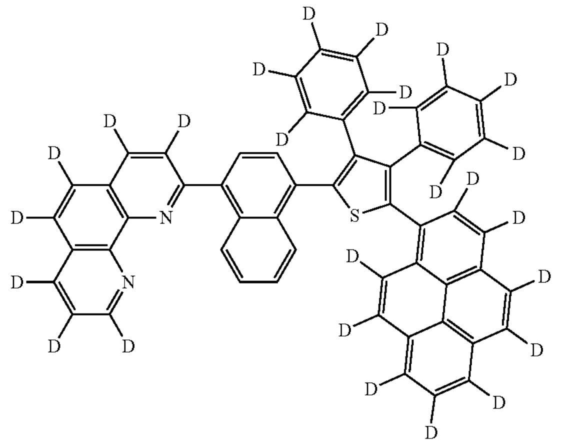

-continued
D350
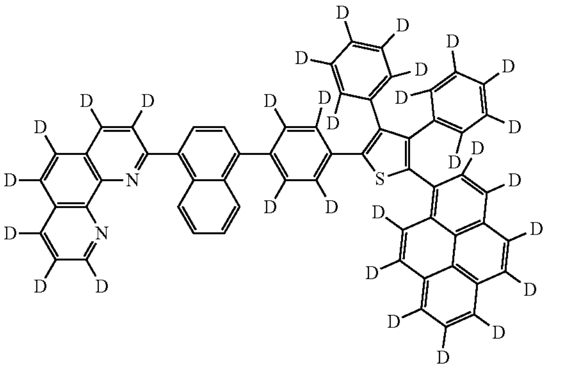
D351
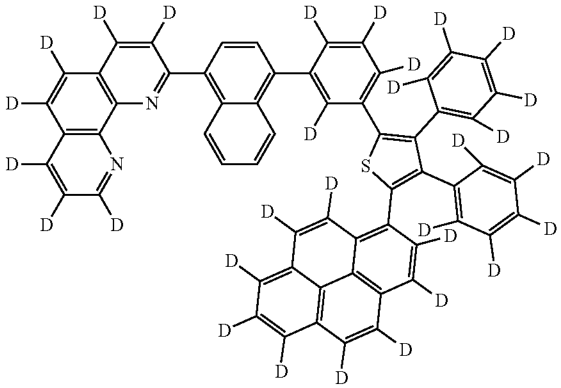
D352
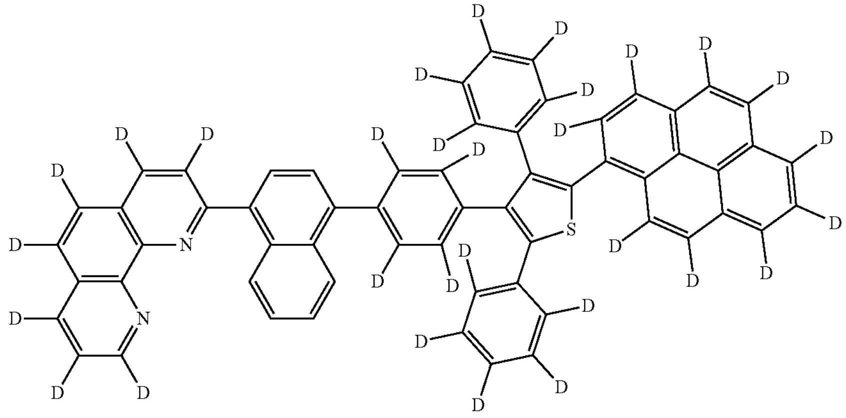
D353
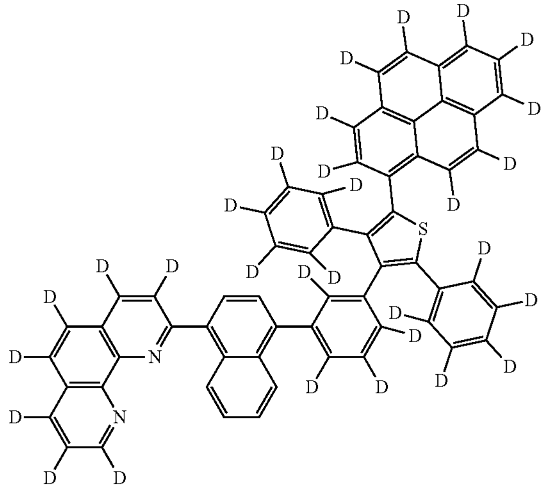
D354
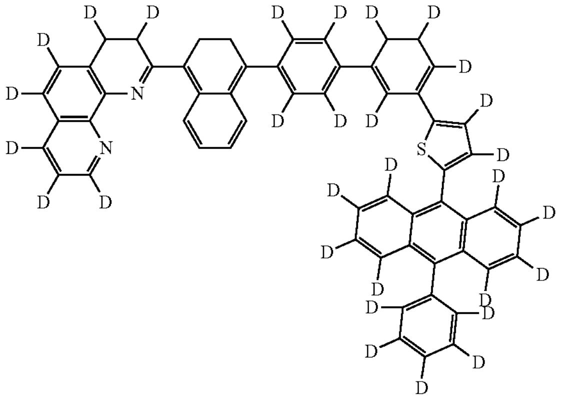

-continued
D355
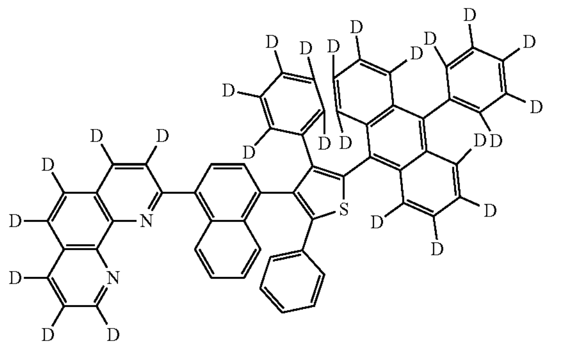
D356
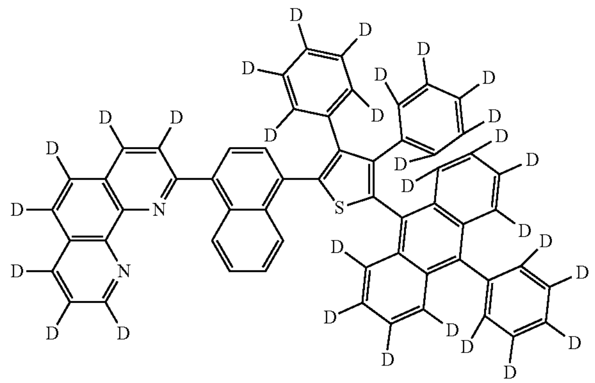
D357
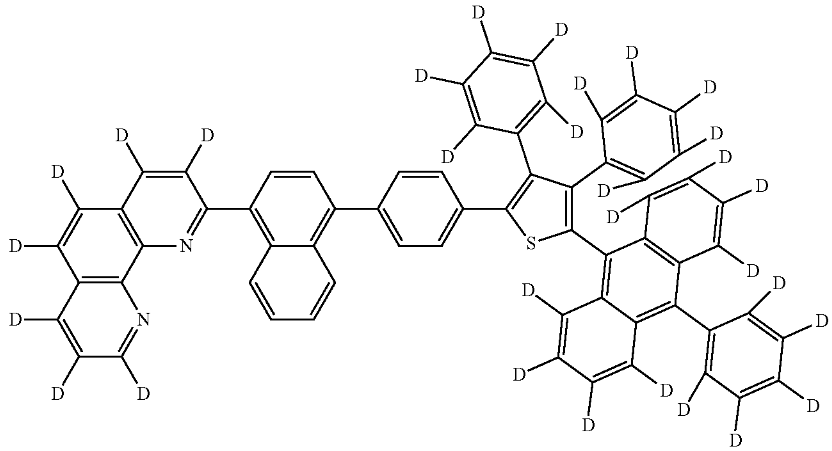
D358
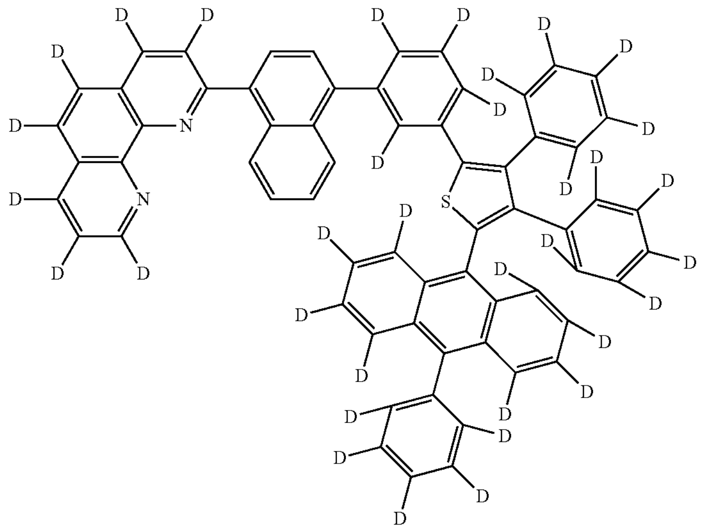

-continued
D359
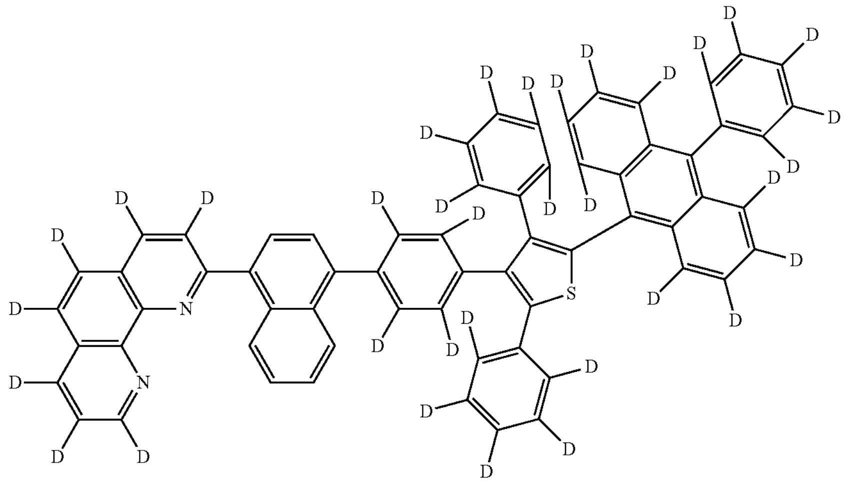
D360
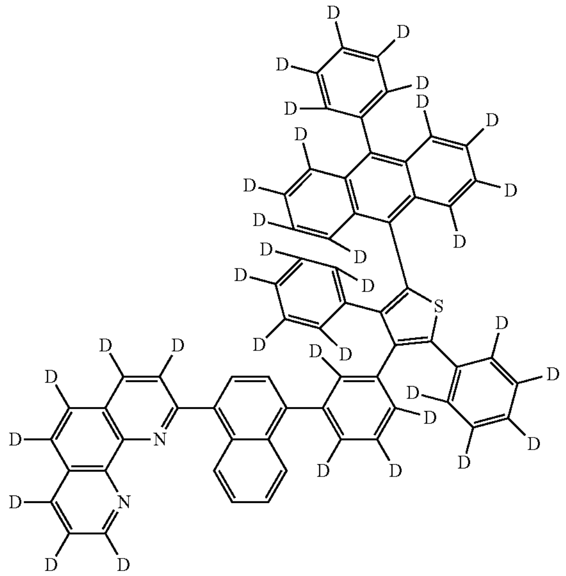
D361
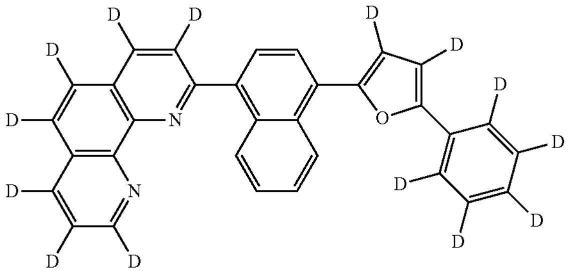
D362
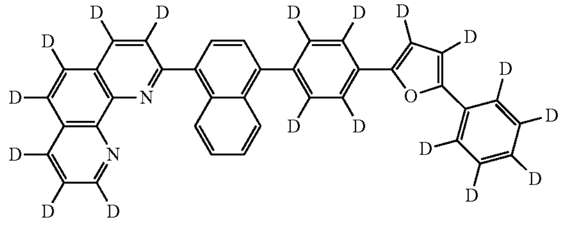
D363
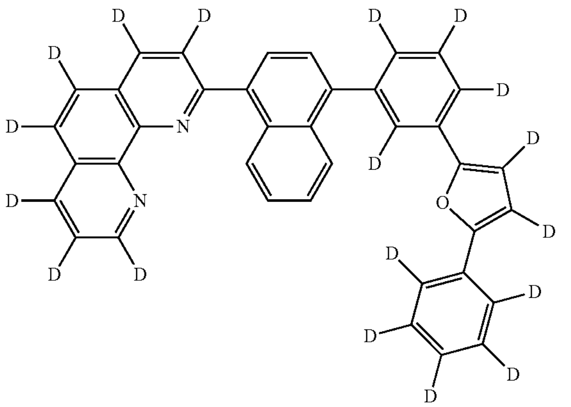

-continued
D364
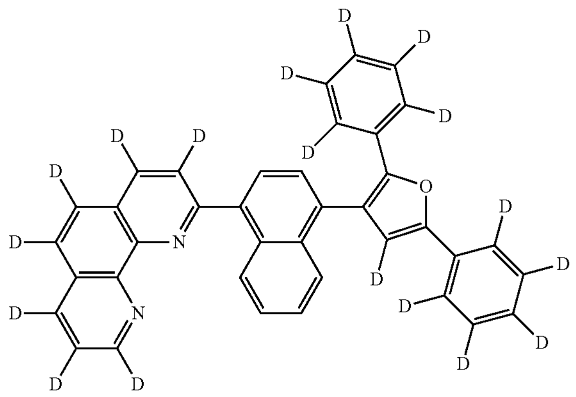
D365
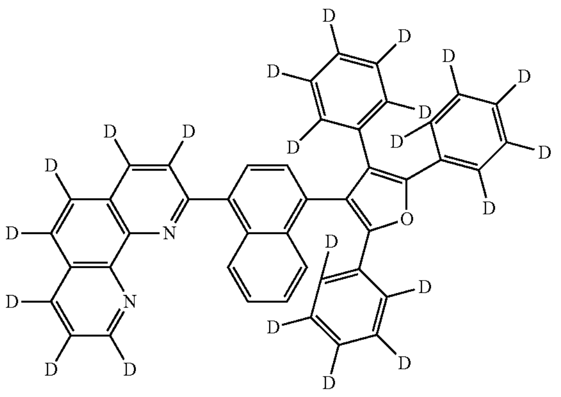
D366
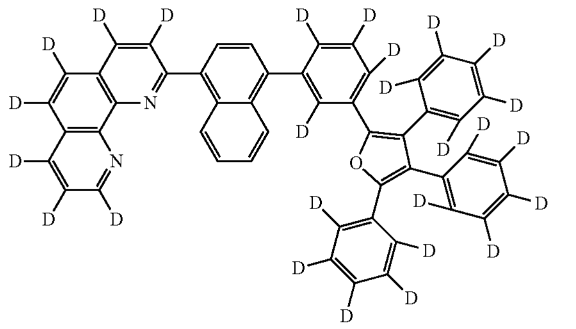
D367
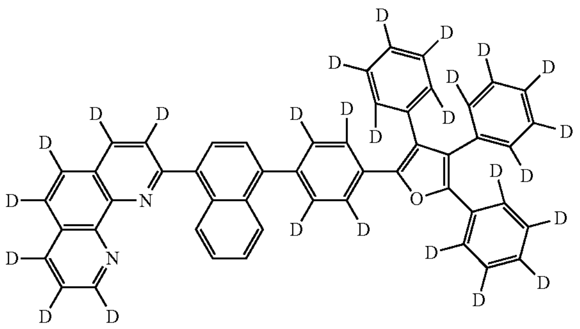
D368
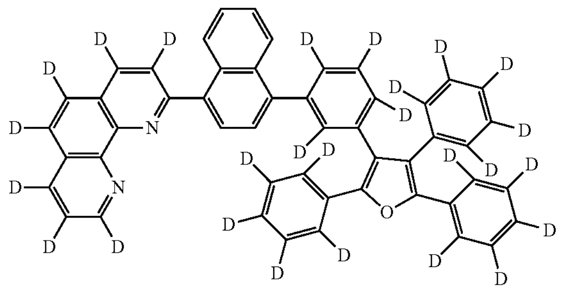
D369
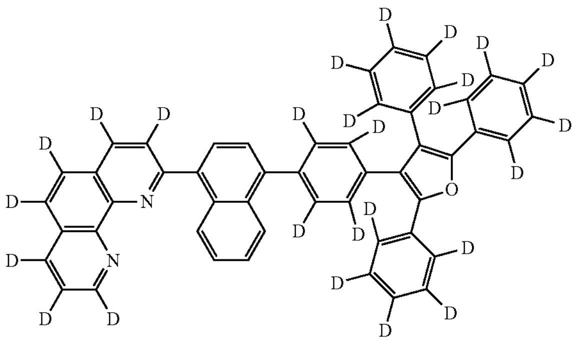
D370
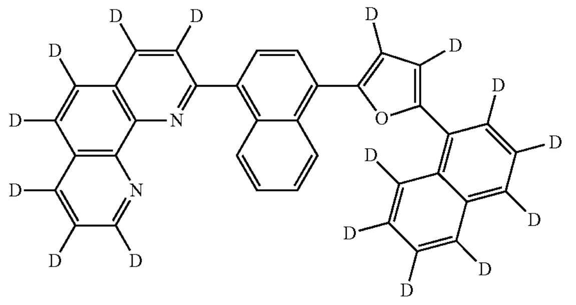
D371
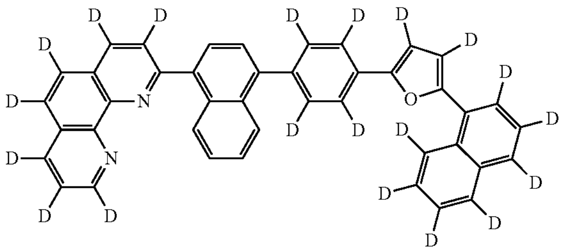

-continued
D372
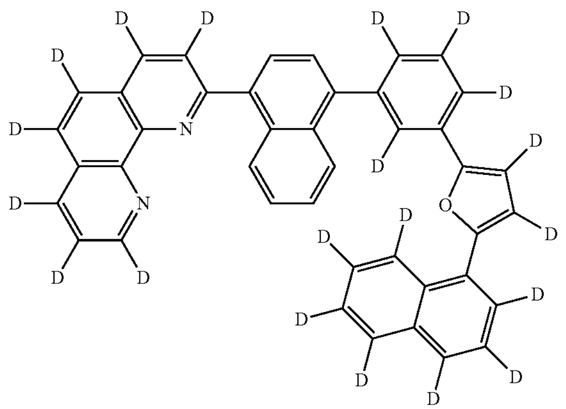
D373
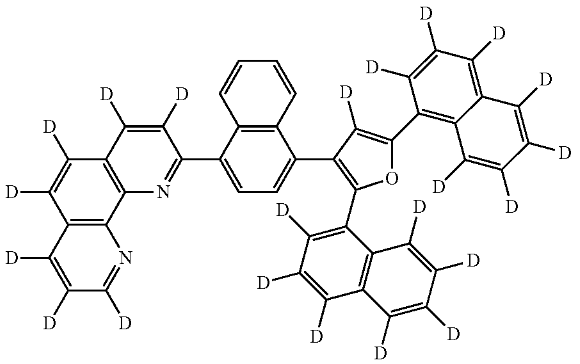
D374
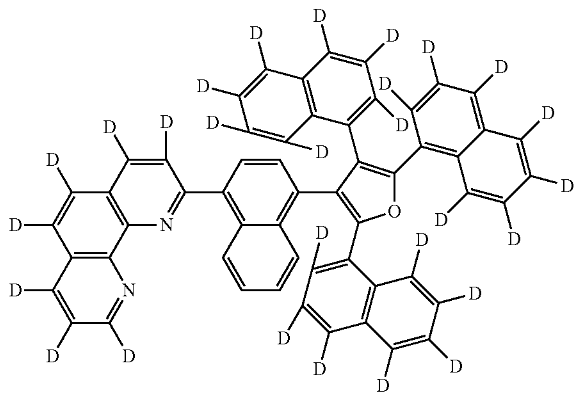
D375
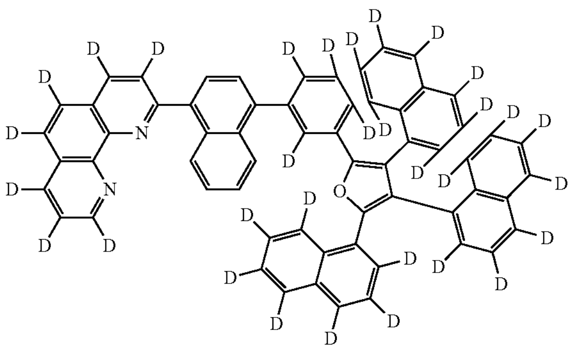
D376
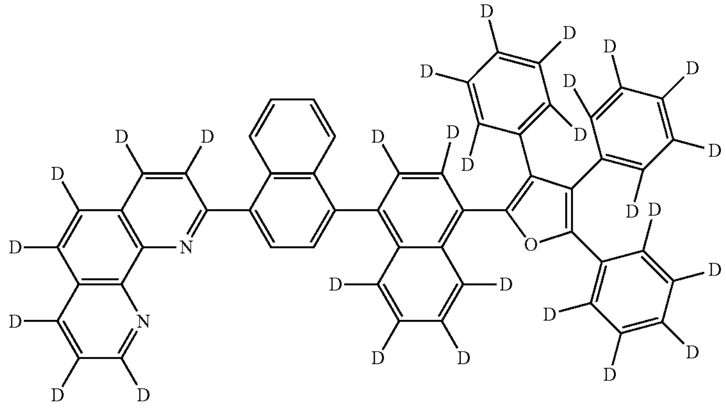

-continued
D377
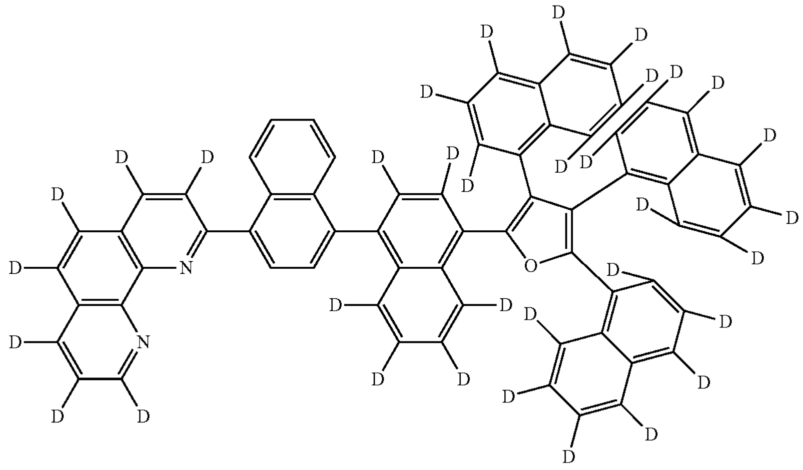
D378
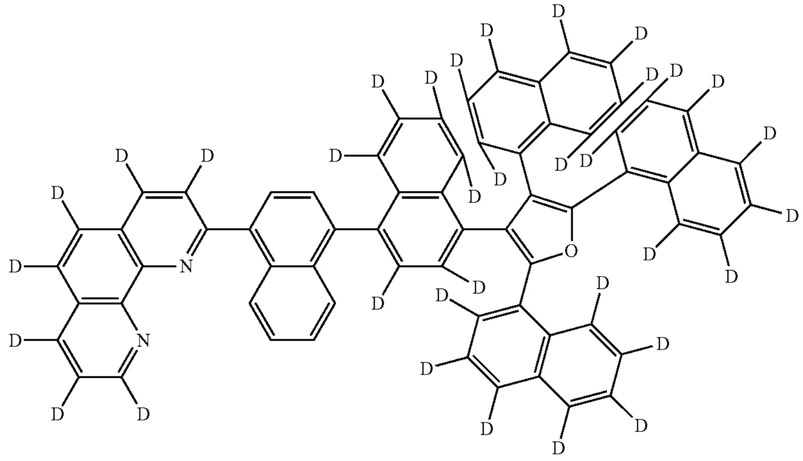
D379
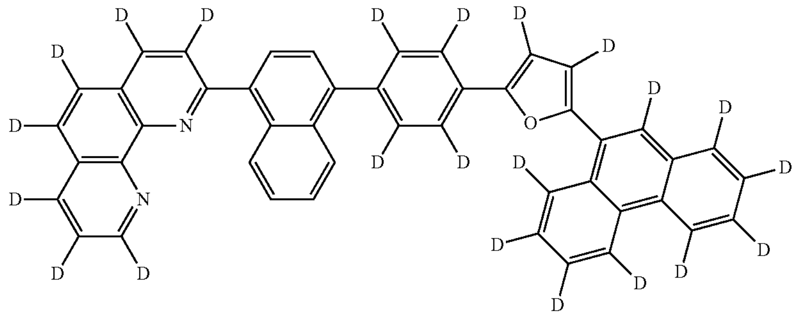

-continued
D380
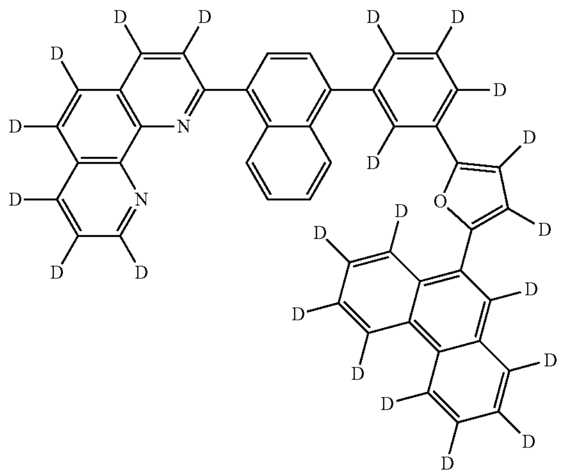
D381
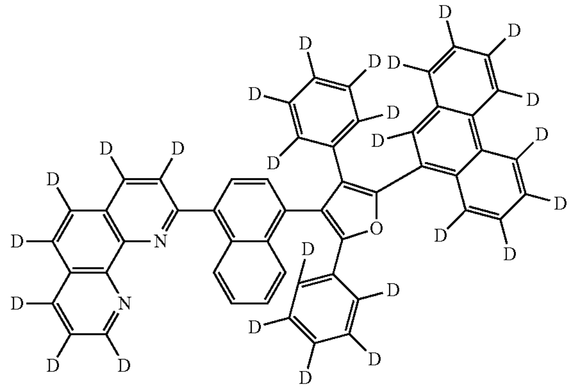
D382
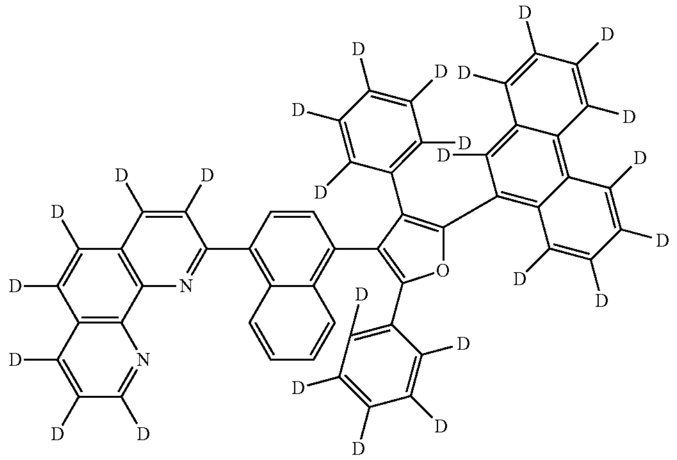
D383
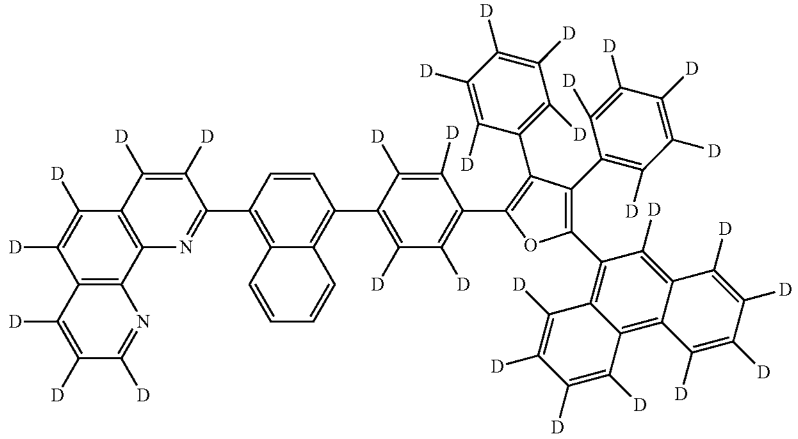

-continued
D384
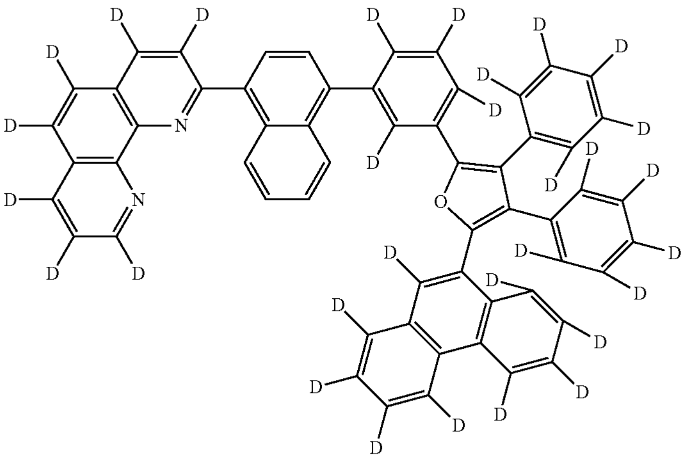
D385
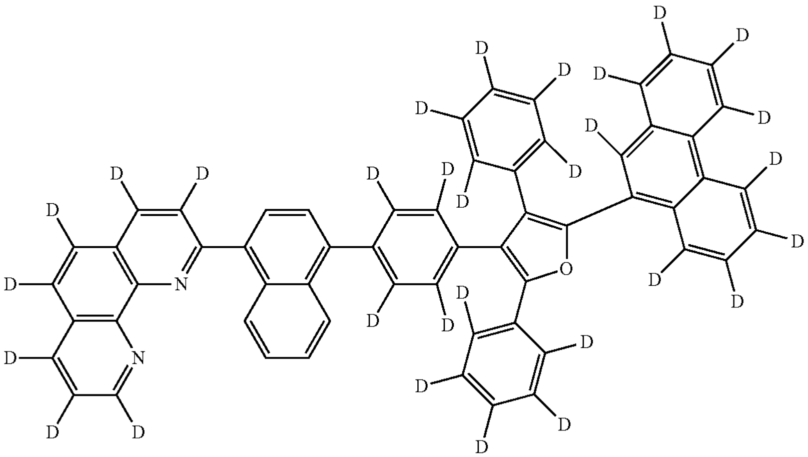
D386
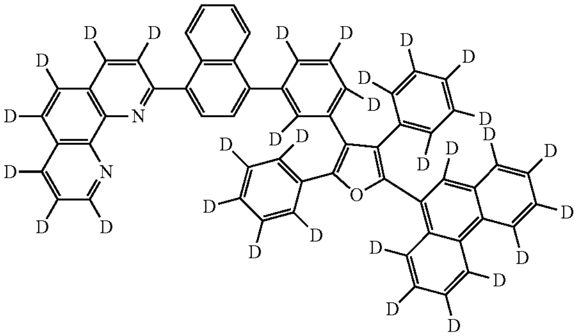
D387
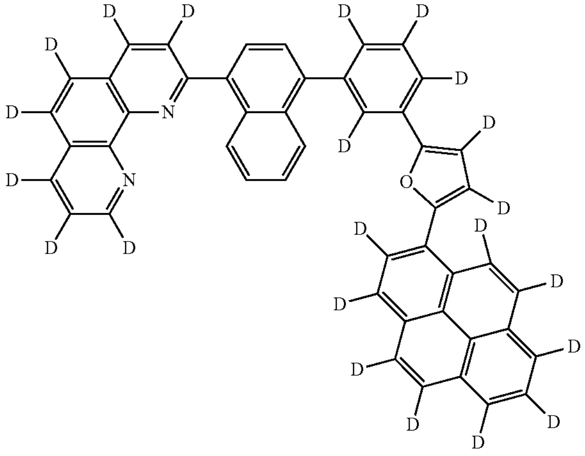

-continued
D388
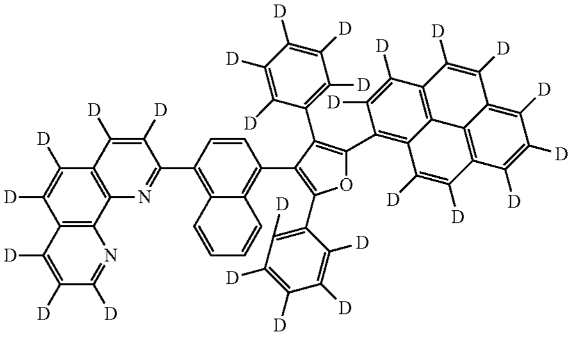
D389
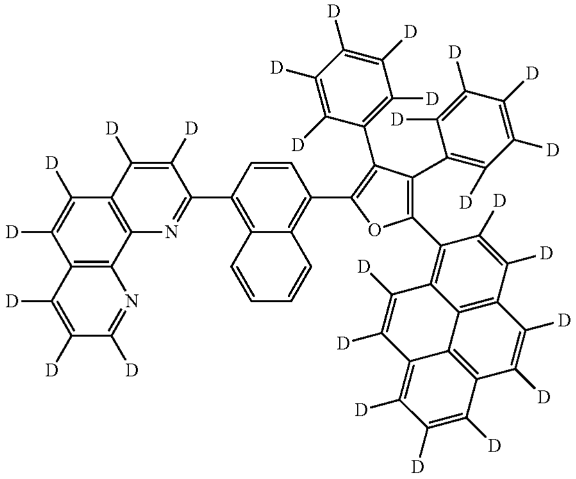
D390
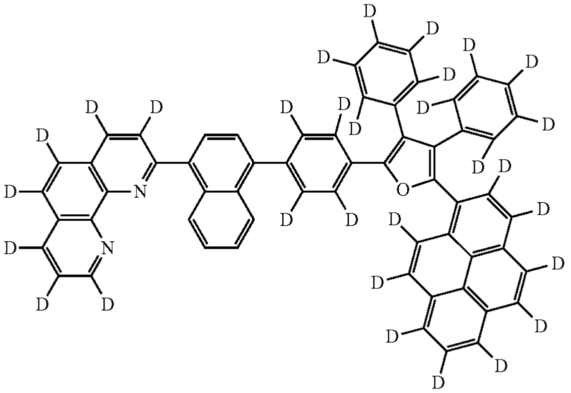
D391
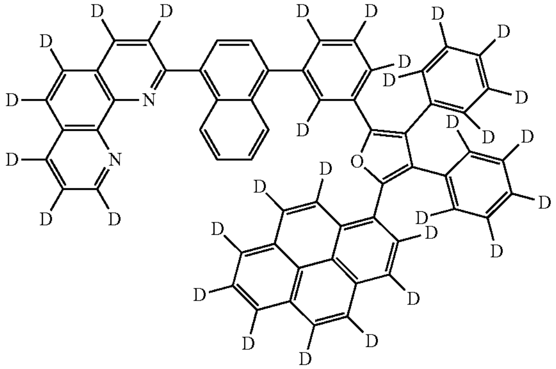
D392
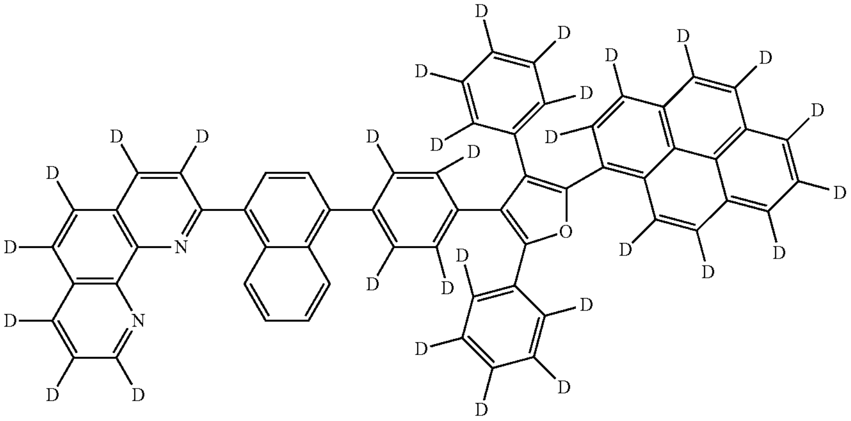

-continued
D393
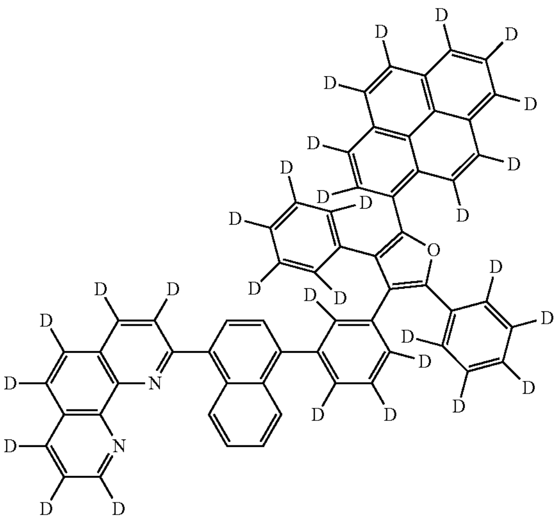
D394
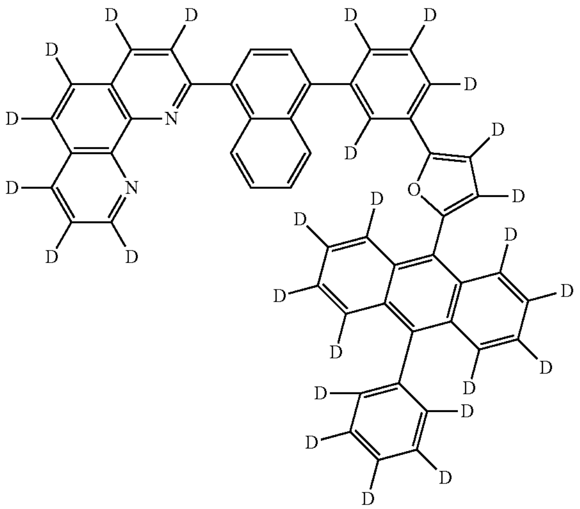
D395
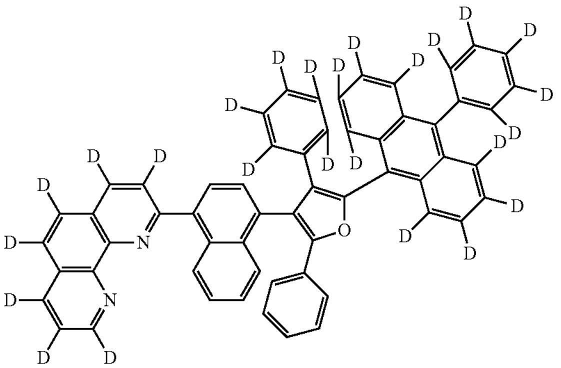
D396
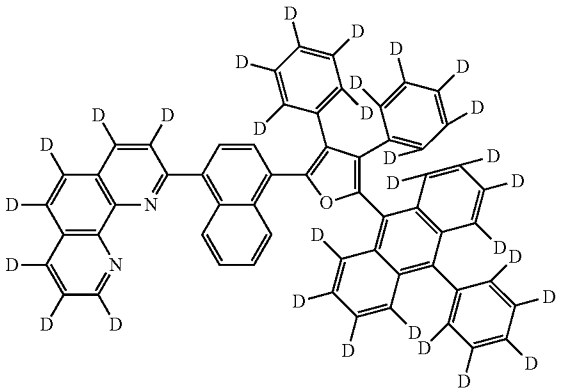
D397
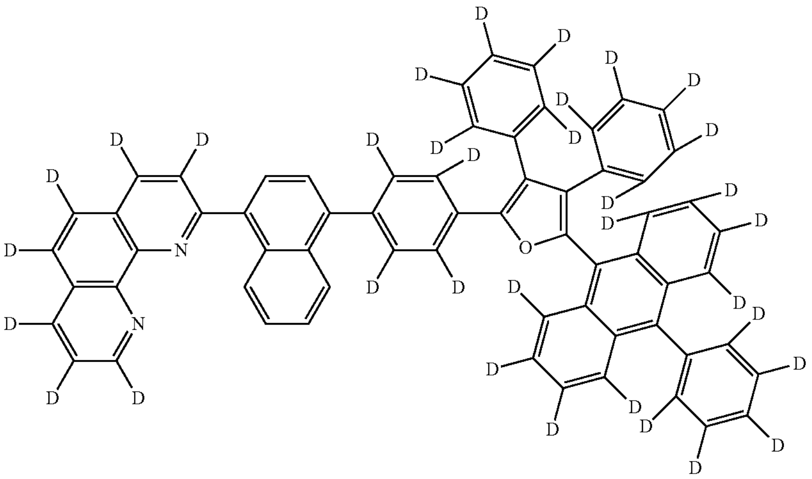

-continued
D398
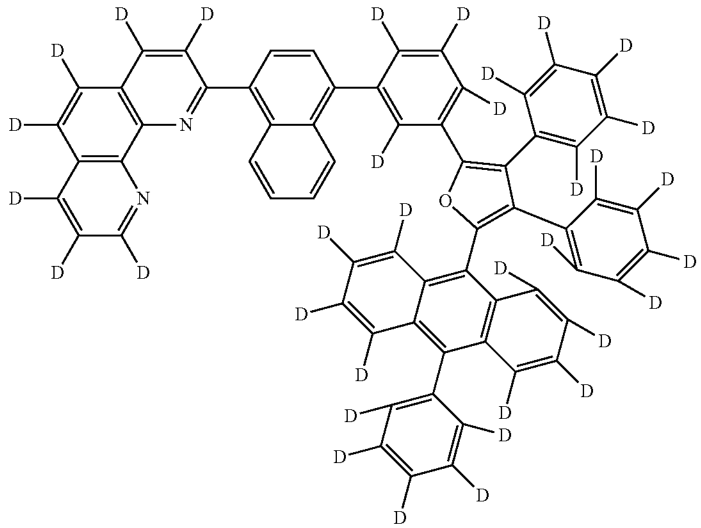
D399
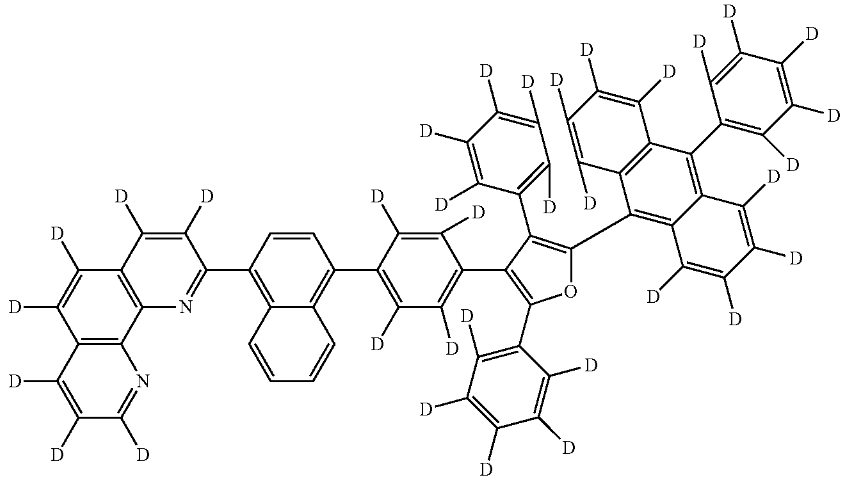
D400
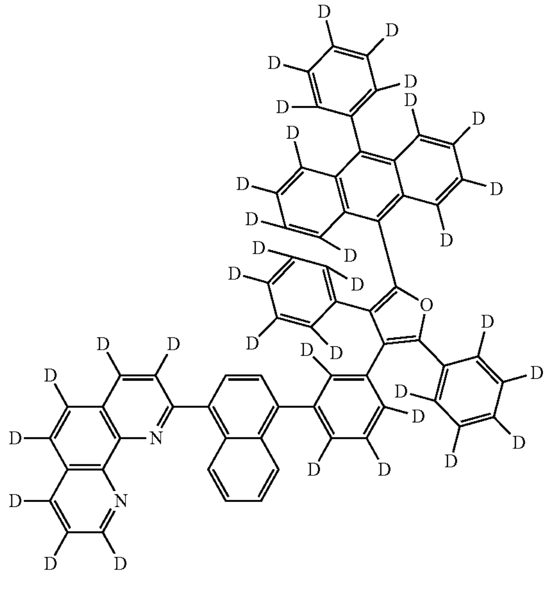
D401
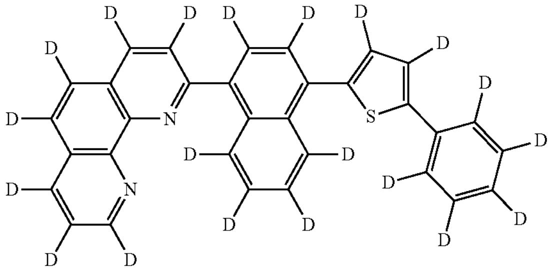

-continued
D402
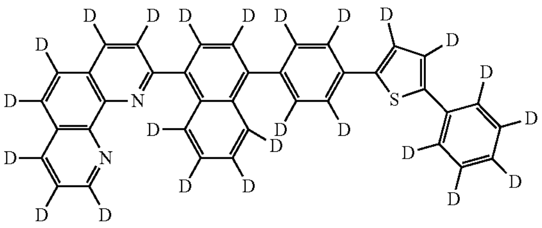
D403
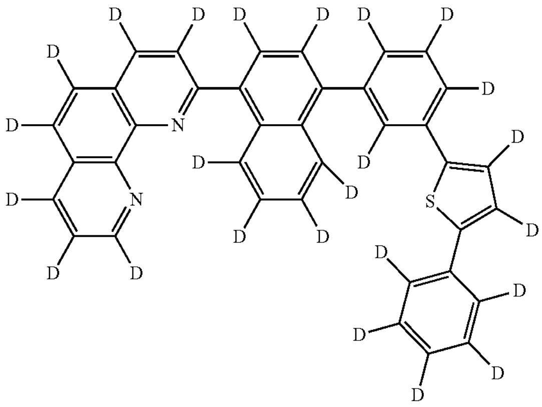
D404
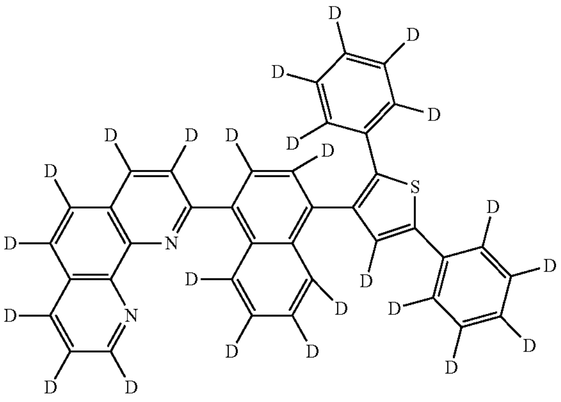
D405
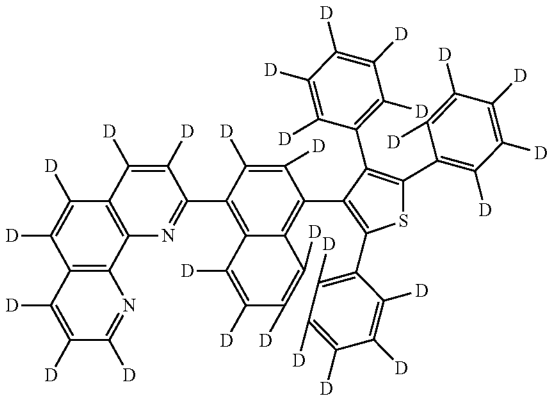
D406
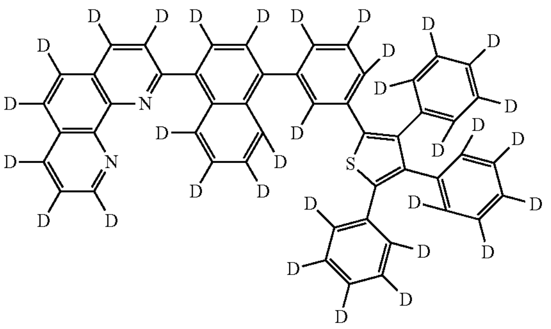
D407
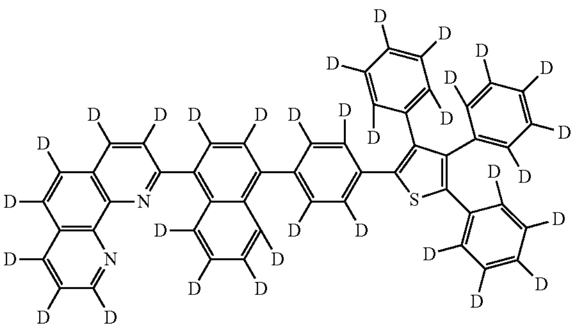
D408
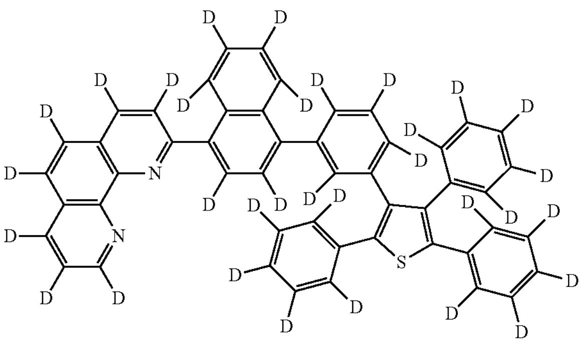
D409
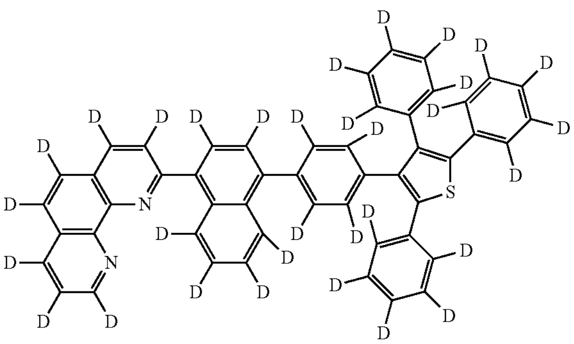

-continued
D410
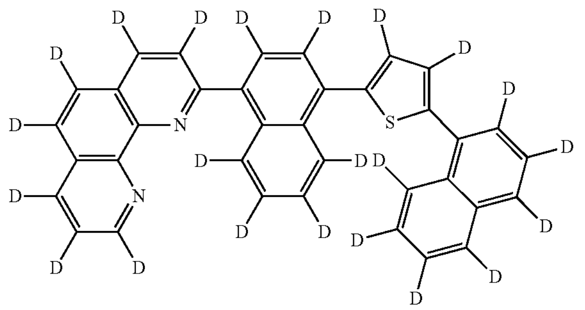
D411
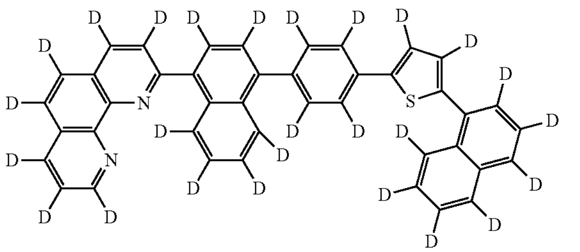
D412
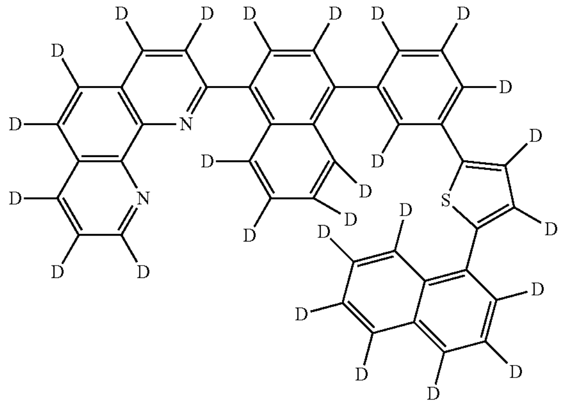
D413
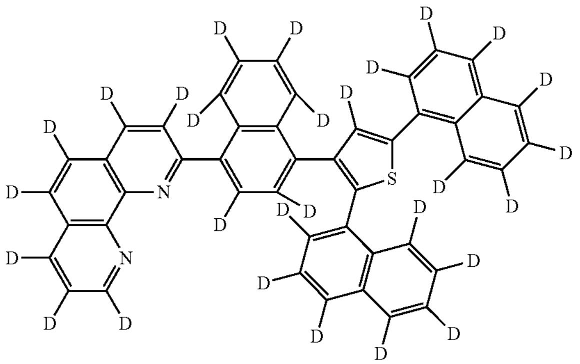
D414
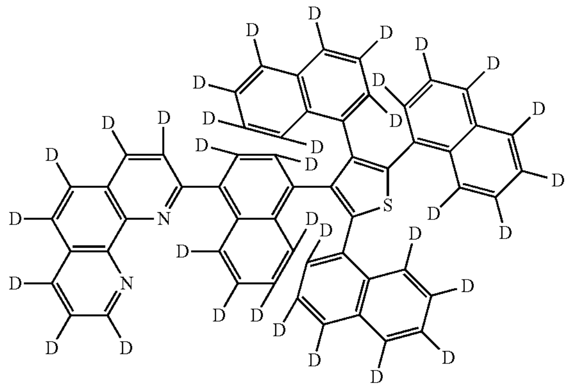
D415
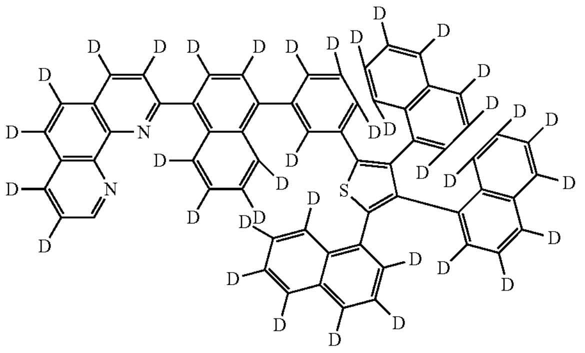
D416
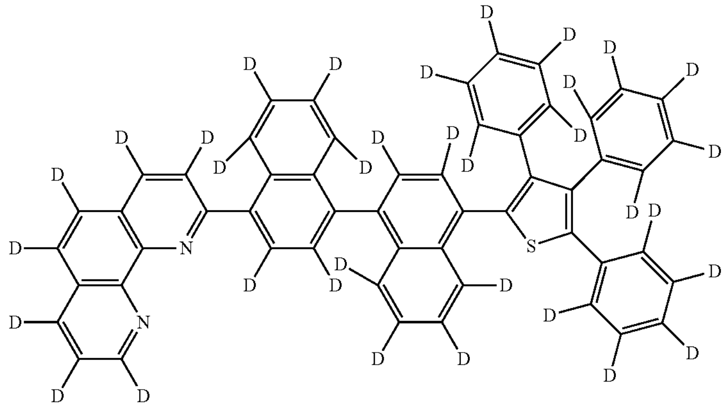

-continued
D417
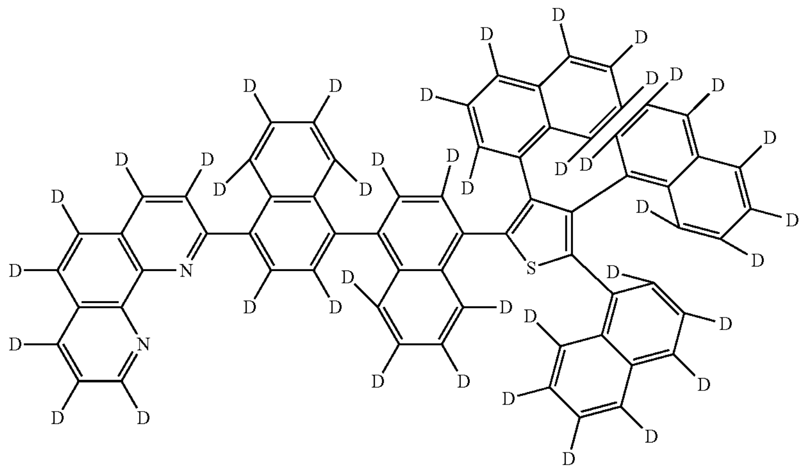
D418
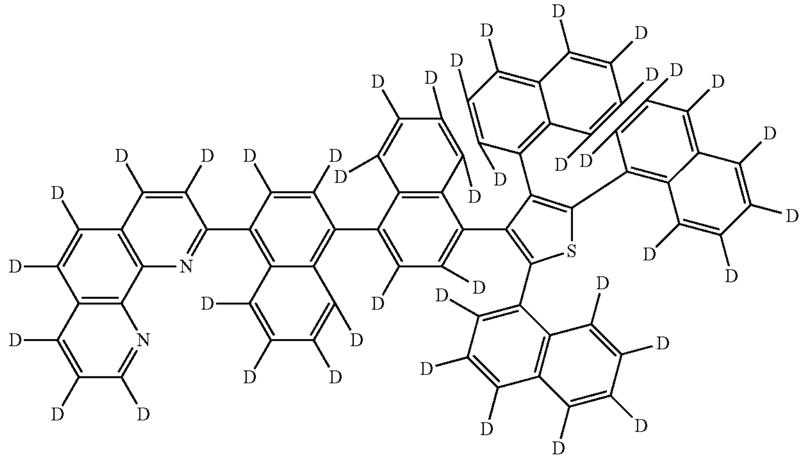
D419
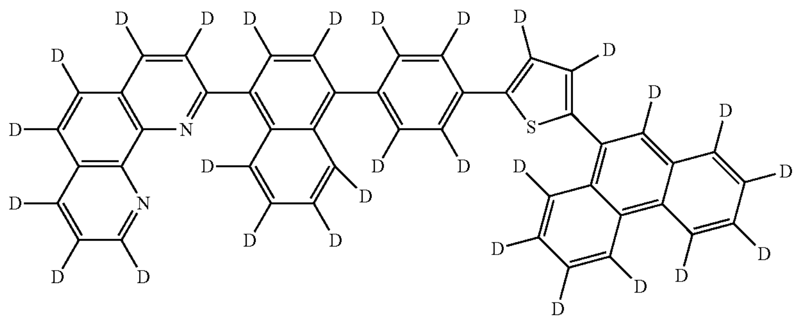

-continued
D420
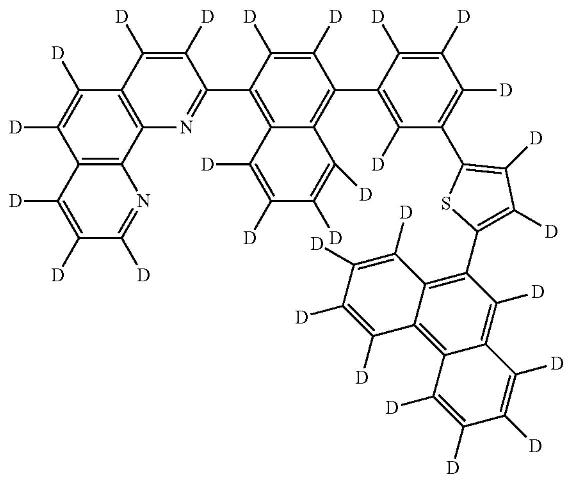
D421
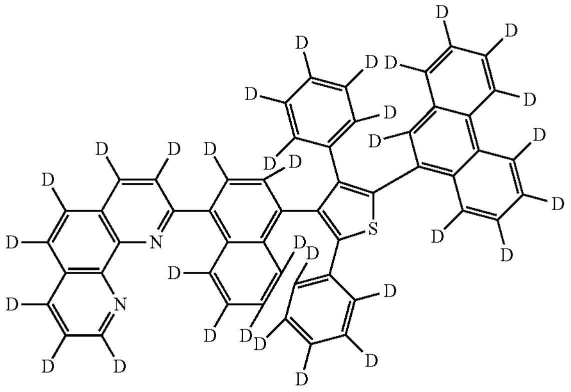
D422
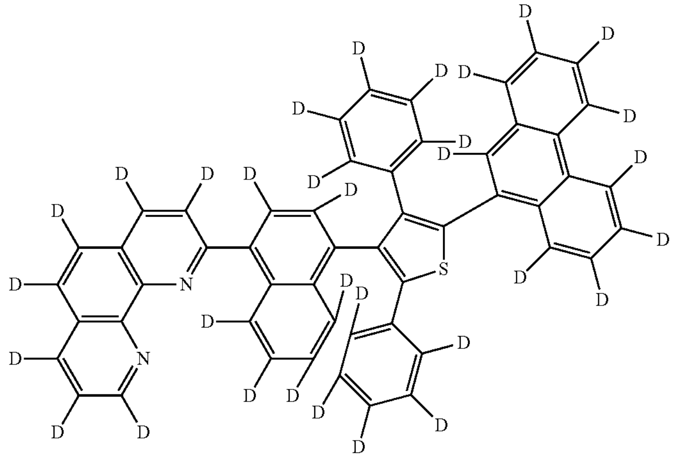
D423
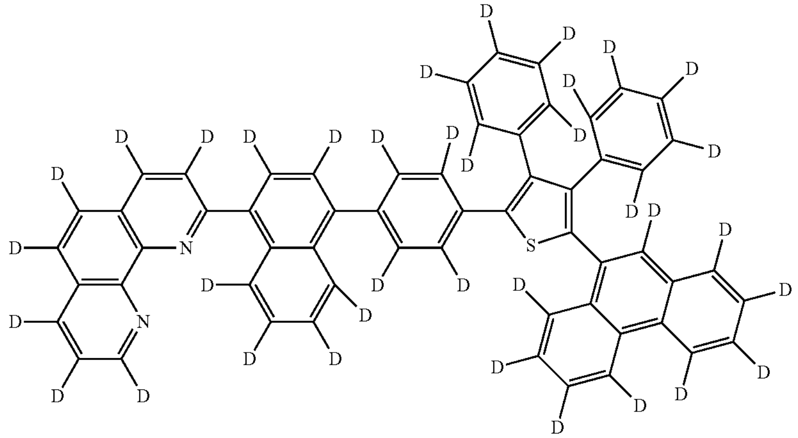

-continued
D424
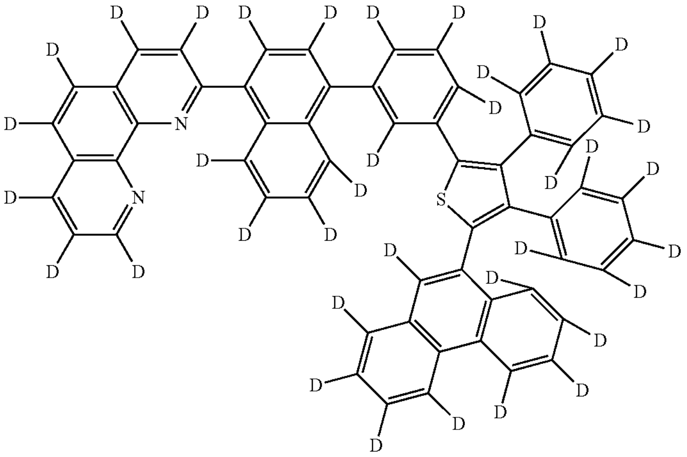
D425
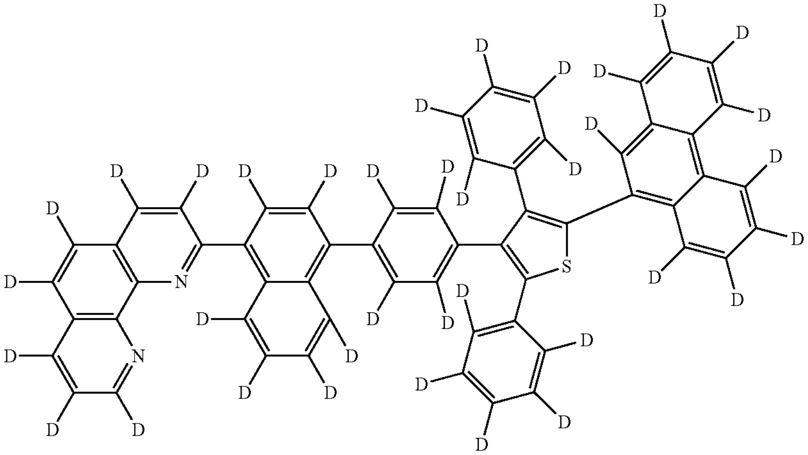
D426
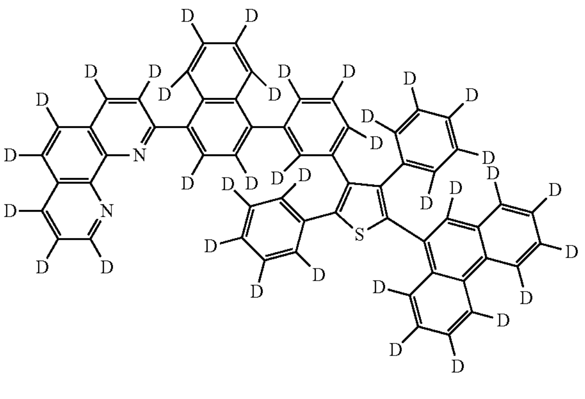
D427
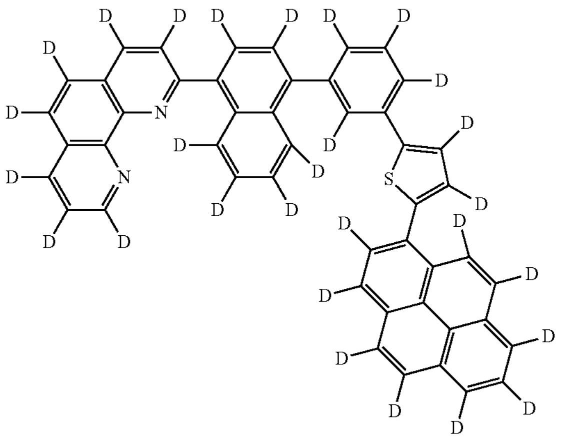

-continued
D428
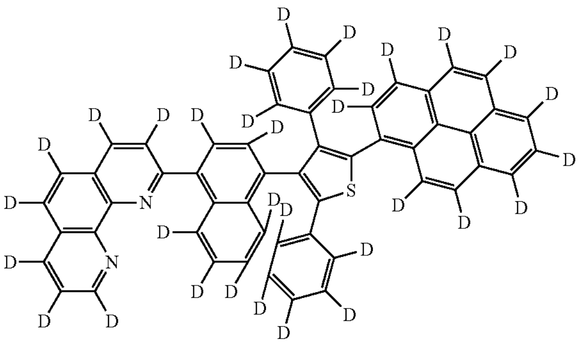
D429
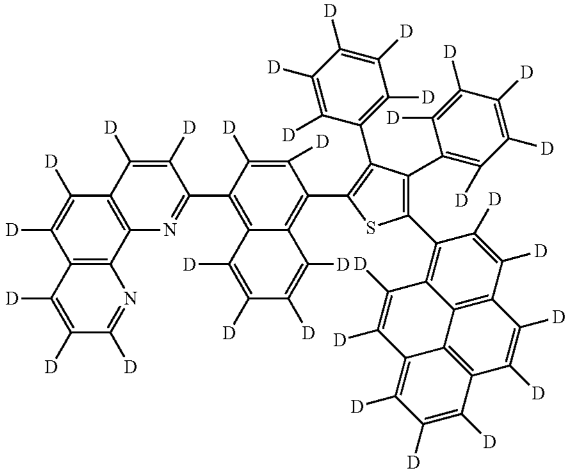
D430
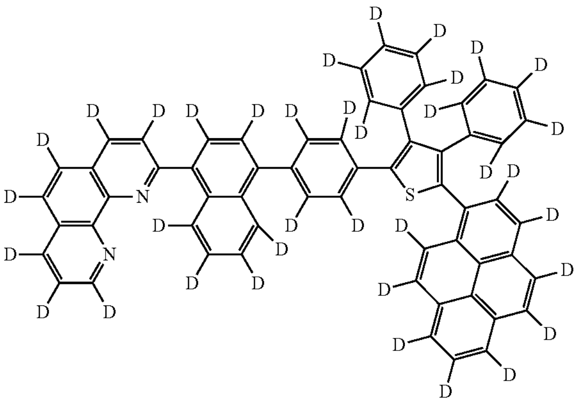
D431
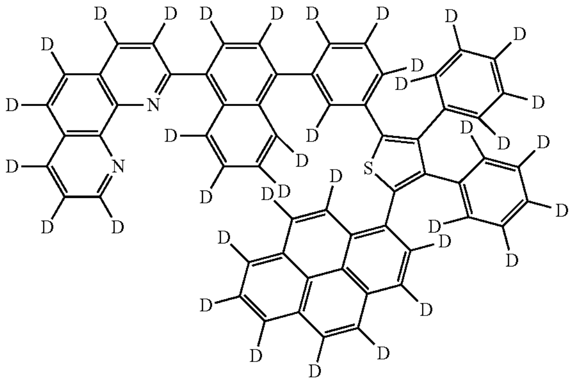
D432
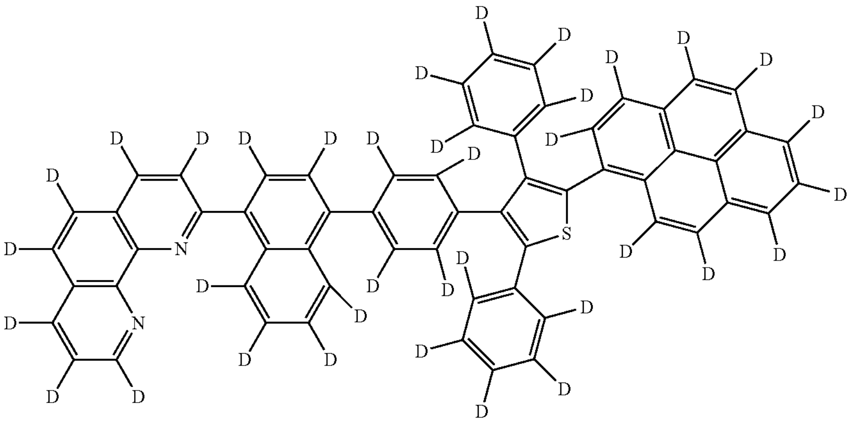

-continued
D433
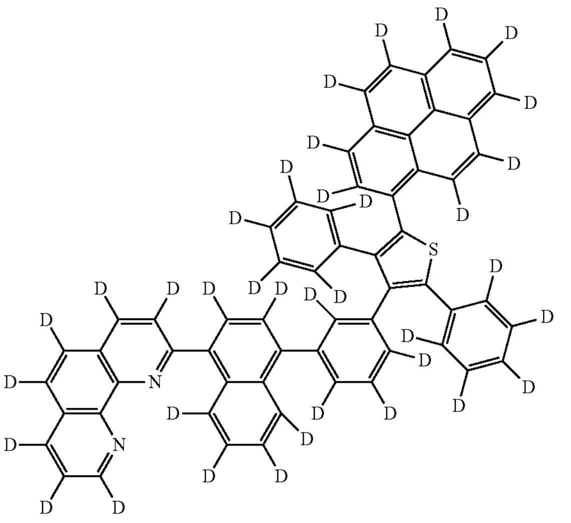
D434
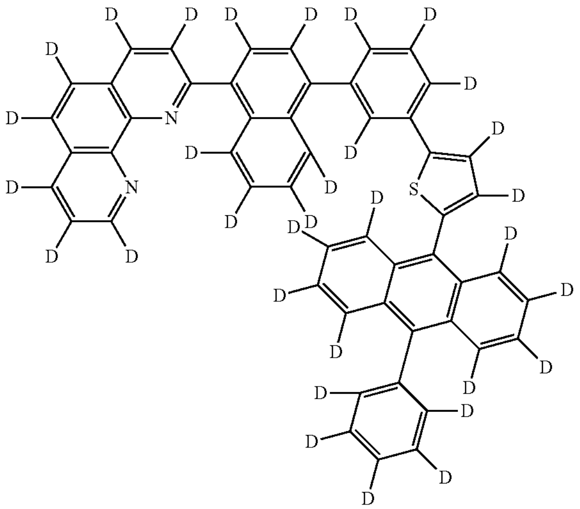
D435
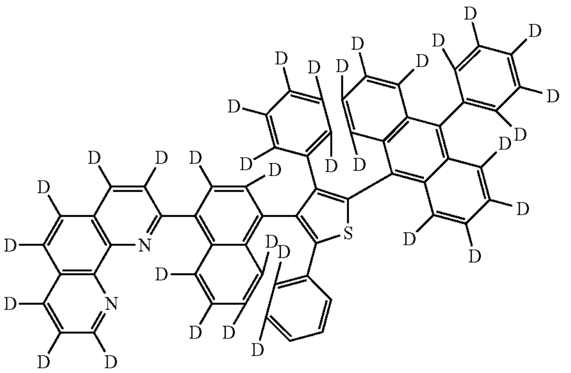
D436
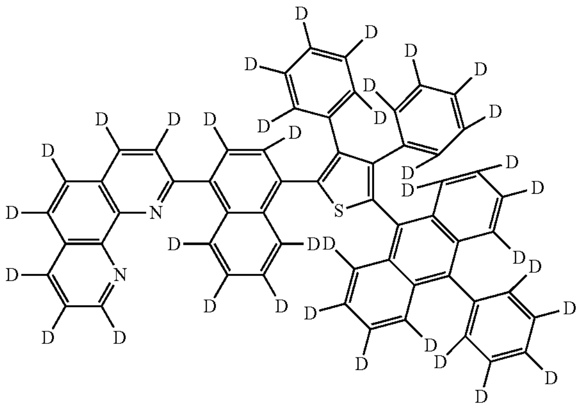
D437
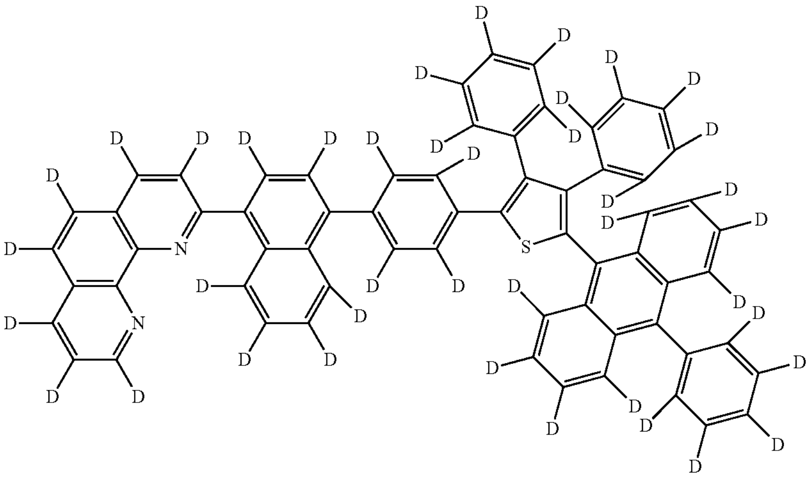

-continued
D438
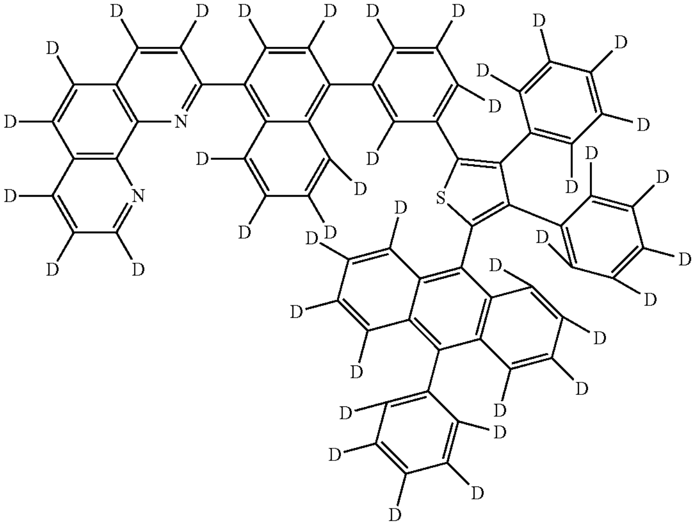
D439
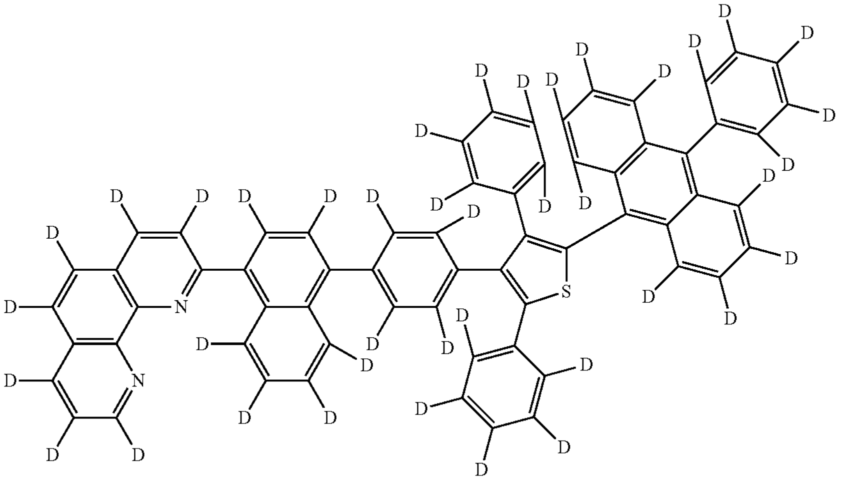
D440
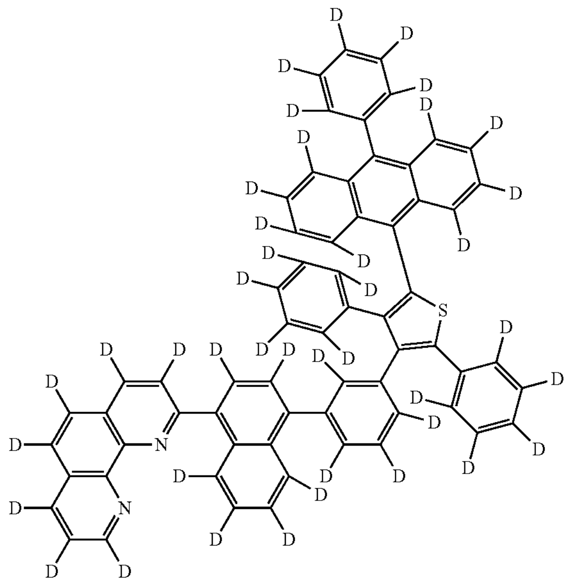
D441
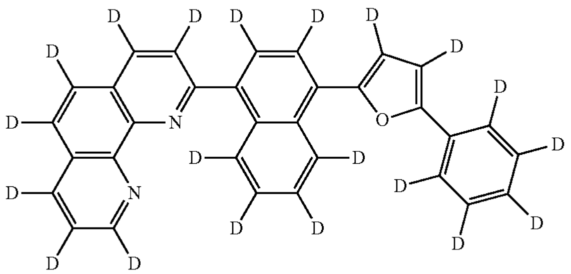

-continued
D442
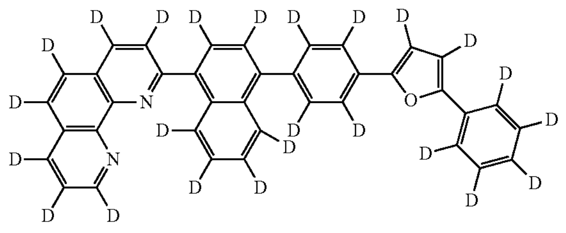
D443
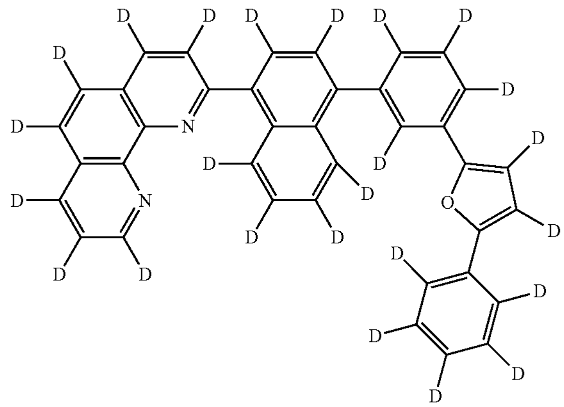
D444
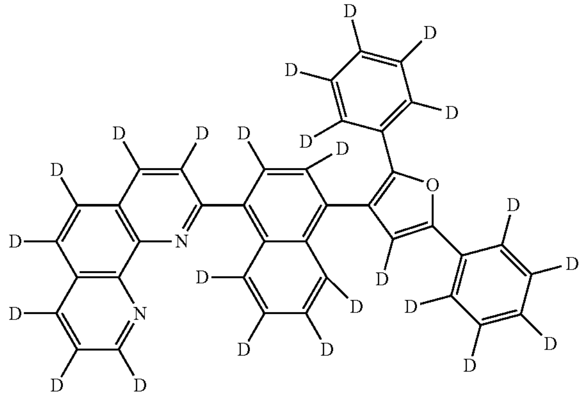
D445
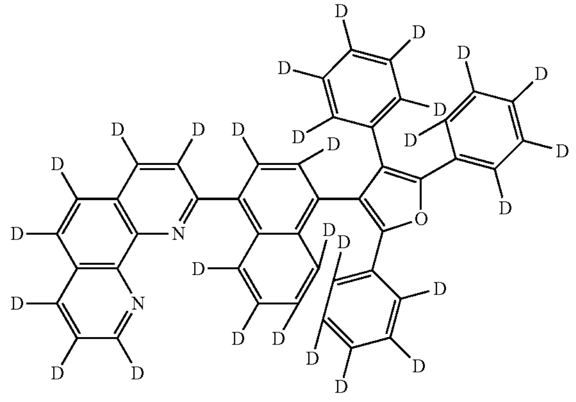
D446
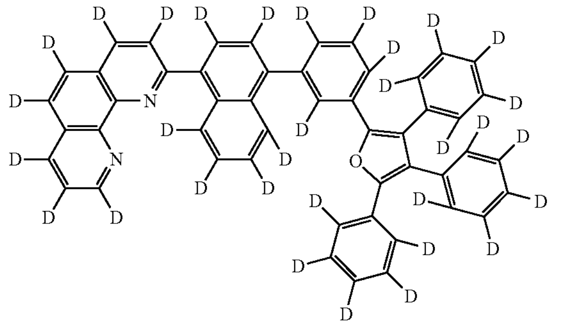
D447
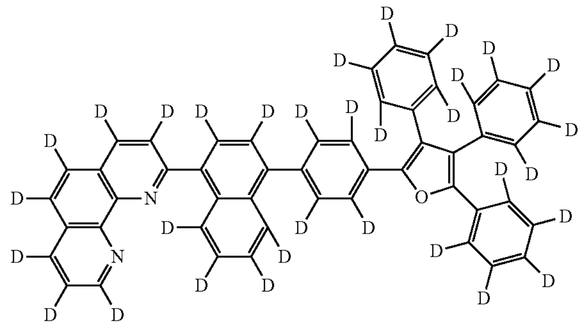
D448
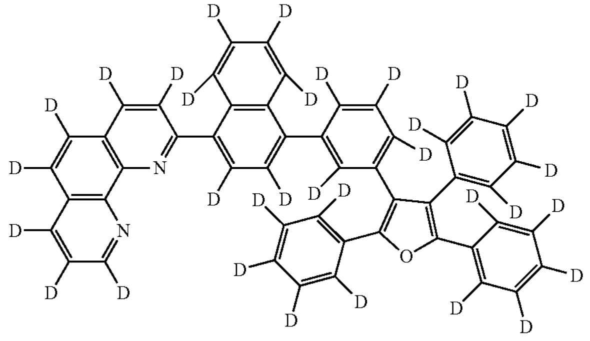
D449
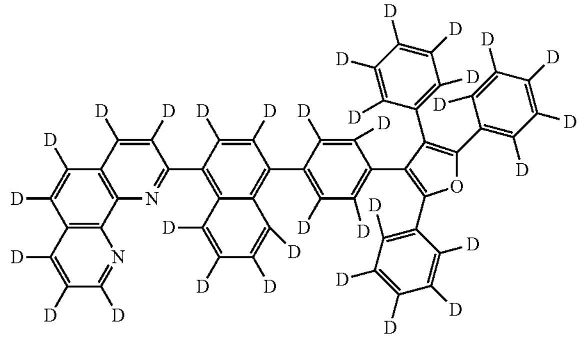

-continued
D450
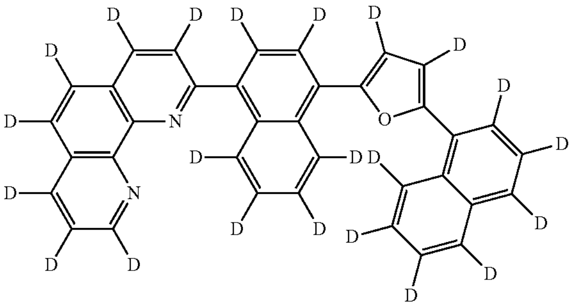
D451
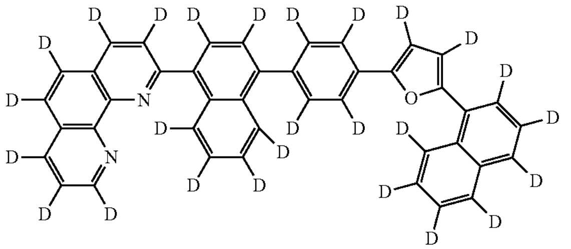
D452
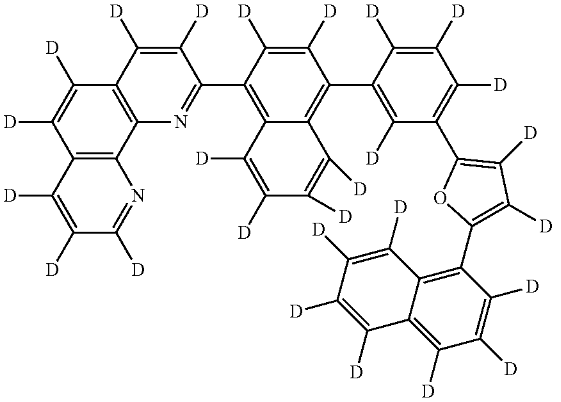
D453
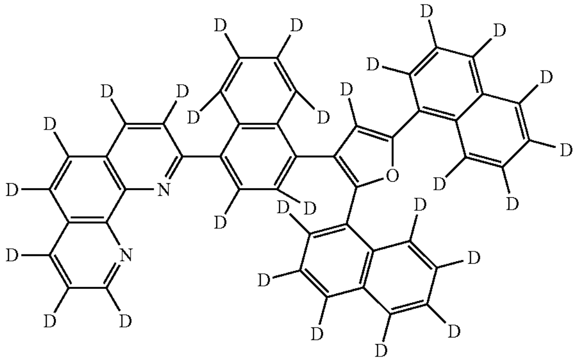
D454
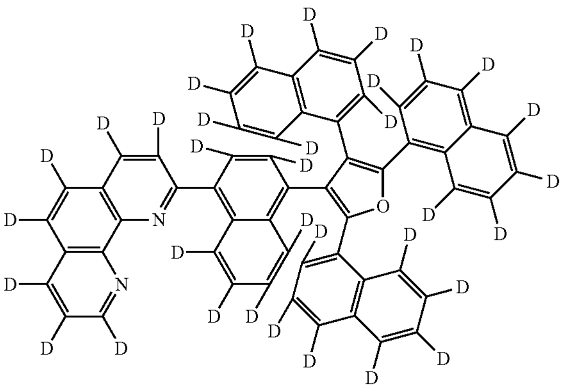
D455
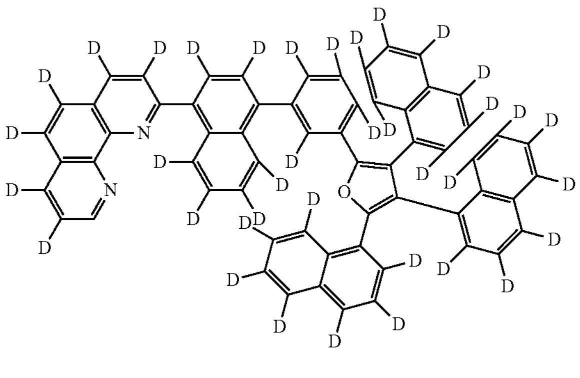
D456
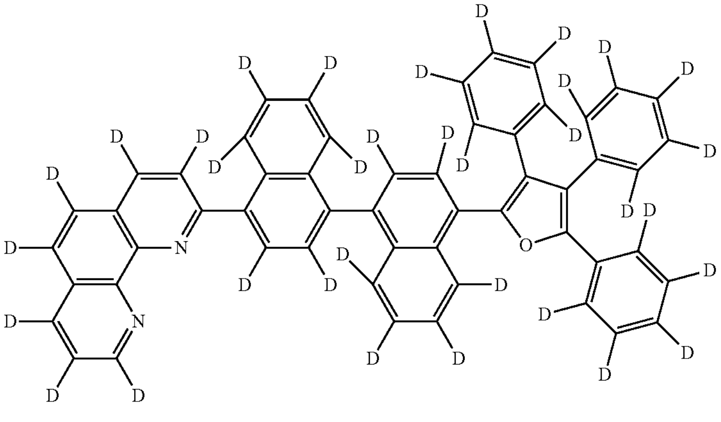

-continued
D457
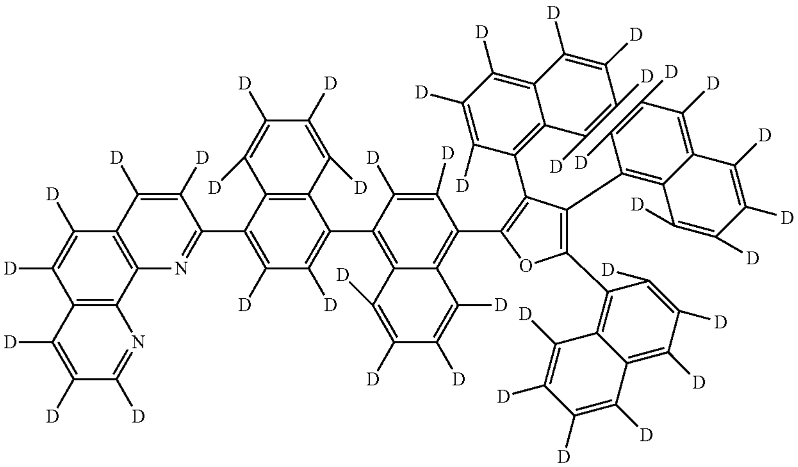
D458
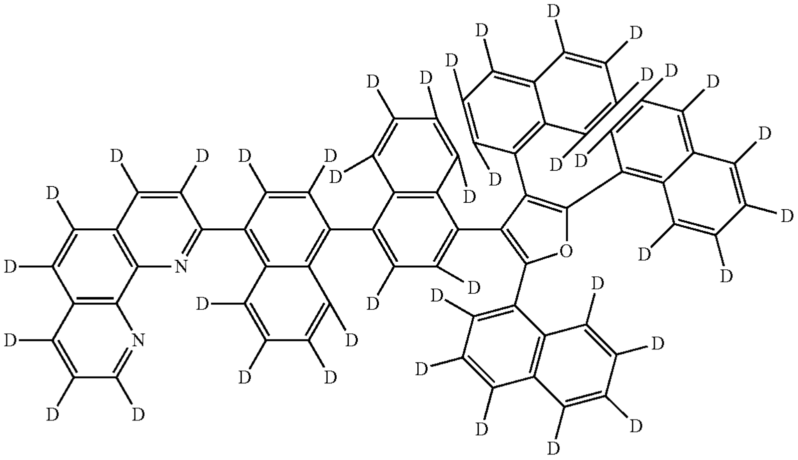
D459
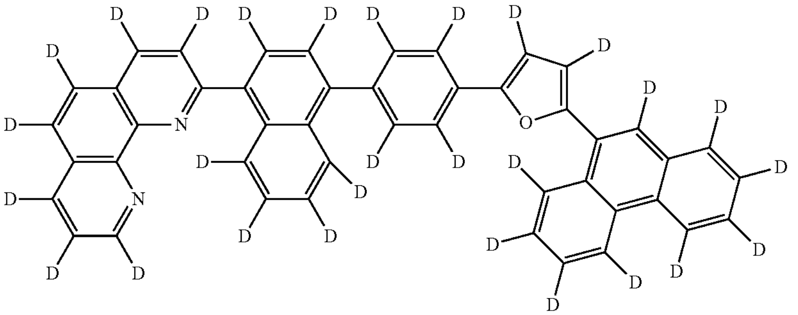

-continued
D460
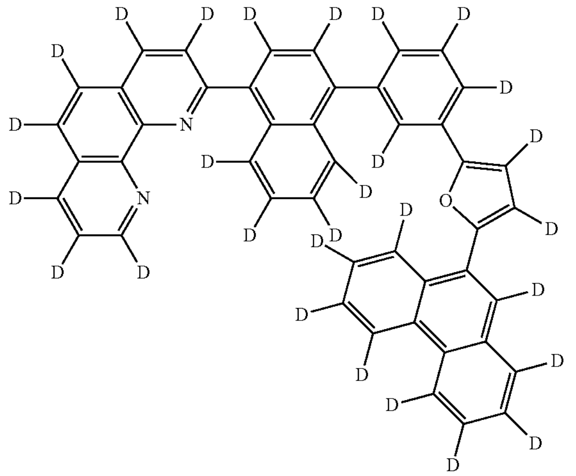
D461
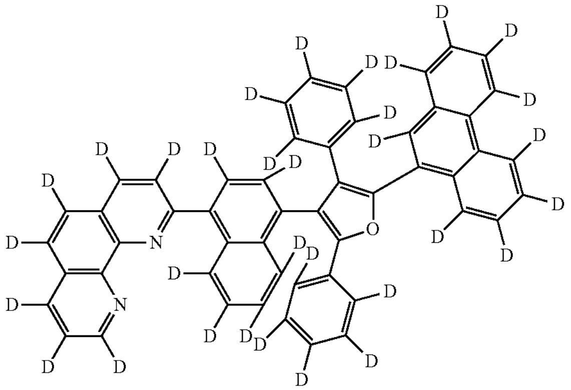
D462
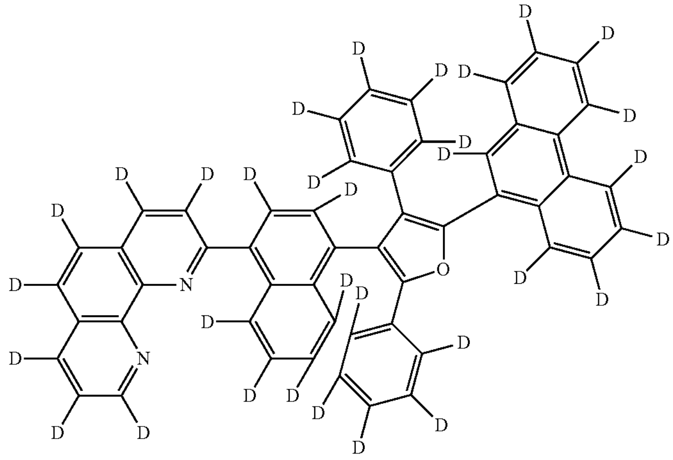
D463
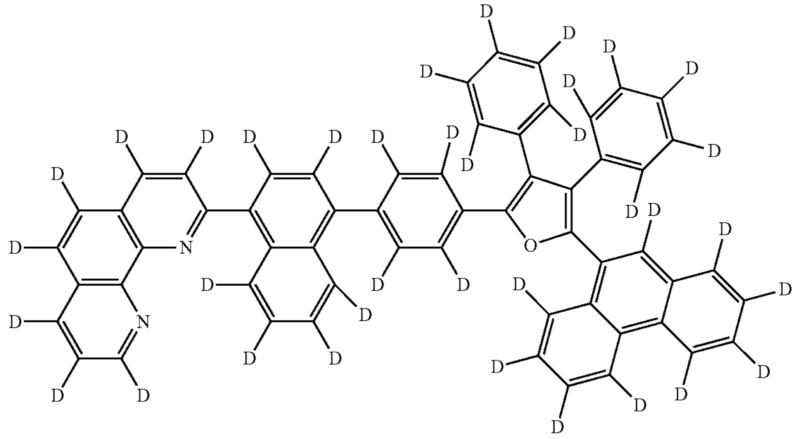

-continued
D464
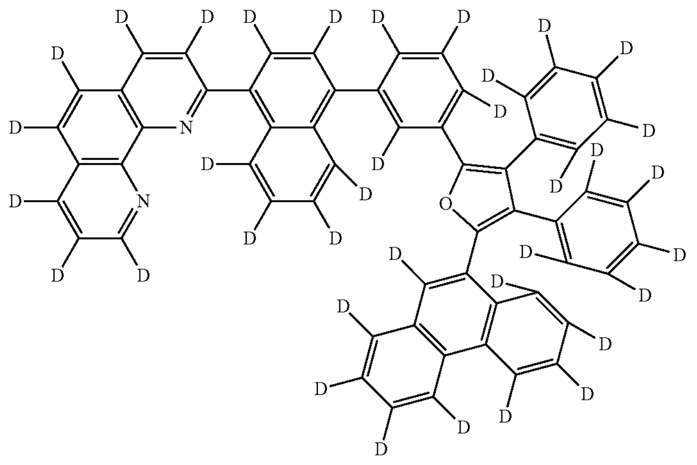
D465
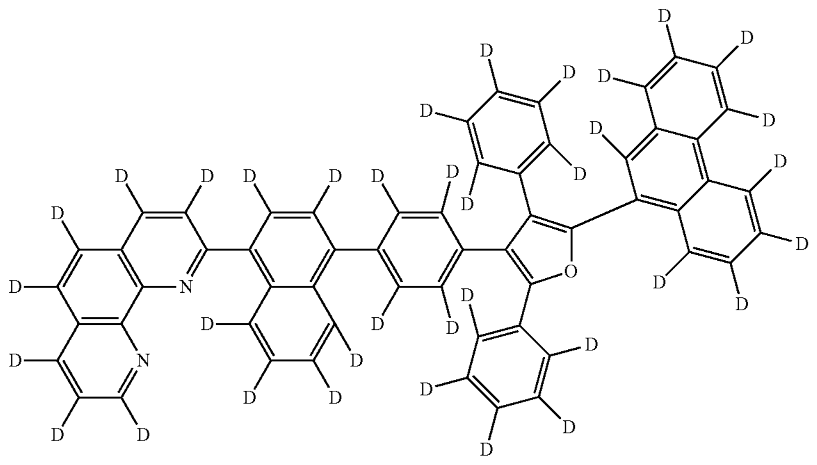
D466
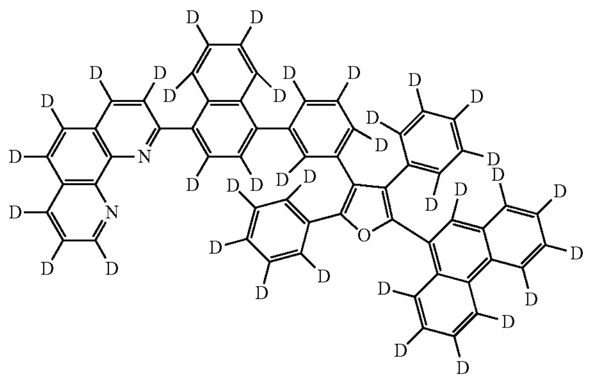
D467
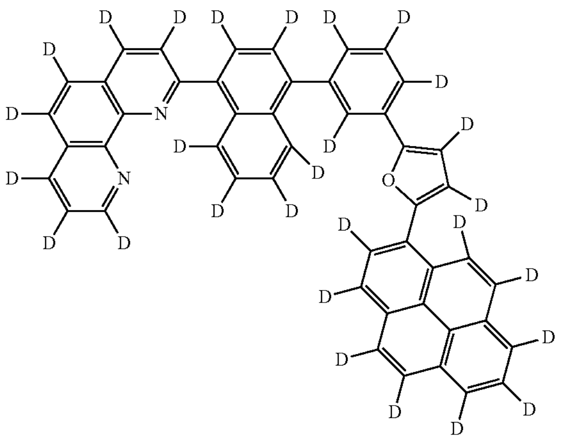

-continued
D468
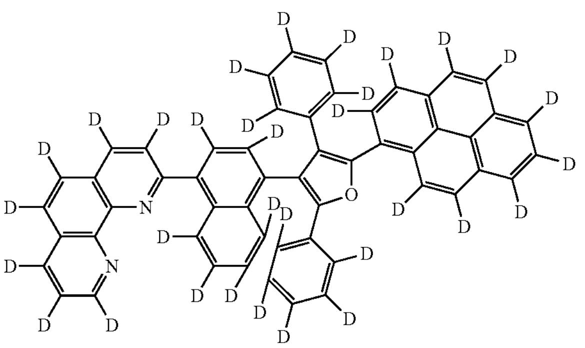
D469
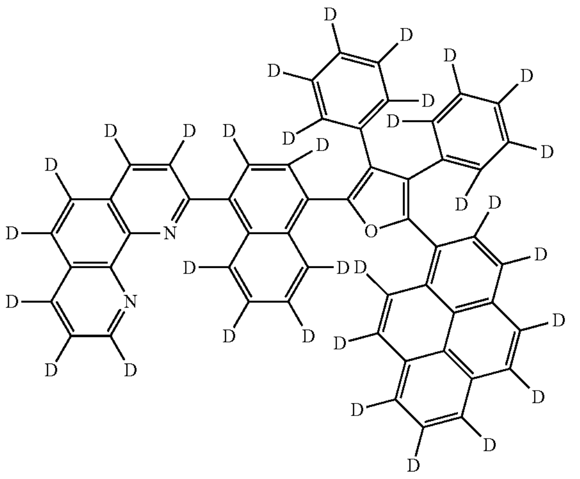
D470
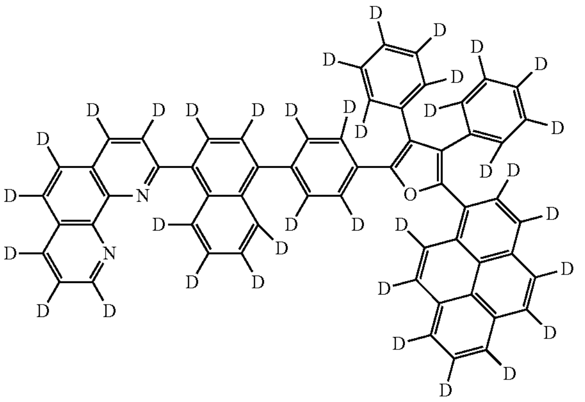
D471
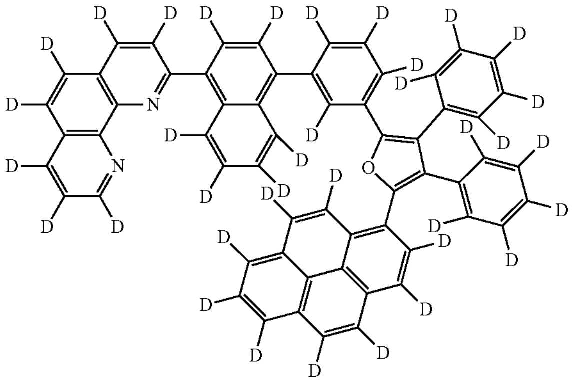
D472
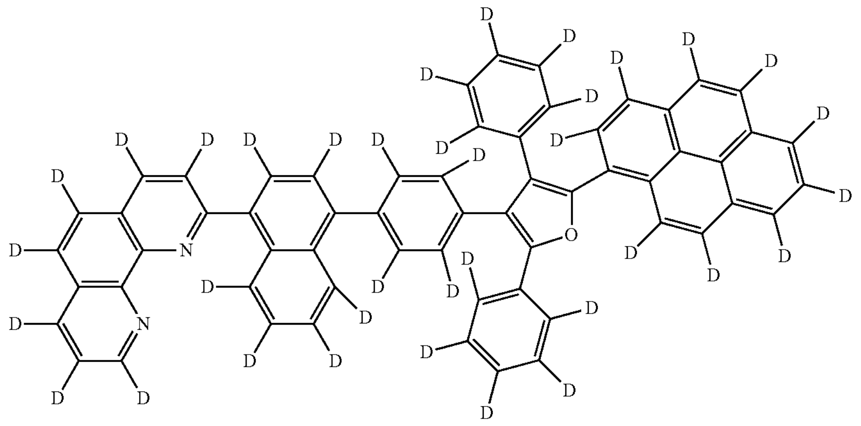

-continued
D473
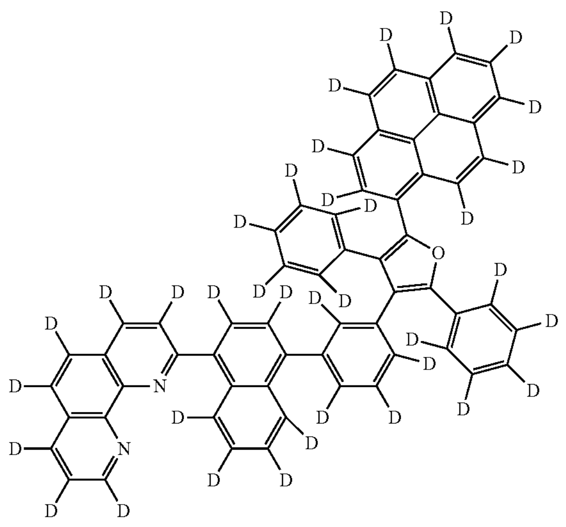
D474
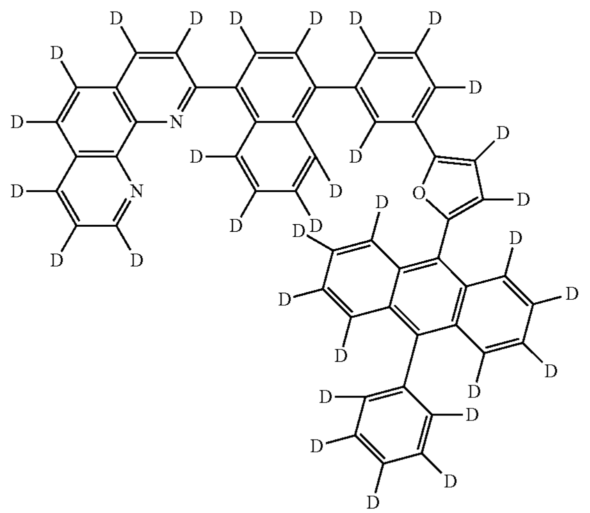
D475
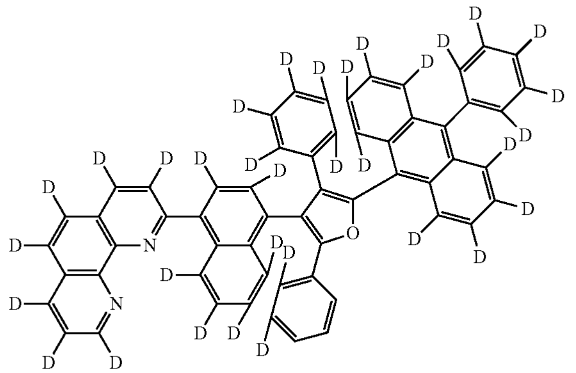
D476
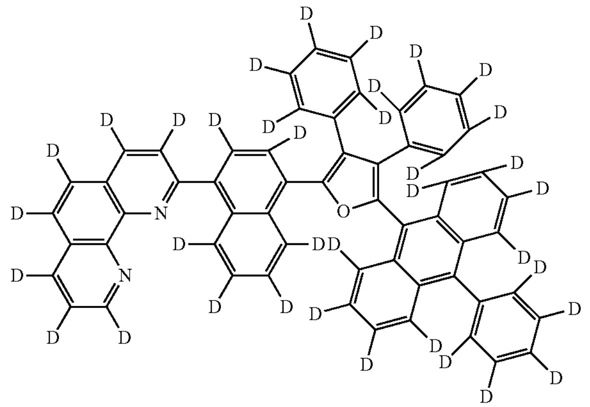
D477
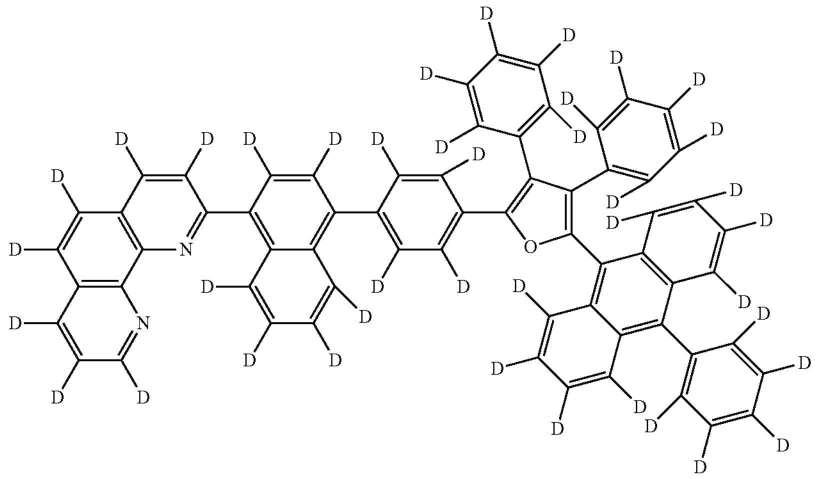

-continued
D478
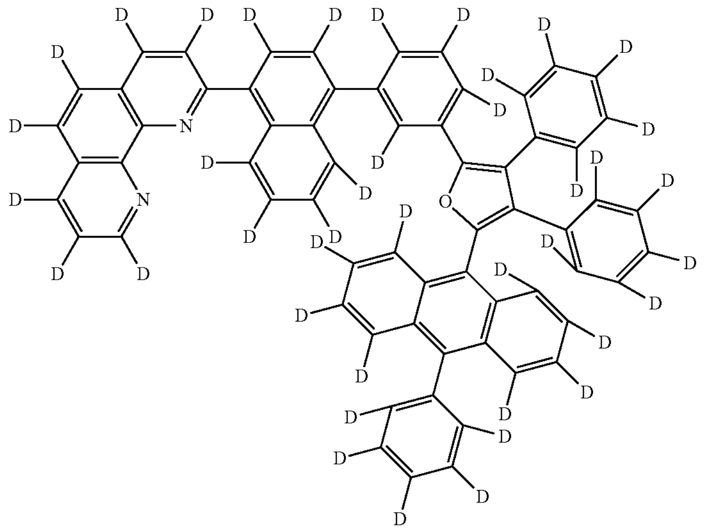
D479
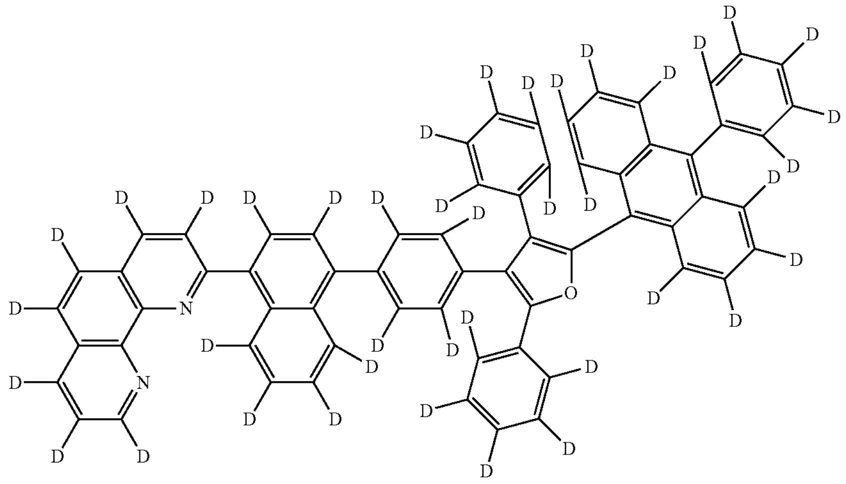

-continued

D480

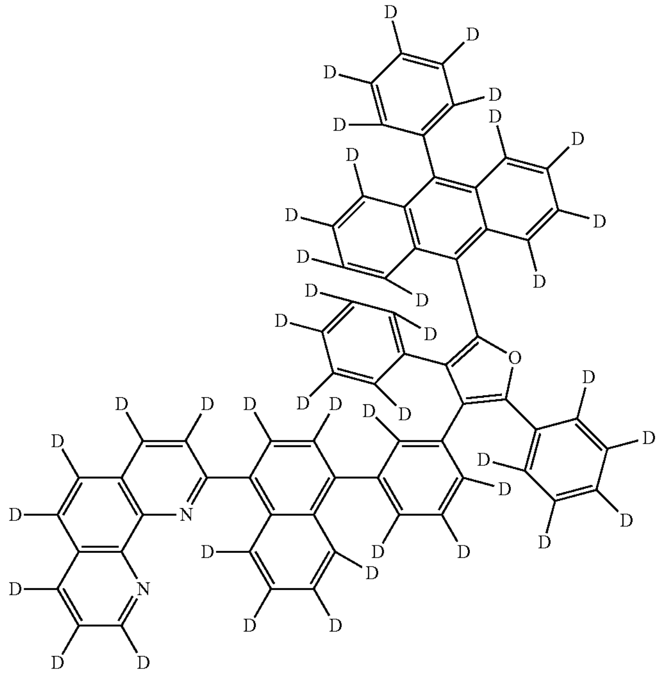

Synthesis

1. Synthesis of Compound D1

(1) Intermediate A

[Reaction Formula 1-1]

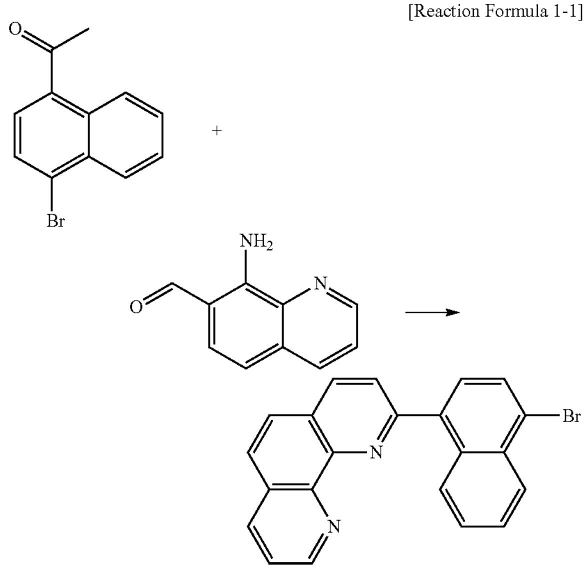

A

In a round-bottom flask, 1-bromo-4-acetylnaphthalene (14.5 g, 0.058 mol), 8-aminoquinoline-7-carbaldehyde (10 g, 0.058 mol), absolute EtOH (ethanol, 800 ml), and KOH (potassium hydroxide, 13 g), 0.232 mol) were added and refluxed for 15 hours. After the reaction mixture was cooled to room temperature, the organic layer was recovered by extraction with $CH_2Cl_2/H_2O$. The organic layer was concentrated under reduced pressure and recrystallized with EtOAc (ethyl acetate) to obtain the intermediate A (10.5 g, 0.027 mol, 47%).

(2) Intermediate B

[Reaction Formula 1-2]

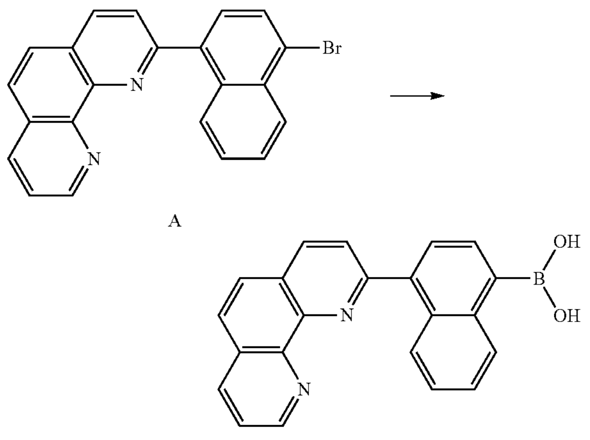

B

In a round-bottom flask, the intermediate A (10 g, 0.026 mol), bis(pinacolato)diboron (7.9 g, 0.04 mol), [1,1'-bis(diphenylphosphino)ferrocene]dichloropalladium(II) (1.1 g, 0.2 mmol), KOAc (potassium acetate, 9.2 g, 0.09 mol) and 1,4-dioxane (200 ml) were added and refluxed for 12 hours. The reaction solution was cooled to room temperature, filtered using celite, and washed with $CHCl_3$. The residual solution was concentrated under reduced pressure and recrystallized with EtOAc to obtain the intermediate B (7.9 g, 0.023 mol, 88%).

(3) Intermediate C

[Reaction Formula 1-3]

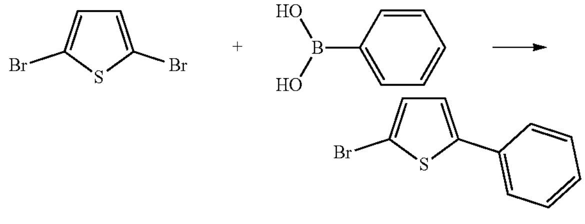

C

In a round-bottom flask, 2,5-dibromothiophene (10.0 g, 0.041 mol), benzene boronic acid (4.88 g, 0.040 mol), tetrakis(triphenylphosphine)Palladium(0) (1.8 g, 0.2 mmol), and $K_2OC_3$ (16.6 g, 0.12) mol) was dissolved in a mixed solvent of toluene (150 mL) and EtOH (60 mL) and refluxed for 12 hours. The reaction mixture was cooled to room temperature, and the reaction solution was filtered to obtain a crude product. After dissolving the crude product in $CH_2Cl_2$, the organic solution was dried using $MgSO_4$ and the solvent was removed. The silica column chromatography (eluent=$CHCl_3$) is performed to the mixture to obtain the intermediate C (8.14 g, 0.034 mol, 85%).

(4) Compound D1

[Reaction Formula 1-4]

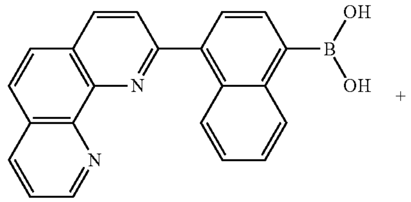

B

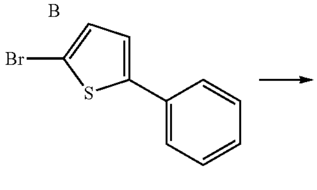

C

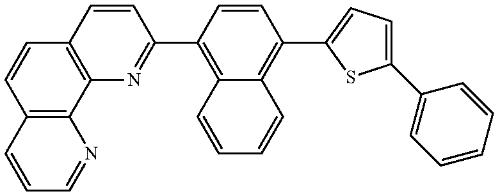

D1

The compound D1 (8.38 g, 0.018 mol, 82%) was obtained by proceeding in the same manner as for the synthesis of the intermediate C using the intermediate B (7.9 g, 0.022 mol) and the intermediate C (6.5 g, 0.027 mol).

2. Synthesis of Compound D5

(1) Intermediate D

[Reaction Formula 2-1]

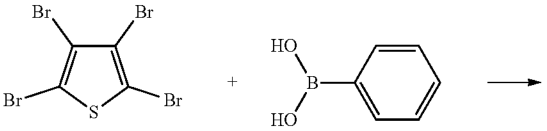

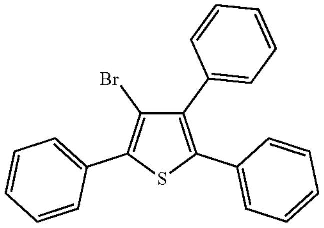

D

The intermediate D (6.3 g, 0.016 mol, 64%) was obtained by proceeding in the same manner as for the synthesis of the Intermediate C using 2,3,4,5-tetrabromothiophene (10.0 g, 0.025 mol) and benzene boronic acid (9.1 g, 0.075 mol).

(2) Compound D5

[Reaction Formula 2-2]

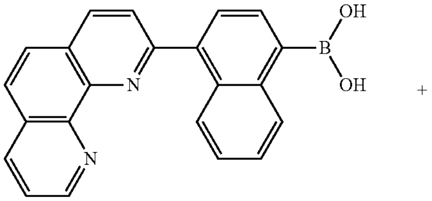

B

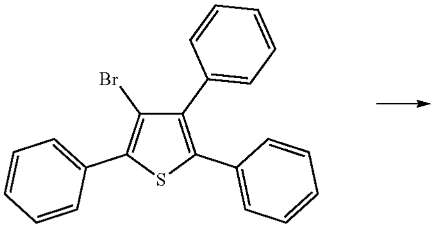

D

-continued

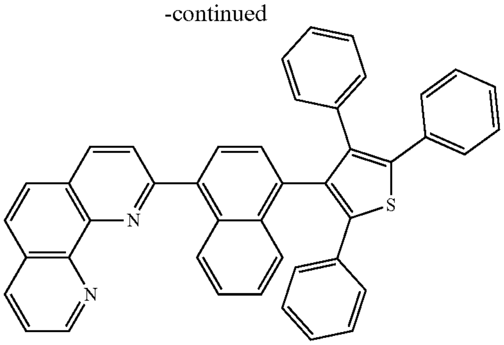

D5

The compound D5 (2.94 g, 0.0048 mol, 80%) was obtained by proceeding in the same manner as for the synthesis of the Intermediate C using the intermediate B (2.1 g, 0.006 mol) and the intermediate D (2.5 g, 0.064 mol).

3. Synthesis of Compound D7

[Reaction Formula 3-1]

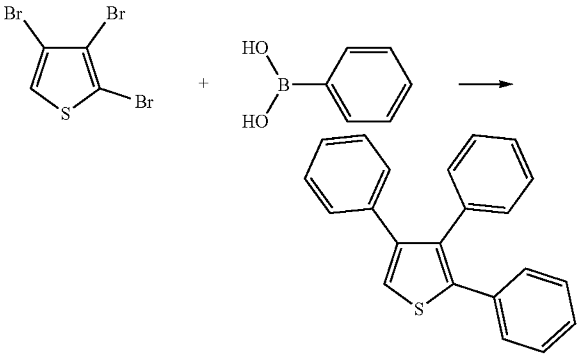

E (1) Intermediate E

The intermediate E (6.3 g, 0.016 mol, 64%) was obtained by proceeding in the same manner as for the synthesis of the Intermediate C using 2,3,4-tribromothiophene (10.0 g, 0.025 mol) and benzene boronic acid (9.1 g, 0.075 mol).

(2) Intermediate F

[Reaction Formula 3-2]

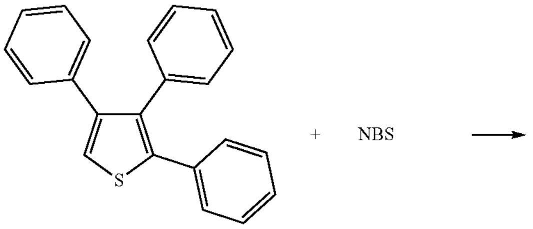

E

-continued

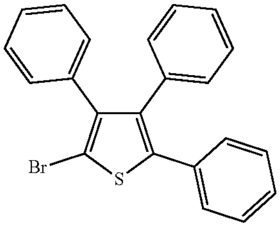

F

The intermediate E (6.0 g, 0.019 mol) and N-bromo succinimide (NBS, 3.7 g, 0.021 mol) were dissolved in $CHCl_3$ (200 mL) and stirred at room temperature for 5 hours. Distilled water (200 mL) was added to the reaction mixture, $Na_2S_2O_3$ (5 g) was added while stirring at room temperature, and the mixture was stirred for 1 hour. The reaction mixture was extracted with $CH_2Cl_2/H_2O$ to recover the organic layer. The organic layer was concentrated under reduced pressure and recrystallized with $CH_2Cl_2$ and petroleum ether to obtain the intermediate F (7.1 g, 0.018 mol, 95%).

(3) Intermediate G

[Reaction Formula 3-3]

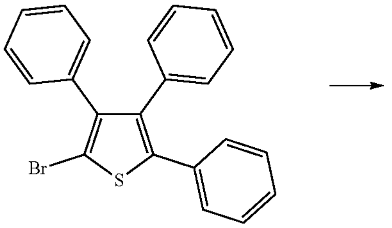

F

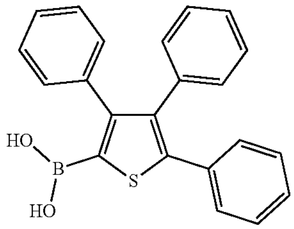

G

The intermediate F (10 g, 0.026 mol), bis(pinacolato) diboron (7.8 g, 0.02 mol), [1,1'-bis(diphenylphosphino)ferrocene]dichloropalladium(II) (0.55 g, 0.1 mmol), KOAc (4.6 g, 0.045 mol) and 1,4-dioxane (150 ml) were added and refluxed for 12 hours. The reaction solution was cooled to room temperature, filtered using celite, and washed with $CHCl_3$. The residual solution was concentrated under reduced pressure and recrystallized with hexane to obtain the intermediate G (7.9 g, 0.022 mol, 85%).

(4) Intermediate H

[Reaction Formula 3-4]

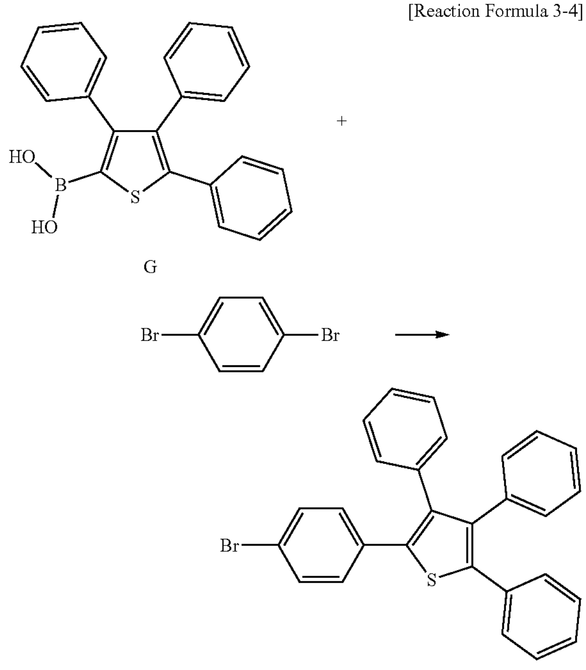

G

H

The intermediate H (5.1 g, 0.011 mol, 79%) was obtained by proceeding in the same manner as for the synthesis of the intermediate C using the intermediate G (5.0 g, 0.014 mol) and 1,4-dibromobenzene (6.6 g, 0.028 mol).

(5) Compound D7

[Reaction Formula 3-5]

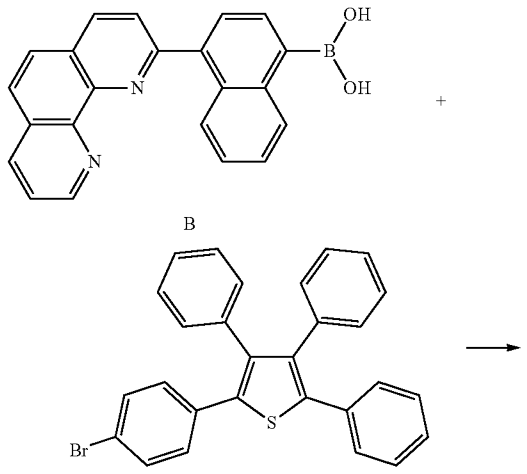

B

H

-continued

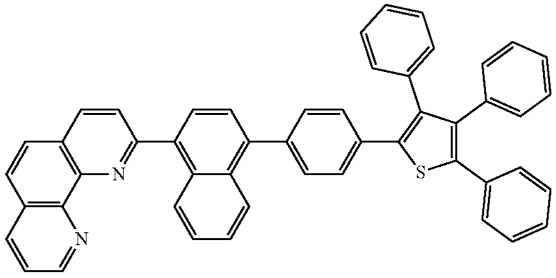

D7

The compound D7 (3.2 g, 4.6 mmol, 87%) was obtained by proceeding in the same manner as for the synthesis of the Intermediate C using the intermediate B (1.9 g, 5.4 mmol) and the intermediate H (2.5 g, 5.3 mmol).

4. Synthesis of Compound D23

(1) Intermediate I

[Reaction Formula 4-1]

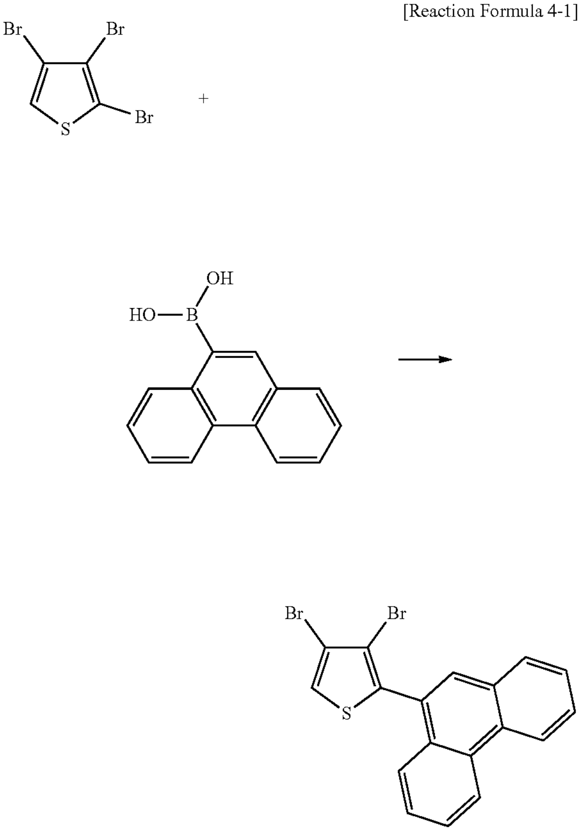

I

The intermediate I (6.2 g, 14.8 mmol, 79%) was obtained by proceeding in the same manner as for the synthesis of the Intermediate C using 2,3,4-tribromothiophene (6.0 g, 18.7 mmol) and phenanthren-9-yl boronic acid (4.2 g, 18.9 mmol).

(2) Intermediate J

[Reaction Formula 4-2]

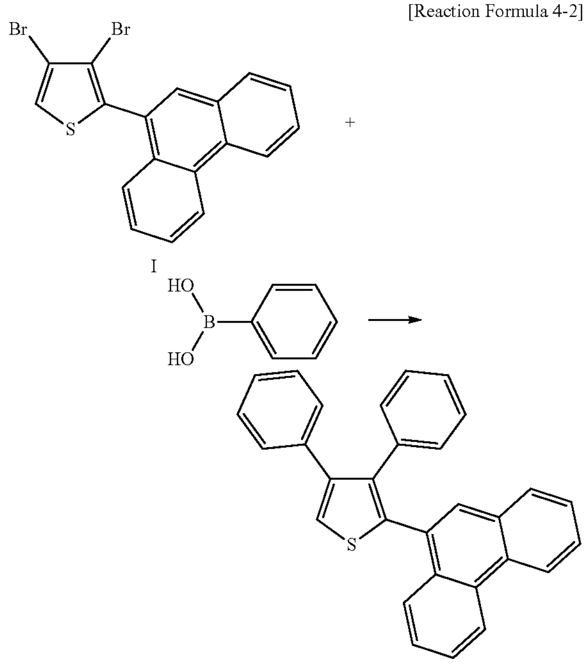

I

J

The intermediate J (5.5 g, 13.3 mmol, 90%) was obtained by proceeding in the same manner as for the synthesis of the Intermediate C using the intermediate I (6.2 g, 14.8 mmol) and benzene boronic acid (4.0 g, 32.8 mmol).

(3) Intermediate L

[Reaction Formula 4-3]

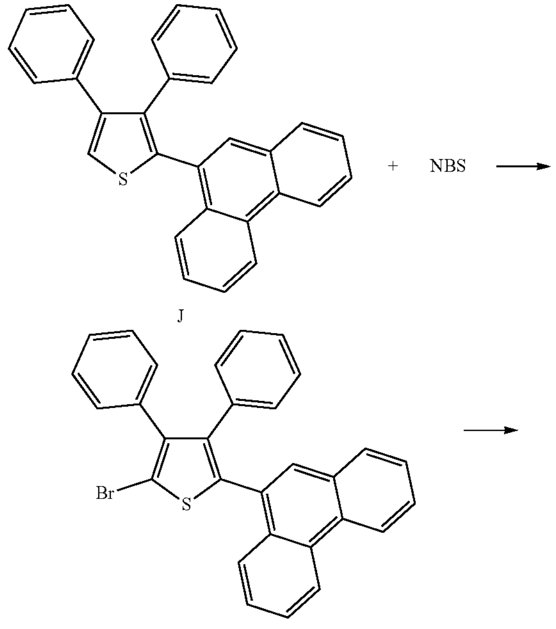

J

K

-continued

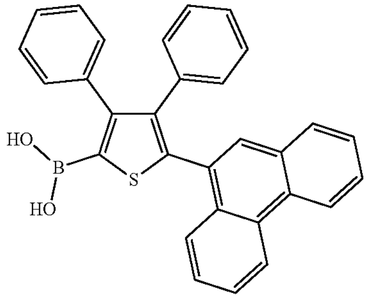

L

The intermediate K was obtained by proceeding in the same manner as for the synthesis of the Intermediate F using the intermediate J (5.5 g, 13.3 mmol), and the intermediate L (4.9 g, 10.7 mmol, 80%) was obtained by proceeding in the same manner as for the synthesis of the Intermediate G using the intermediate K.

(4) Intermediate M

[Reaction Formula 4-4]

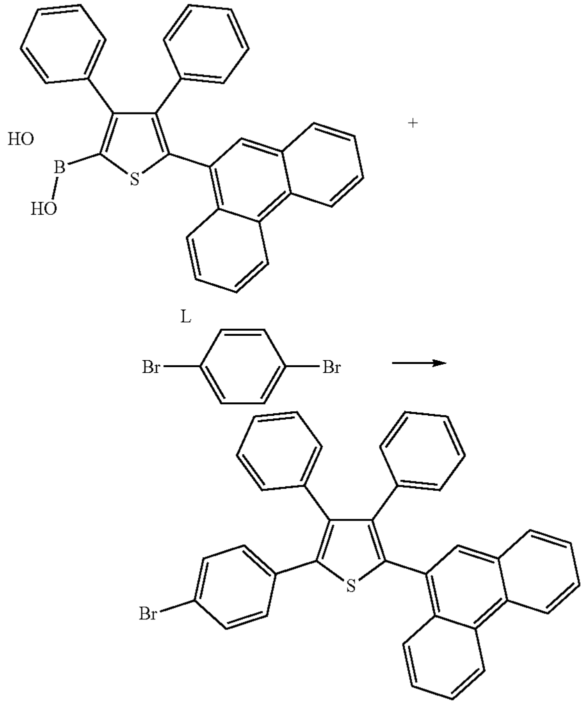

L

M

The intermediate M (3.9 g, 6.9 mmol, 78%) was obtained by proceeding in the same manner as for the synthesis of the Intermediate C using the intermediate L (4.0 g, 8.8 mmol) and 1,4-dibromobenzene (3.0 g, 12.7 mmol).

(5) Compound D23

[Reaction Formula 4-5]

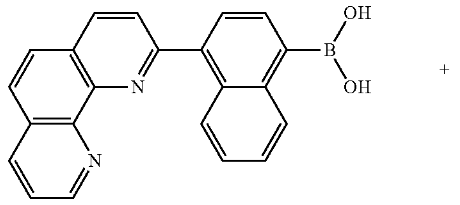

B

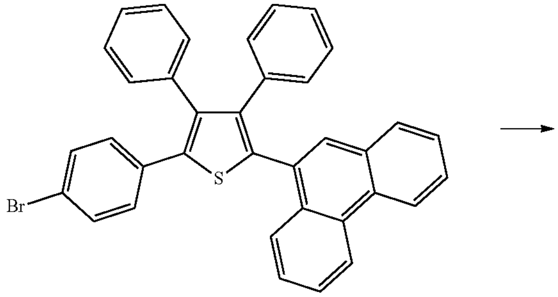

M

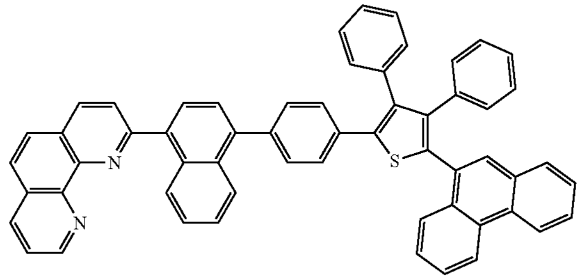

D23

The compound D23 (3.8 g, 4.8 mmol, 70%) was obtained by proceeding in the same manner as for the synthesis of the Intermediate C using the intermediate B (2.4 g, 6.9 mmol) and the intermediate M (3.9 g, 6.9 mmol).

5. Synthesis of Compound D29

(1) Intermediate N

[Reaction Formula 5-1]

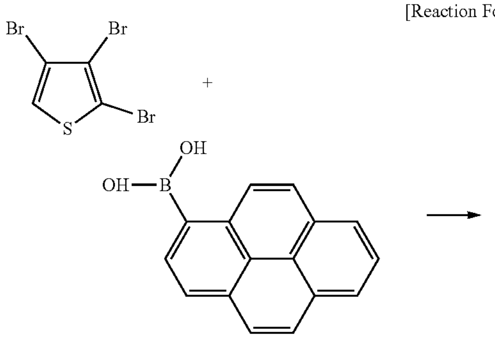

-continued

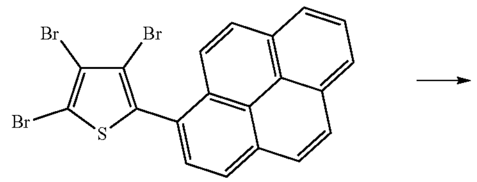

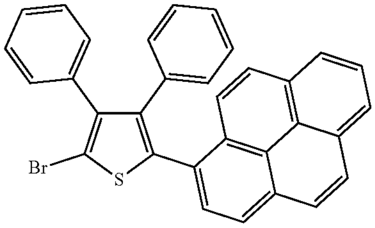

N

The intermediate N (5.3 g, 10.3 mmol, 69%) was obtained by proceeding in the same manner as for the synthesis of the intermediate C using 2,3,4-tribromothiophene (4.9 g, 15.3 mmol) and pyren-1-yl boronic acid (3.7 g, 15.0 mmol).

(2) Compound D29

[Reaction Formula 5-2]

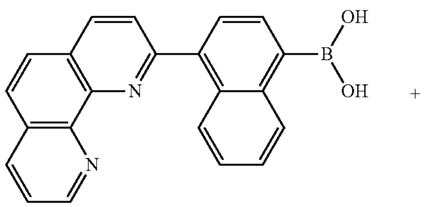

B

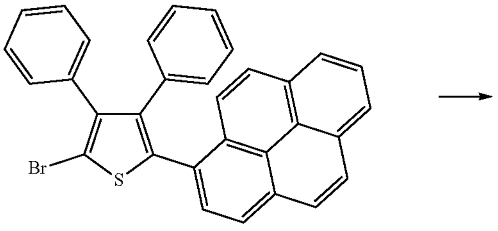

N

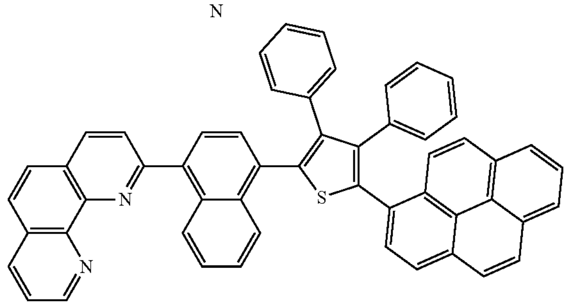

D29

The compound D29 (5.8 g, 7.8 mmol, 76%) was obtained by proceeding in the same manner as for the synthesis of the intermediate C using the intermediate B (3.7 g, 10.6 mmol) and the intermediate N (5.3 g, 10.3 mmol).

6. Synthesis of compound D38

(1) Intermediate O

[Reaction Formula 6-1]

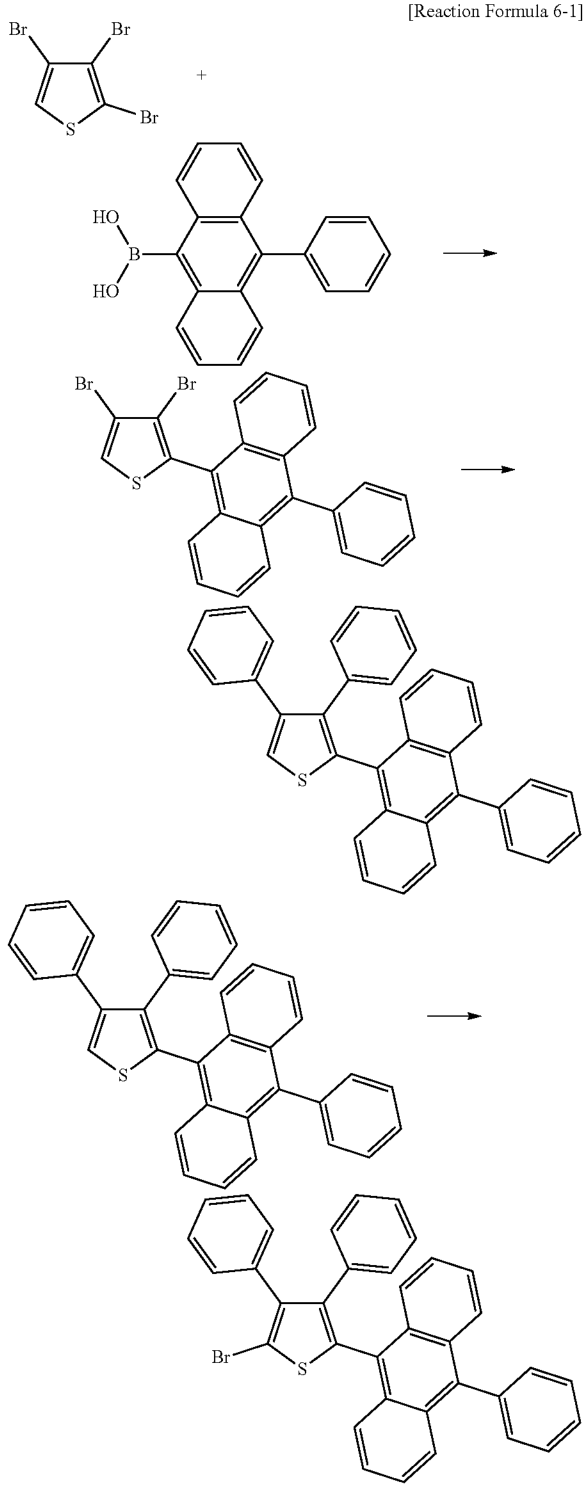

O

The intermediate O (5.2 g, 9.16 mmol, 61%) was obtained by proceeding in the same manner as for the synthesis of the Intermediate K using 2,3,4-tribromothiophene (4.9 g, 15.3 mmol) and 10-phenyl-anthracene-9-yl boronic acid (4.5 g, 15.1 mmol).

(2) Intermediate P

[Reaction Formula 6-2]

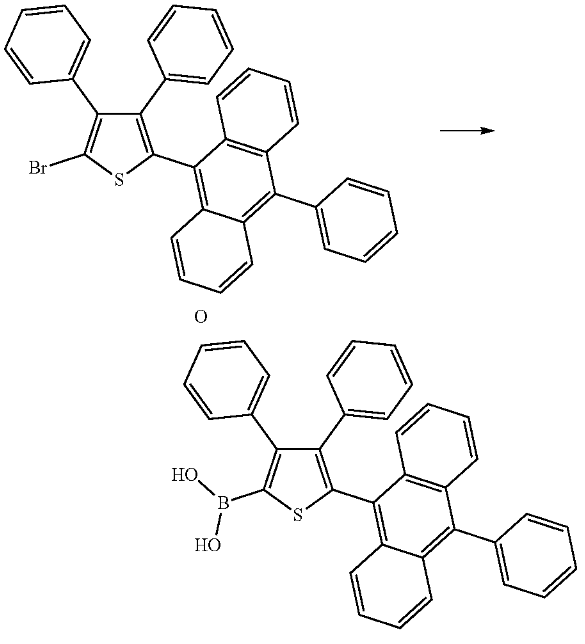

O

P

The intermediate P (4.6 g, 8.64 mmol, 94%) was obtained by proceeding in the same manner as for the synthesis of the Intermediate B using the intermediate O (5.2 g, 9.16 mmol).

(3) Intermediate Q

[Reaction Formula 6-3]

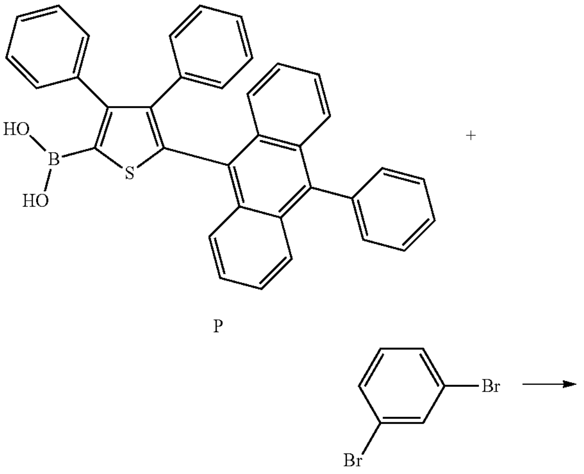

P

-continued

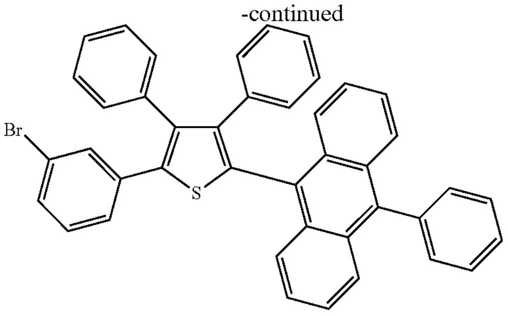

Q

The intermediate Q (5.1 g, 7.9 mmol, 92%) was obtained by proceeding in the same manner as for the synthesis of the Intermediate C using the intermediate P (4.6 g, 8.6 mmol) and 1,3-dibromobenzene (3.0 g, 12.7 mmol).

(4) Compound D38

[Reaction Formula 6-4]

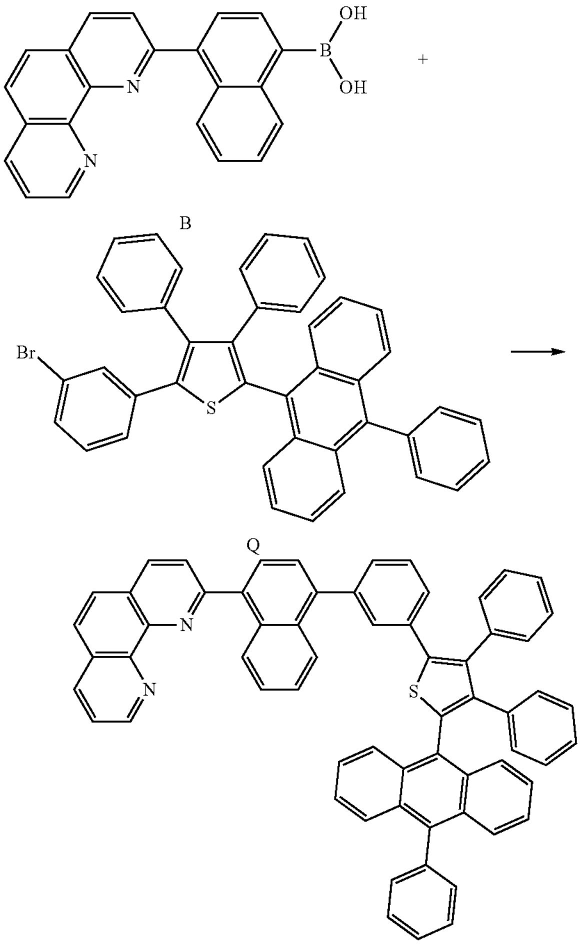

B

Q

D38

The compound D38 (4.2 g, 4.8 mmol, 61%) was obtained by proceeding in the same manner as for the synthesis of the Intermediate C using the intermediate B (3.0 g, 8.6 mmol) and the intermediate Q (5.1 g, 7.9 mmol).

7. Synthesis of Compound D41

(1) Intermediate S

[Reaction Formula 7-1]

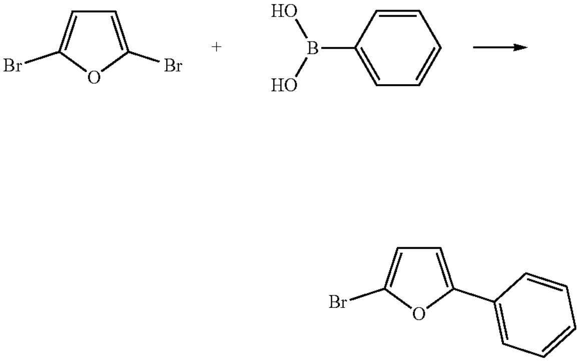

S

The intermediate S (8.5 g, 0.038 mol, 86%) was obtained by proceeding in the same manner as for the synthesis of the intermediate C using 2,5-dibromofuran (10.0 g, 0.044 mol) and benzene boronic acid (6.0 g, 0.049 mol).

(2) Compound D41

[Reaction Formula 7-2]

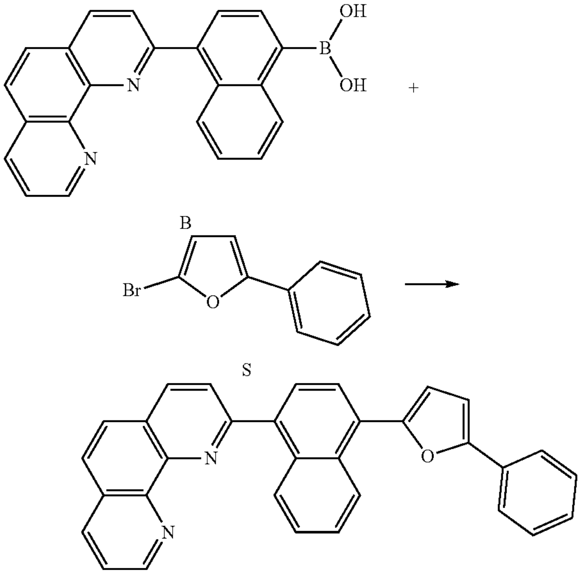

B

S

D41

The compound D41 (8.4 g, 0.019 mol, 83%) was obtained by proceeding in the same manner as for the synthesis of the Intermediate C using the intermediate B (8.0 g, 0.023 mol) and the intermediate S (6.5 g, 0.029 mol).

8. Synthesis of Compound D45

(1) Intermediate T

[Reaction Formula 8-1]

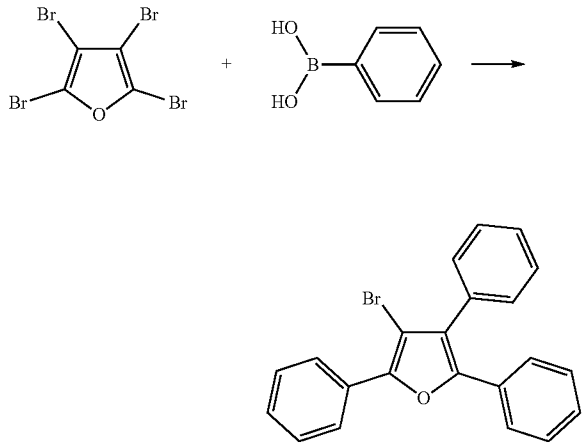

T

The intermediate T (4.92 g, 0.0131 mol, 50%) was obtained by proceeding in the same manner as for the synthesis of the intermediate C using 2,3,4,5-tetrabromofuran (10.0 g, 0.0261 mol) and benzene boronic acid (10.0 g, 0.0820 mol).

(2) Compound D45

[Reaction Formula 8-2]

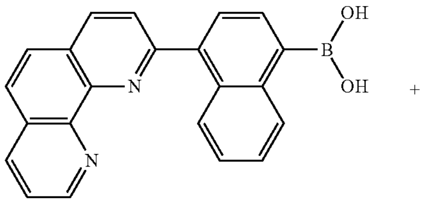

B

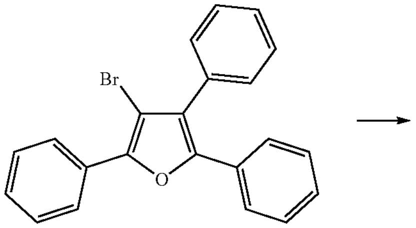

T

-continued

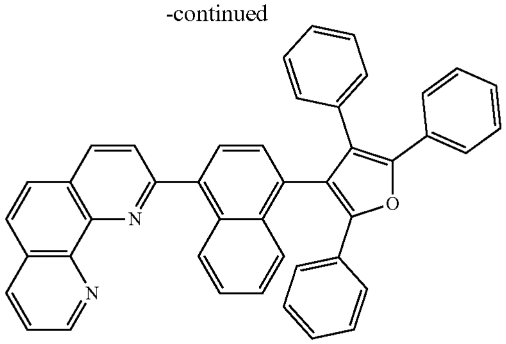

D45

The compound D45 (5.20 g, 0.00866 mol, 72%) was obtained by proceeding in the same manner as for the synthesis of the Intermediate C using the intermediate B (4.20 g, 0.0120 mol) and the intermediate T (4.92 g, 0.0131 mol).

9. Synthesis of Compound D47

(1) Intermediate U

[Reaction Formula 9-1]

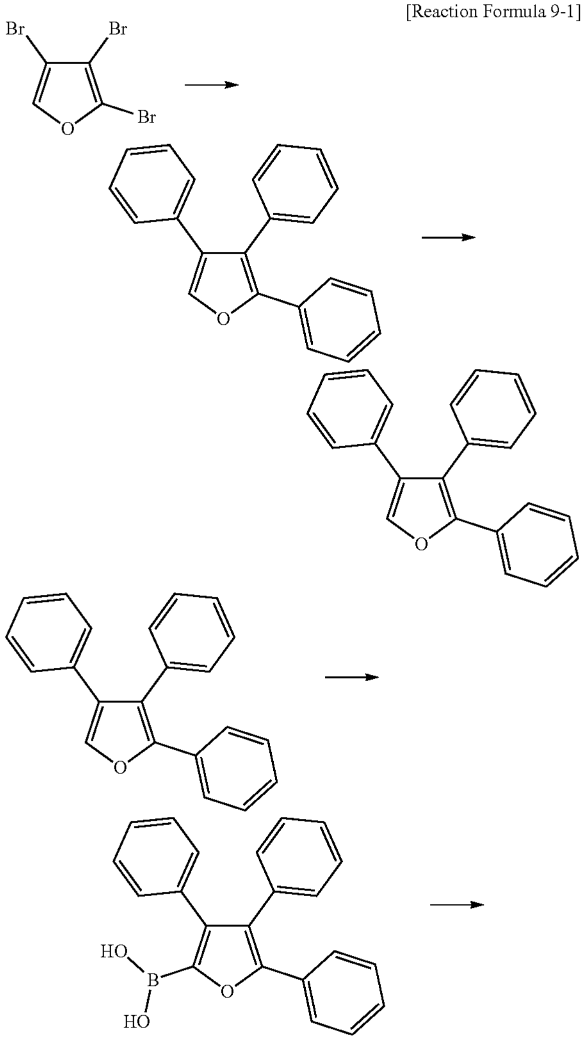

-continued

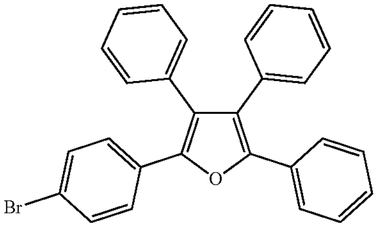

U

The intermediate U (5.3 g, 0.0117 mol, 36%) was obtained by sequentially proceeding in the same manner as for the synthesis of the intermediate E, the synthesis of the intermediate F, the synthesis of the intermediate G, and the synthesis of the intermediate H using 2,3,4-tribromofuran (10.0 g, 0.0328 mol).

(2) Compound D47

[Reaction Formula 9-2]

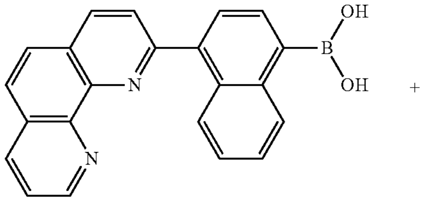

B

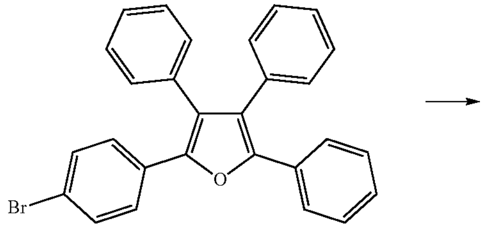

U

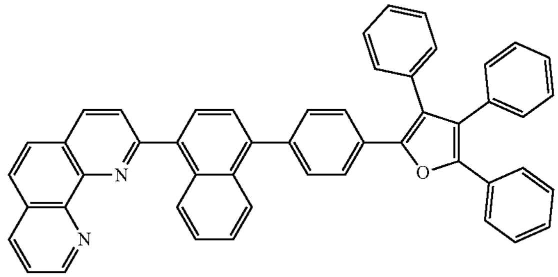

D47

The compound D47 (5.3 g, 0.0078 mol, 65%) was obtained by proceeding in the same manner as for the synthesis of the Intermediate C using the intermediate B (4.8 g, 0.014 mol) and the intermediate U (5.3 g, 0.012 mol).

10. Synthesis of Compound D63

(1) Intermediate V

[Reaction Formula 10-1]

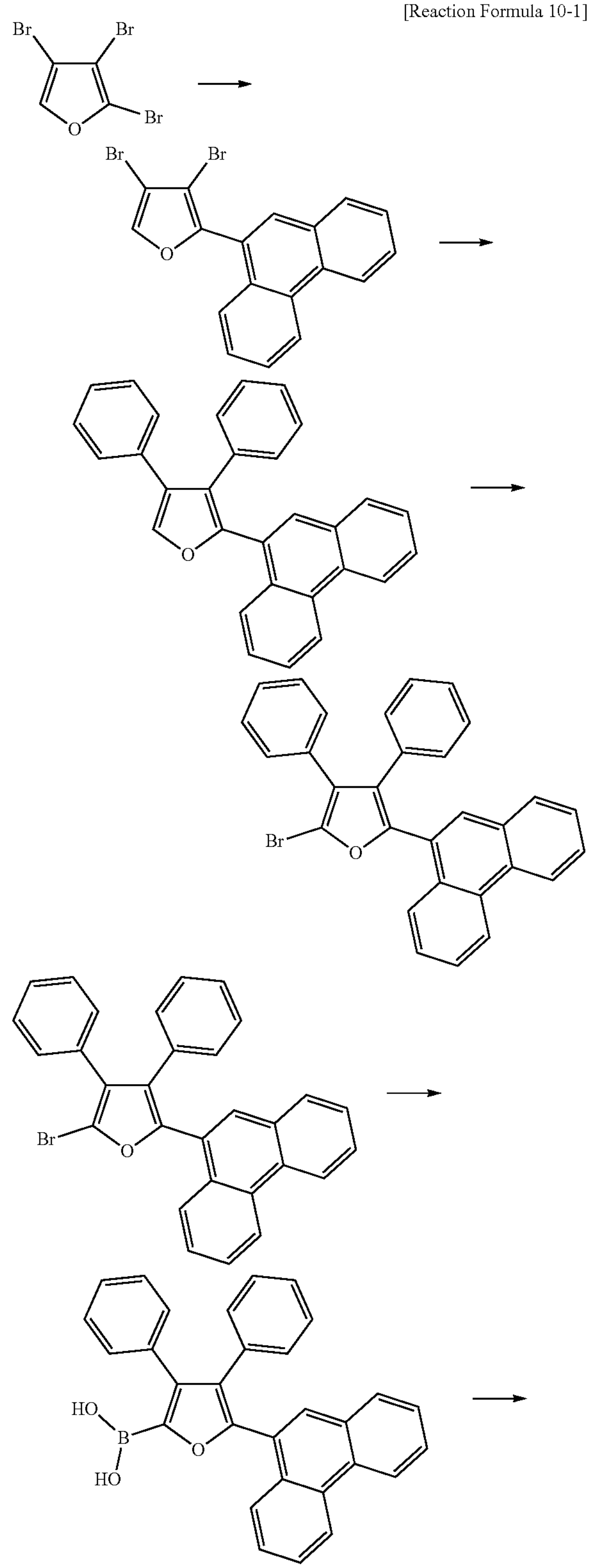

-continued

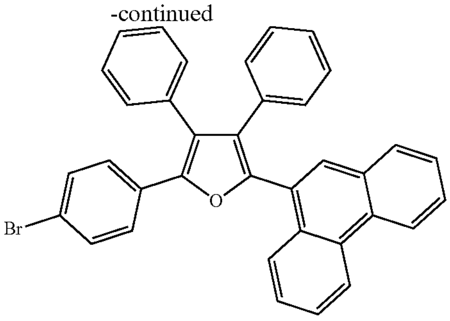

V

The intermediate V (6.82 g, 0.0124 mol, 38%) was obtained by sequentially proceeding in the same manner as for the synthesis of the intermediate I, the synthesis of the intermediate J, the synthesis of the intermediate K, the synthesis of the intermediate L, and the synthesis of the intermediate M using 2,3,4-tribromofuran (10.0 g, 0.0328 mol).

(2) Compound D63

[Reaction Formula 10-2]

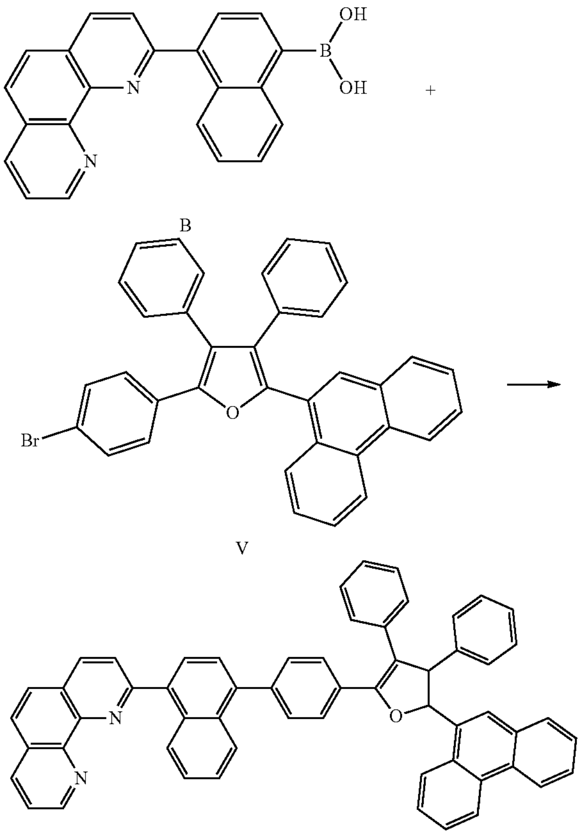

B

V

D63

The compound D63 (7.1 g, 0.0091 mol, 76%) was obtained by proceeding in the same manner as for the synthesis of the Intermediate C using the intermediate B (4.8 g, 0.014 mol) and the intermediate V (6.8 g, 0.012 mol).

11. Synthesis of Compound D69

(1) Intermediate W

[Reaction Formula 11-1]

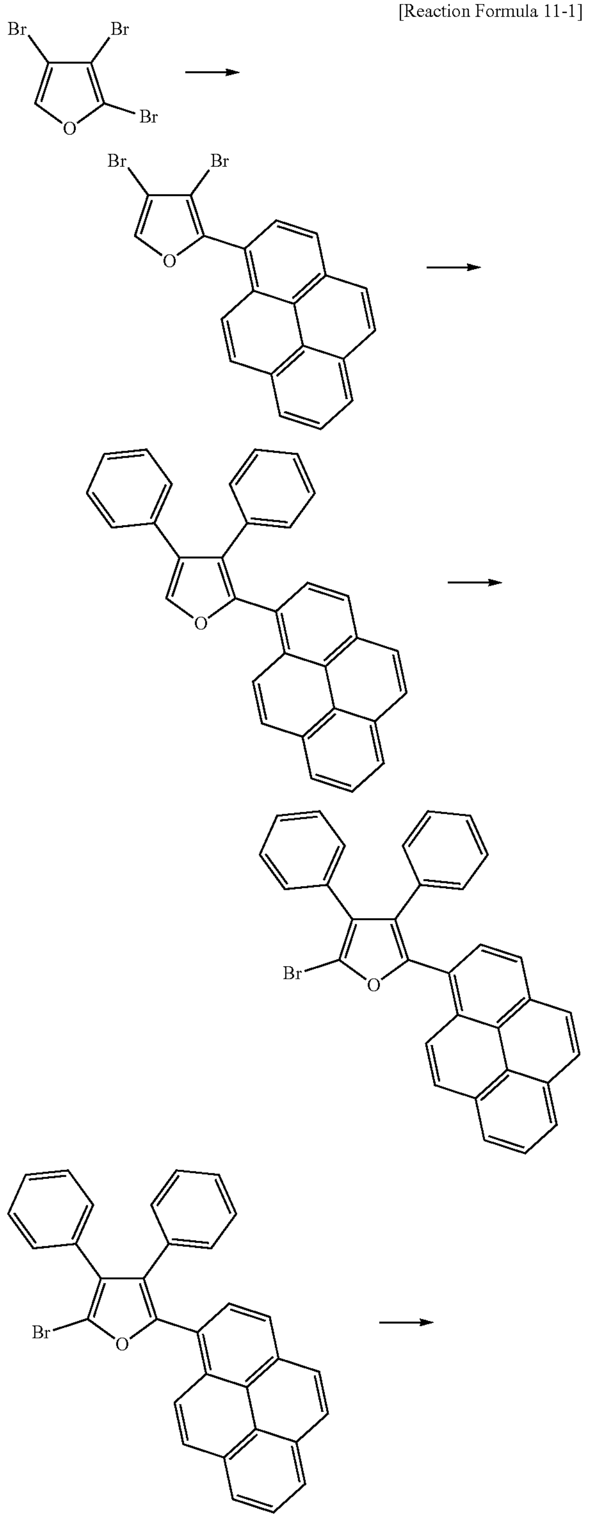

-continued

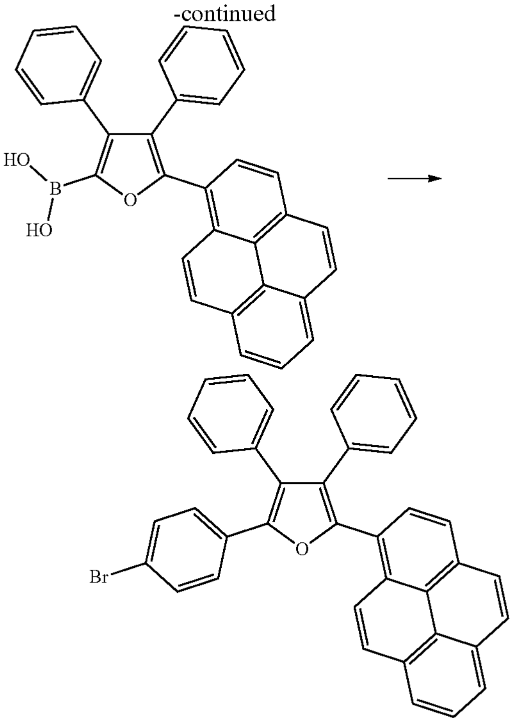

W

The intermediate W (5.7 g, 0.00990 mol, 30%) was obtained by sequentially proceeding in the same manner as for the synthesis of the intermediate I, the synthesis of the intermediate J, the synthesis of the intermediate K, the synthesis of the intermediate L, and the synthesis of the intermediate M using 2,3,4-tribromofuran (10.0 g, 0.0328 mol).

(2) Compound D69

[Reaction Formula 11-2]

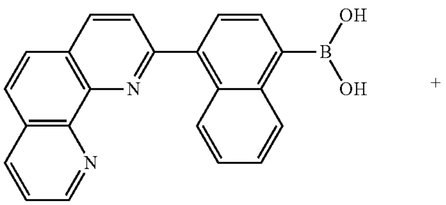

B

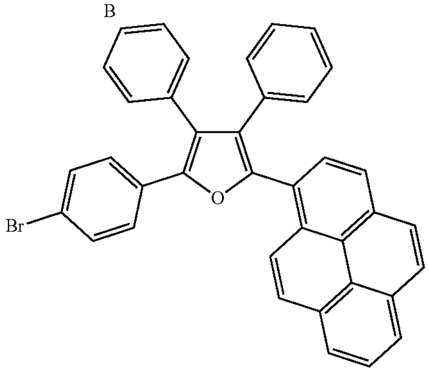

V

-continued

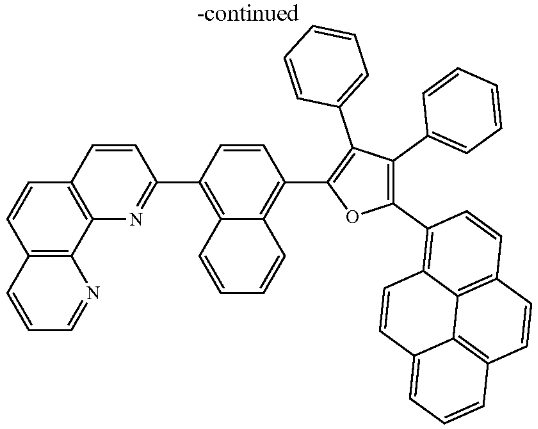

D69

The compound D69 (5.2 g, 0.0072 mol, 72%) was obtained by proceeding in the same manner as for the synthesis of the Intermediate C using the intermediate B (4.0 g, 0.011 mol) and the intermediate W (5.7 g, 0.0099 mol).

12. Synthesis of Compound D78

(1) Intermediate X

[Reaction Formula 12-1]

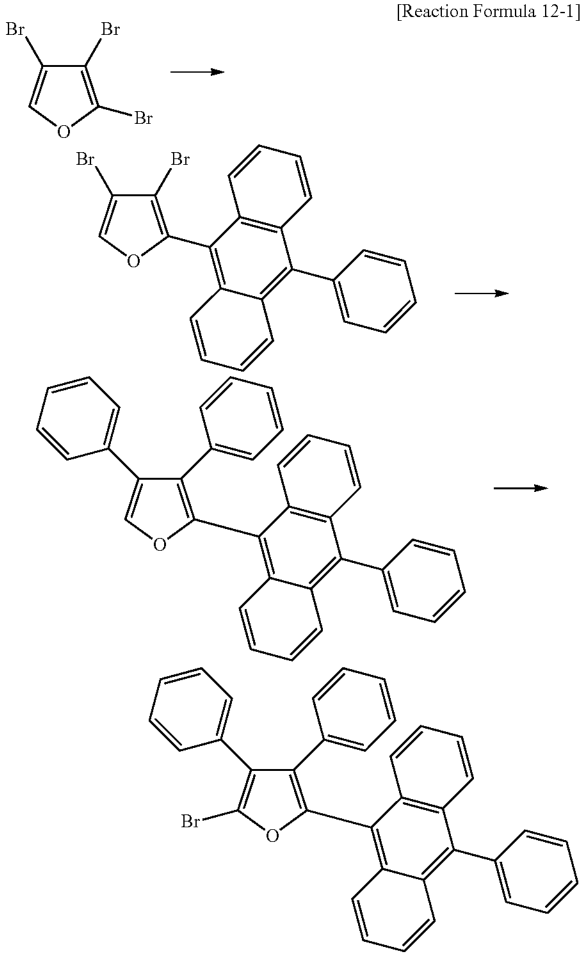

-continued

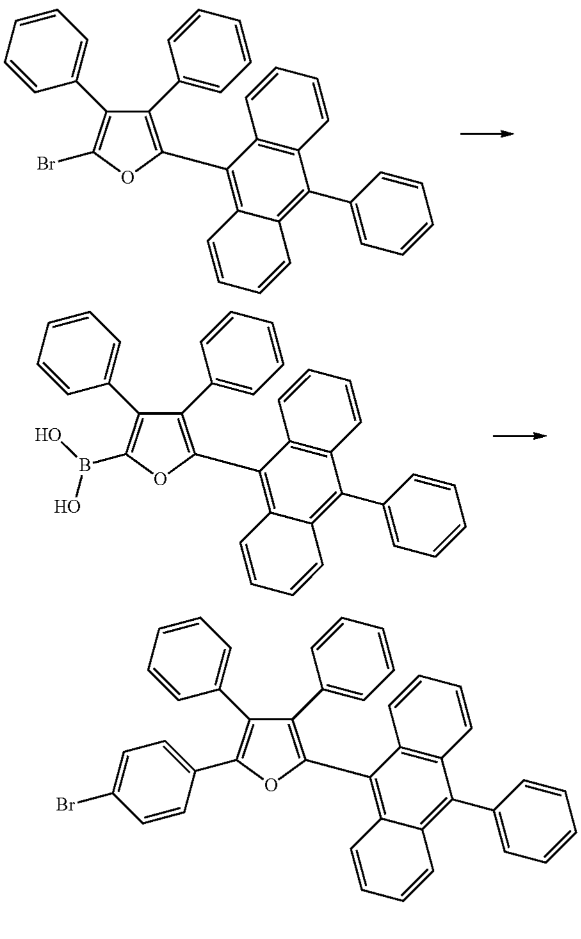

X

The intermediate X (5.2 g, 0.0083 mol, 25%) was obtained by sequentially proceeding in the same manner as for the synthesis of the intermediate I, the synthesis of the intermediate J, the synthesis of the intermediate K, the synthesis of the intermediate L, and the synthesis of the intermediate M using 2,3,4-tribromofuran (10.0 g, 0.0328 mol).

(2) Compound D78

[Reaction Formula 12-2]

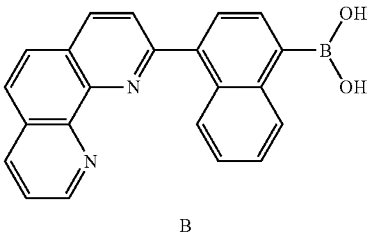

B

+

-continued

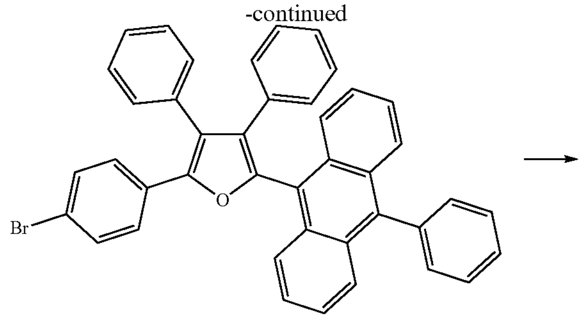

X

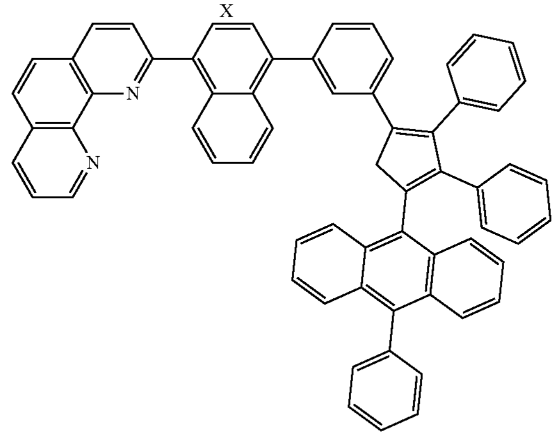

D78

The compound D78 (4.8 g, 0.0056 mol, 67%) was obtained by proceeding in the same manner as for the synthesis of the Intermediate C using the intermediate B (3.3 g, 0.0094 mol) and the intermediate X (5.2 g, 0.0083 mol).

In the OLED D, since the ETL 250 includes the electron transporting material 252 being the organic compound of the present disclosure, the electron transporting property from the second electrode 164 as the cathode into (or toward) the EML 240 is improved. Accordingly, in the OLED D and the organic light emitting display device 100, the driving voltage is decreased, and the emitting efficiency and the lifespan are increased.

[OLED]

On an anode (ITO), an HIL (100 Å, the compound in Formula 3), an HTL (1000 Å, the compound in Formula 4), an EML (250 Å, host (the compound in Formula 5) and dopant (the compound in Formula 6), 3 wt %)), an ETL (300 Å), an EIL (20 Å, LiF) and a cathode (Al) are sequentially stacked to form the OLED.

1. Comparative Example (Ref)

The ETL is formed by using the compound in Formula 7.

2. Examples (1) Example 1 (Ex1)

The ETL is formed by using the compound D1 in Formula 2.

(2) Example 2 (Ex2)

The ETL is formed by using the compound D5 in Formula 2.

(3) Example 3 (Ex3)

The ETL is formed by using the compound D7 in Formula 2.

(4) Example 4 (Ex4)

The ETL is formed by using the compound D23 in Formula 2.

(5) Example 5 (Ex5)

The ETL is formed by using the compound D29 in Formula 2.

(6) Example 6 (Ex6)

The ETL is formed by using the compound D38 in Formula 2.

(7) Example 7 (Ex7)

The ETL is formed by using the compound D41 in Formula 2.

(8) Example 8 (Ex8)

The ETL is formed by using the compound D45 in Formula 2.

(9) Example 9 (Ex9)

The ETL is formed by using the compound D47 in Formula 2.

(10) Example 10 (Ex10)

The ETL is formed by using the compound D63 in Formula 2.

(11) Example 11 (Ex11)

The ETL is formed by using the compound D69 in Formula 2.

(12) Example 12 (Ex12)

The ETL is formed by using the compound D78 in Formula 2.

[Formula 3]

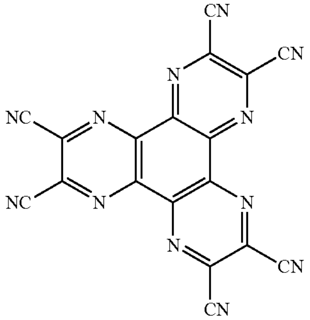

-continued

[Formula 4]

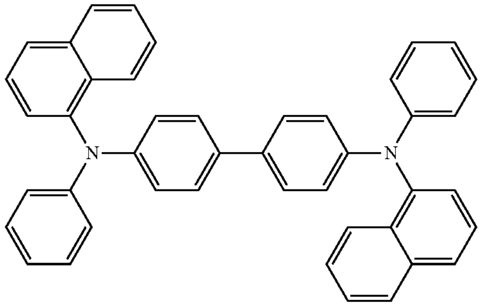

[Formula 5]

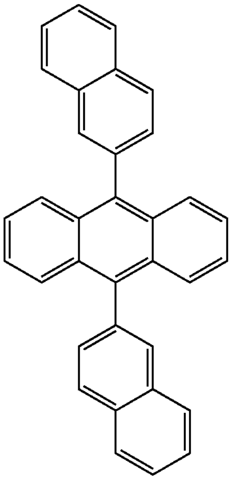

[Formula 6]

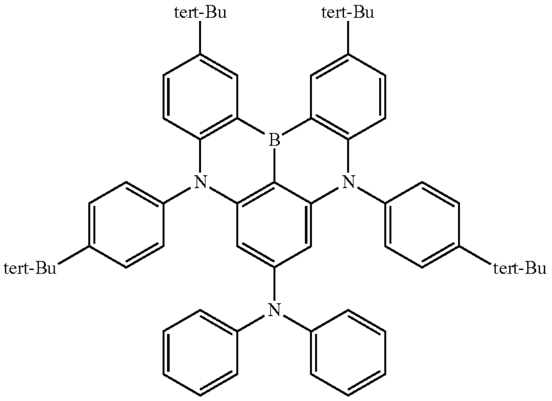

[Formula 7]

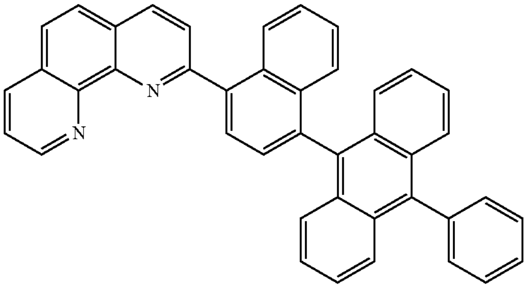

The emitting properties, i.e., the driving voltage (ΔV), the efficiency and the lifespan, of the OLED in Comparative Example and Examples 1 to 12 are measured and listed in Table 1.

TABLE 1

| | ETL | ΔV | efficiency | lifespan |
|---|---|---|---|---|
| Ref | Formula7 | 0.00 | 100 | 100 |
| Ex1 | D1 | −0.14 | 99 | 84 |
| Ex2 | D5 | −0.14 | 108 | 105 |
| Ex3 | D7 | −0.18 | 114 | 113 |
| Ex4 | D23 | −0.23 | 110 | 118 |
| Ex5 | D29 | −0.28 | 118 | 115 |
| Ex6 | D38 | −0.25 | 112 | 109 |
| Ex7 | D41 | −0.10 | 88 | 81 |
| Ex8 | D45 | −0.13 | 99 | 100 |
| Ex9 | D47 | −0.15 | 108 | 110 |
| Ex10 | D63 | −0.21 | 113 | 115 |
| Ex11 | D69 | −0.22 | 115 | 108 |
| Ex12 | D78 | −0.19 | 119 | 114 |

As shown in Table 1, in comparison to the OLED of Ref, the ETL of the OLED of Ex1 to Ex12 includes the organic compound of the present disclosure having a structure, where a thiophene moiety or a furan moiety is combined to a phenanthroline moiety directly or through a linker, the OLED has advantages in the driving voltage, the emitting efficiency and the lifespan.

In addition, in comparison to the OLED of Ex1 and Ex7 using the organic compound, in which hydrogen is presented in a meta-position of the thiophene moiety or a meta-position of the furan moiety, in the OLED of Ex2 to Ex6 using the organic compound, in which aryl substituent is presented in the meta-position of the thiophene moiety, and the OLED of Ex8 to Ex12, in which aryl substituent is presented in the meta-position of the furan moiety, the driving voltage is significantly reduced, and the emitting efficiency and the lifespan are significantly improved.

Moreover, in comparison to the OLED of Ex1 to Ex3, in which only monocyclic aryl substituent is presented at the thiophene moiety, and the OLED of Ex7 to Ex9, in which only monocyclic aryl substituent is presented at the furan moiety, in the OLED of Ex4 to Ex6, in which a polycyclic aryl substituent is presented at the thiophene moiety, and the OLED of Ex10 to Ex12, in which a polycyclic aryl substituent is presented at the furan moiety, the driving voltage is further reduced, and the emitting efficiency and the lifespan are further improved.

FIG. 4 is a schematic cross-sectional view of an organic light emitting device according to a third embodiment of the present disclosure. FIG. 5 is a schematic cross-sectional view of an OLED according to a fourth embodiment of the present disclosure, and FIG. 6 is a schematic cross-sectional view of an OLED device according to a fifth embodiment of the present disclosure.

As shown in FIG. 4, the organic light emitting display device 300 includes a first substrate 310, where a red pixel BP, a green pixel GP and a blue pixel BP are defined, a second substrate 370 facing the first substrate 310, an OLED D, which is positioned between the first and second substrates 310 and 370 and providing white emission, and a color filter layer 380 between the OLED D and the second substrate 370.

Each of the first and second substrates 310 and 370 may be a glass substrate or a flexible substrate. For example, each of the first and second substrates 310 and 370 may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 320 is formed on the substrate, and the TFT Tr corresponding to each of the red, green and blue pixels RP, GP and BP is formed on the buffer layer 320. The buffer layer 320 may be omitted.

A semiconductor layer 322 is formed on the buffer layer 320. The semiconductor layer 322 may include an oxide semiconductor material or polycrystalline silicon.

A gate insulating layer 324 is formed on the semiconductor layer 322. The gate insulating layer 324 may be formed of an inorganic insulating material such as silicon oxide or silicon nitride.

A gate electrode 330, which is formed of a conductive material, e.g., metal, is formed on the gate insulating layer 324 to correspond to a center of the semiconductor layer 322.

An interlayer insulating layer 332, which is formed of an insulating material, is formed on the gate electrode 330. The interlayer insulating layer 332 may be formed of an inorganic insulating material, e.g., silicon oxide or silicon nitride, or an organic insulating material, e.g., benzocyclobutene or photo-acryl.

The interlayer insulating layer 332 includes first and second contact holes 334 and 336 exposing both ends of the semiconductor layer 322. The first and second contact holes 334 and 336 are positioned at both sides of the gate electrode 330 to be spaced apart from the gate electrode 330.

A source electrode 340 and a drain electrode 342, which are formed of a conductive material, e.g., metal, are formed on the interlayer insulating layer 332.

The source electrode 340 and the drain electrode 342 are spaced apart from each other with respect to the gate electrode 330 and respectively contact both ends of the semiconductor layer 322 through the first and second contact holes 334 and 336.

The semiconductor layer 322, the gate electrode 330, the source electrode 340 and the drain electrode 342 constitute the TFT Tr. The TFT Tr serves as a driving element. Namely, the TFT Tr may correspond to the driving TFT Td (of FIG. 1).

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 350, which includes a drain contact hole 352 exposing the drain electrode 342 of the TFT Tr, is formed to cover the TFT Tr.

A first electrode 360, which is connected to the drain electrode 342 of the TFT Tr through the drain contact hole 352, is separately formed in each pixel and on the planarization layer 350. The first electrode 360 may be an anode and may be formed of a conductive material, e.g., a transparent conductive oxide (TCO), having a relatively high work function. The first electrode 360 may further include a reflection electrode or a reflection layer. For example, the reflection electrode or the reflection layer may be formed of silver (Ag) or aluminum-palladium-copper (APC) alloy. In the top-emission type organic light emitting display device 300, the first electrode 360 may have a triple-layered structure of ITO/Ag/ITO or ITO/APC/ITO.

A bank layer 366 is formed on the planarization layer 350 to cover an edge of the first electrode 360. Namely, the bank layer 366 is positioned at a boundary of the pixel and exposes a center of the first electrode 360 in the pixel. Since the OLED D emits the white light in the red, green and blue pixels RP, GP and BP, the organic emitting layer 362 may be formed as a common layer in the red, green and blue pixels RP, GP and BP without separation. The bank layer 366 may be formed to prevent a current leakage at an edge of the first electrode 360 and may be omitted.

An organic emitting layer 362 is formed on the first electrode 360.

Referring to FIG. 5, the organic light emitting layer 362 includes a first emitting part 410 including a first EML 416 and a first ETL 420, a second emitting part 430 including a second EML 434 and a second ETL 440, and a charge generation layer (CGL) 450 between the first and second emitting parts 410 and 430.

The CGL 450 is positioned between the first and second emitting parts 410 and 430, and the first emitting part 410, the CGL 450 and the second emitting part 430 are sequentially stacked on the first electrode 360. Namely, the first emitting part 410 is positioned between the first electrode 360 and the CGL 450, and the second emitting part 420 is positioned between the second electrode 364 and the CGL 450.

The first emitting part 410 may further include a first HTL 414 between the first electrode 360 and the first EML 416. In addition, the first emitting part 410 may further include an HIL 412 between the first electrode 360 and the first HTL 414.

Although not shown, the first emitting part 410 may further include at least one of an EBL between the first HTL 414 and the first EML 416 and an HBL between the first EML 416 and the first ETL 420.

The second emitting part 430 may further include a second HTL 432 between the second EML 434 and the CGL 450. In addition, the second emitting part 430 may further include an EIL 436 between the second ETL 440 and the second electrode 364.

Although not shown, the second emitting part 430 may further include at least one of an EBL between the second HTL 432 and the second EML 434 and an HBL between the second EML 434 and the second ETL 440.

One of the first and second EMLs 416 and 434 provides the blue emission, and the other one of the first and second EMLs 416 and 434 provides the yellow-green emission. For example, the first EML 416, which may provide the blue emission, may include a host and a blue dopant, and the second EML 434, which may provide the yellow-green emission, may include a host and a yellow-green dopant. Alternatively, the second EML 434 may have a double-layered structure including a first layer, which provides the red emission, and a second layer, which provides the green emission. In this instance, the first layer, which may provide the red emission, may include a host and a red dopant, and the second layer, which may provide the green emission, may include a host and a green dopant.

For example, in the first EML 416 providing the blue emission, the host may be an anthracene derivative, the blue dopant may be a boron derivative.

The CGL 450 includes an n-type CGL 452 and a p-type CGL 454. The n-type CGL 452 is positioned between the first ETL 418 and the second HTL 432, and the p-type CGL 454 is positioned between the n-type CGL 452 and the second HTL 432.

The n-type CGL 452 provides the electron toward the first ETL 418, and the electron is transferred into the first EML 416 through the first ETL 418. The p-type CGL 454 provides the hole toward the second HTL 432, and the hole is transferred into the second EML 434 through the second HTL 432. As a result, in the OLED D having a two-stack (double-stack) structure, the driving voltage is reduced, and the emitting efficiency is improved.

The p-type CGL 454 may be formed of an organic material doped with a metal or a p-type dopant. For example, the metal doped in the p-type CGL 454 may be selected from the group consisting of Al, Cu, Fe, Pb, Zn, Au, Pt, W, In, Mo, Ni, and Ti, and the p-type dopant may be F4-TCNQ. The organic material in the p-type CGL 454 may be selected from the group consisting of NPB, TPD, N,N,N',N'-tetranaphthalenyl-benzidine (TNB), and HAT-CN.

Alternatively, the p-type CGL 454 may include a compound represented by Formula 8-1 or 8-2.

[Formula 8-1]

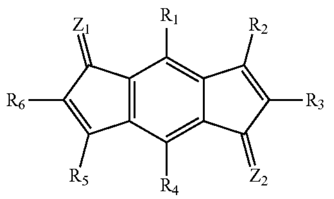

[Formula 8-2]

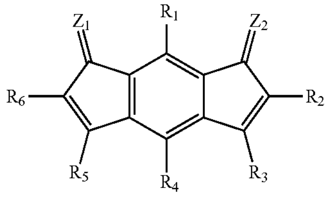

In Formulas 8-1 and 8-2, each of R1 to R6 is independently selected from the group consisting of hydrogen, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy, and trimethylsilyl, and at least one of R1 to R6 is cyano.

Each of Z1 and Z2 is independently represented by Formula 9.

[Formula 9]

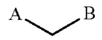

In Formula 9, each of A and B is independently selected from the group consisting of hydrogen, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy, and trimethylsilyl.

Each of aryl group, heteroaryl group, alkyl group, alkoxy group, and ether group may be unsubstituted or substituted with at least one of C6 to C30 aryl group, C6 to C30 heteroaryl group, C1 to C12 alkyl group, cyano, fluorine, trifluoromethyl, trifluoromethoxy, and trimethylsilyl.

The compound in the p-type CGL 454, which is represented by Formula 8-1 or 8-2, may be one of the compounds in Formula 10.

[Formula 10]
A01
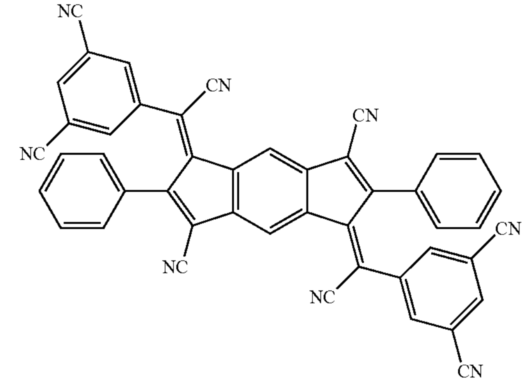
A02
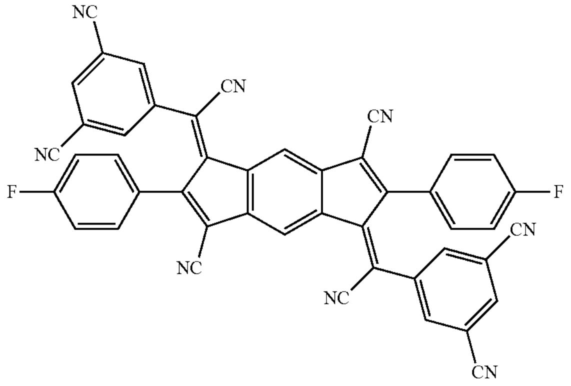
A03
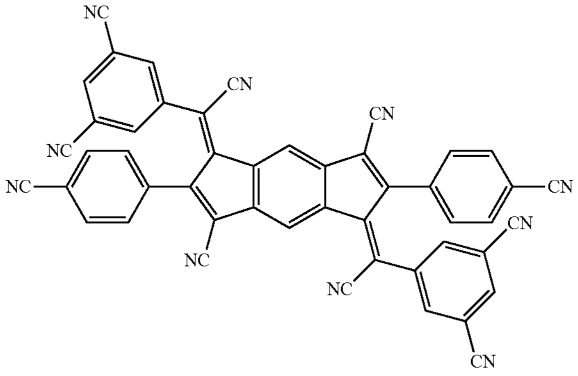
A04
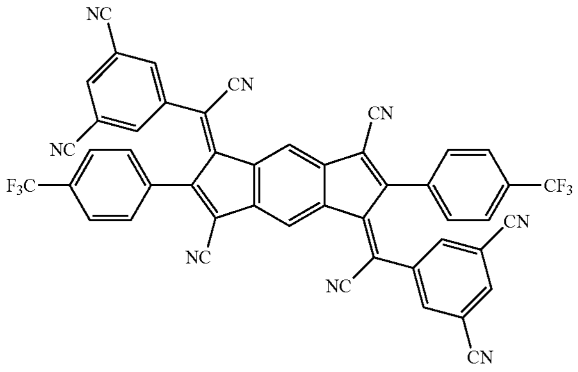
-continued
A05
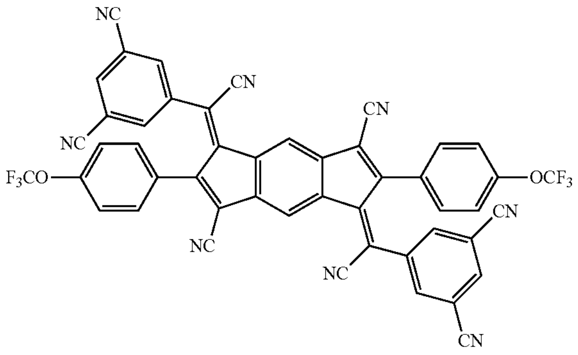
A06
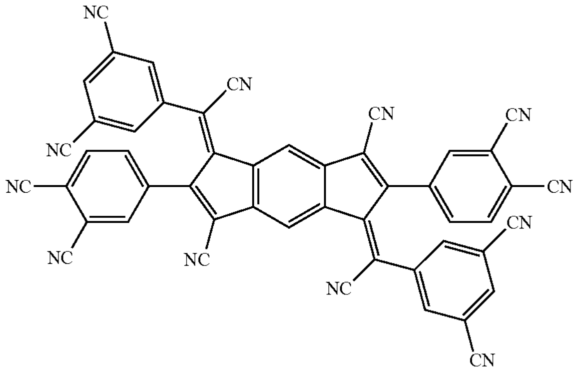
A07
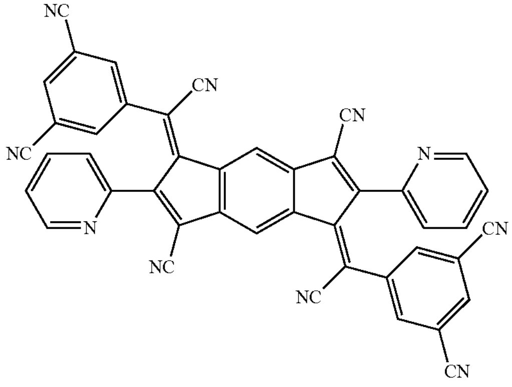
A08
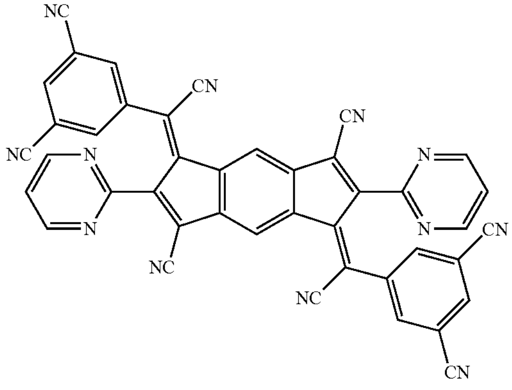

-continued
A09
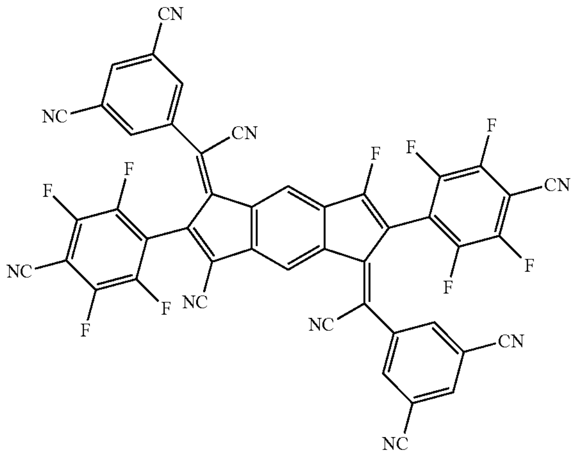
A10
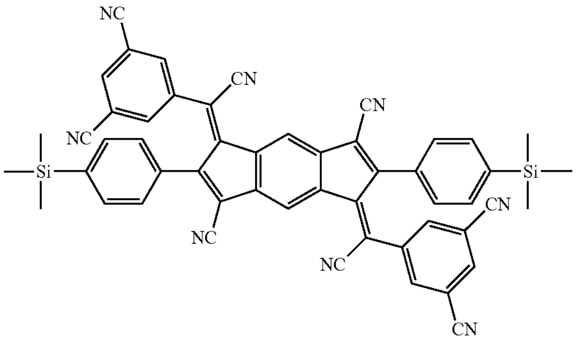
A11
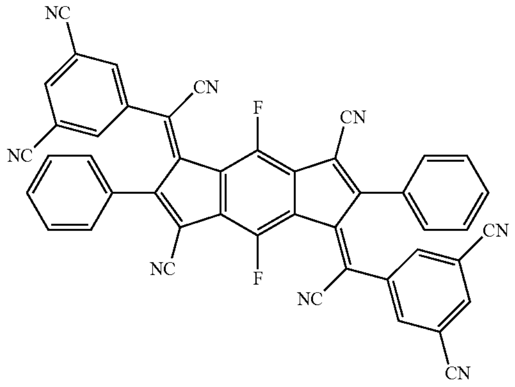
A12
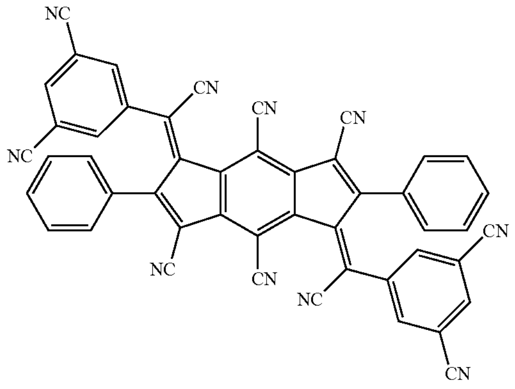
-continued
A13
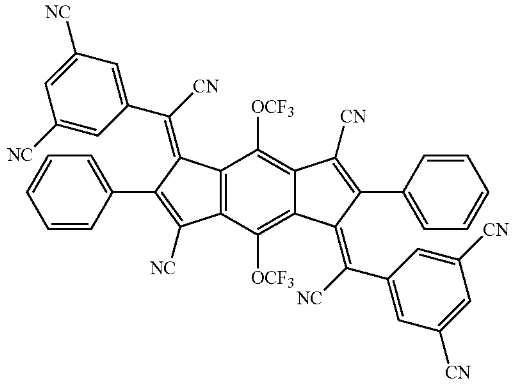
A14
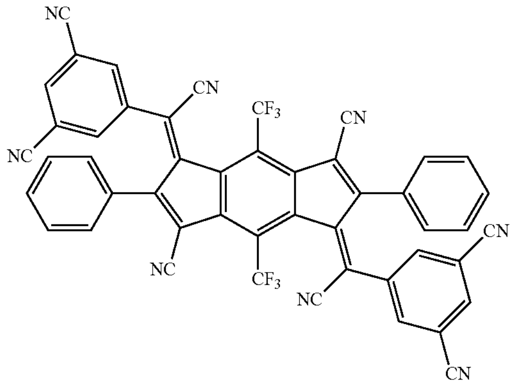
A15
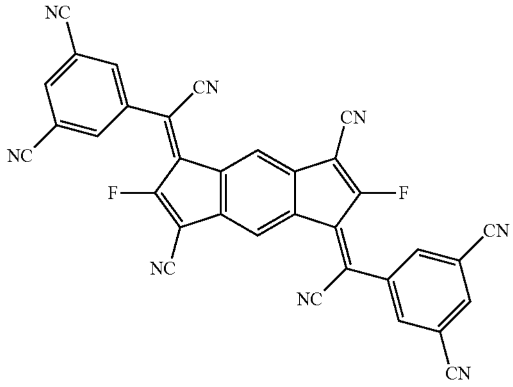
A16
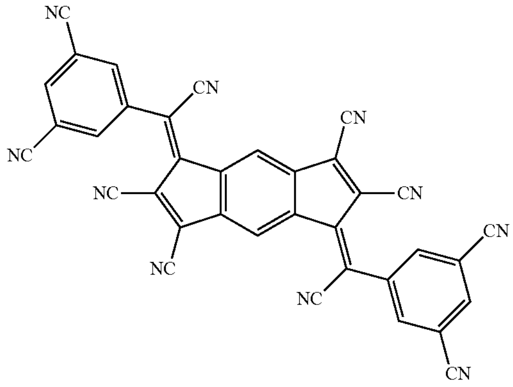

-continued
A17
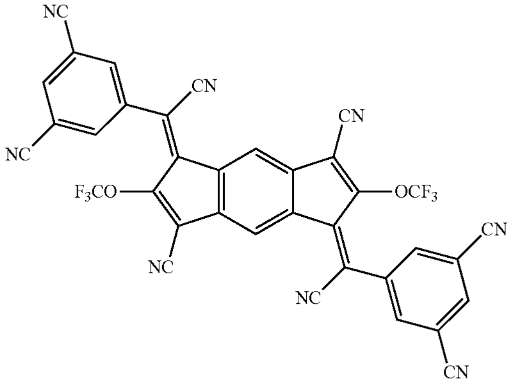
A18
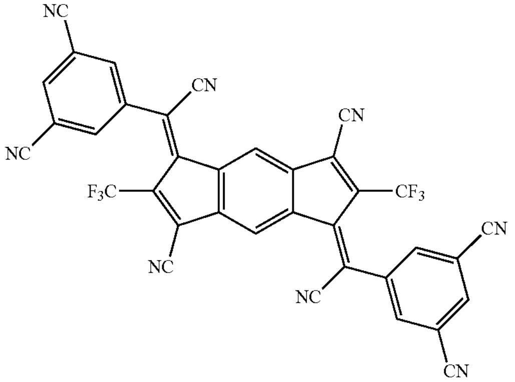
A19
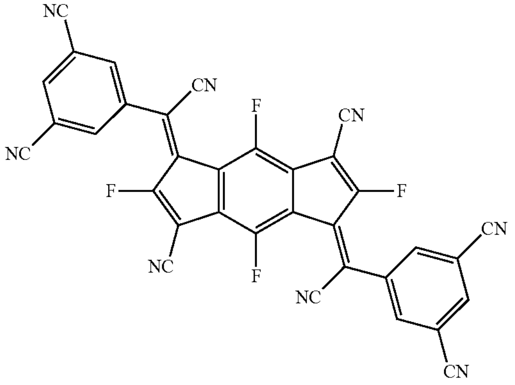
A20
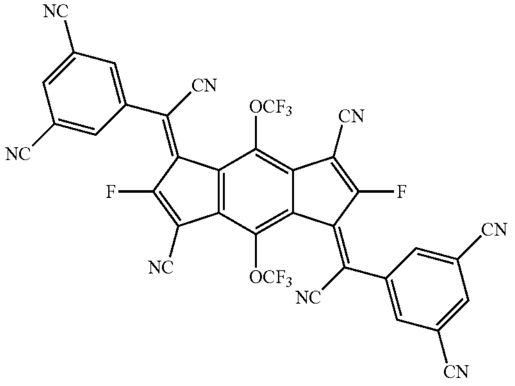
-continued
A21
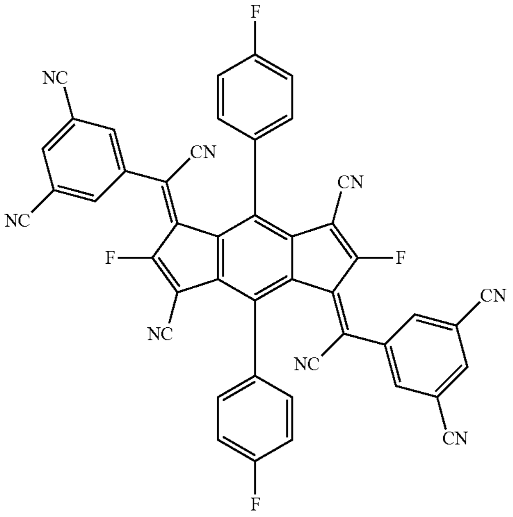
A22
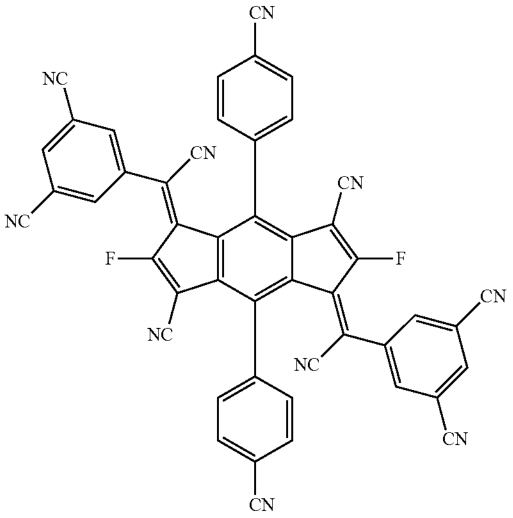
A23
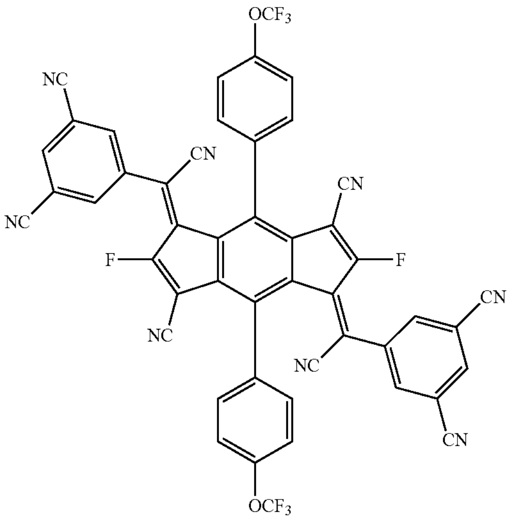

-continued
A24
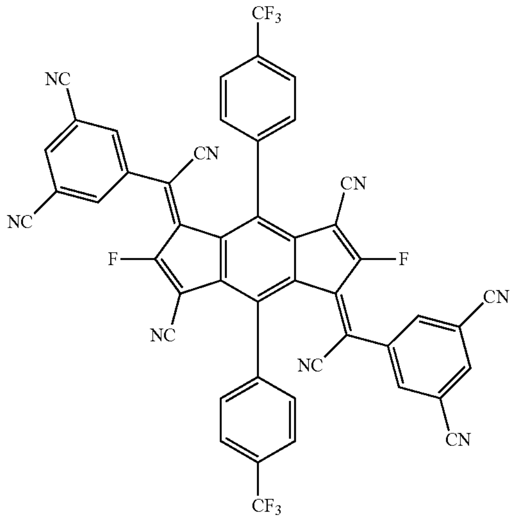
A25
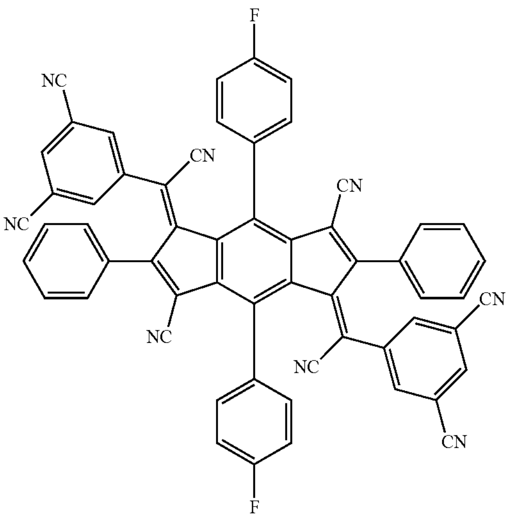
A26
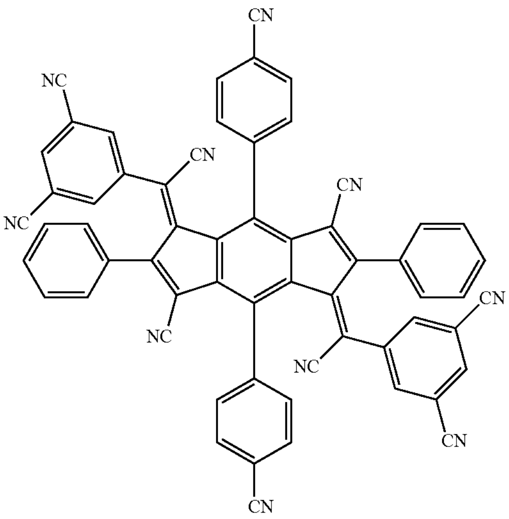
-continued
A27
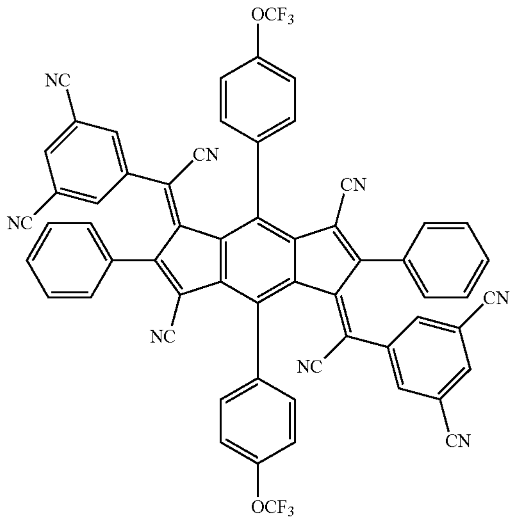
A28
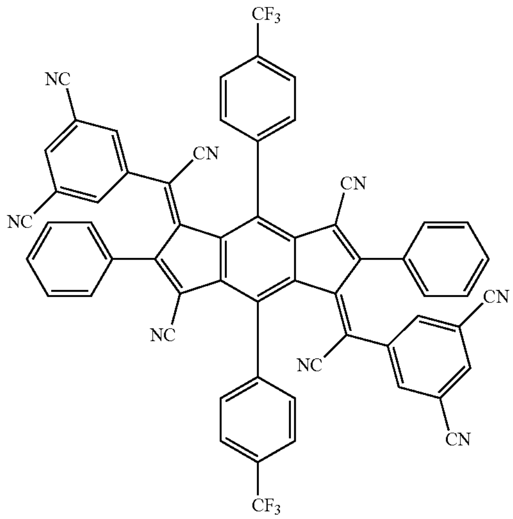
A29
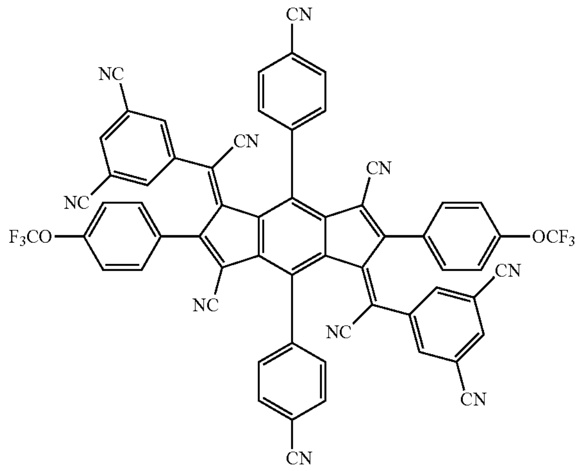

-continued
A30
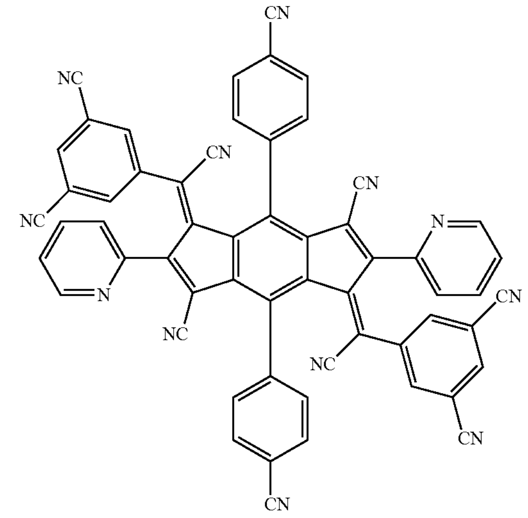
A31
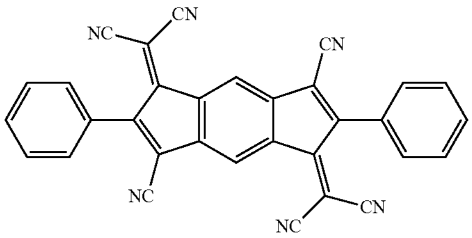
A32
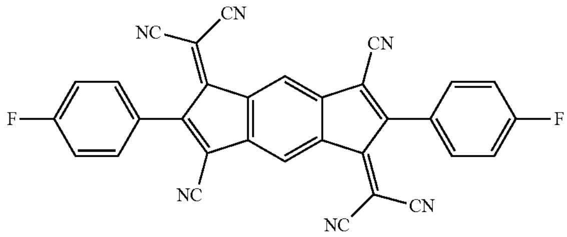
A33
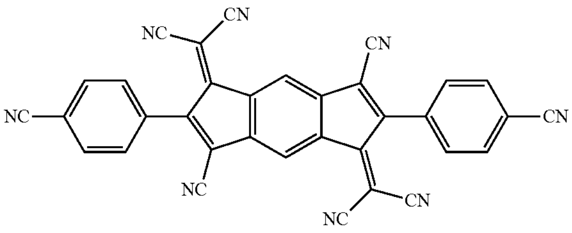
A34
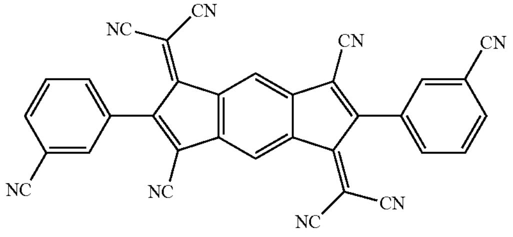
-continued
A35
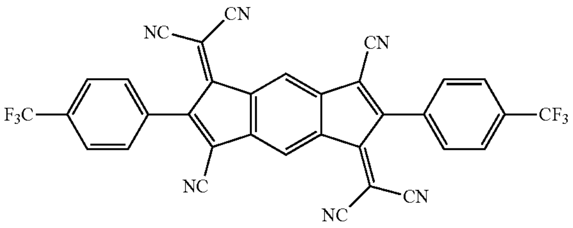
A36
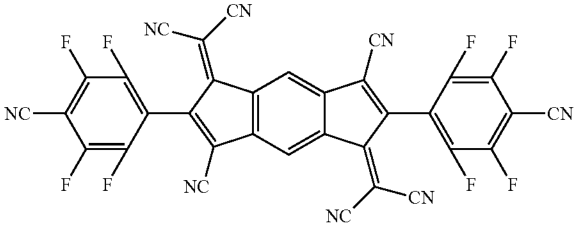
A37
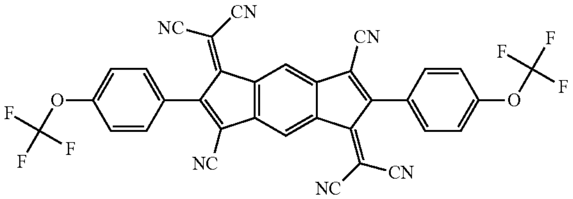
A38
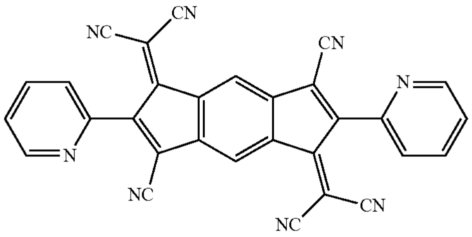
A39
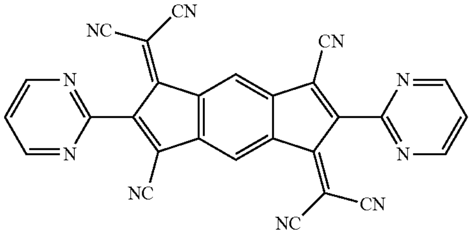
A40
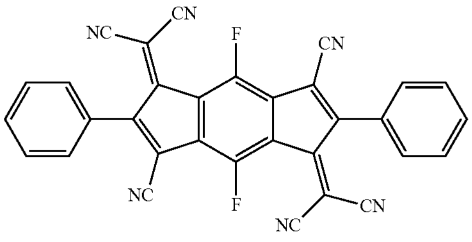

-continued
A41
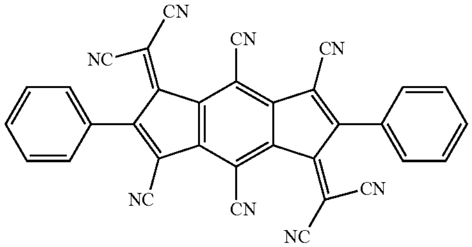
A42
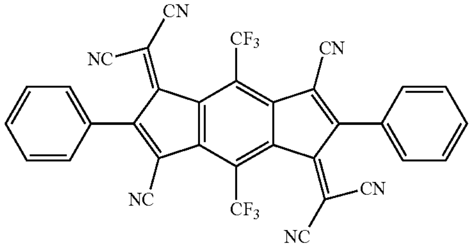
A43
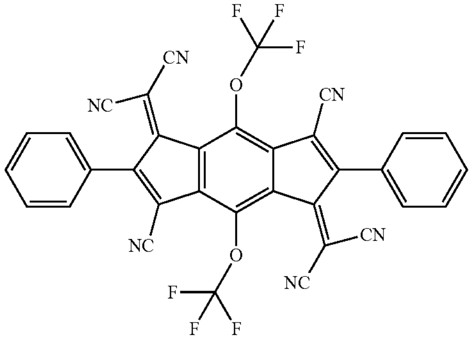
A44
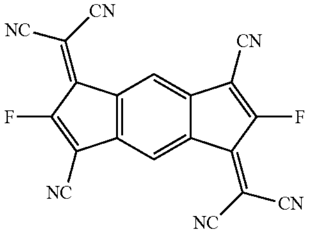
A45
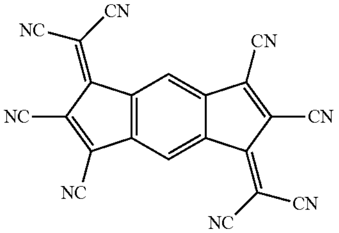
A46
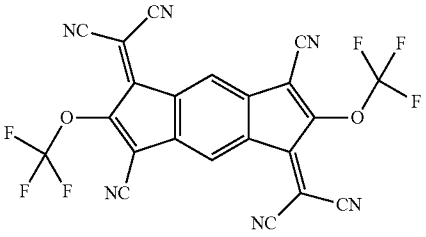
-continued
A47
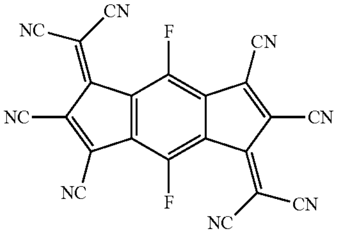
A48
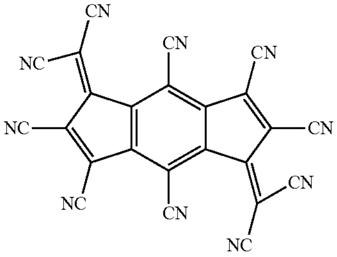
A49
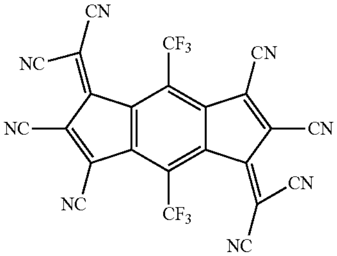
A50
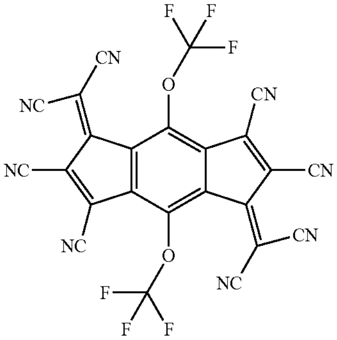
A51
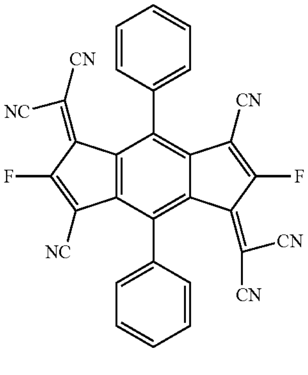

-continued
A52
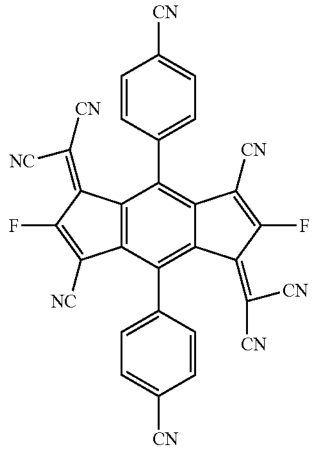
A53
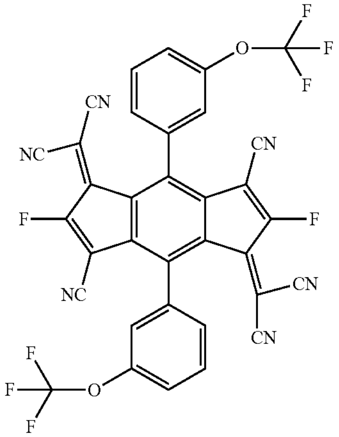
A54
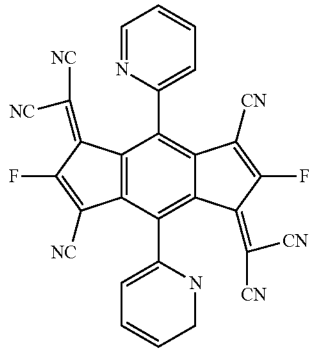
A55
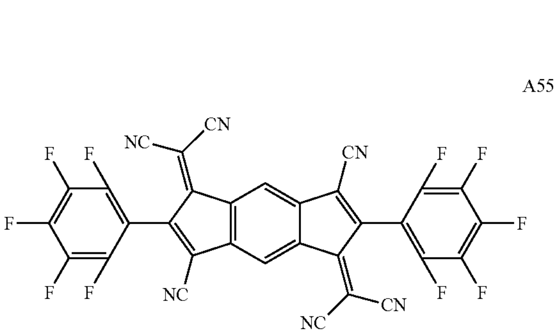
-continued
A56
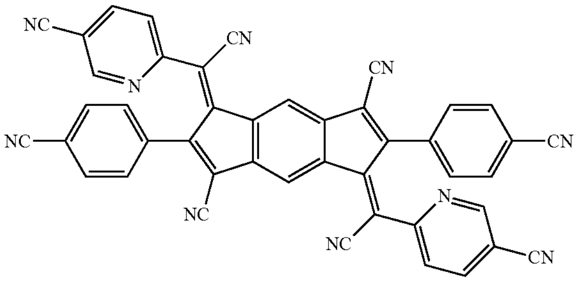
A57
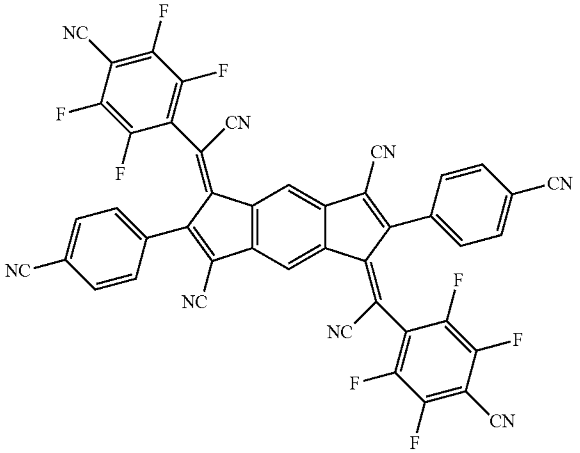
A58
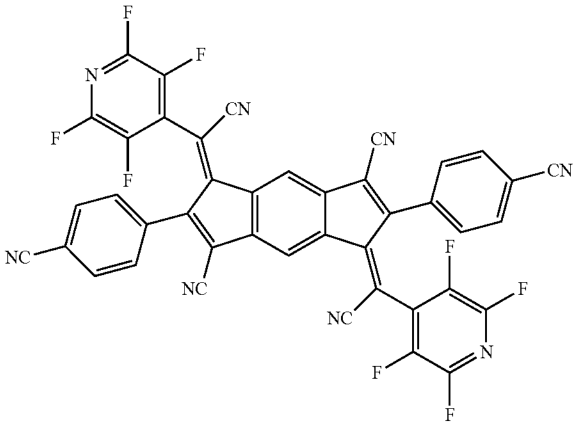
A59
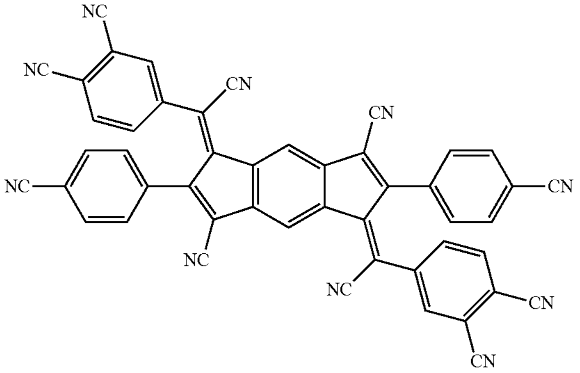

-continued
A60
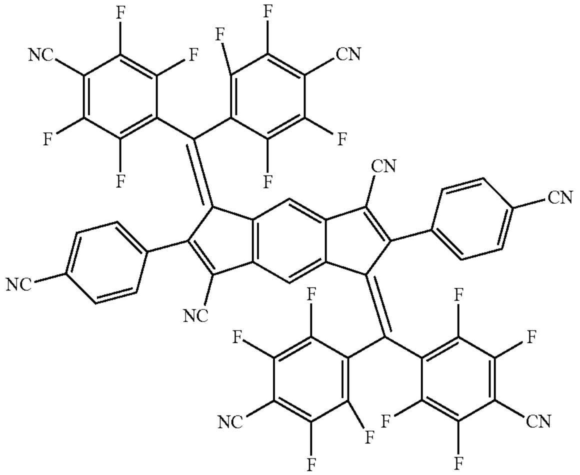
A61
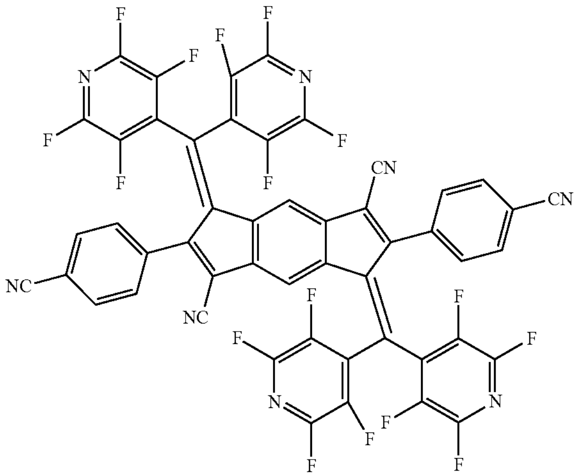
A62
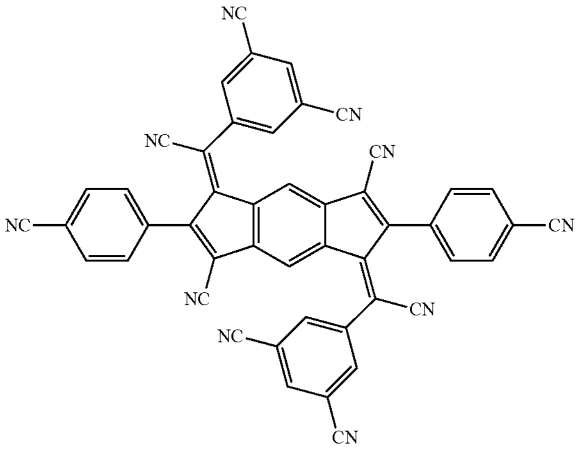
-continued
A63
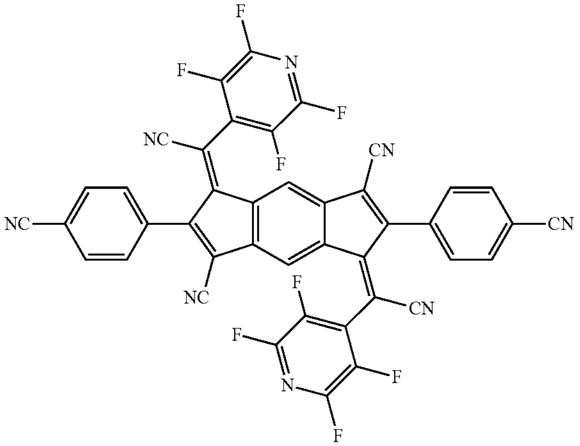
A64
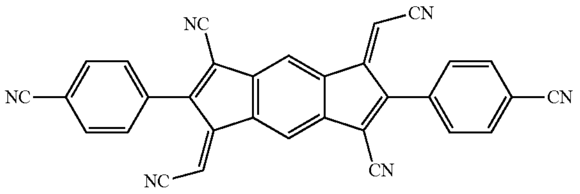
B1
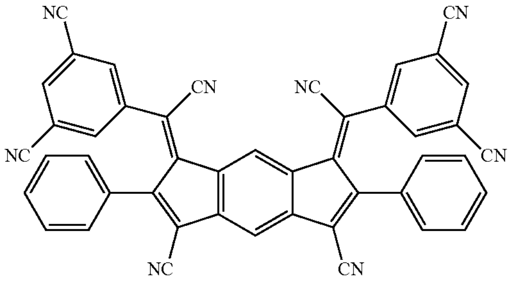
B2
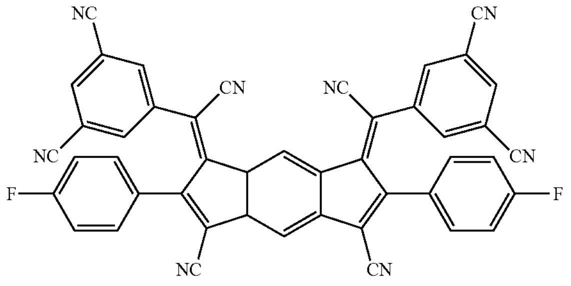
B3
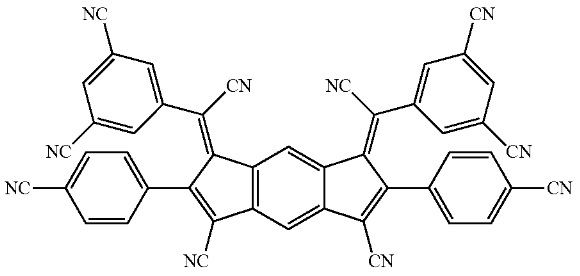

-continued
B4
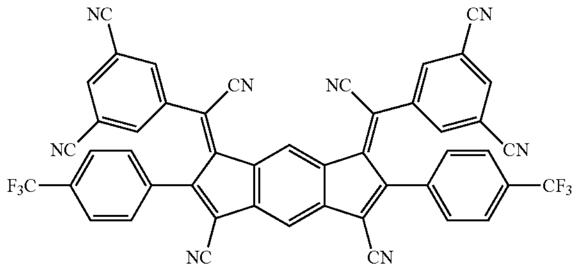
B5
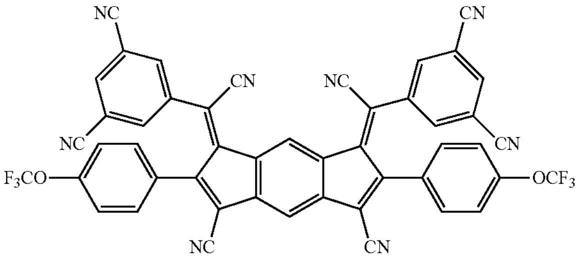
B6
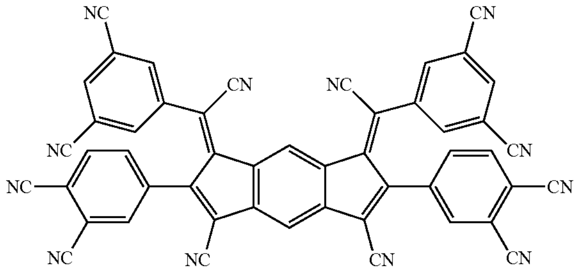
B7
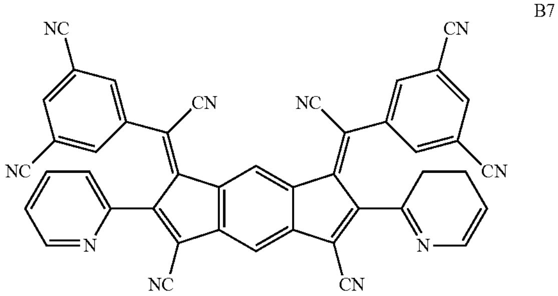
B8
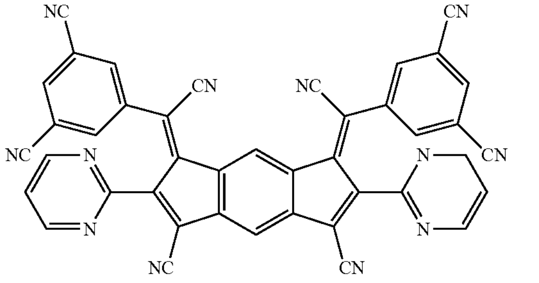
-continued
B9
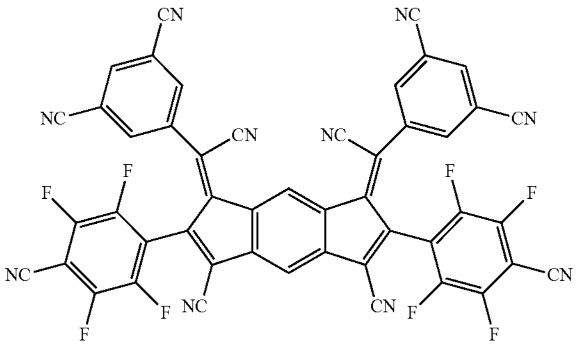
B10
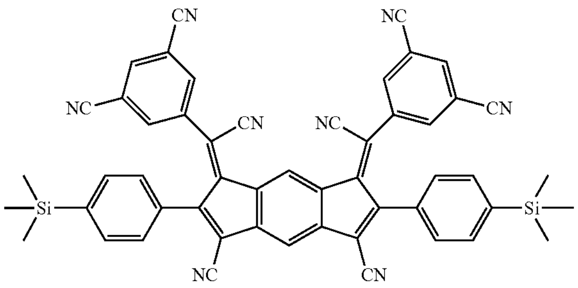
B11
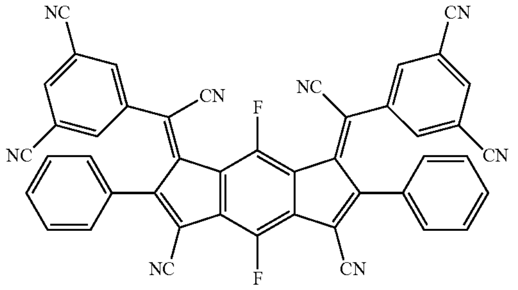
B12
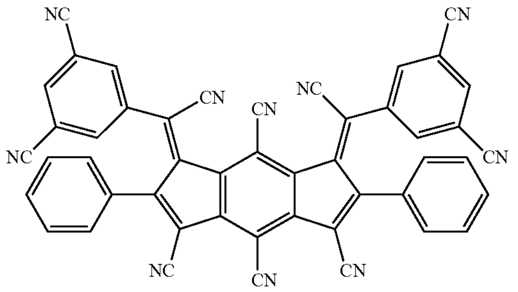
B13
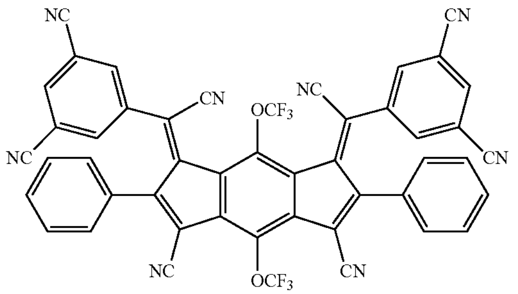

-continued
B14
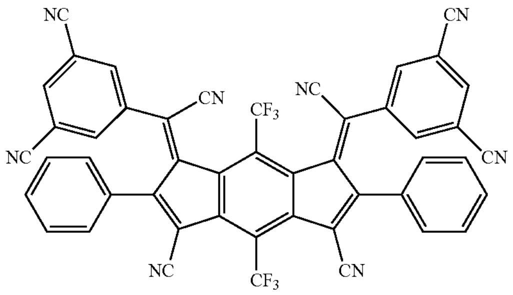
B15
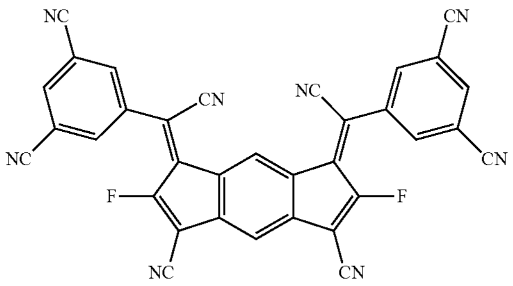
B16
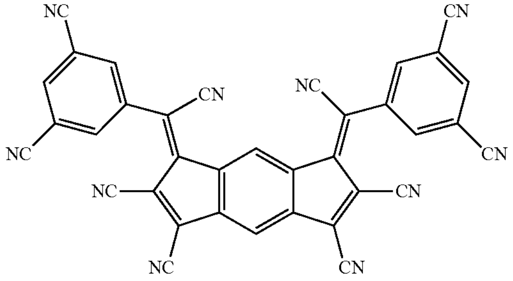
B17
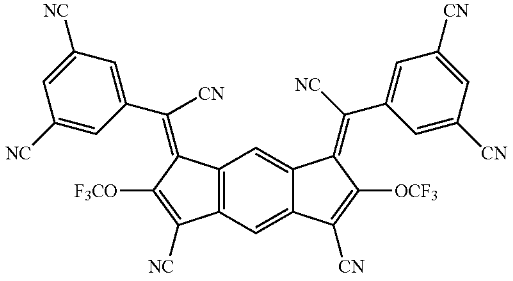
B18
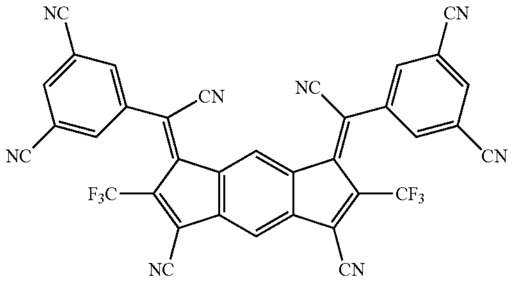
-continued
B19
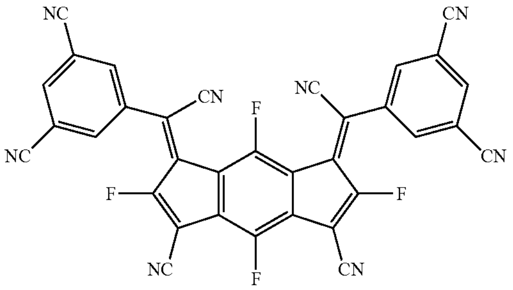
B20
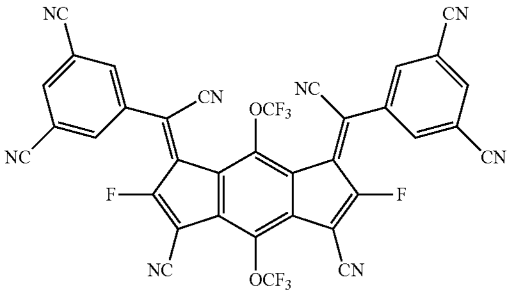
B21
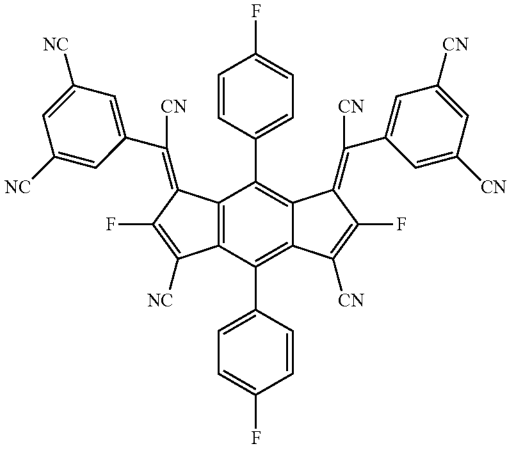
B22
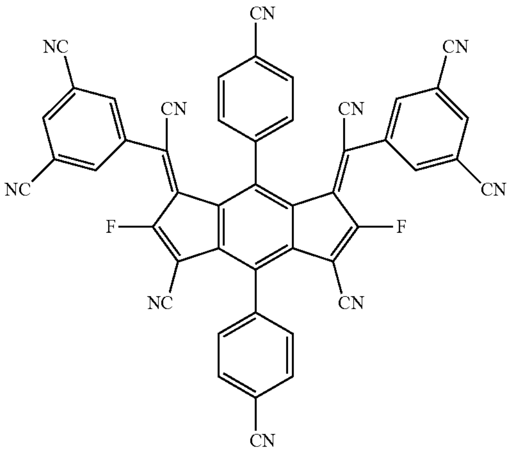

-continued
B23
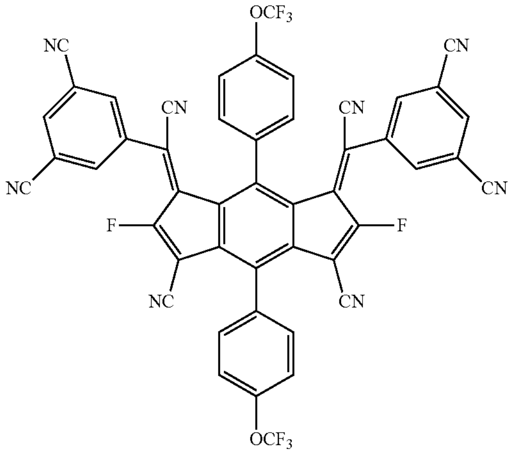
B24
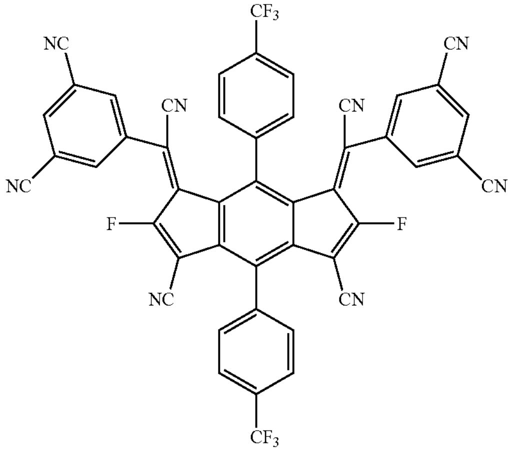
B25
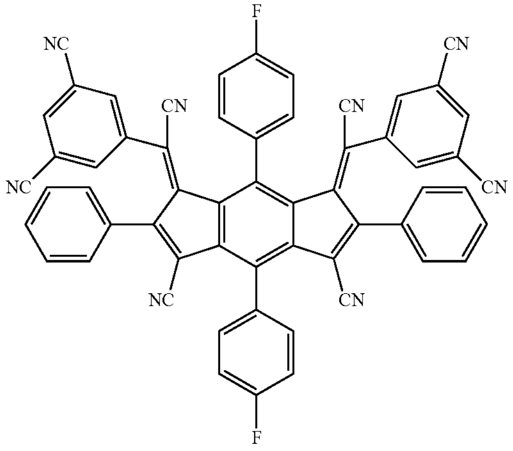
-continued
B26
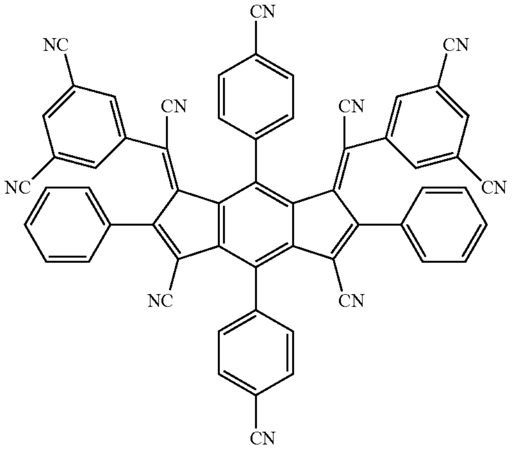
B27
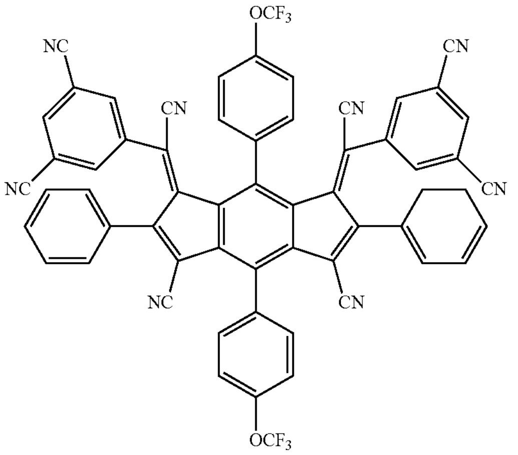
B28
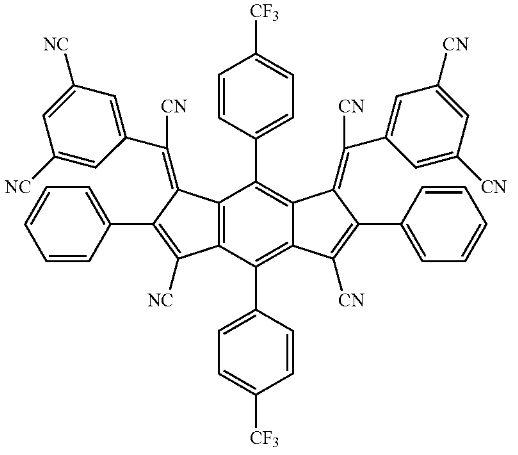

-continued
B29
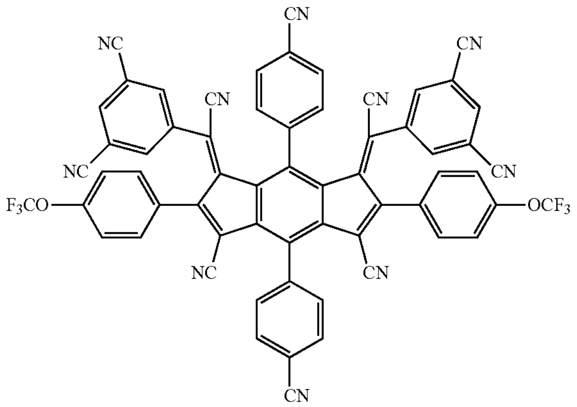
B30
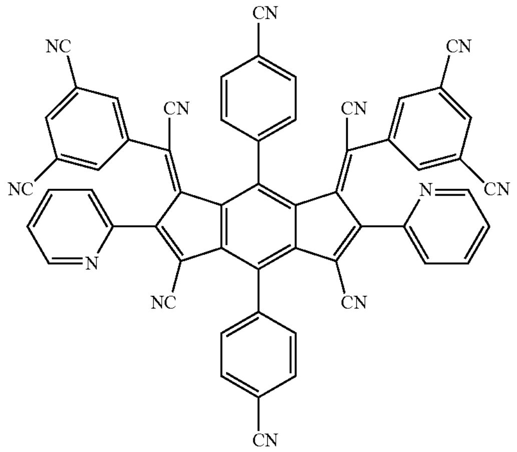
B31
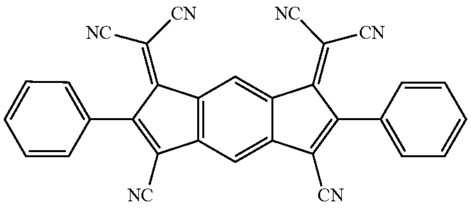
B32
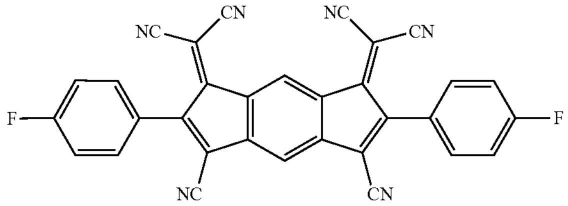
B33
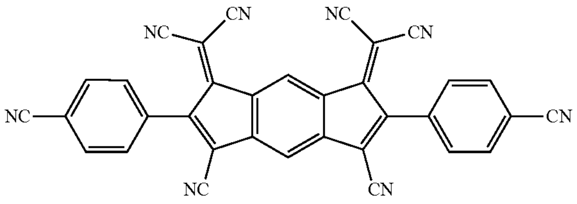
-continued
B34
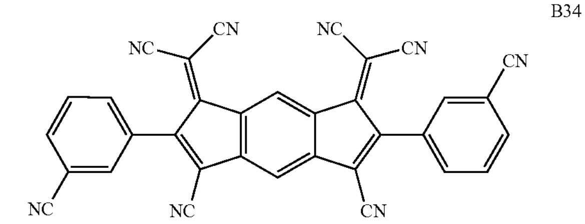
B35
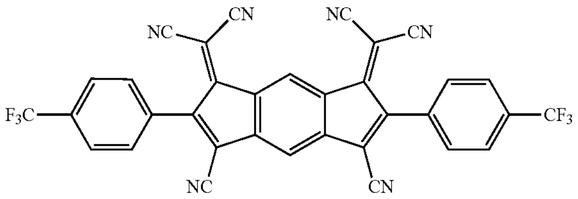
B36
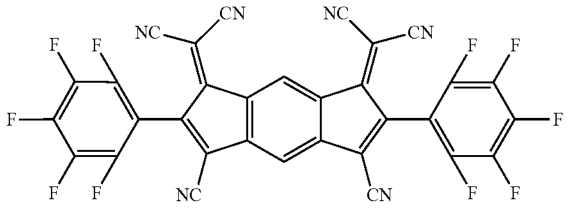
B37
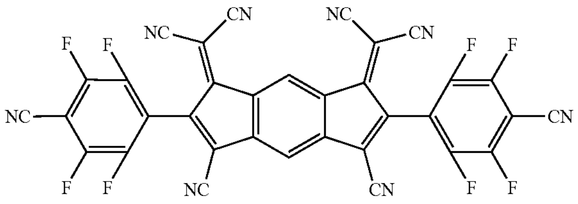
B38
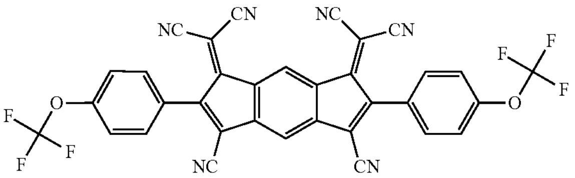
B39
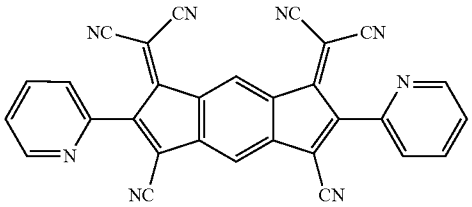
B40
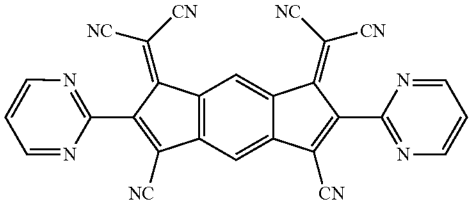

-continued
B41
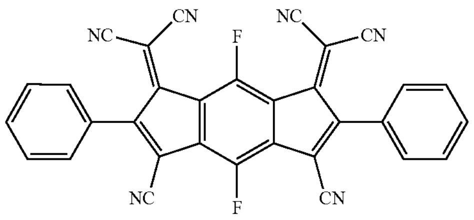
B42
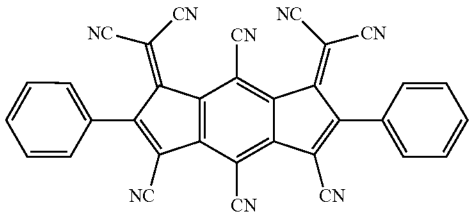
B43
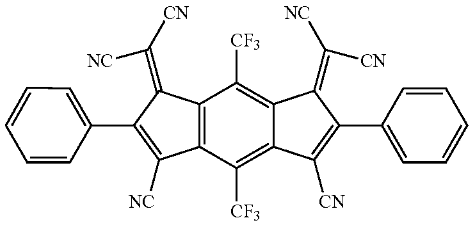
B44
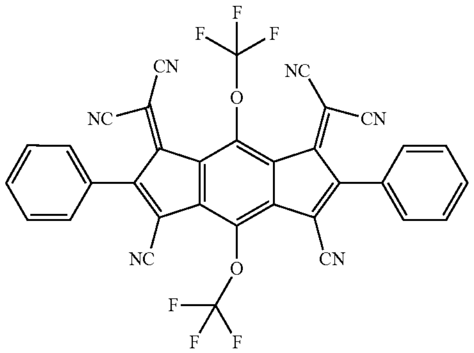
B45
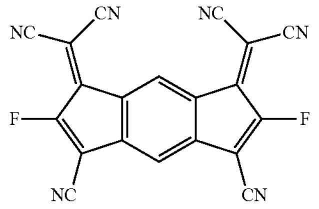
B46
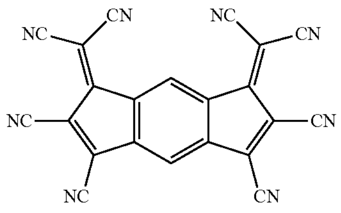
-continued
B47
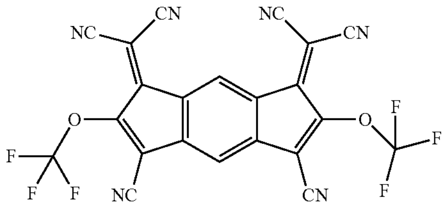
B48
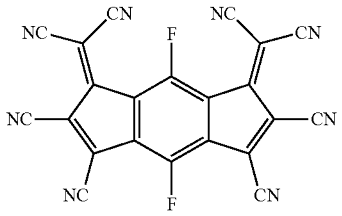
B49
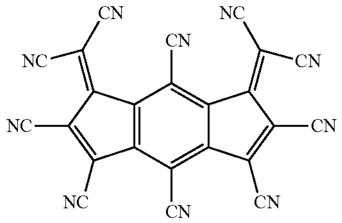
B50
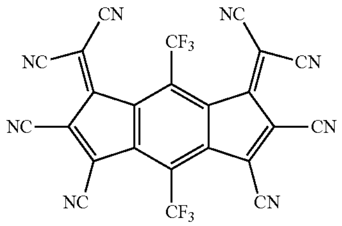
B51
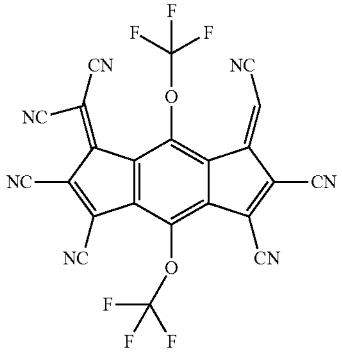
B52
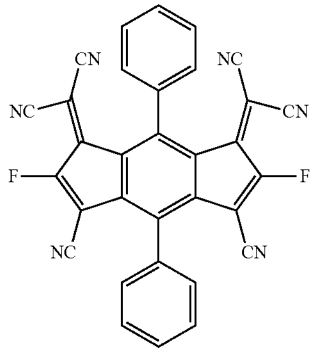

-continued

B53

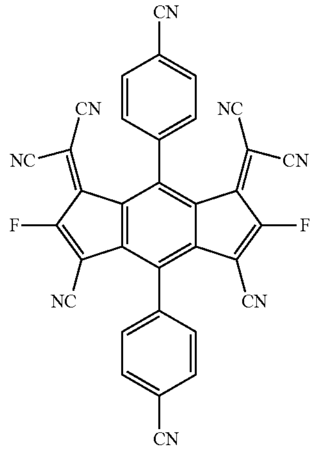

B54

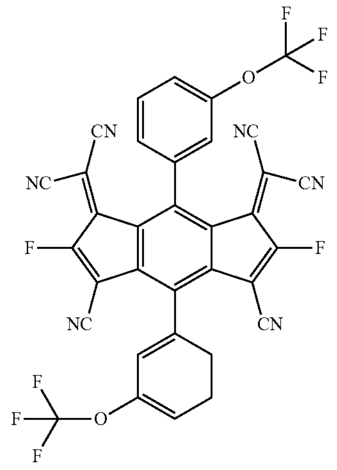

B55

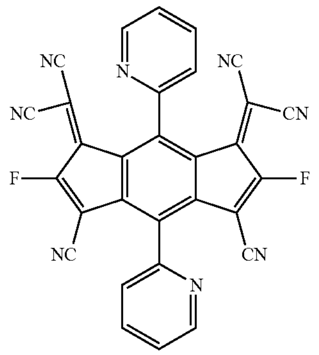

B56

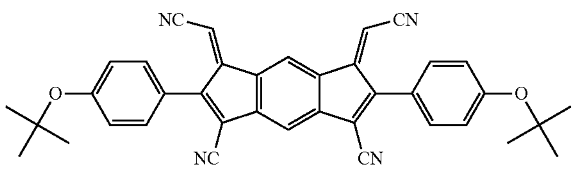

At least one of the first ETL 420, the n-type CGL 452 and the second ETL 440 includes the organic compound in Formula 1-1. For example, the first ETL 420 may include the organic compound of the present disclosure as a first electron transporting material 422. The second ETL 440 may include the organic compound of the present disclosure as a second electron transporting material 442. The n-type CGL 452 may include the organic compound of the present disclosure as an n-type charge generation material 456.

The first electron transporting material 422 of the first ETL 420, the second electron transporting material 442 of the second ETL 440, and the n-type charge generation material 456 of the n-type CGL 452 may be same or different.

When the n-type CGL 452 includes the organic compound of the present disclosure as the n-type charge generation material 456, the n-type CGL 452 may further include an auxiliary n-type charge generation material (not shown). For example, the auxiliary n-type charge generation material may be alkali metal, e.g., Li, Cs, K, Rb, Na or Fr, or alkali earth metal, e.g., Be, Mg, Ca, Sr, Ba or Ra. In the n-type CGL 452, the auxiliary n-type charge generation material may have a weight % of about 0.1 to 10 wt %, preferably about 0.5 to 5 wt %.

The OLED D including the first emitting part 410 providing the blue emission and the second emitting part 430 providing the yellow-green emission provides the white emission, and the CGL 450 including the organic compound of the present disclosure is provided between the first and second emitting parts 410 and 430. As a result, the OLED D has advantages in the driving voltage, the emitting efficiency and the lifespan.

Referring to FIG. 6, the organic emitting layer 362 includes a first emitting part 510 including a first EML 516 and a first ETL 520, a second emitting part 530 including a second EML 534 and a second ETL 540, a third emitting part 550 including a third EML 554 and a third ETL 560, a first CGL 570 between the first and second emitting parts 510 and 530 and a second CGL 580 between the second and third emitting parts 530 and 550.

The first CGL 570 is positioned between the first and second emitting parts 510 and 530, and the second CGL 580 is positioned between the second and third emitting parts 530 and 550. Namely, the first emitting part 510, the first CGL 570, the second emitting part 530, the second CGL 580 and the third emitting part 550 are sequentially stacked on the first electrode 360. In other words, the first emitting part 510 is positioned between the first electrode 360 and the first CGL 570, the second emitting part 530 is positioned between the first and second CGLs 570 and 580, and the third emitting part 550 is positioned between the second electrode 360 and the second CGL 580.

The first emitting part 510 may further include a first HTL 514 between the first electrode 360 and the first EML 516. In addition, the first emitting part 510 may further include an HTL 512 between the first electrode 360 and the first HTL 514.

Although not shown, the first emitting part 510 may further include at least one of an EBL between the first HTL 514 and the first EML 516 and an HBL between the first EML 516 and the first ETL 520.

The second emitting part 530 may further include a second HTL 532 under the second EML 534.

Although not shown, the second emitting part 510 may further include at least one of an EBL between the second HTL 532 and the second EML 534 and an HBL between the second EML 534 and the second ETL 550.

The third emitting part 550 may further include a third HTL 552 between the third EML 554 and the second CGL 580. In addition, the third emitting part 550 may further include an EIL 556 between the third ETL 560 and the second electrode 364.

Although not shown, the third emitting part 550 may further include at least one of an EBL between the third HTL

552 and the third EML 554 and an HBL between the third EML 554 and the third ETL 560.

Each of the first and third EMLs 516 and 554 provides the blue emission, and the third EML 534 provides the yellow-green emission. For example, the first and third EMLs 516 and 554, each of which may provide the blue emission, may include a host and a blue dopant, and the second EML 534, which may provide the yellow-green emission, may include a host and a yellow-green dopant. Alternatively, the second EML 534 may have a double-layered structure including a first layer, which provides the red emission, and a second layer, which provides the green emission. In addition, the second EML 534 may have a triple-layered structure including a first layer, which provides the red emission and includes a host and a red dopant, a second layer, which provides the yellow-green emission and includes a host and a yellow-green dopant, and a third layer, which provides the green emission and includes a host and a green dopant.

For example, in the first and third EMLs 516 and 554 each providing the blue emission, the host may be an anthracene derivative, the blue dopant may be a boron derivative.

The first CGL 570 includes a first n-type CGL 572 and a first p-type CGL 574. The first n-type CGL 572 is positioned between the first ETL 520 and the second HTL 532, and the first p-type CGL 574 is positioned between the first n-type CGL 572 and the second HTL 532.

The second CGL 580 includes a second n-type CGL 582 and a second p-type CGL 584. The second n-type CGL 582 is positioned between the second ETL 540 and the third HTL 552, and the second p-type CGL 584 is positioned between the second n-type CGL 582 and the third HTL 552.

The first n-type CGL 572 provides the electron toward the first ETL 520, and the electron is transferred into the first EML 516 through the first ETL 520. The first p-type CGL 574 provides the hole toward the second HTL 532, and the hole is transferred into the second EML 534 through the second HTL 532.

The second n-type CGL 582 provides the electron toward the second ETL 540, and the electron is transferred into the second EML 534 through the second ETL 540. The second p-type CGL 584 provides the hole toward the third HTL 552, and the hole is transferred into the third EML 554 through the third HTL 552.

As a result, in the OLED D having a three-stack (triple-stack) structure, the driving voltage is reduced, and the emitting efficiency is improved.

For example, each of the first and second p-type CGLs 574 and 584 may include one of HAT-CN, and the compound represented by Formula 8-1 or 8-2. In addition, each of the first and second p-type CGLs 574 and 584 may further include a metal or a p-type dopant.

At least one of the first ETL 520, the first n-type CGL 572, the second ETL 540, the second n-type CGL 582, and the third ETL 560 includes the organic compound in Formula 1-1. For example, the first ETL 520 may include the organic compound of the present disclosure as a first electron transporting material 522. The second ETL 540 may include the organic compound of the present disclosure as a second electron transporting material 542. The third ETL 560 may include the organic compound of the present disclosure as a third electron transporting material 562. The first n-type CGL 572 may include the organic compound of the present disclosure as a first n-type charge generation material 576. The second n-type CGL 582 may include the organic compound of the present disclosure as a second n-type charge generation material 586.

The first electron transporting material 522 of the first ETL 520, the second electron transporting material 542 of the second ETL 540, the third electron transporting material 562 of the third ETL 560, the first n-type charge generation material 576 of the first n-type CGL 572, and the second n-type charge generation material 586 of the second n-type CGL 582 may be same or different.

When each of the first and second n-type CGLs 572 and 582 includes the organic compound of the present disclosure as the first and second n-type charge generation materials 576 and 586, respectively, each of the first and second n-type CGLs 572 and 582 may further include an auxiliary n-type charge generation material (not shown). For example, the auxiliary n-type charge generation material may be alkali metal, e.g., Li, Cs, K, Rb, Na or Fr, or alkali earth metal, e.g., Be, Mg, Ca, Sr, Ba or Ra. In each of the first and second n-type CGLs 572 and 582, the auxiliary n-type charge generation material may have a weight % of about 0.1 to 10 wt %, preferably about 0.5 to 5 wt %.

The OLED D including the first and third emitting part 510 and 550 each providing the blue emission and the second emitting part 530 providing the yellow-green emission provides the white emission, and the first and second CGLs 570 and 580 including the organic compound of the present disclosure is provided between the first and second emitting parts 510 and 530 and between the second and third emitting parts 530 and 550, respectively. As a result, the OLED D has advantages in the driving voltage, the emitting efficiency and the lifespan.

Referring to FIG. 4 again, a second electrode 364 is formed over the substrate 310 where the organic emitting layer 362 is formed.

In the organic light emitting display device 300, since the light emitted from the organic emitting layer 362 is incident to the color filter layer 380 through the second electrode 364, the second electrode 364 has a thin profile for transmitting the light.

The first electrode 360, the organic emitting layer 362 and the second electrode 364 constitute the OLED D.

The color filter layer 380 is positioned over the OLED D and includes a red color filter 382, a green color filter 384 and a blue color filter 386 respectively corresponding to the red, green and blue pixel regions RP, GP and BP. The red color filter 382 may include at least one of red dye and red pigment, the green color filter 384 may include at least one of green dye and green pigment, and the blue color filter 386 may include at least one of blue dye and blue pigment.

Although not shown, the color filler layer 380 may be attached to the OLED D by using an adhesive layer. Alternatively, the color filter layer 380 may be formed directly on the OLED D.

An encapsulation film (not shown) may be formed to prevent penetration of moisture into the OLED D. For example, the encapsulation film may include a first inorganic insulating layer, an organic insulating layer and a second inorganic insulating layer sequentially stacked, but it is not limited thereto. The encapsulation film may be omitted.

A polarization plate (not shown) for reducing an ambient light reflection may be disposed over the top-emission type OLED D. For example, the polarization plate may be a circular polarization plate.

In the OLED of FIG. 4, the first and second electrodes 360 and 364 are a reflection electrode and a transparent (or semi-transparent) electrode, respectively, and the color filter layer 380 is disposed over the OLED D. Alternatively, when the first and second electrodes 360 and 364 are a transparent (or semi-transparent) electrode and a reflection electrode, respectively, the color filter layer 380 may be disposed between the OLED D and the first substrate 310.

A color conversion layer (not shown) may be formed between the OLED D and the color filter layer 380. The color conversion layer may include a red color conversion layer, a green color conversion layer and a blue color conversion layer respectively corresponding to the red, green and blue pixel regions RP, GP and BP. The white light from the OLED D is converted into the red light, the green light and the blue light by the red, green and blue color conversion layer, respectively. For example, the color conversion layer may include a quantum dot. Accordingly, the color purity of the organic light emitting display device 300 may be further improved.

The color conversion layer may be included instead of the color filter layer 380.

As described above, in the organic light emitting display device 300, the OLED D in the red, green and blue pixel regions RP, GP and BP emits the white light, and the white light from the organic light emitting diode D passes through the red color filter 382, the green color filter 384 and the blue color filter 386. As a result, the red light, the green light and the blue light are provided from the red pixel region RP, the green pixel region GP and the blue pixel region BP, respectively.

In FIG. 4, the OLED D emitting the white light is used for a display device. Alternatively, the OLED D may be formed on an entire surface of a substrate without at least one of the driving element and the color filter layer to be used for a lightening device. The display device and the lightening device each including the OLED D of the present disclosure may be referred to as an organic light emitting device.

In the OLED D and the organic light emitting display device 300, at least one of the ETL and the n-type CGL includes the organic compound of the present disclosure such that the electron transporting property into the EML is improved. Accordingly, in the OLED and the display device 300, the driving voltage is decreased, and the emitting efficiency and the lifespan are increased.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of patents, patent application publications, patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound of Formula 1-6:

[Formula 1-6]

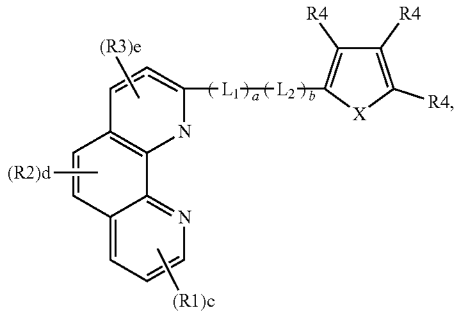

wherein X is oxygen (O) or sulfur (S), and each of R1 to R3 is independently selected from the group consisting of deuterium, halogen, cyano, C1 to C10 alkyl group, C1 to C10 alkoxy group, C3 to C30 cycloalkyl group, C6 to C30 aryl group, C6 to C30 arylamino group, and C5 to C30 heteroaryl group, wherein R4 is independently selected from the group consisting of C6 to C30 aryl group, wherein each of L1 and L2 is independently selected from the group consisting of C6 to C30 arylene group and C5 to C30 heteroarylene group, and wherein each of a and b is independently 0 or 1, c is an integer of 0 to 3, and each of d and e is independently an integer of 0 to 2.

2. An organic light emitting diode, comprising:

a first electrode;

a second electrode facing the first electrode; and a first emitting part including a first emitting material layer and a first electron transporting layer and positioned between the first and second electrodes, wherein the first electron transporting layer includes a first electron transporting material and is positioned between the first emitting material layer and the second electrode, wherein the first electron transporting material is an organic compound of Formula 1-6:

[Formula 1-6]

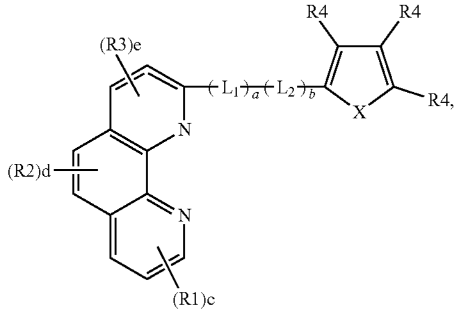

wherein X is oxygen (O) or sulfur (S), and each of R1 to R3 is independently selected from the group consisting of deuterium, halogen, cyano, C1 to C10 alkyl group, C1 to C10 alkoxy group, C3 to C30 cycloalkyl group, C6 to C30 aryl group, C6 to C30 arylamino group, and C5 to C30 heteroaryl group, wherein R4 is independently selected from the group consisting of C6 to C30 aryl group, wherein each of L1 and L2 is independently selected from the group consisting of C6 to C30 arylene group and C5 to C30 heteroarylene group, and wherein each of a and b is independently 0 or 1, c is an integer of 0 to 3, and each of d and e is independently an integer of 0 to 2.

3. The organic light emitting diode according to claim 2, further comprising:

a second emitting part including a second emitting material layer and a second electron transporting layer and positioned between the first emitting part and the second electrode, the second electron transporting layer including a second electron transporting material and positioned between the second emitting material layer and the second electrode; and a first n-type charge generation layer including a first n-type charge generation material and positioned between the first and second emitting parts.

4. The organic light emitting diode according to claim 3, wherein at least one of the second electron transporting material and the first n-type charge generation material is the organic compound of Formula 1.

5. The organic light emitting diode according to claim 3, wherein the first emitting material layer emits a blue light, and the second emitting material layer emits a yellow-green light.

6. The organic light emitting diode according to claim 3, wherein the first emitting material layer emits a blue light, and the second emitting material layer includes a first layer emitting a red light and a second layer emitting a green light.

7. The organic light emitting diode according to claim 3, further comprising:

a third emitting part including a third emitting material layer and a third electron transporting layer and positioned between the second emitting part and the second electrode, the third electron transporting layer including a third electron transporting material and positioned between the third emitting material layer and the second electrode; and a second n-type charge generation layer including a second n-type charge generation material and positioned between the second and third emitting parts.

8. The organic light emitting diode according to claim 7, wherein at least one of the second electron transporting material, the third electron transporting material, the first n-type charge generation material, and the second n-type charge generation material is the organic compound of Formula 1.

9. The organic light emitting diode according to claim 7, wherein each of the first and third emitting material layers emits a blue light, and the second emitting material layer emits a yellow-green light.

10. The organic light emitting diode according to claim 7, wherein each of the first and third emitting material layers emits a blue light, and the second emitting material layer includes a first layer emitting a red light and a second layer emitting a green light.

11. An organic light emitting diode, comprising:

a first electrode;

a second electrode facing the first electrode;

a first emitting part including a first emitting material layer and positioned between the first and second electrodes;

a second emitting part including a second emitting material layer and positioned between the first emitting part and the second electrode; and a first n-type charge generation layer including a first n-type charge generation material and positioned between the first and second emitting parts, wherein the first n-type charge generation material is an organic compound of Formula 1-6:

[Formula 1-6]

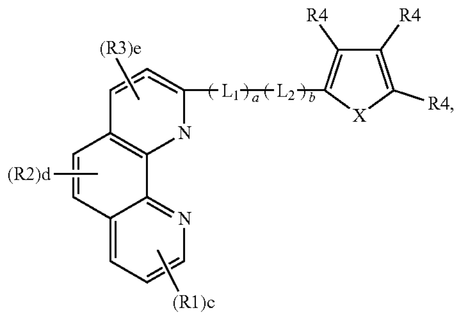

wherein X is oxygen (O) or sulfur (S), and each of R1 to R3 is independently selected from the group consisting of deuterium, halogen, cyano, C1 to C10 alkyl group, C1 to C10 alkoxy group, C3 to C30 cycloalkyl group, C6 to C30 aryl group, C6 to C30 arylamino group, and C5 to C30 heteroaryl group, wherein R4 is independently selected from the group consisting of C6 to C30 aryl group, wherein each of L1 and L2 is independently selected from the group consisting of C6 to C30 arylene group and C5 to C30 heteroarylene group, and wherein each of a and b is independently 0 or 1, c is an integer of 0 to 3, and each of d and e is independently an integer of 0 to 2.

12. The organic light emitting diode according to claim 11, wherein the first n-type charge generation layer further includes a metal or a p-type dopant.

13. The organic light emitting diode according to claim 11, further comprising:

a third emitting part including a third emitting material layer and positioned between the second emitting part and the second electrode; and a second n-type charge generation layer including a second n-type charge generation material and positioned between the second and third emitting parts.

14. The organic light emitting diode according to claim 13, wherein the second n-type charge generation material is the organic compound of Formula 1.

15. An organic light emitting device, comprising:

a substrate;

the organic light emitting diode according to claim 2 over the substrate; and an encapsulation film covering the organic light emitting diode.

16. The organic light emitting device according to claim 15, wherein a red pixel region, a green pixel region and a blue pixel region are defined on the substrate, and the organic light emitting diode corresponds to each of the red, green and blue pixel regions, and wherein the organic light emitting device further includes:

a color filter layer disposed between the substrate and the organic light emitting diode or on the organic light emitting diode and corresponding to the red, green and blue pixel regions.

17. The organic compound according to claim 1, wherein the organic compound is one of compounds in Formula 2:

[Formula 2]
D5
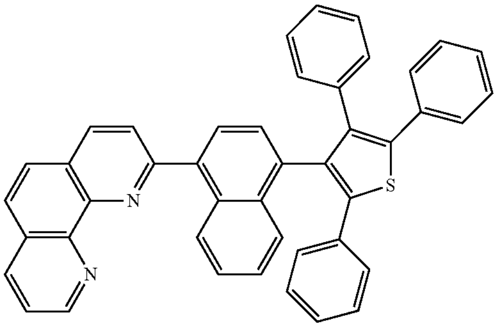
D6
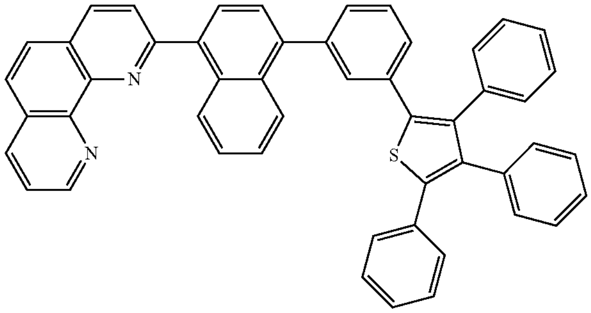
D7
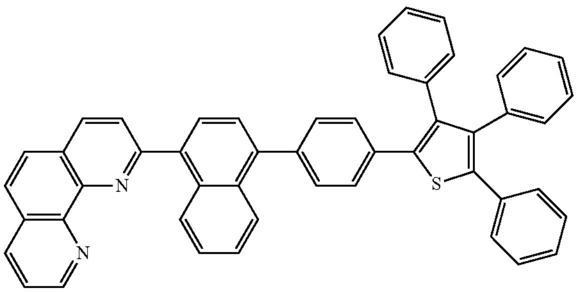
D8
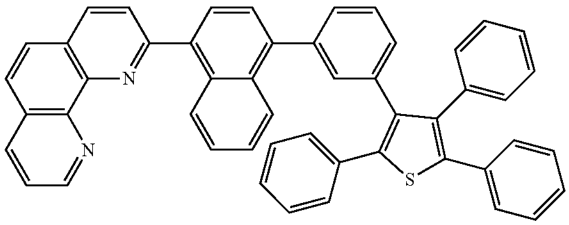
D9
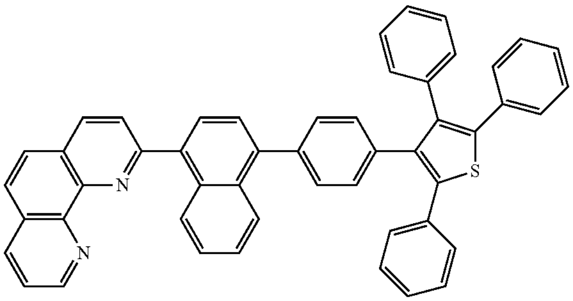
D14
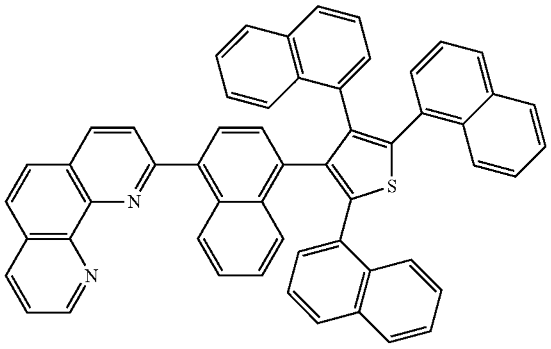
D15
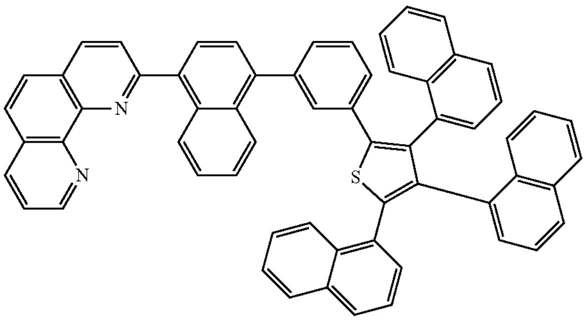
D16
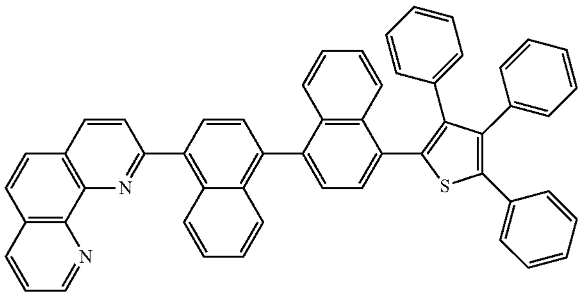

-continued
D17
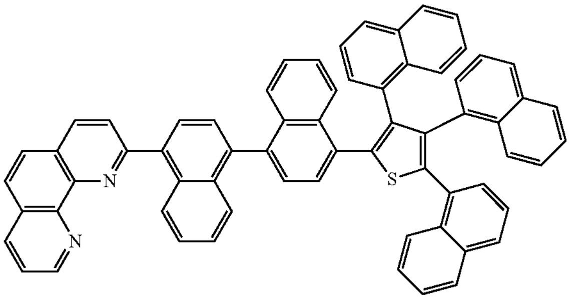
D18
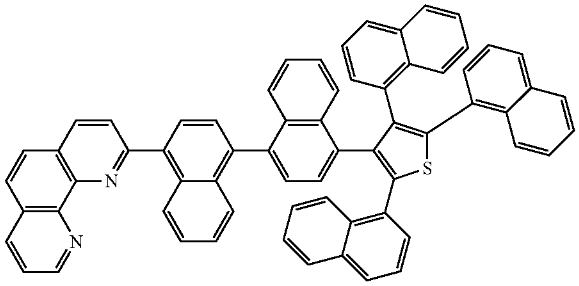
D21
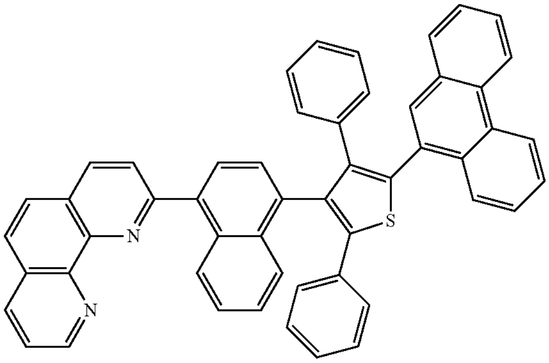
D22
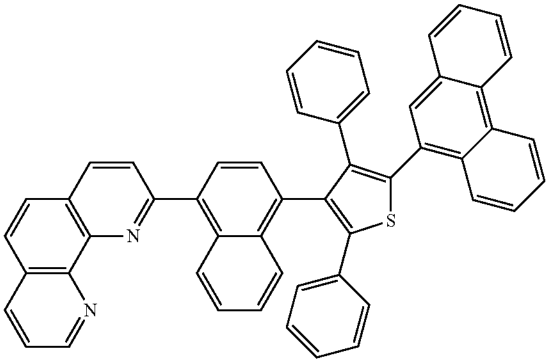
D23
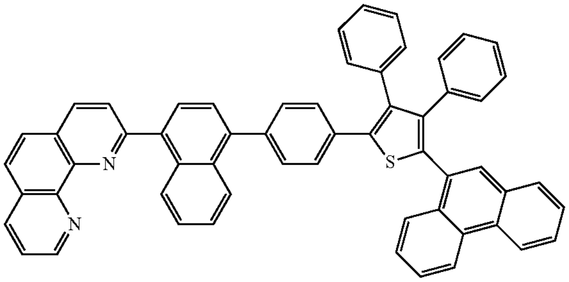
D24
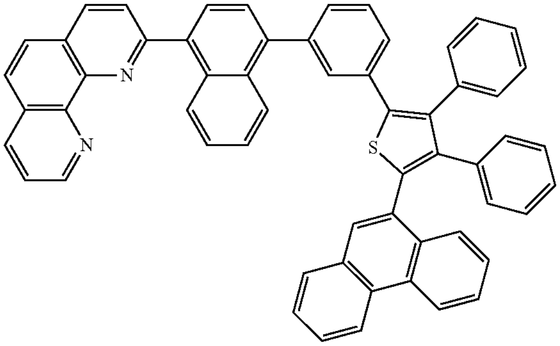
D25
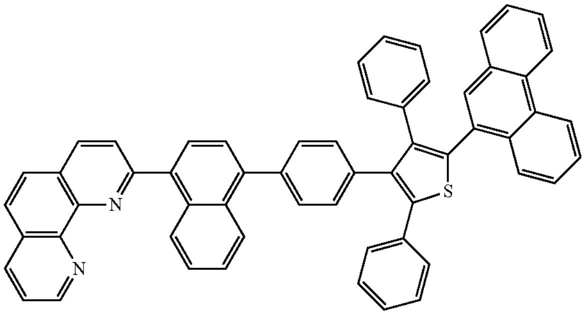
D26
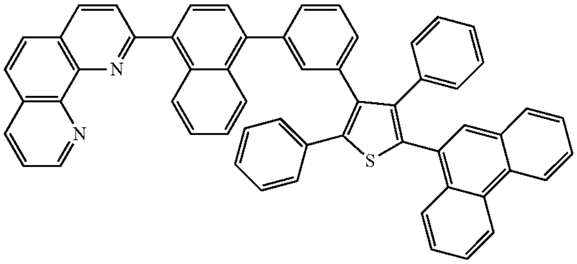

-continued
D28
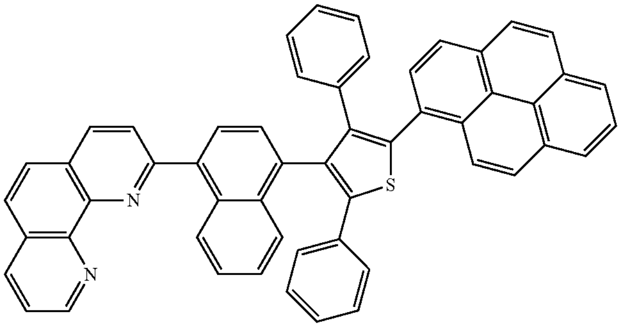
D29
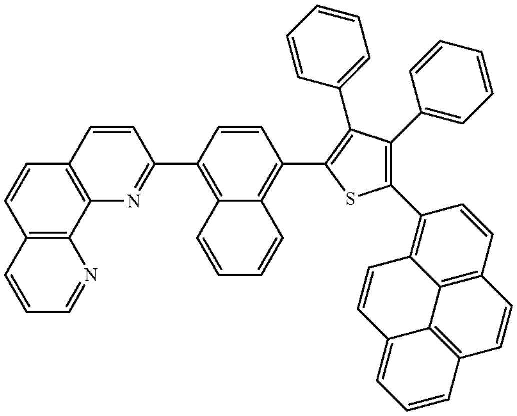
D30
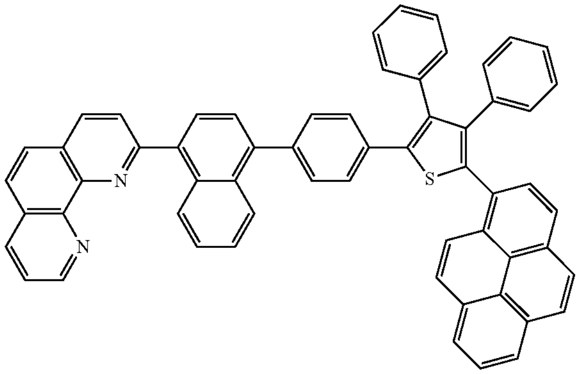
D31
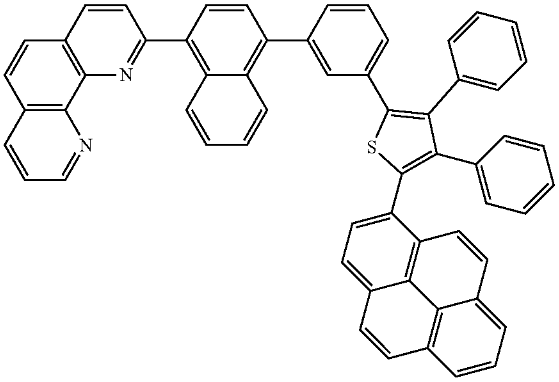
D32
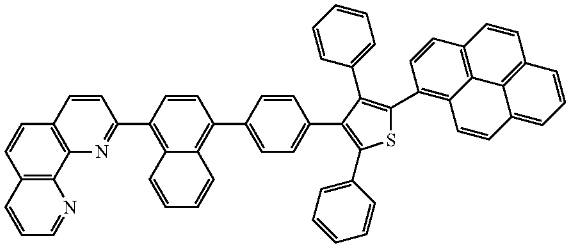
D33
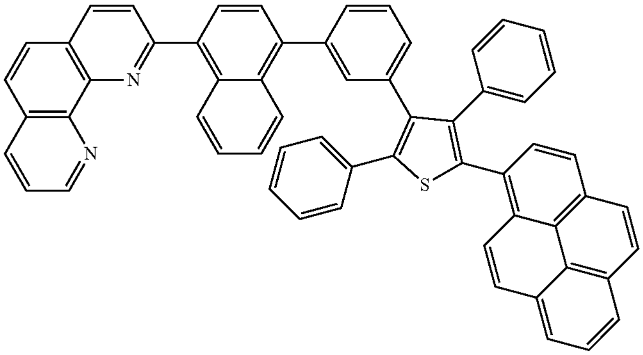

-continued
D35
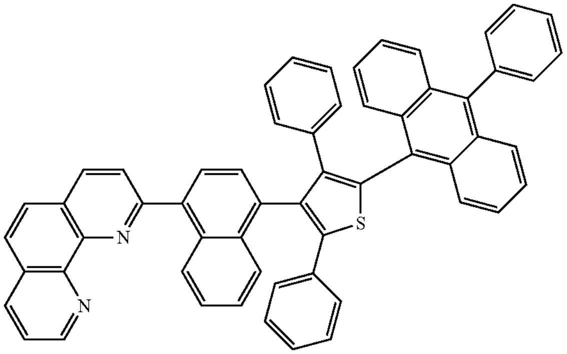
D36
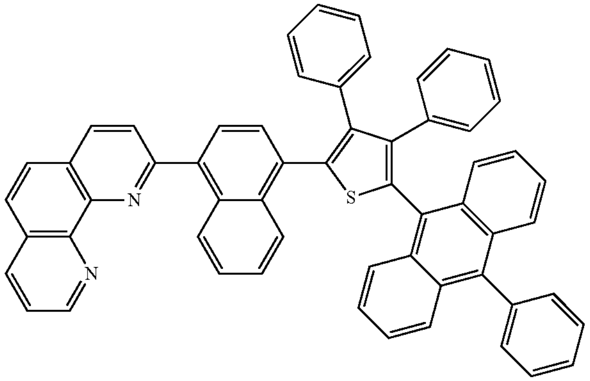
D37
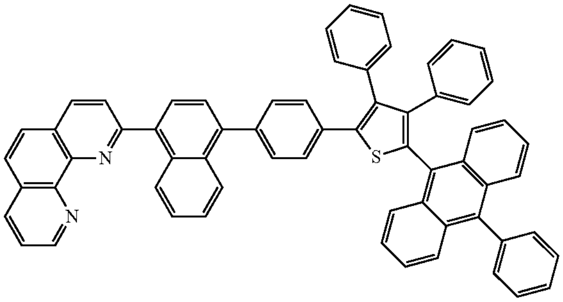
D38
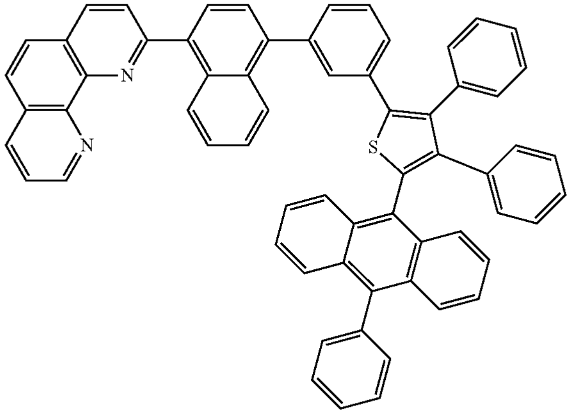
D39
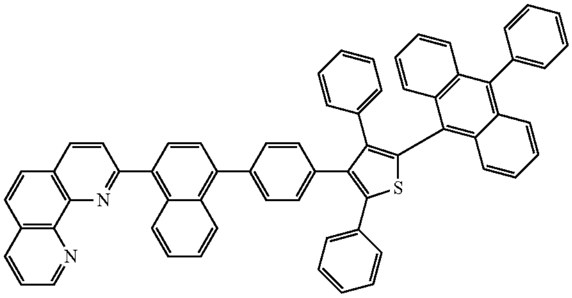
D40
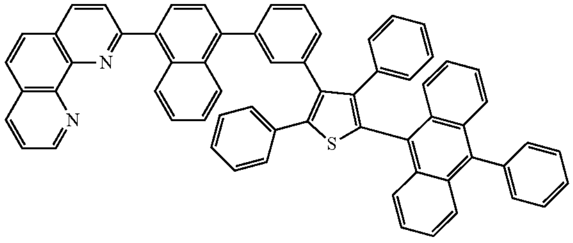
D45
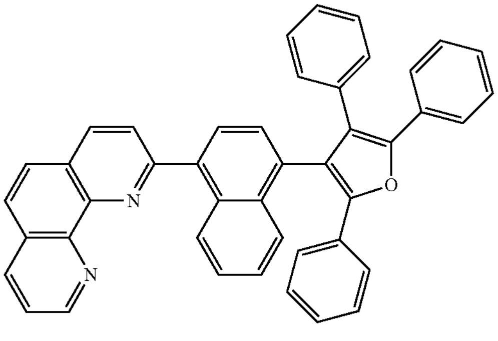
D46
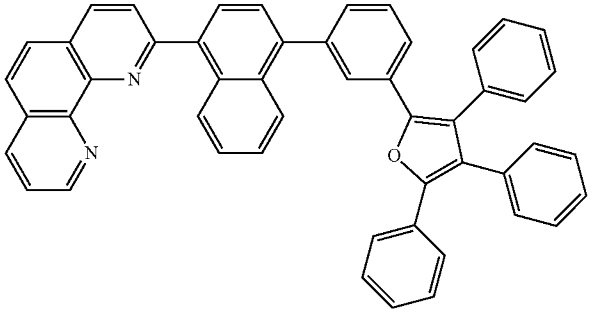

-continued
D47
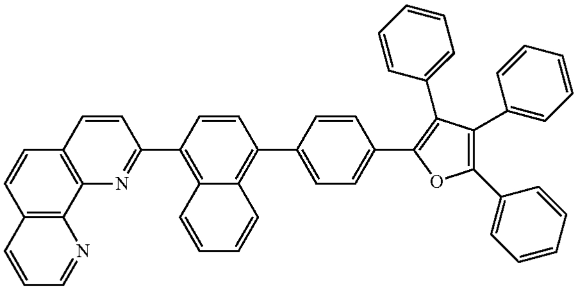
D48
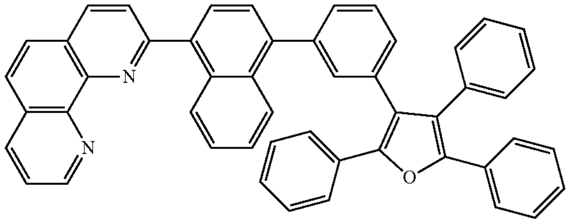
D49
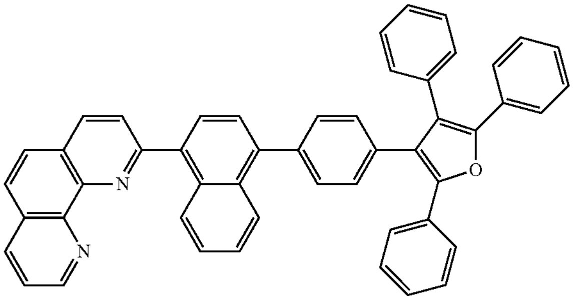
D54
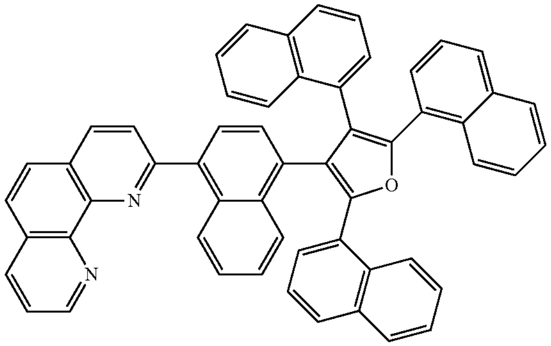
D55
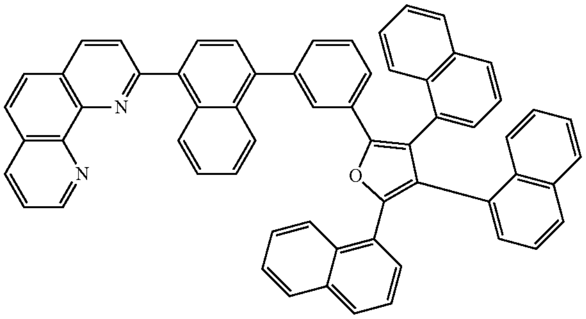
D56
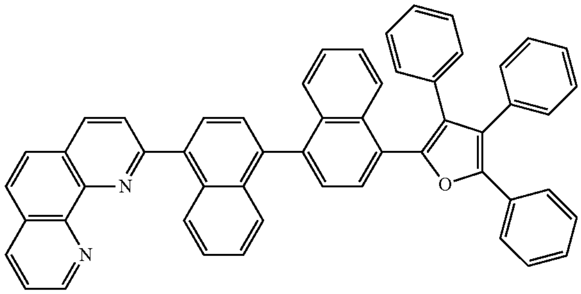
D57
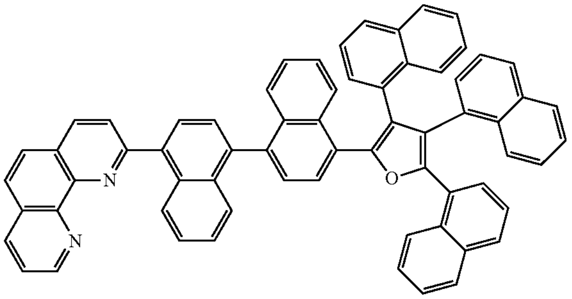
D58
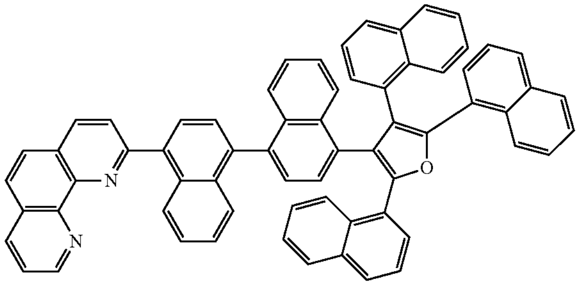

-continued
D61
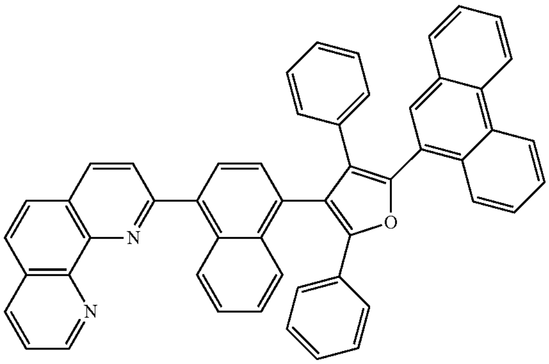
D62
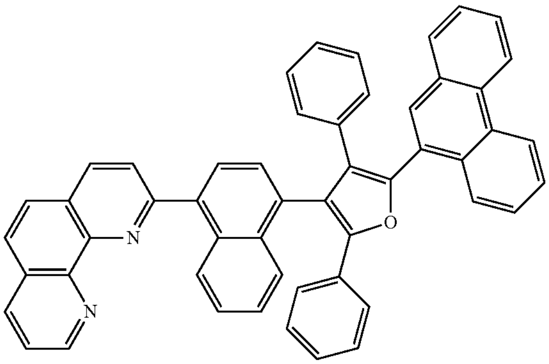
D63
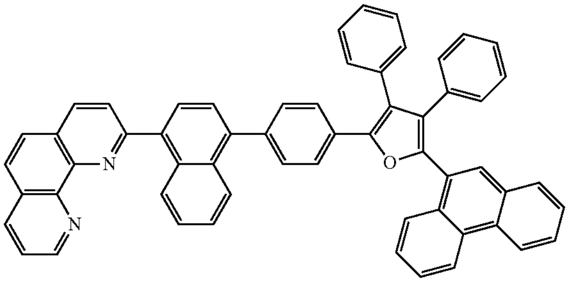
D64
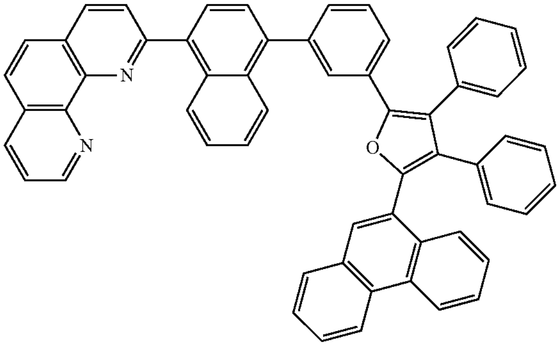
D65
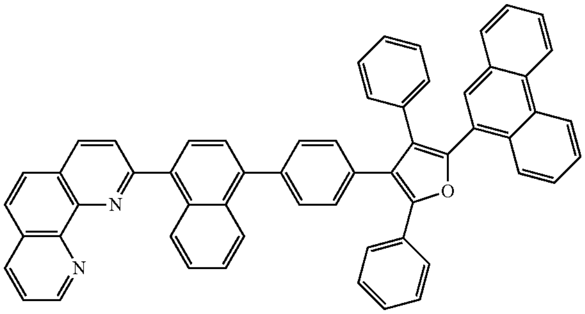
D66
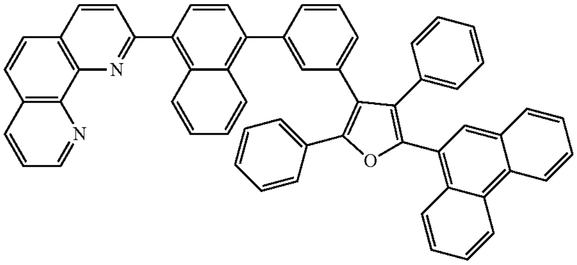
-continued
D68
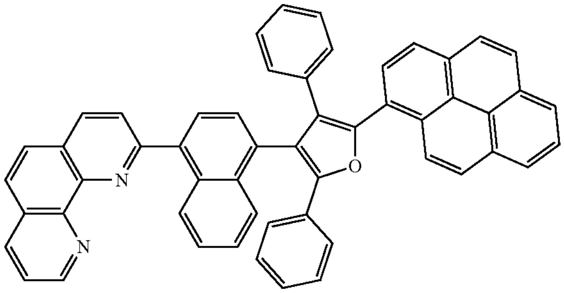
D69
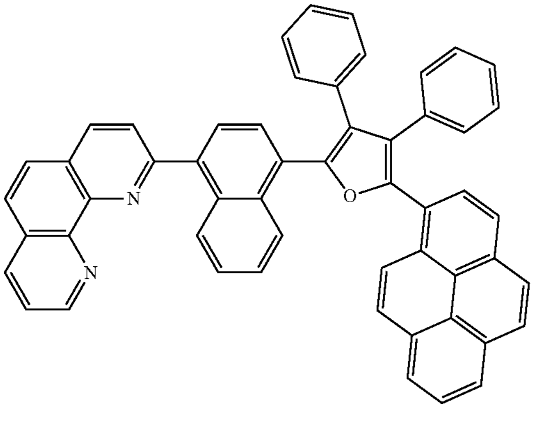

-continued
D70
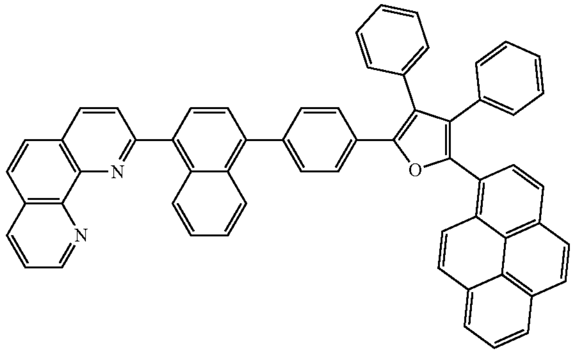
D71
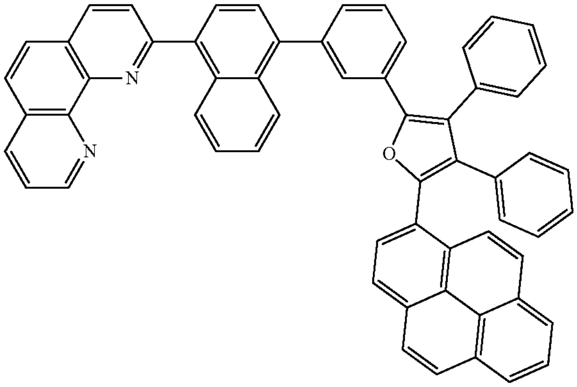
D72
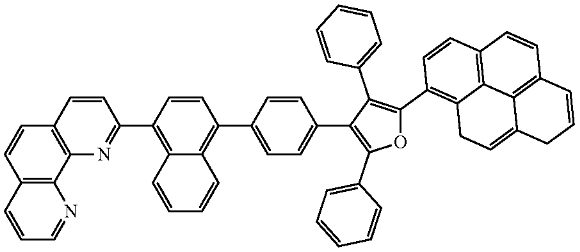
D73
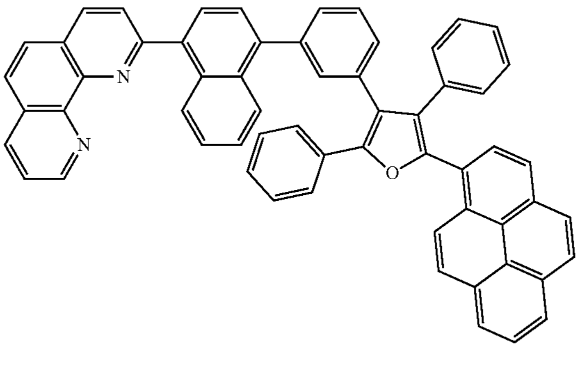
-continued
D75
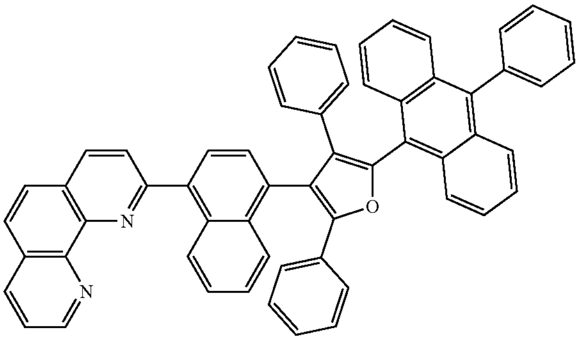
D76
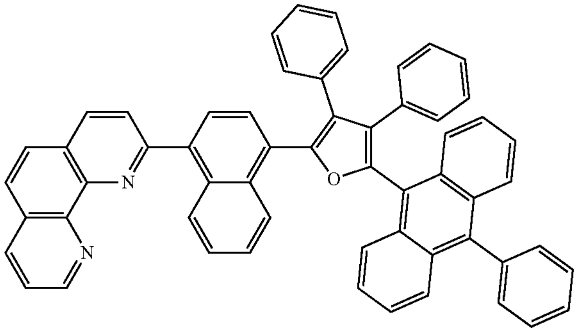
D77
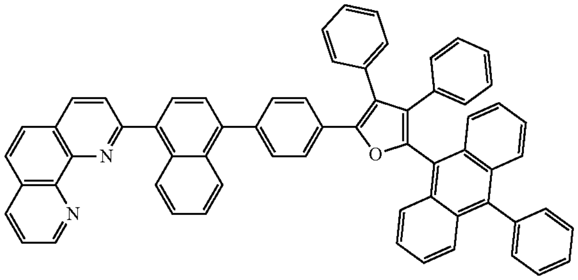
D78
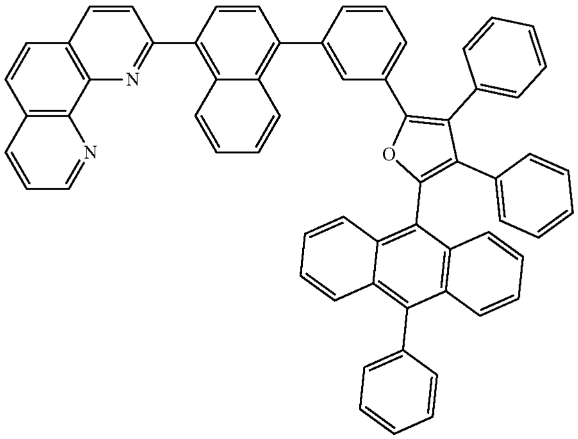

-continued
D79
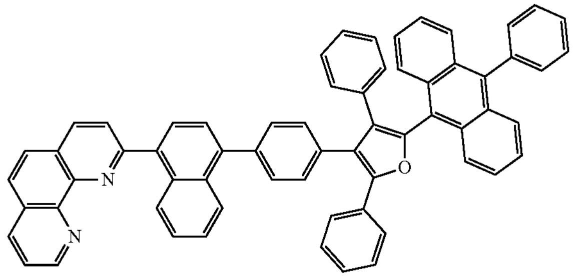
D80
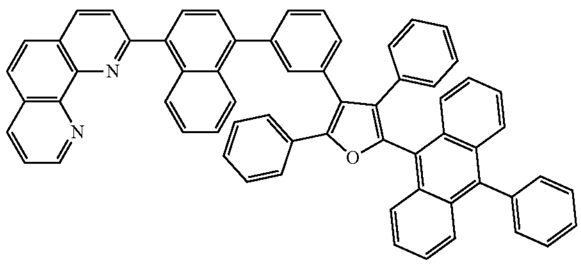
D85
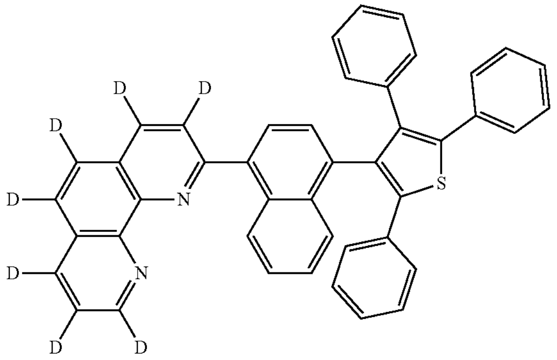
D86
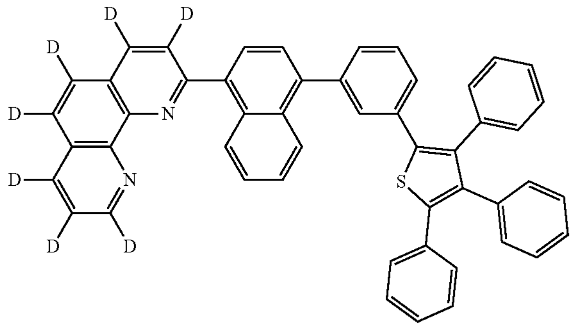
D87
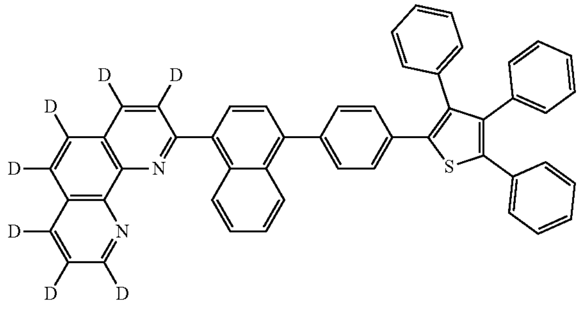
-continued
D88
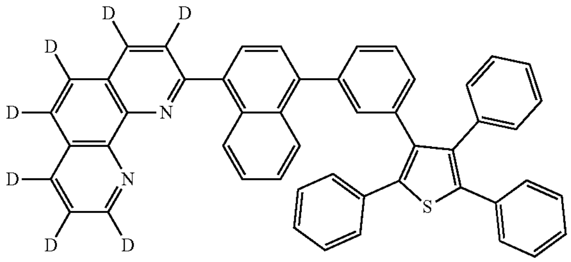
D89
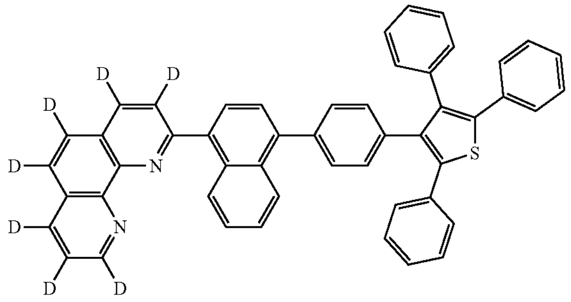
D94
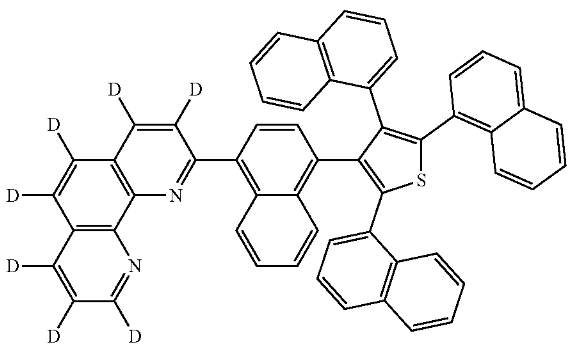
D95
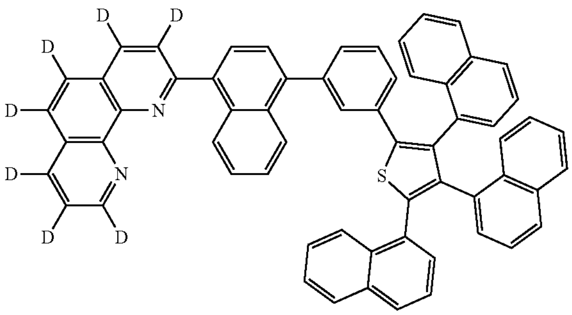
D96
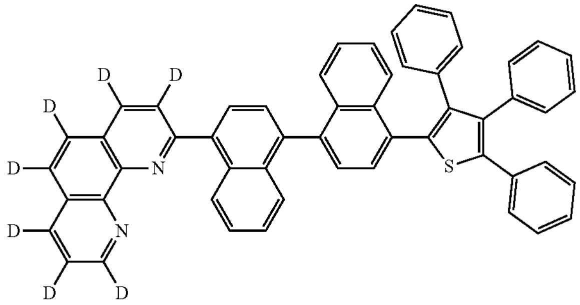

-continued
D97
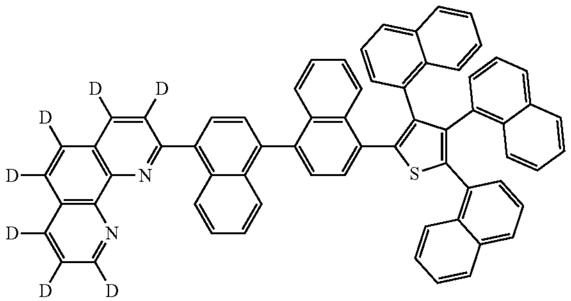
D98
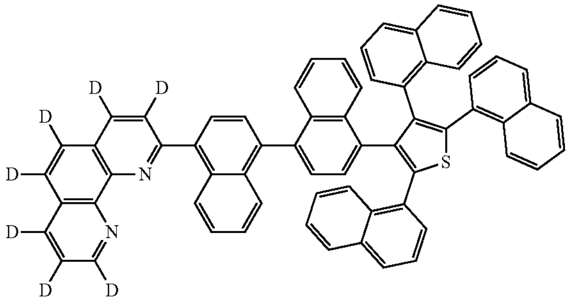
D101
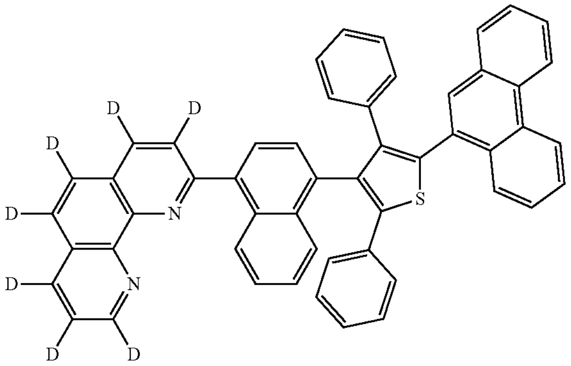
D102
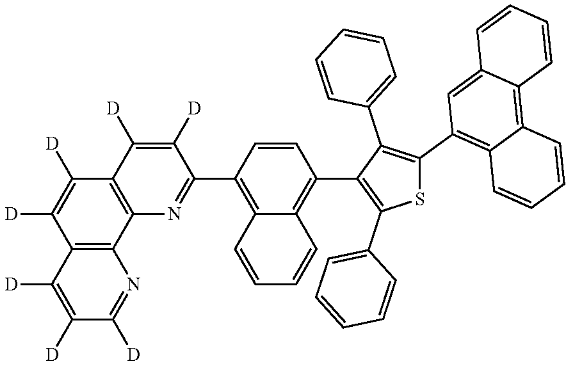
-continued
D103
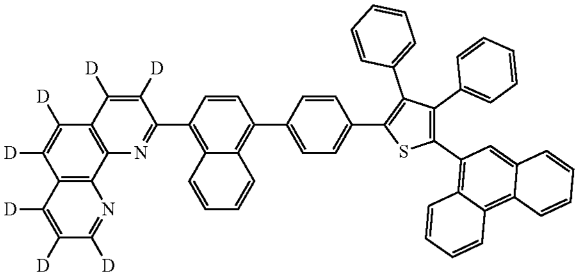
D104
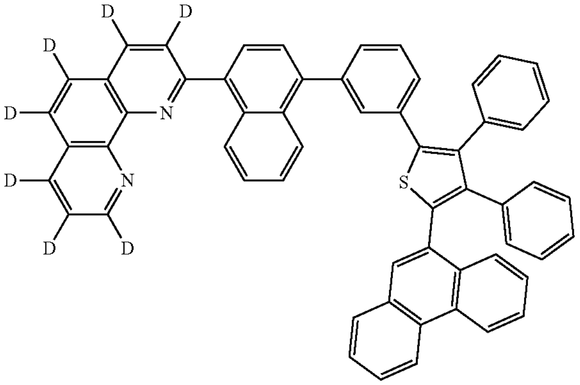
D105
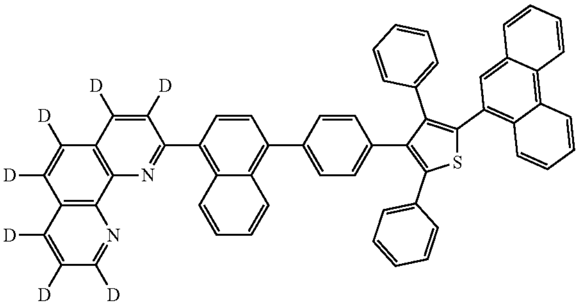
D106
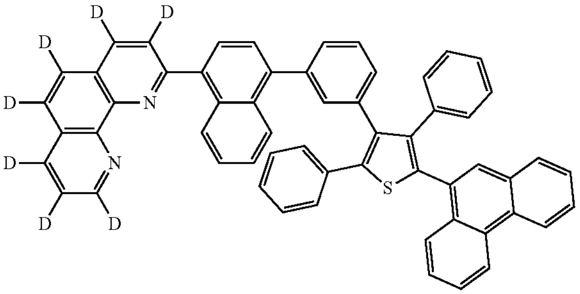

-continued
D108
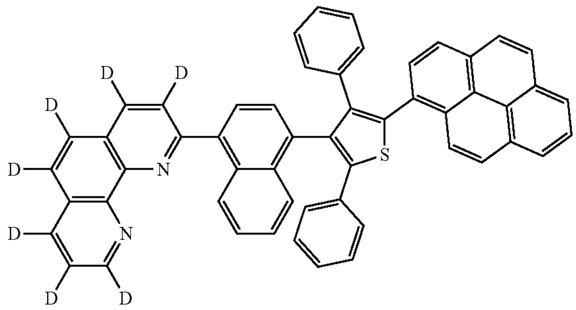
D109
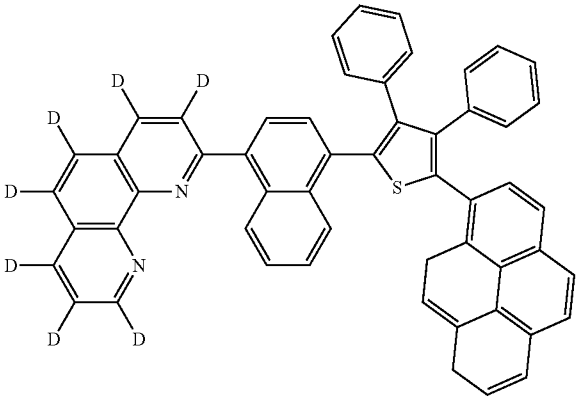
D110
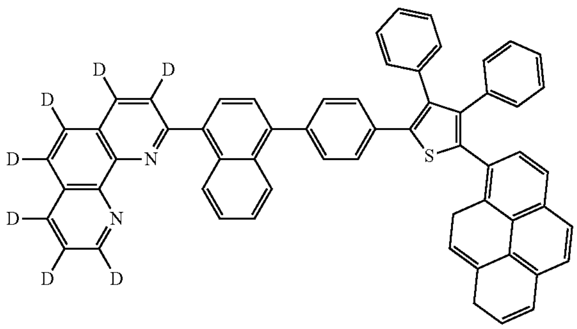
D111
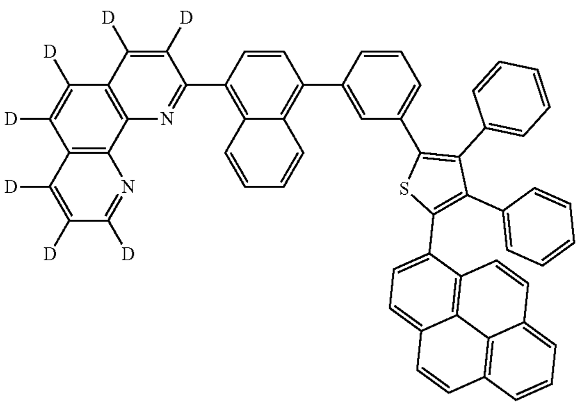
-continued
D112
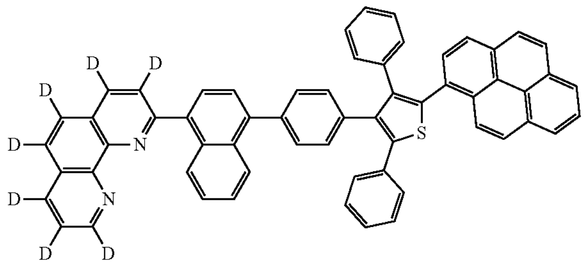
D113
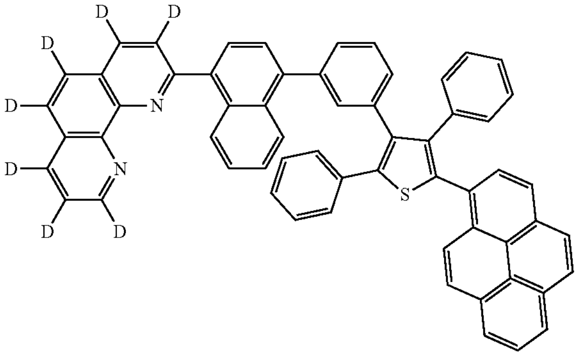
D115
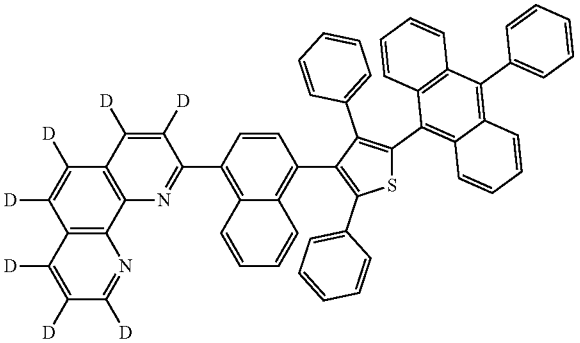
D116
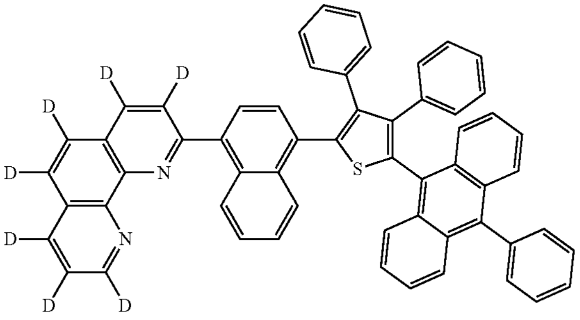

-continued
D117
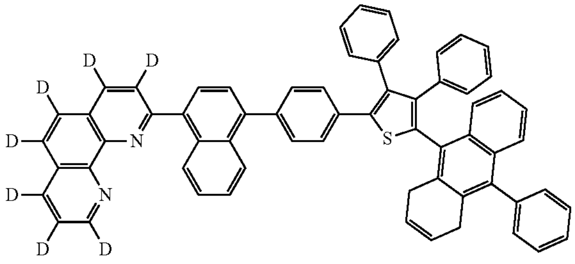
D118
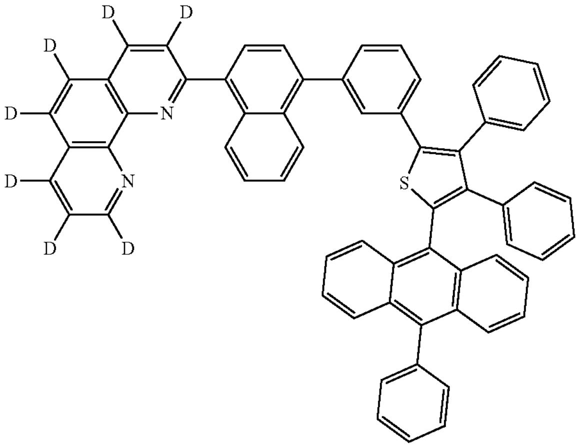
D119
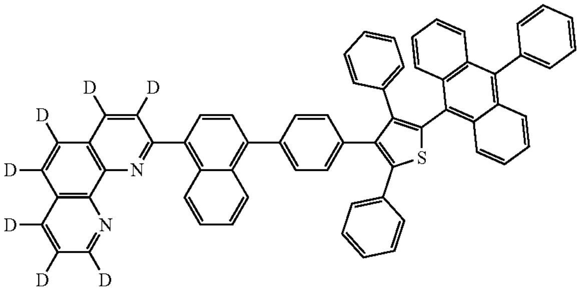
D120
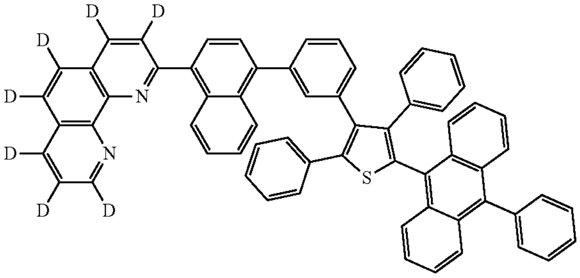
-continued
D125
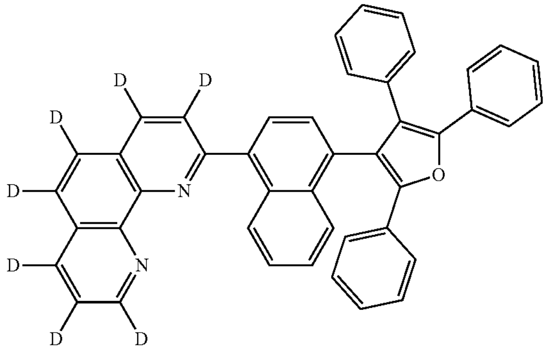
D126
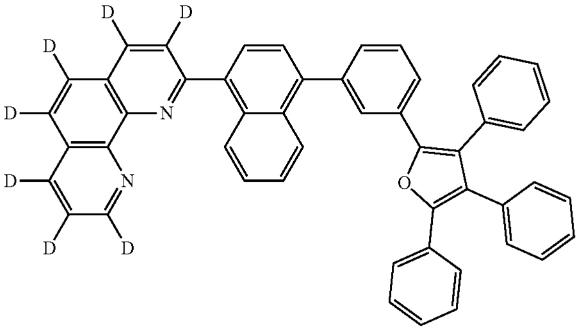
D127
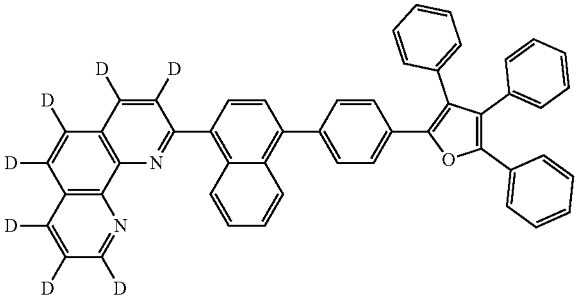
D128
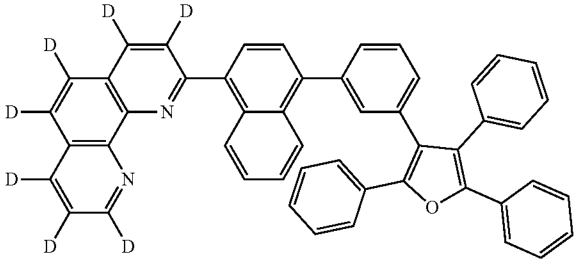

-continued
D129
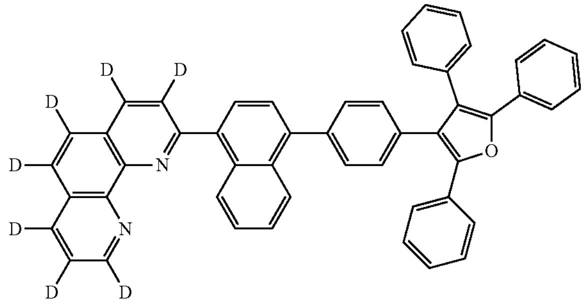
D134
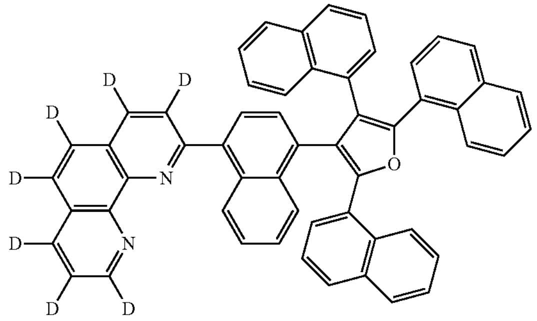
D135
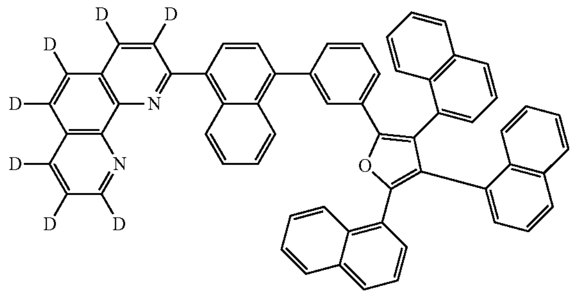
D136
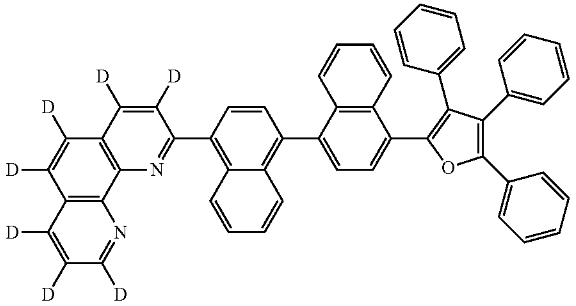
D137
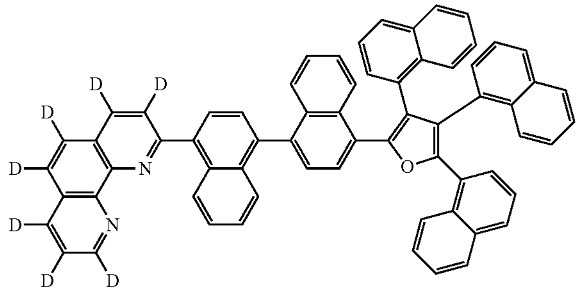
D138
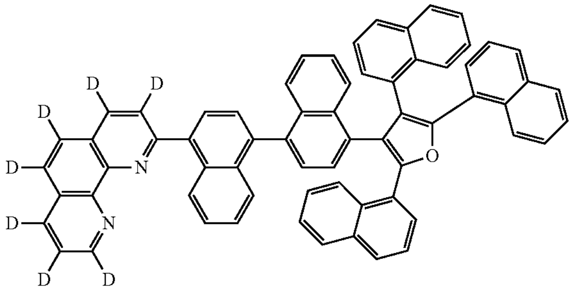

-continued
D141
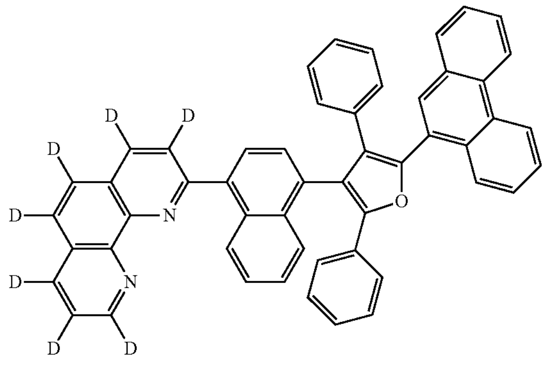
D142
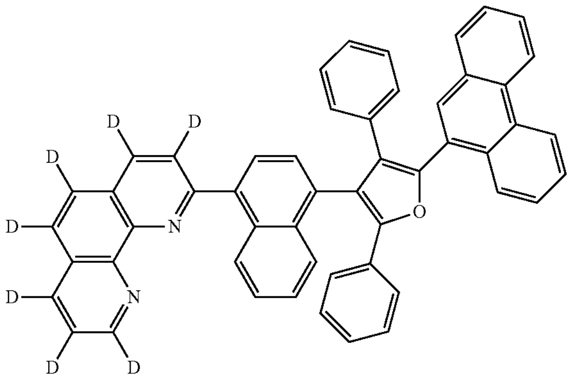
D143
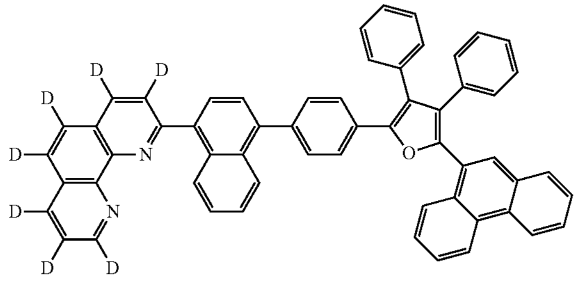
D144
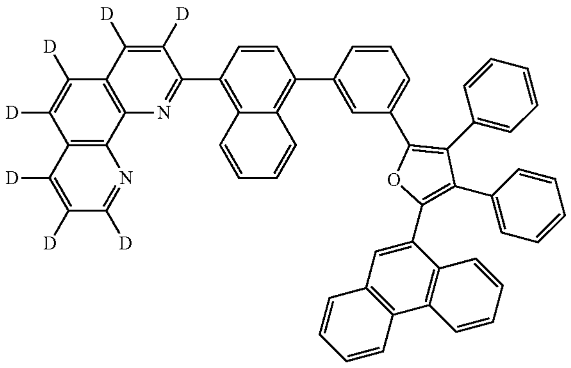
D145
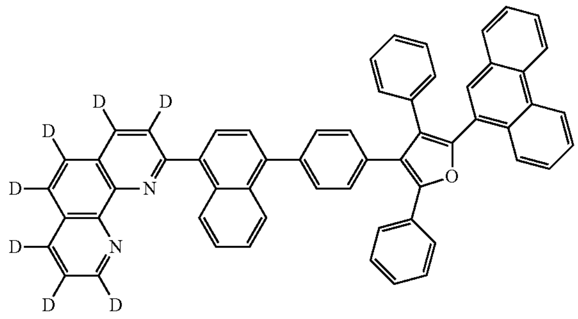
D146
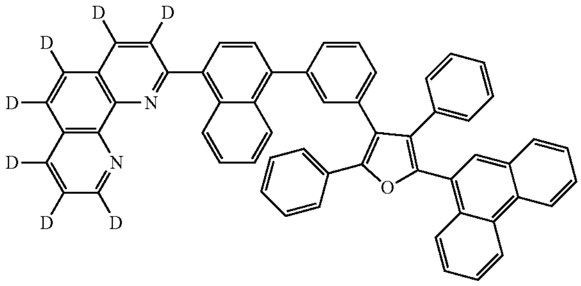
D148
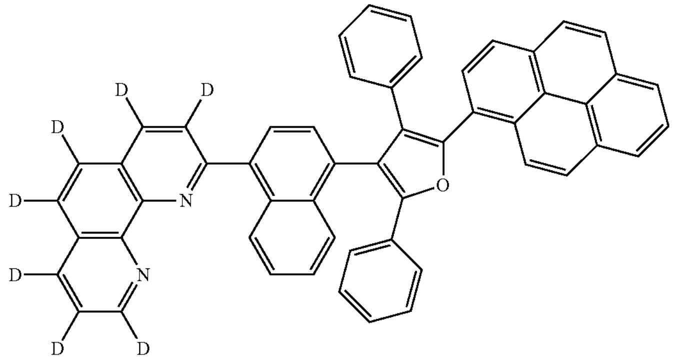

-continued
D149
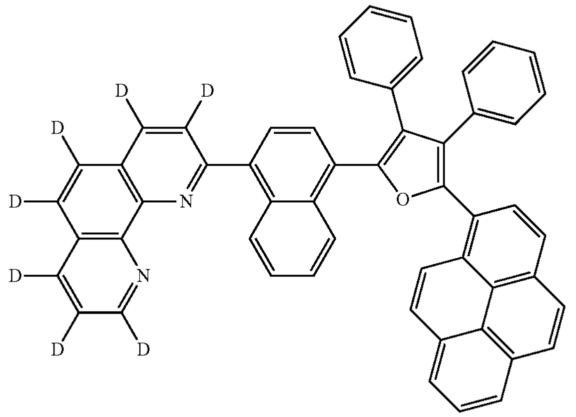
D150
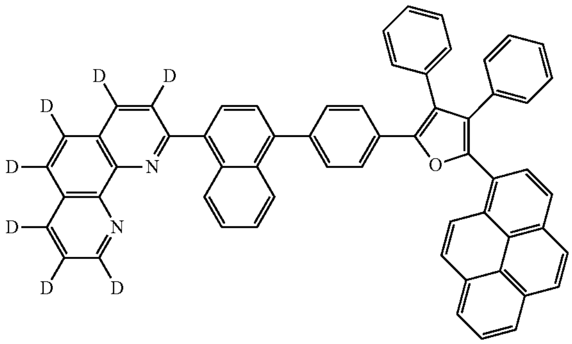
D151
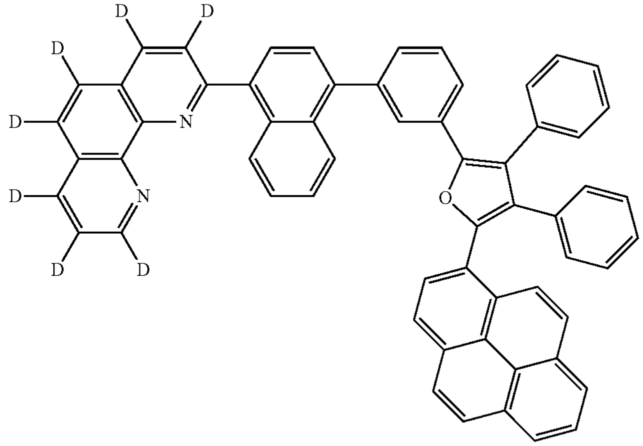
D152
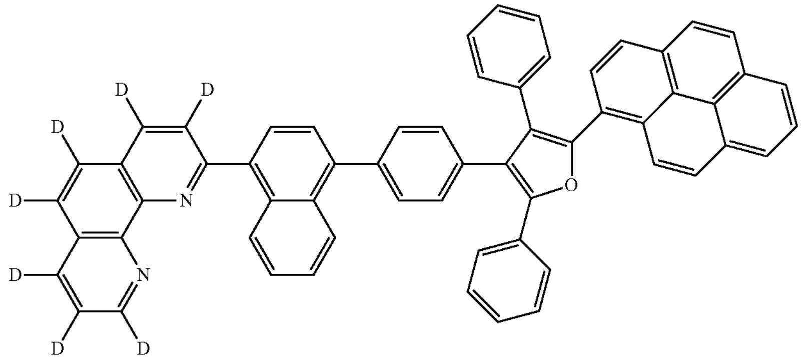
D153
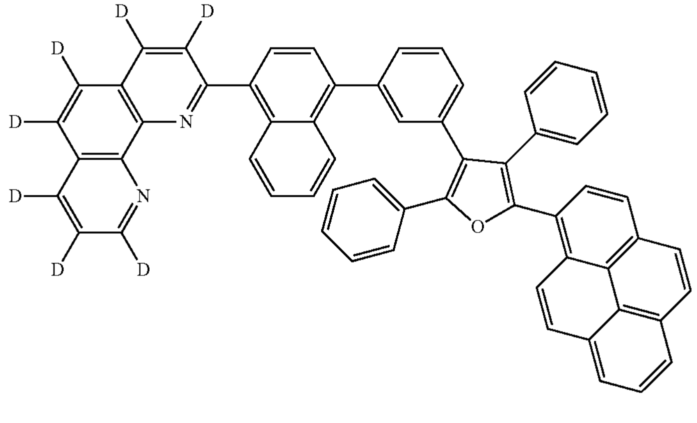

-continued
D155
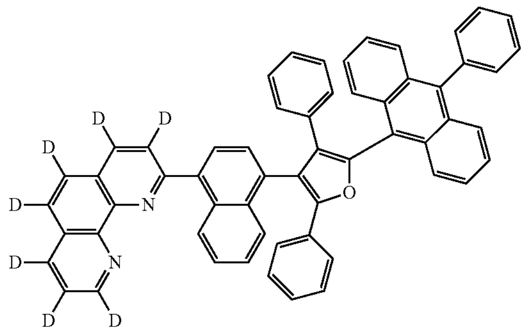
D156
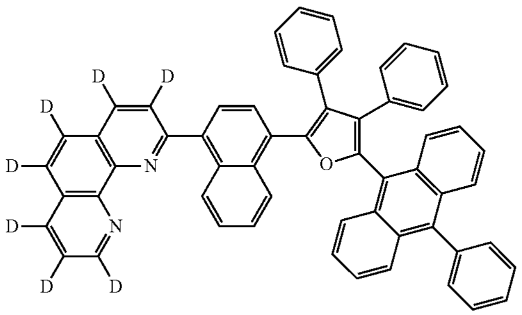
D157
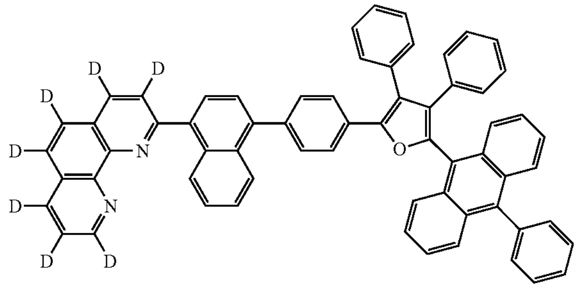
D158
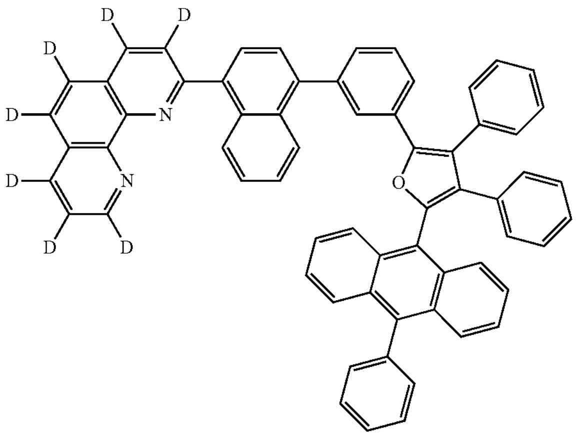
D159
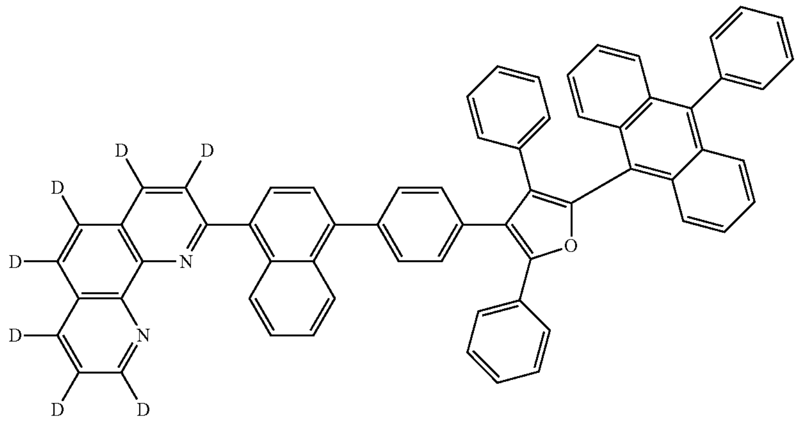
D160
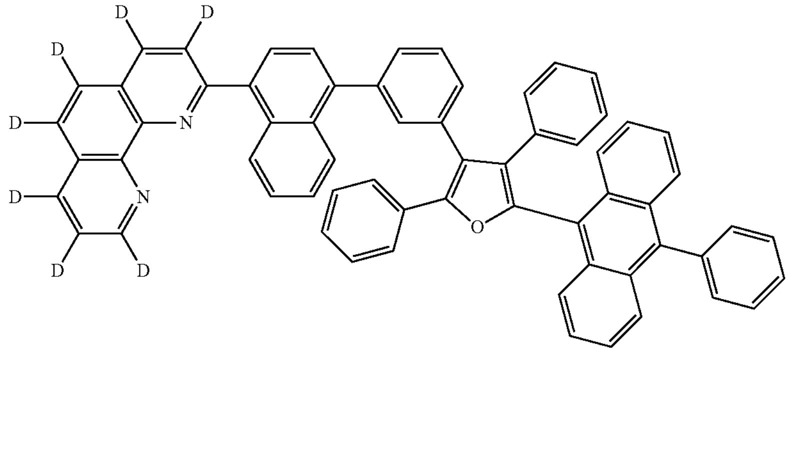

-continued
D165
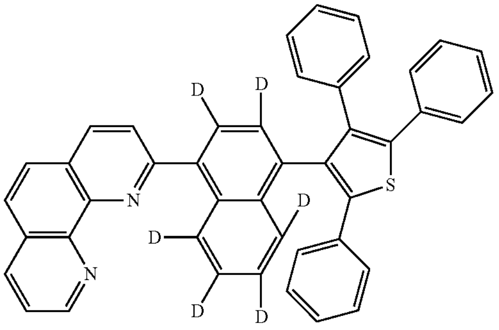
D166
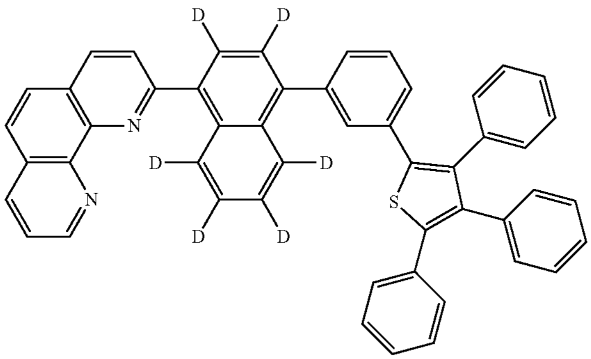
D167
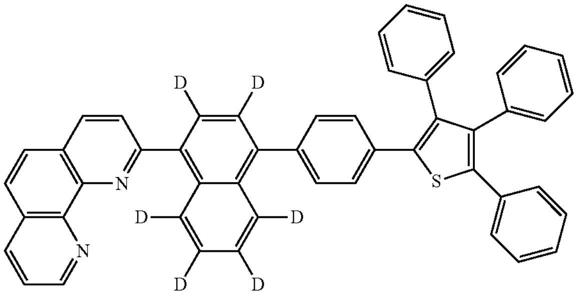
D168
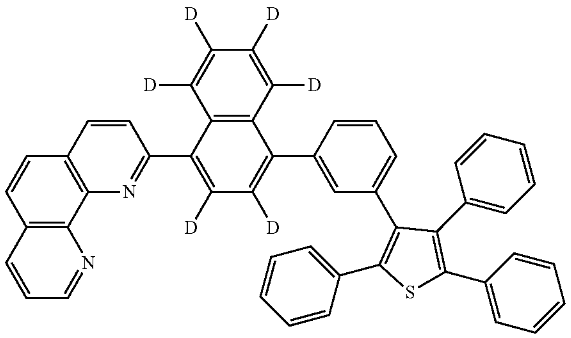
D169
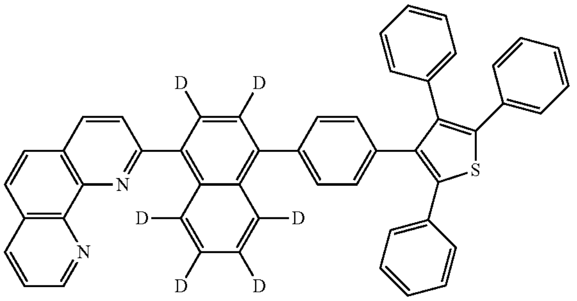
D174
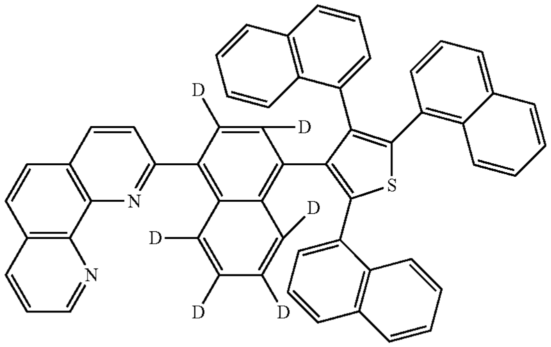
D175
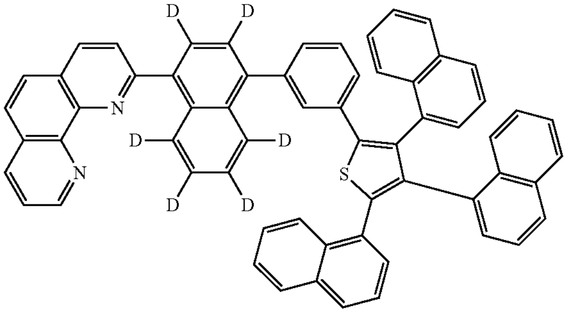
D176
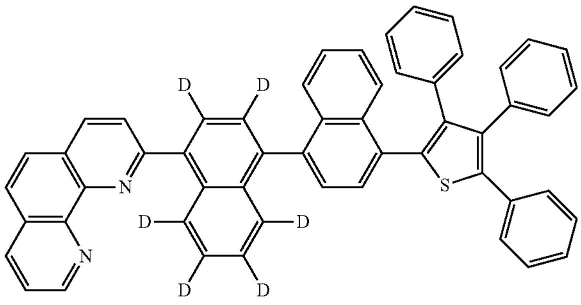

-continued
D177
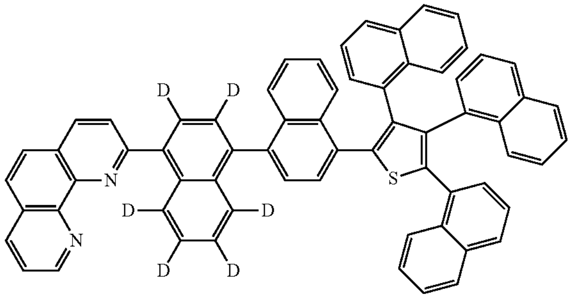
D178
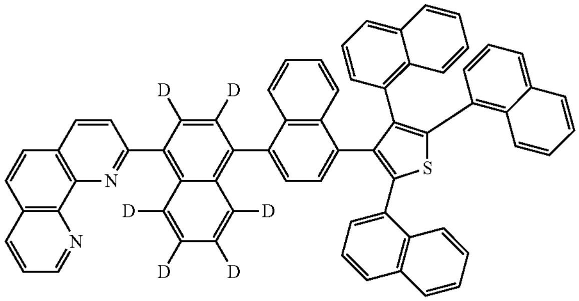
D181
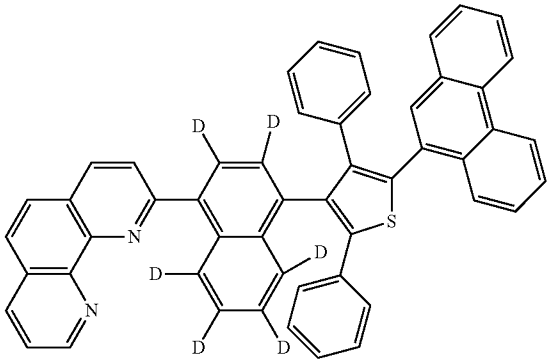
D182
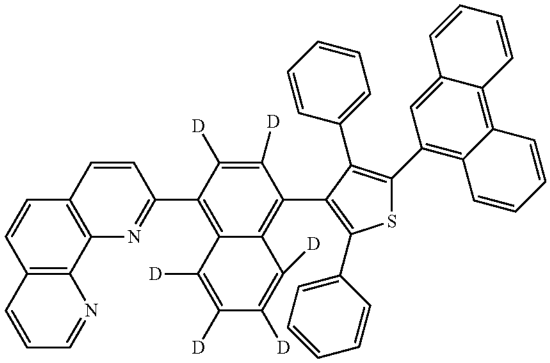
D183
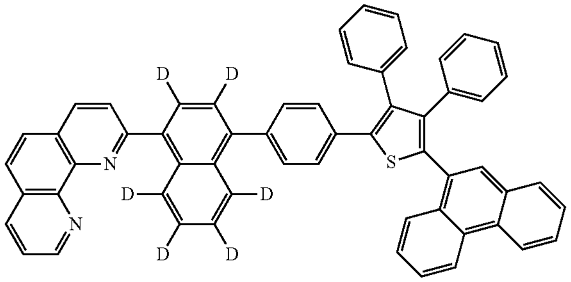
D184
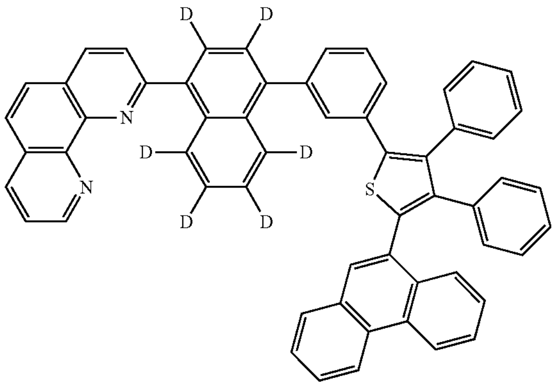
D185
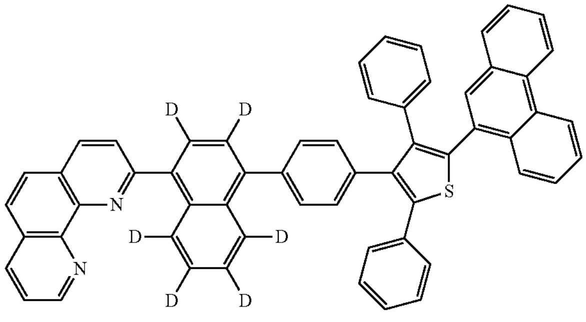
D186
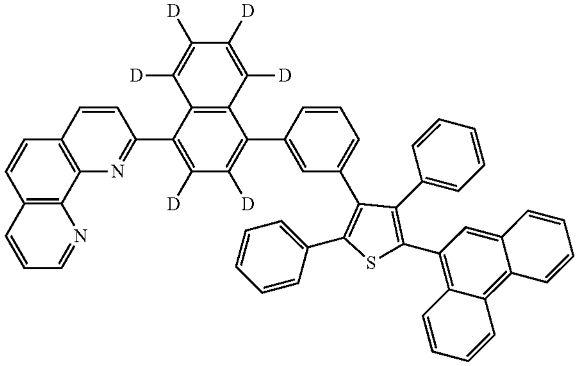

-continued
D188
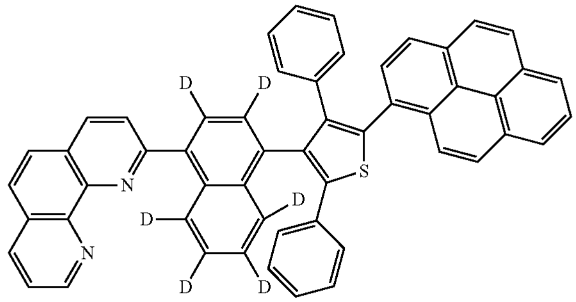
D189
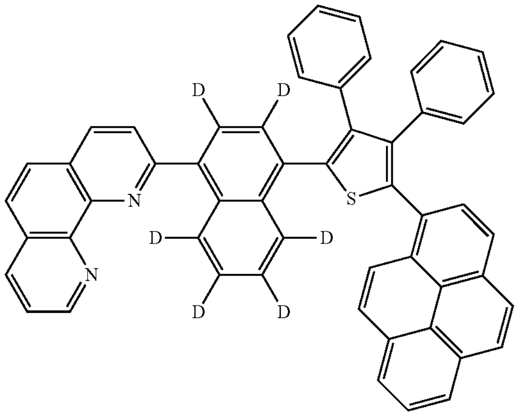
D190
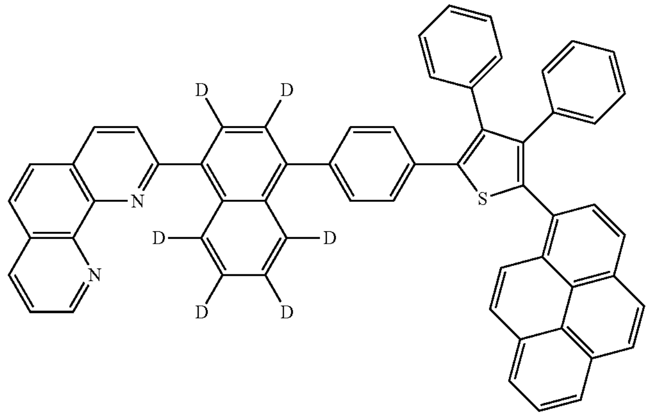
D191
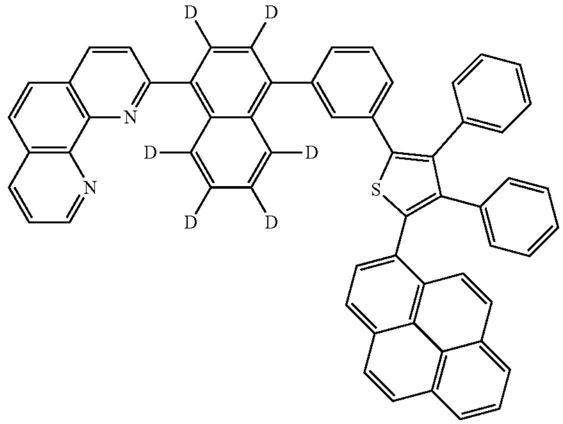
D192
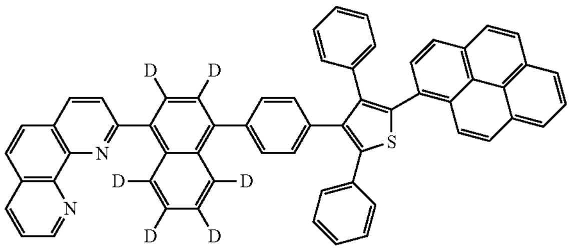

-continued
D193
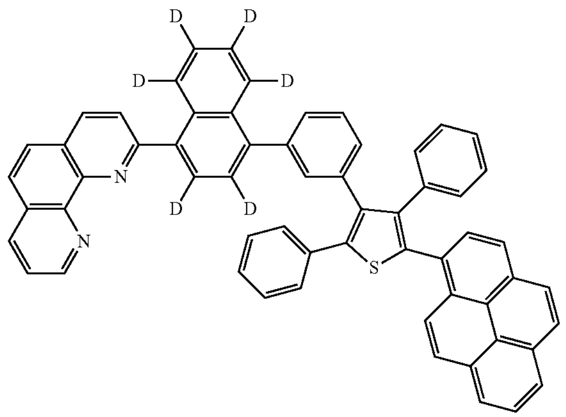
D195
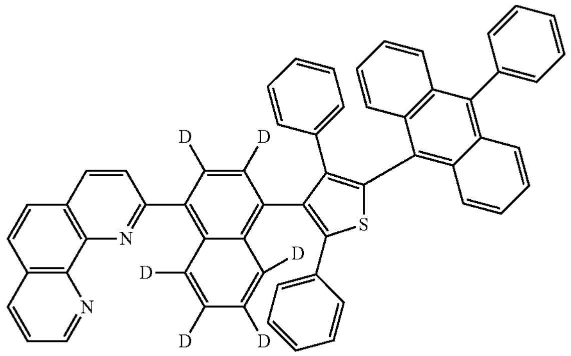
D196
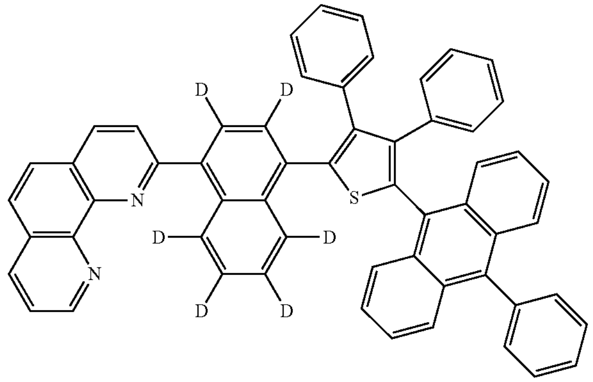
D197
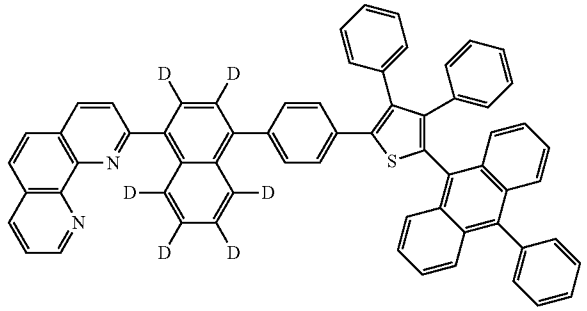
D198
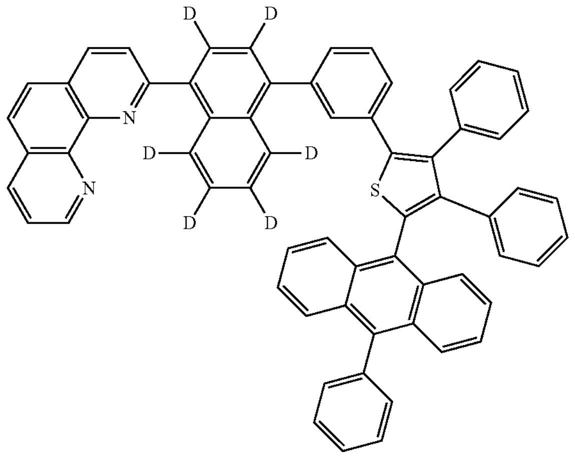
D199
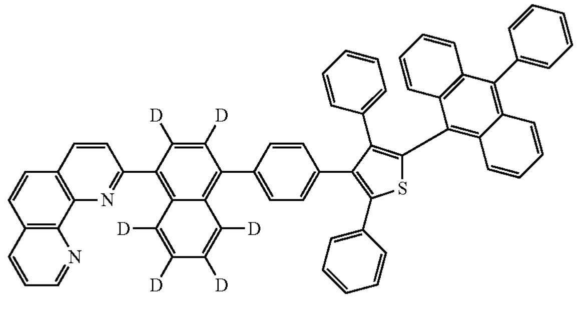
D200
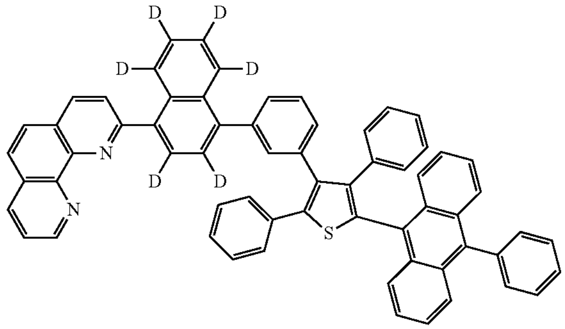

-continued
D205
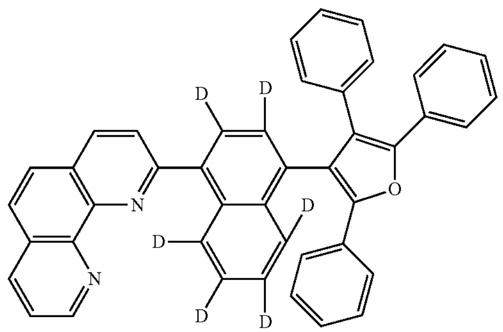
D206
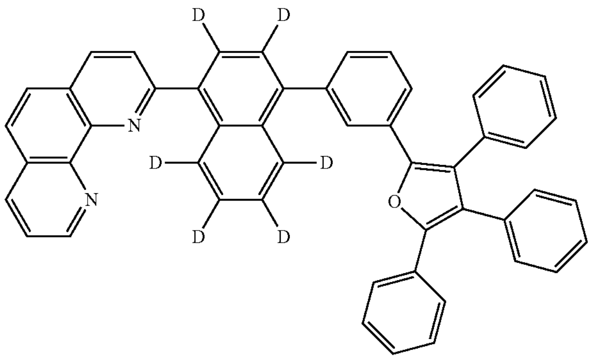
D207
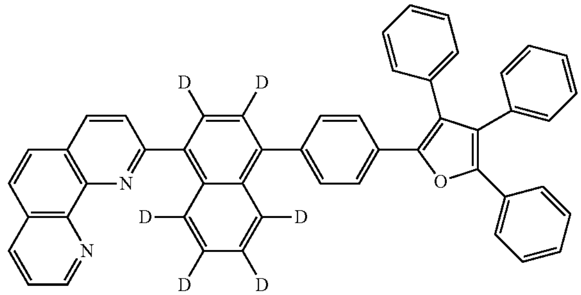
D208
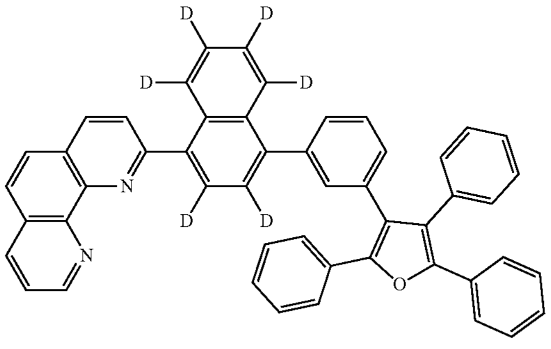
D209
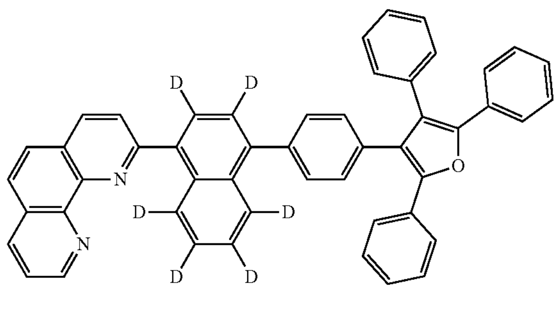
-continued
D214
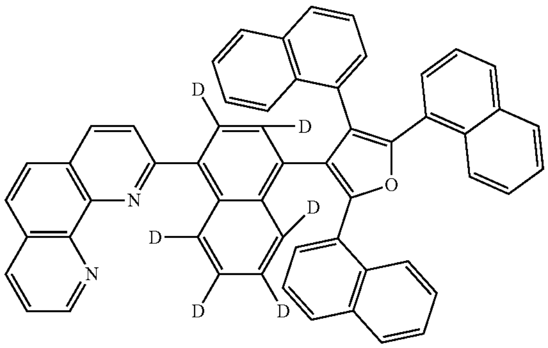
D215
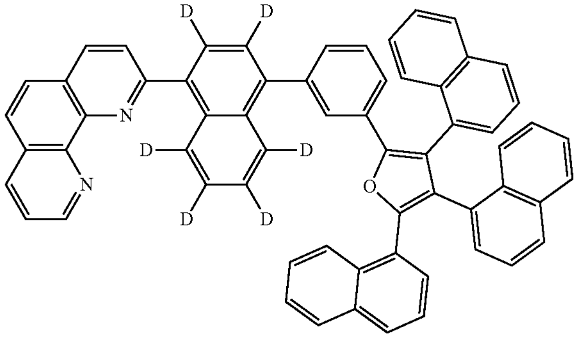

-continued
D216
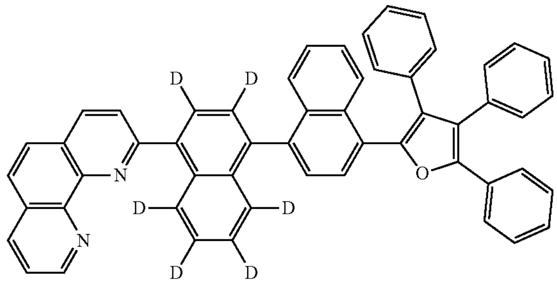
D217
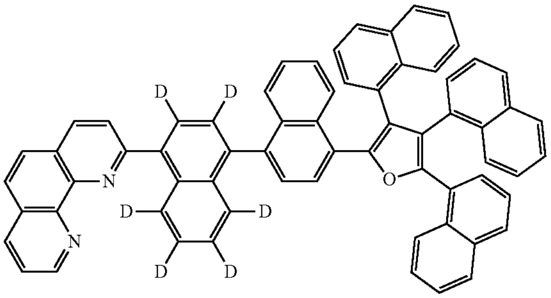
D218
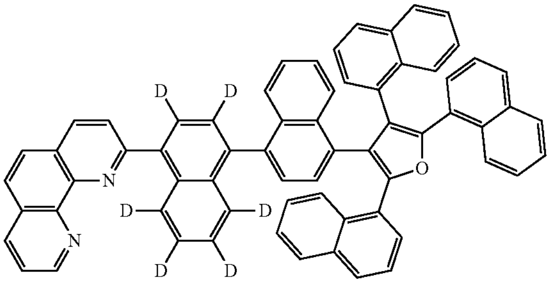
D221
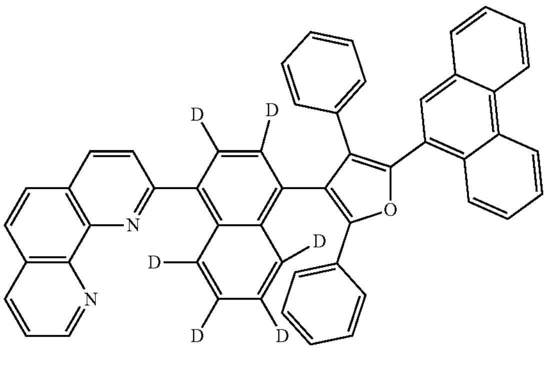
-continued
D222
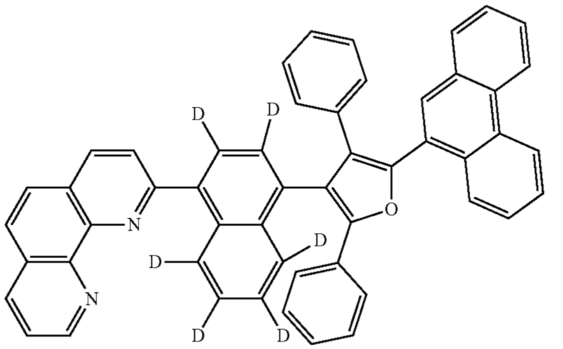
D223
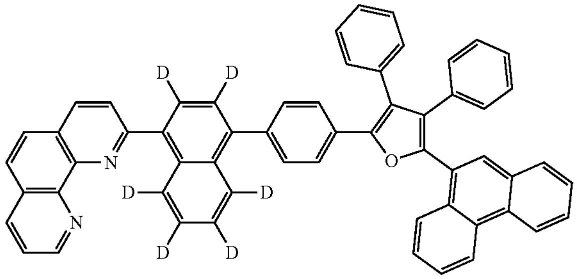
D224
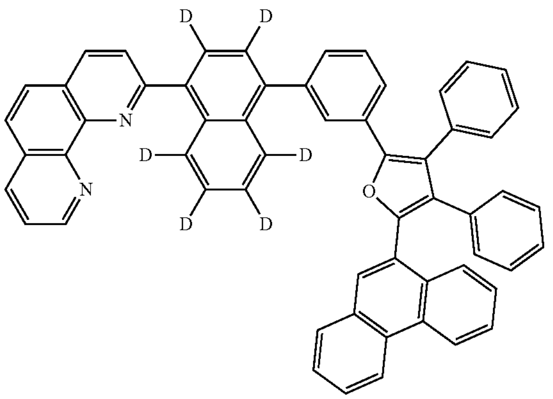
D225
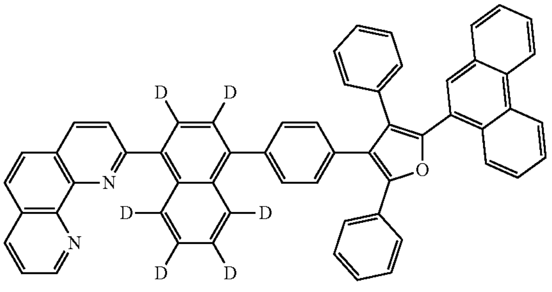

-continued
D226
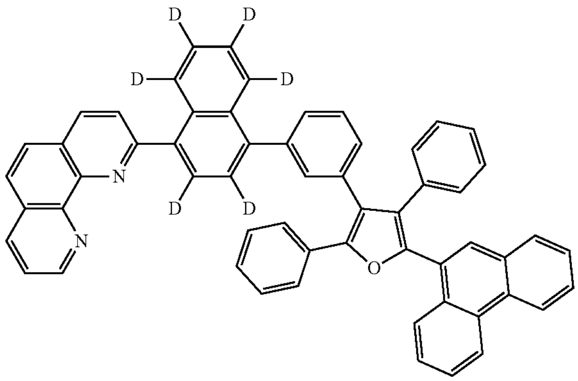
D228
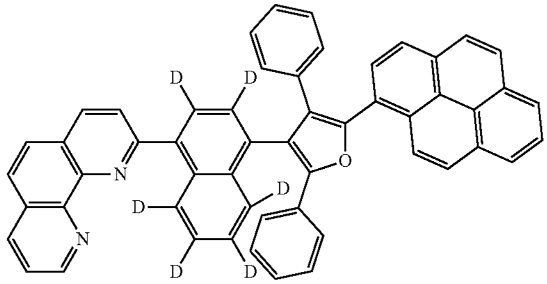
D229
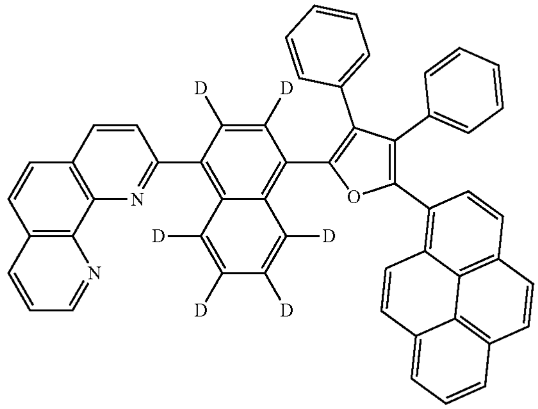
D230
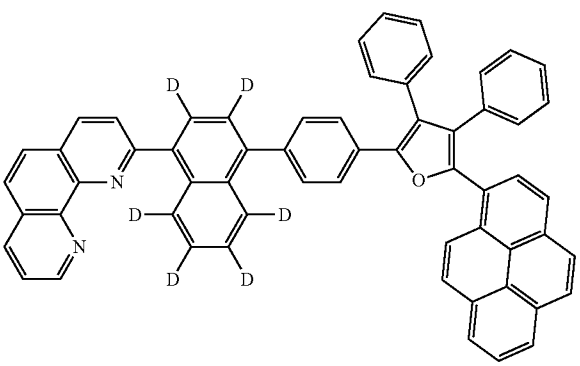
-continued
D231
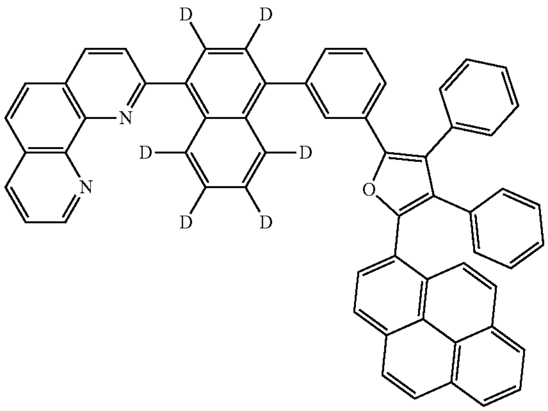
D232
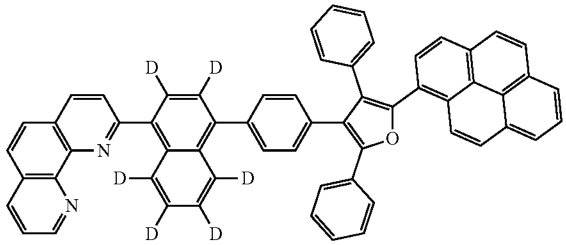
D233
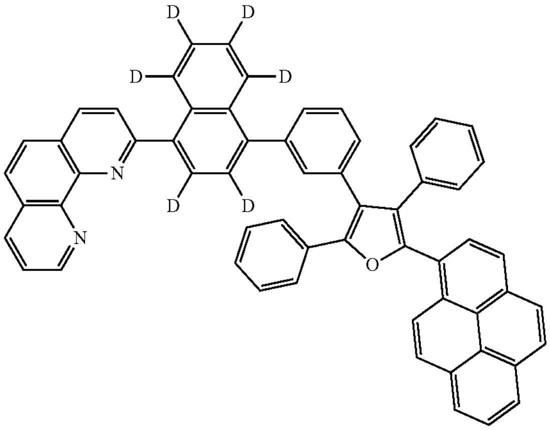
D235
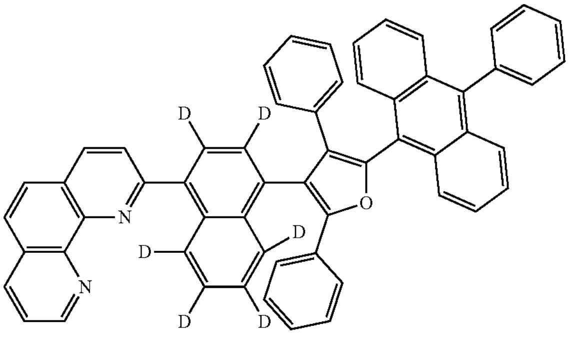

-continued
D236
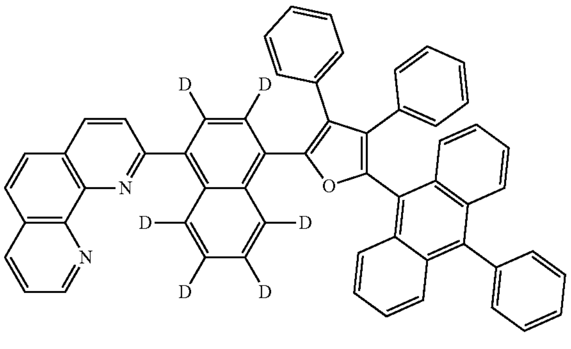
D237
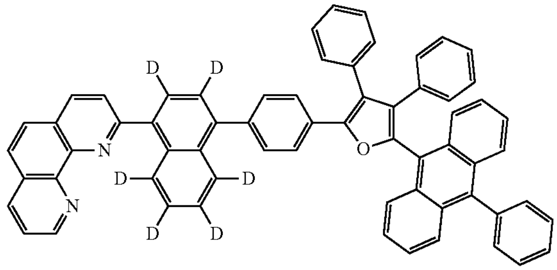
D238
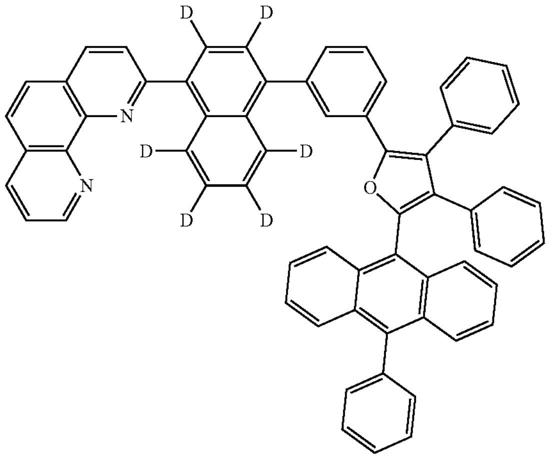
D239
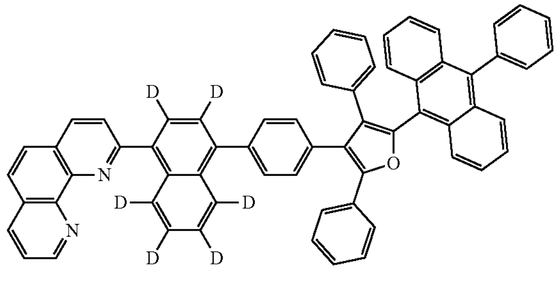
-continued
D240
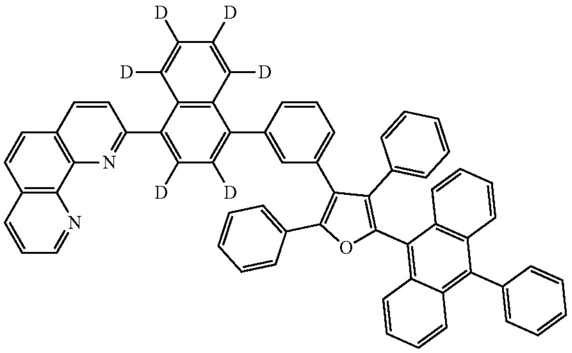
D245
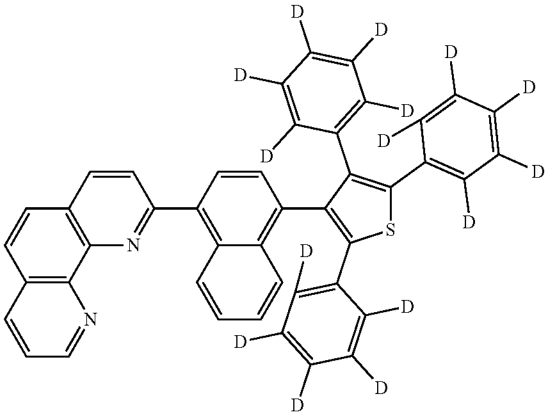
D246
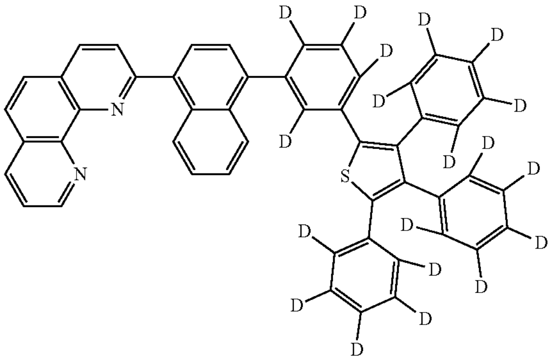
D247
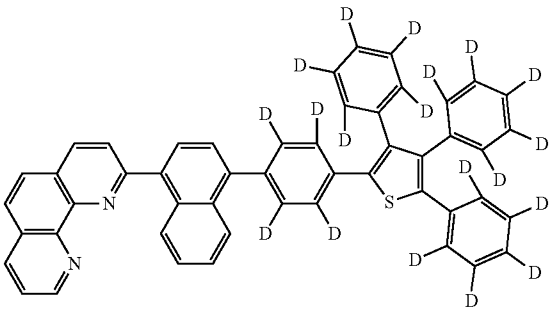

-continued
D248
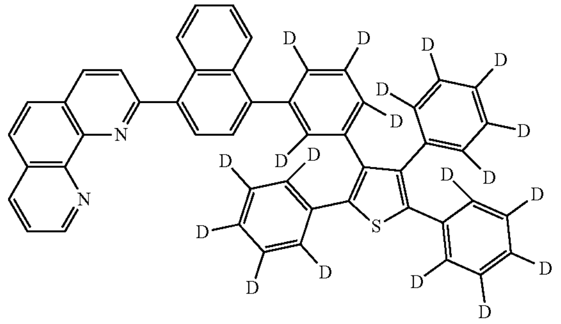
D249
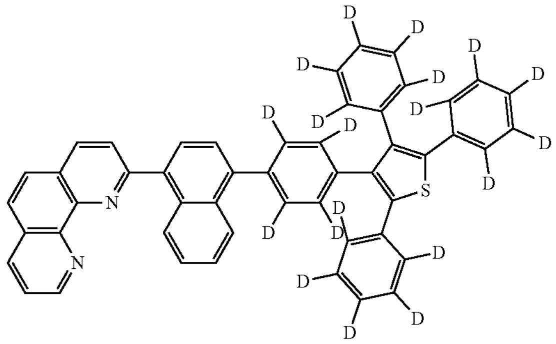
D254
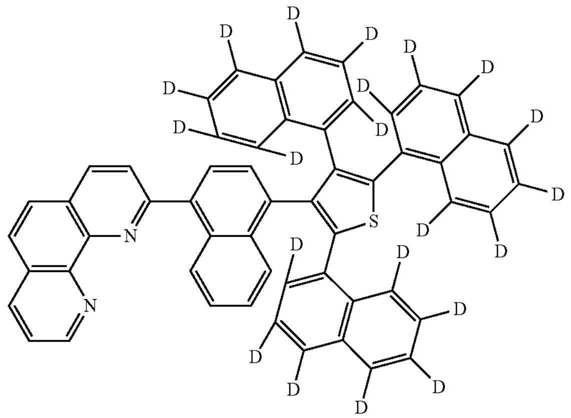
D255
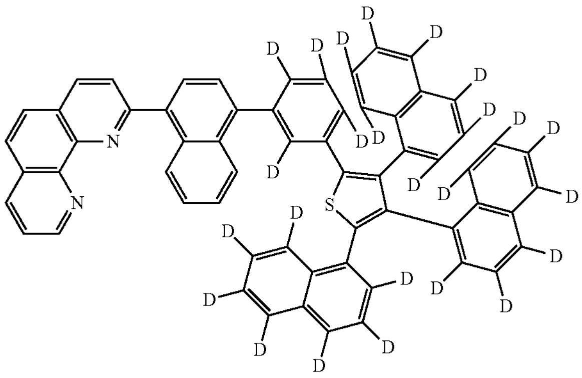
D256
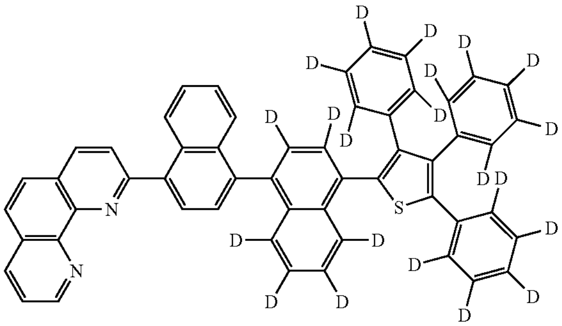
D257
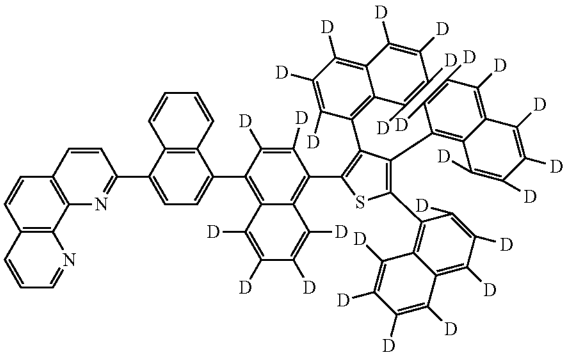

-continued
D258
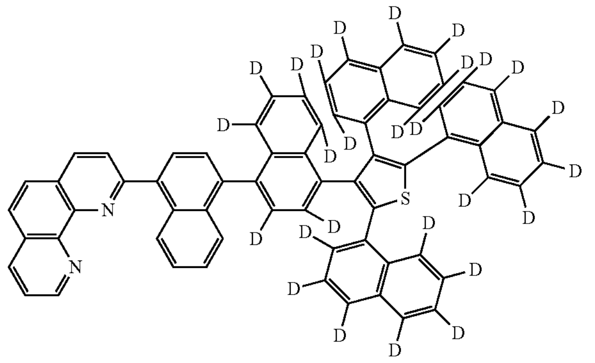
D261
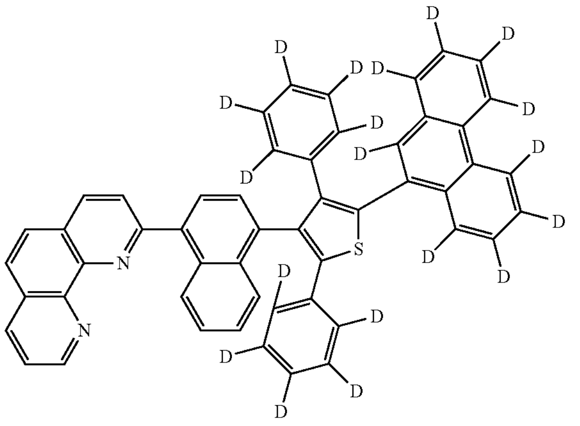
D262
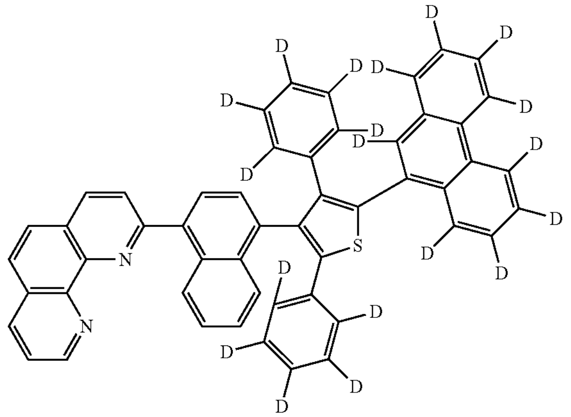
D263
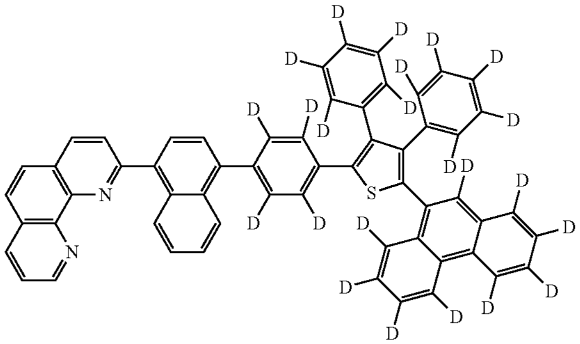
D264
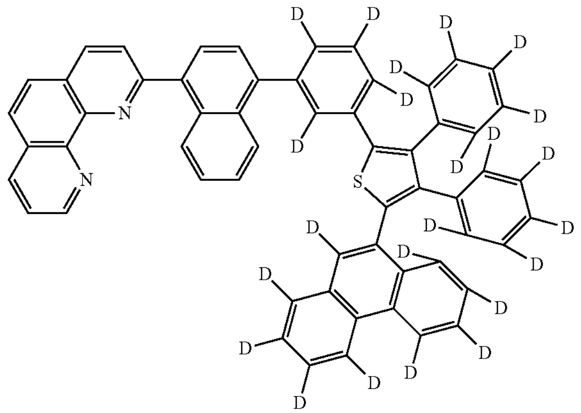
D265
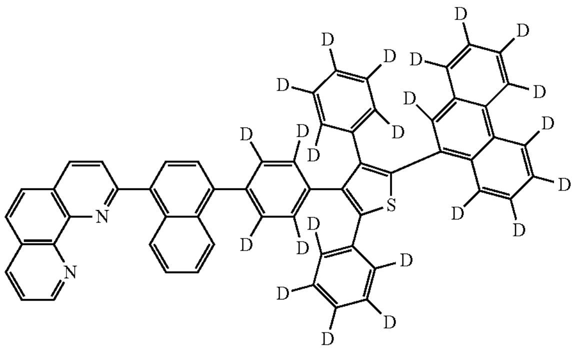

-continued
D266
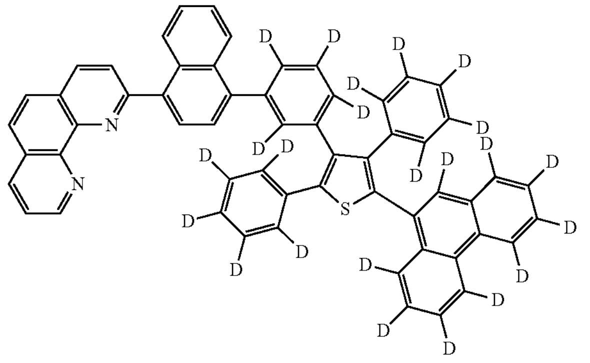
D268
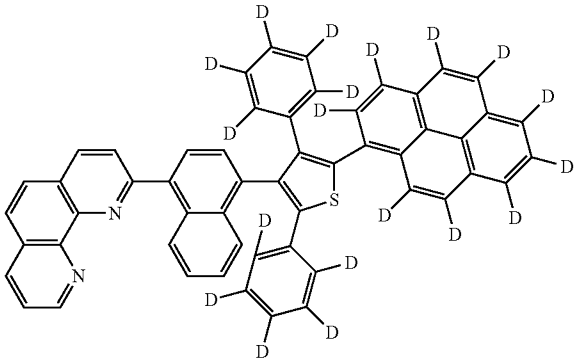
D269
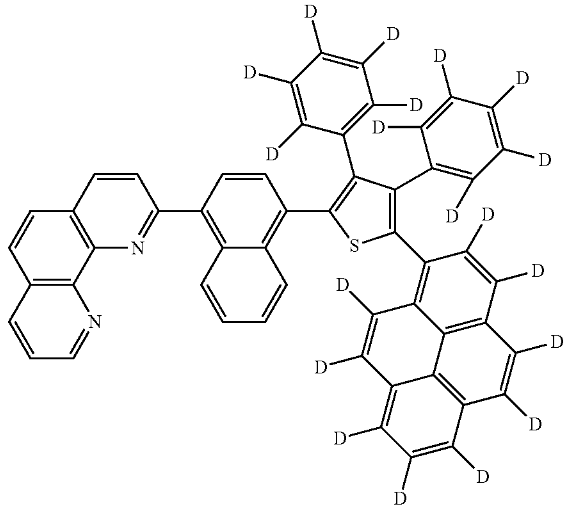
D270
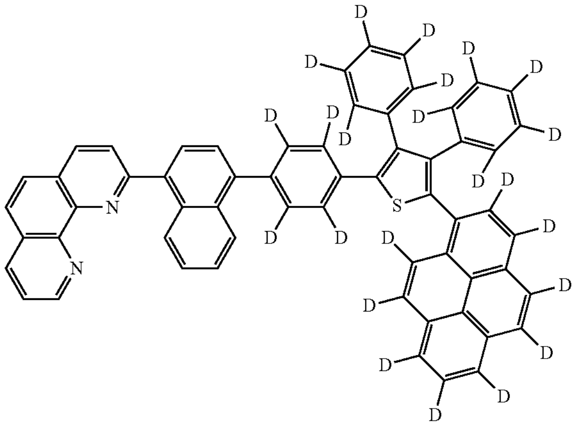
D271
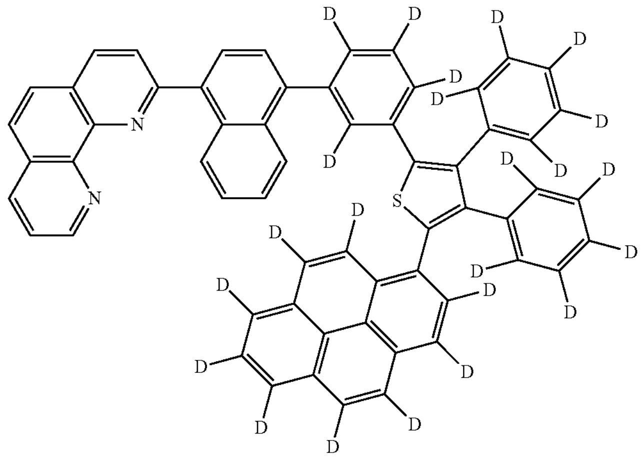

-continued
D272
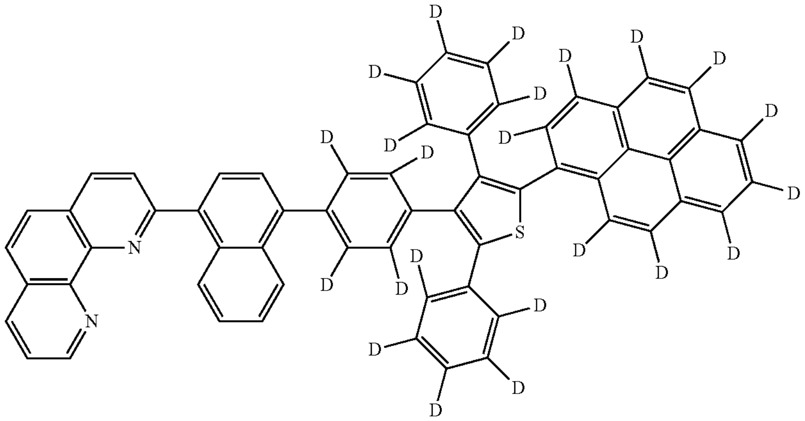
D273
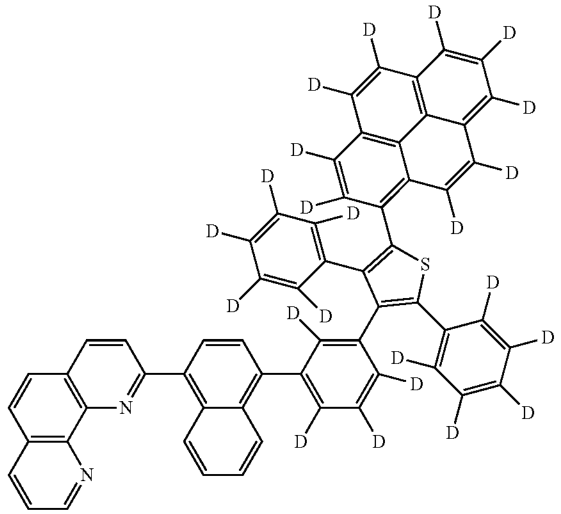
D275
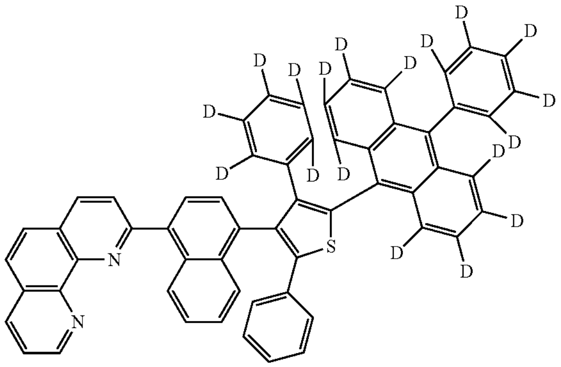
D276
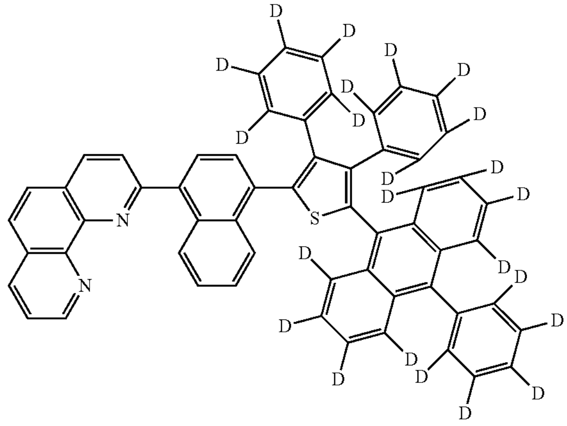
D277
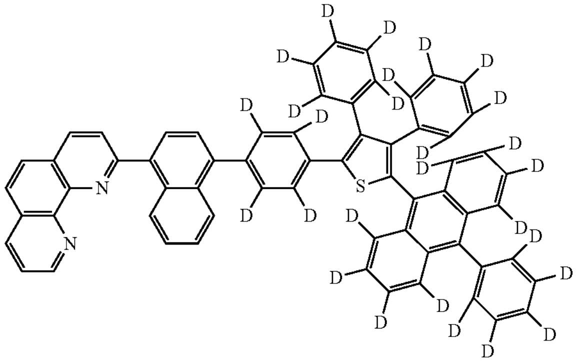

-continued
D278
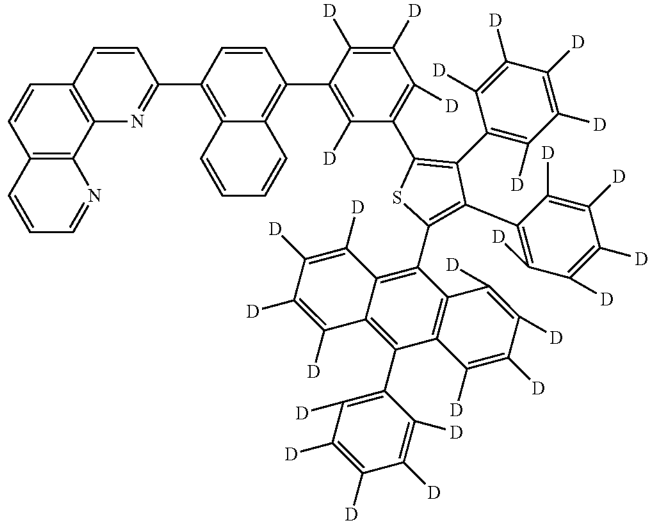
D279
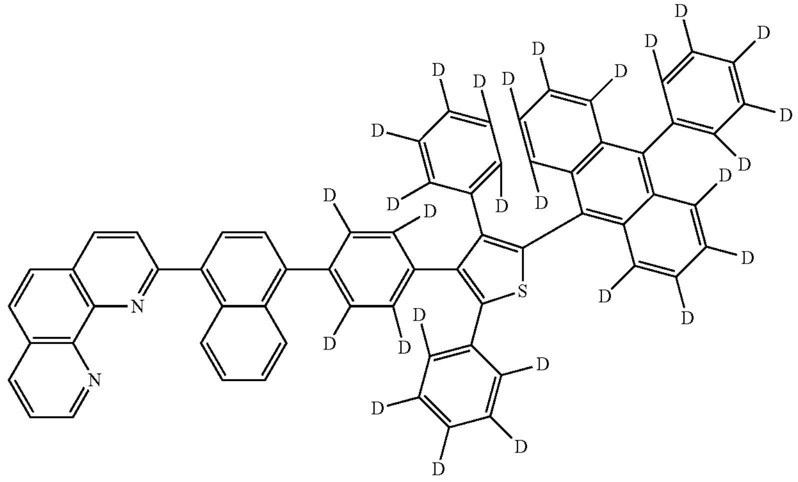
D280
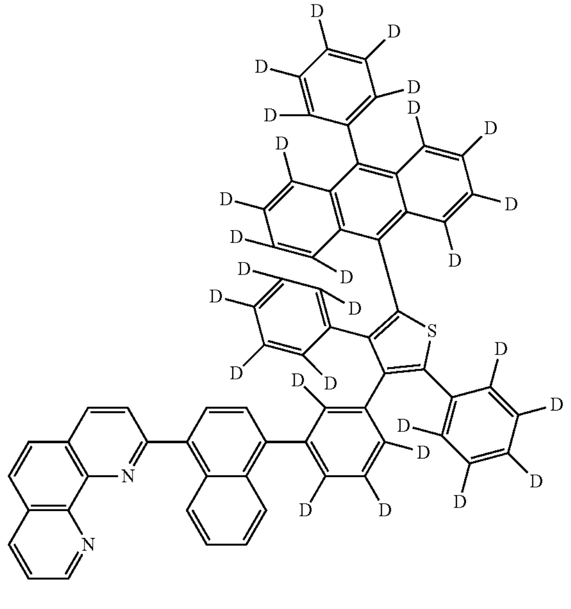
D285
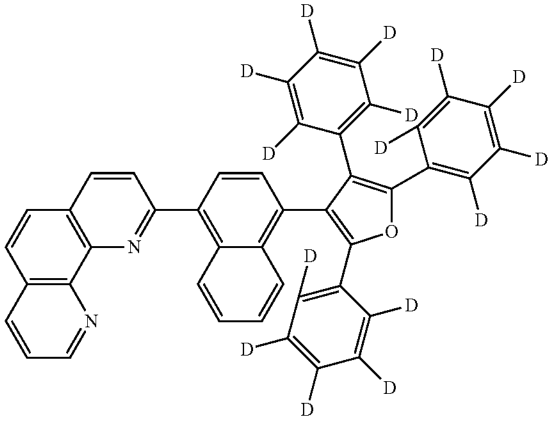

-continued
D286
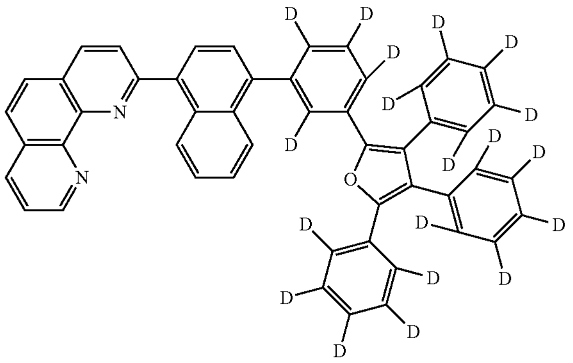
D287
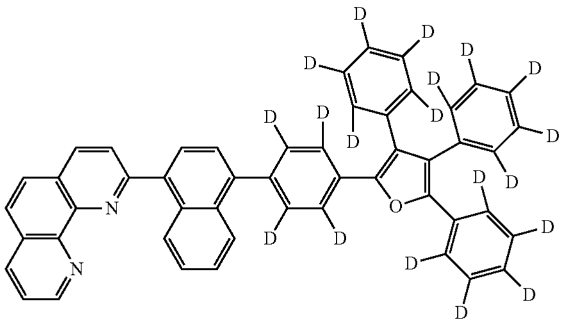
D288
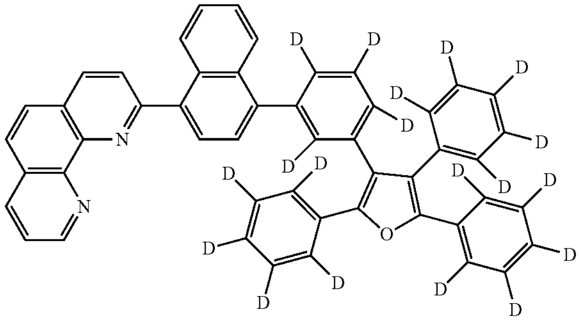
D289
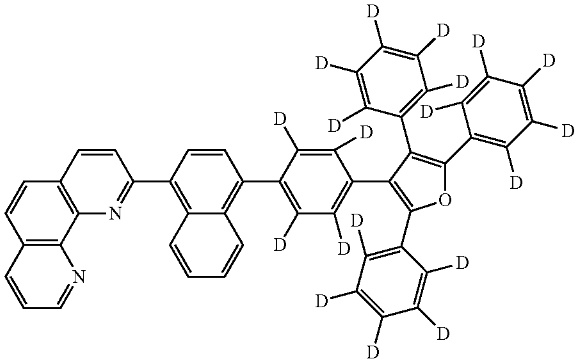
D294
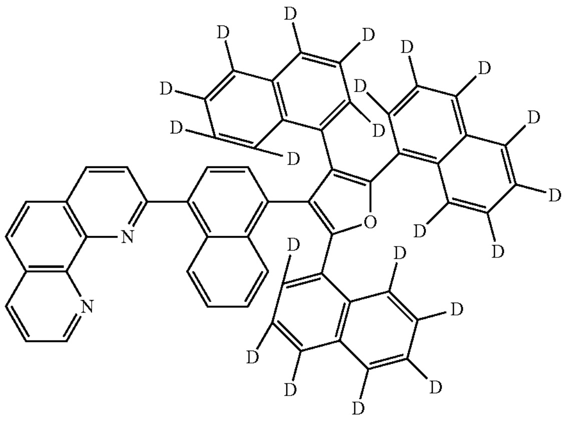
D295
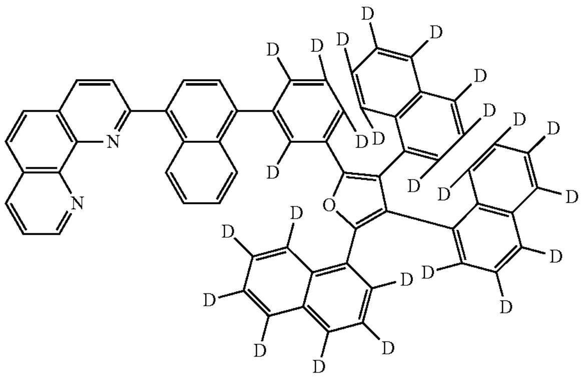
D296
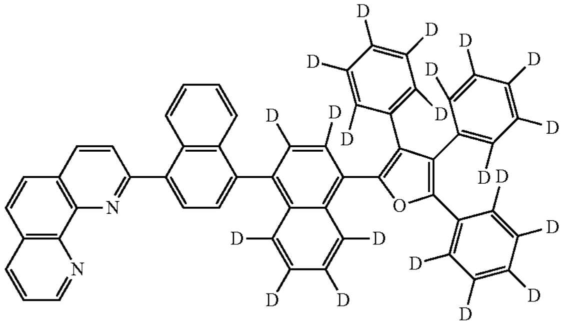
D297
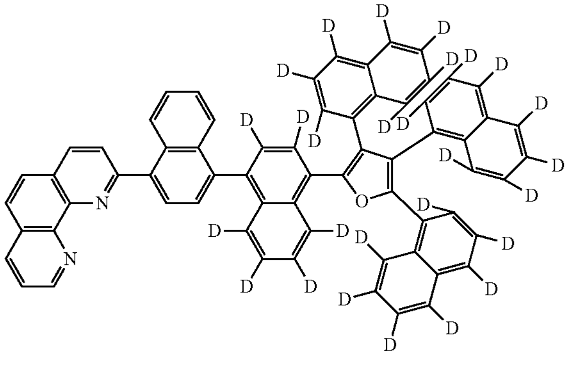

-continued
D298
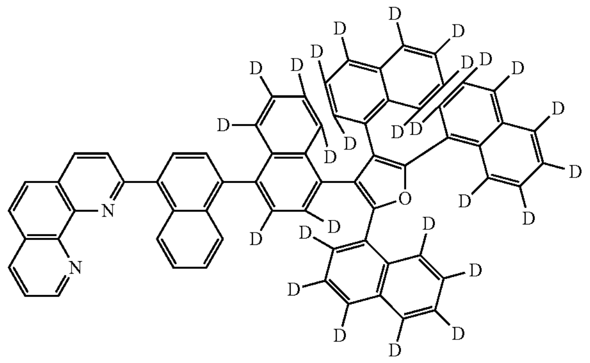
D301
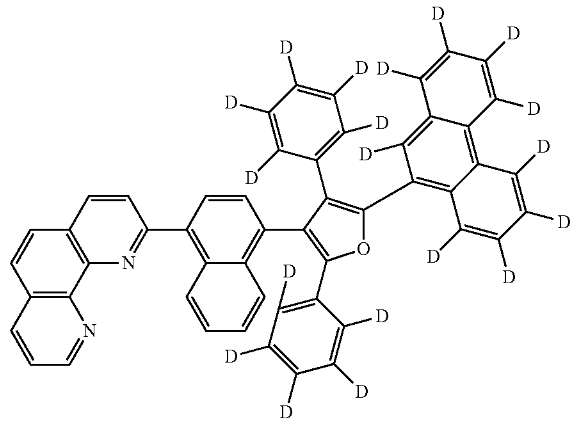
D302
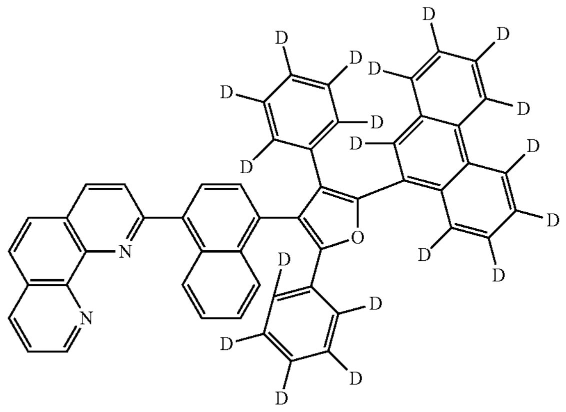
D303
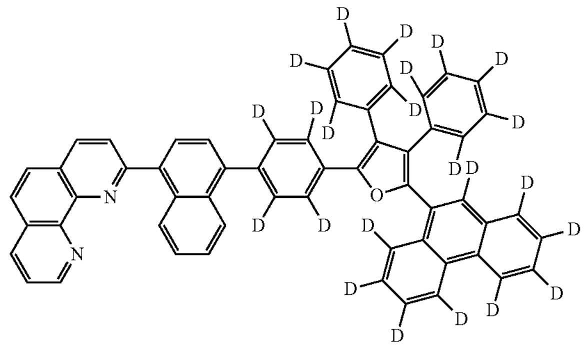
D304
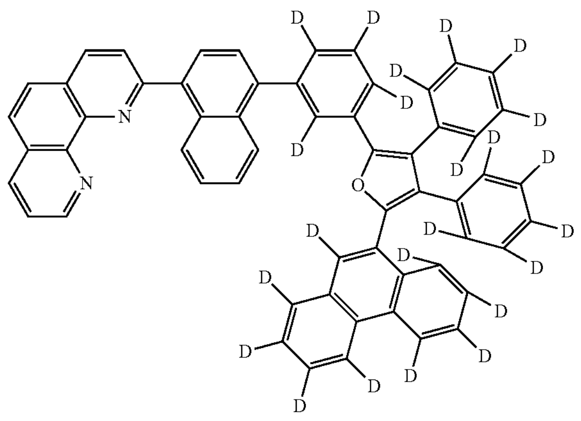
D305
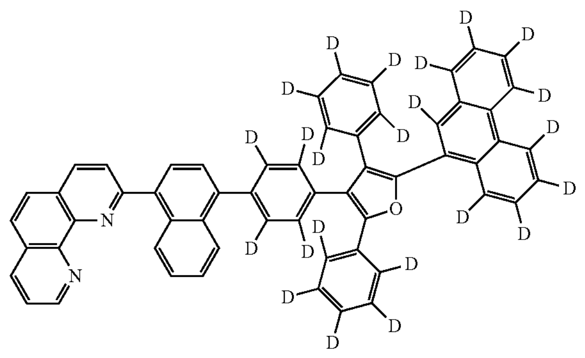

-continued
D306
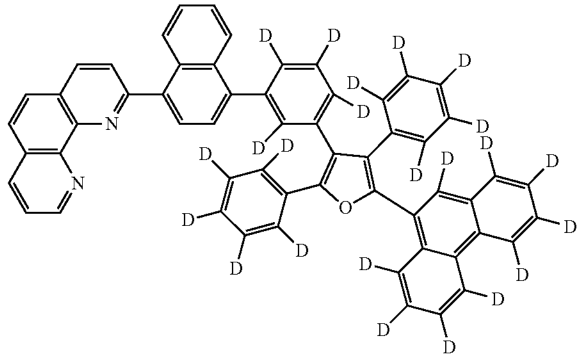
D308
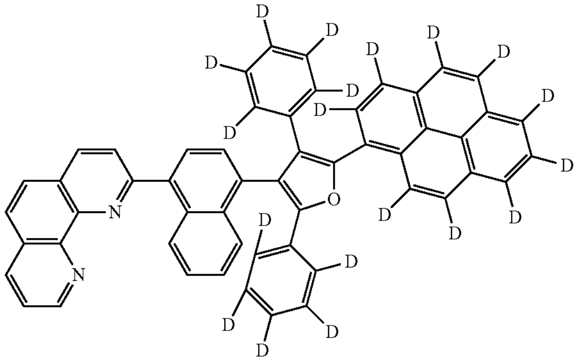
D309
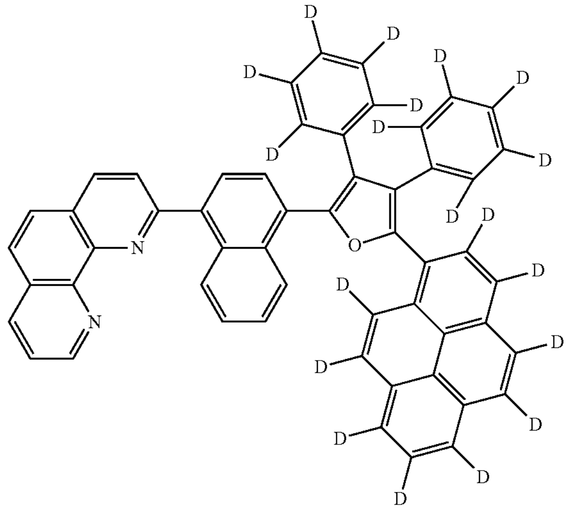
D310
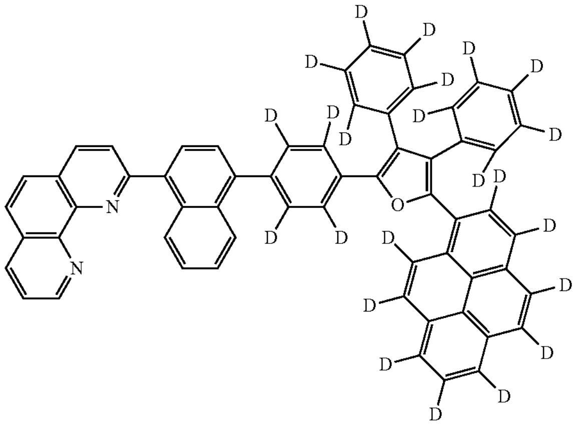
D311
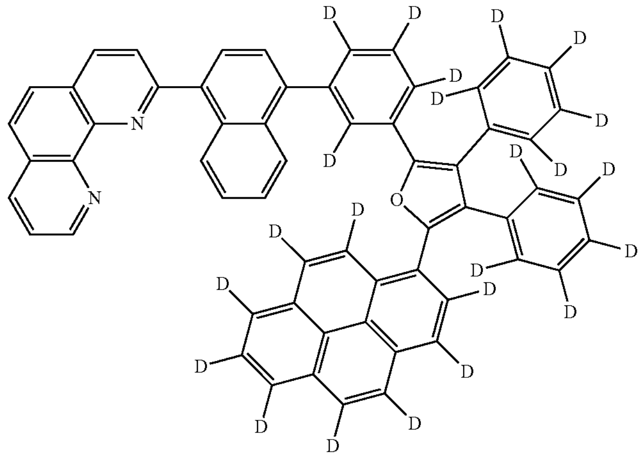

-continued
D312
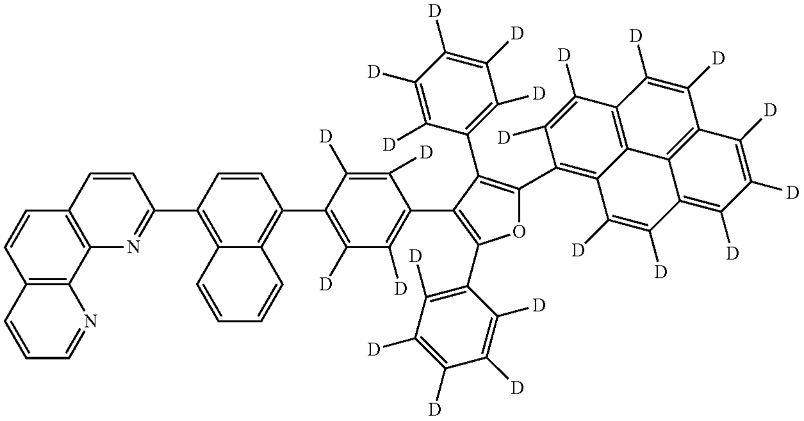
D313
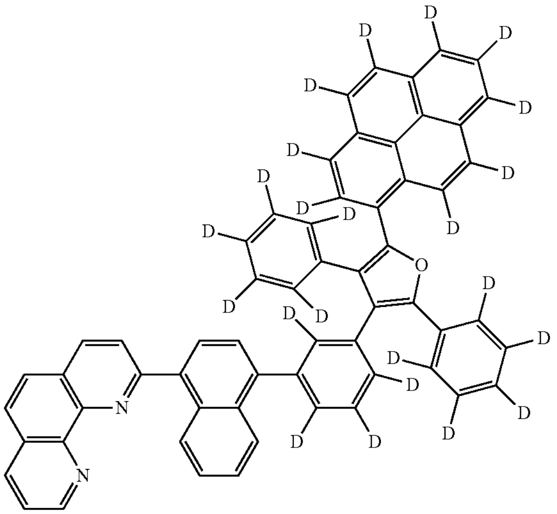
D315
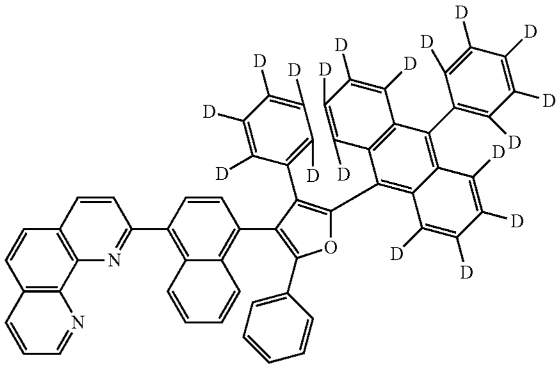
D316
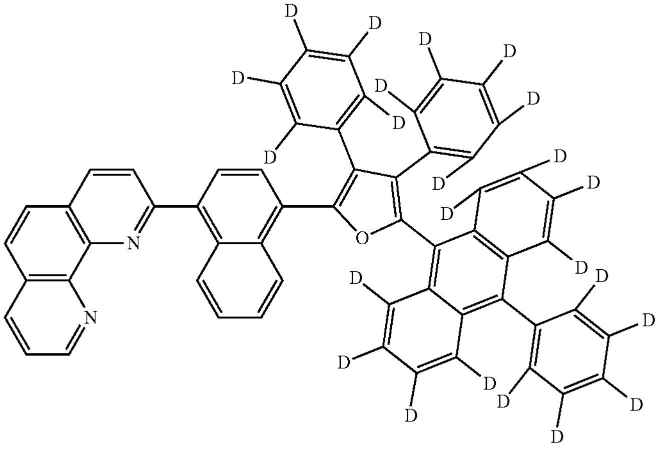

-continued
D317
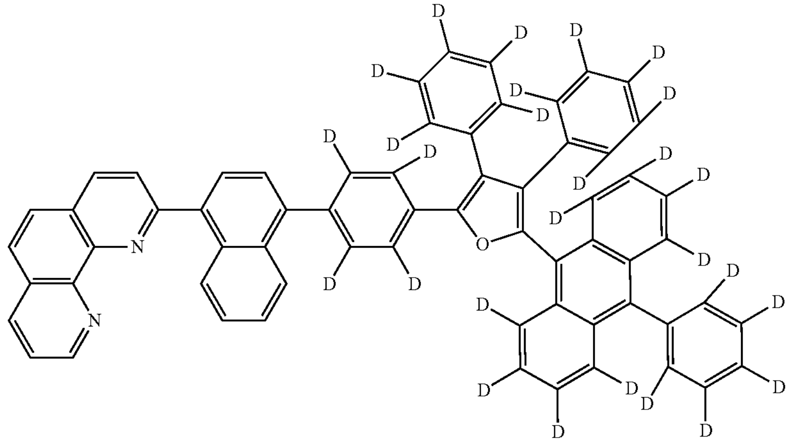
D318
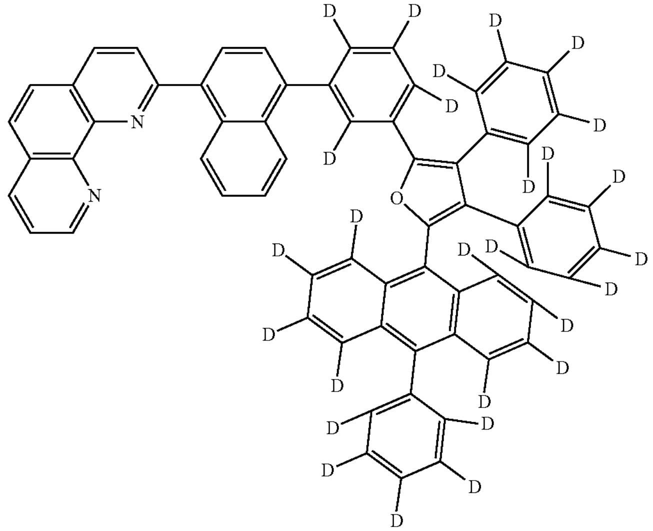
D319
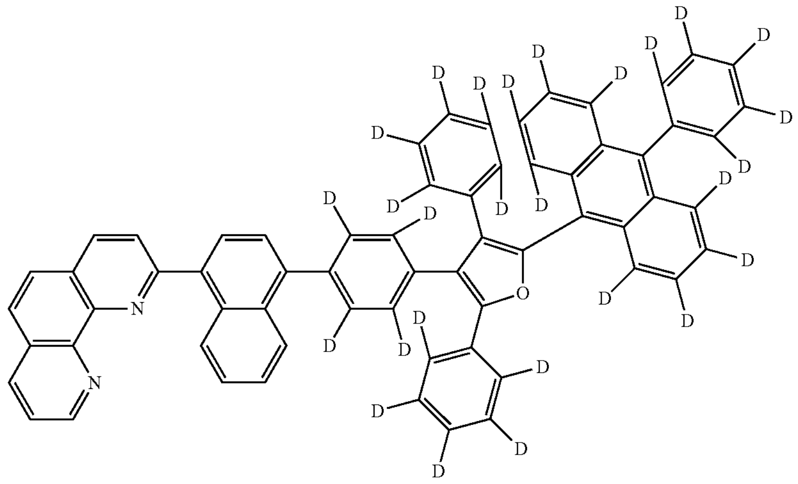

-continued
D320
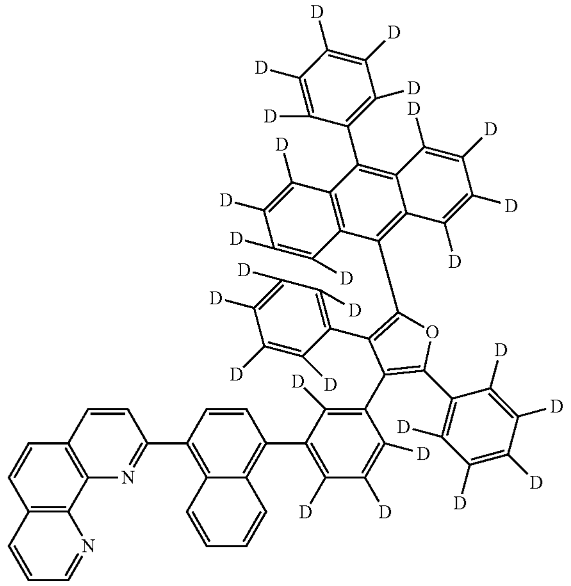
D325
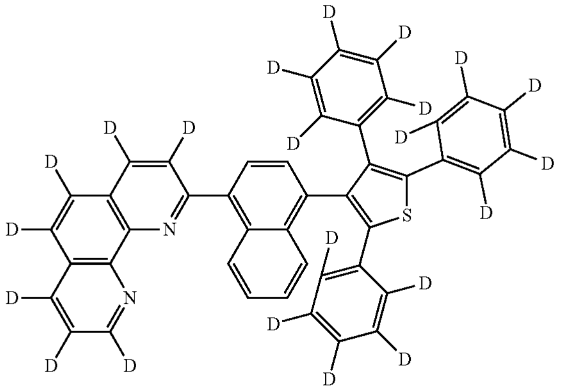
D326
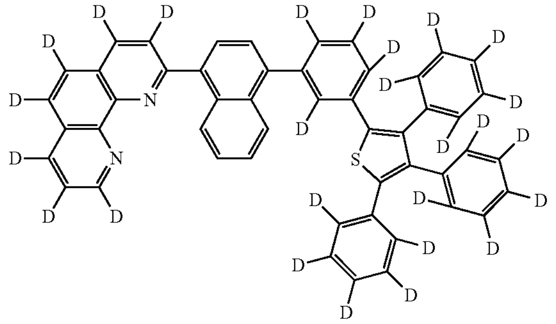
D327
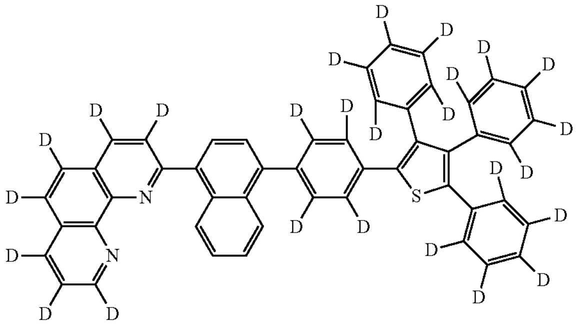
D328
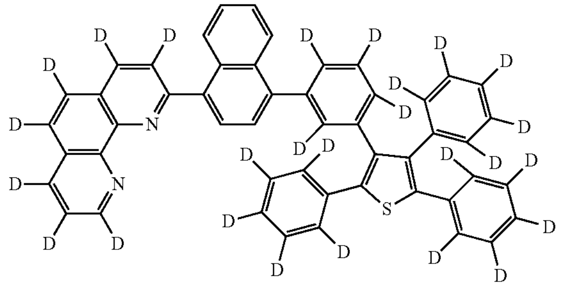
D329
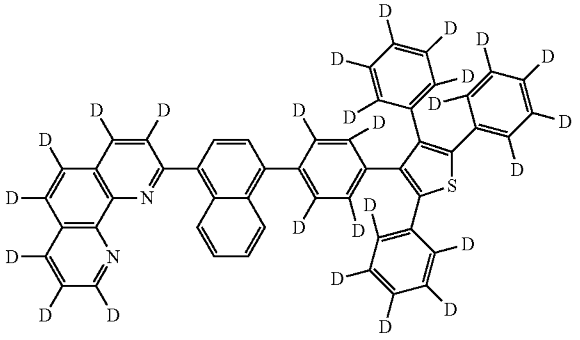

D334
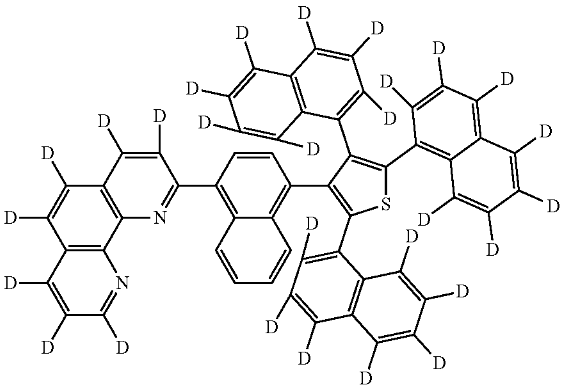
D335
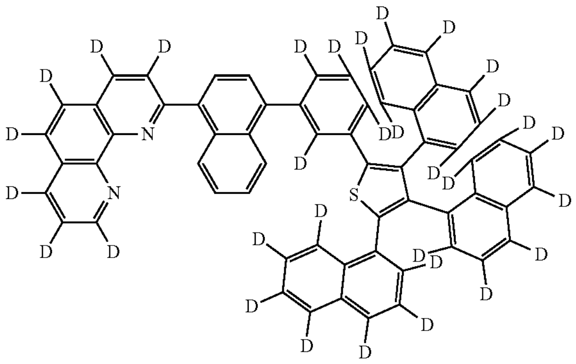
D336
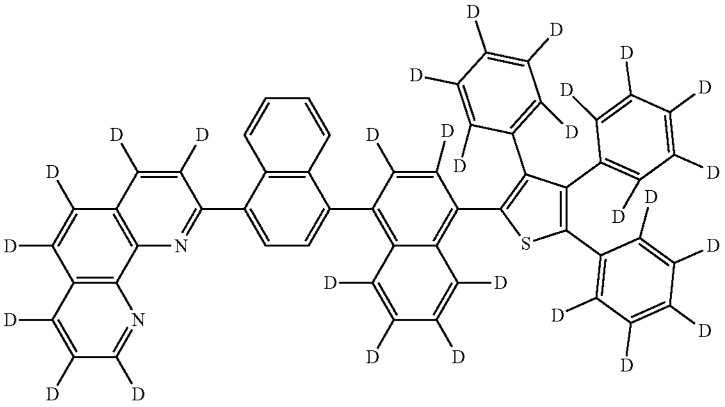
D337
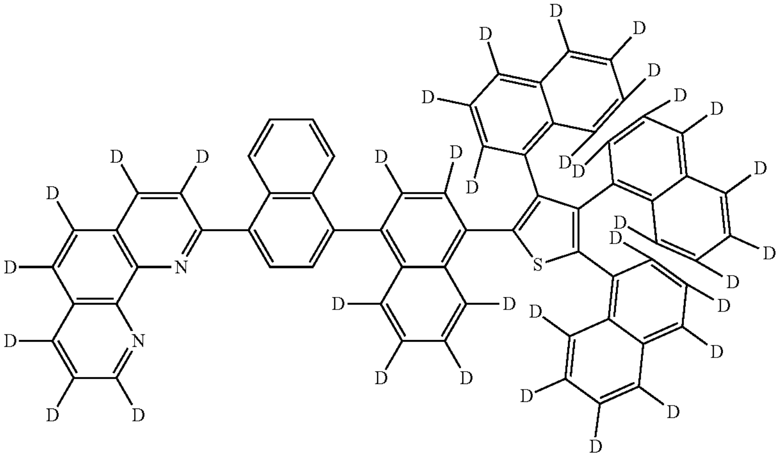

-continued
D338
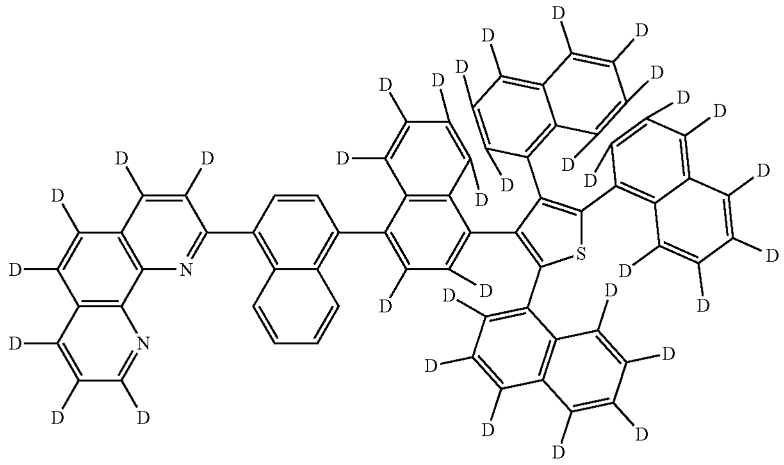
D341
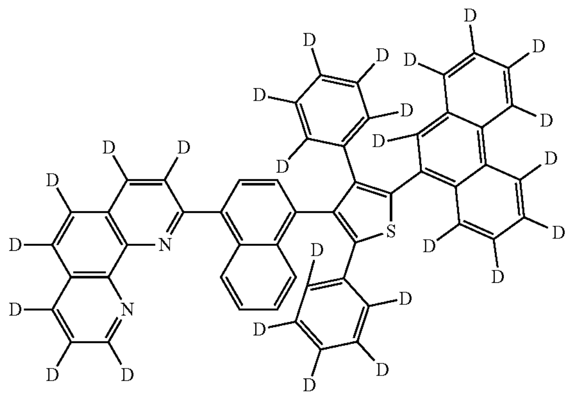
D342
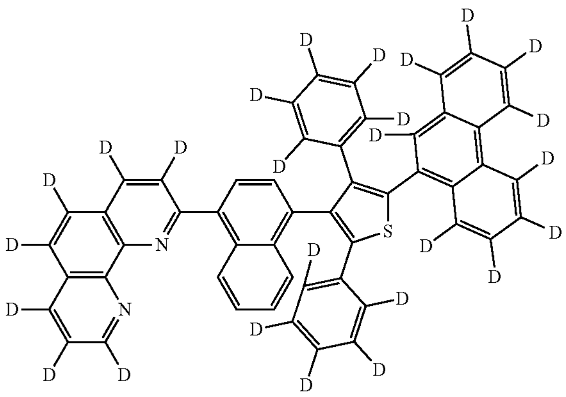
D343
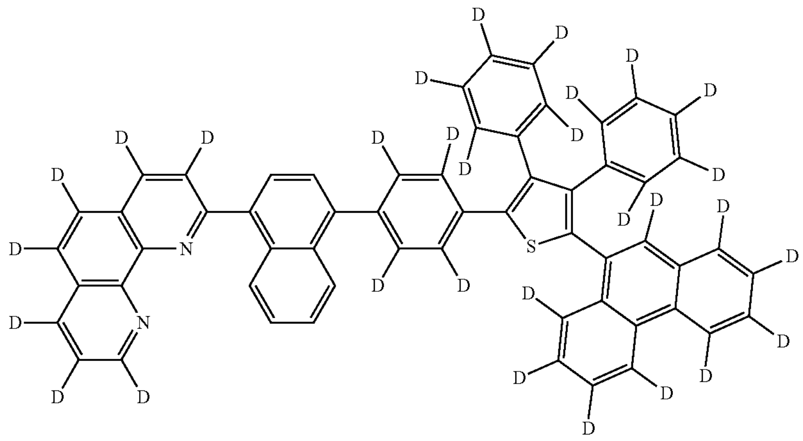

-continued
D344
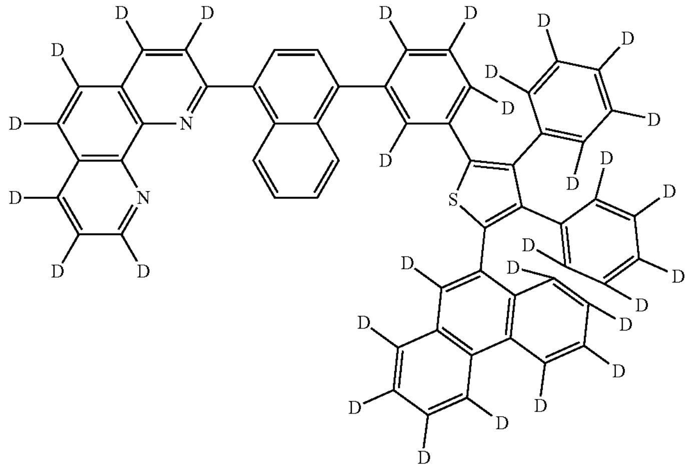
D345
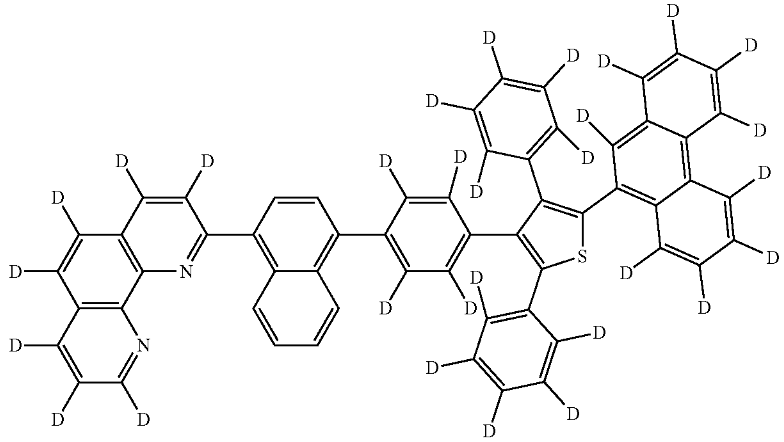
D346
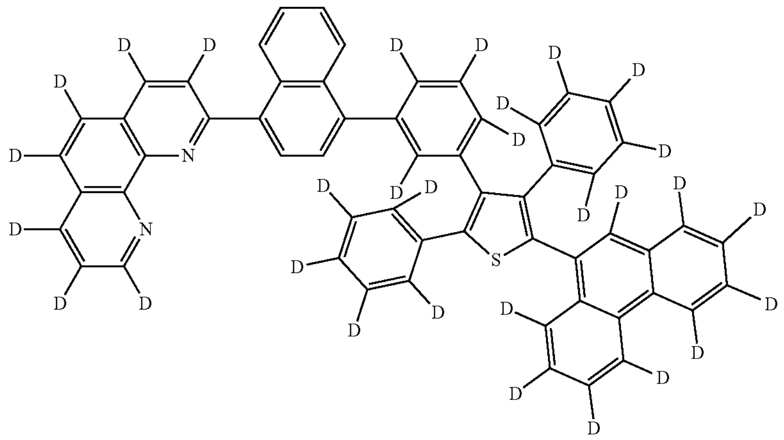

-continued
D348
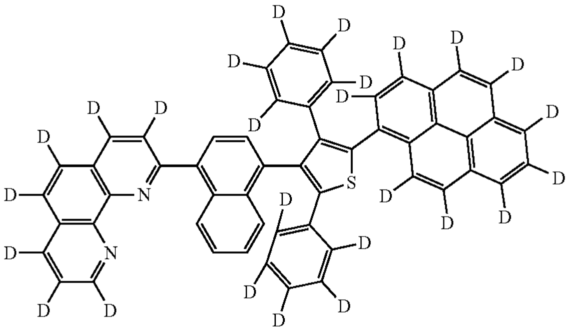
D349
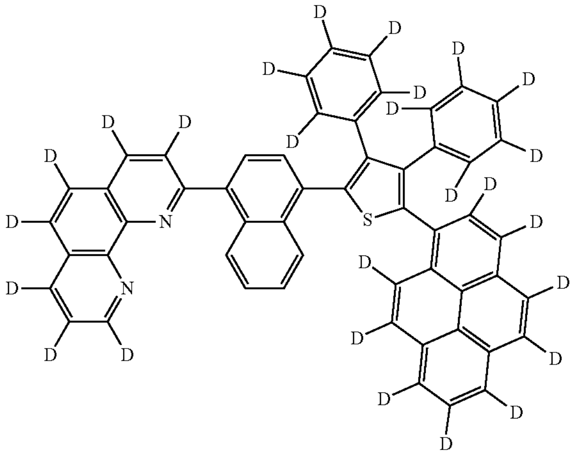
D350
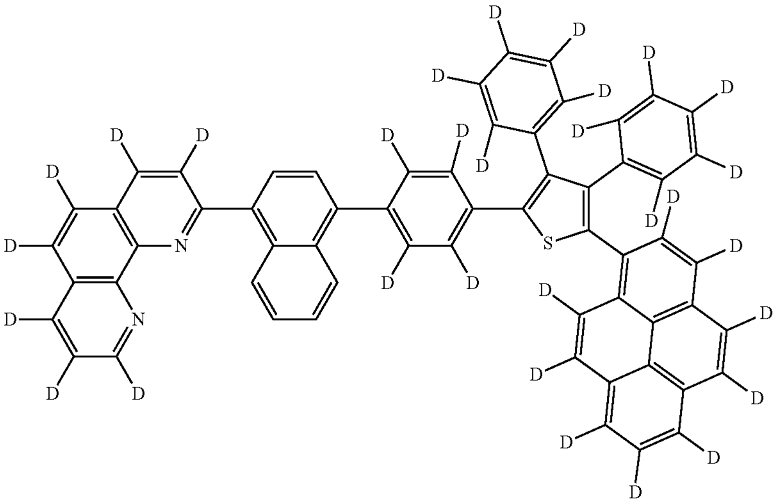
D351
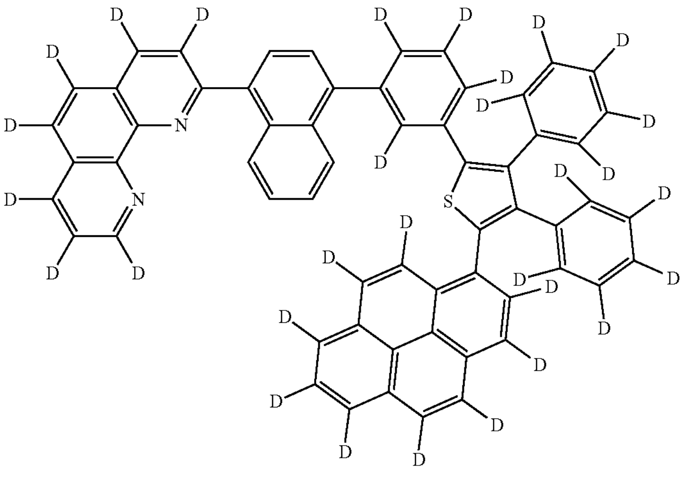

-continued
D352
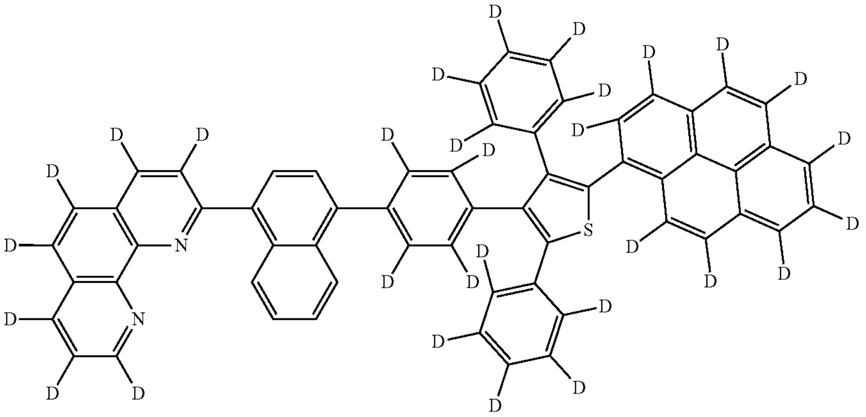
D353
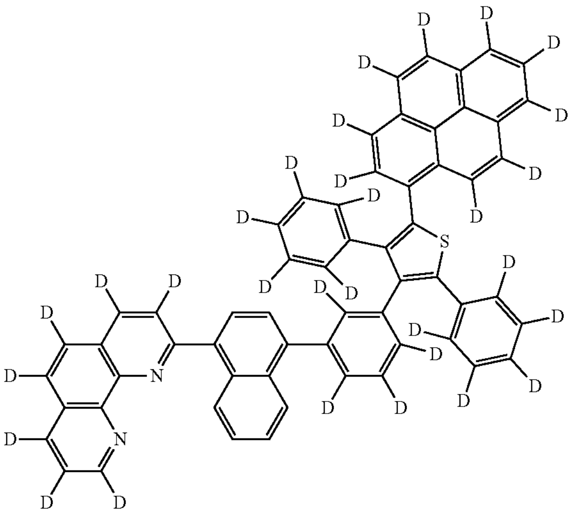
D355
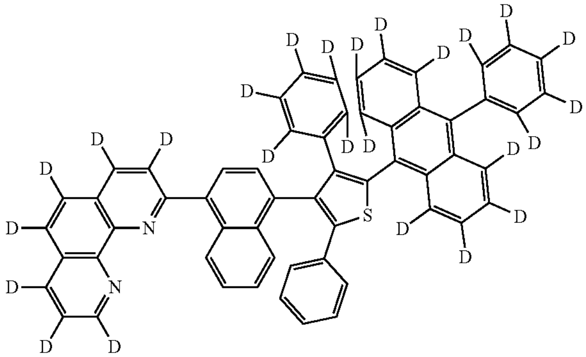
D356
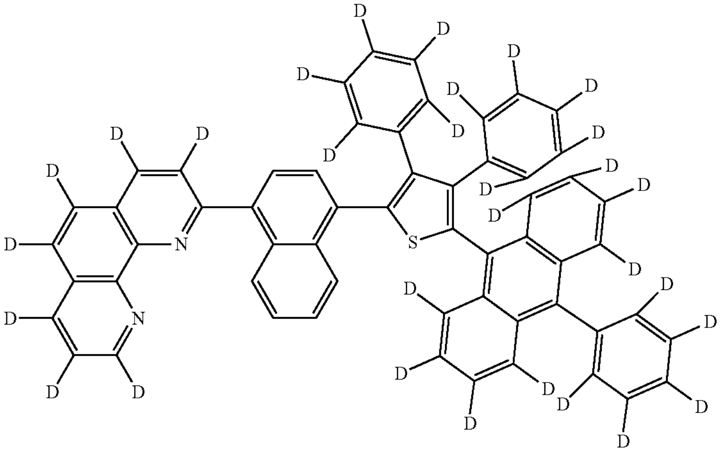

-continued
D357
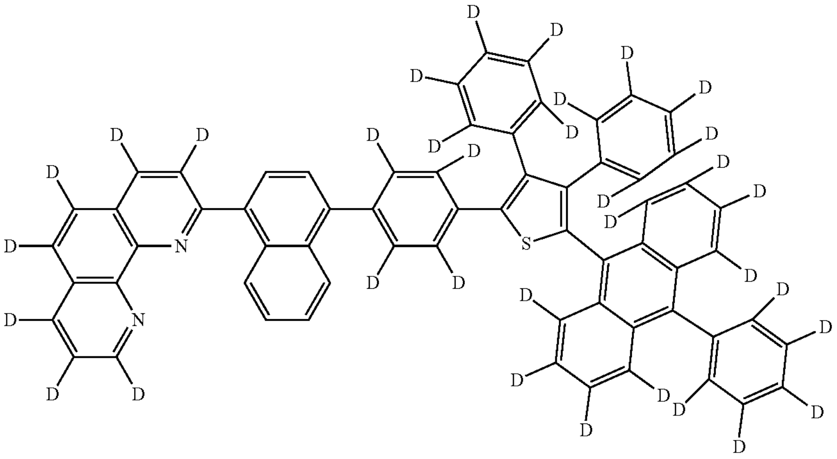
D358
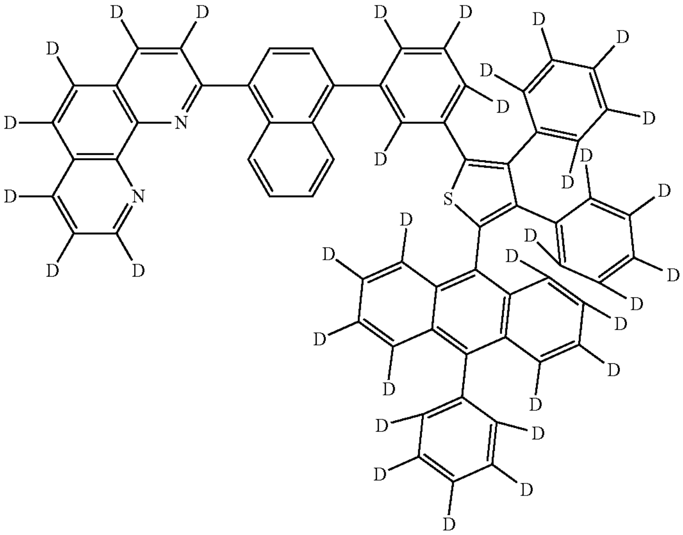
D359
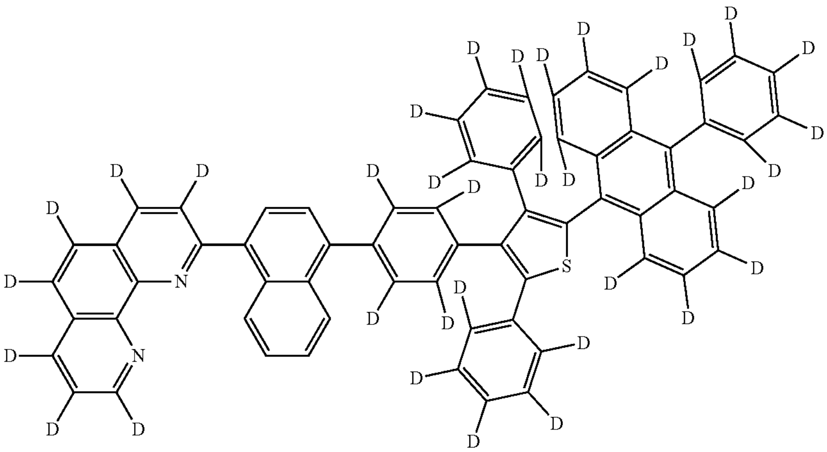

-continued
D360
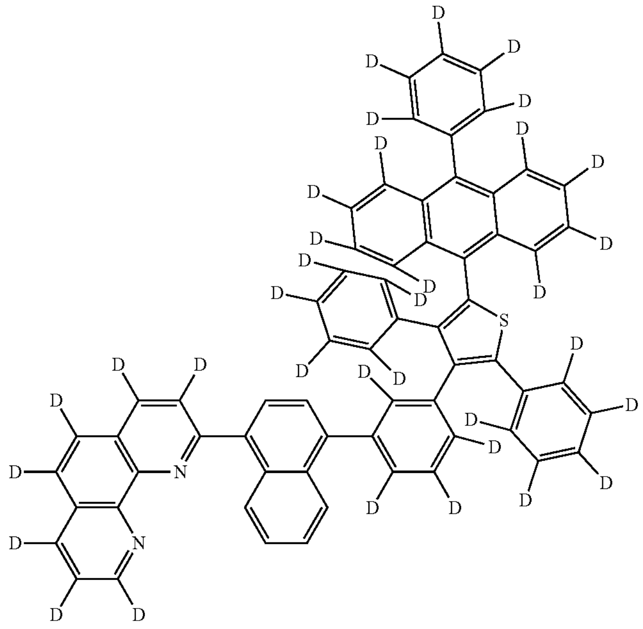
D365
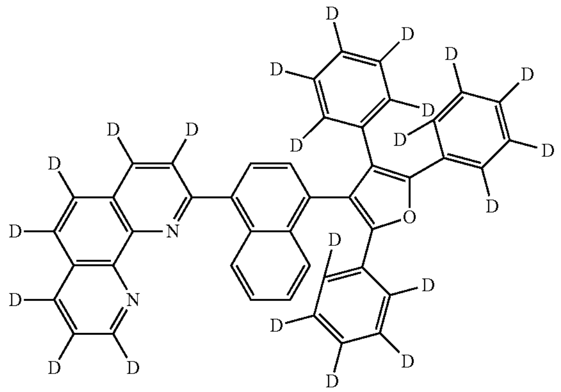
D366
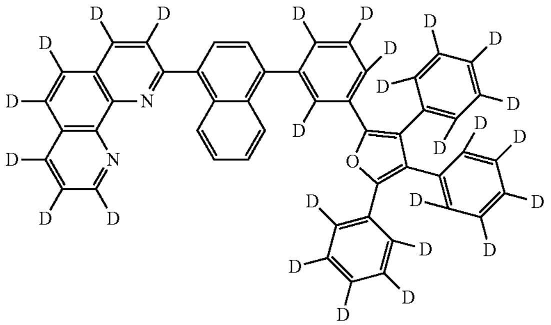
D367
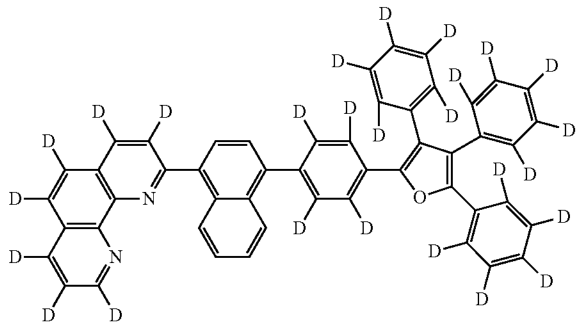
D368
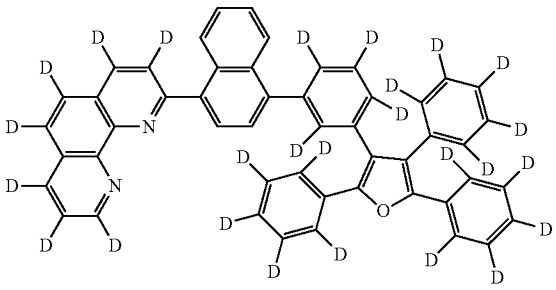

-continued
D369
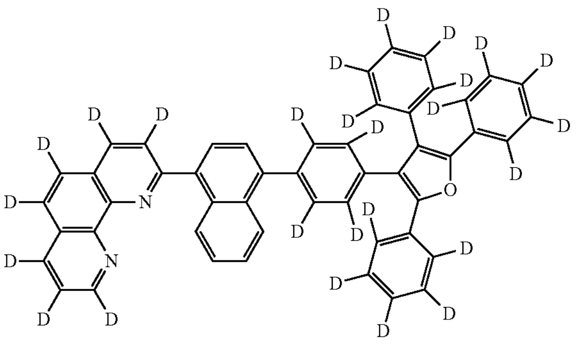
D374
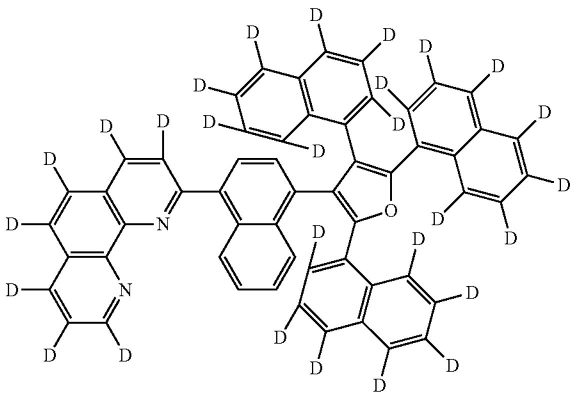
D375
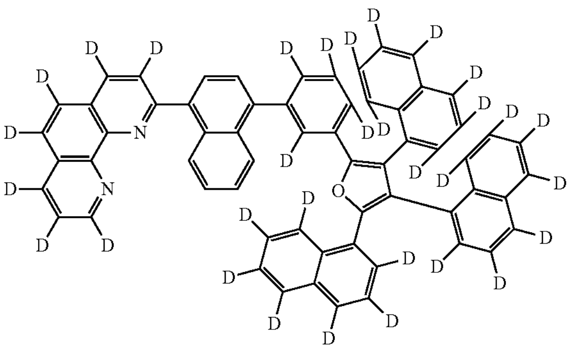
D376
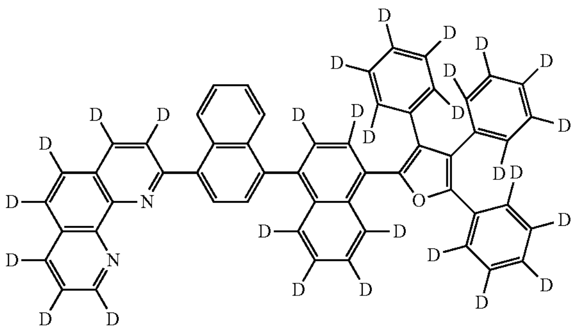
D377
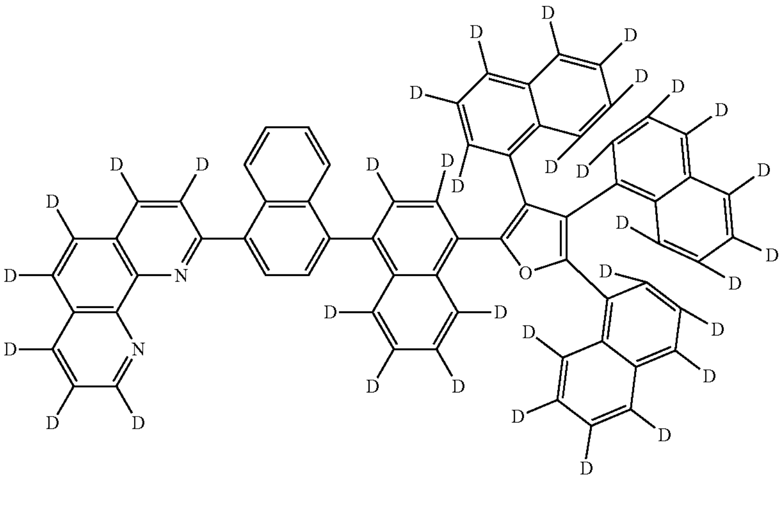

-continued
D378
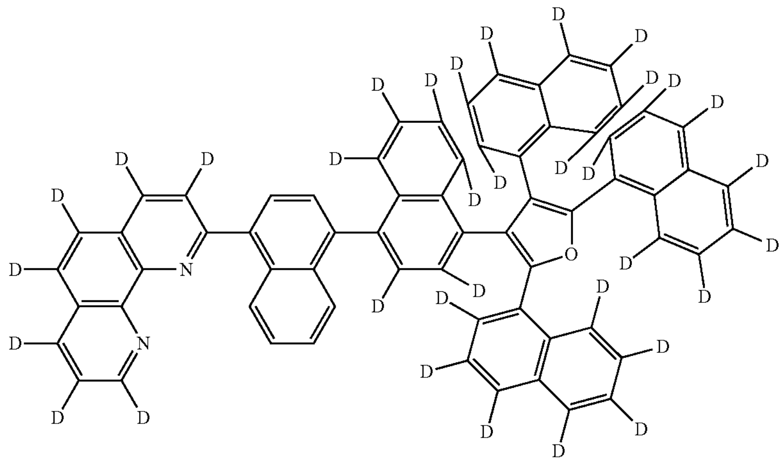
D381
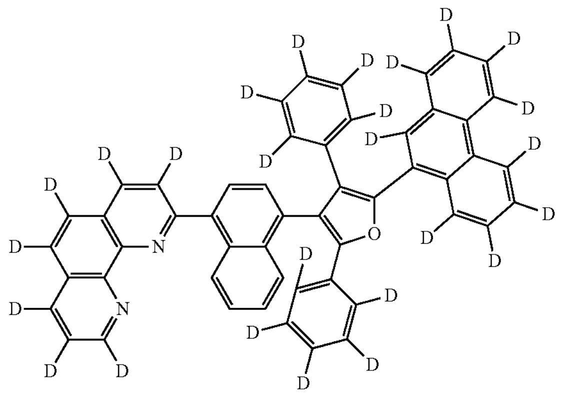
D382
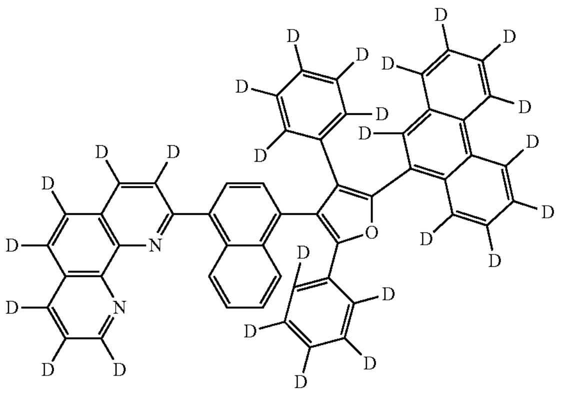
D383
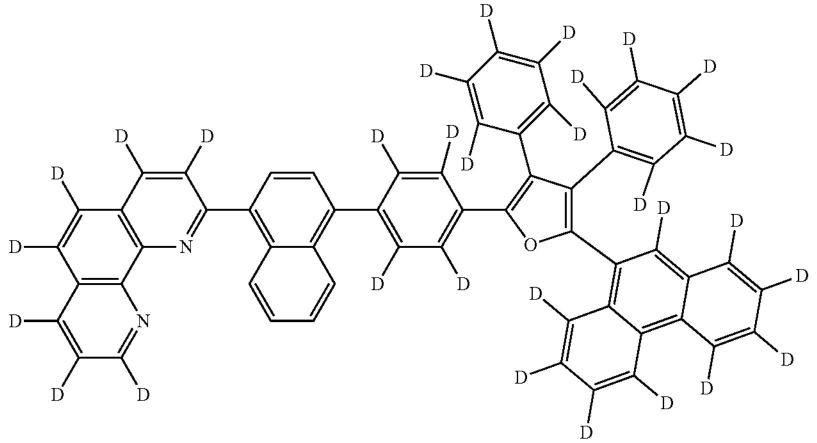

-continued
D384
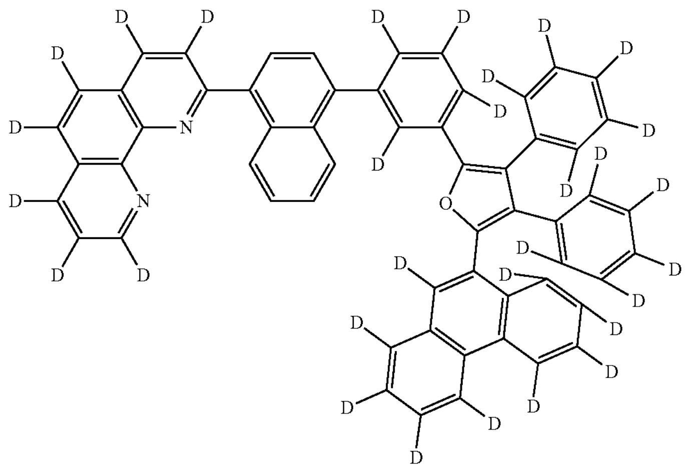
D385
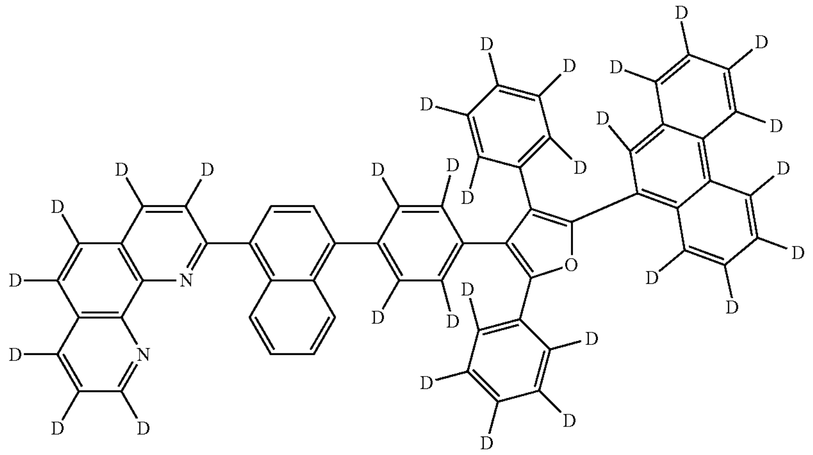
D386
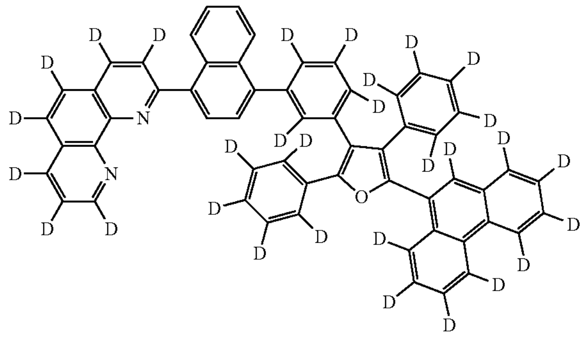
D388
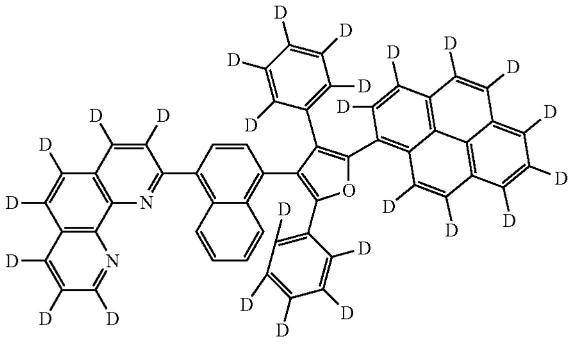

-continued
D389
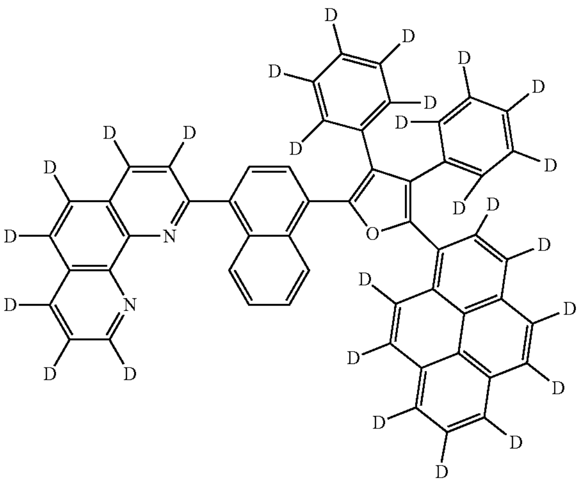
D390
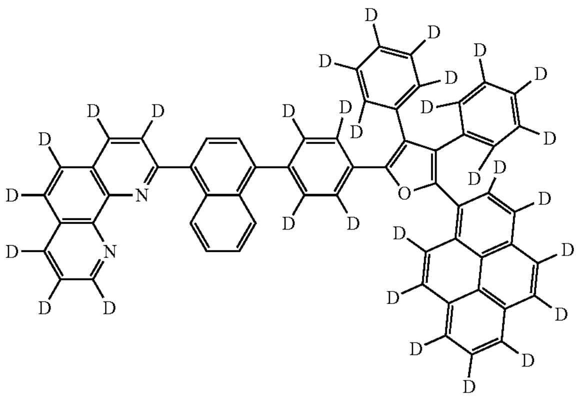
D391
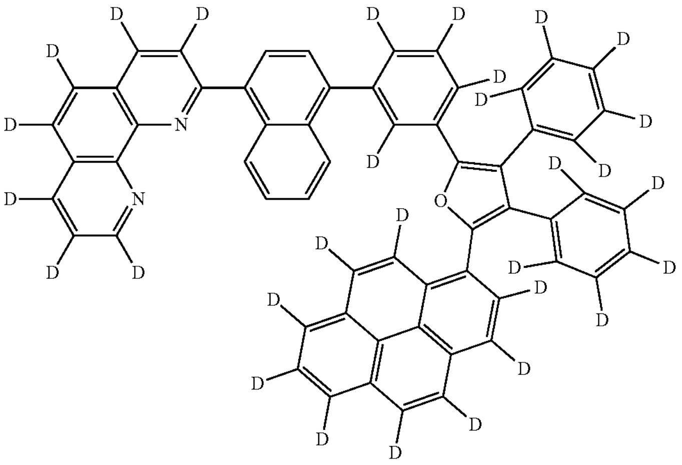
D392
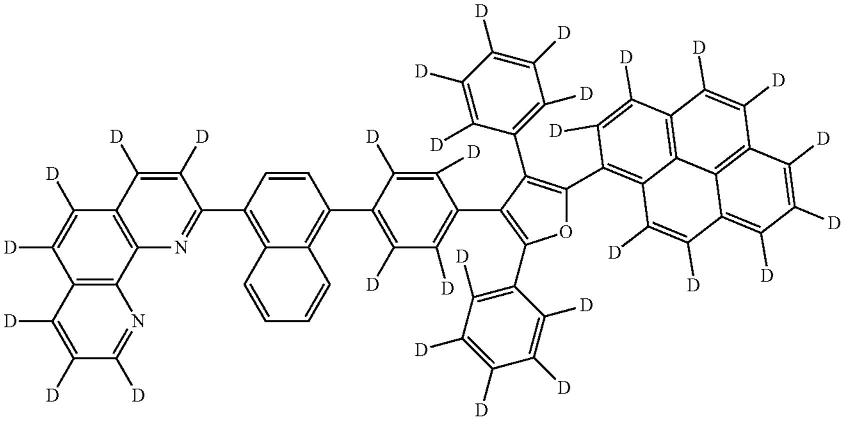

-continued
D393
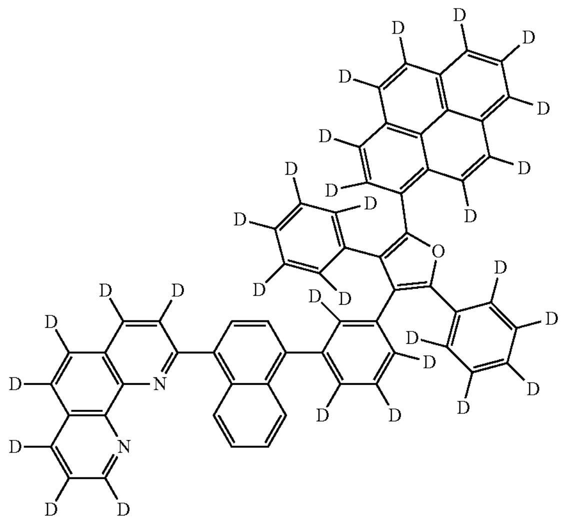
D395
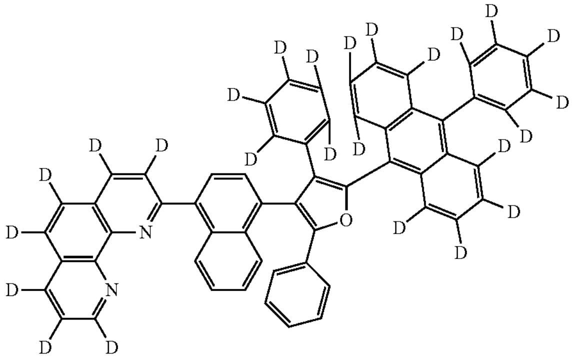
D396
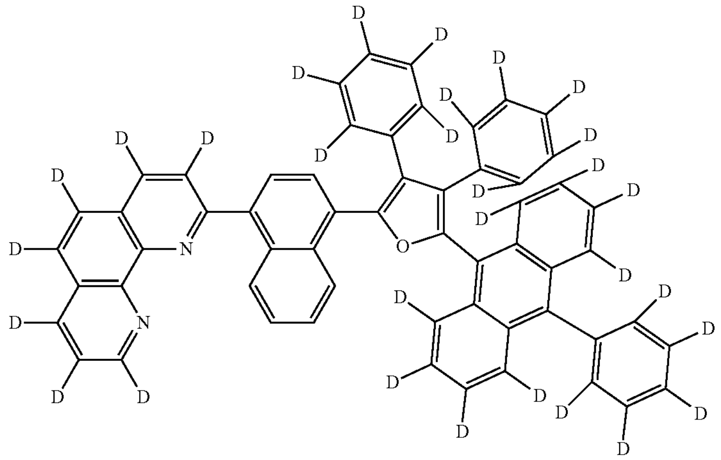
D397
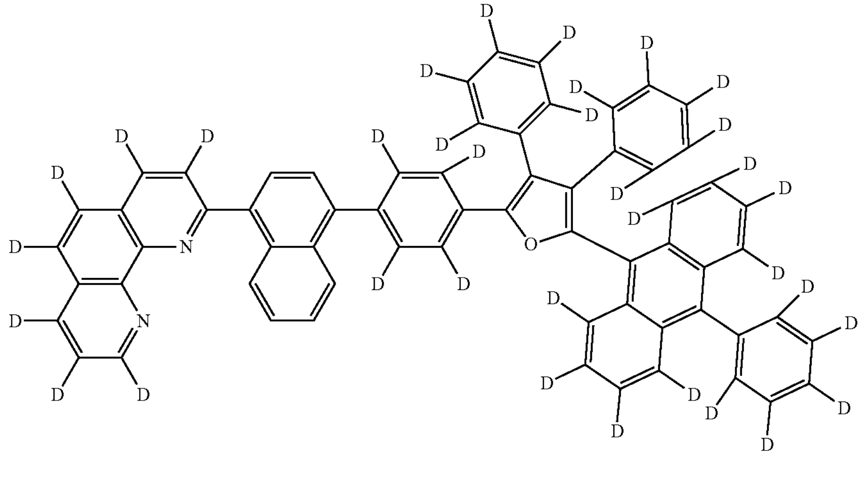

-continued
D398
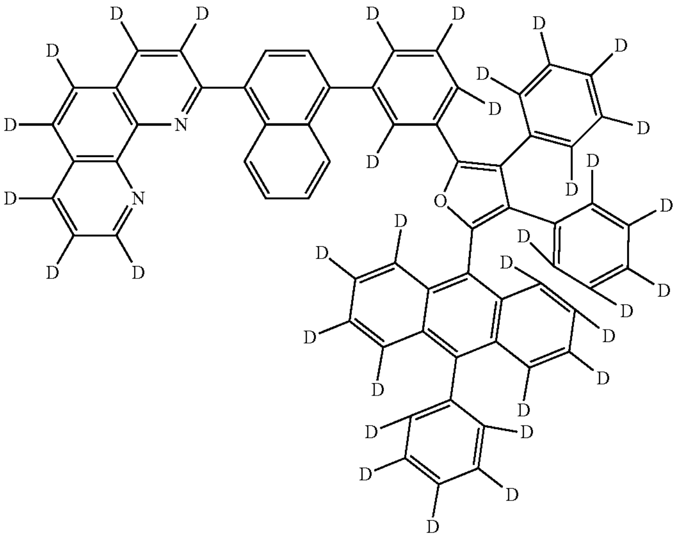
D399
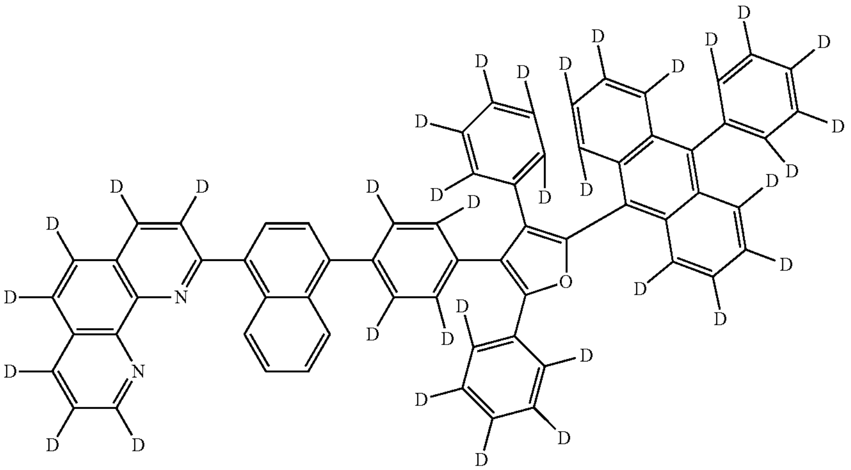
D400
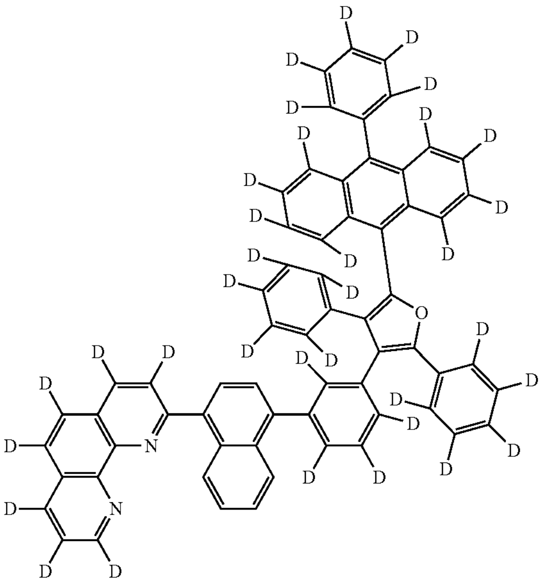
D405
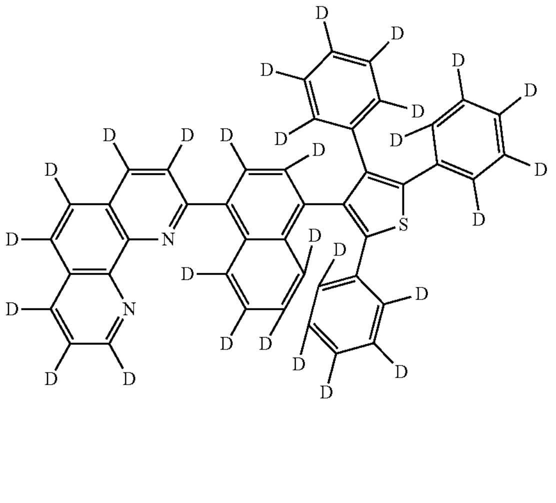

-continued
D406
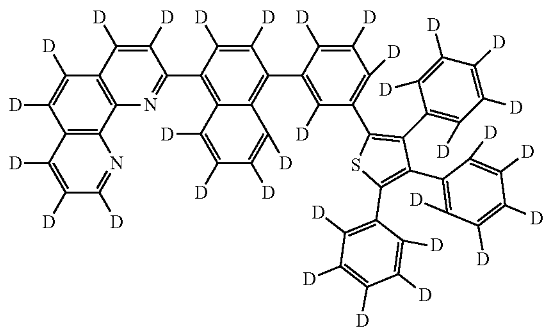
D407
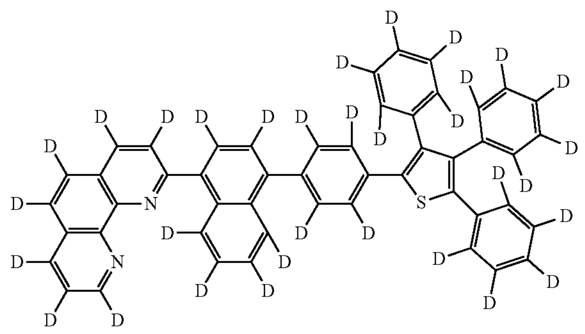
D408
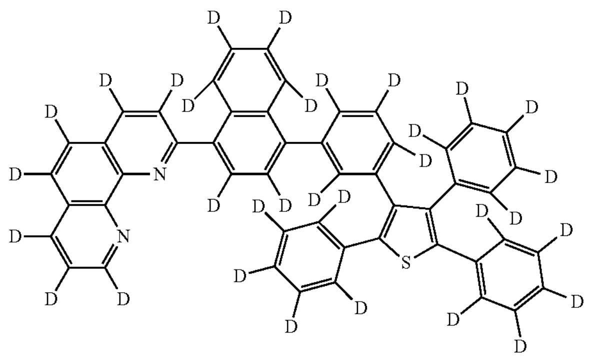
D409
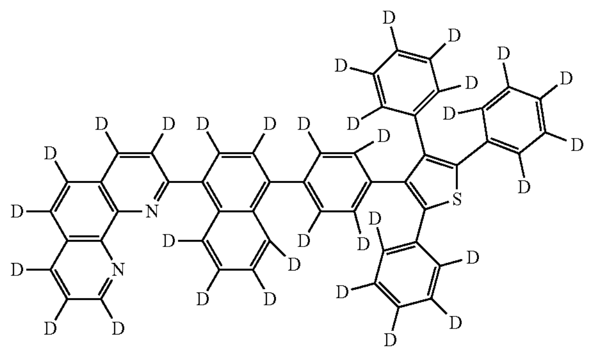
D414
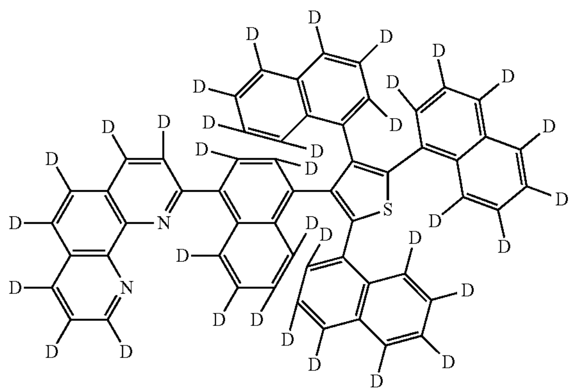
D415
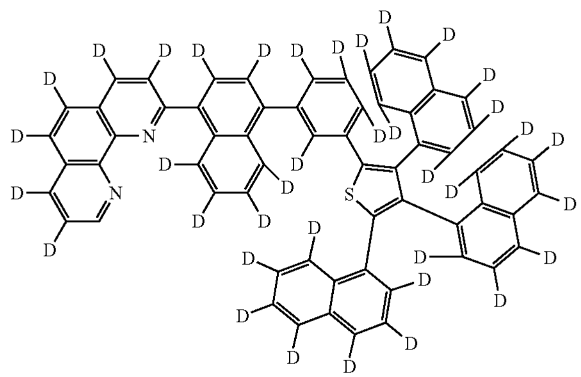
D416
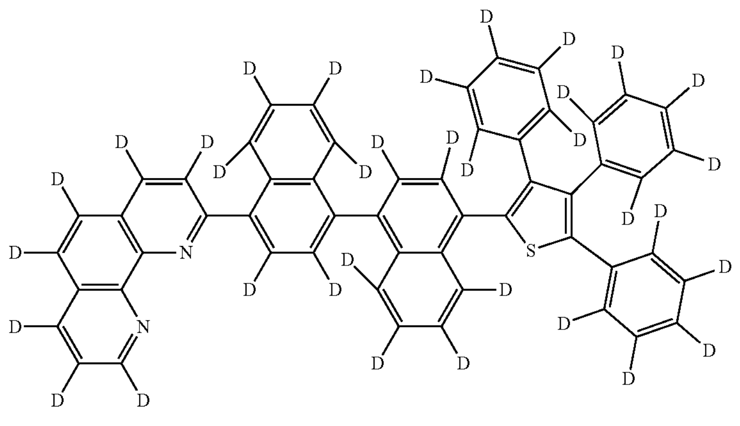

-continued
D417
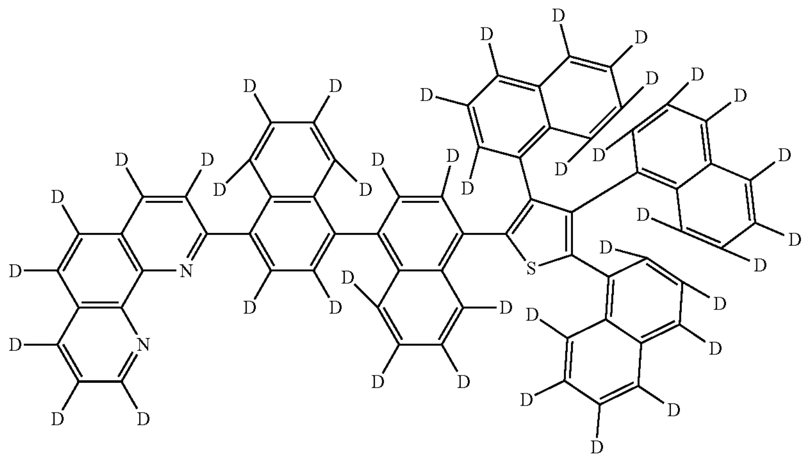
D418
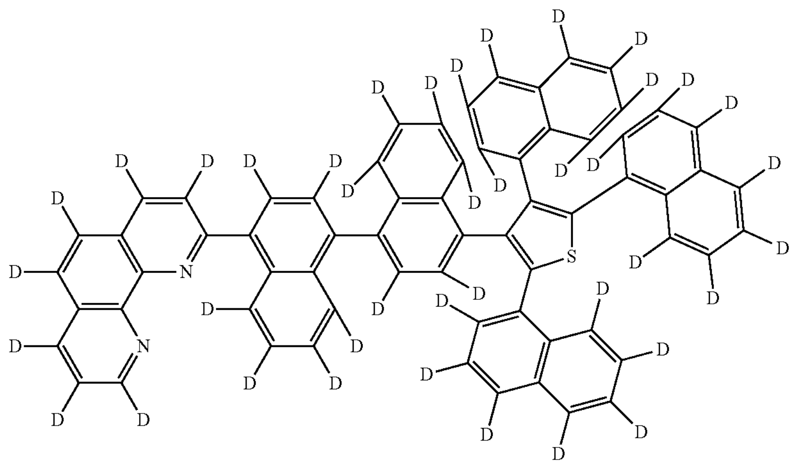
D421
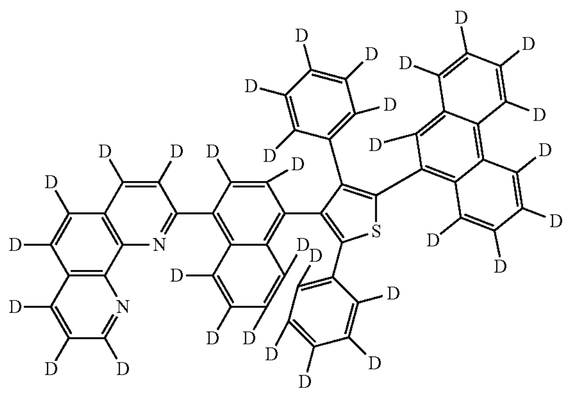
D422
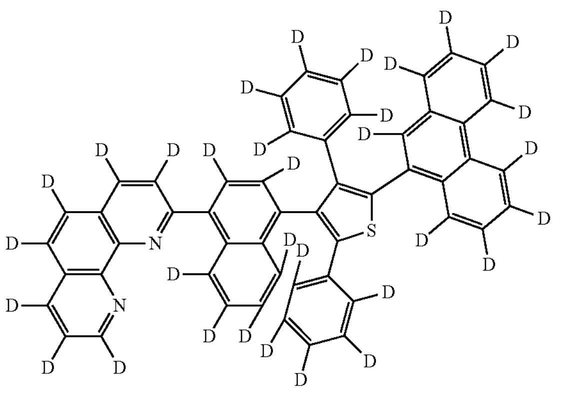

-continued
D423
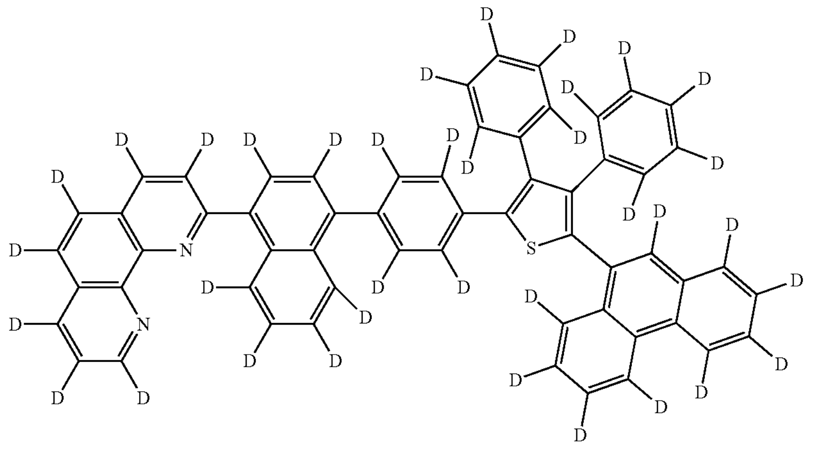
D424
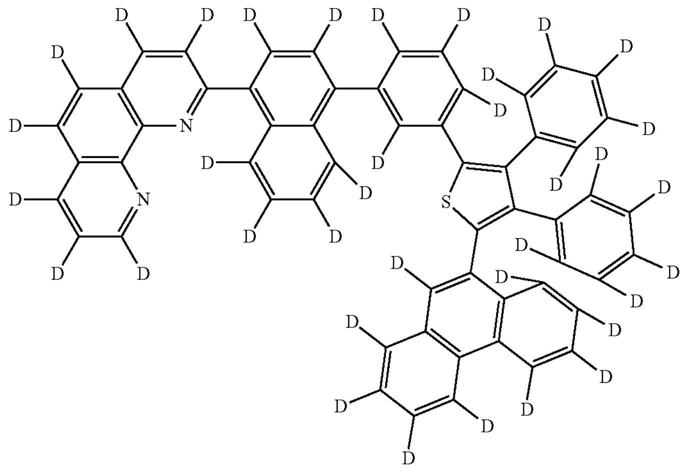
D425
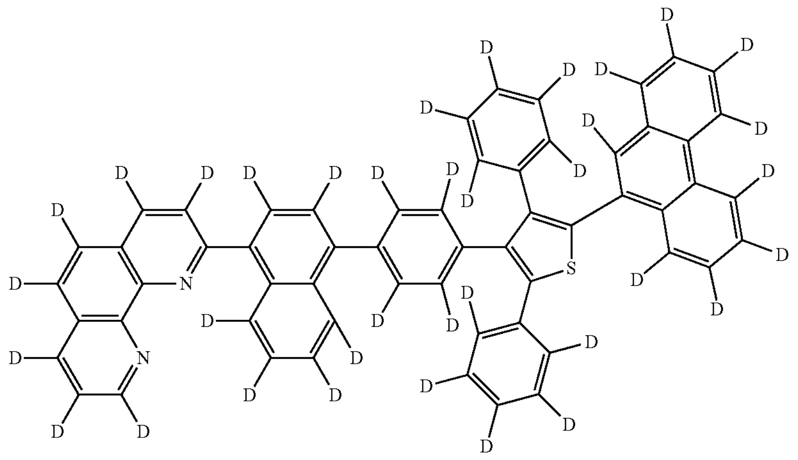

-continued
D426
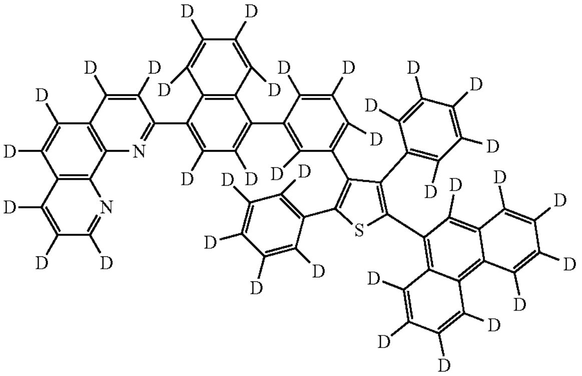
D428
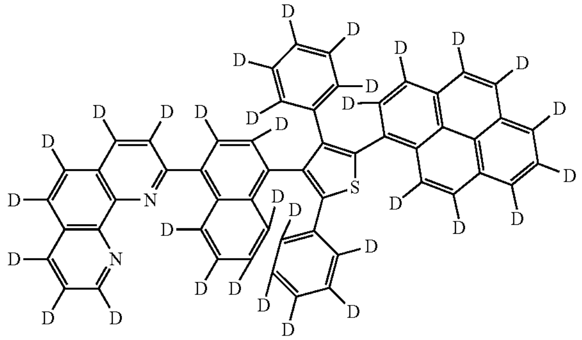
D429
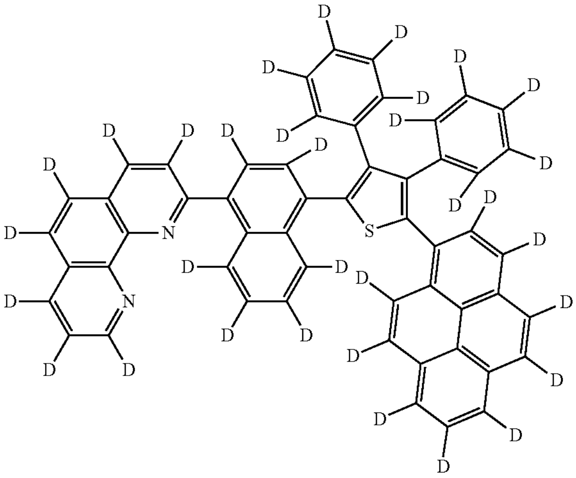
D430
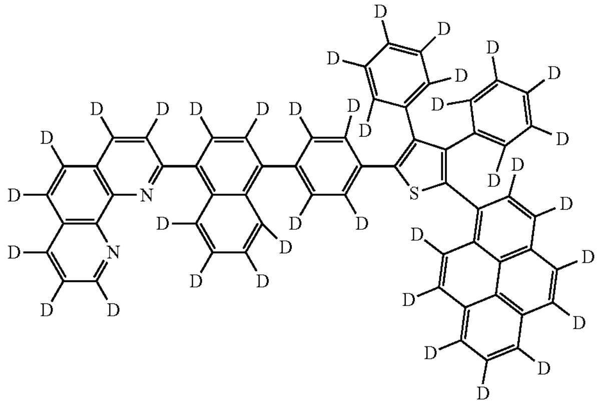
D431
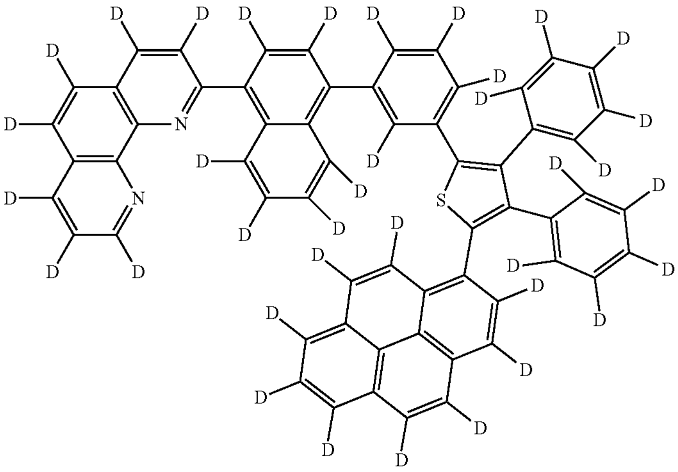

-continued
D432
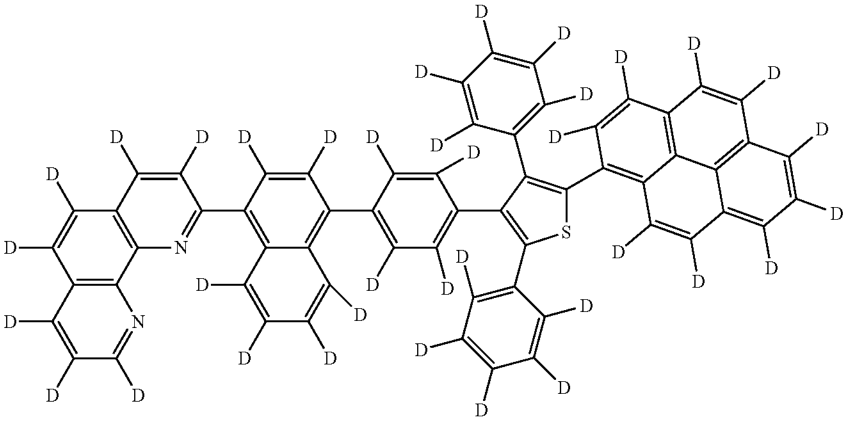
D433
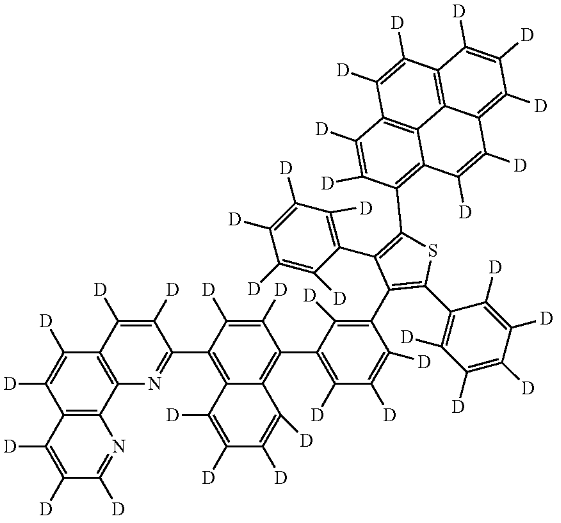
D435
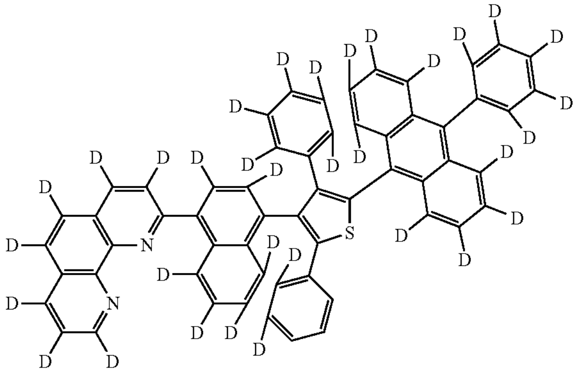
D436
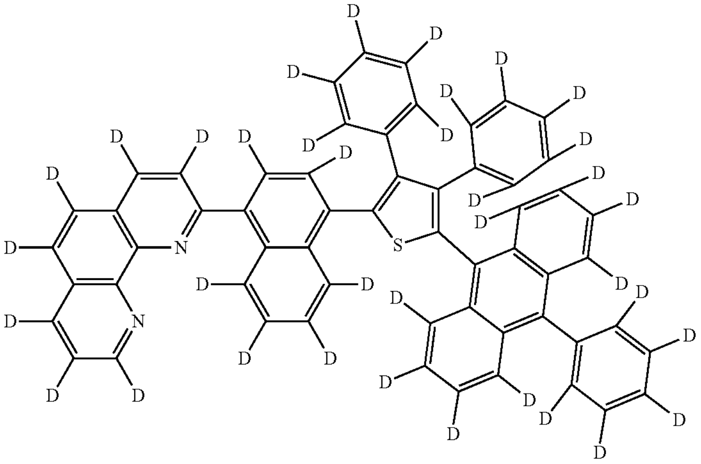

-continued
D437
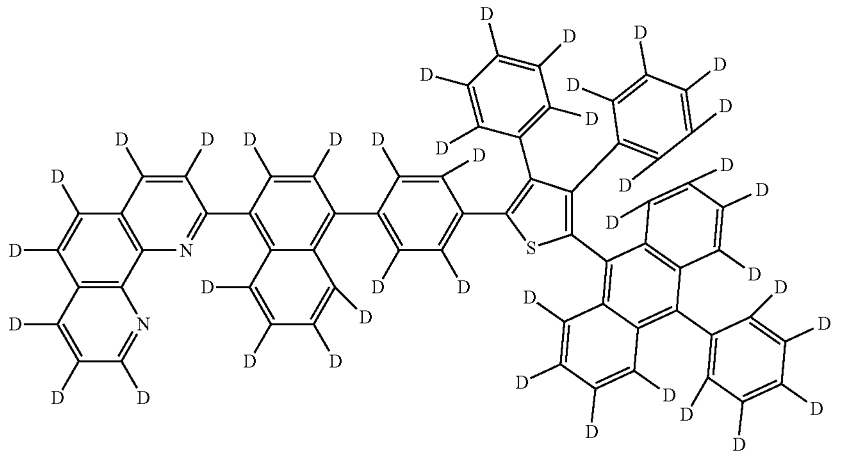
D438
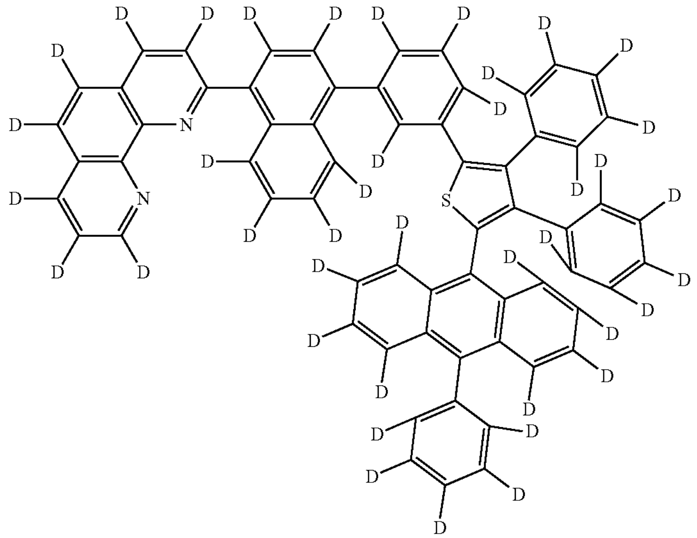
D439
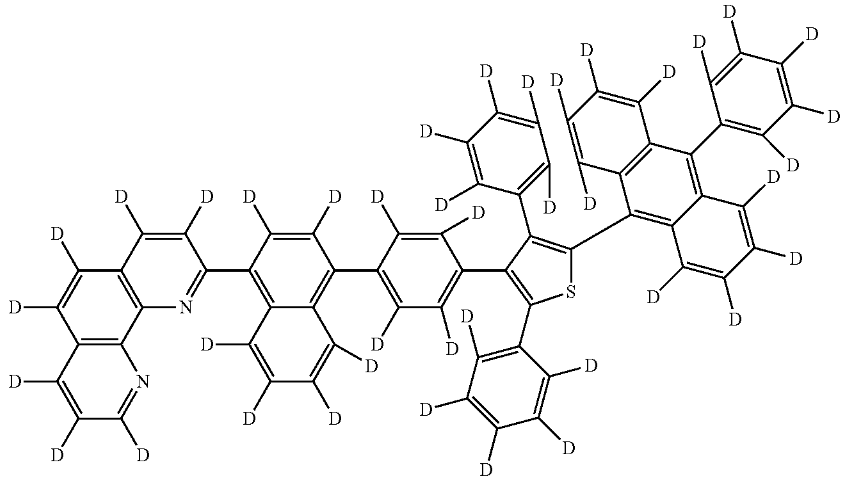

-continued
D440
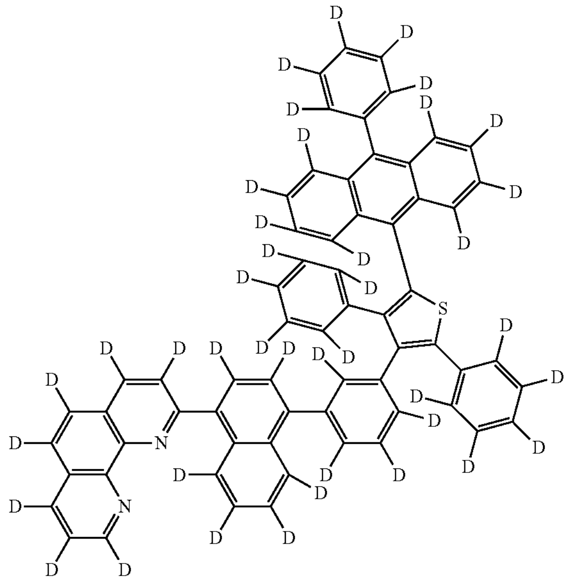
D445
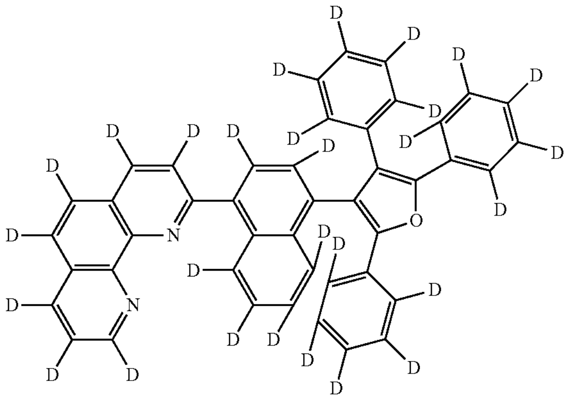
D446
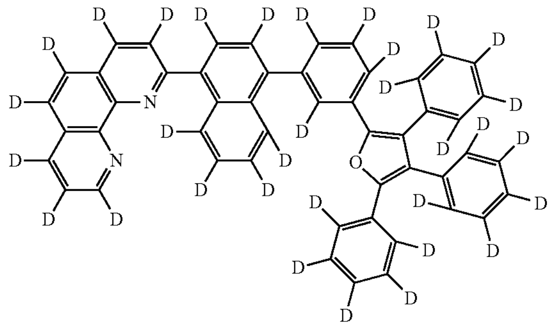
D447
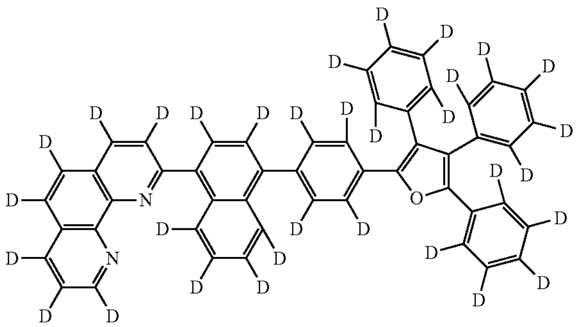
D448
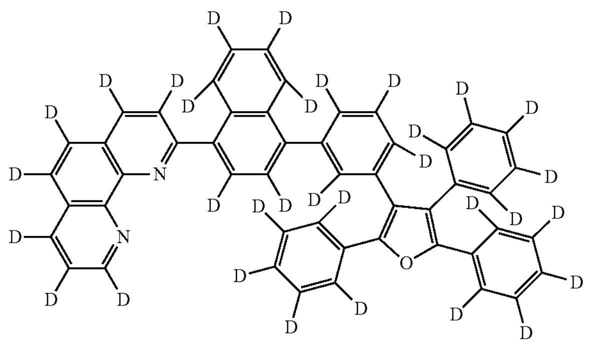
D449
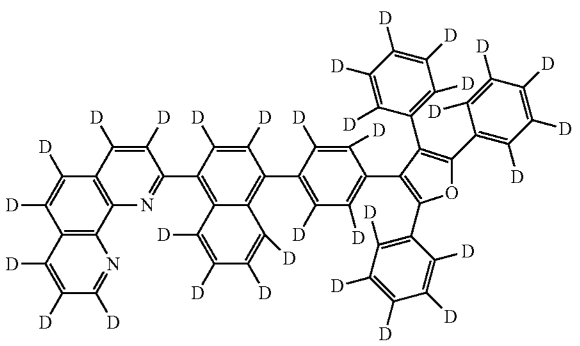

-continued
D454
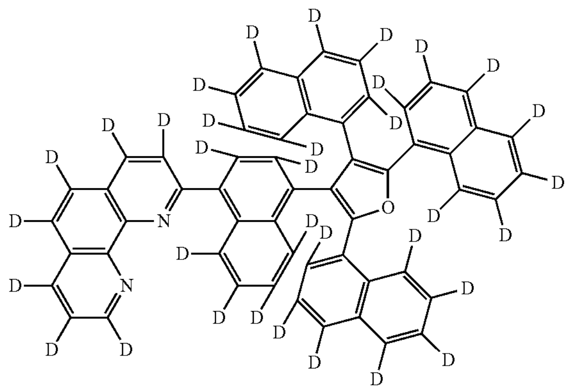
D455
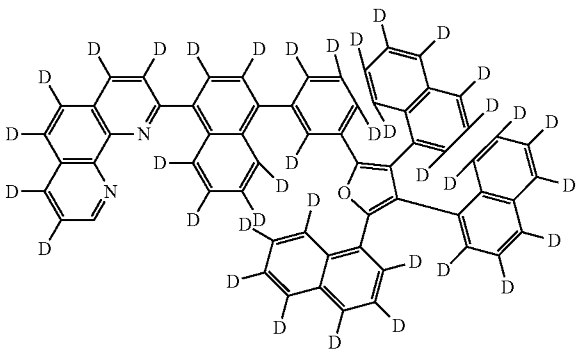
D456
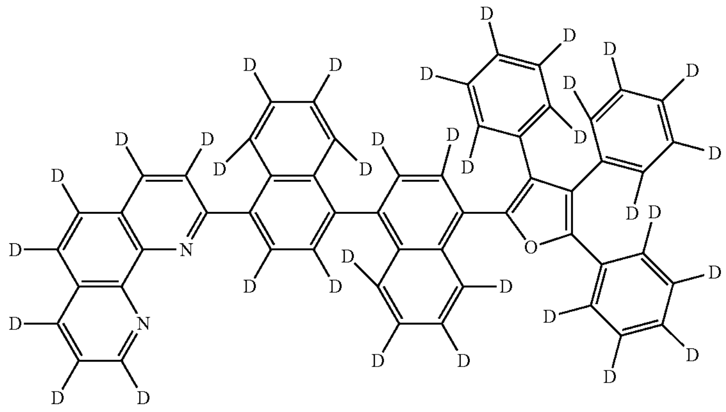
D457
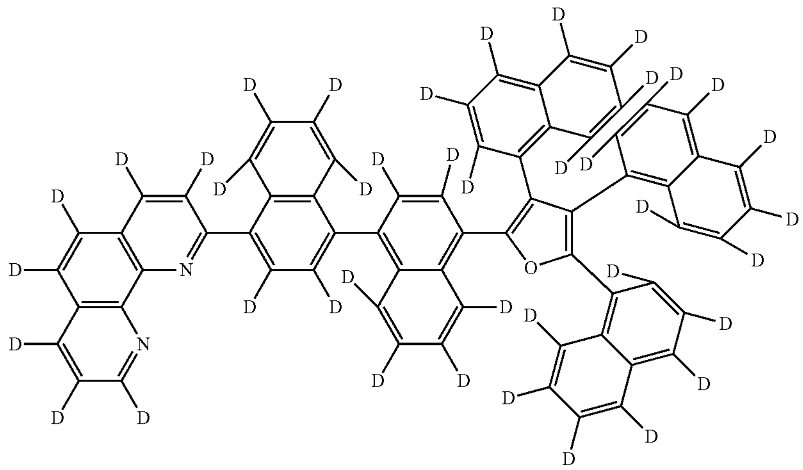

-continued
D458
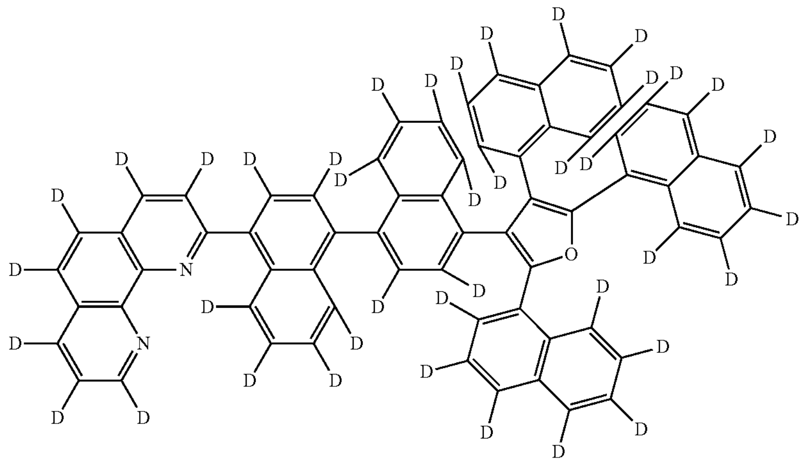
D461
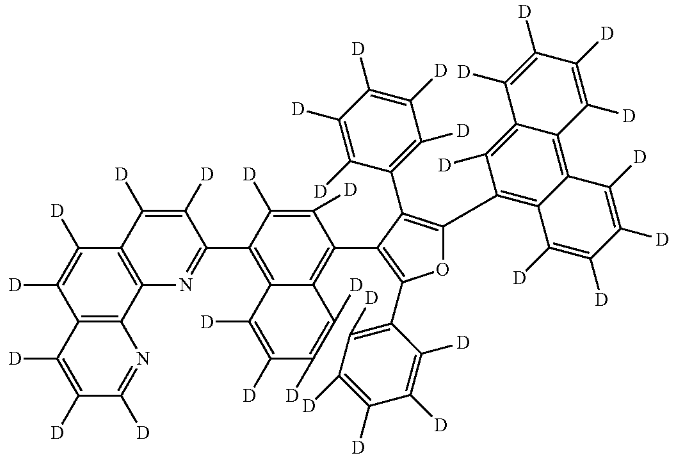
D462
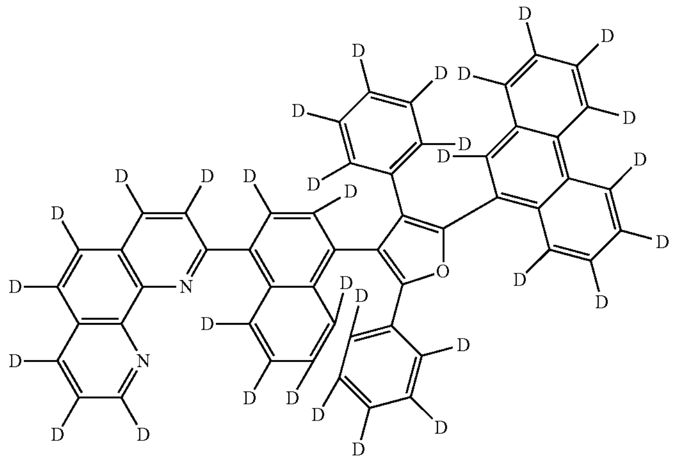

-continued
D463
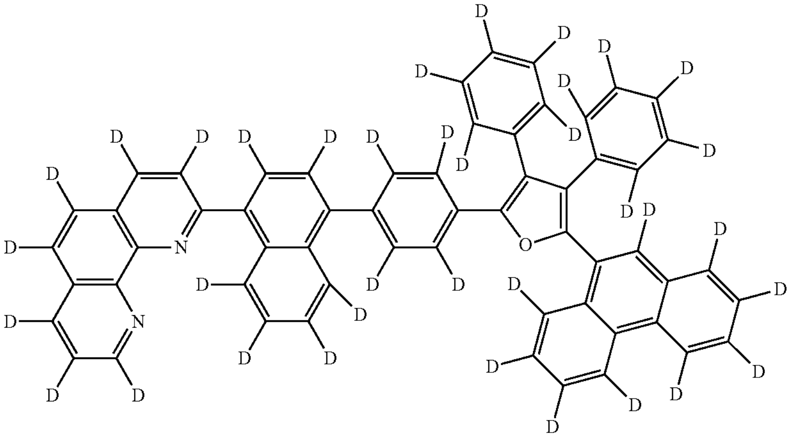
D464
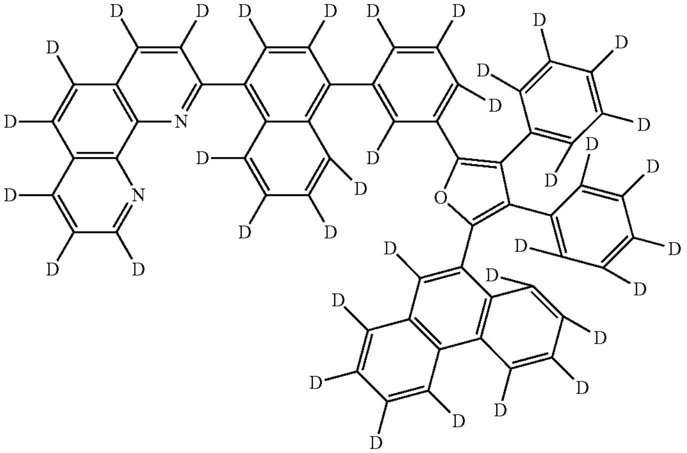
D465
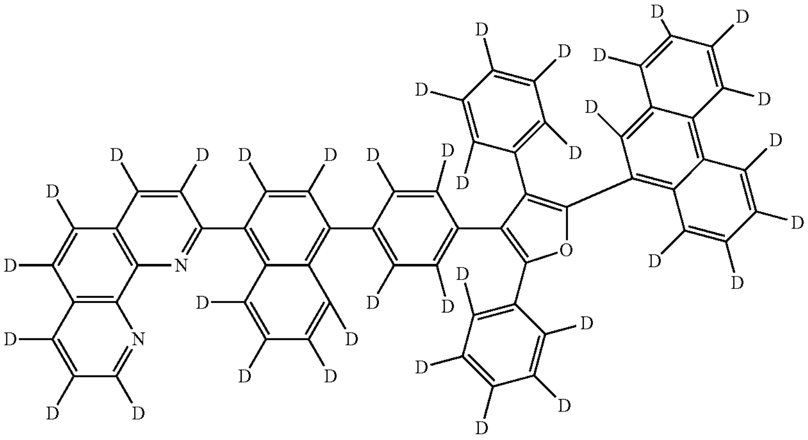

-continued
D466
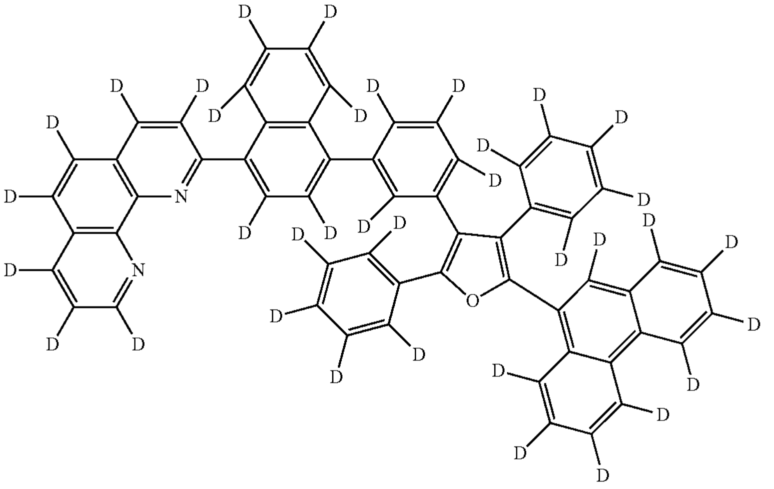
D468
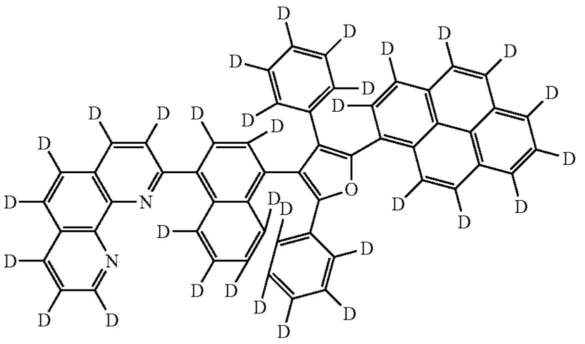
D469
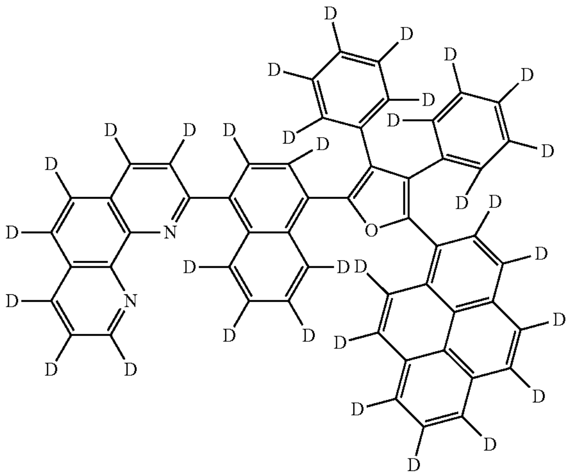
D470
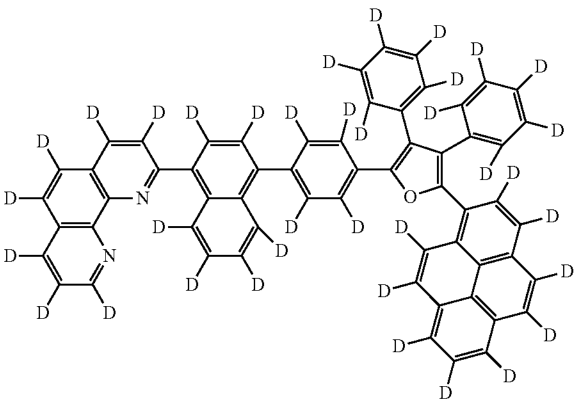
D471
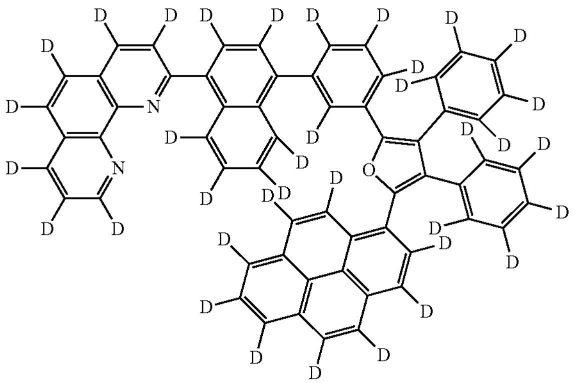

-continued
D472
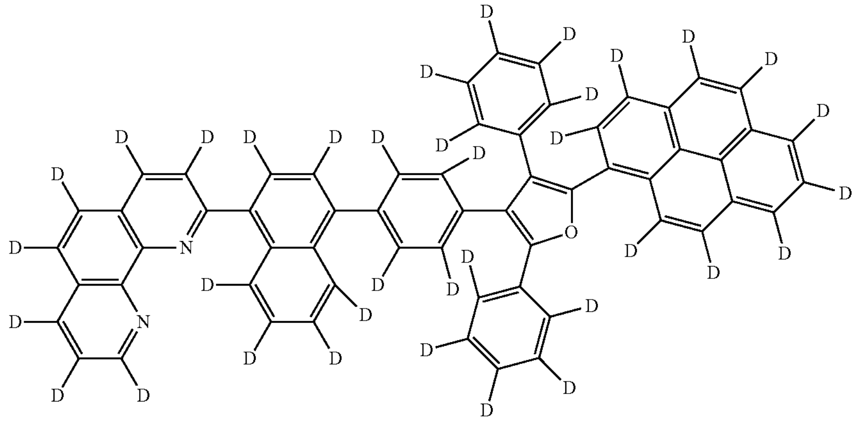
D473
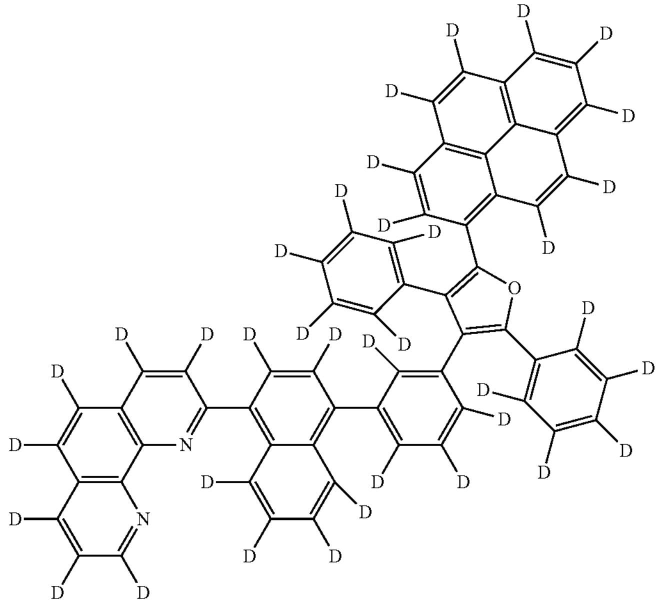
D475
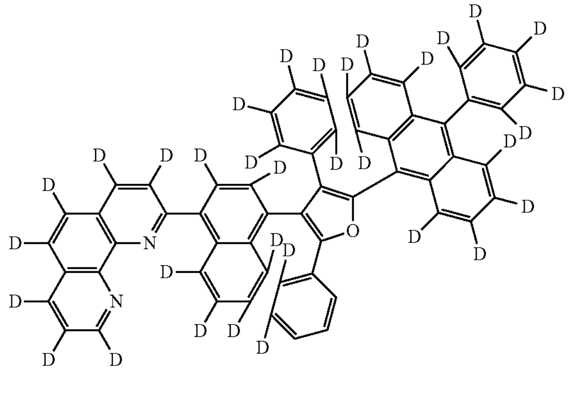
D476
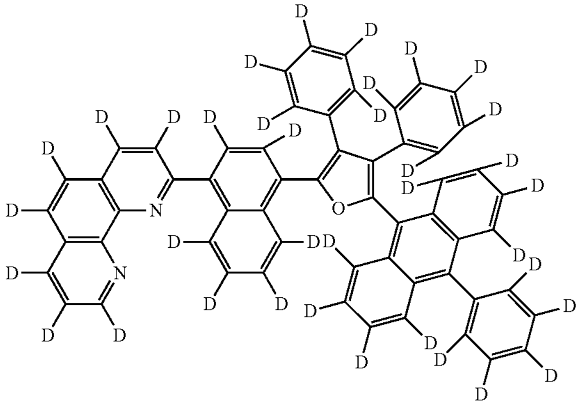

-continued
D477
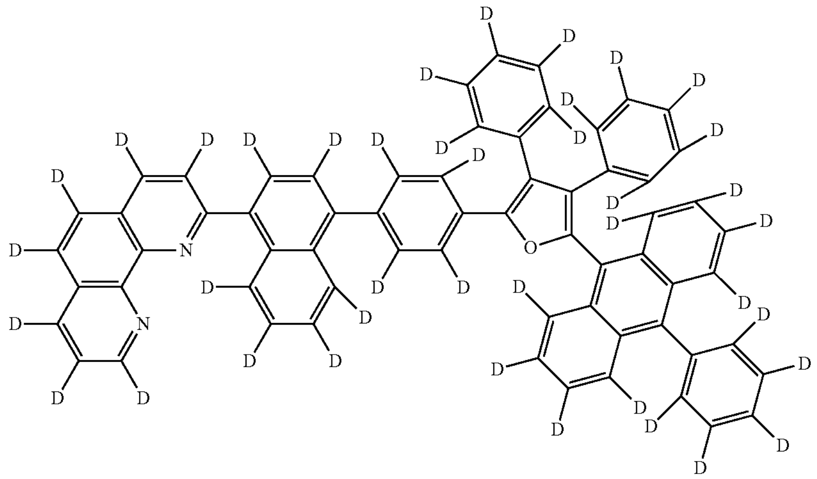
D478
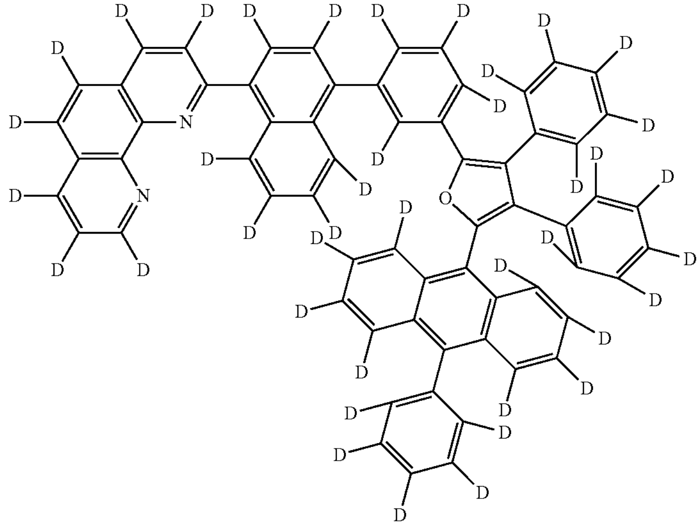
D479
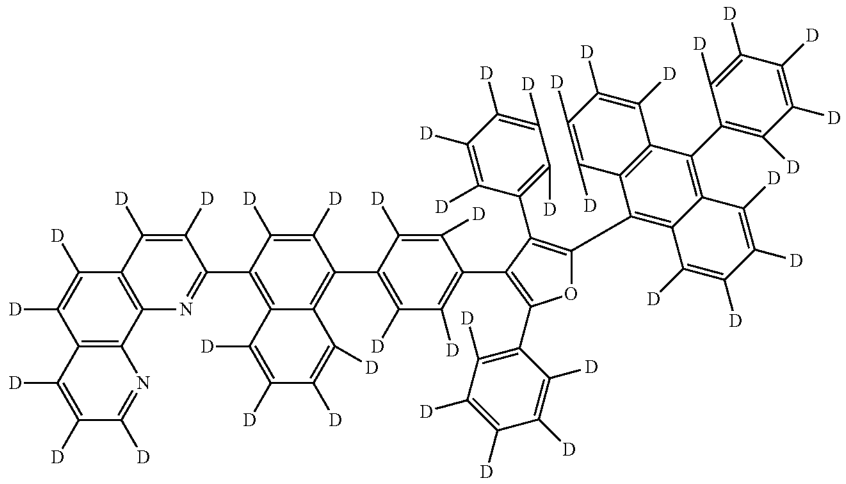

-continued
D480
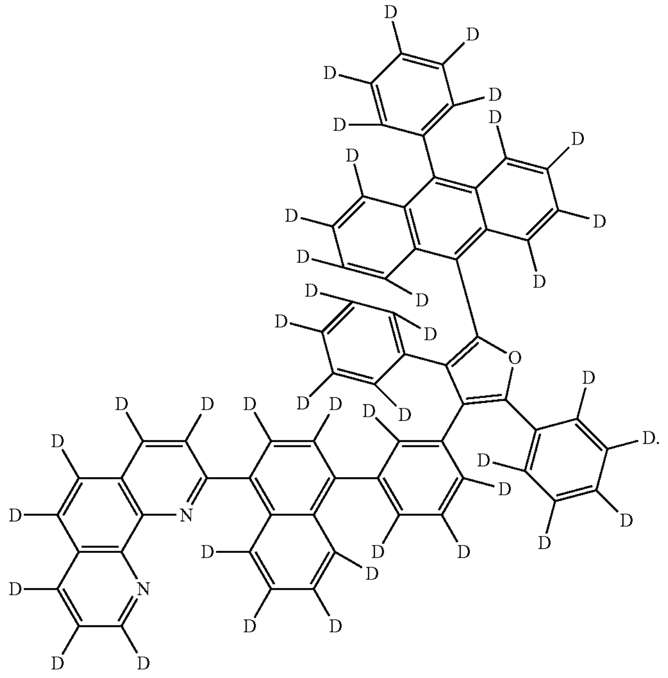
18. The organic light emitting diode according to claim 2, wherein the organic compound is one of compounds in Formula 2:
[Formula 2]
D5
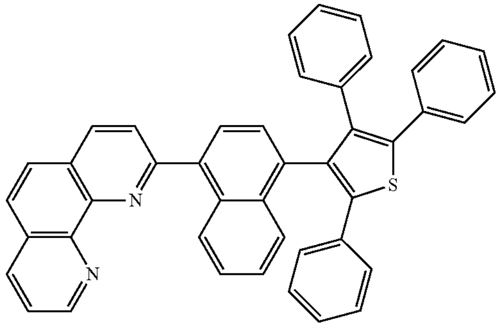
D6
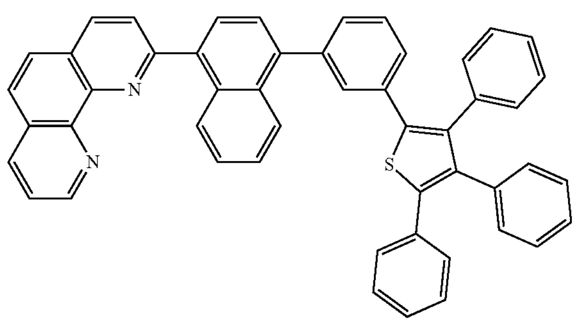
-continued
D7
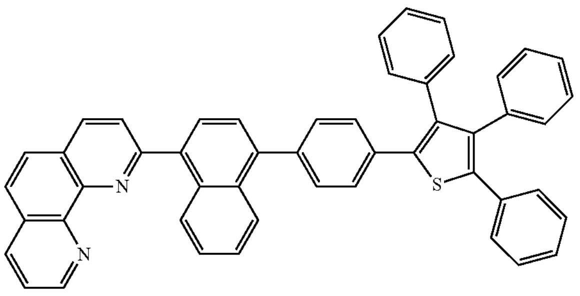
D8
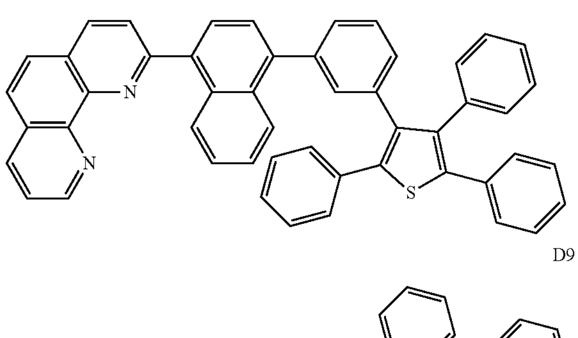
D9
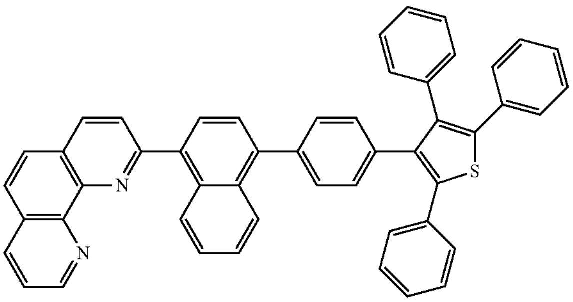

-continued
D14
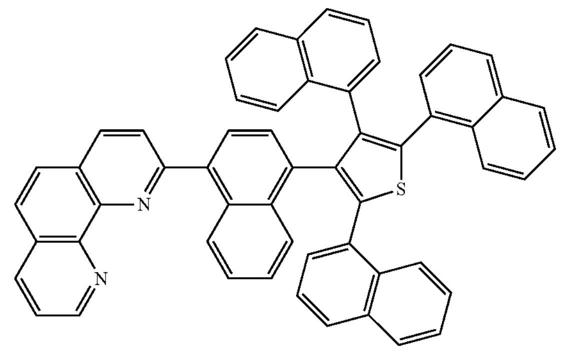
D15
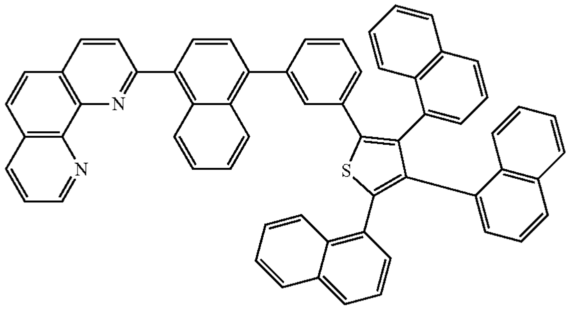
D16
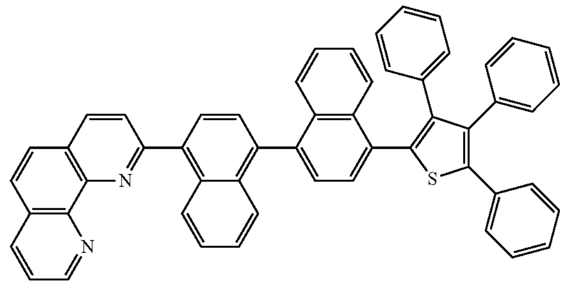
D17
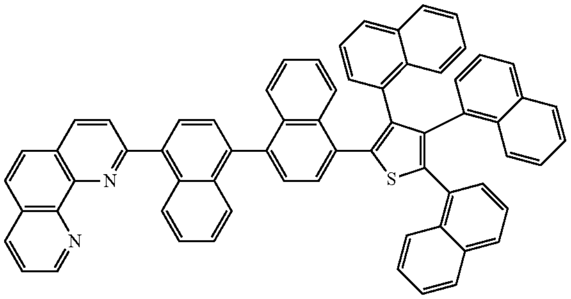
D18
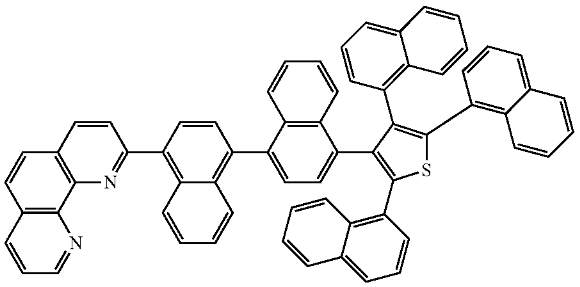
-continued
D21
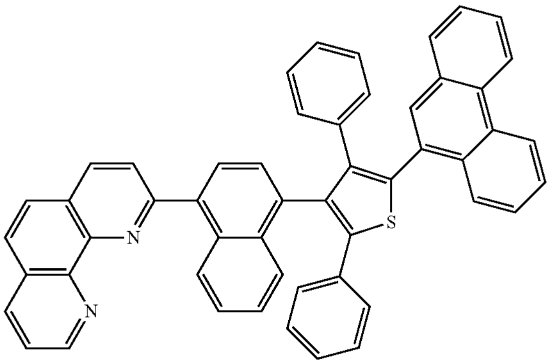
D22
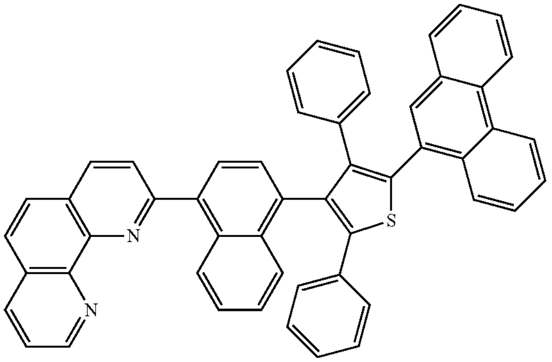
D23
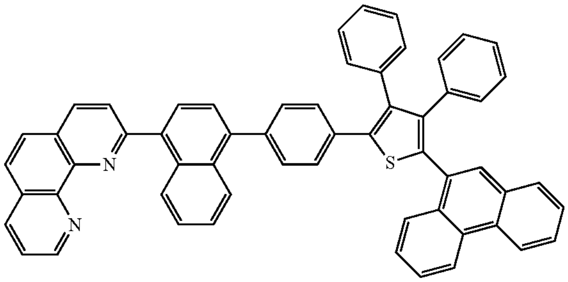
D24
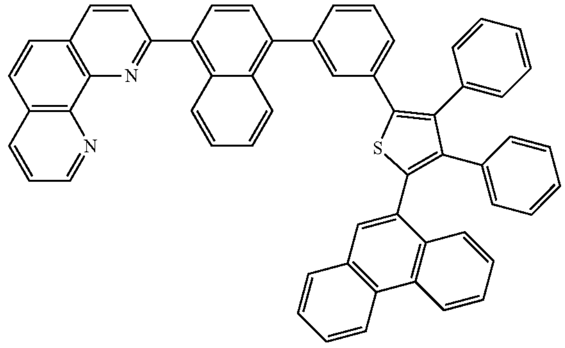

-continued
D25
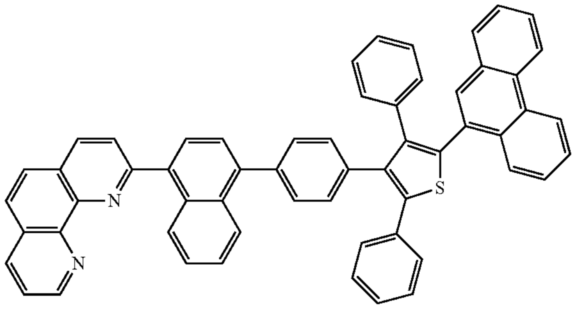
D26
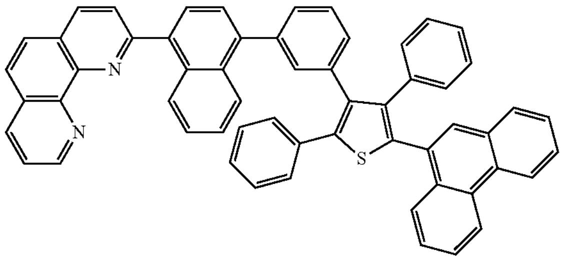
D28
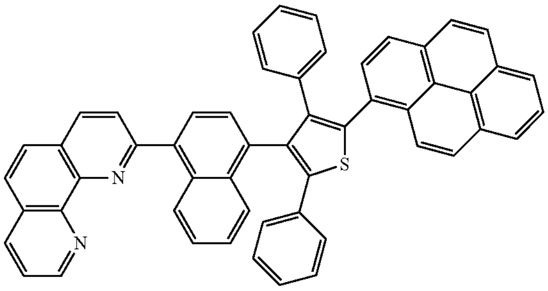
D29
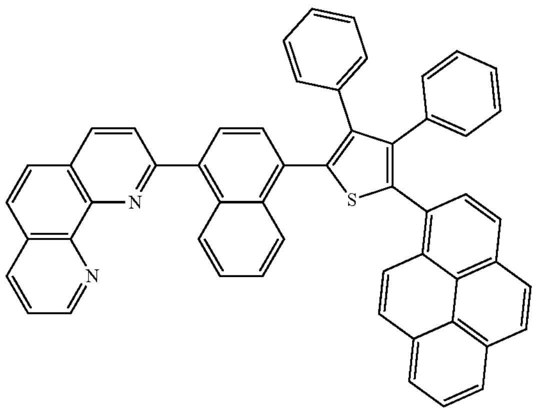
-continued
D30
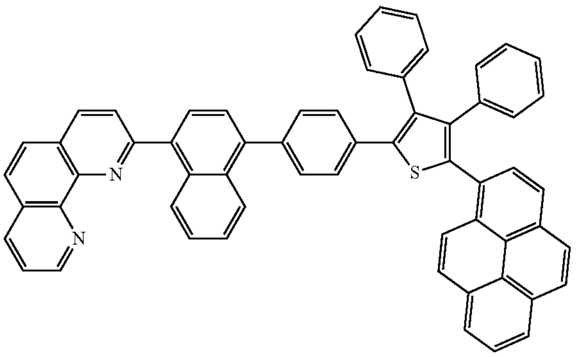
D31
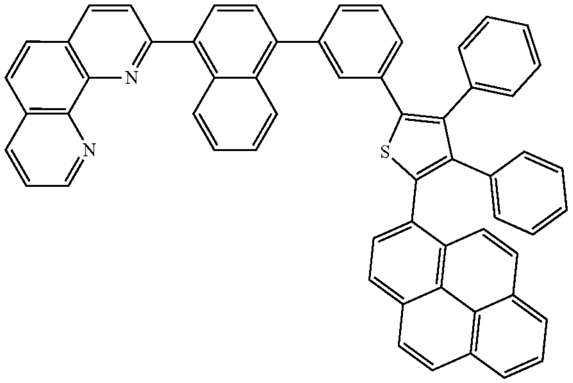
D32
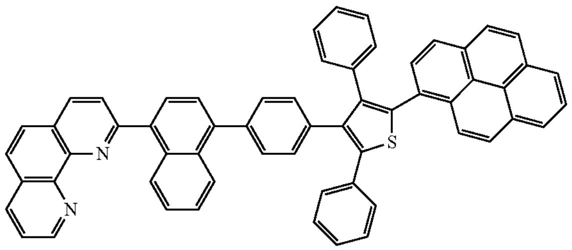
D33
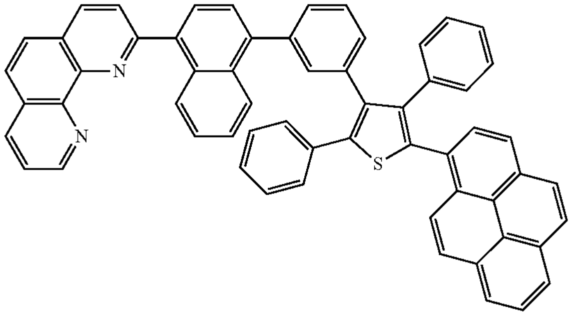

D35
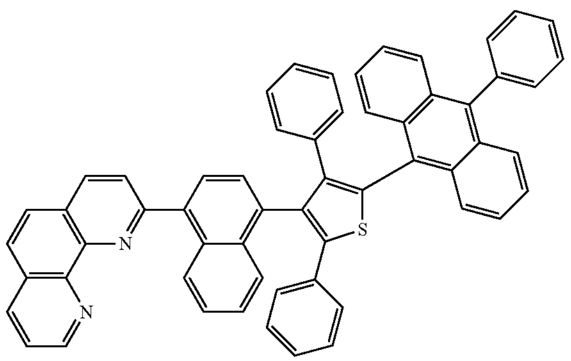
D36
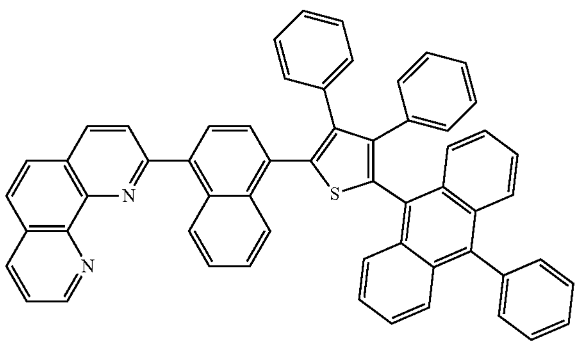
D37
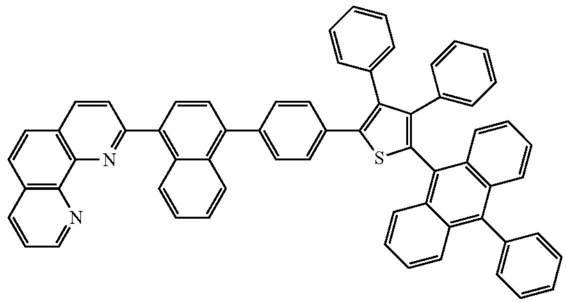
D38
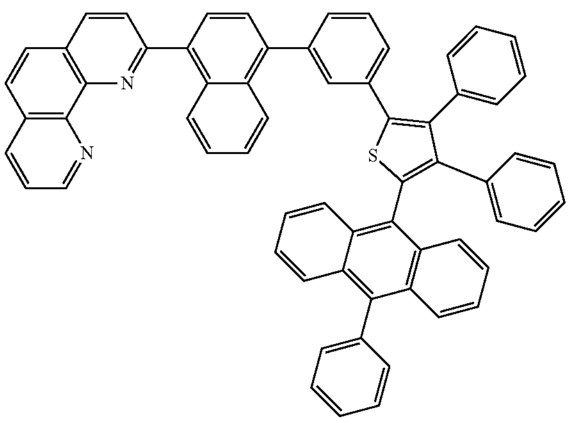
D39
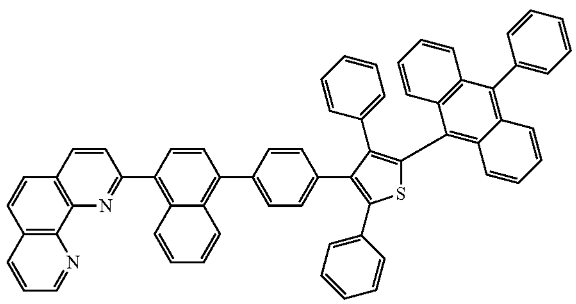
D40
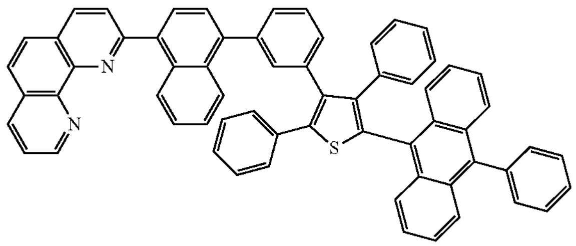
D45
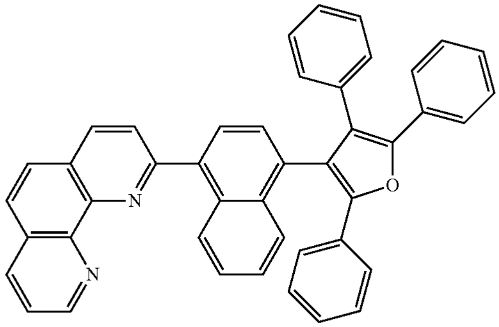
D46
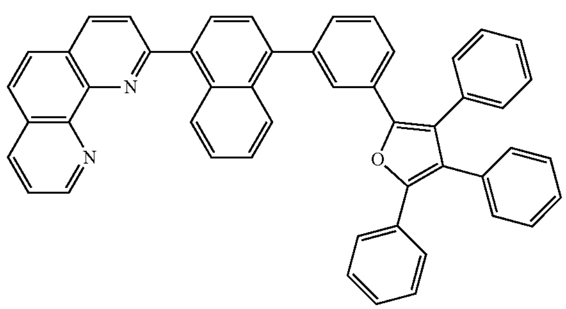
D47
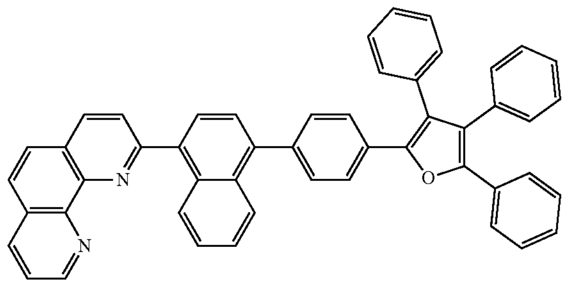

-continued
D48
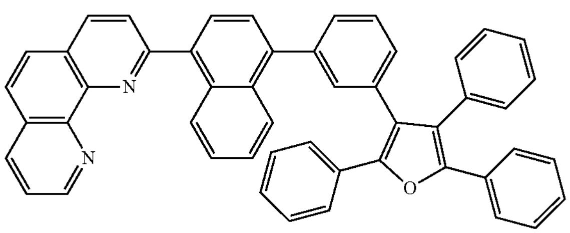
D49
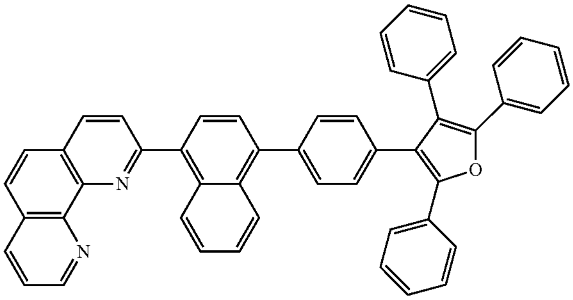
D54
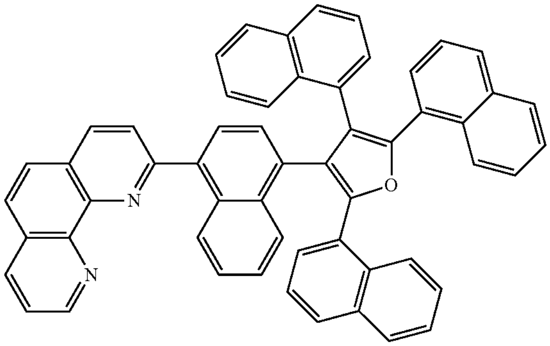
D55
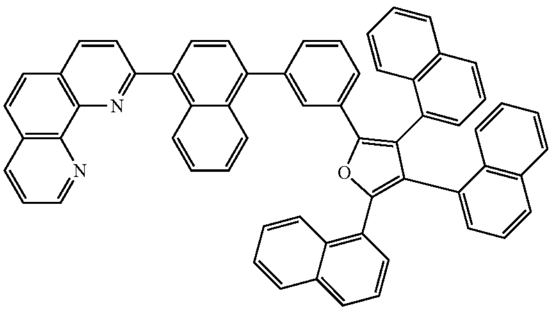
D56
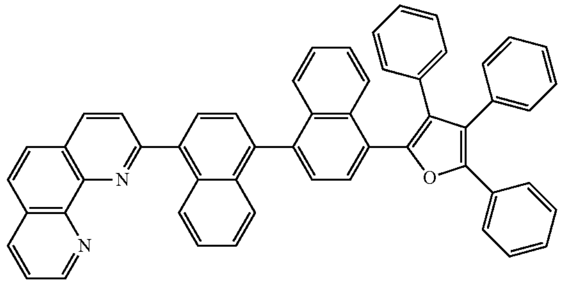
-continued
D57
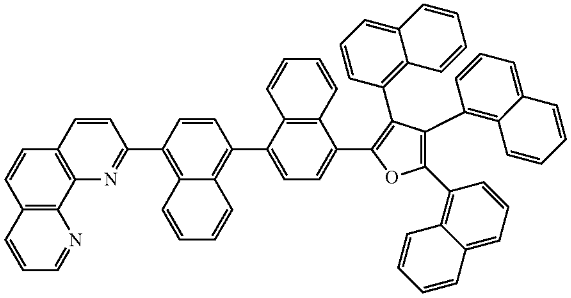
D58
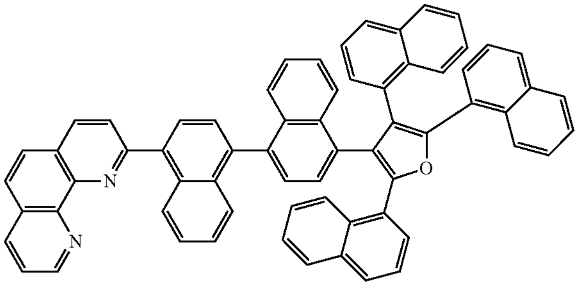
D61
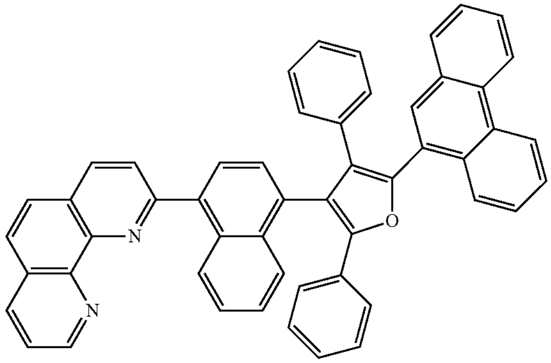
D62
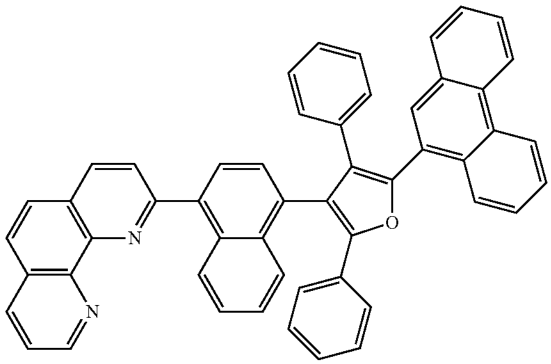

-continued
D63
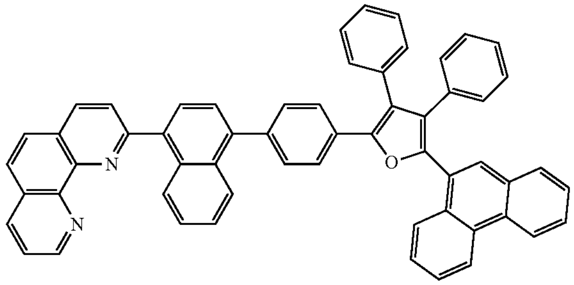
D64
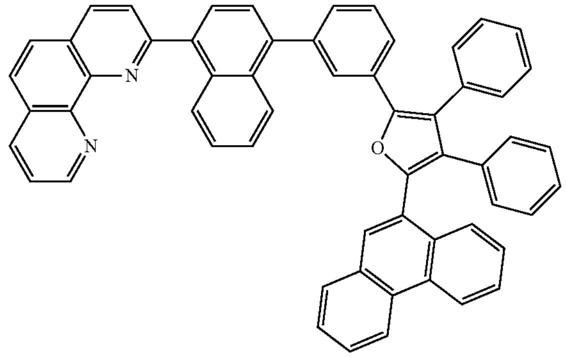
D65
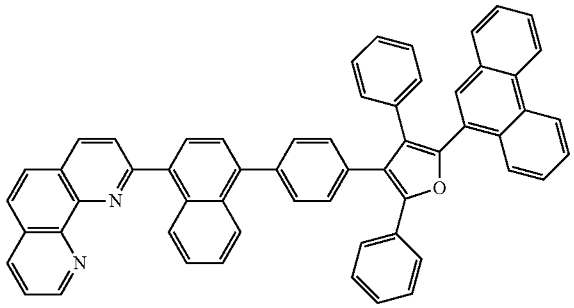
D66
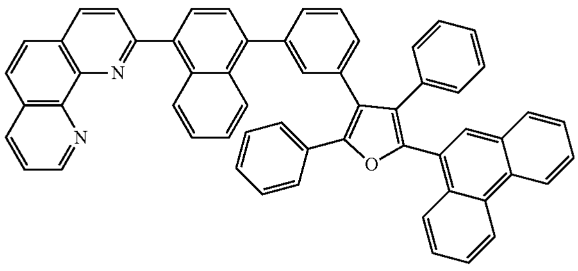
D68
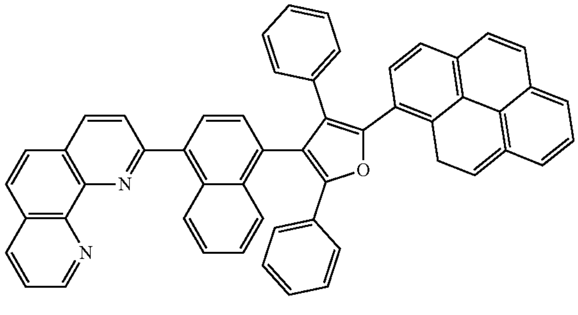
-continued
D69
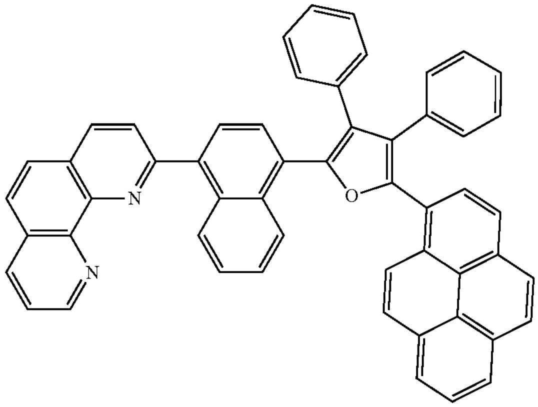
D70
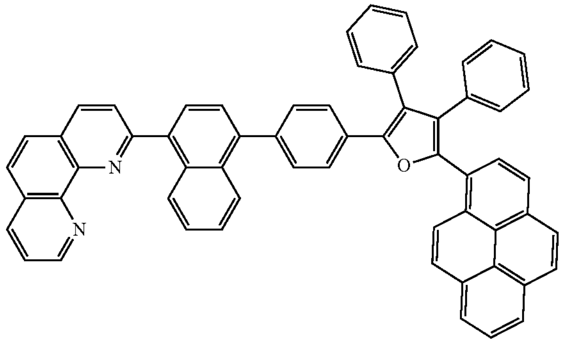
D71
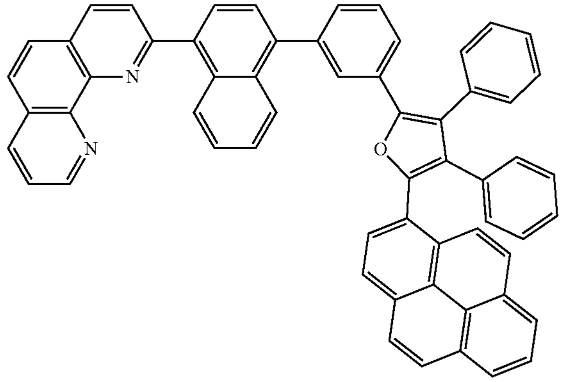
D72
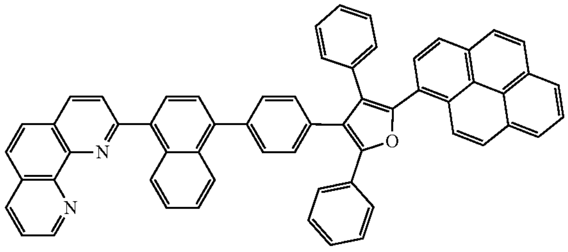

-continued
D73
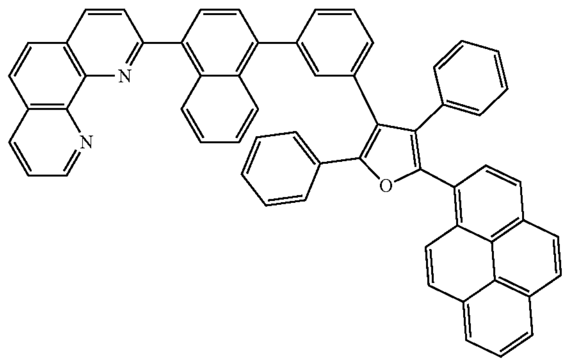
-continued
D75
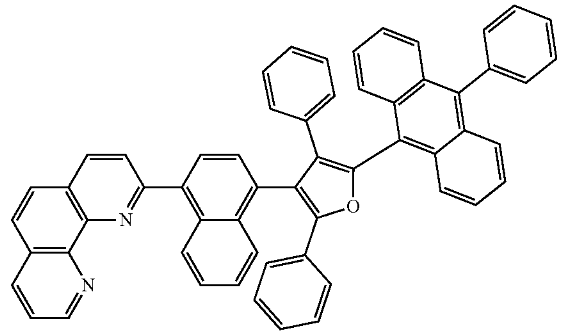
D76
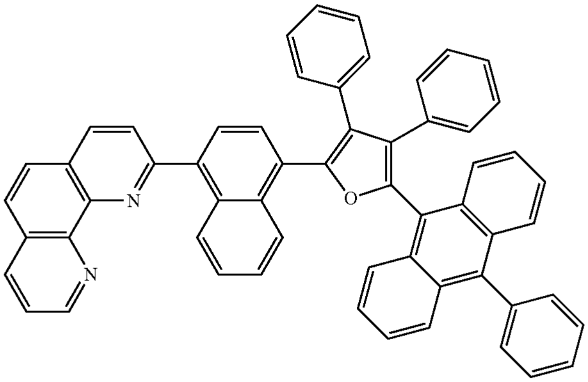
D77
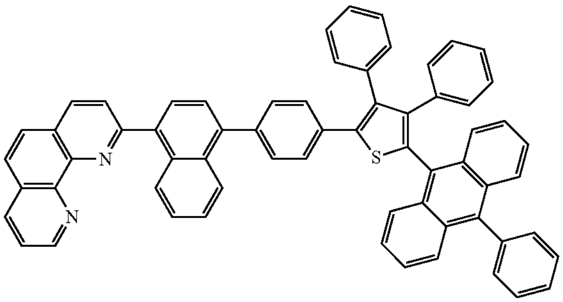
D78
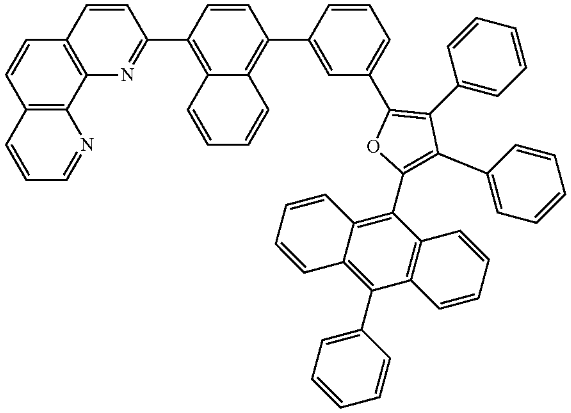
D79
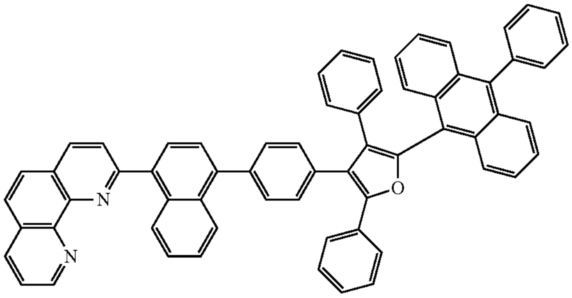
D80
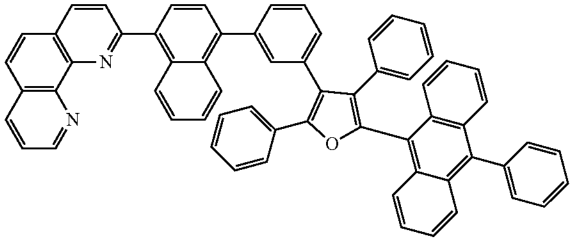

-continued
D85
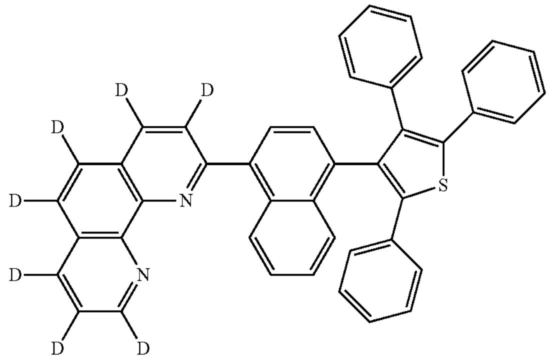
D86
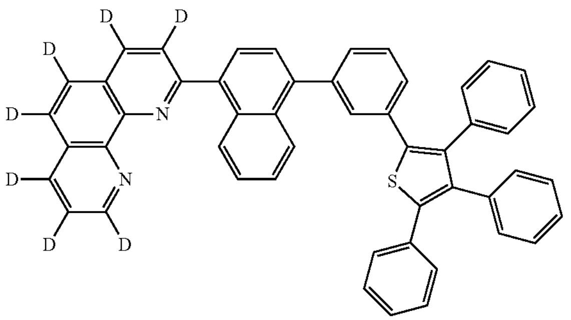
D87
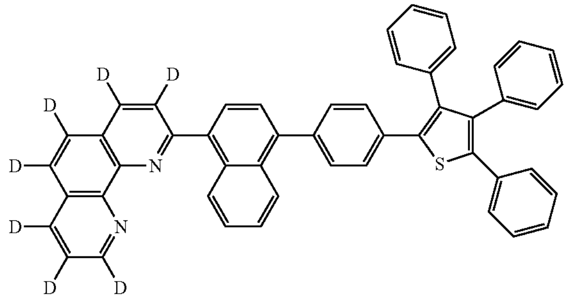
D88
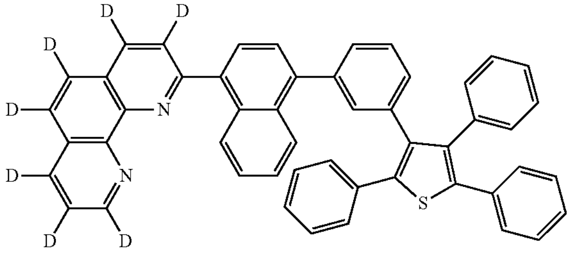
D89
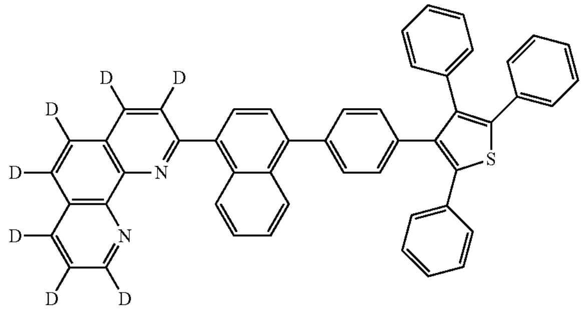
D94
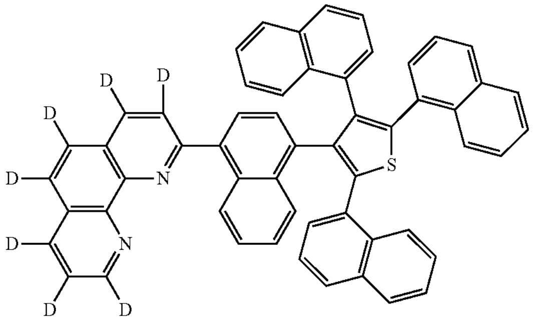
D95
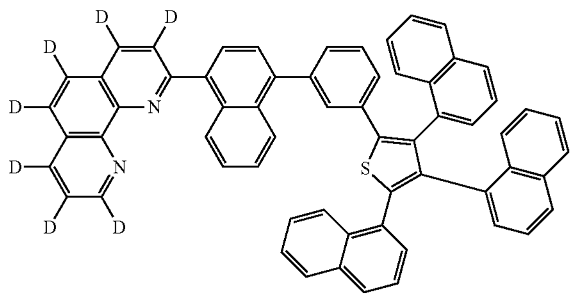
D96
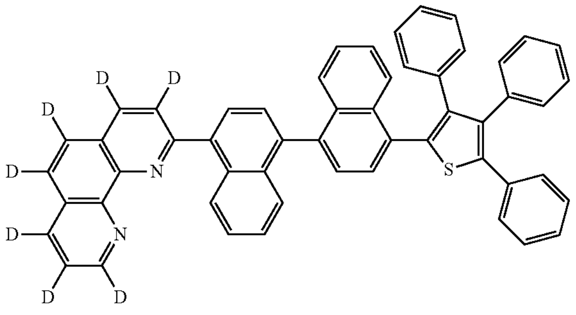

-continued
D97
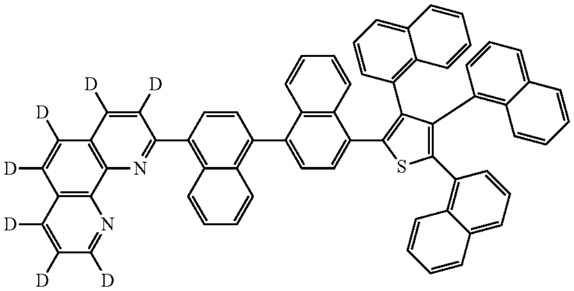
D98
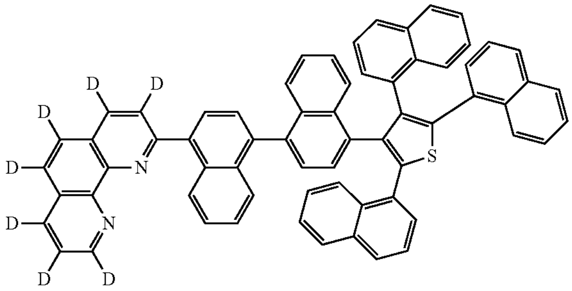
D101
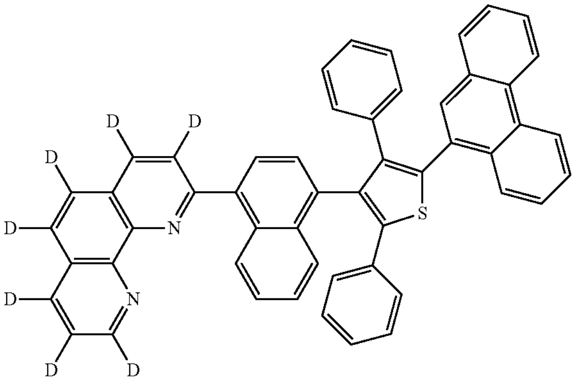
D102
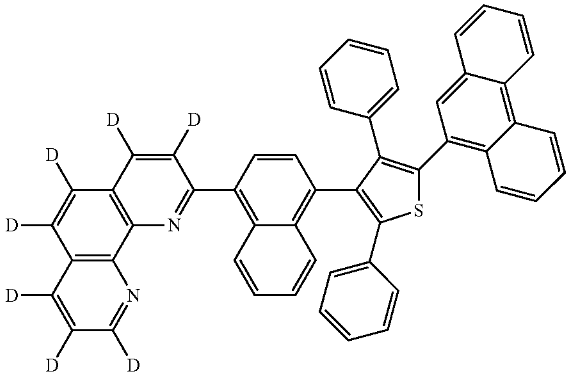
D103
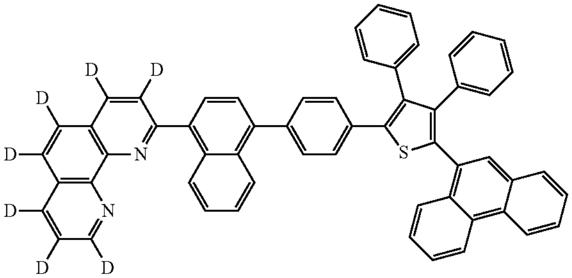
D104
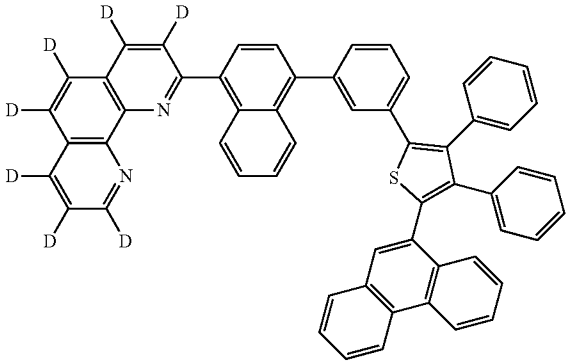
D105
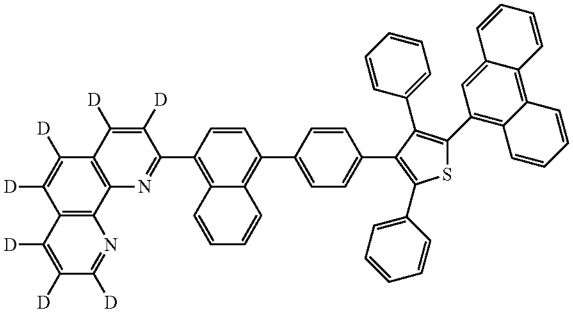
D106
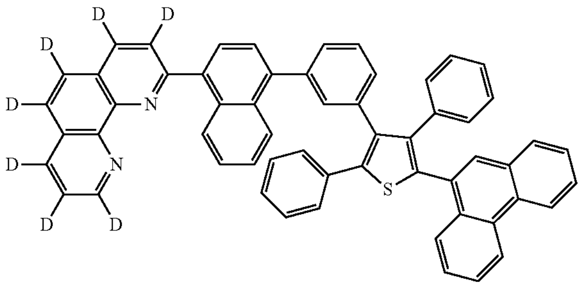

-continued
D108
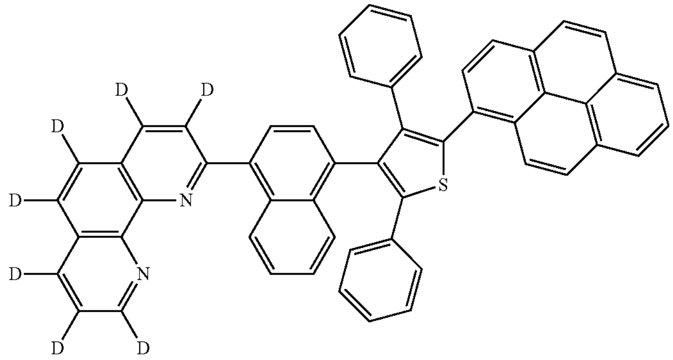
D109
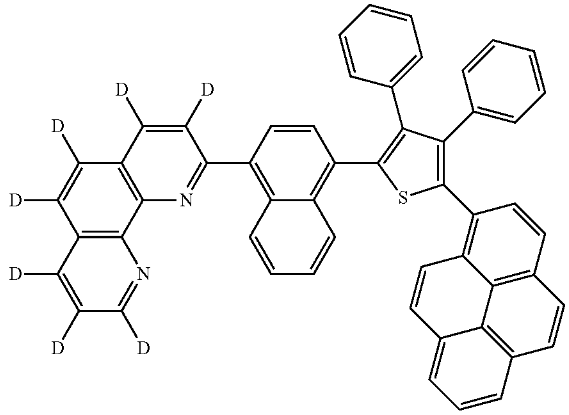
D110
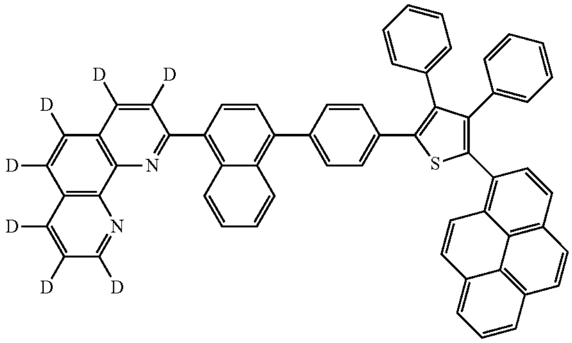
D111
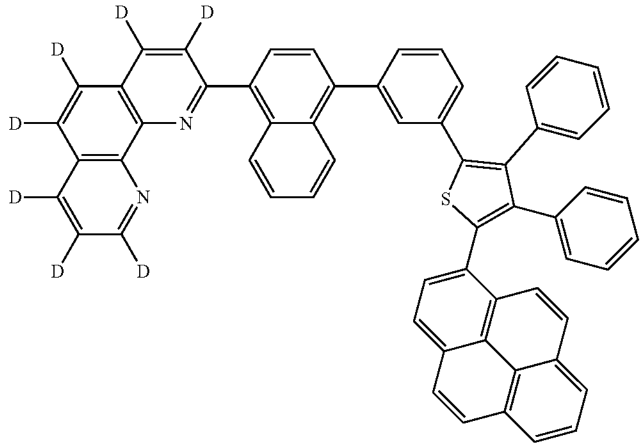
D112
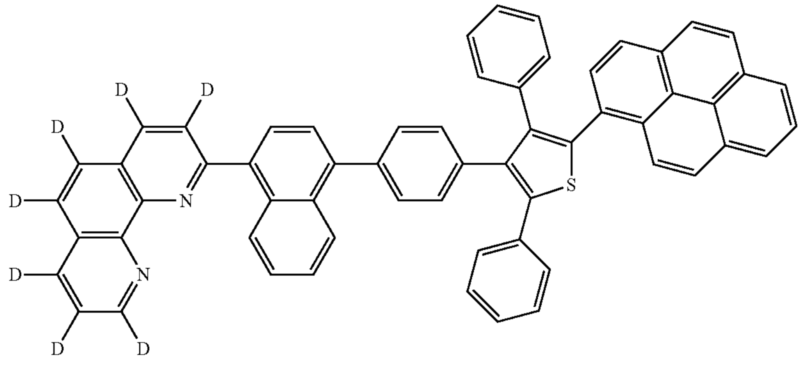

-continued
D113
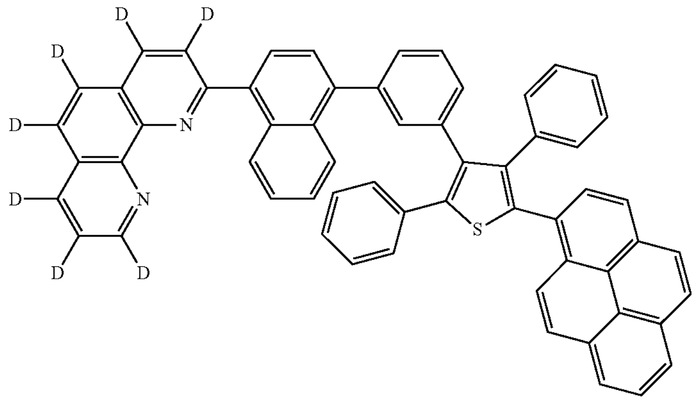
D115
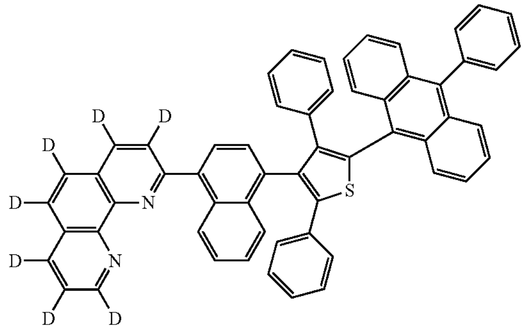
D116
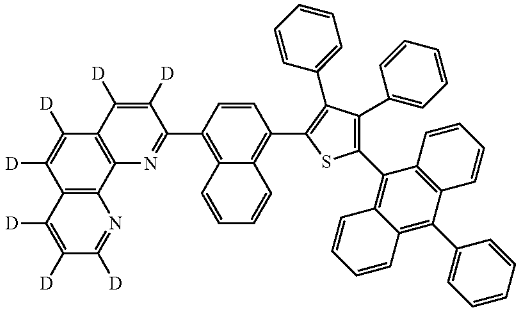
D117
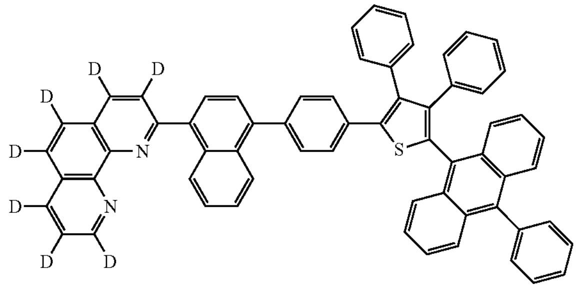
D118
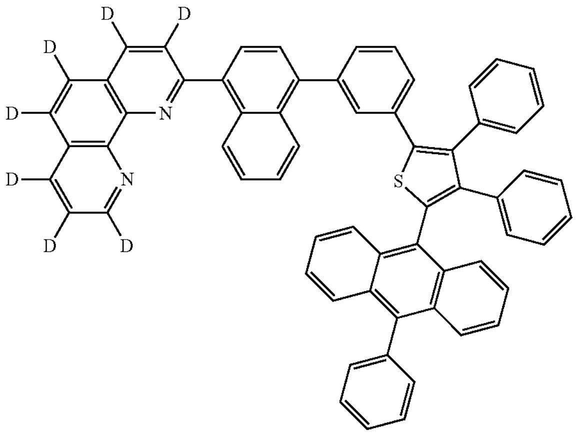
D119
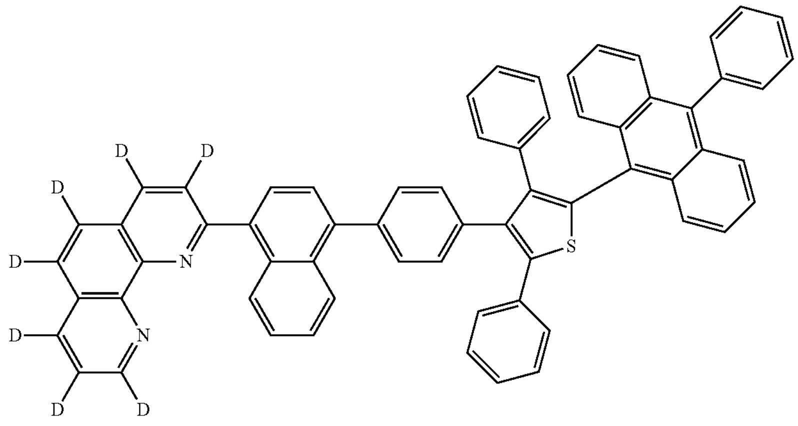

-continued
D120
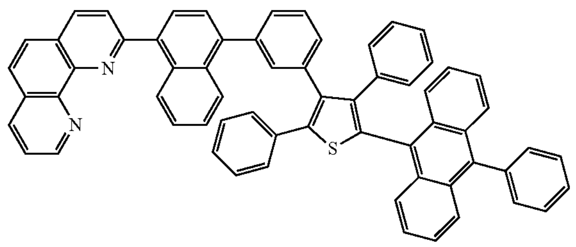
D125
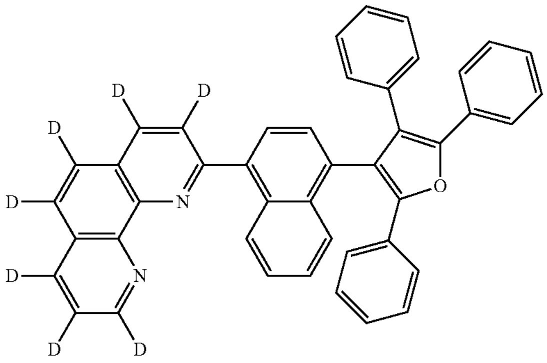
D126
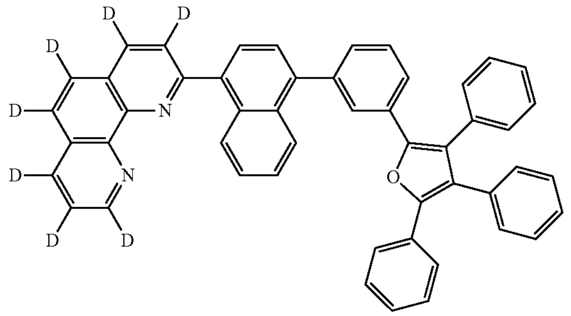
D127
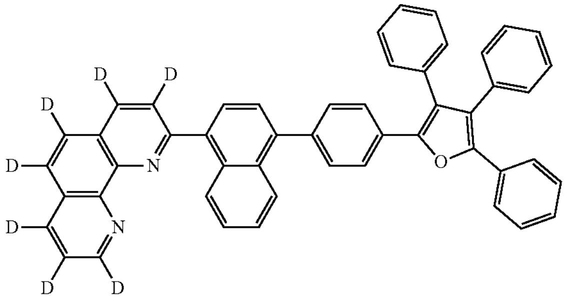
D128
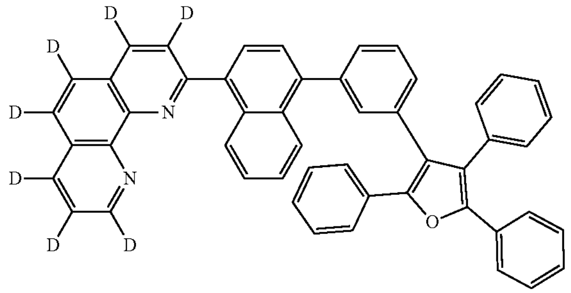
D129
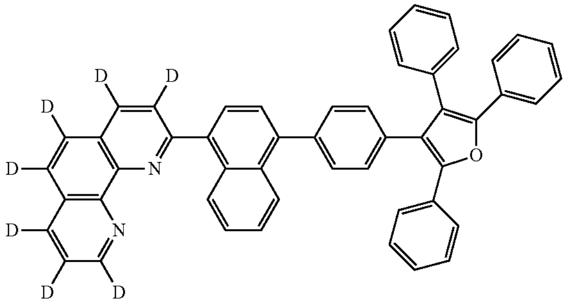
D134
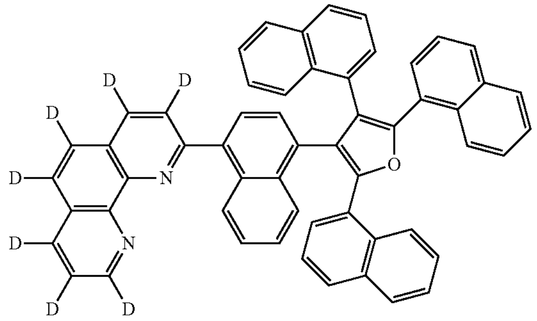
D135
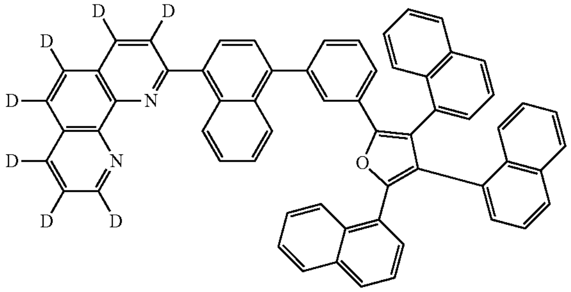

-continued
D136
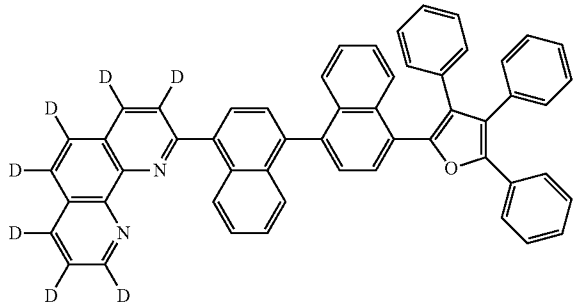
D137
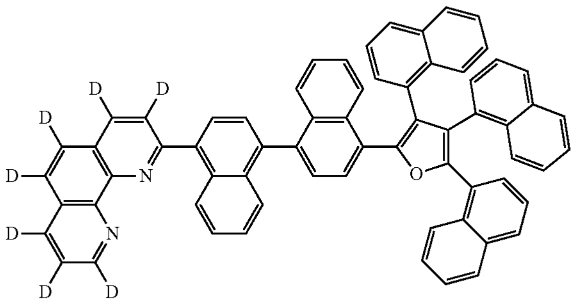
D138
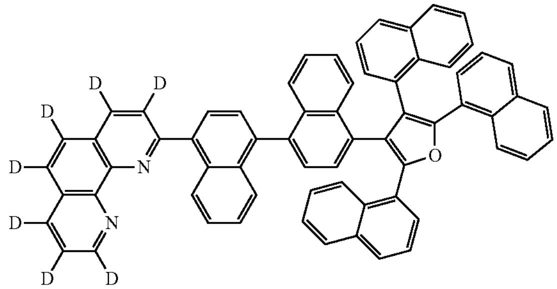
D141
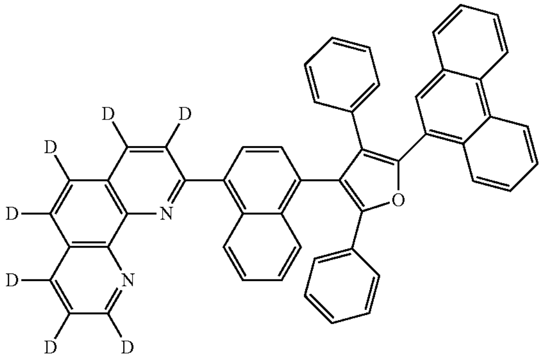
D142
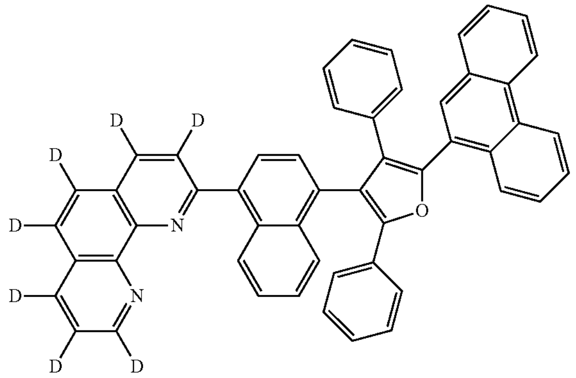
D143
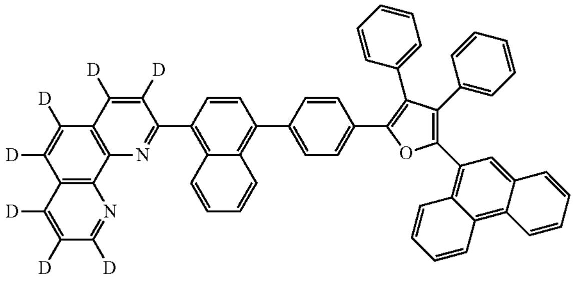
D144
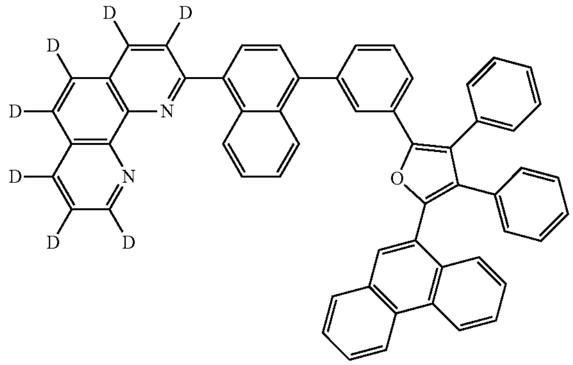
D145
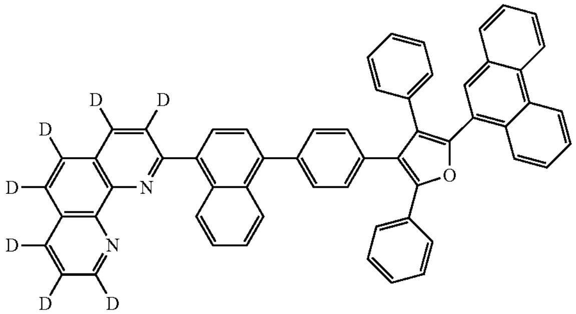

-continued
D146
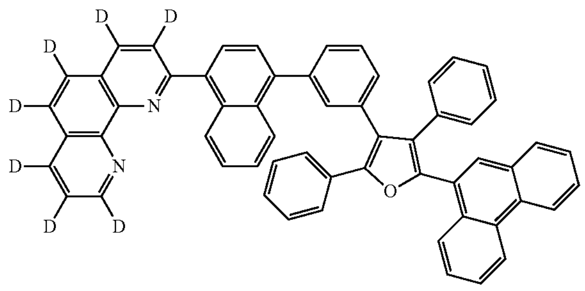
D148
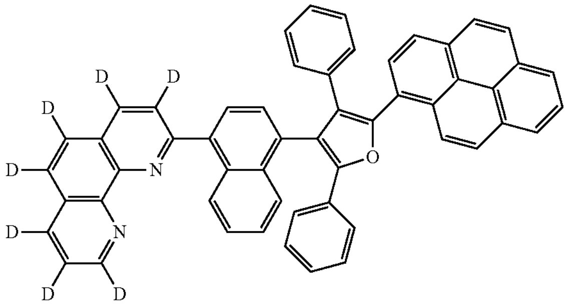
D149
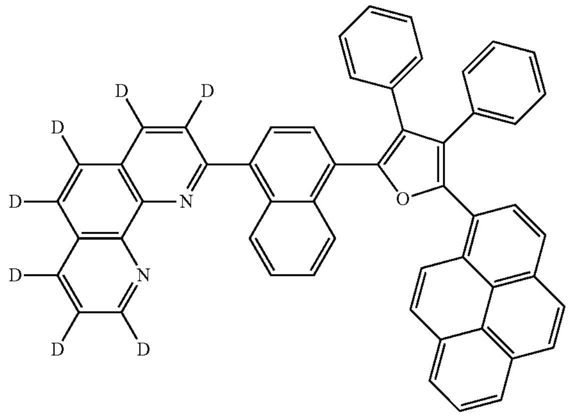
D150
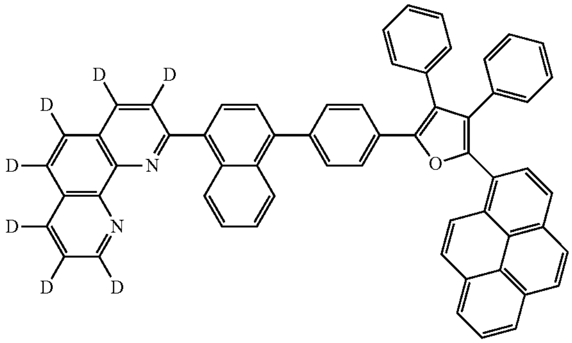
D151
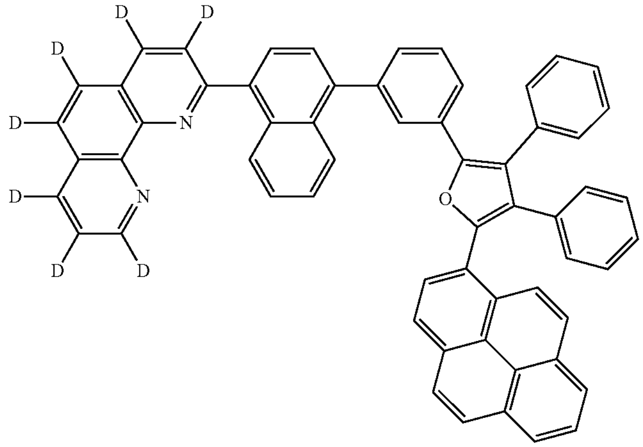
D152
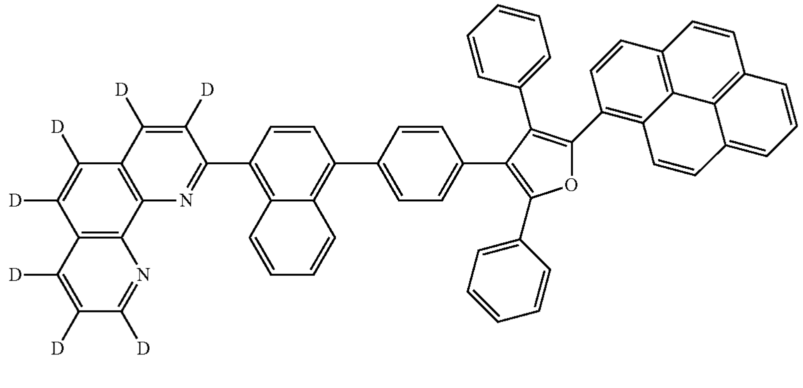

-continued
D153
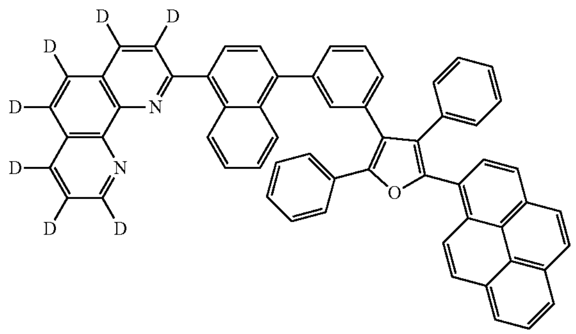
D155
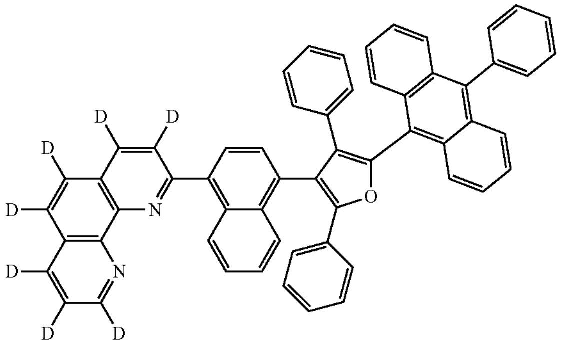
D156
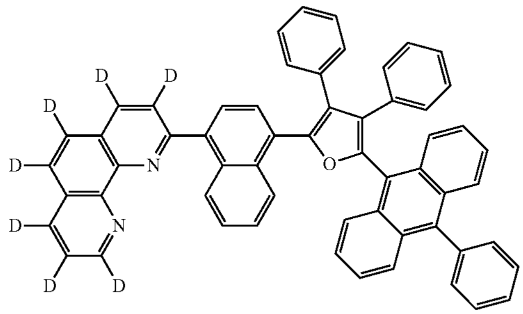
D157
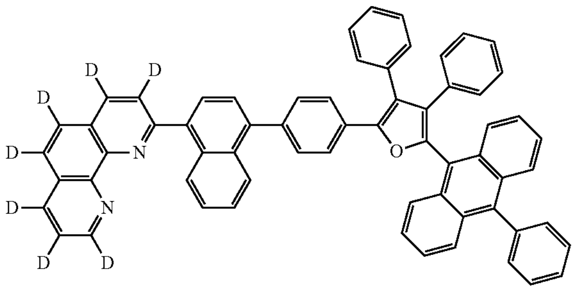
D158
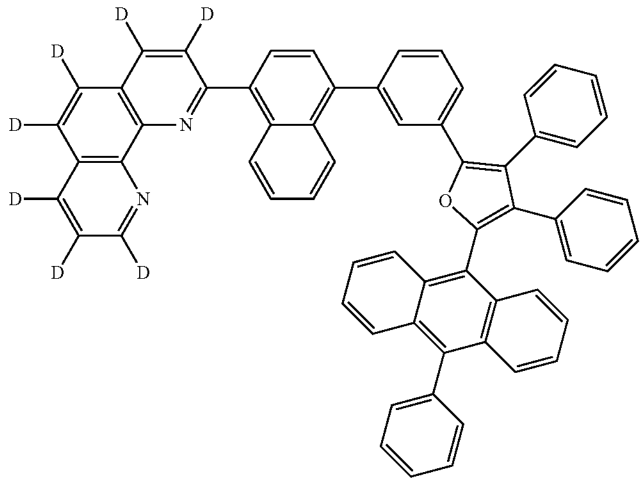
D159
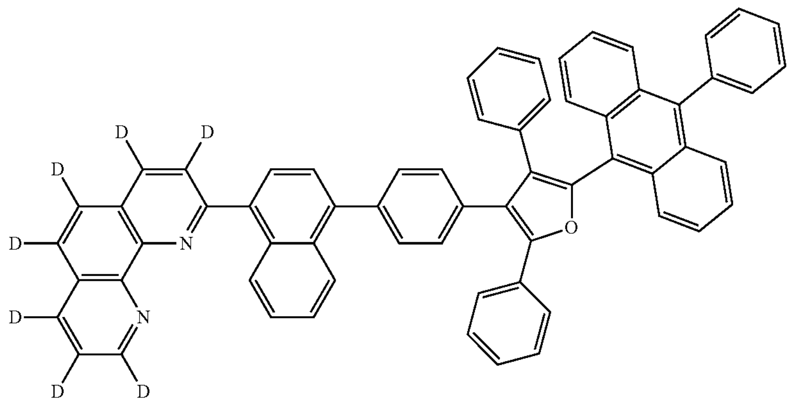

-continued
D160
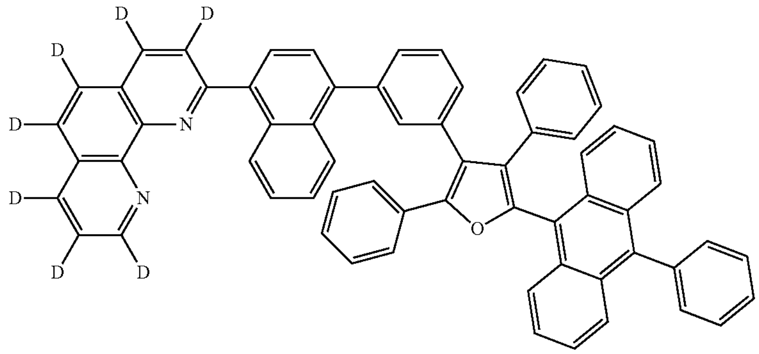
D165
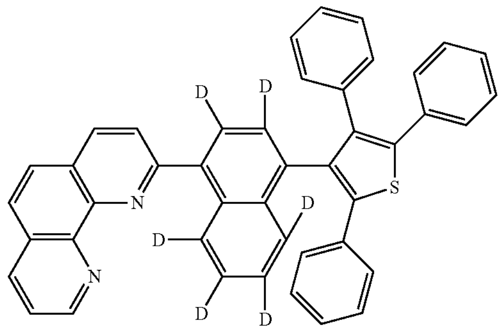
D166
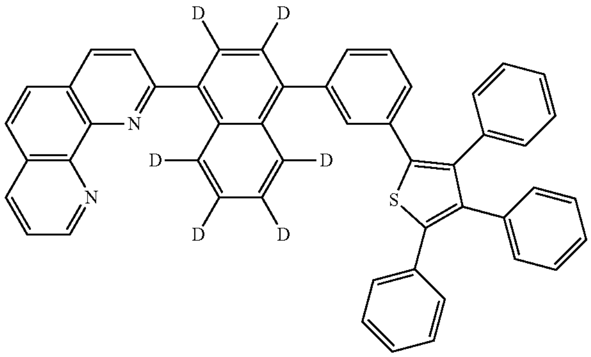
D167
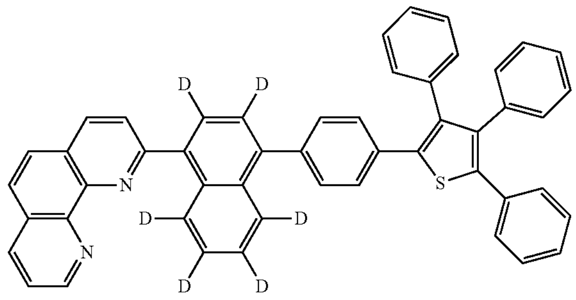
D168
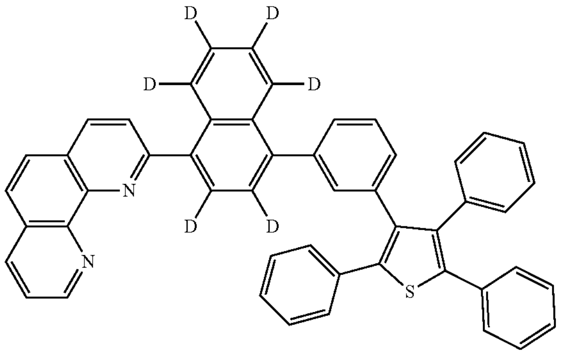
D169
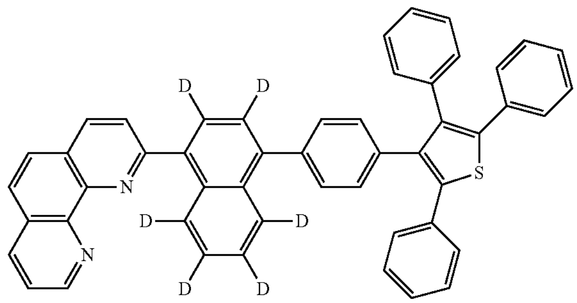
D174
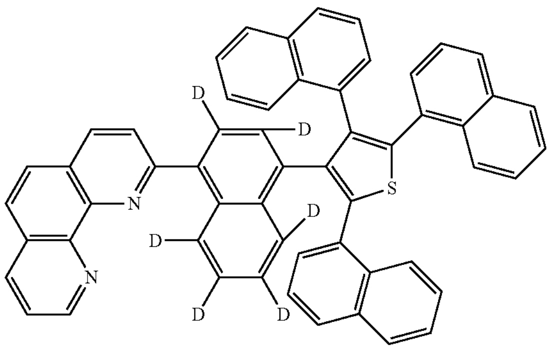

-continued
D175
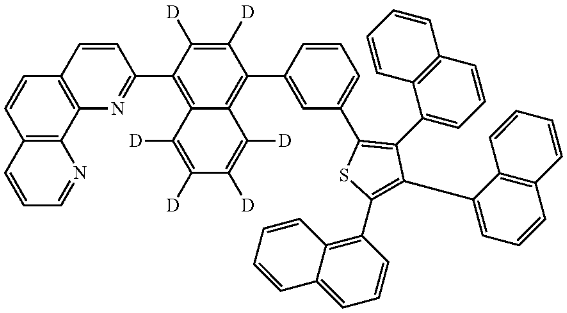
D176
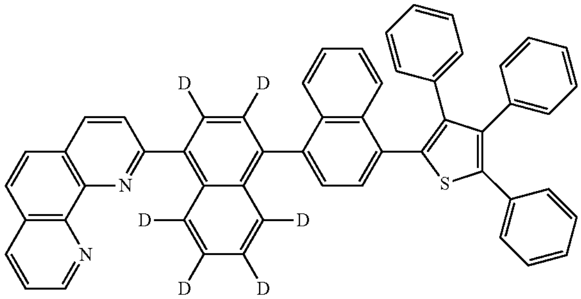
D177
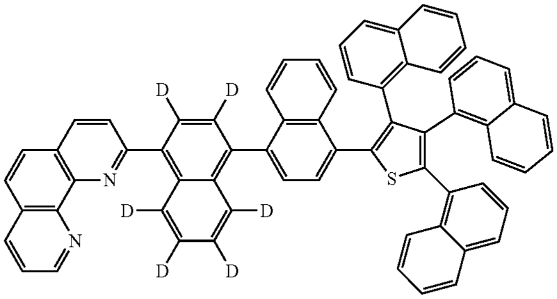
D178
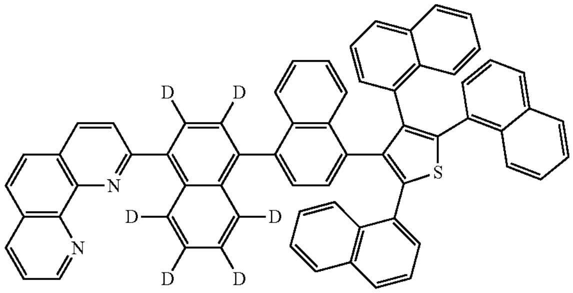
D181
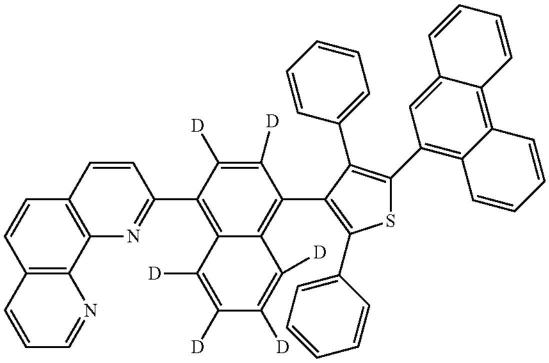
D182
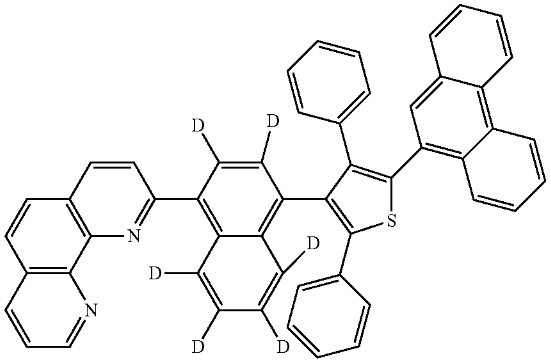
D183
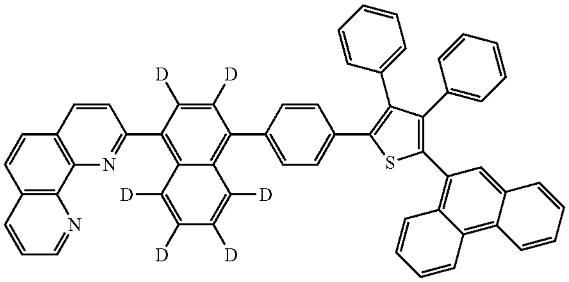
D184
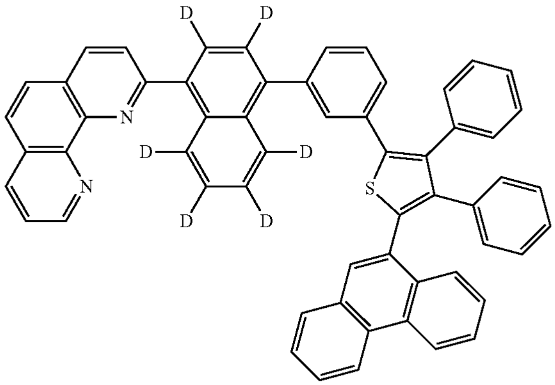

-continued
D185
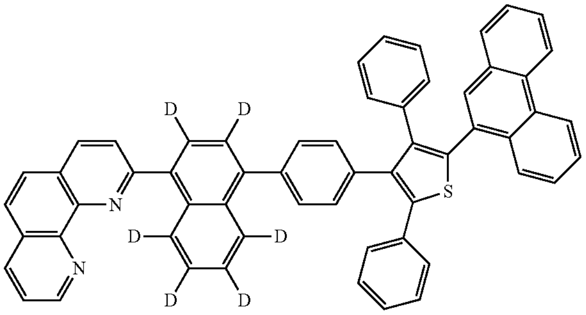
D186
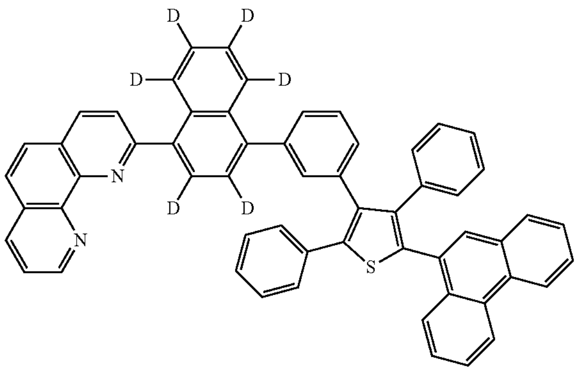
D188
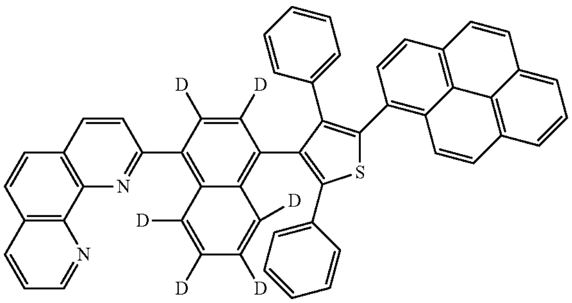
D189
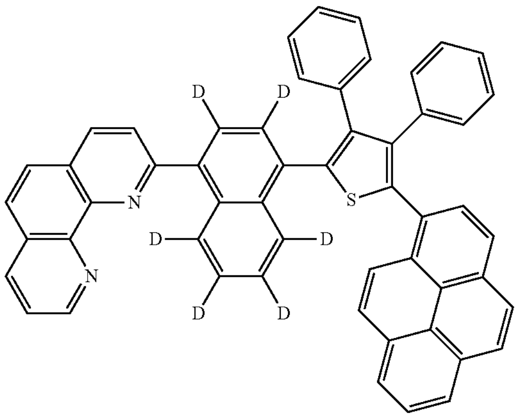
D190
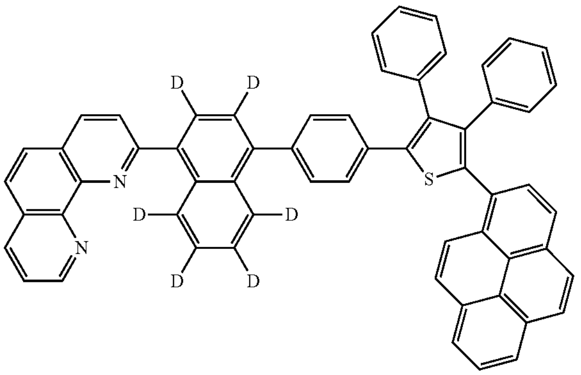
D191
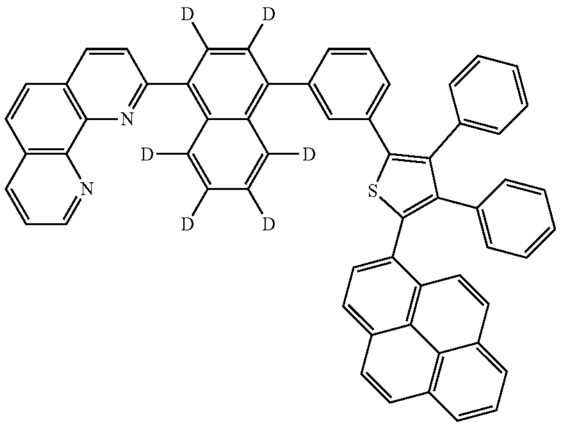

-continued
D192
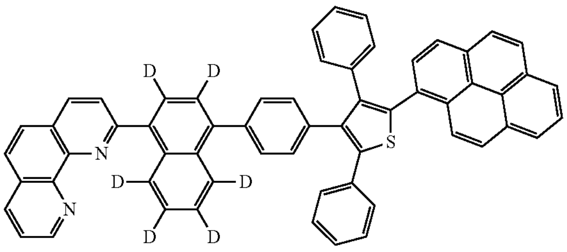
D193
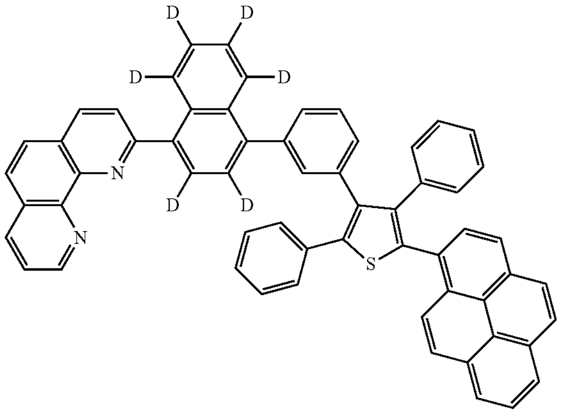
D195
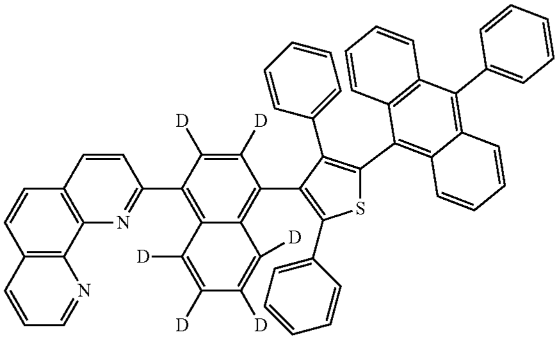
D196
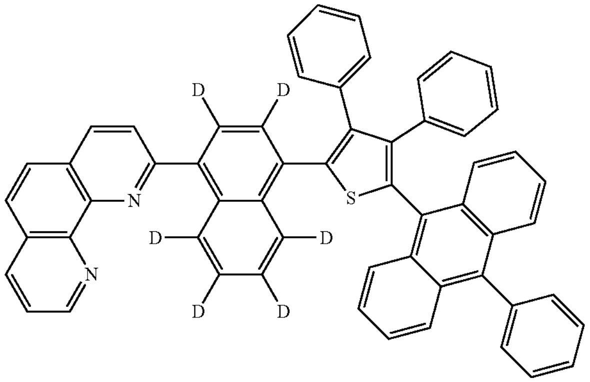
D197
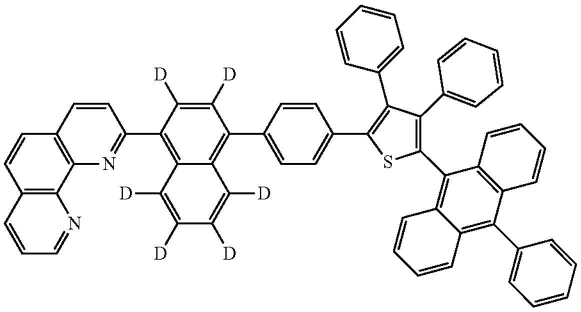
D198
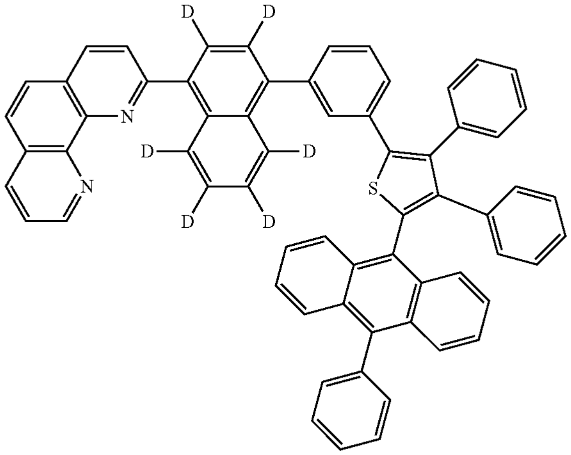

-continued
D199
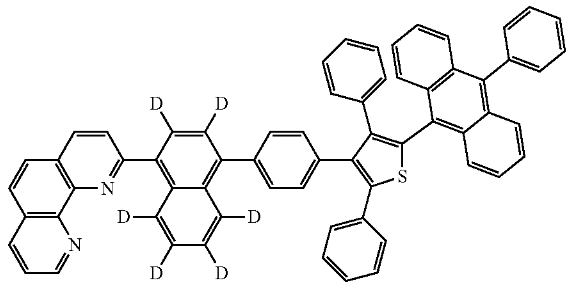
D200
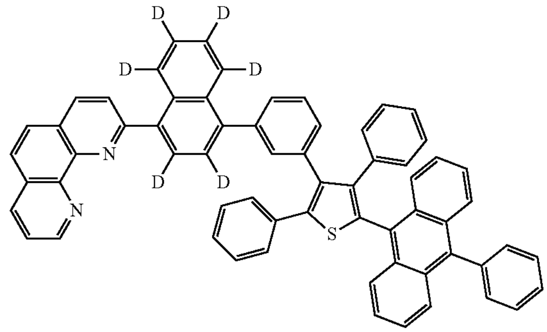
D205
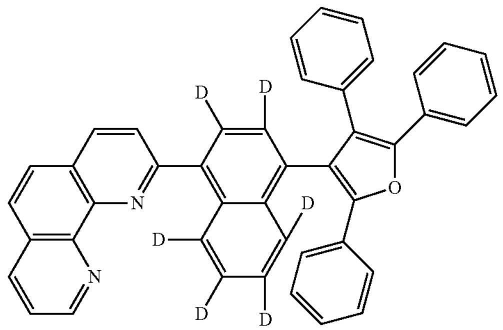
D206
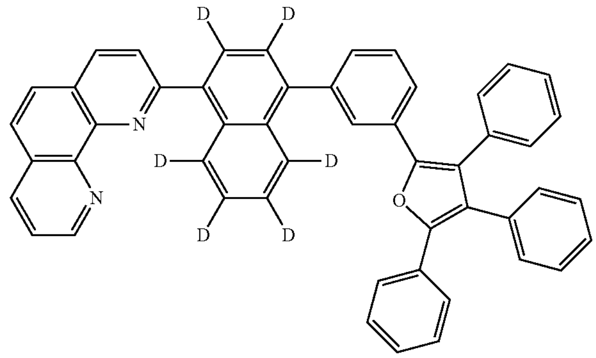
D207
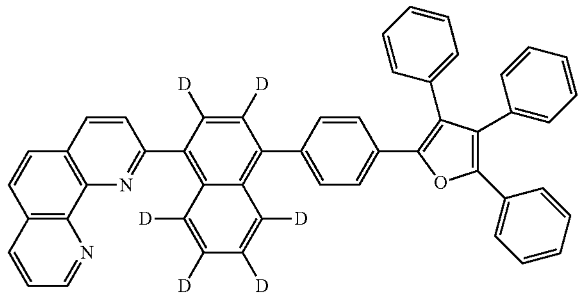
D208
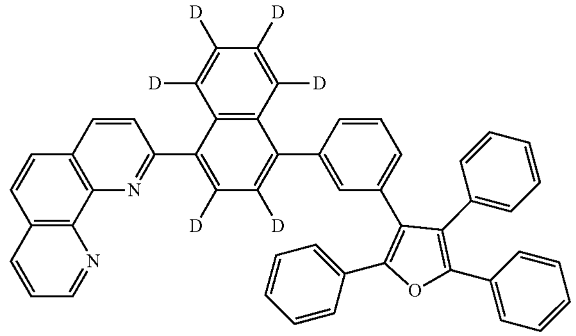
D209
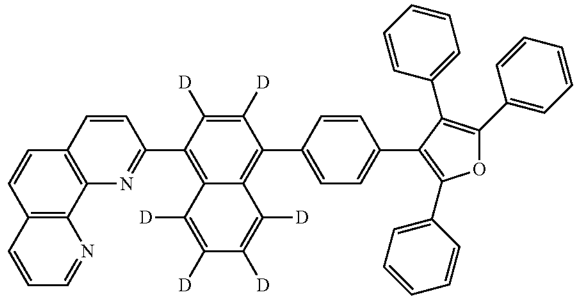
D214
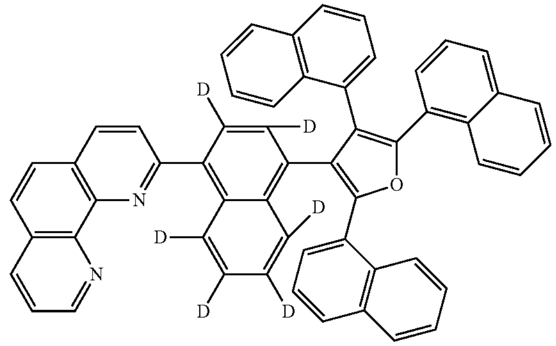

-continued
D215
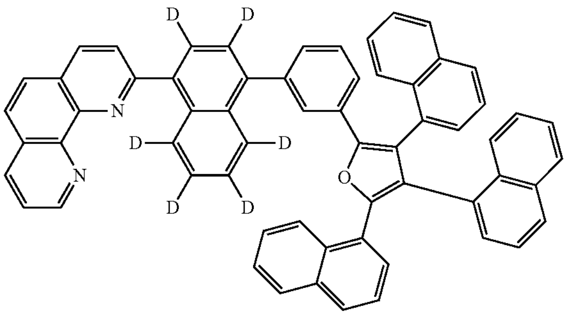
D216
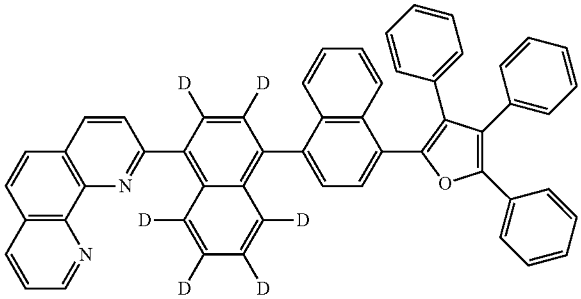
D217
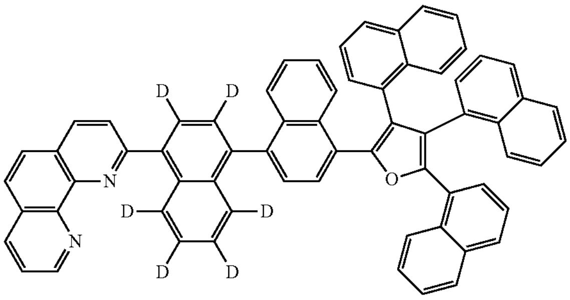
D218
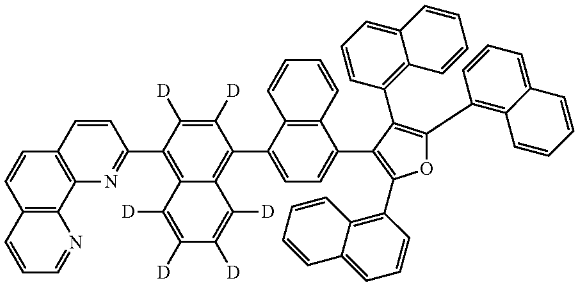
D221
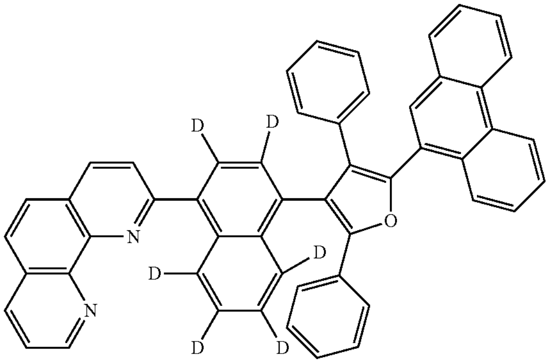
D222
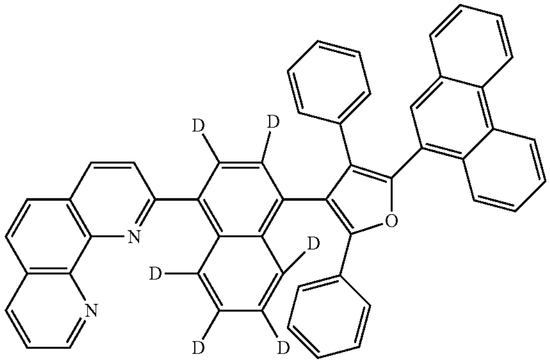
D223
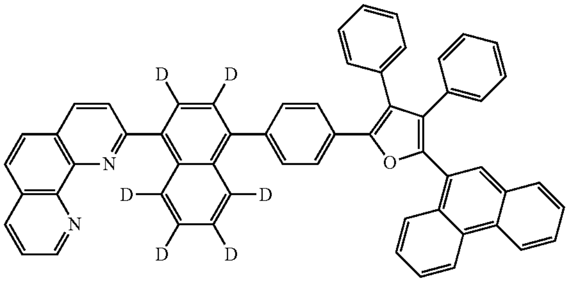
D224
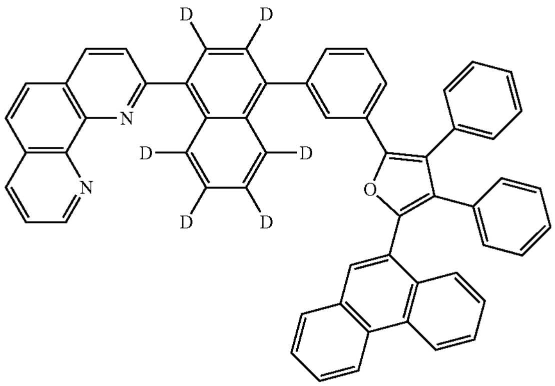

-continued
D225
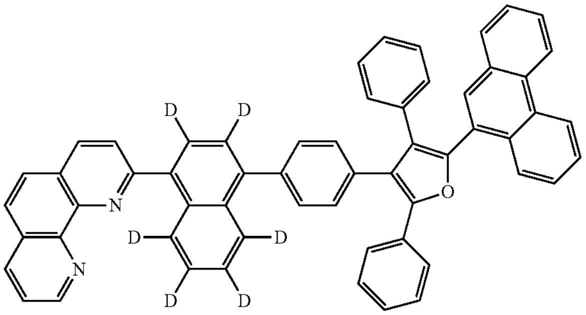
D226
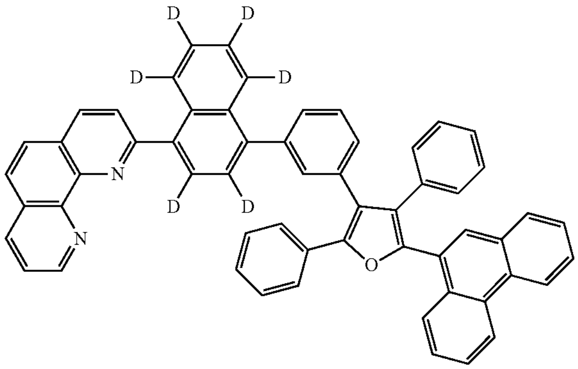
D228
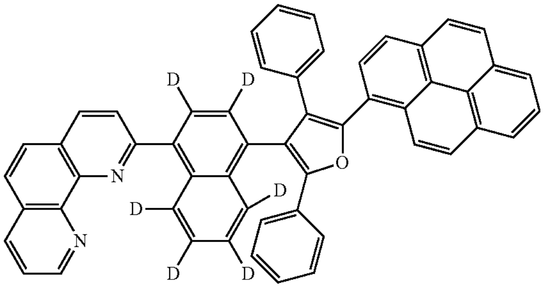
D229
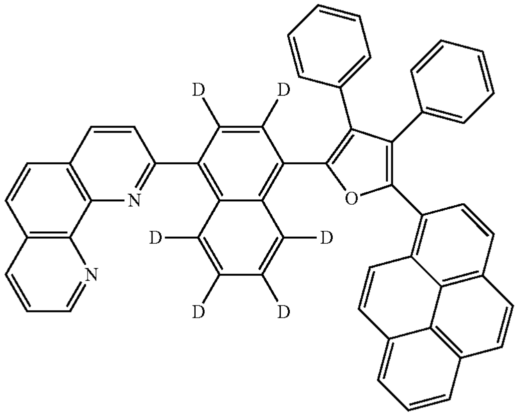
D230
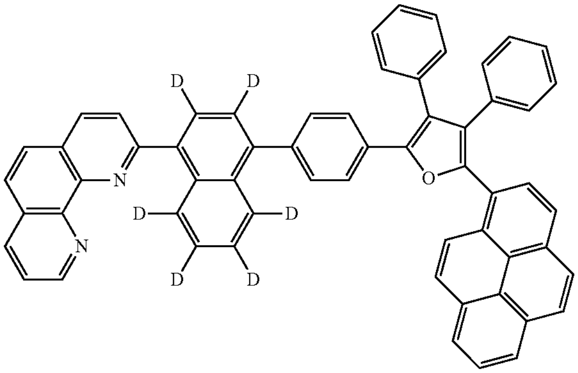
D231
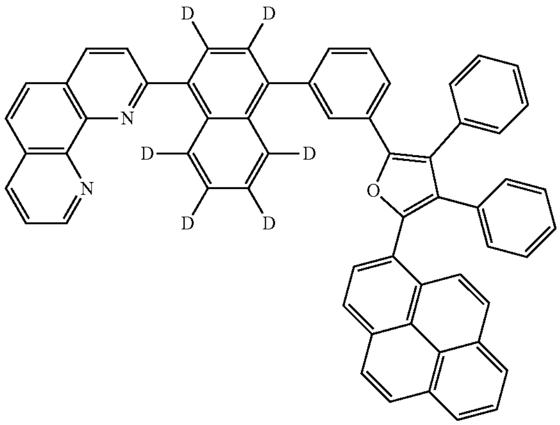

-continued
D232
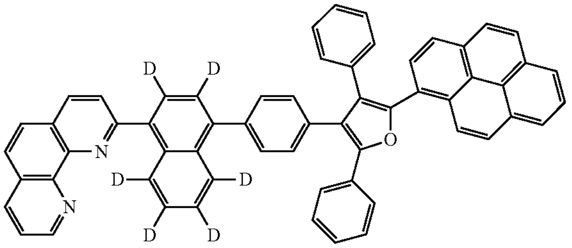
D233
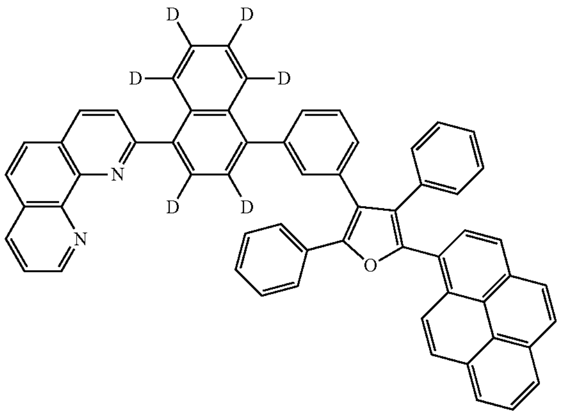
D235
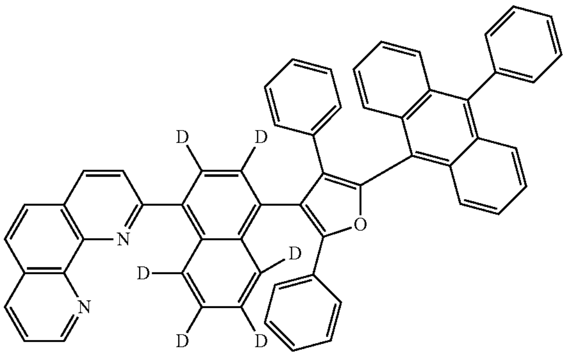
D236
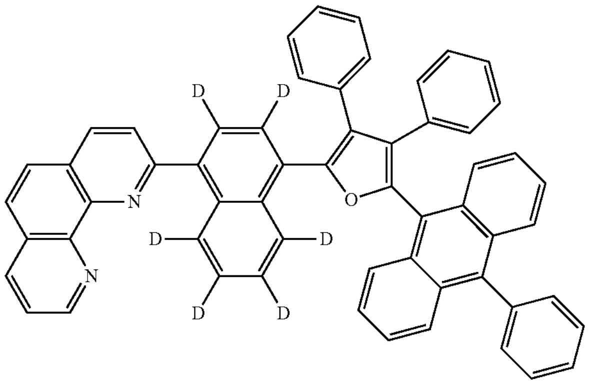
D237
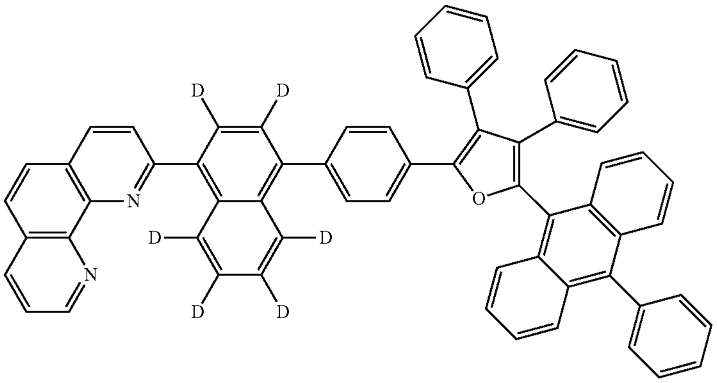

-continued
D238
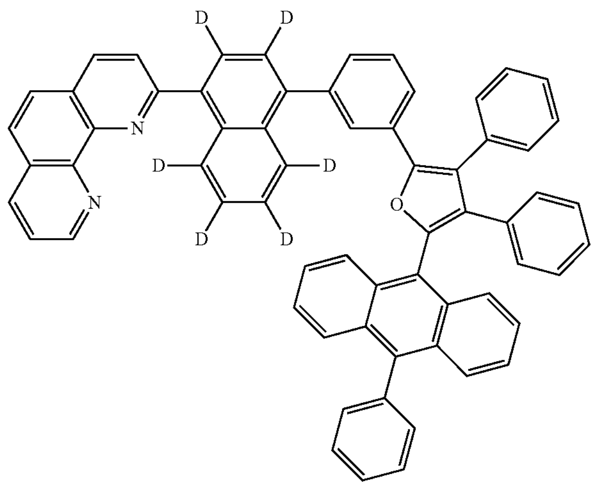
D239
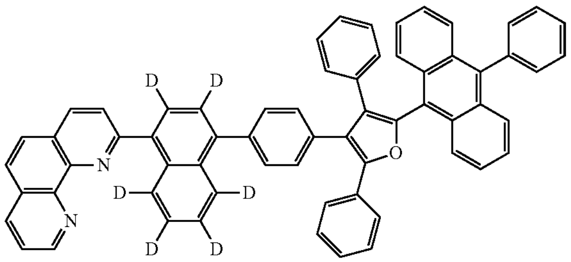
D240
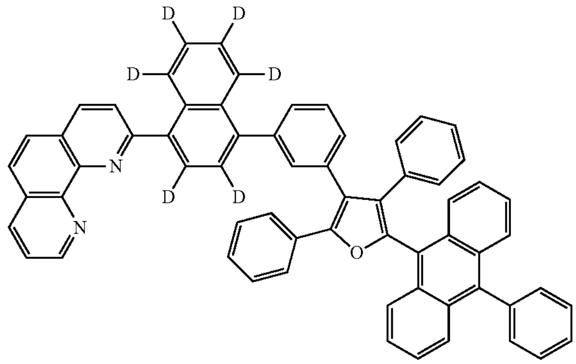
D245
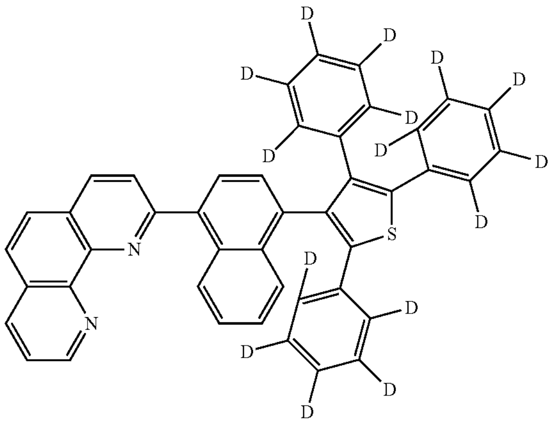
D246
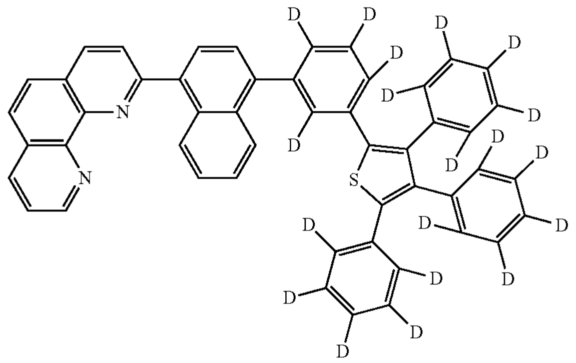
D247
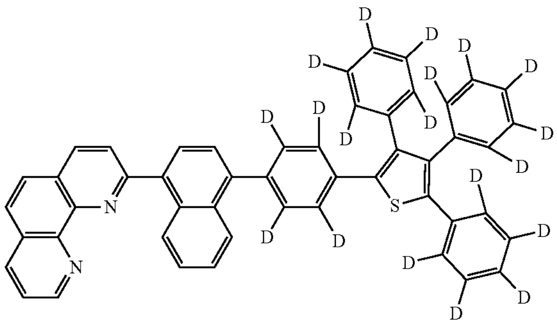

-continued
D248
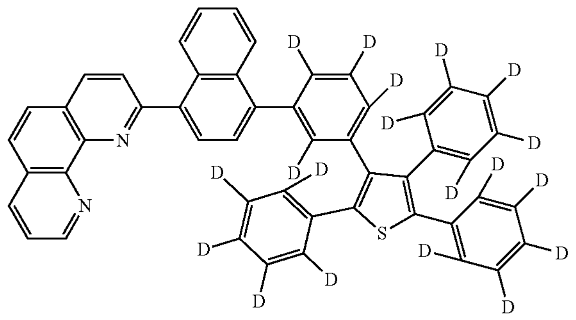
D249
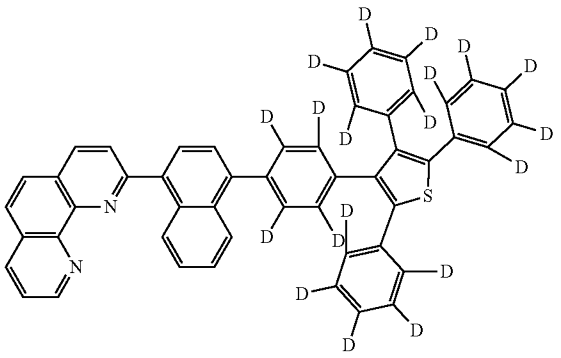
D254
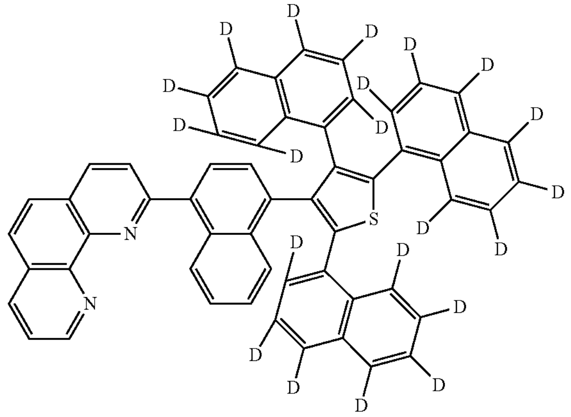
D255
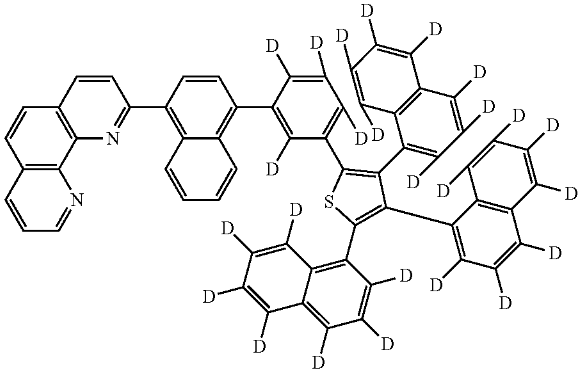
D256
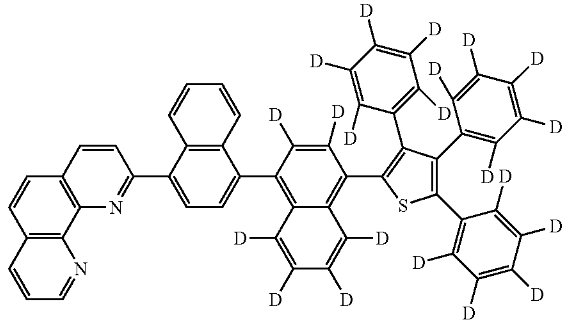
D257
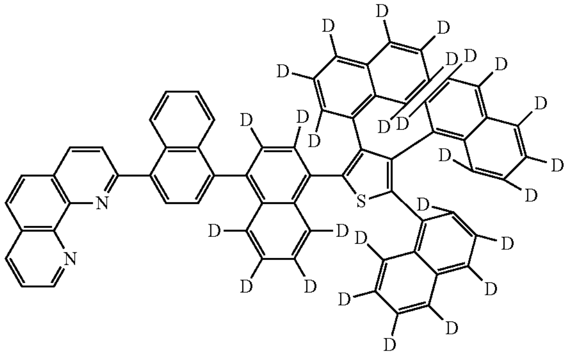

-continued
D258
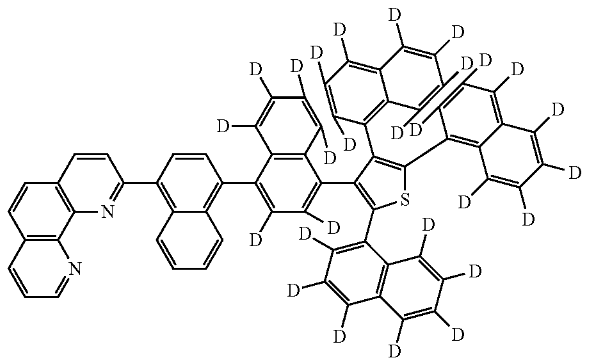
D261
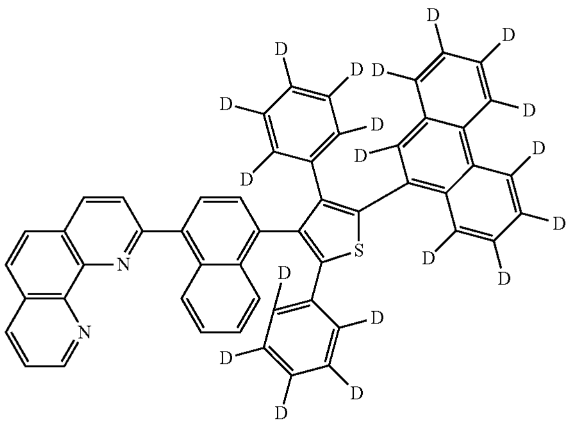
D262
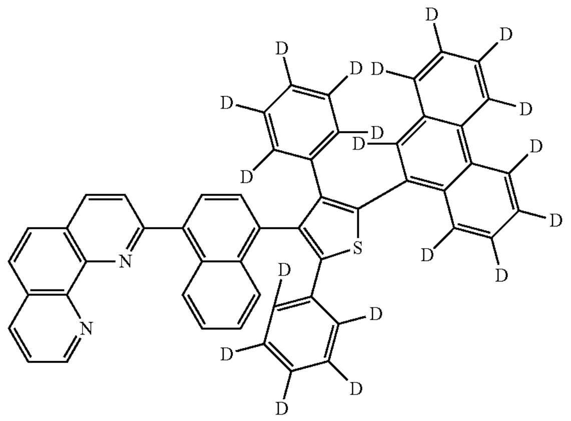
D263
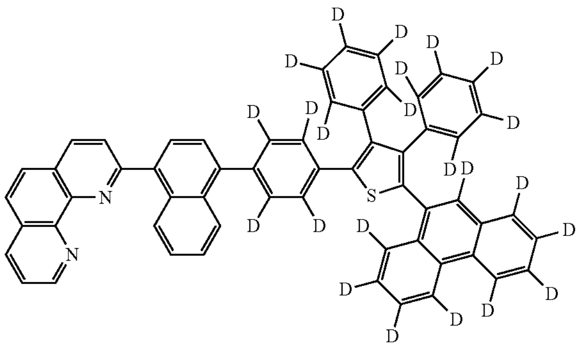
D264
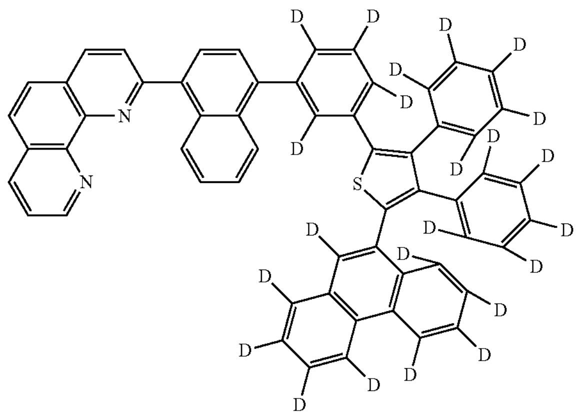
D265
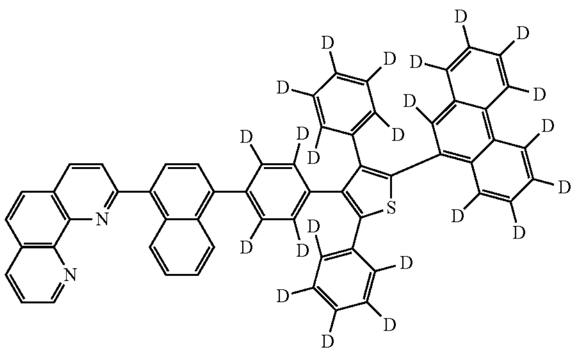

-continued
D266
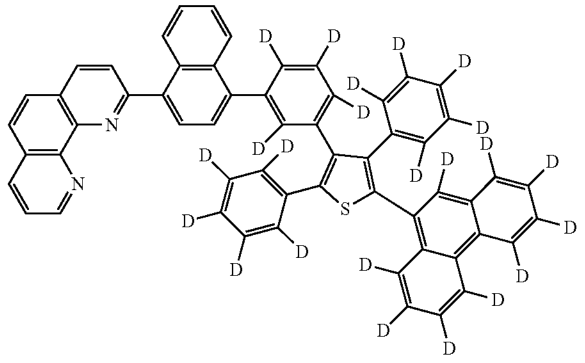
D268
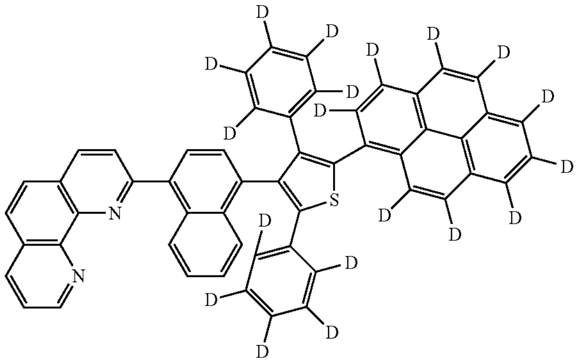
D269
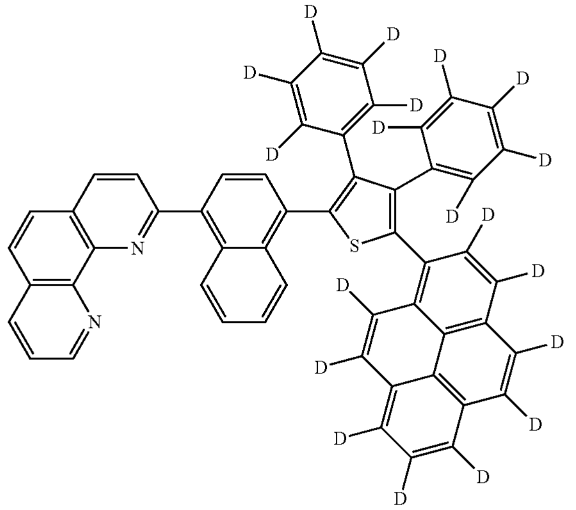
D270
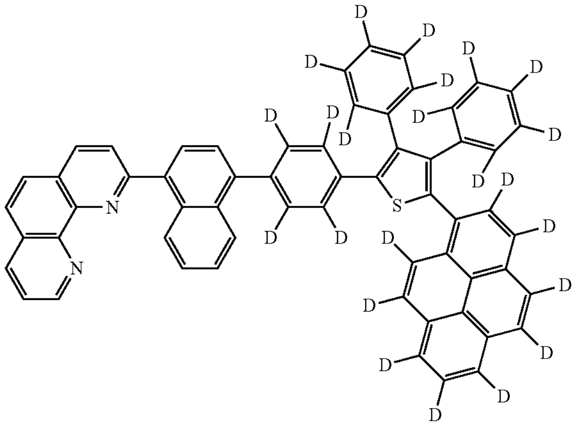
D271
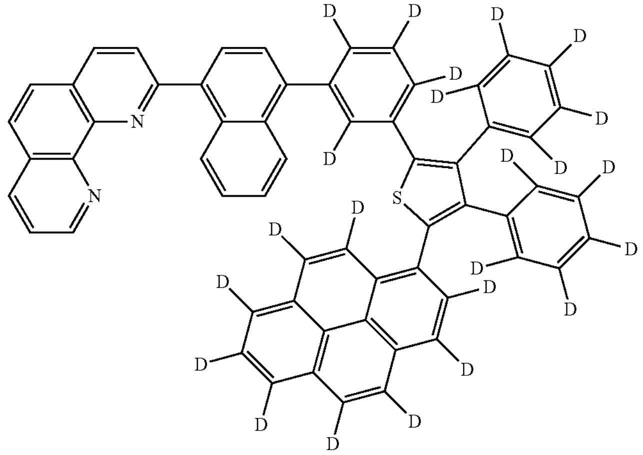

-continued
D272
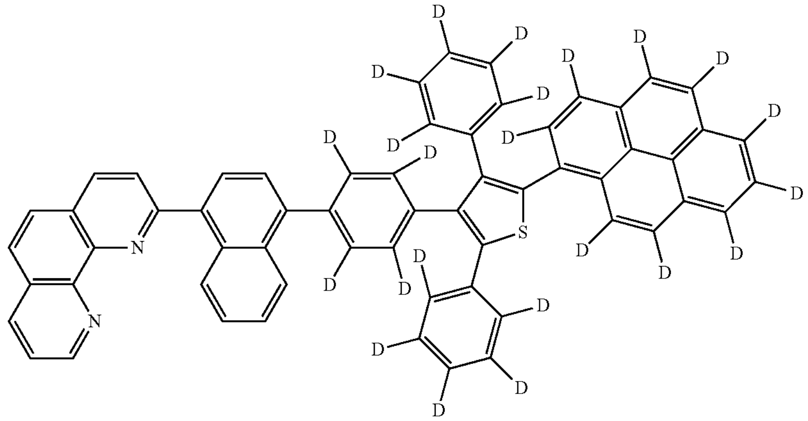
D273
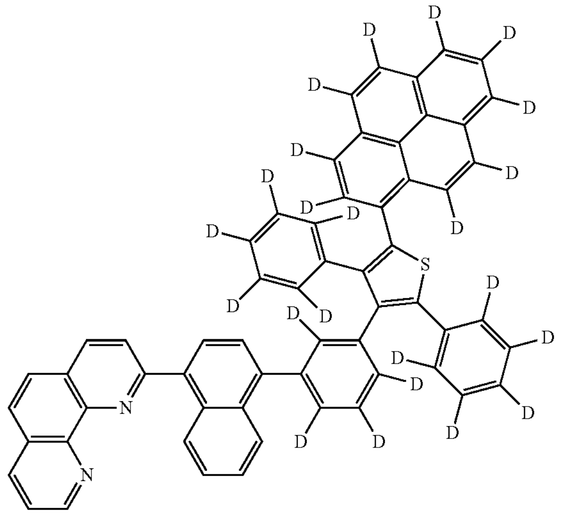
D275
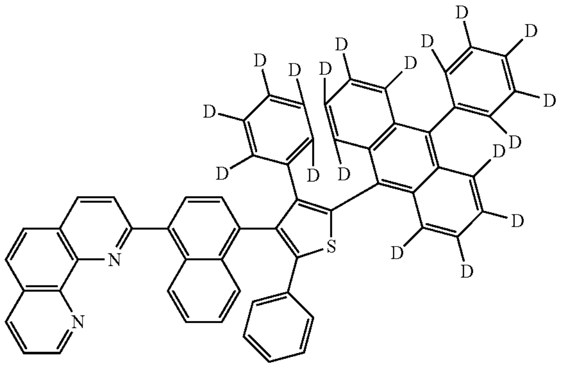
D276
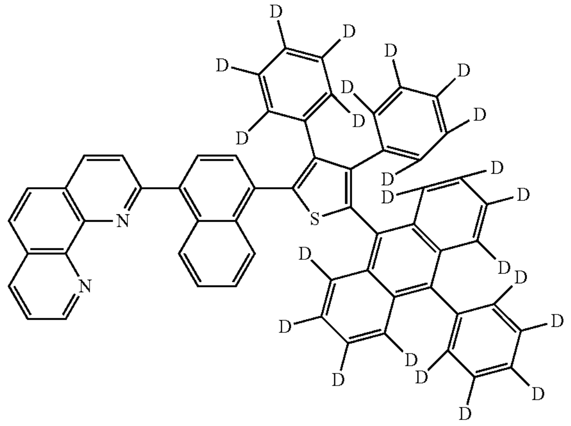
D277
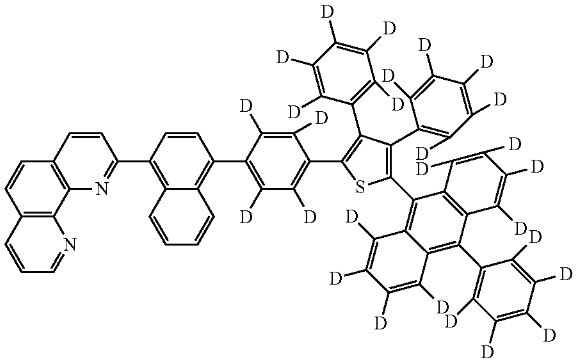

-continued
D278
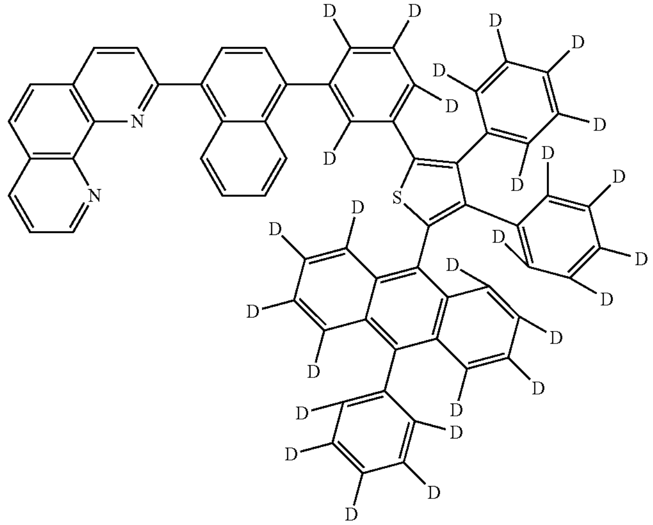
D279
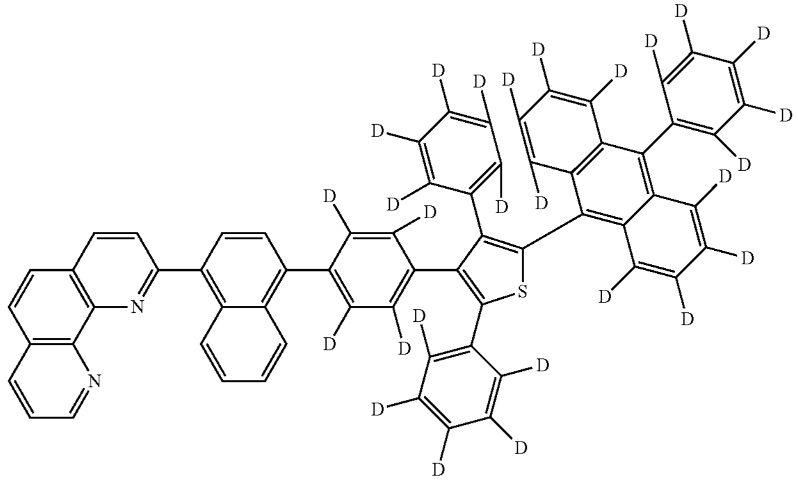
D280
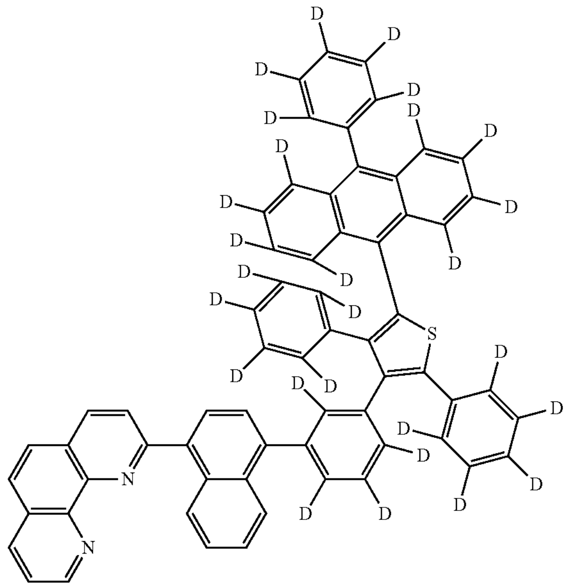
D285
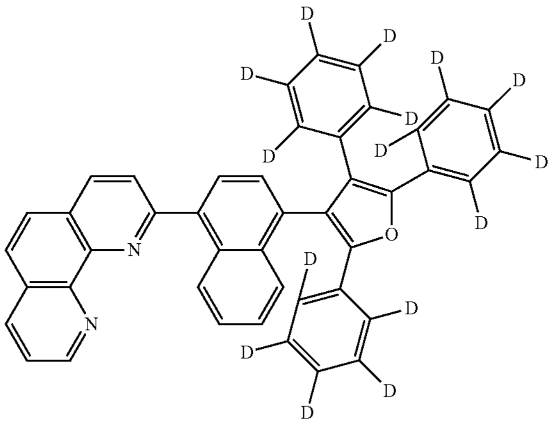

-continued
D286
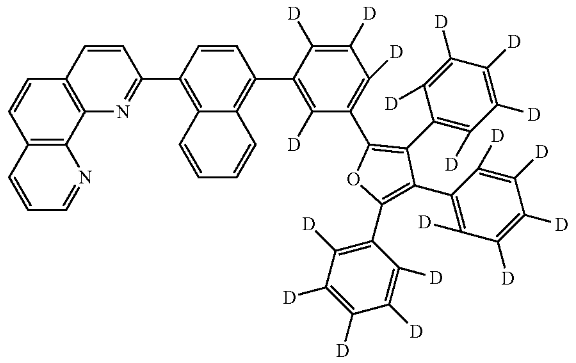
D287
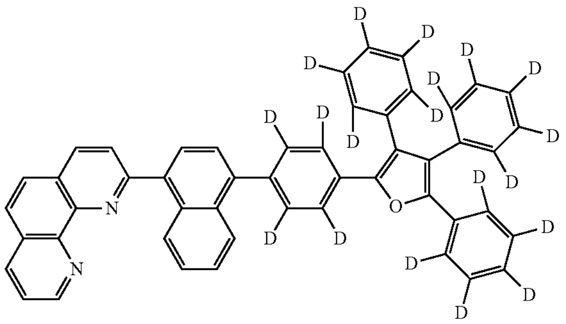
D288
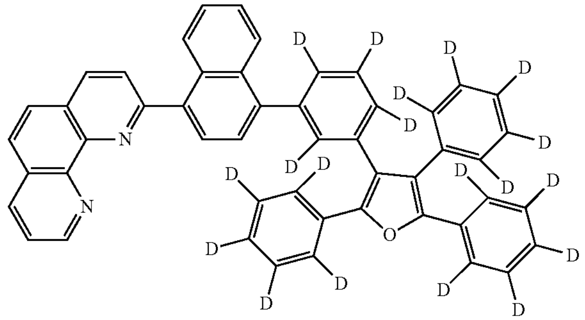
D289
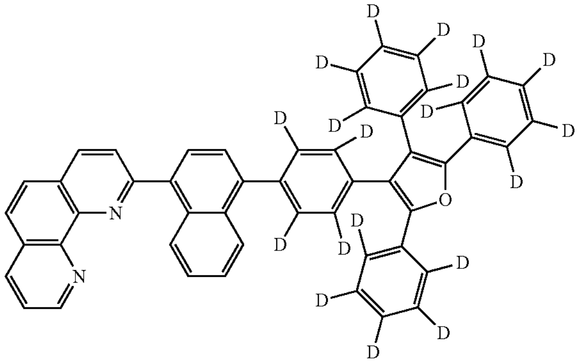
D294
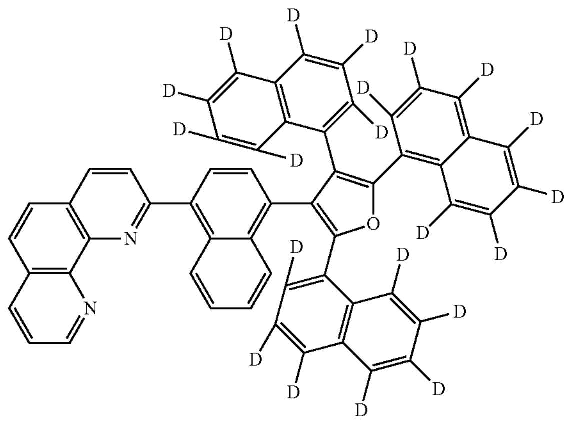
D295
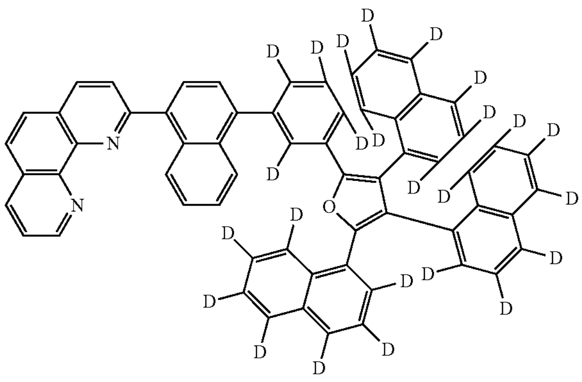
D296
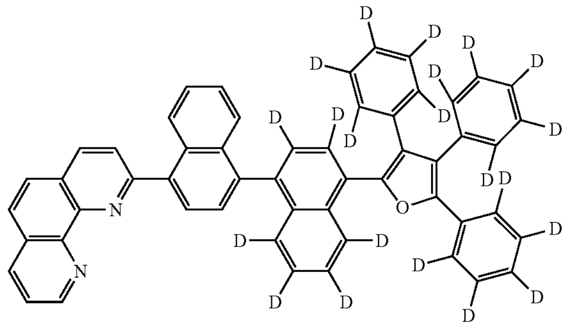
D297
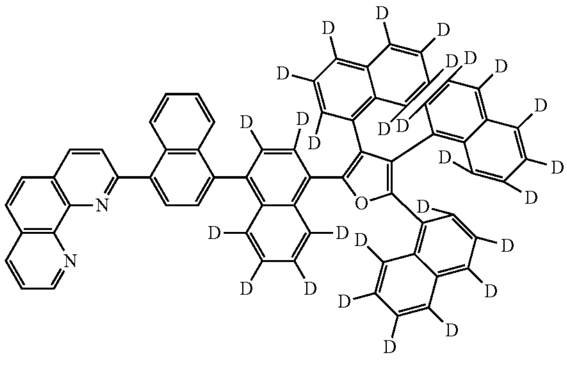

-continued
D298
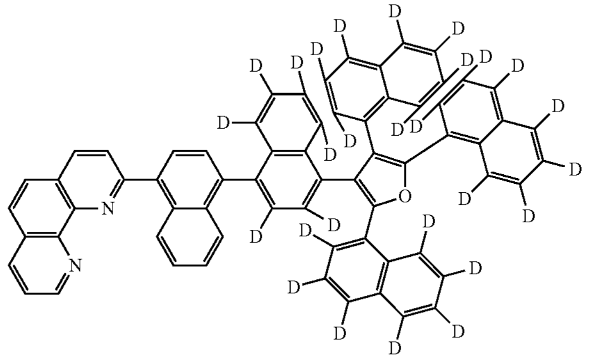
D301
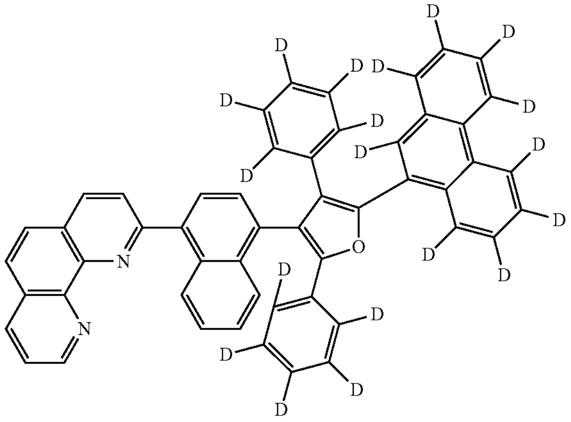
D302
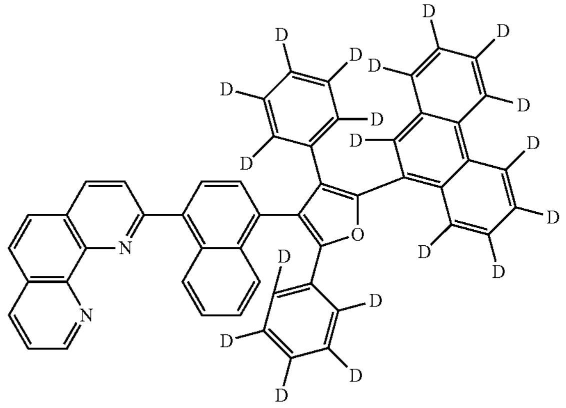
D303
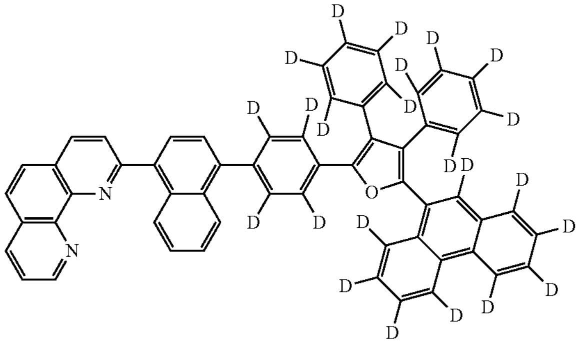
D304
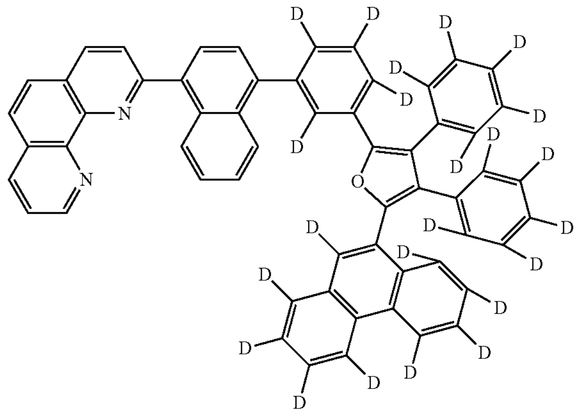
D305
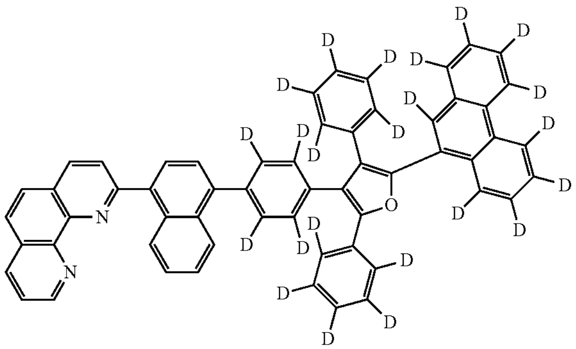

-continued
D306
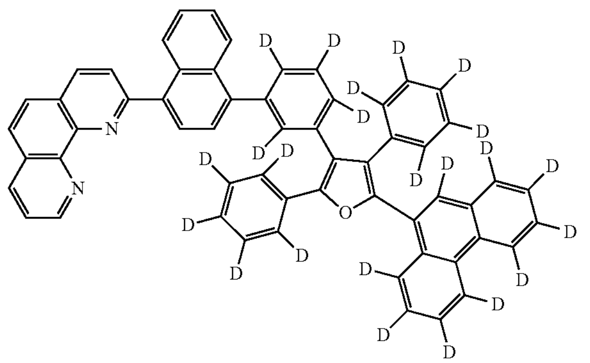
D308
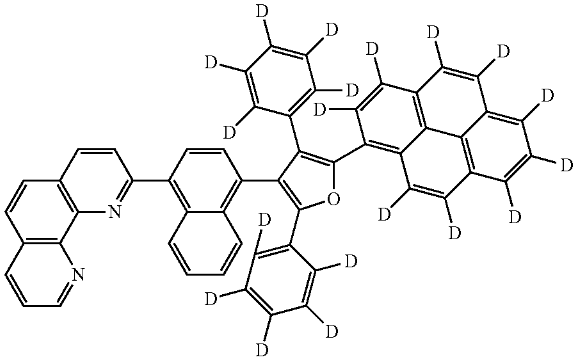
D309
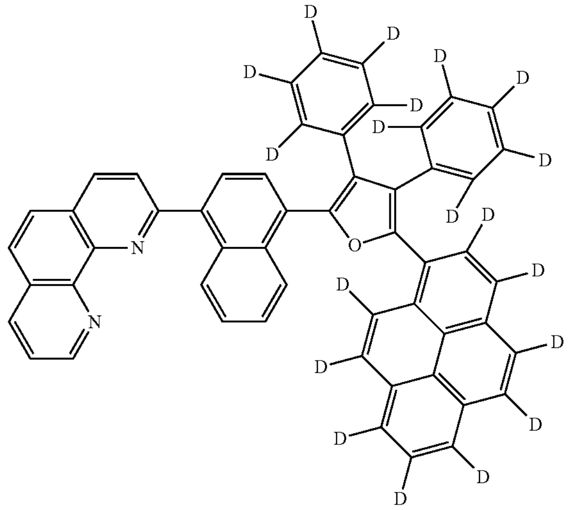
D310
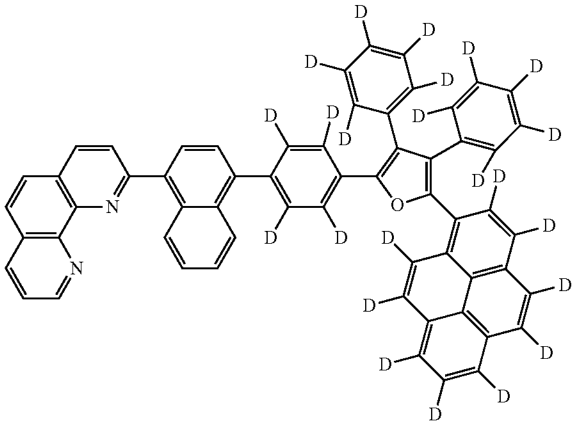
D311
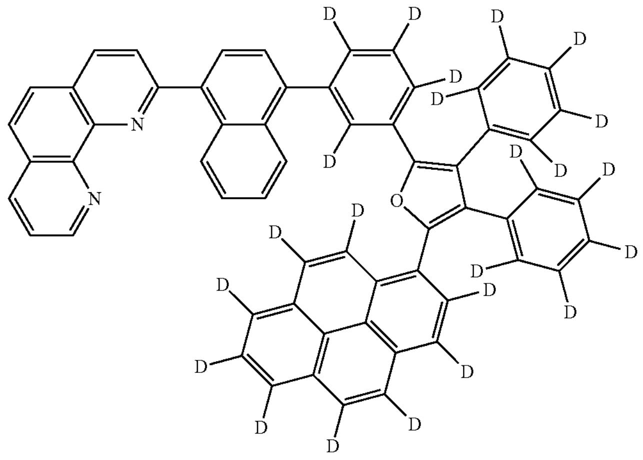

-continued
D312
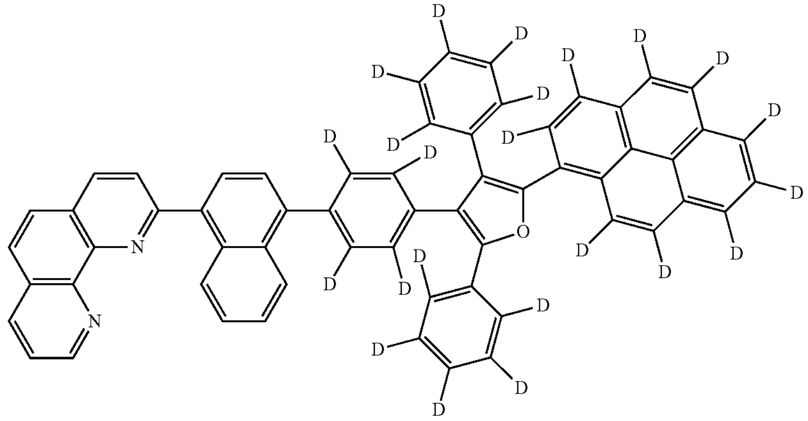
D313
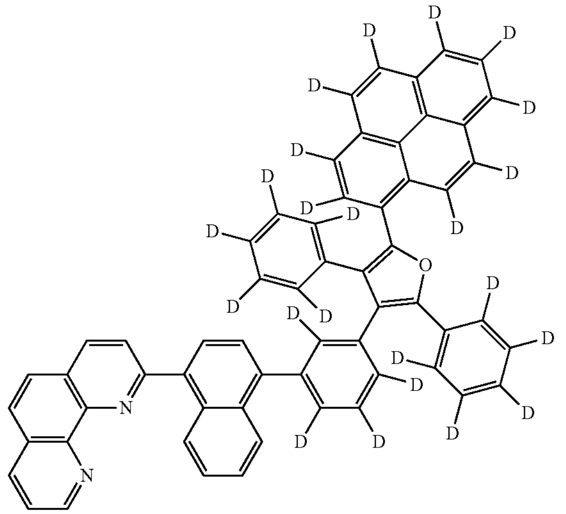
D315
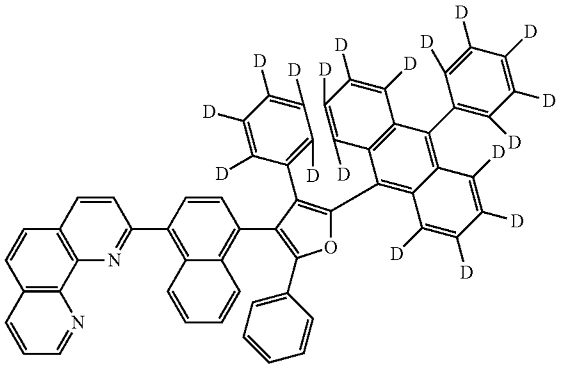
D316
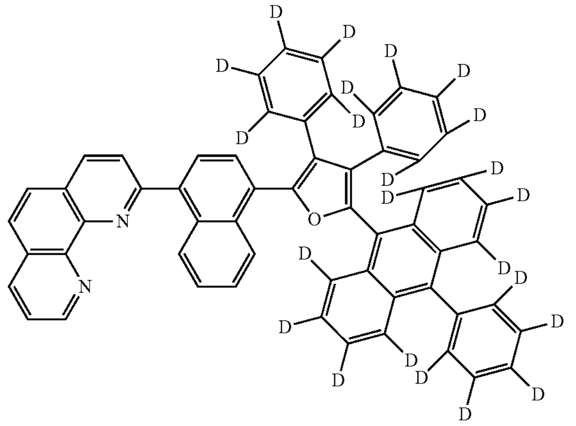
D317
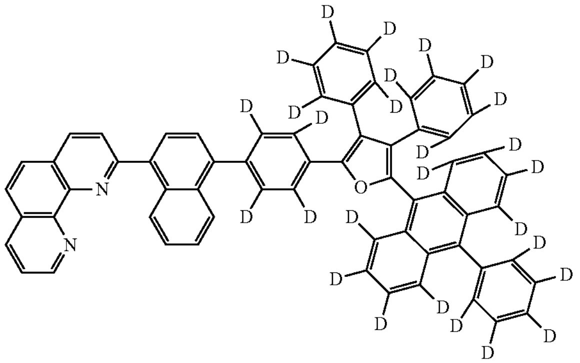

-continued
D318
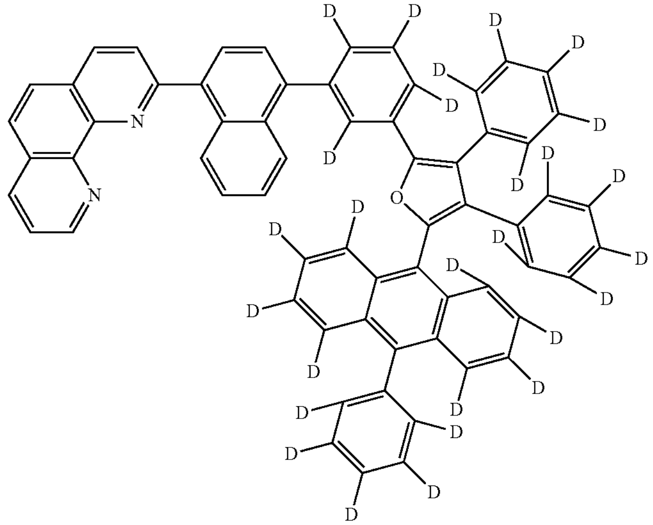
D319
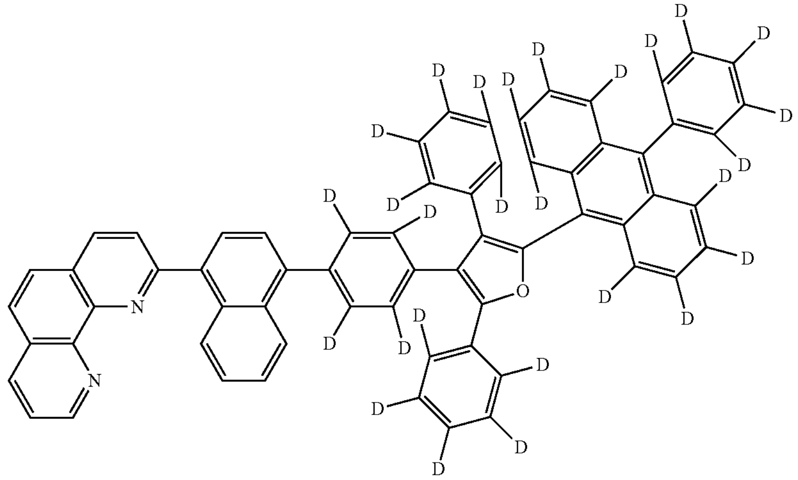
D320
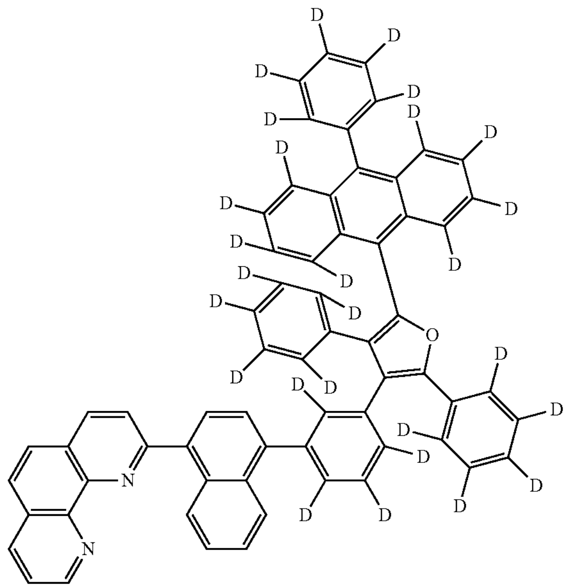
D325
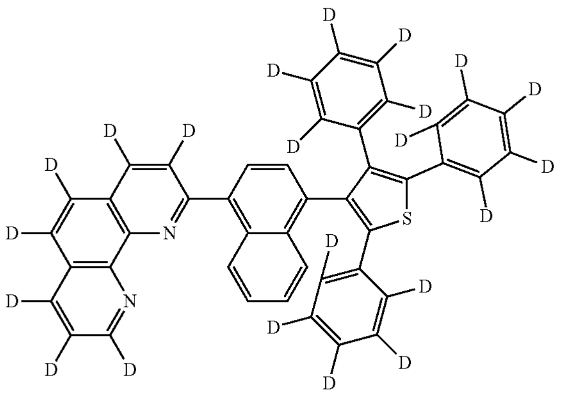

-continued
D326
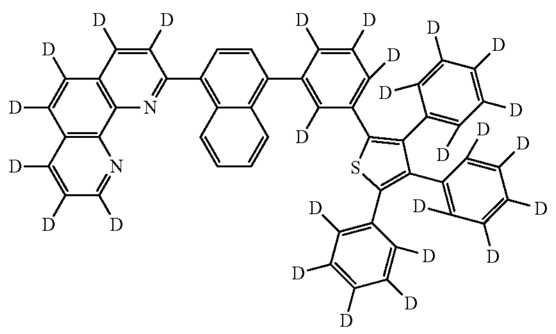
D327
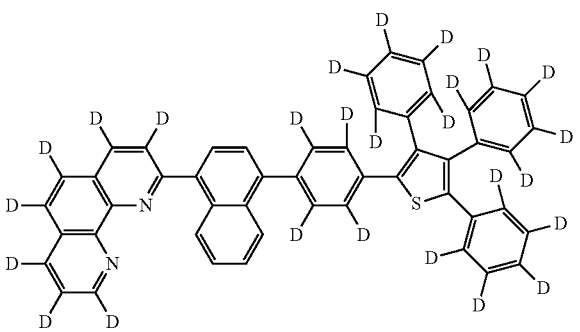
D328
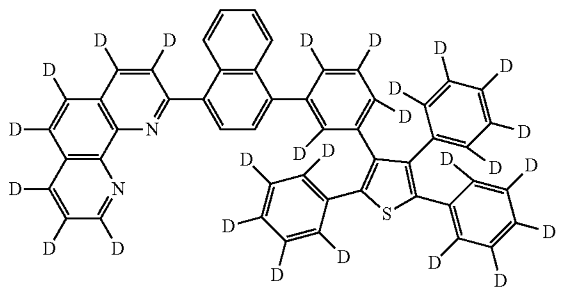
D329
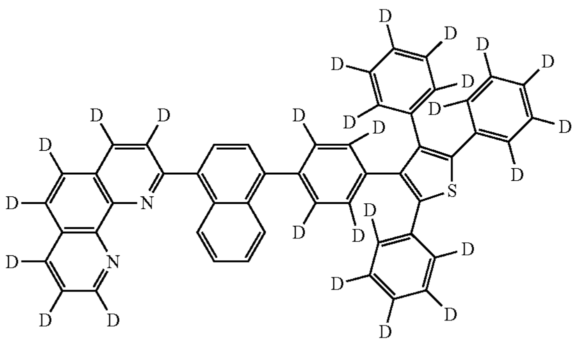
D334
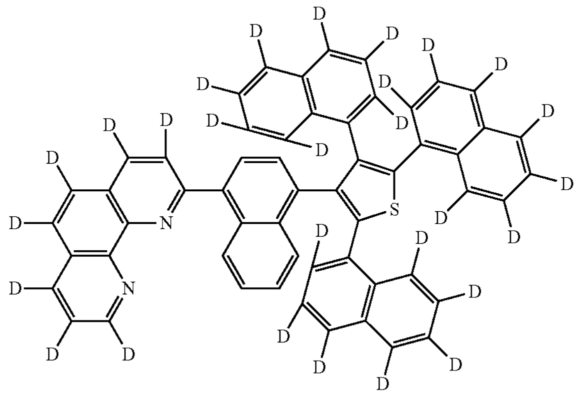
D335
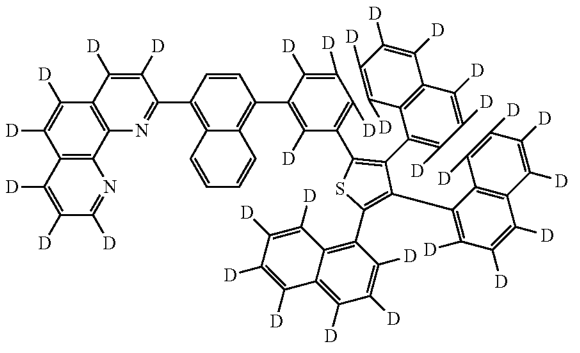
D336
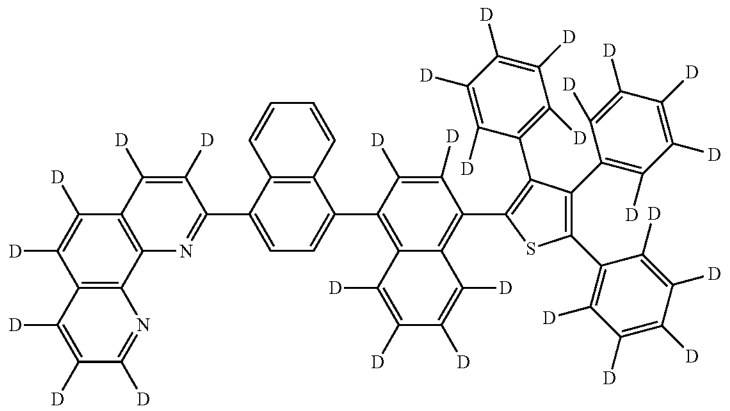

-continued
D337
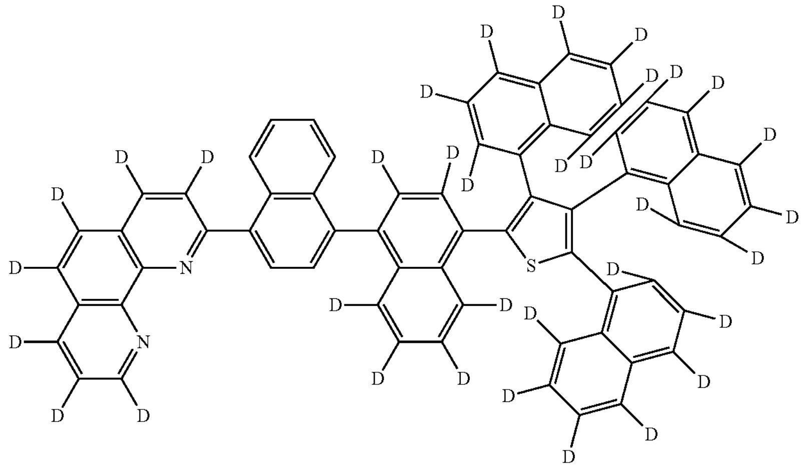
D338
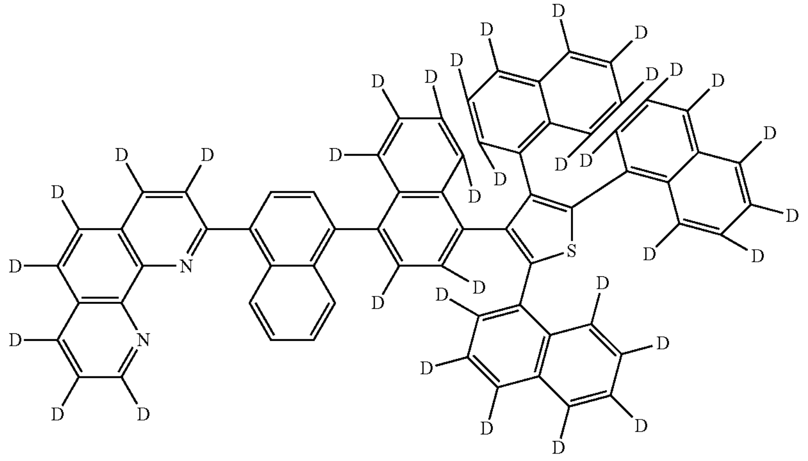
D341
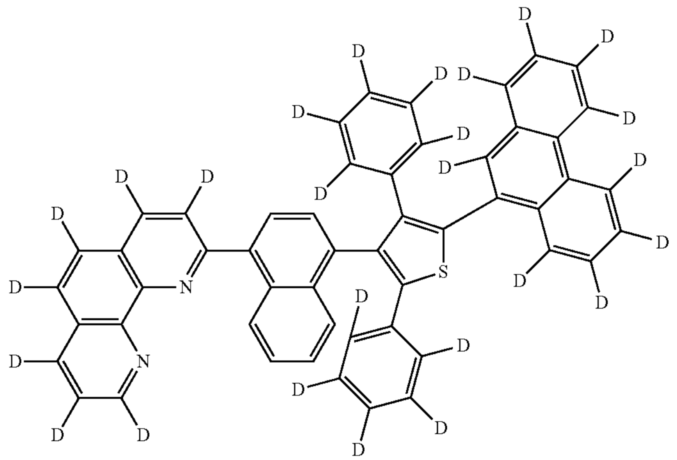

-continued
D342
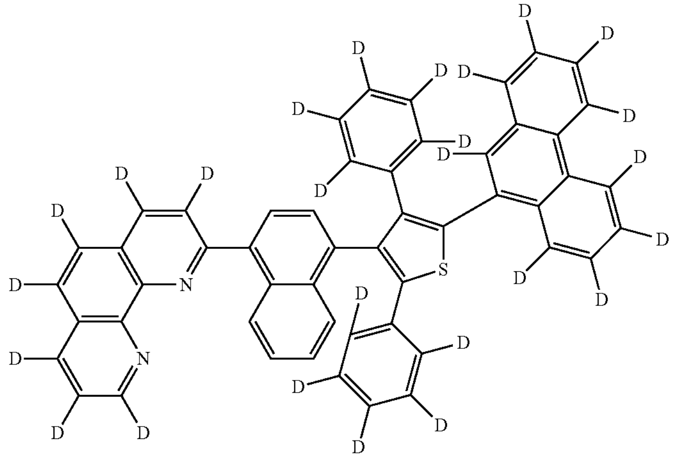
D343
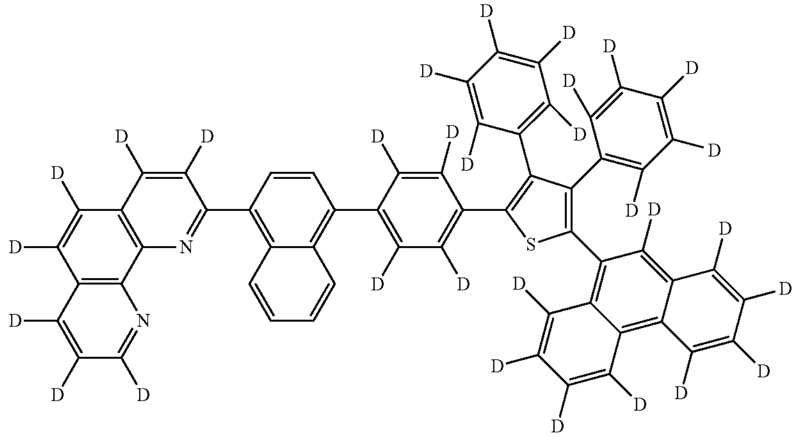
D344
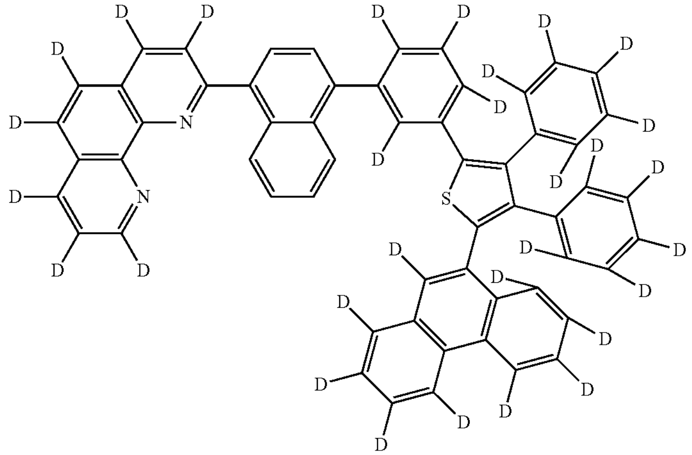

-continued
D345
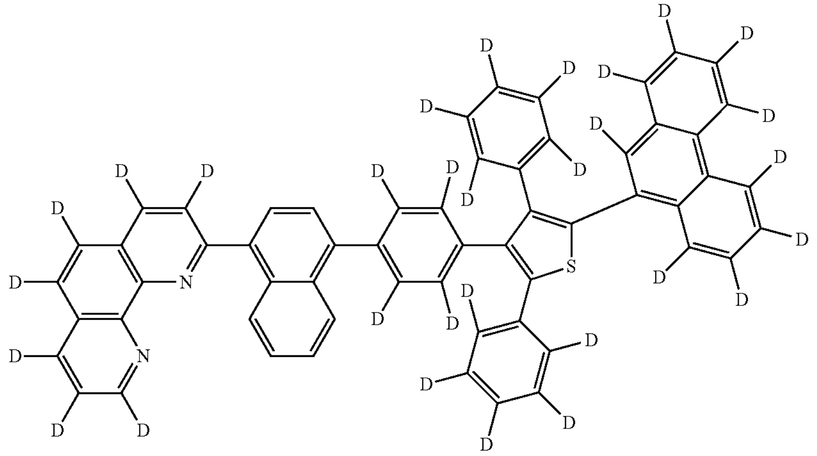
D346
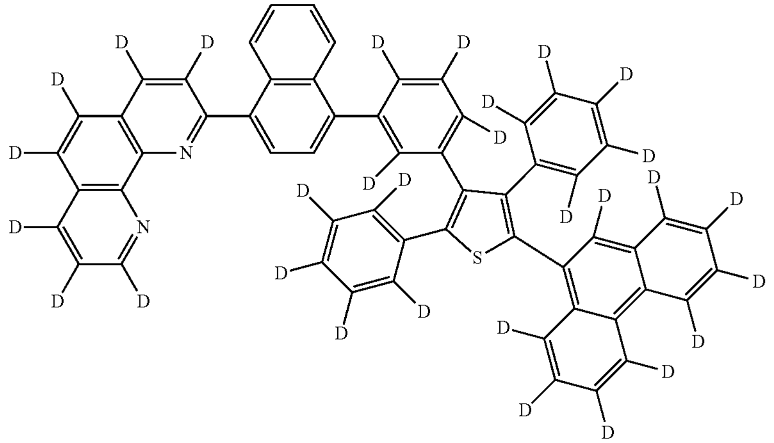
D348
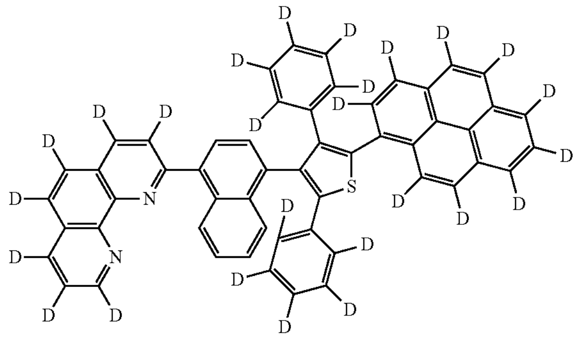
D349
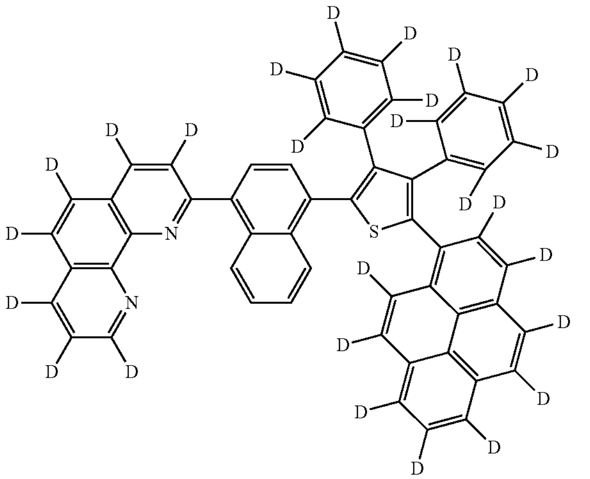

-continued
D350
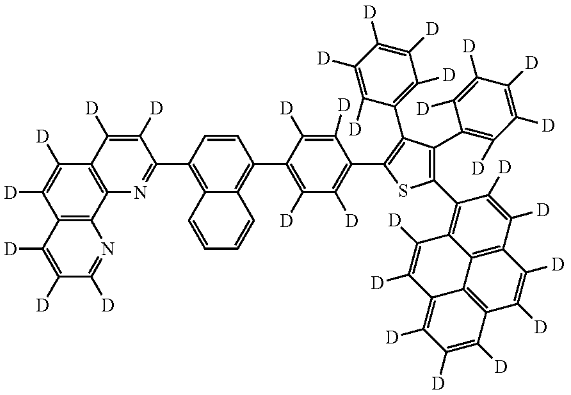
D351
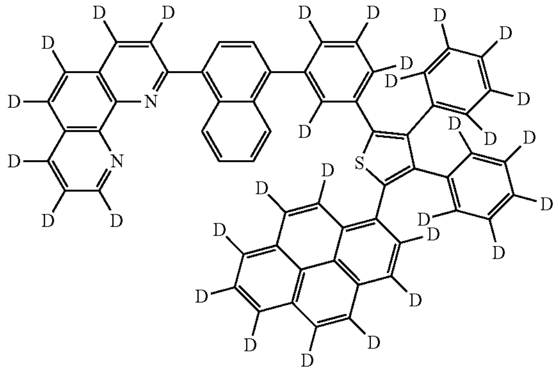
D352
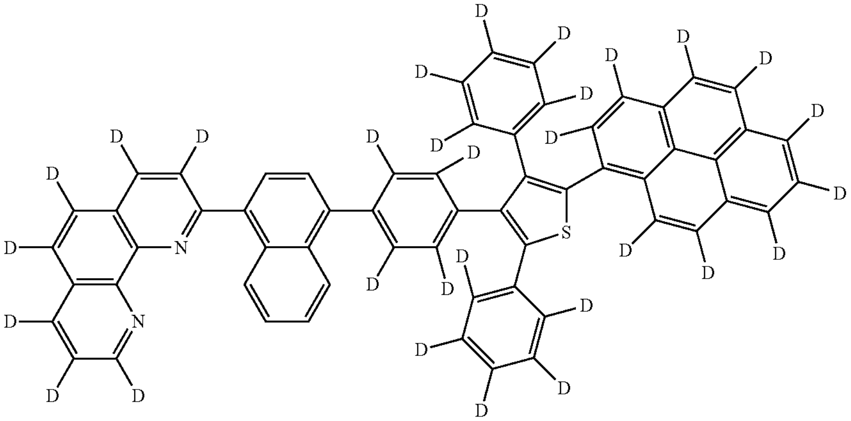
D353
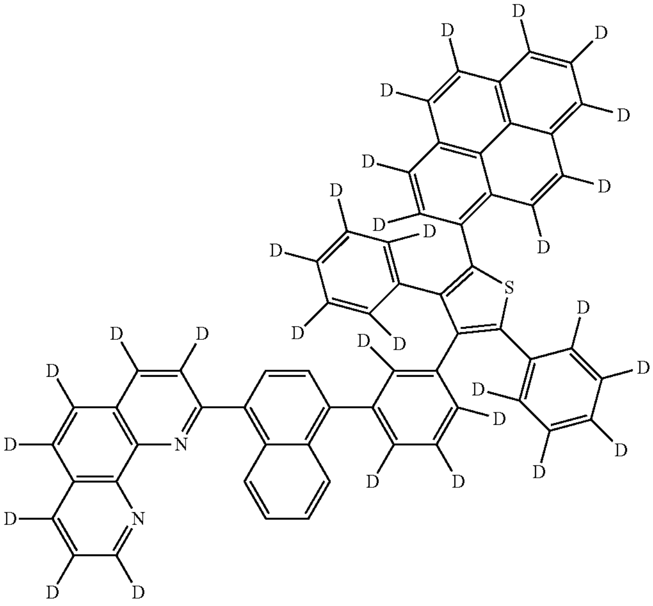

-continued
D355
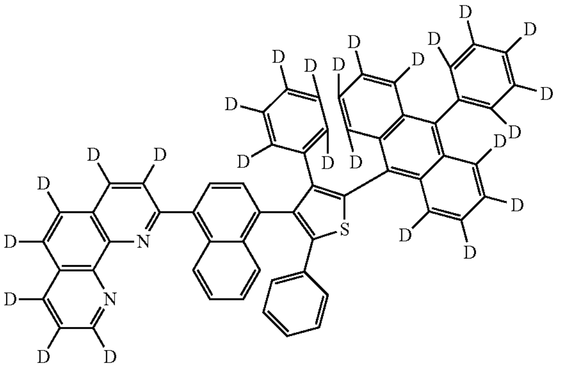
D356
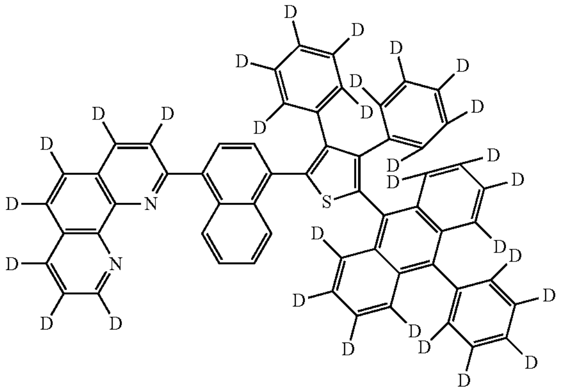
D357
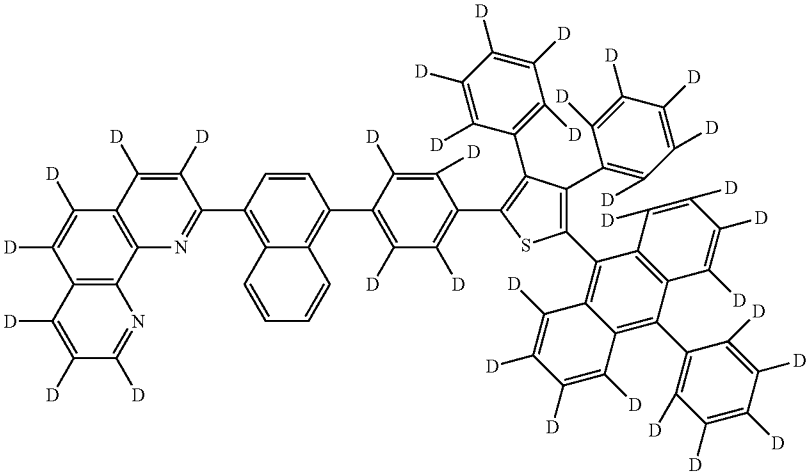
D358
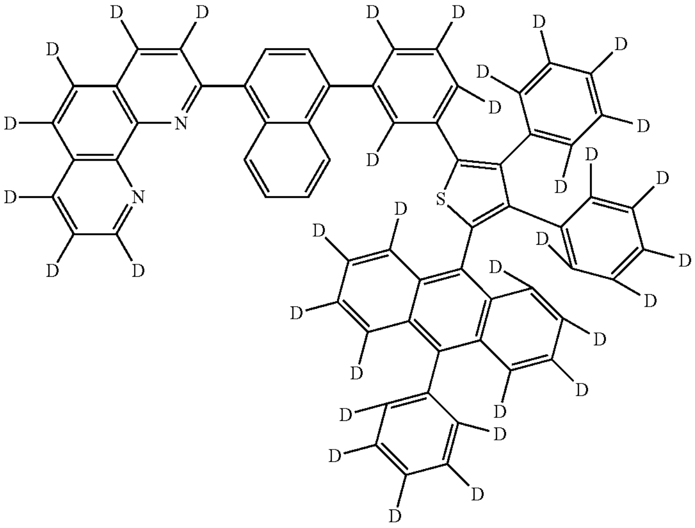

-continued
D359
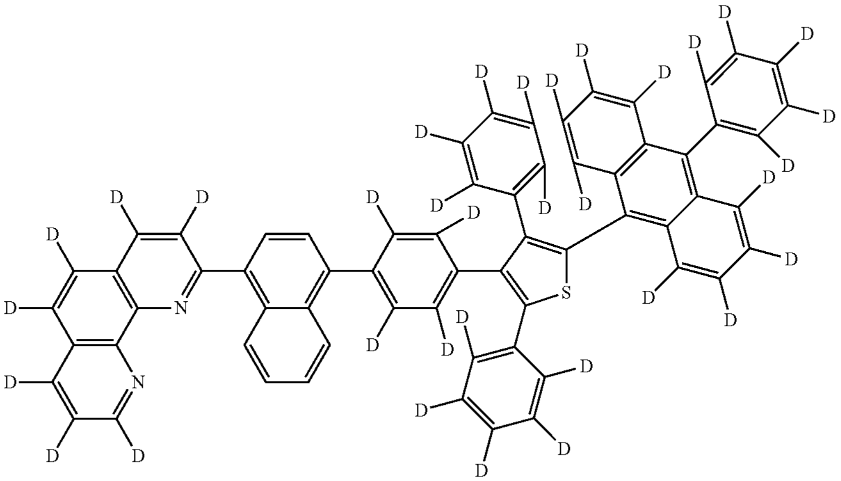
D360
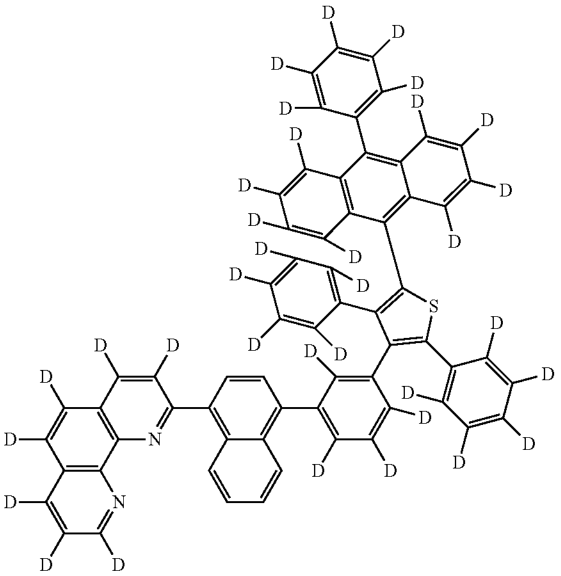
D365
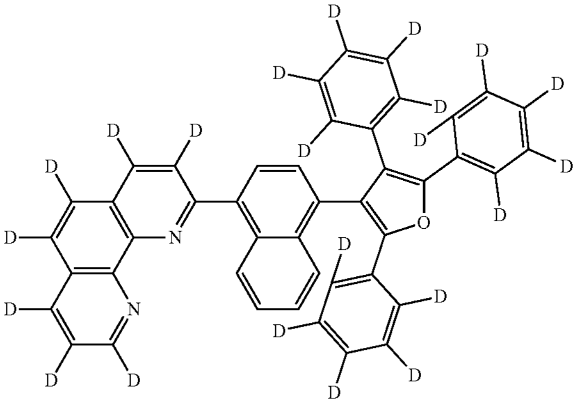
D366
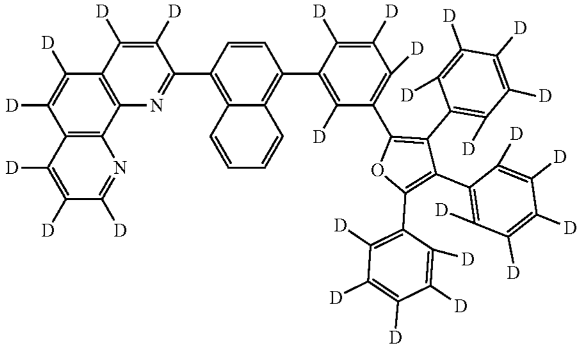

-continued
D367
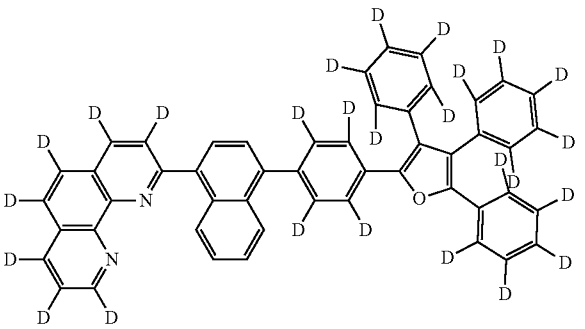
D368
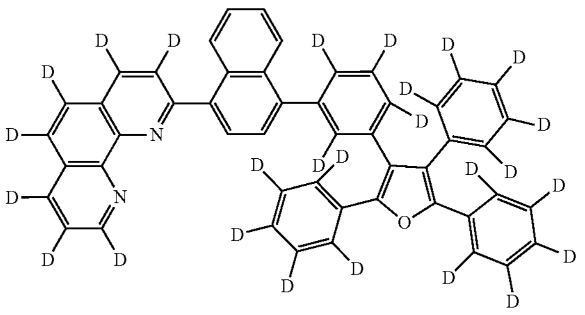
D369
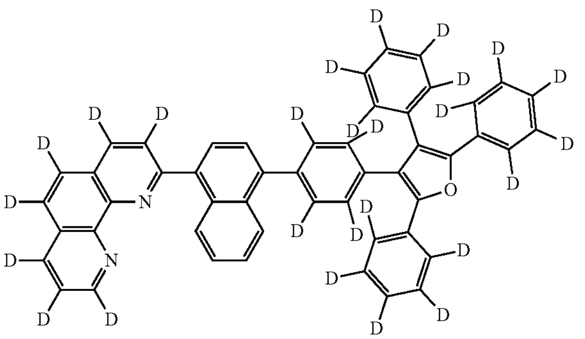
D374
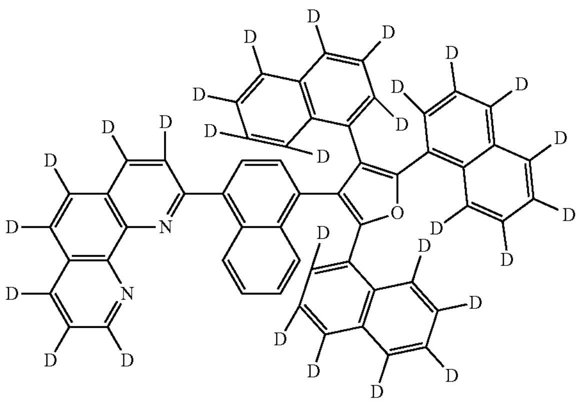
D375
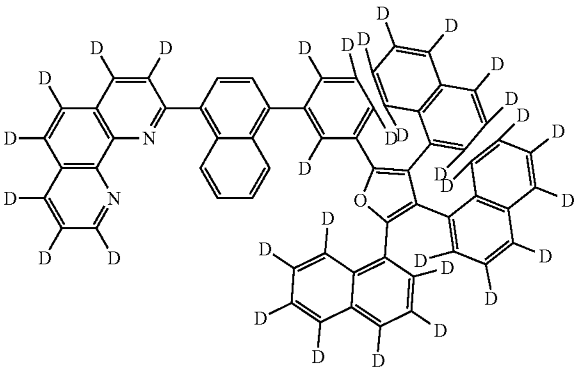
D376
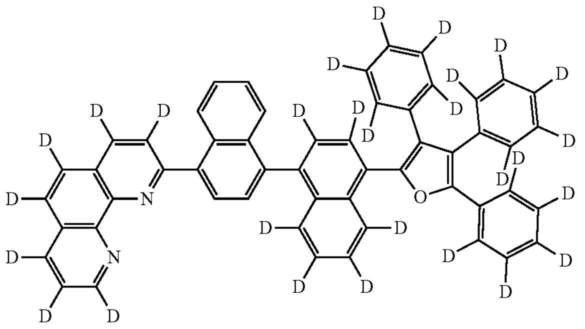
D377
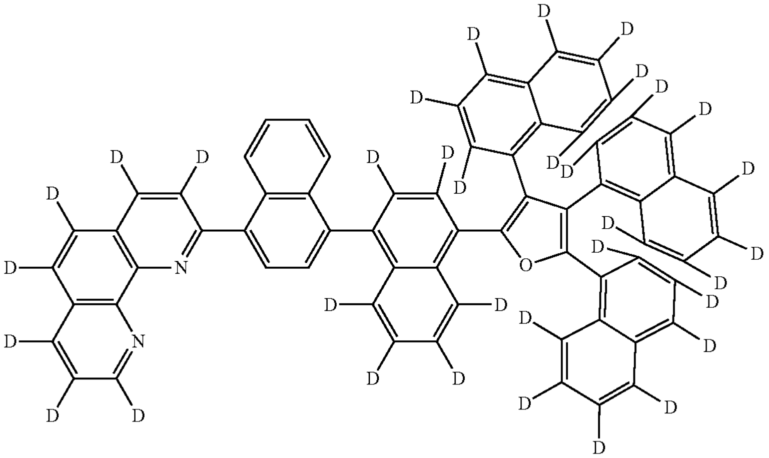

-continued
D378
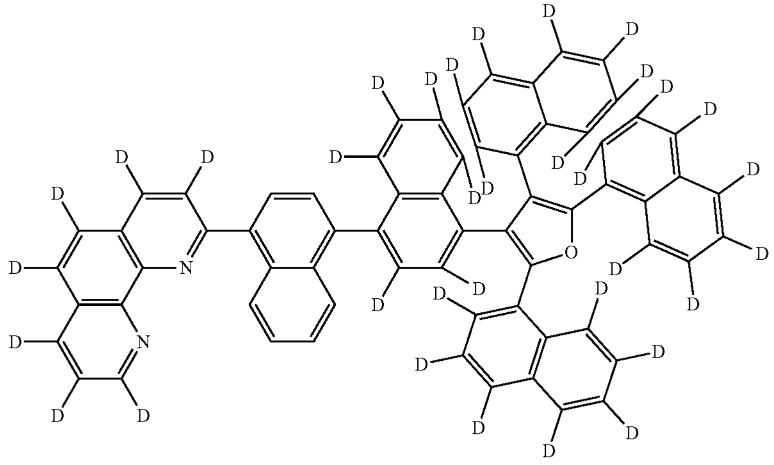
D381
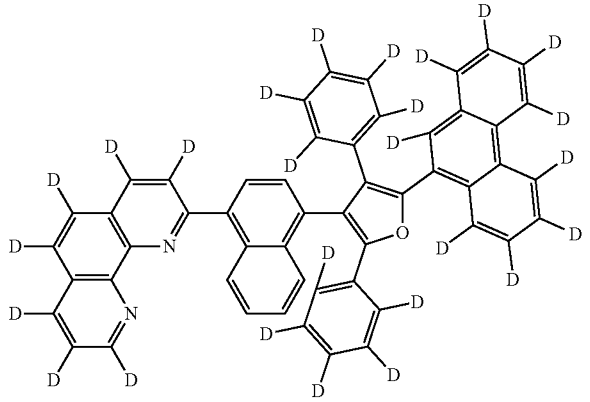
D382
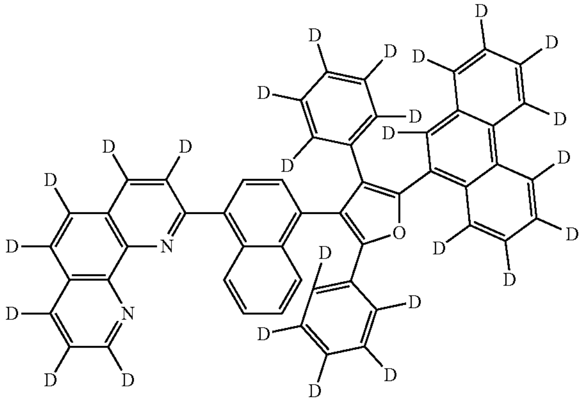
D383
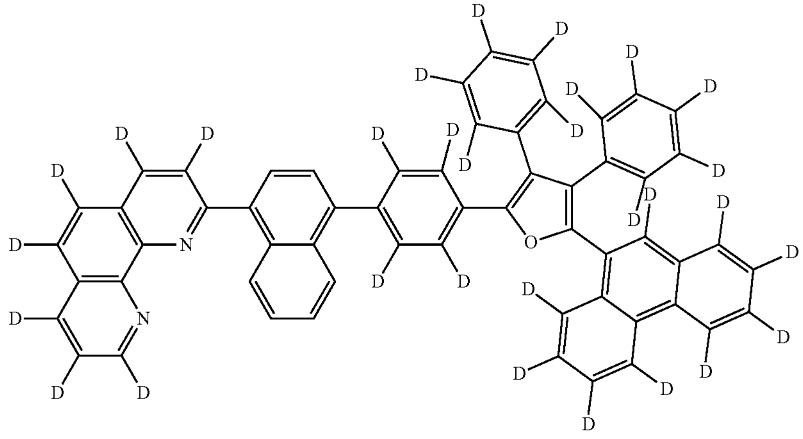

-continued
D384
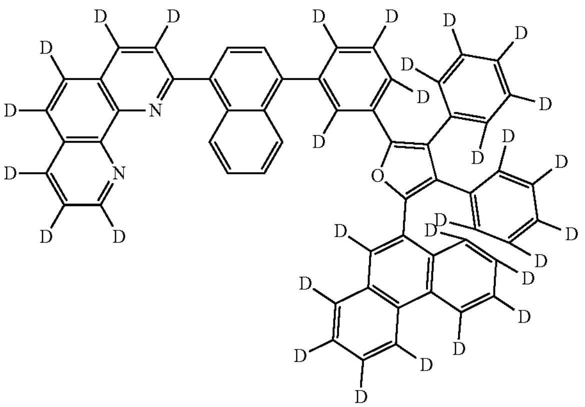
D385
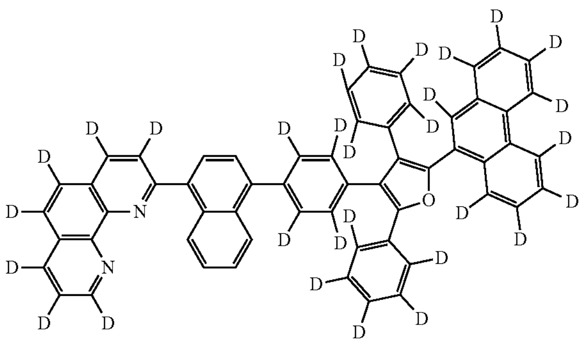
D386
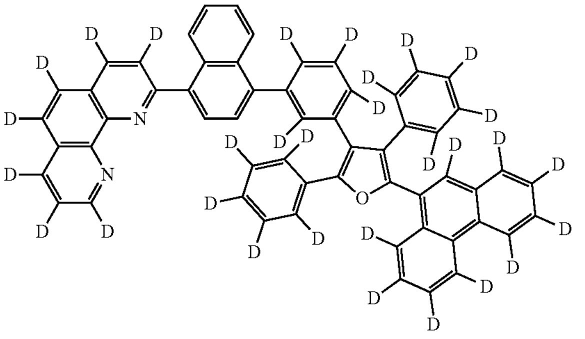
D388
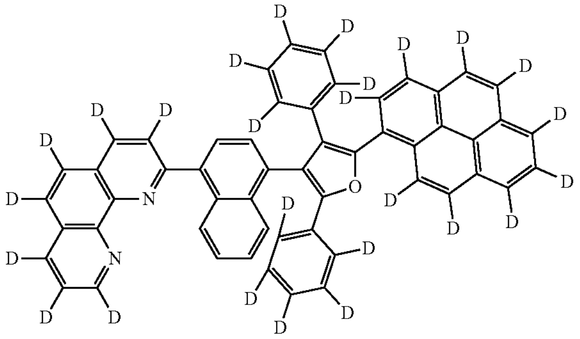
D389
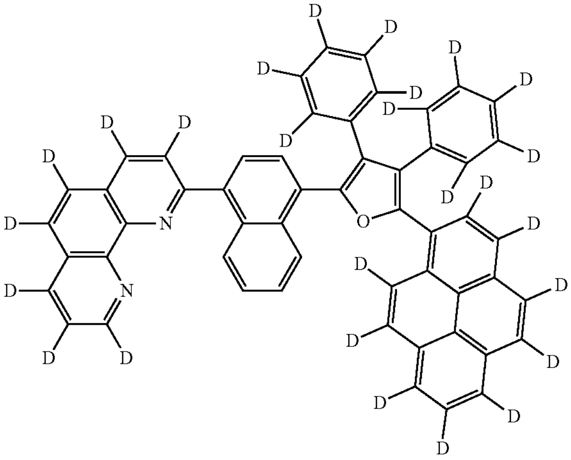
D390
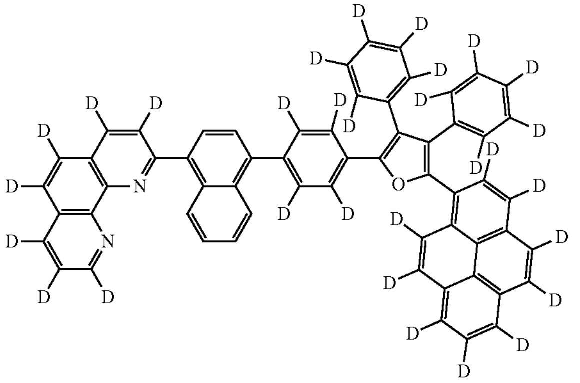

-continued
D391
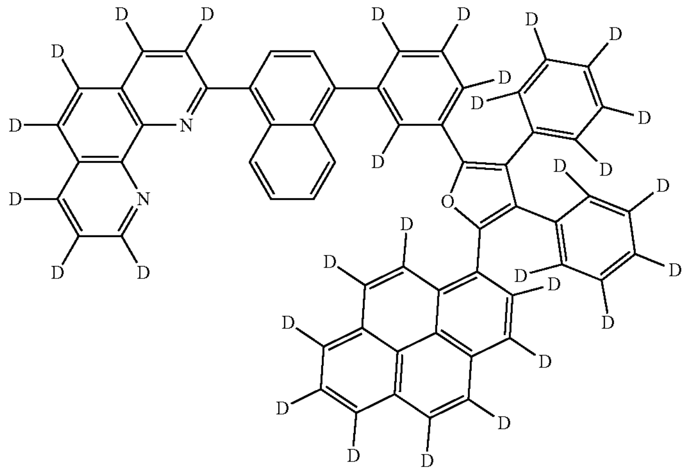
D392
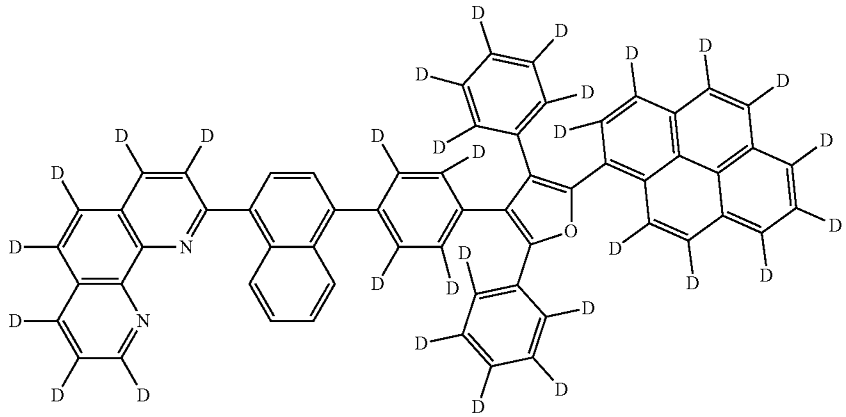
D393
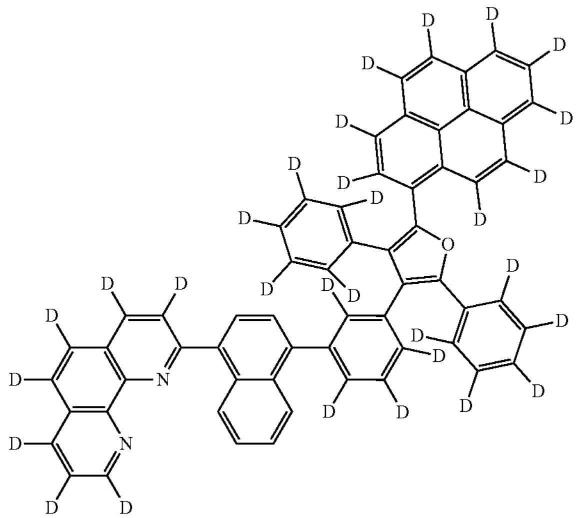
D395
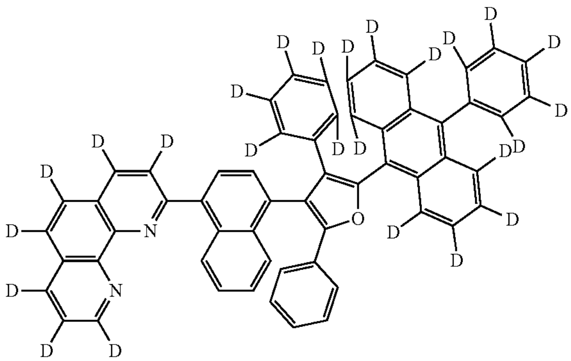

-continued
D396
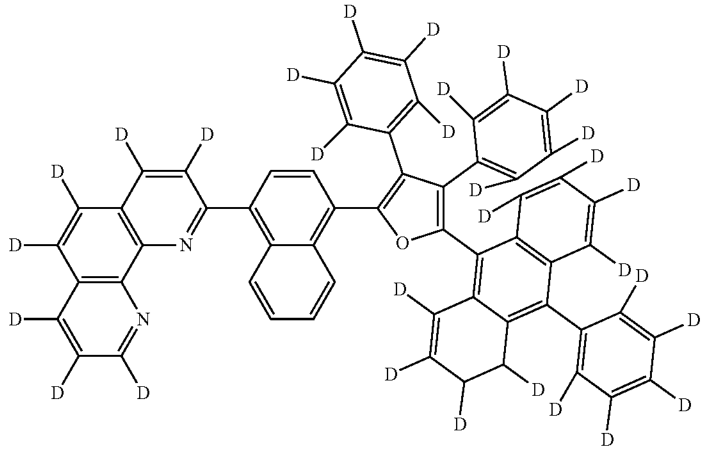
D397
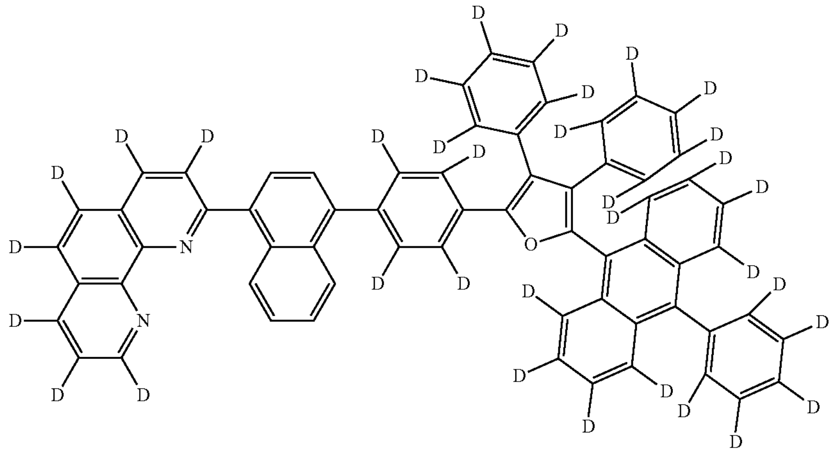
D398
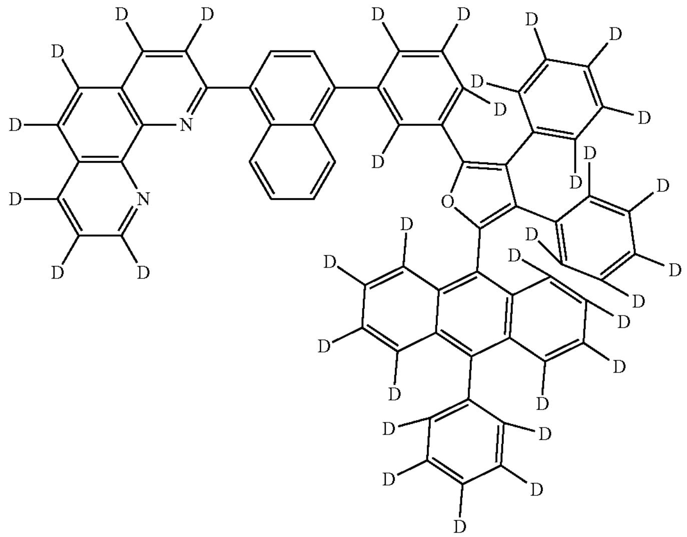

-continued
D399
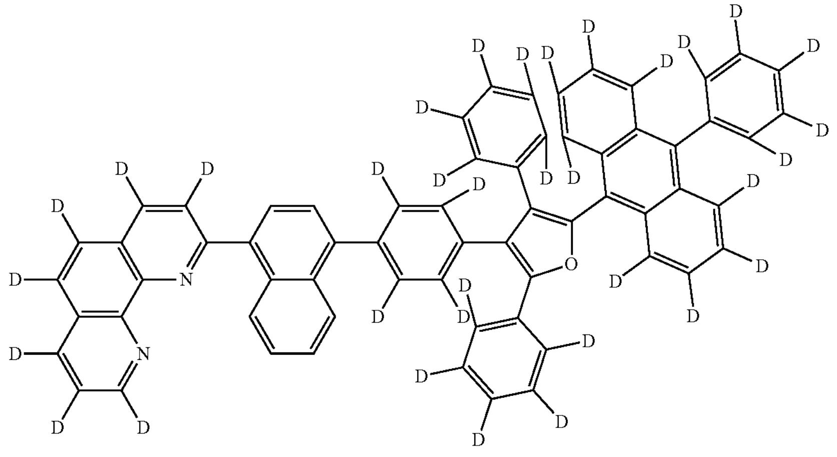
D400
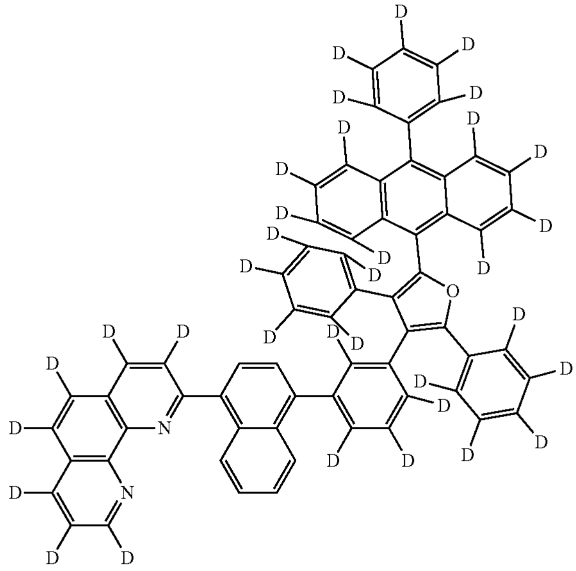
D405
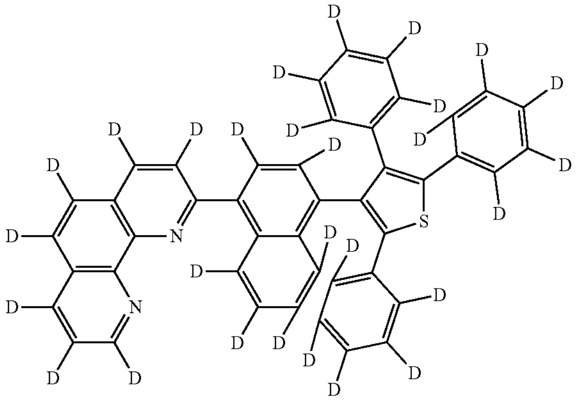
D406
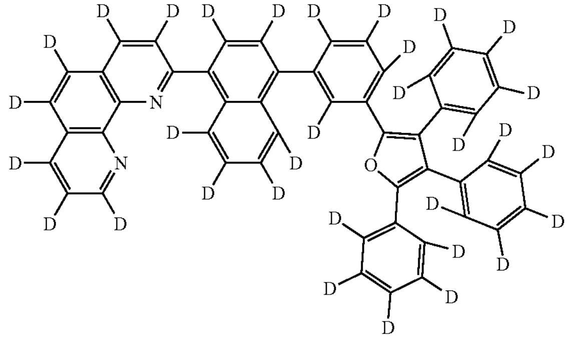
D407
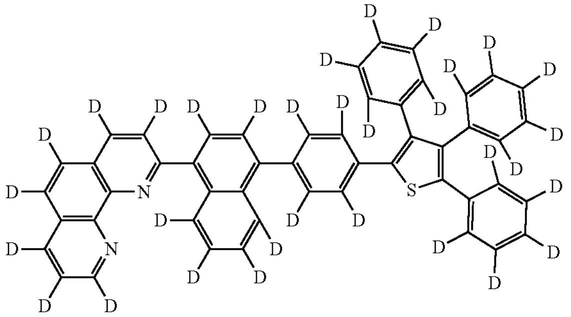

-continued
D408
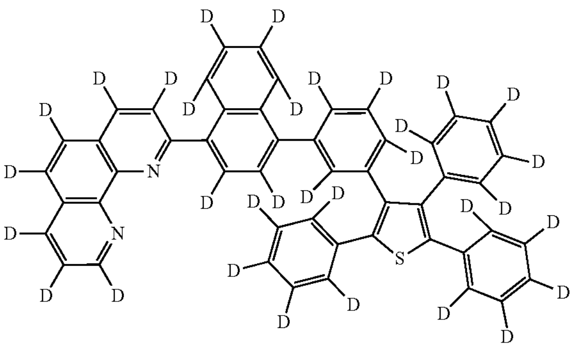
D409
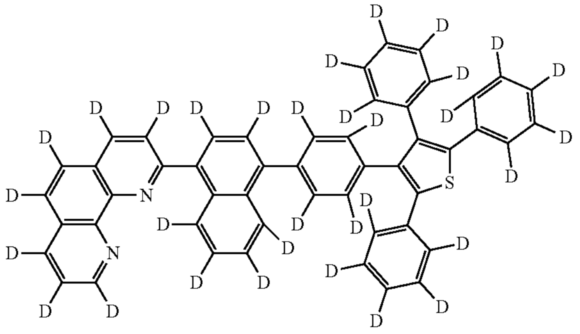
D414
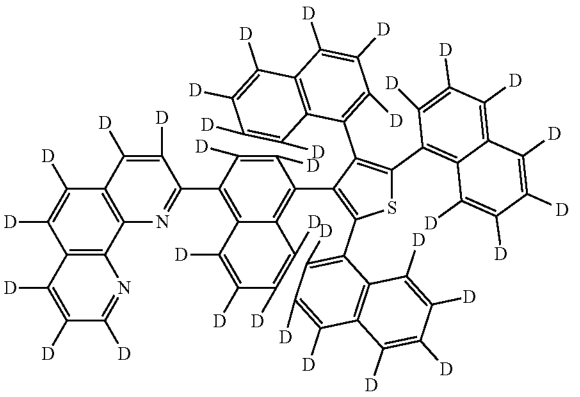
D415
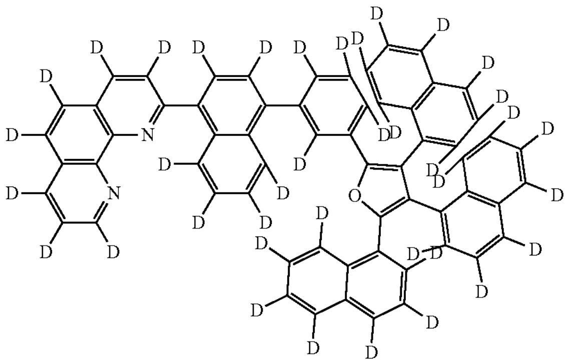
D416
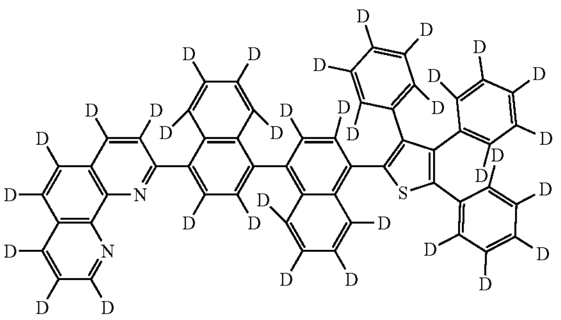
D417
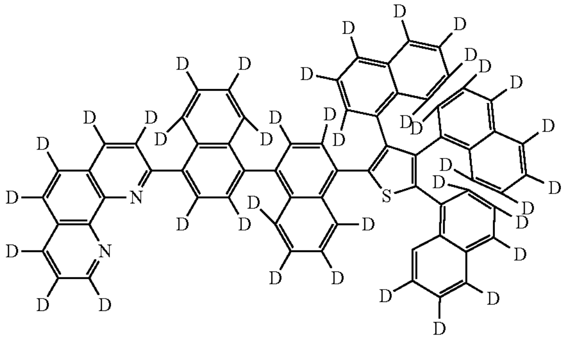
D418
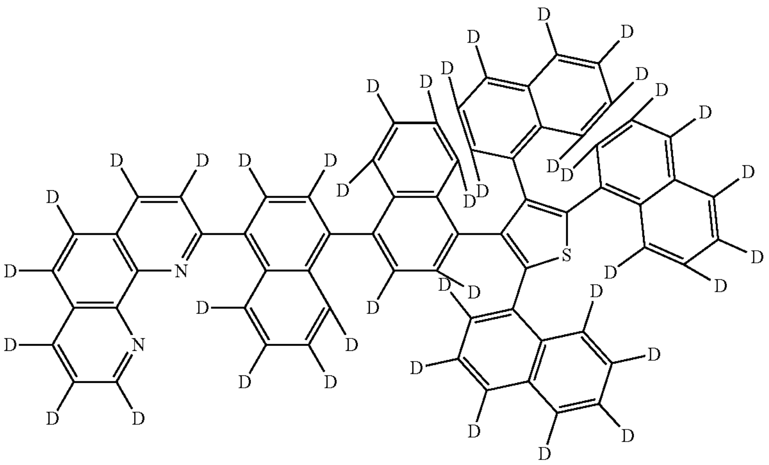

-continued
D421
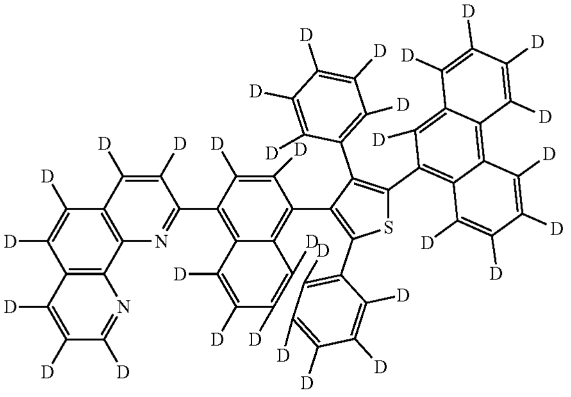
D422
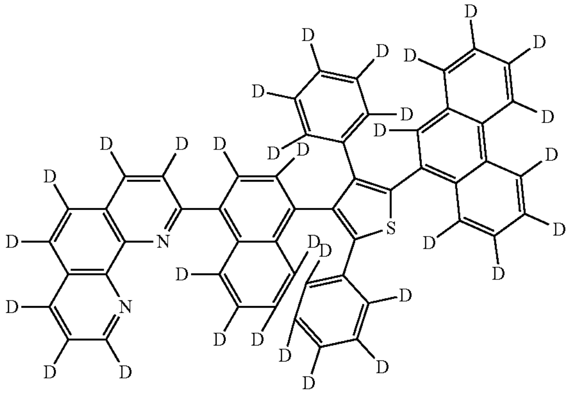
D423
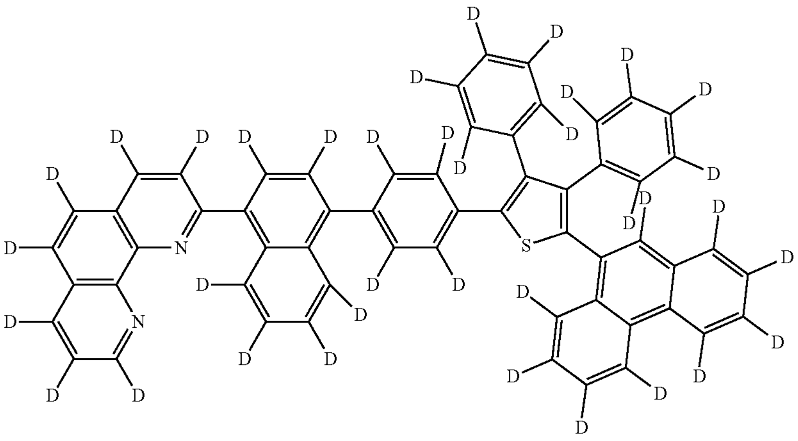
D424
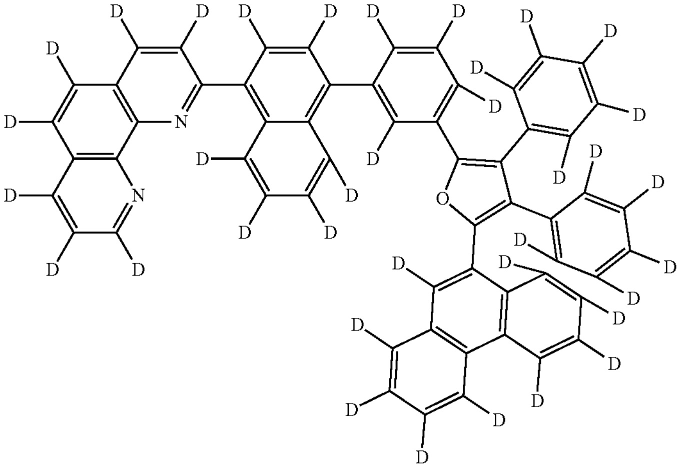

-continued
D425
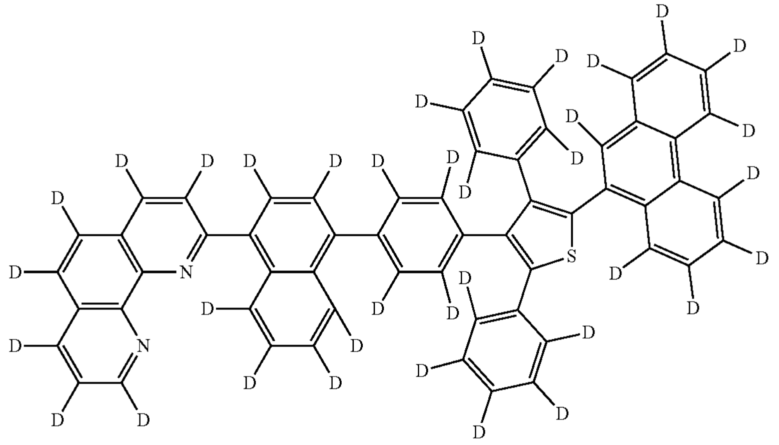
D426
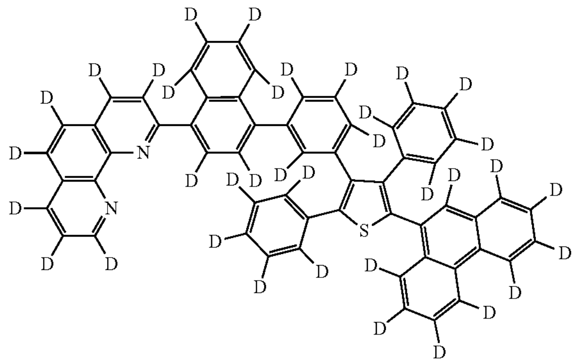
D428
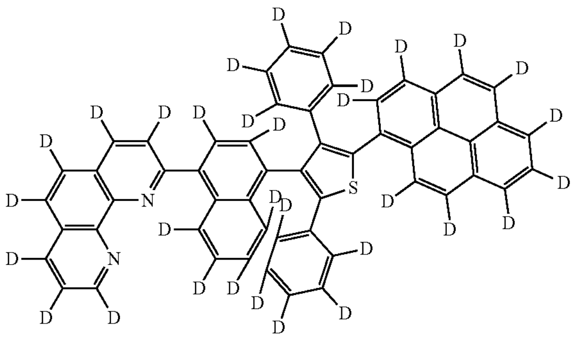
D429
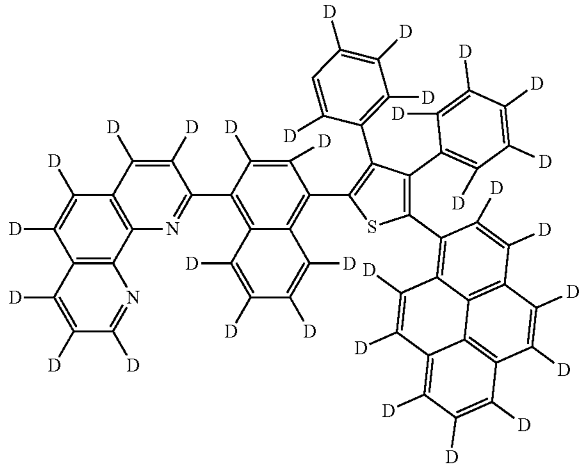
D430
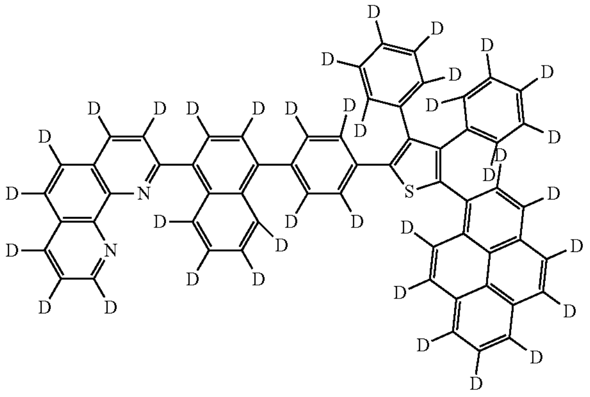

-continued
D431
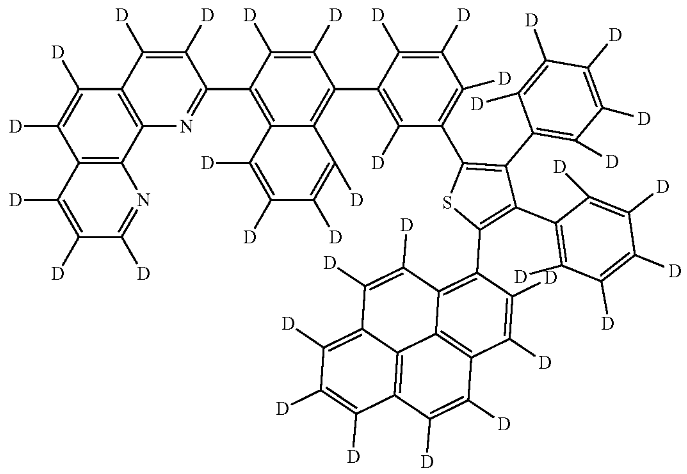
D432
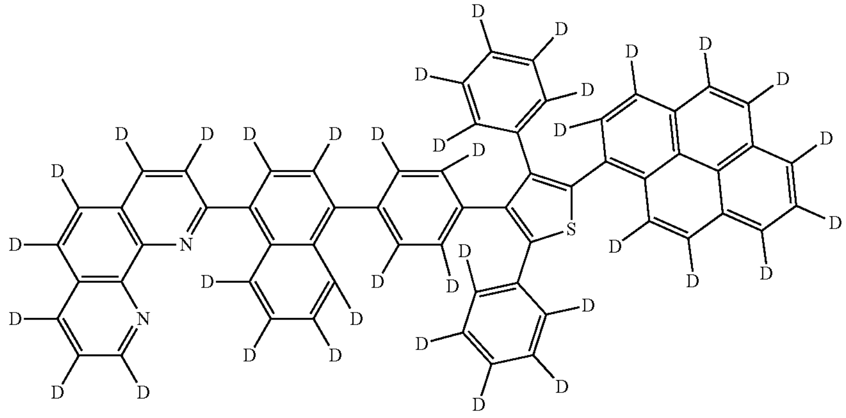
D433
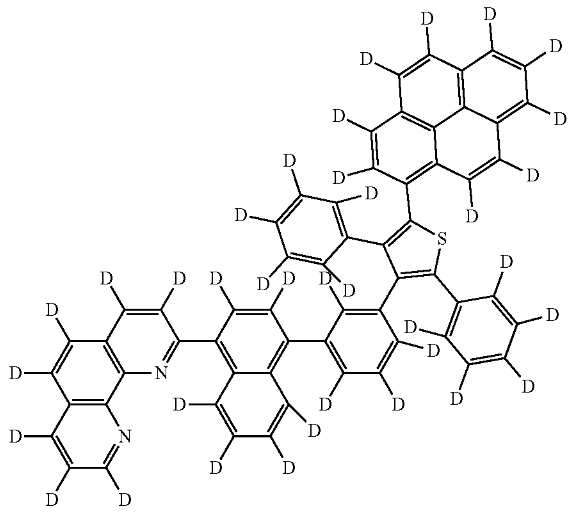
D435
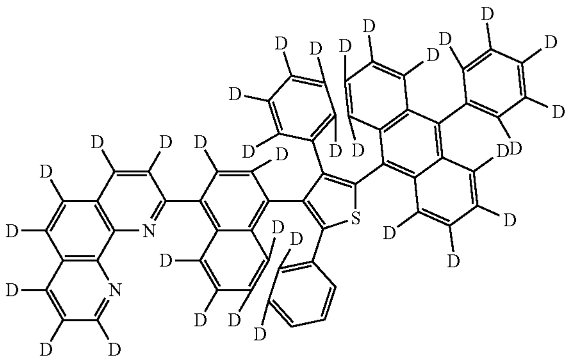

-continued
D436
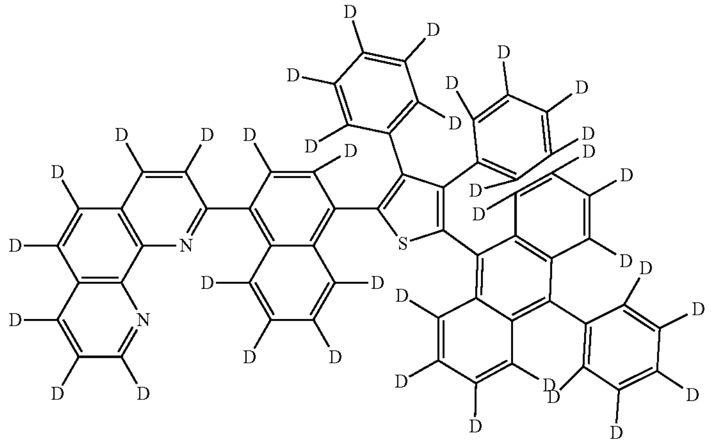
D437
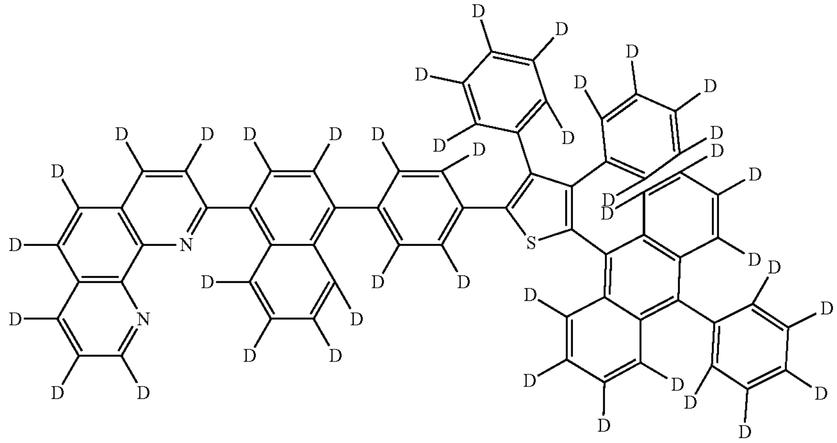
D438
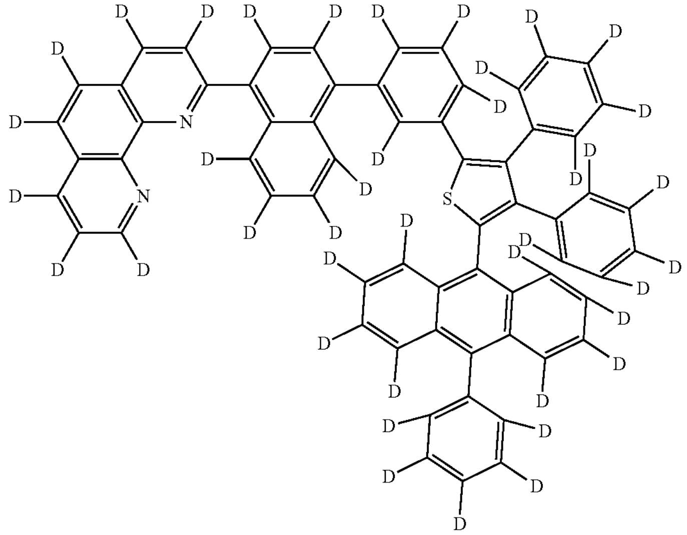

D439
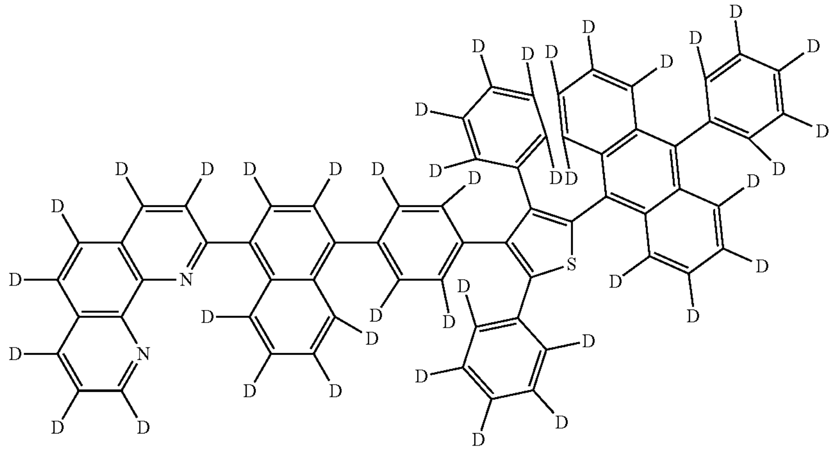
D440
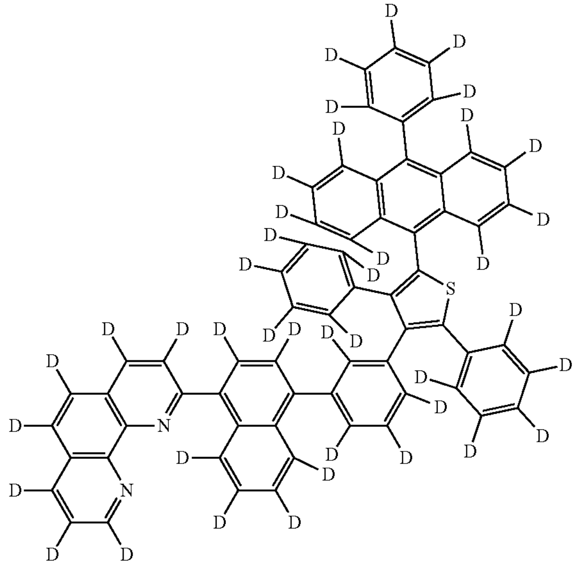
D445
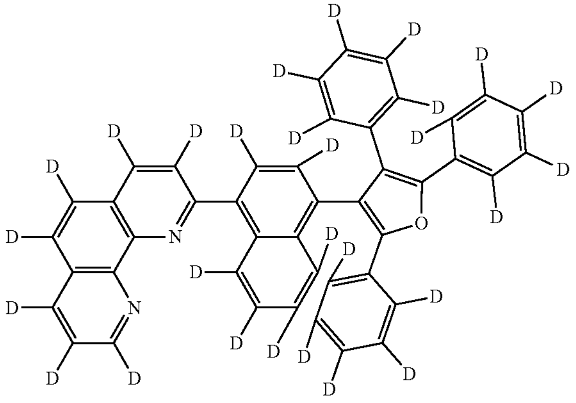
446
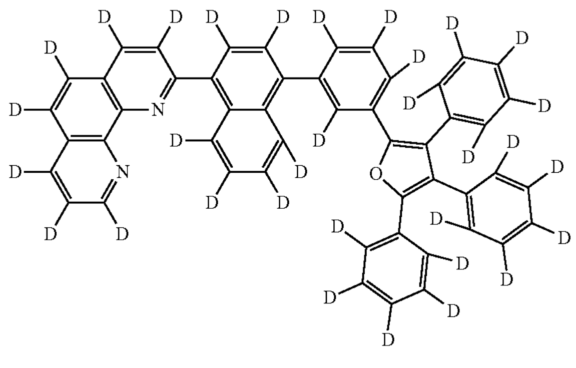
447
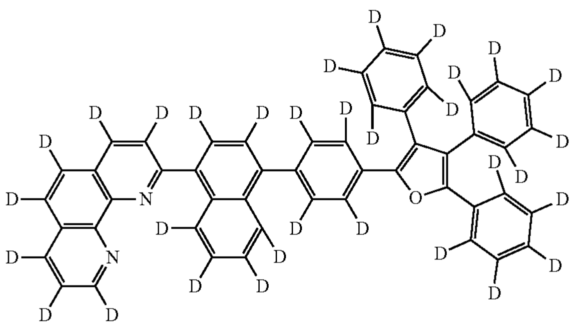

-continued
D448
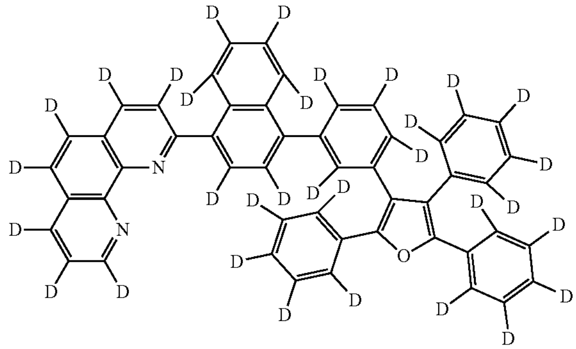
D449
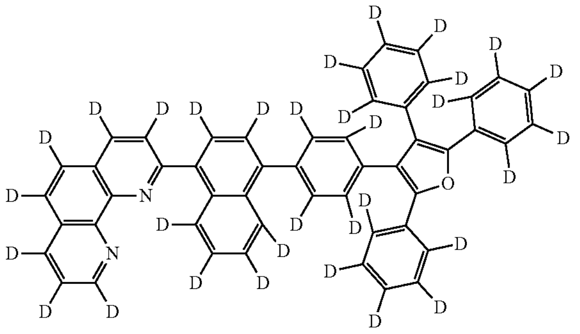
D454
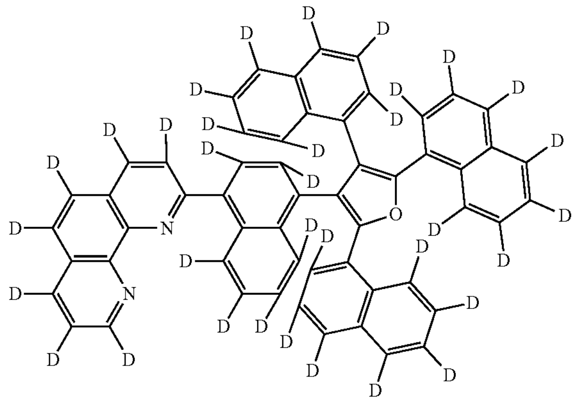
D455
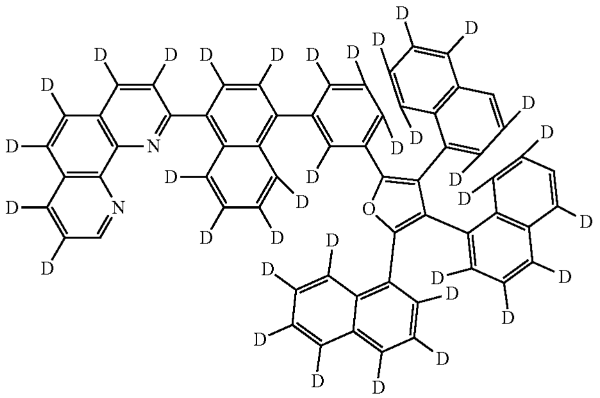
D456
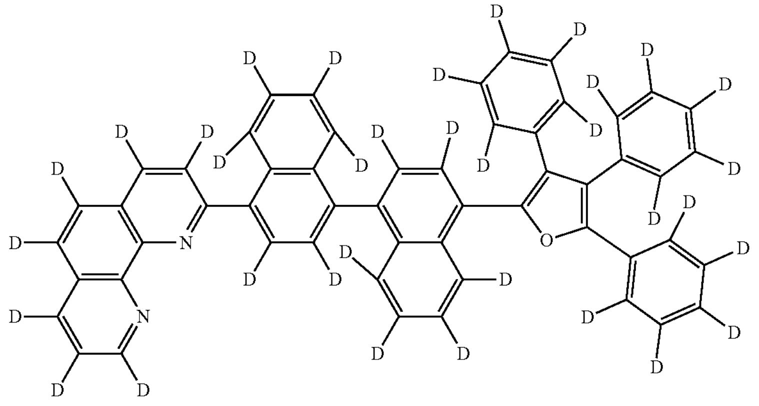
D457
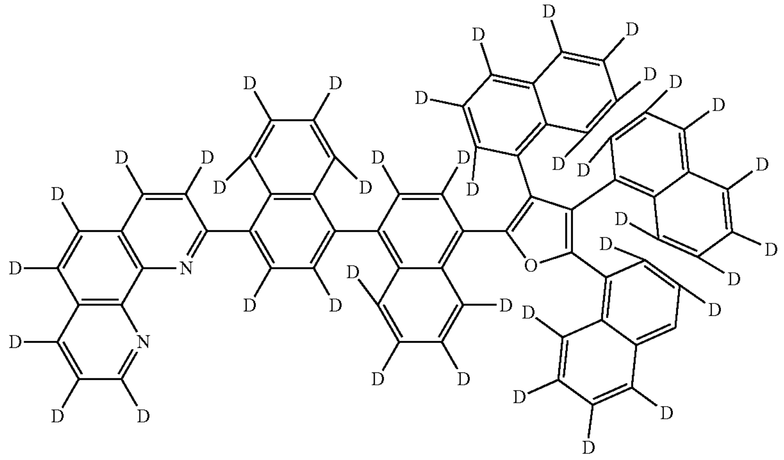

-continued
D458
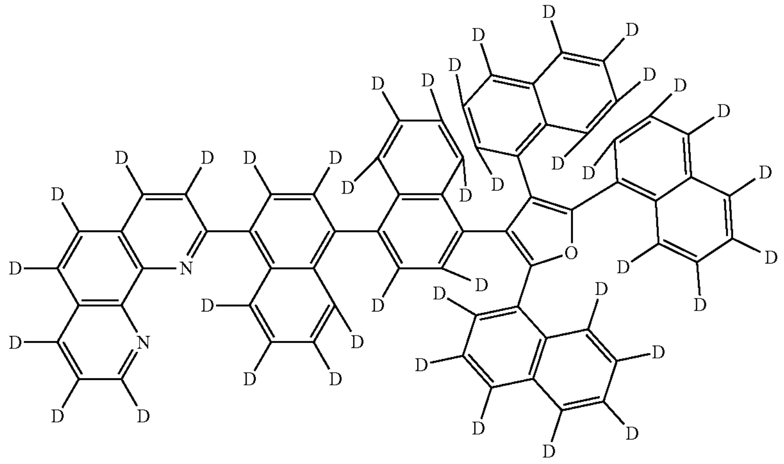
D461
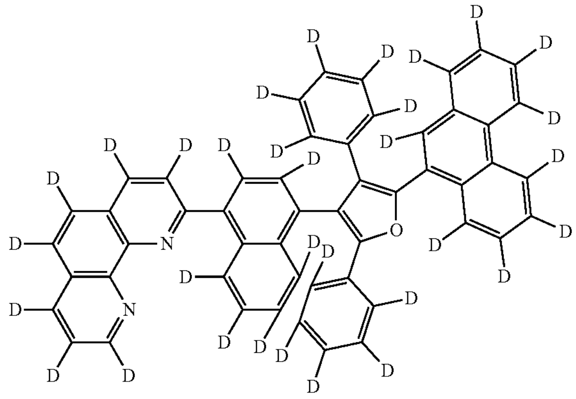
D462
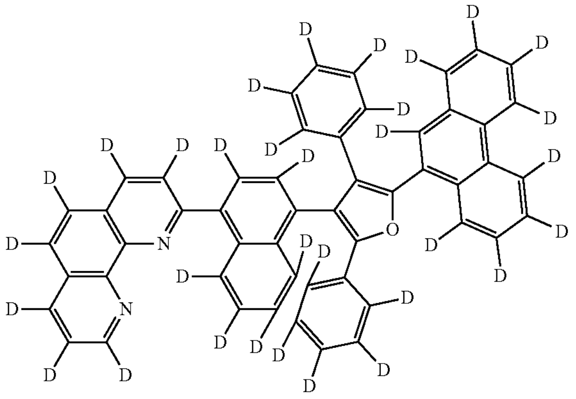
D463
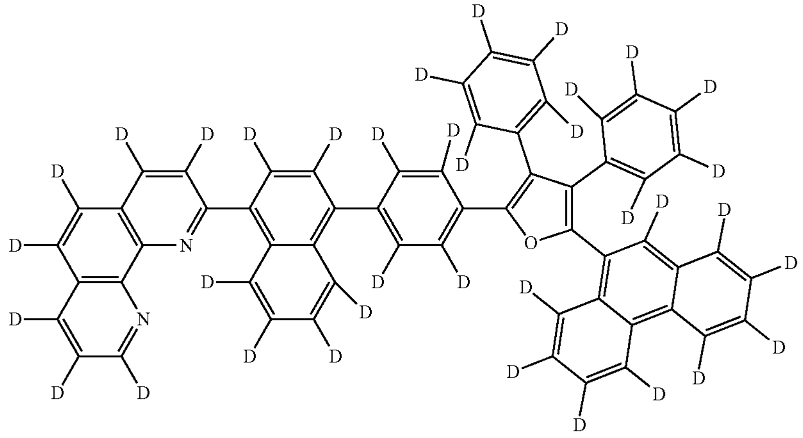

-continued
D464
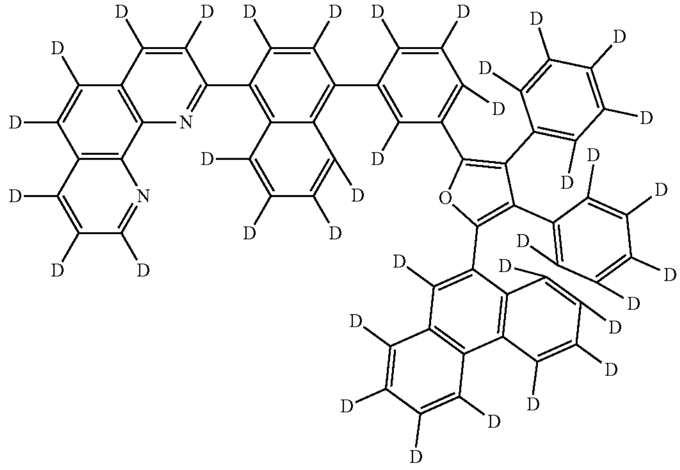
D465
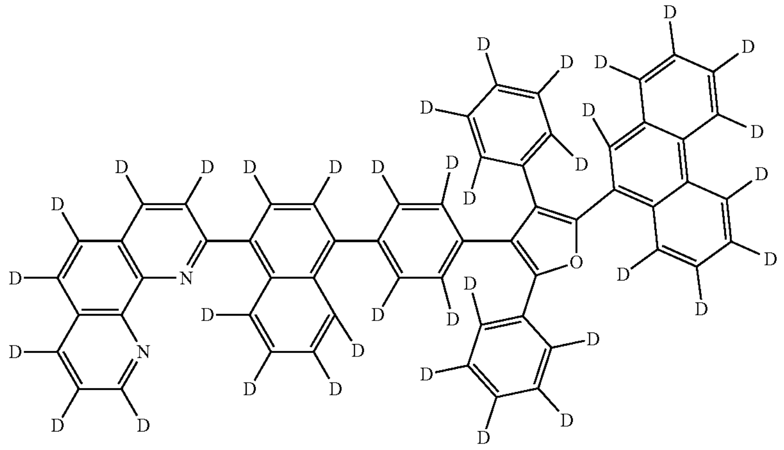
D466
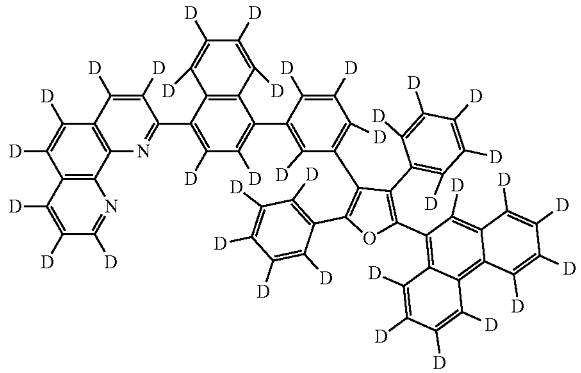
D468
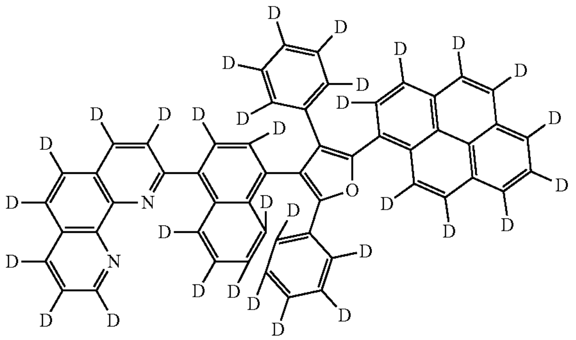

-continued
D469
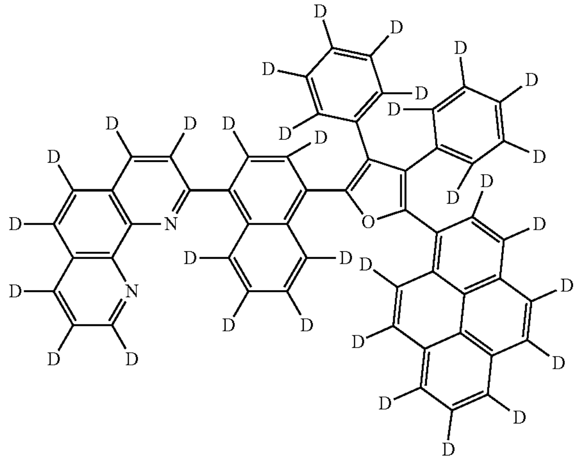
470
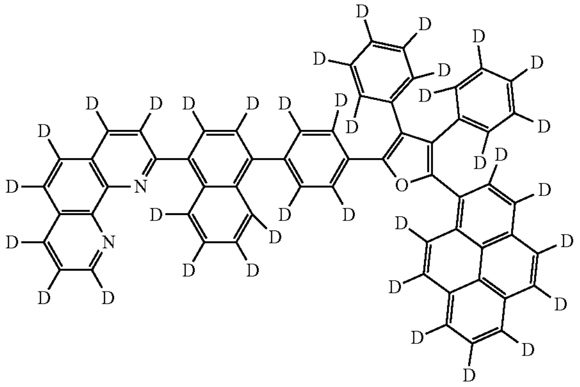
D471
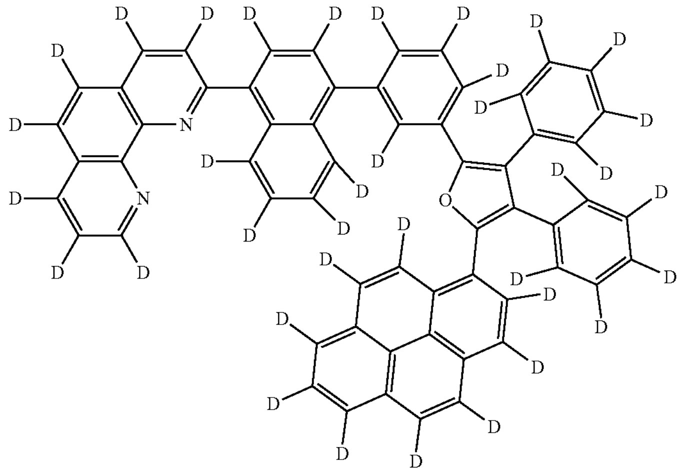
D472
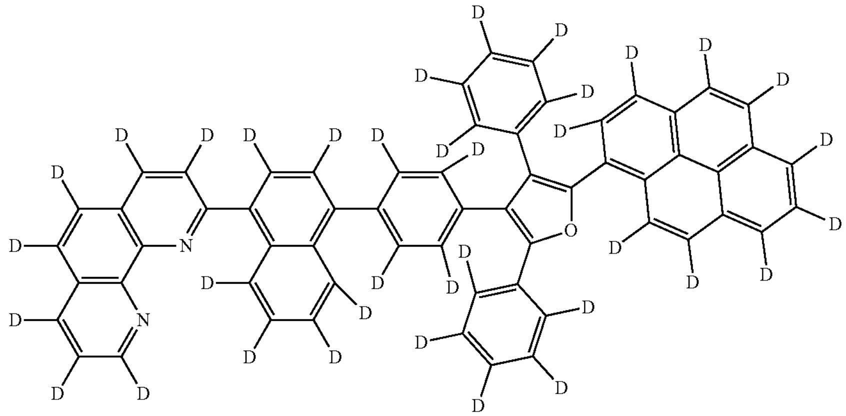

-continued
D473
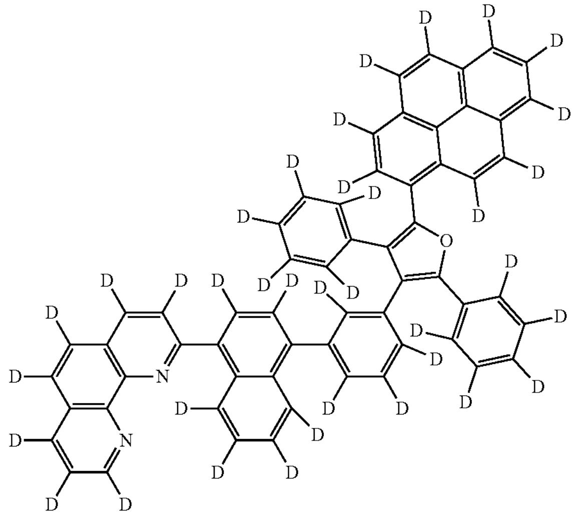
D475
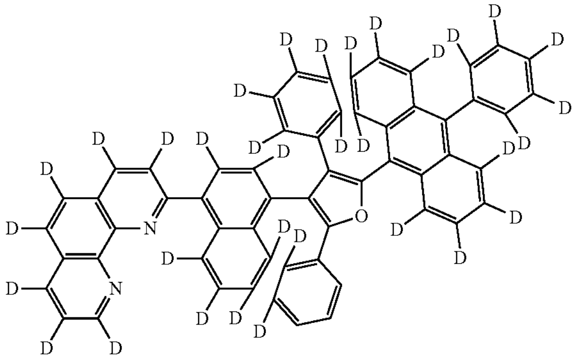
D476
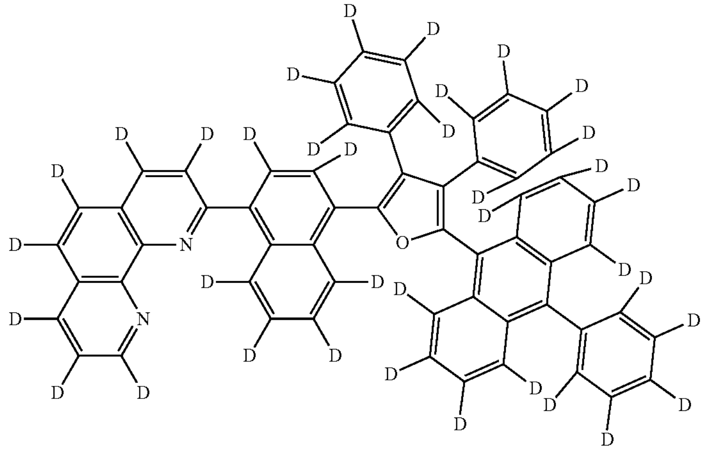
D477
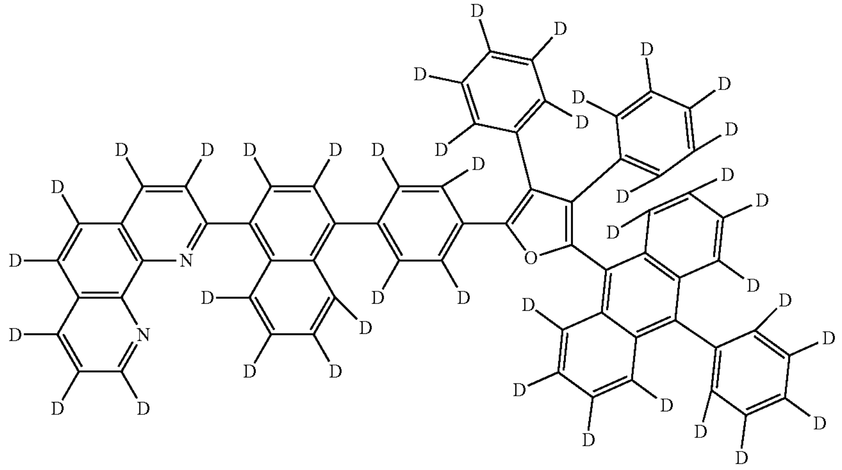

-continued
D478
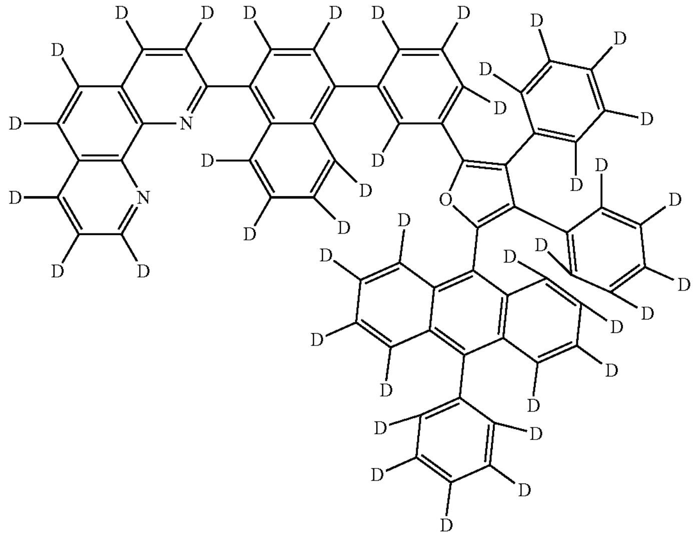
D479
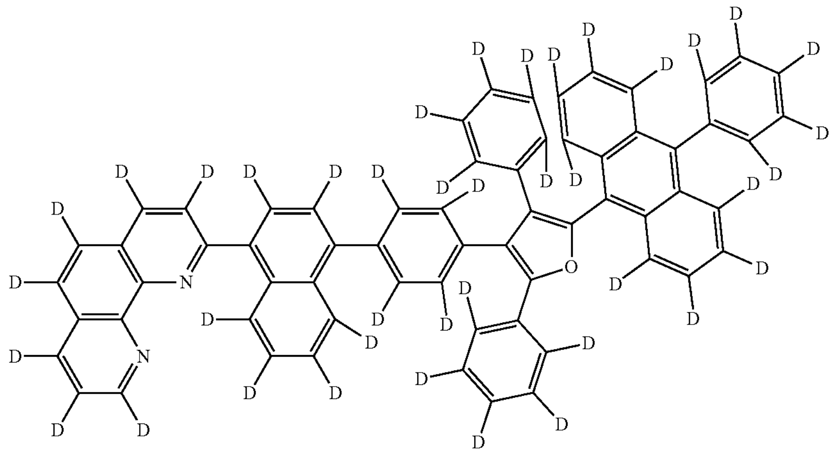
D480
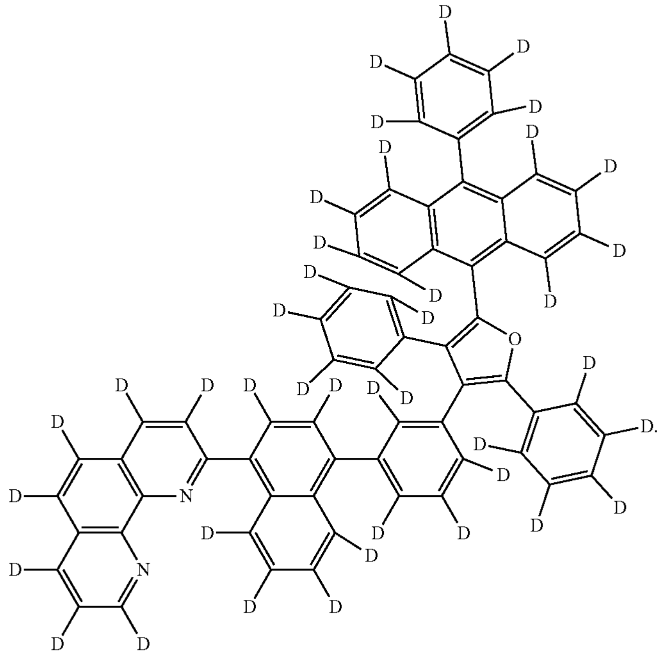

19. The organic light emitting diode according to claim 11, wherein the organic compound is one of compounds in Formula 2:
[Formula 2]
D5
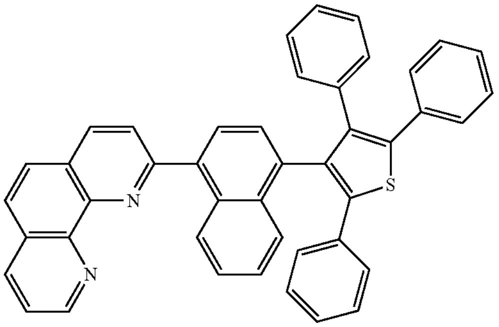
D6
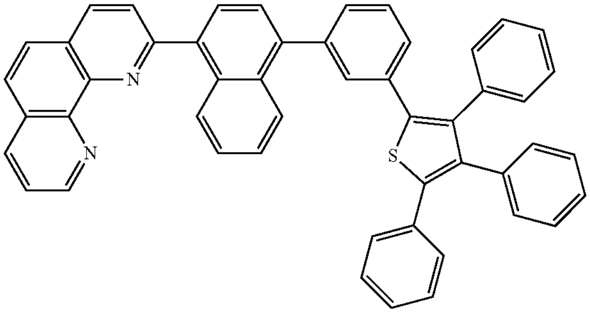
D7
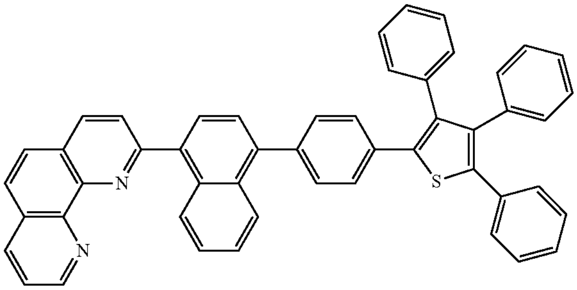
D8
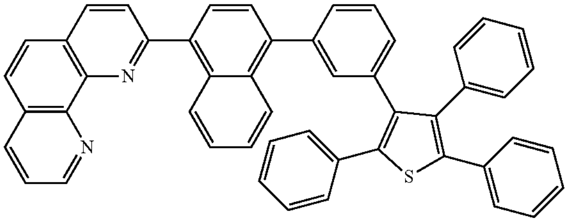
D9
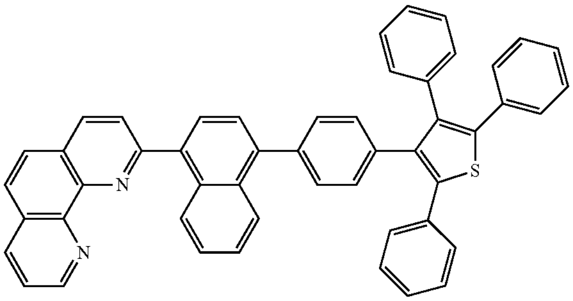
D14
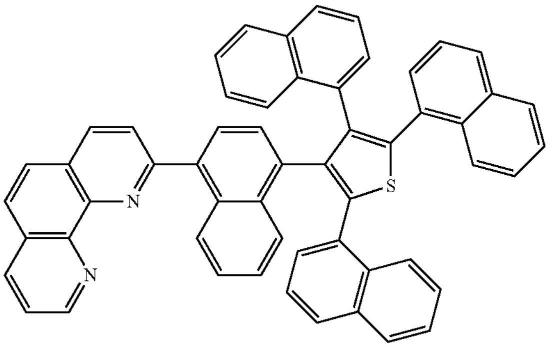
D15
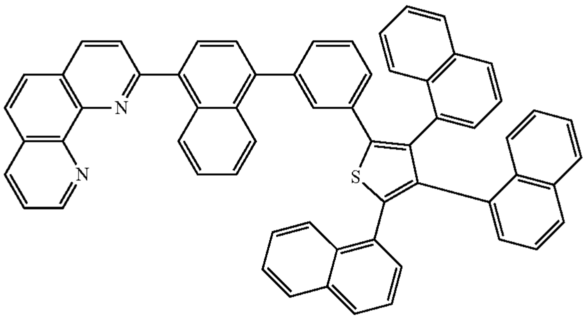
D16
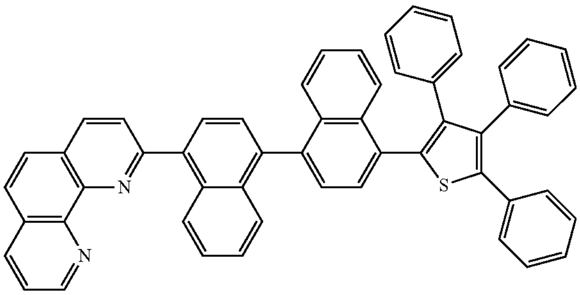

-continued
D17
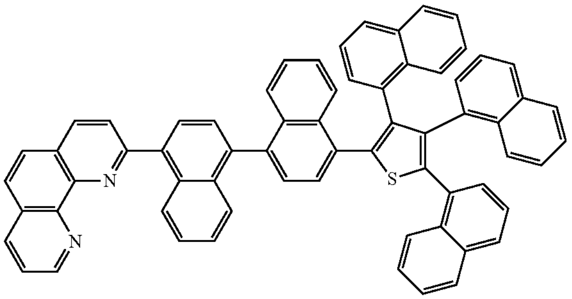
D18
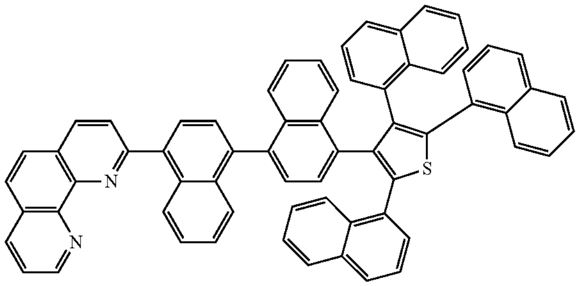
D21
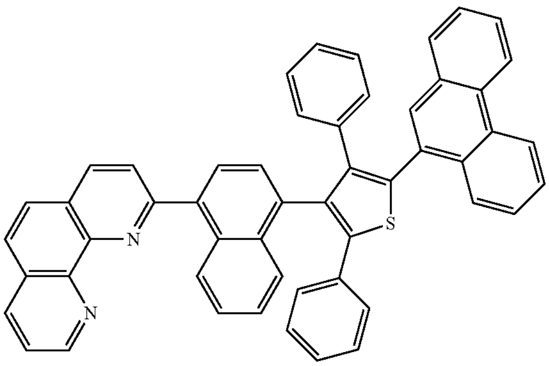
D22
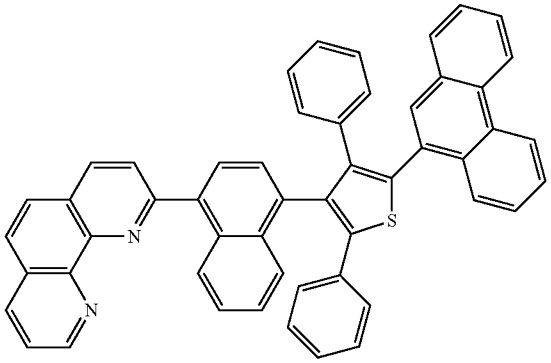
D23
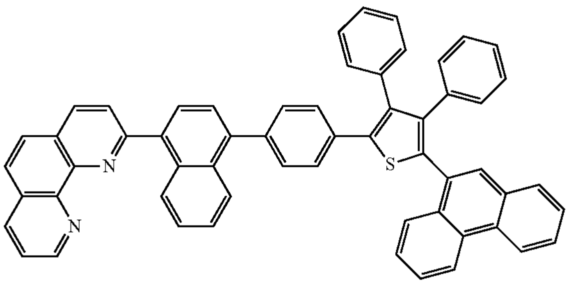
D24
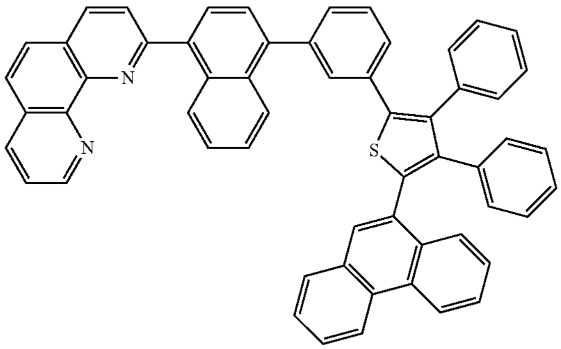
D25
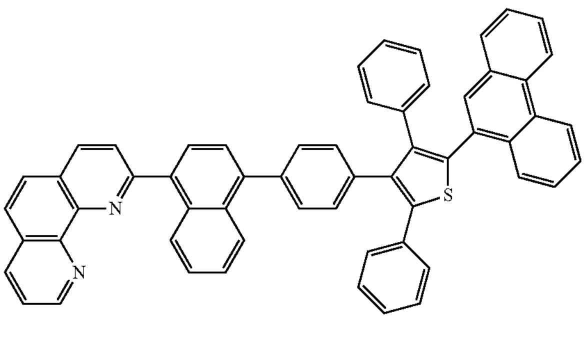
D26
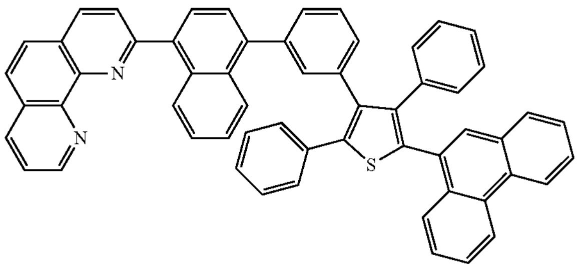

-continued
D28
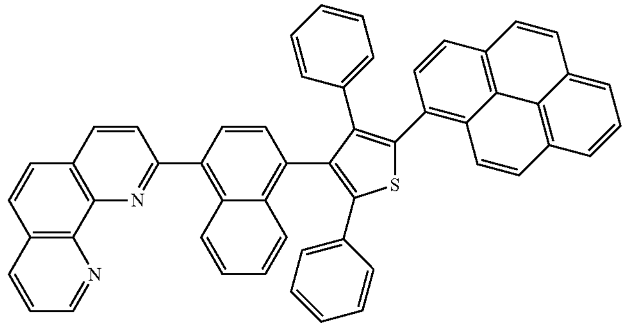
D29
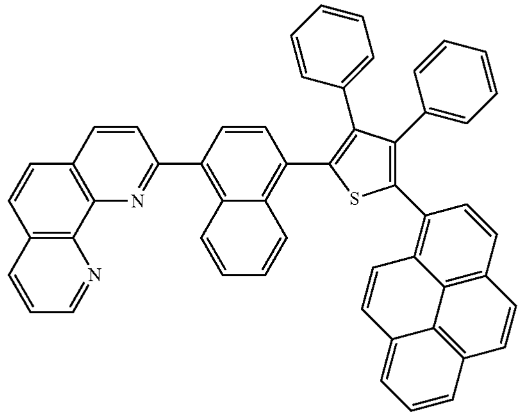
D30
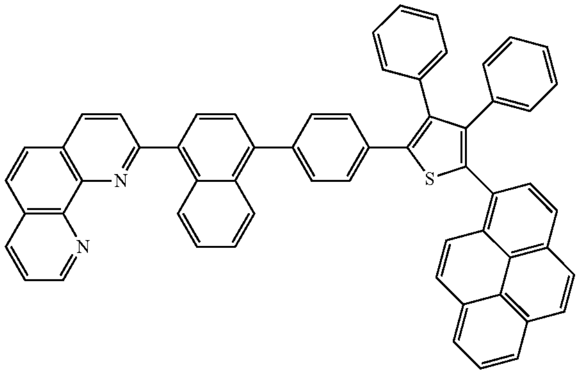
D31
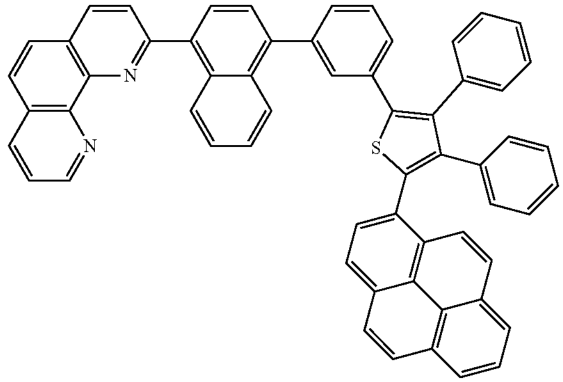
D32
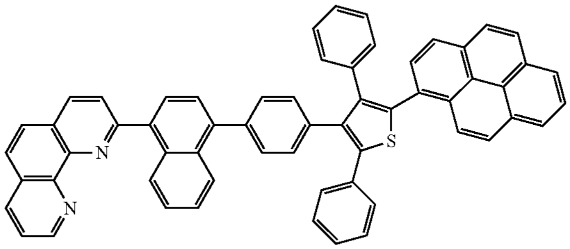
D33
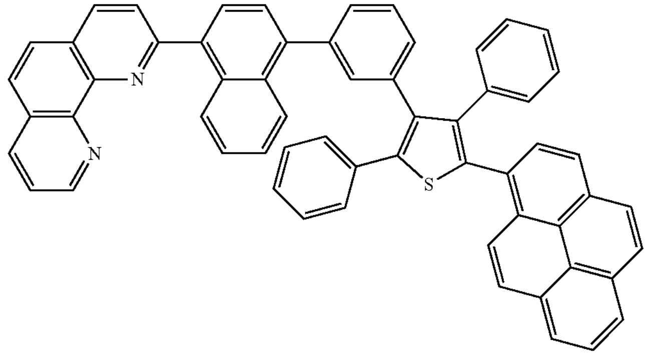

-continued
D35
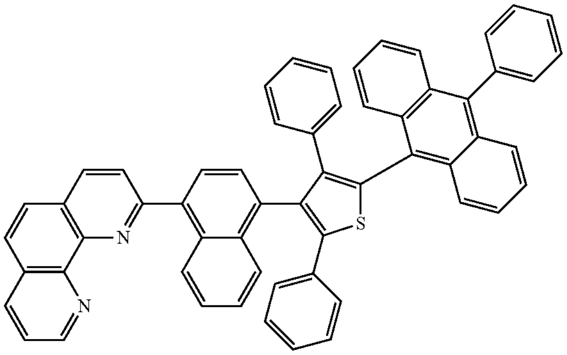
D36
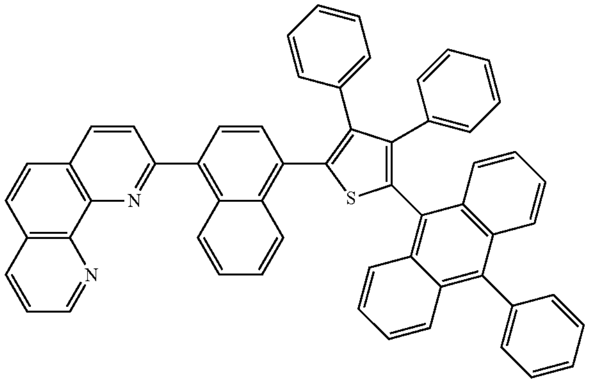
D37
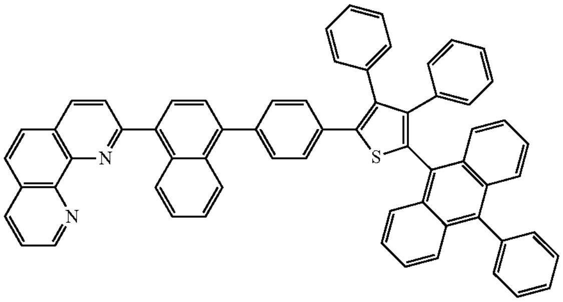
D38
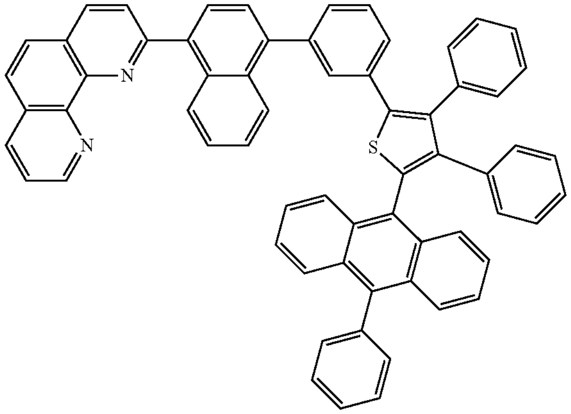
D39
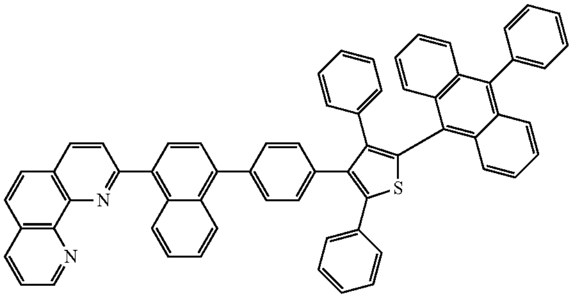
D40
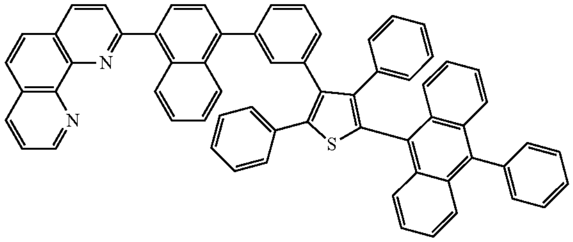
D45
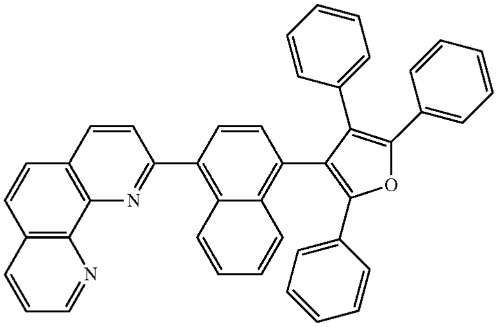
D46
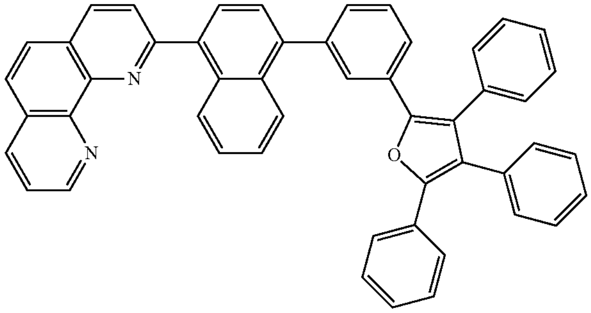

-continued
D47
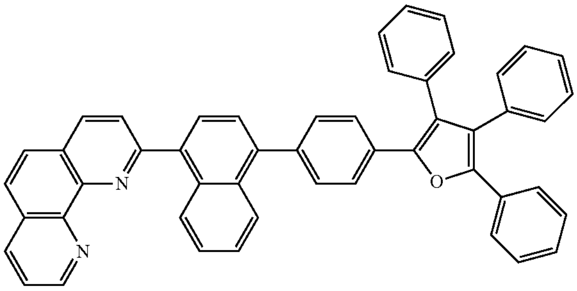
D48
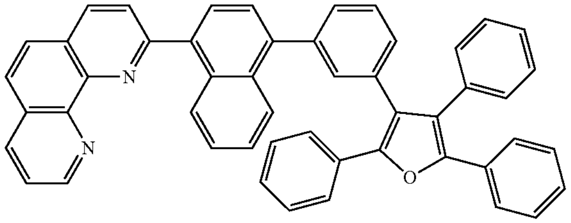
D49
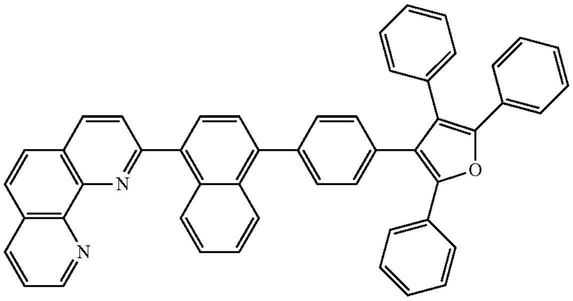
D54
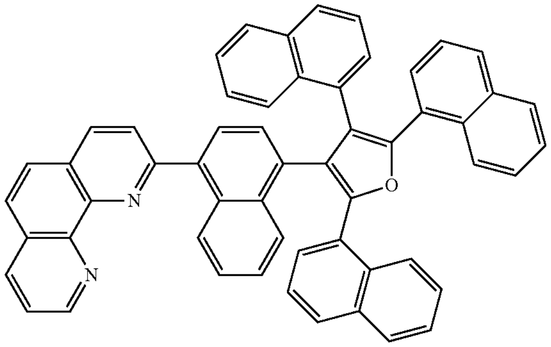
D55
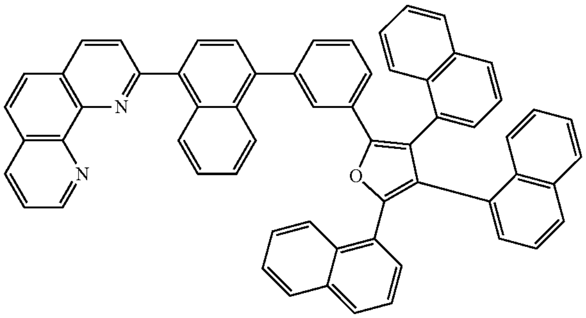
D56
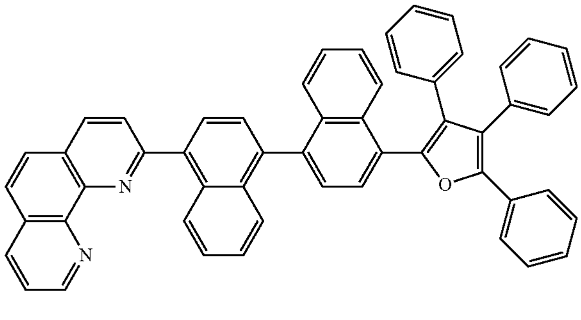
D57
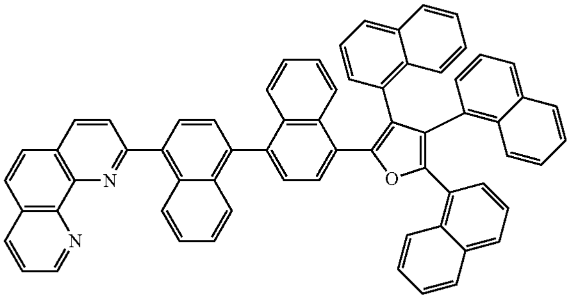
D58
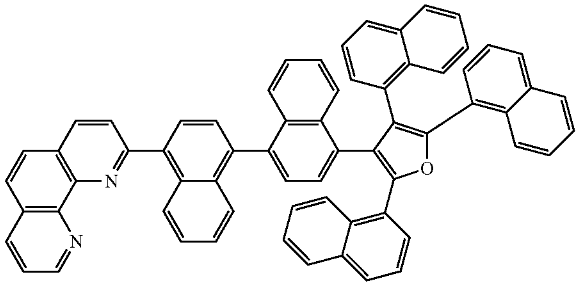

-continued
D61
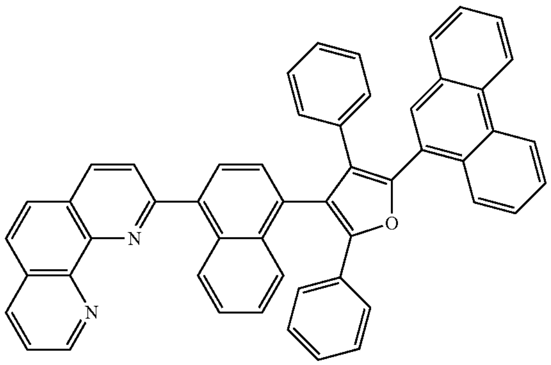
D62
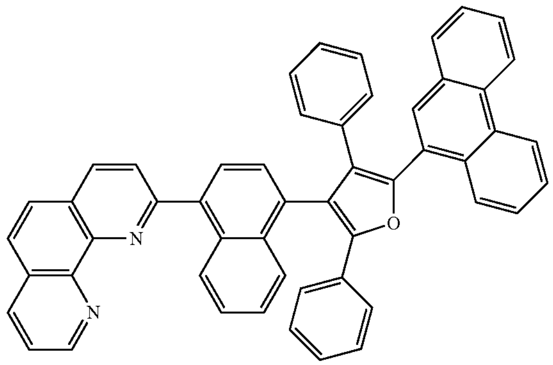
D63
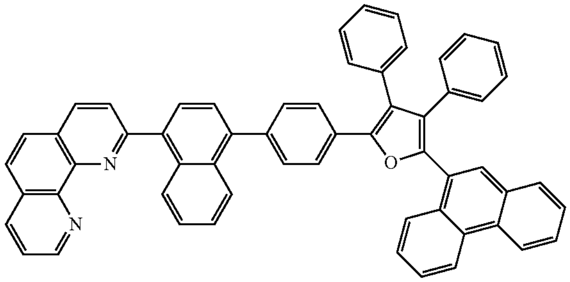
D64
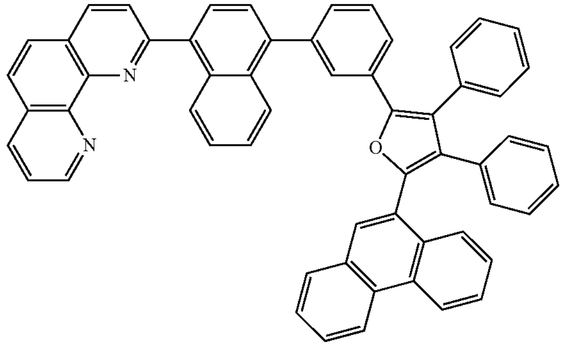
D65
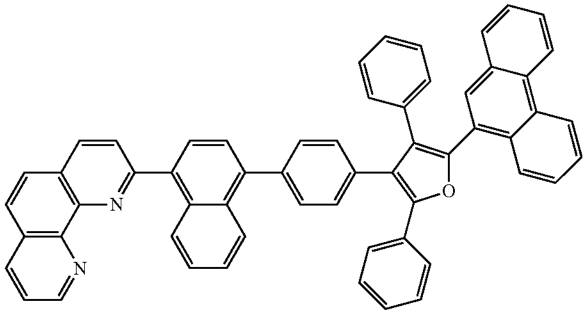
D66
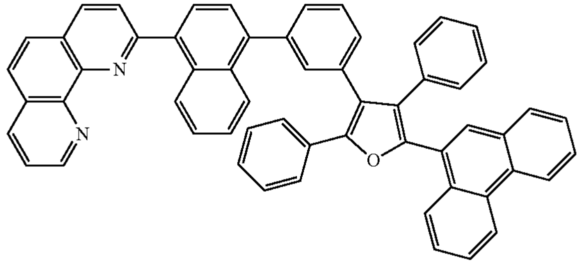
D68
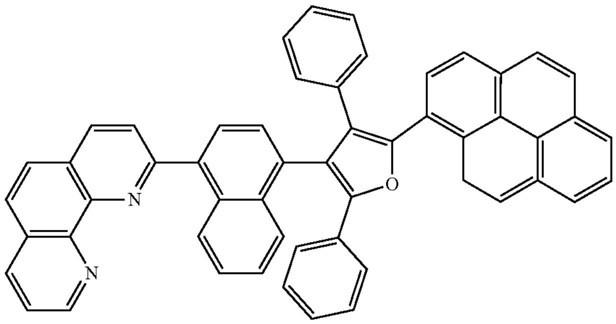
D69
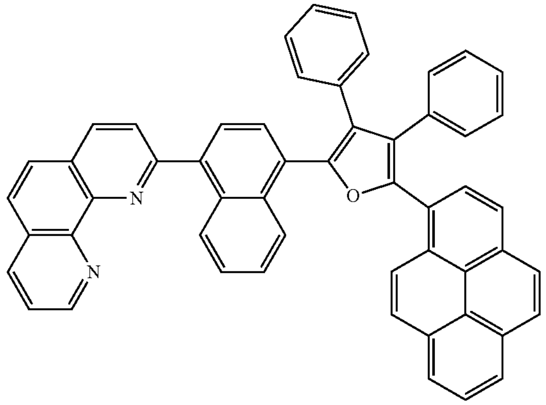

-continued
D70
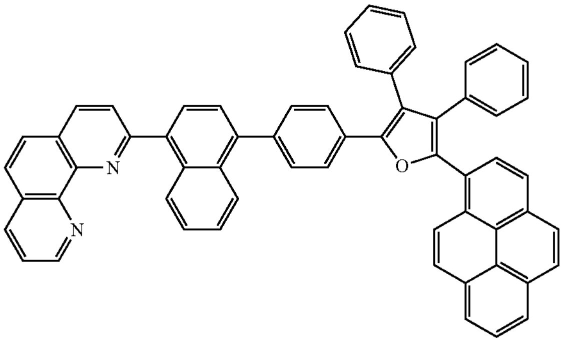
D71
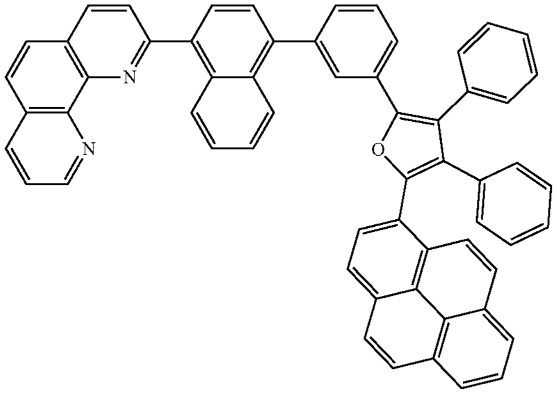
D72
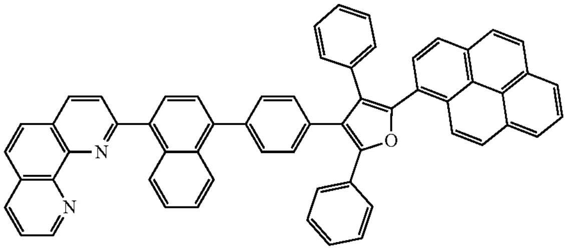
D73
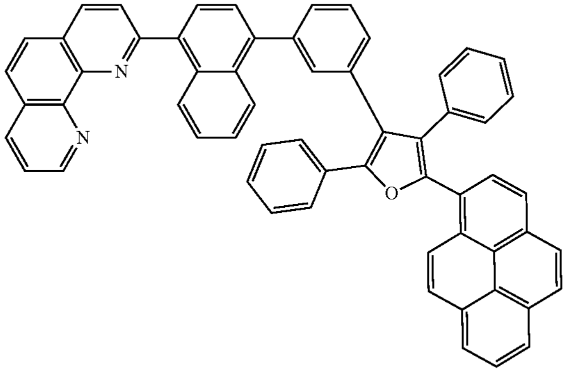
D75
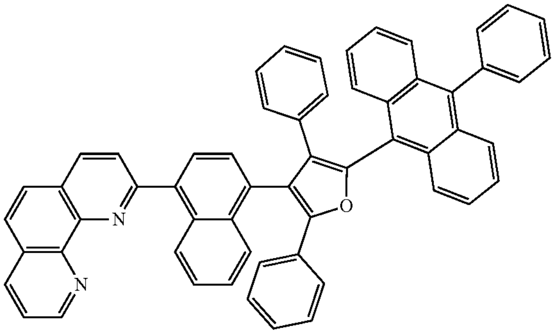
D76
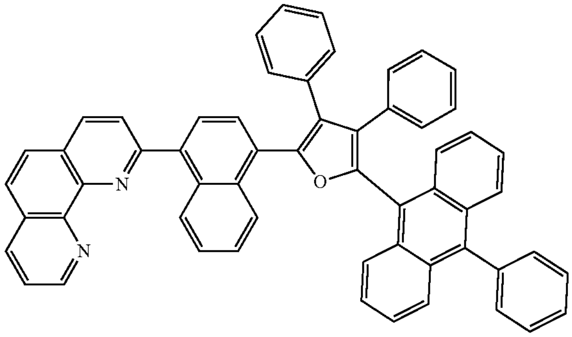

-continued
D77
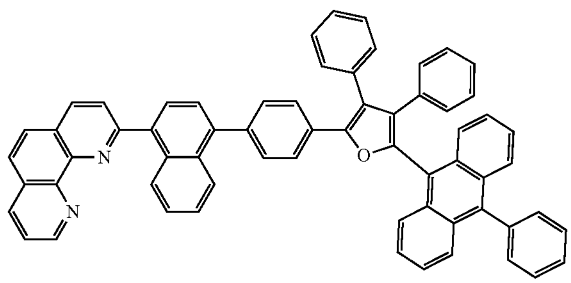
D78
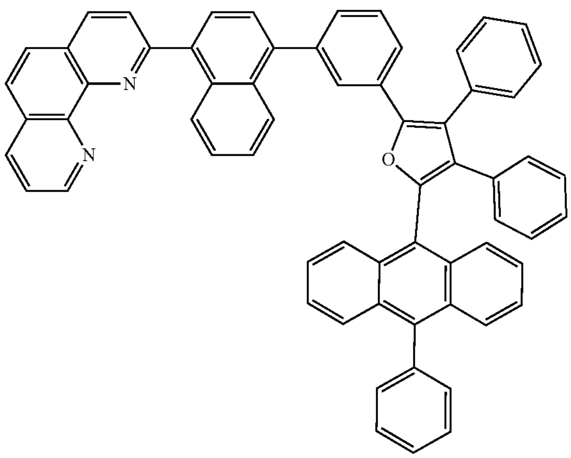
D79
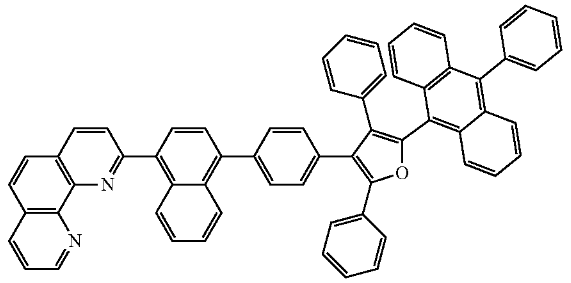
D80
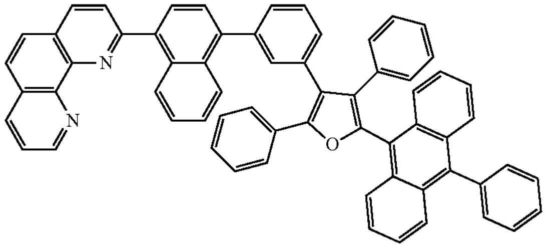
D85
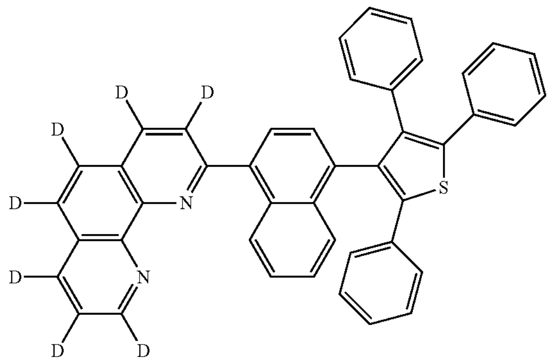
D86
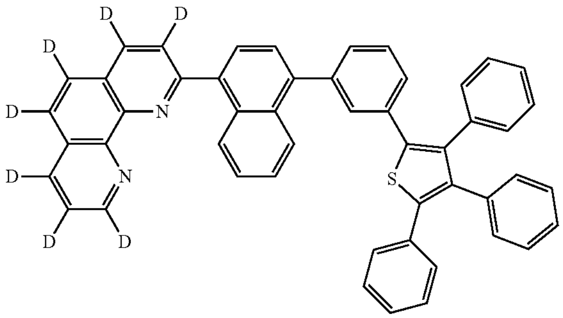
D87
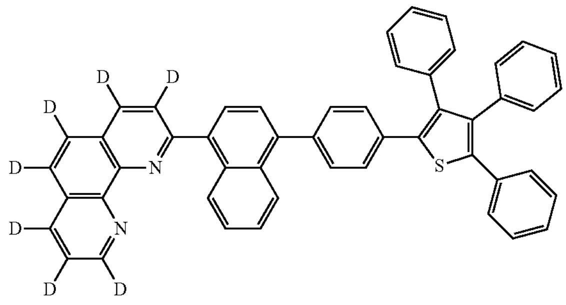
D88
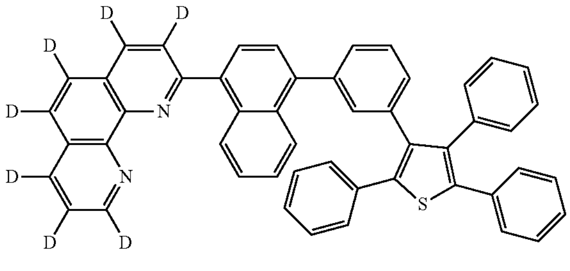

-continued
D89
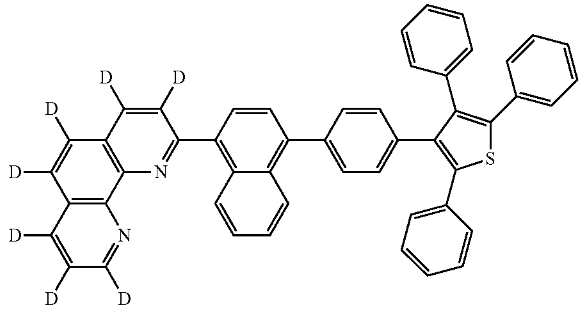
D94
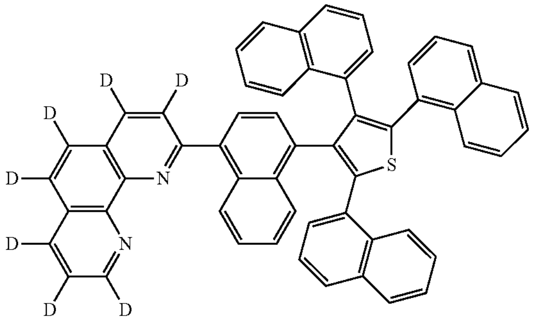
D95
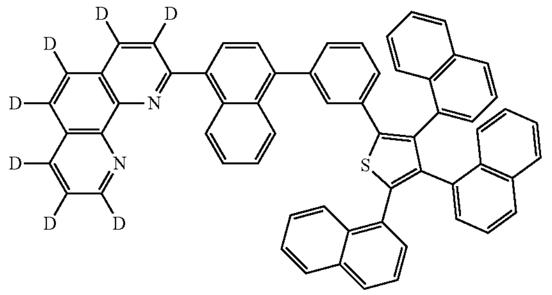
D96
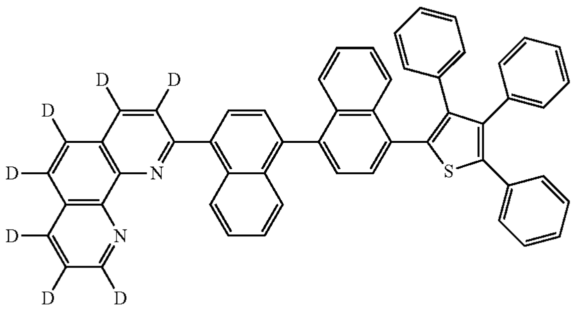
D97
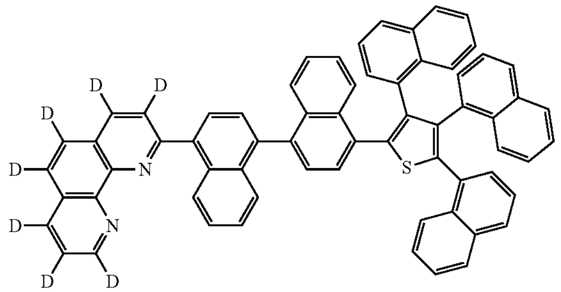
D98
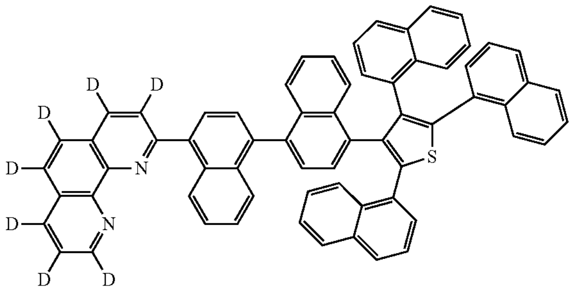
D101
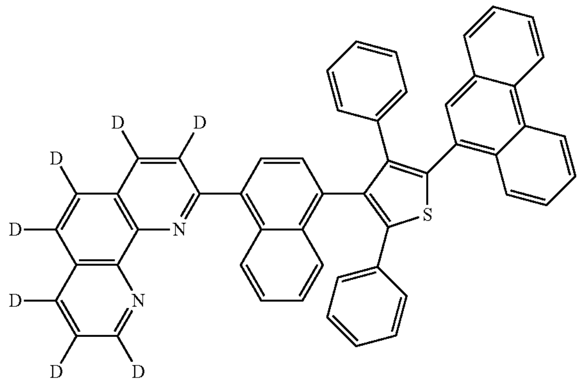
D102
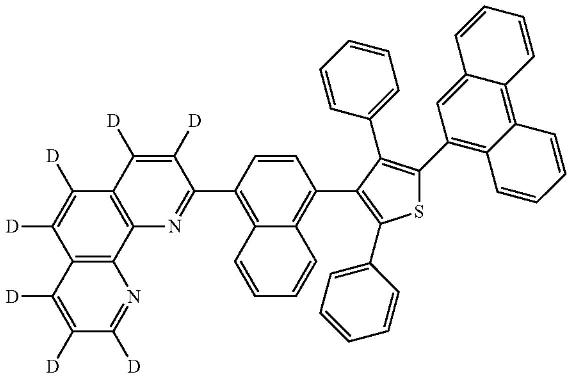

-continued
D103
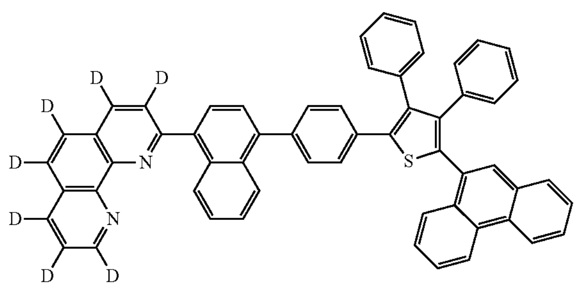
D104
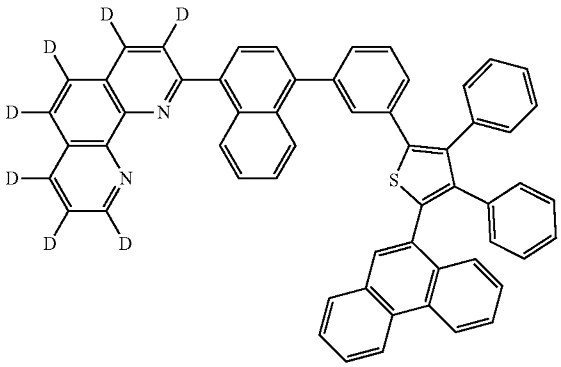
D105
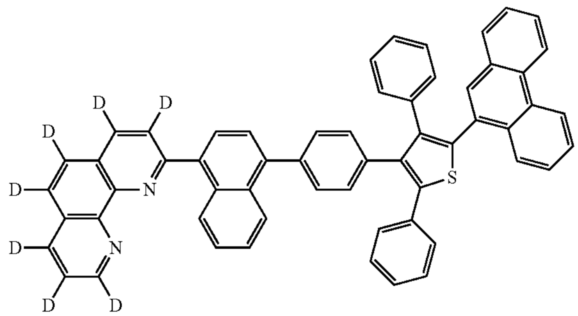
D106
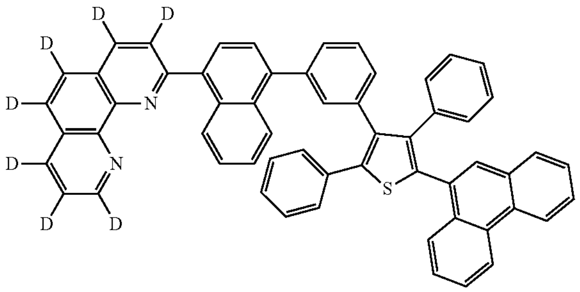
D108
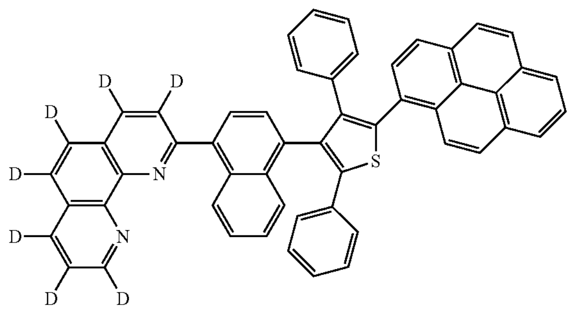
D109
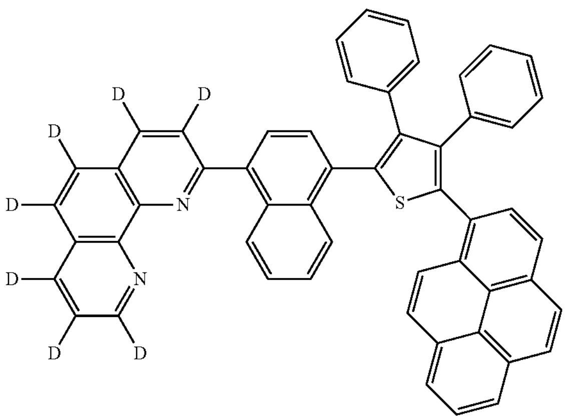
D110
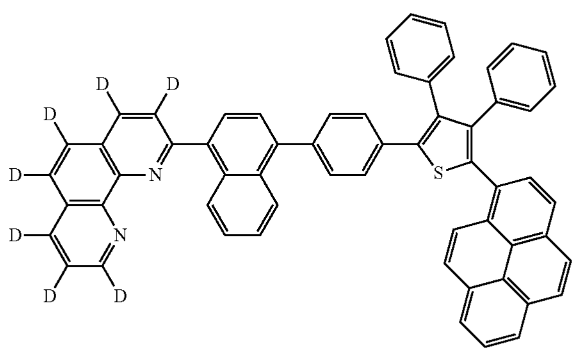
D111
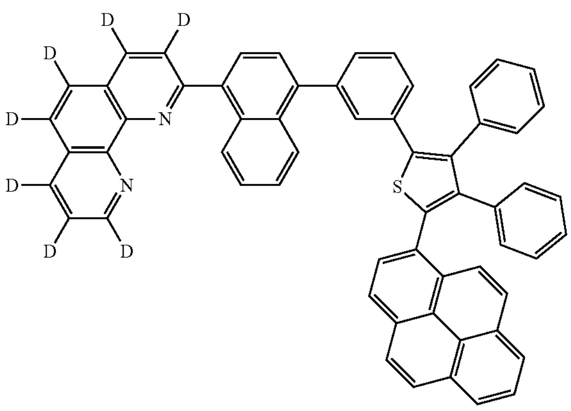

-continued
D112
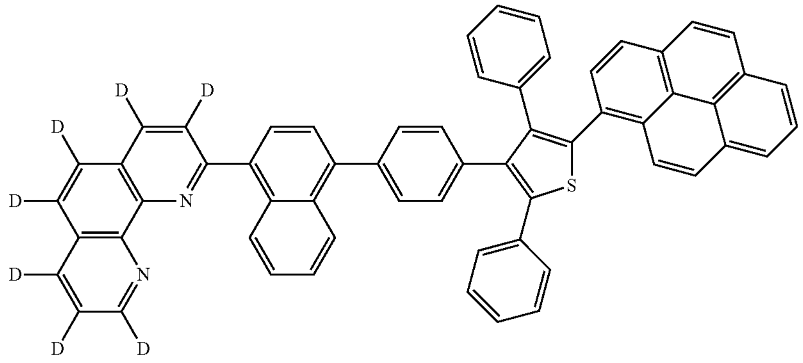
D113
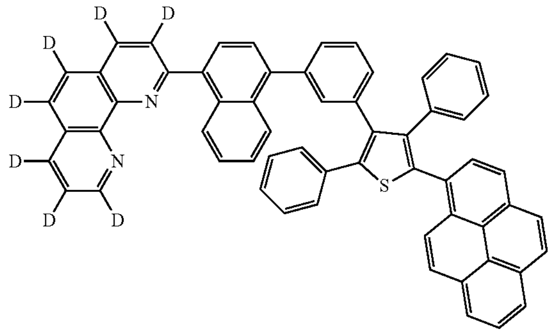
D115
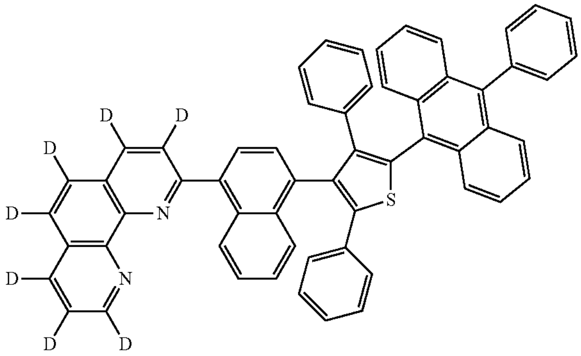
D116
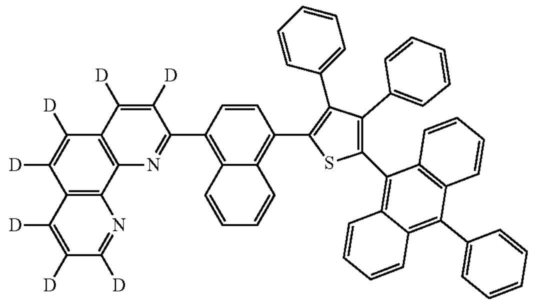
D117
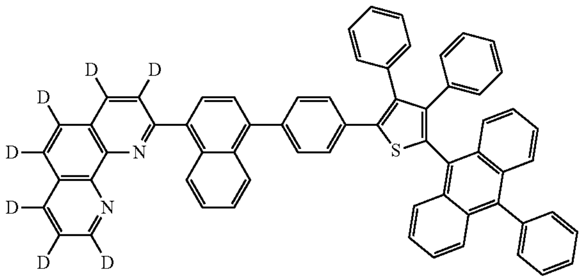
D118
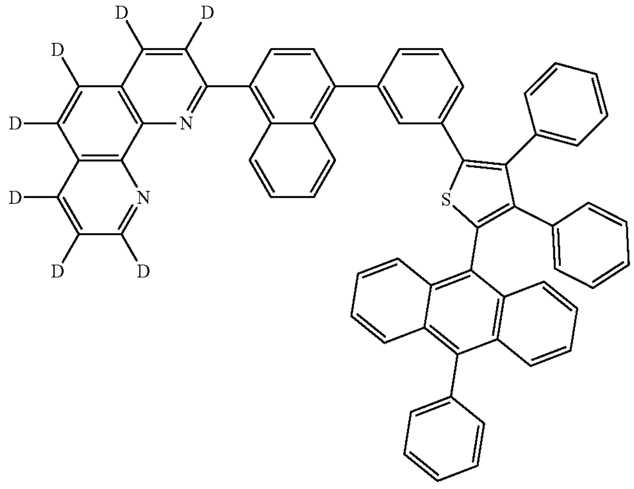

-continued
D119
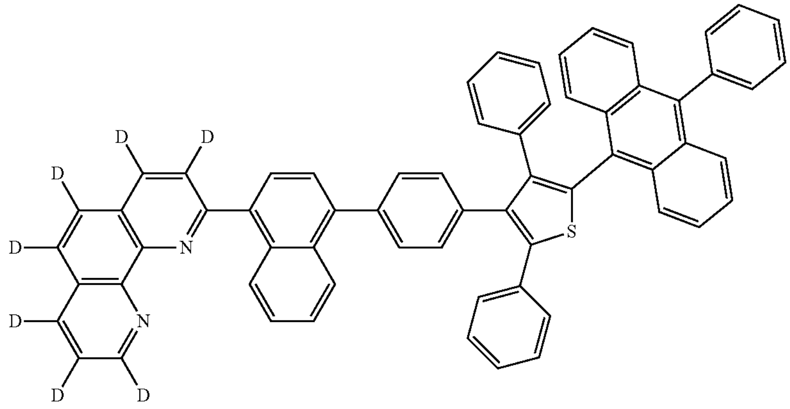
D120
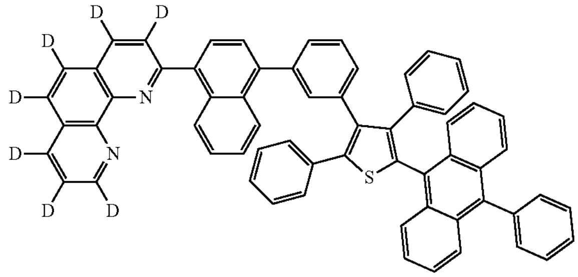
D125
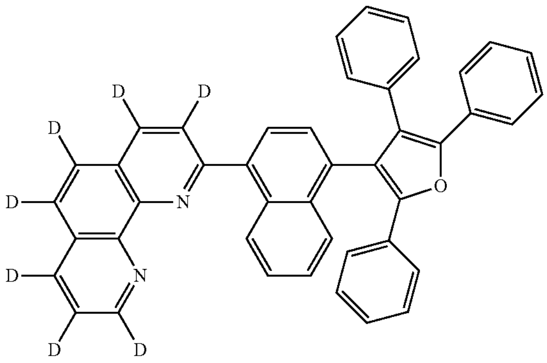
D126
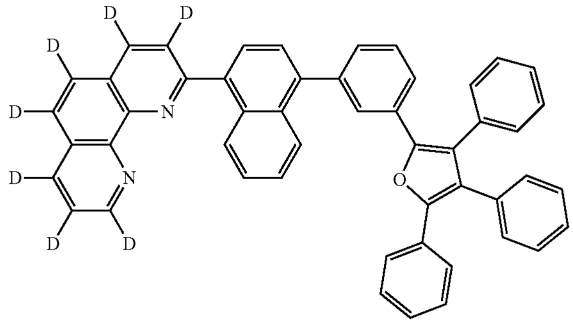
D127
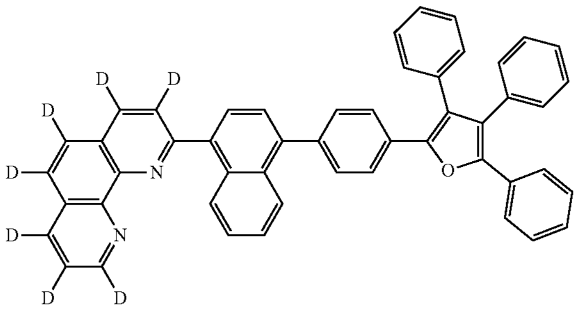
D128
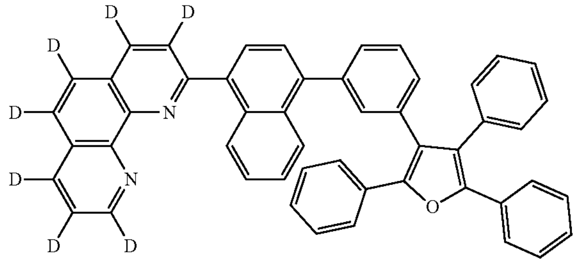
D129
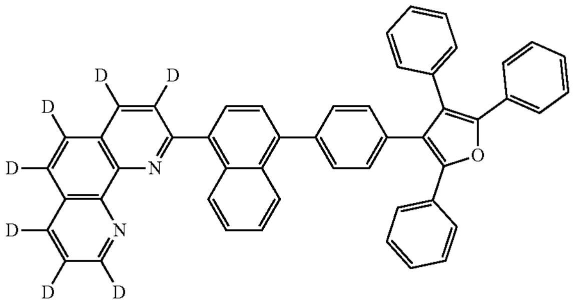

D134
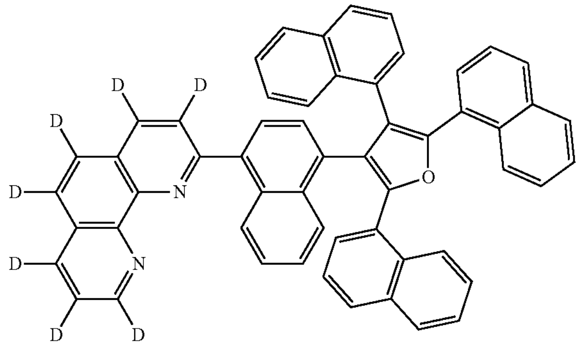
D135
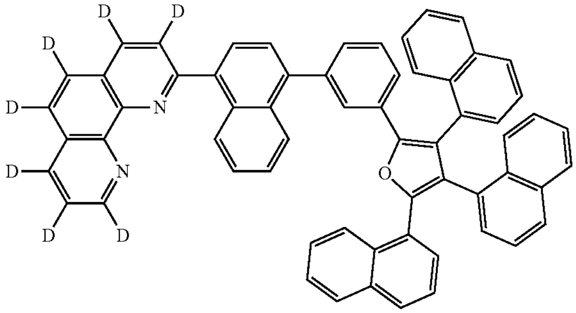
D136
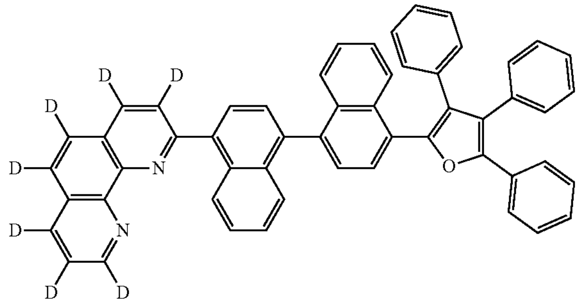
D137
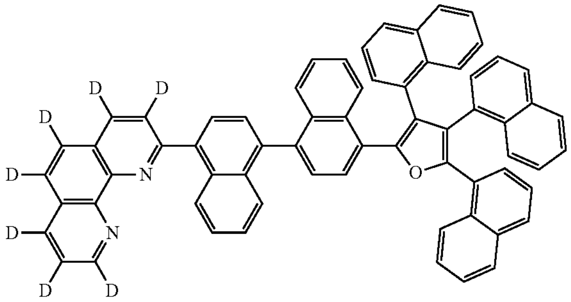
D138
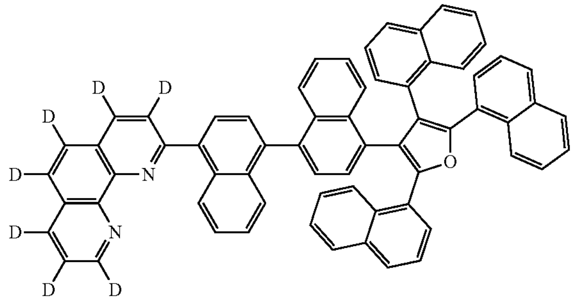
D141
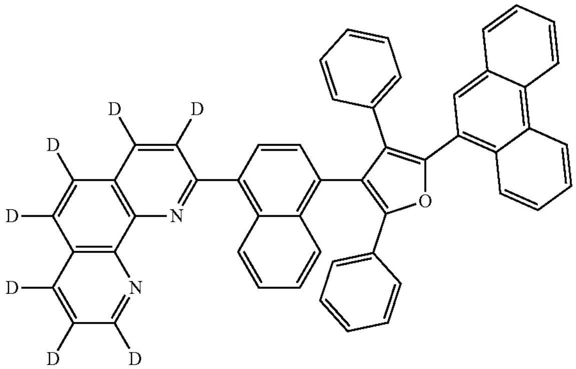
D142
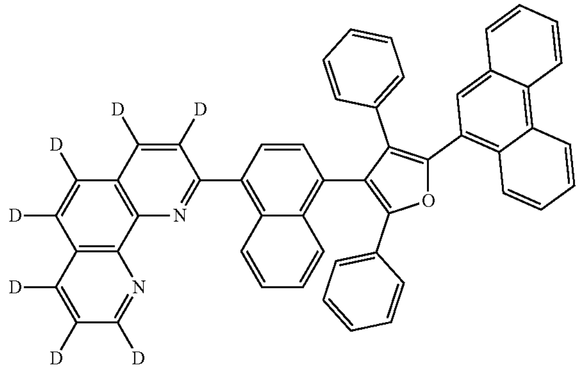
D143
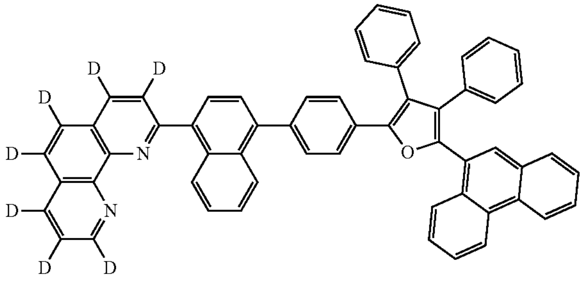

-continued
D144
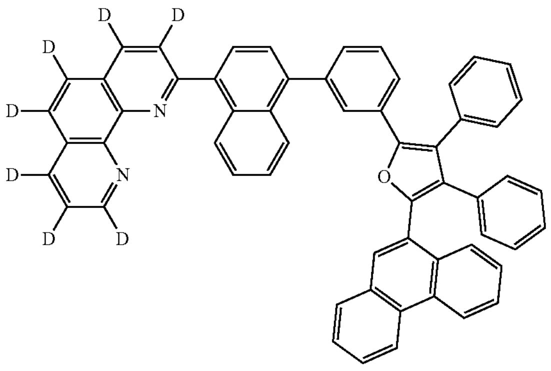
D145
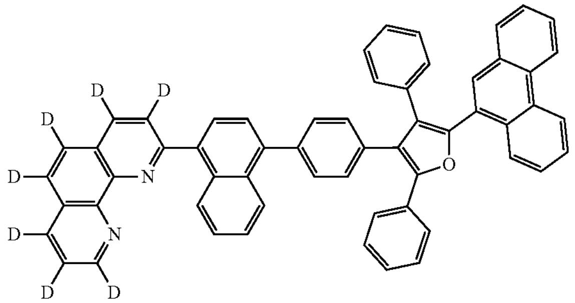
D146
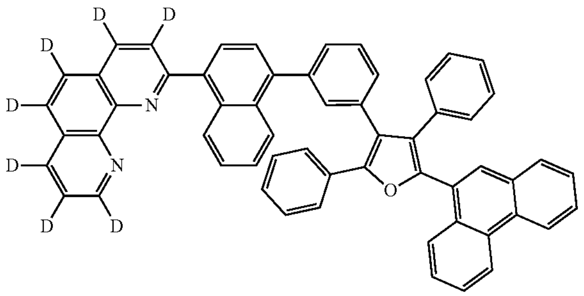
D148
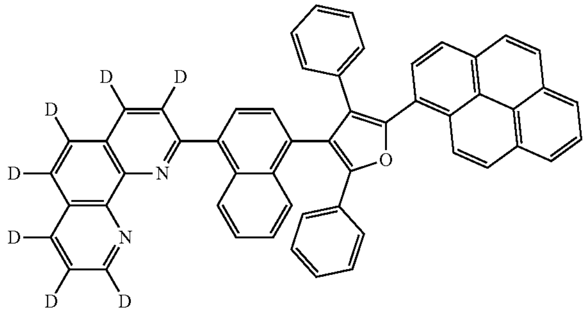
D149
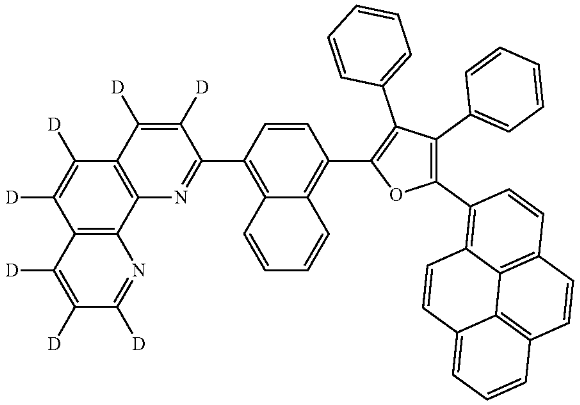
D150
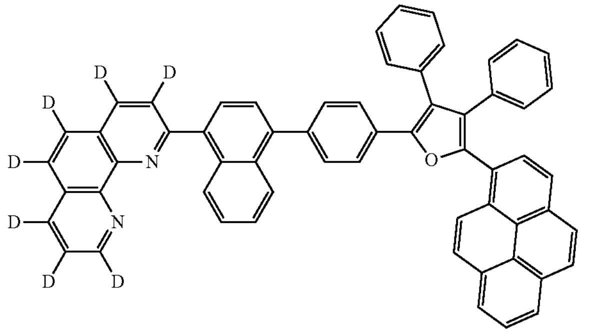
D151
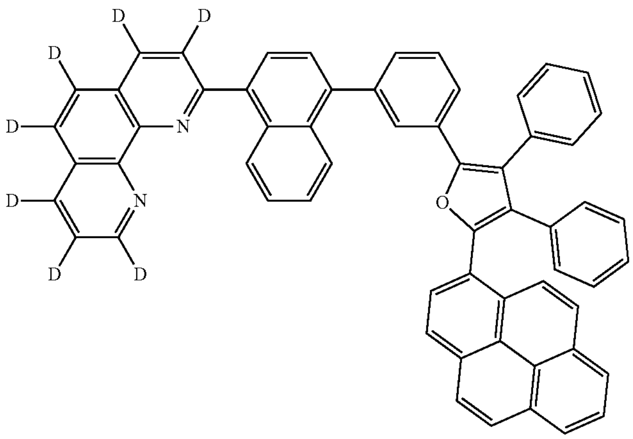

-continued
D152
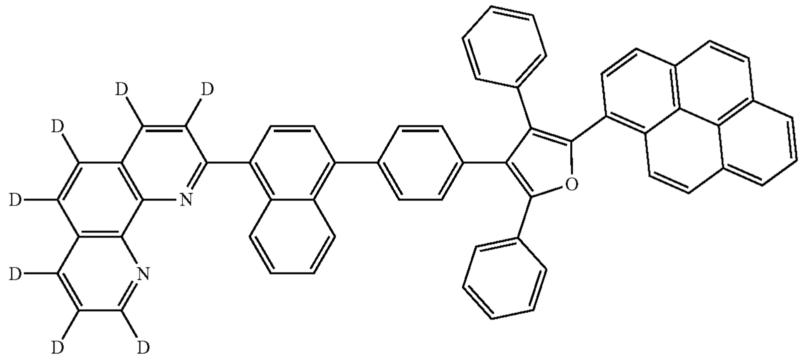
D153
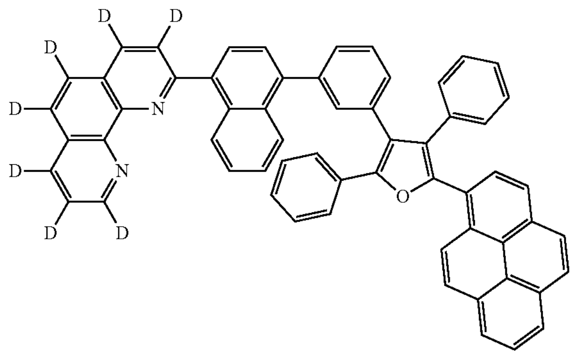
D155
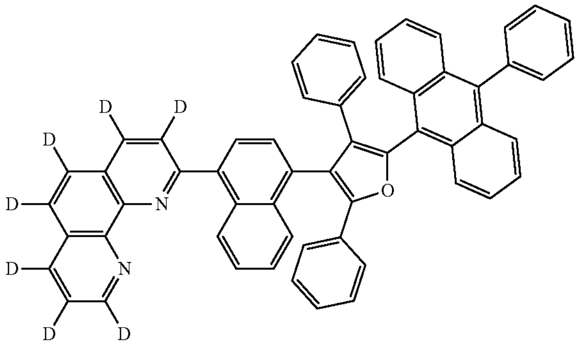
D156
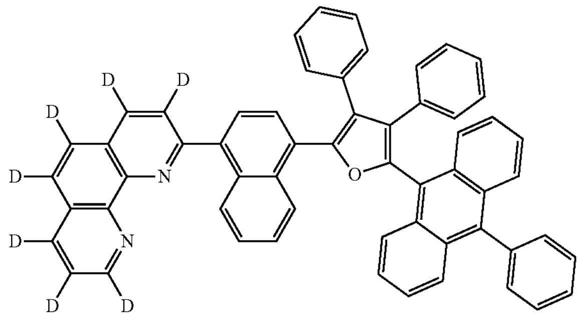
D157
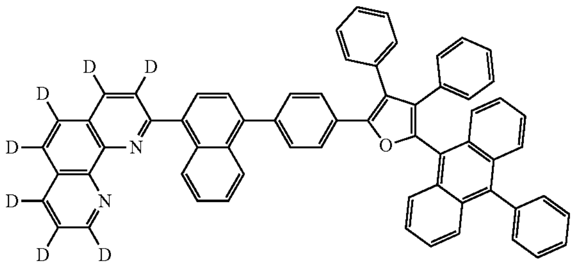
D158
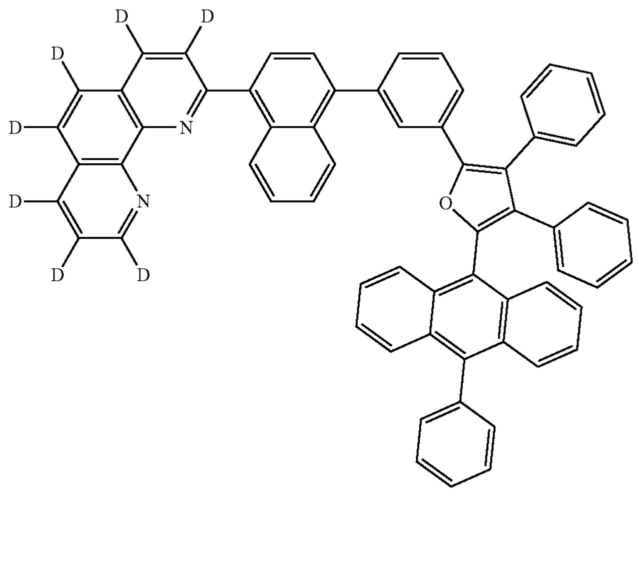

-continued
D159
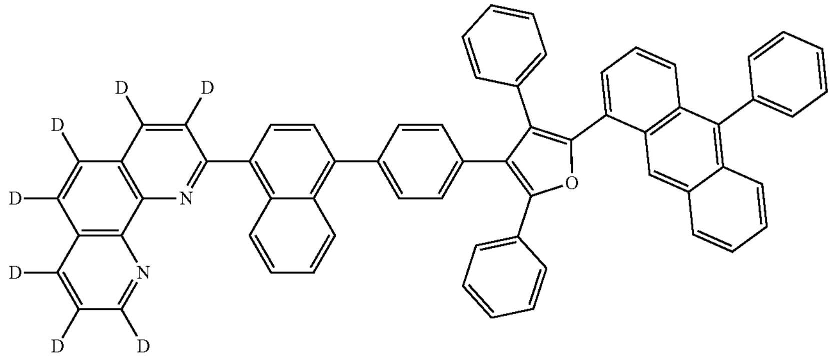
D160
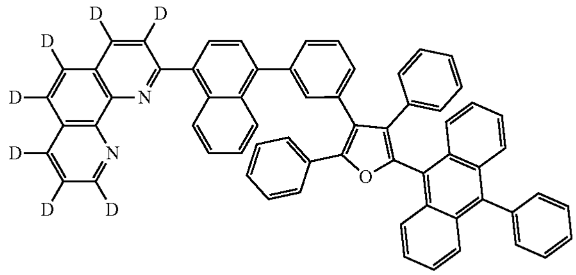
D165
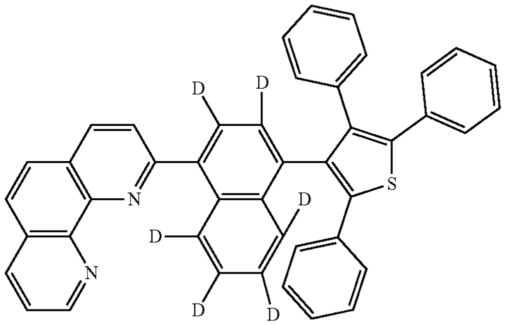
D166
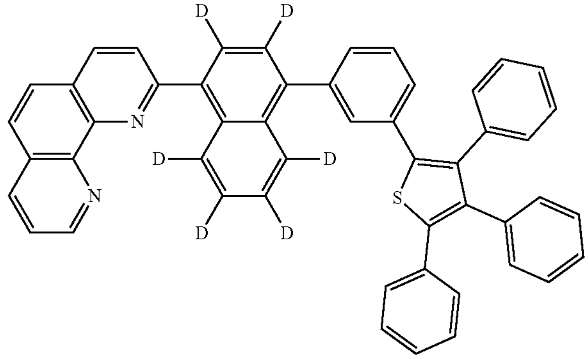
D167
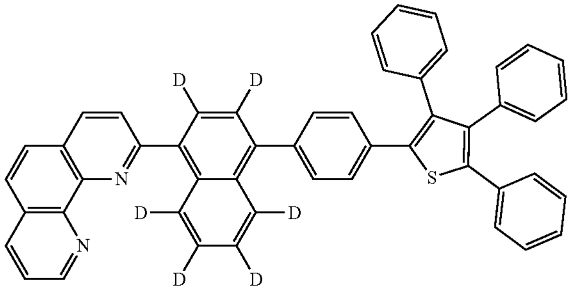
D168
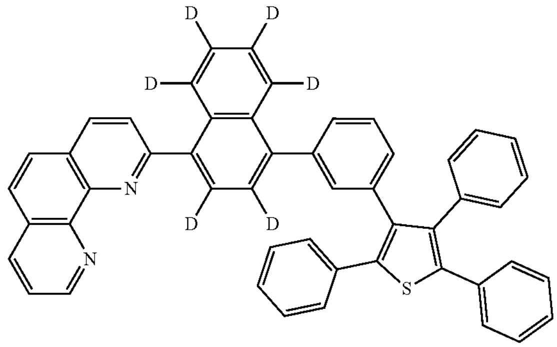
D169
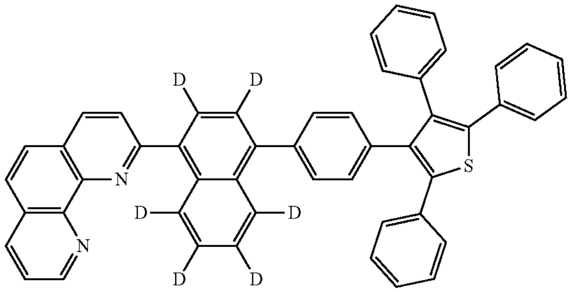

-continued
D174
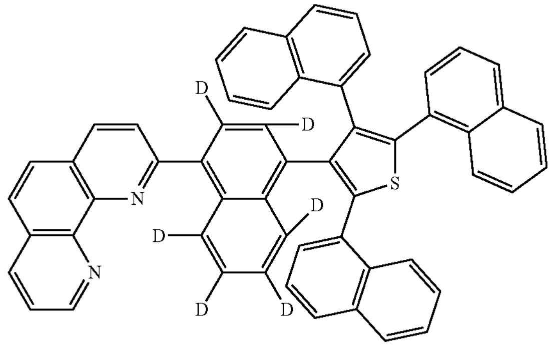
D175
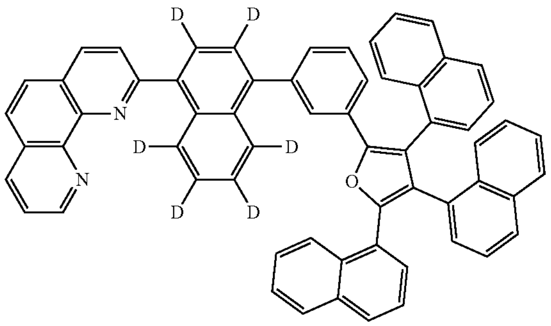
D176
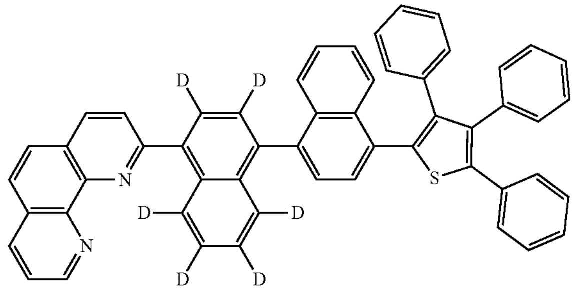
D177
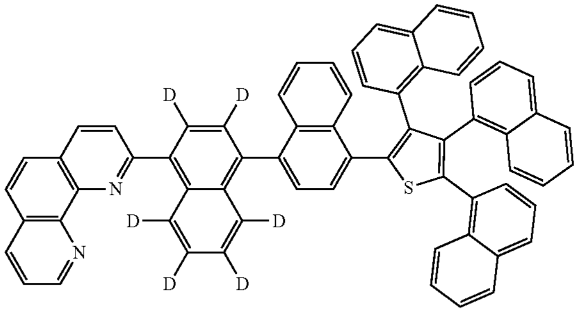
D178
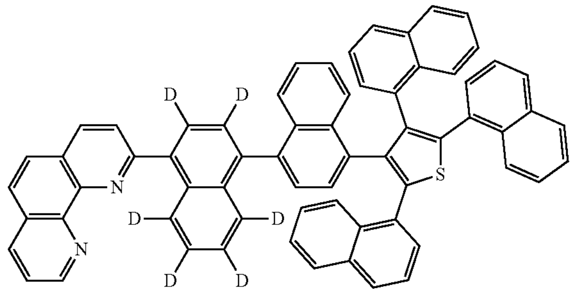
D181
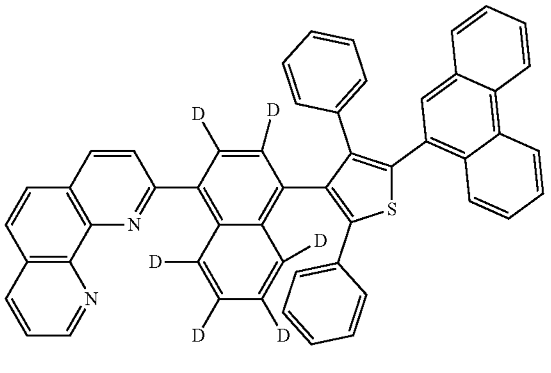
D182
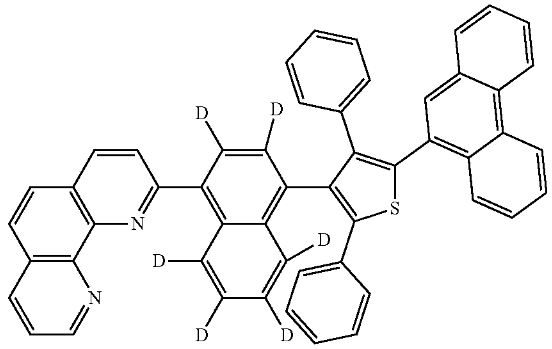
D183
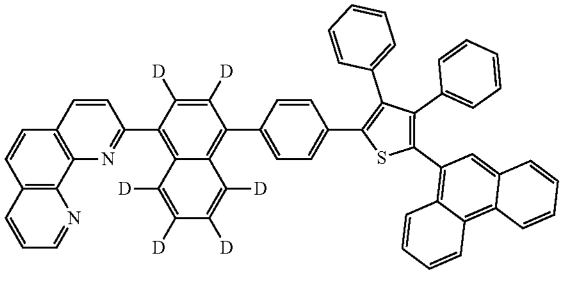

-continued
D184
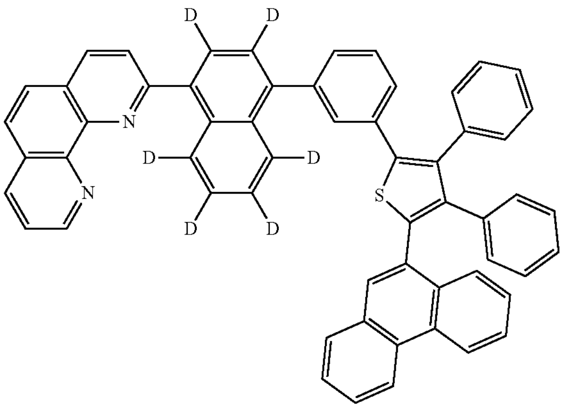
D185
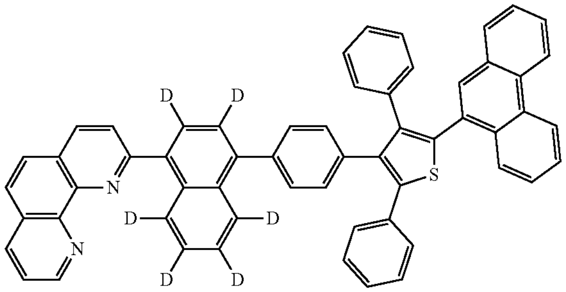
D186
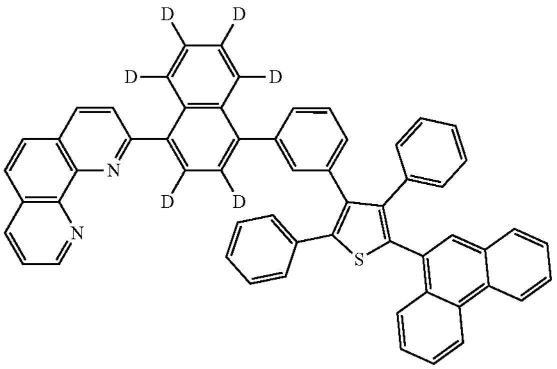
D188
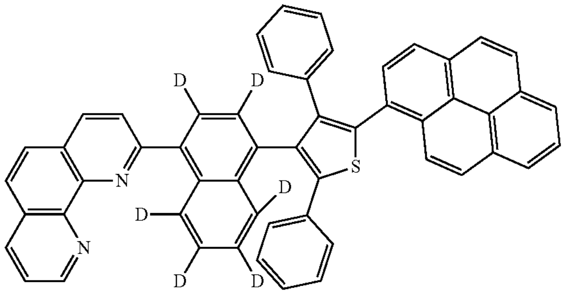
D189
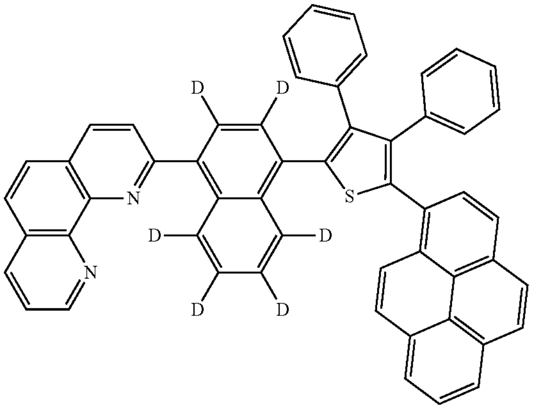
D190
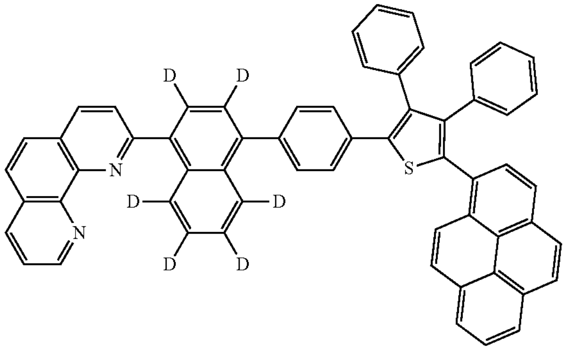

-continued
D191
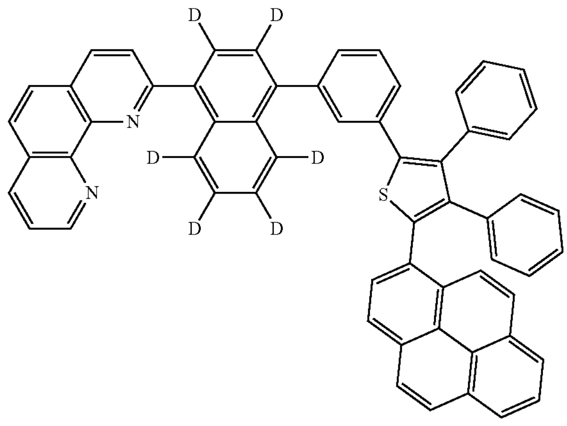
D192
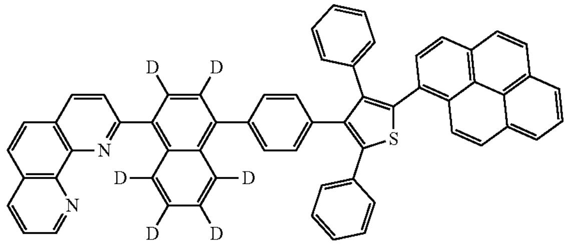
D193
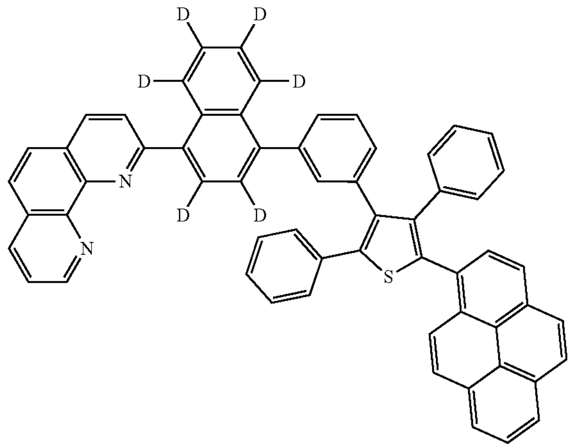
D195
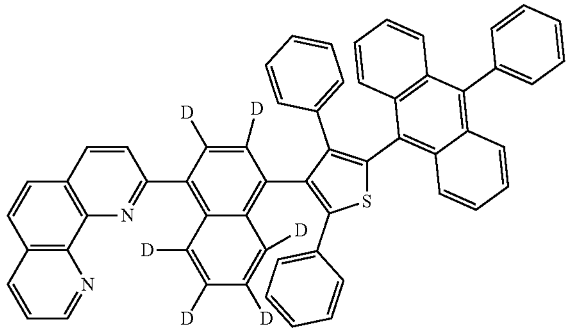
D196
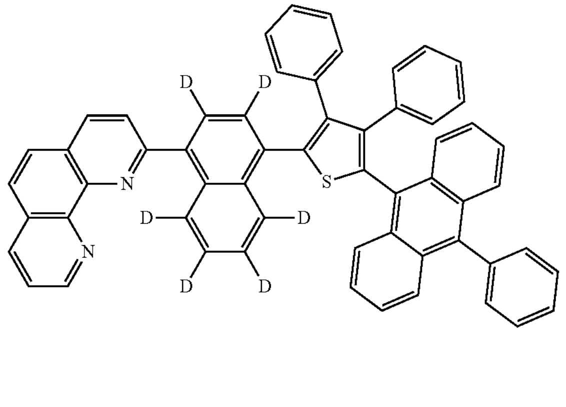
D197
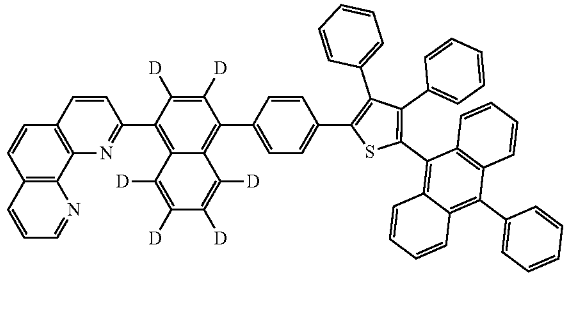

-continued
D198
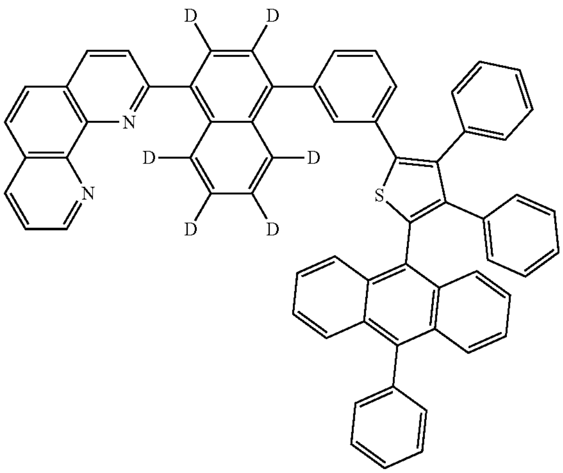
D199
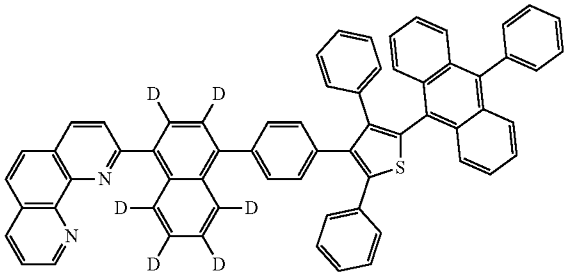
D200
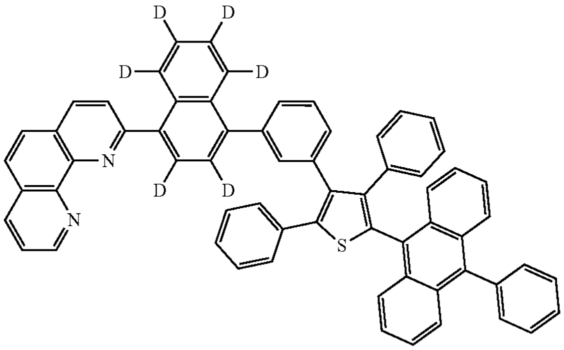
D205
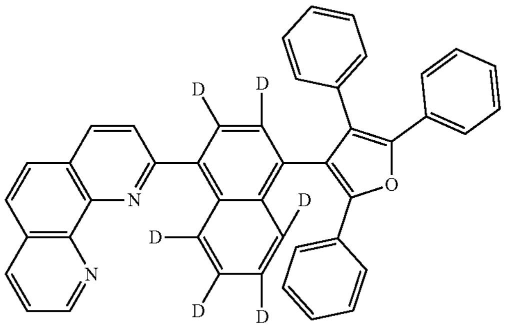
D206
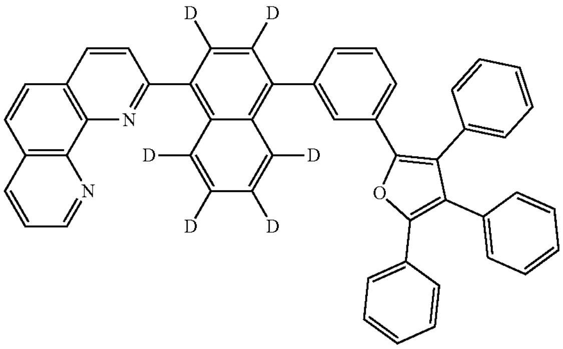
D207
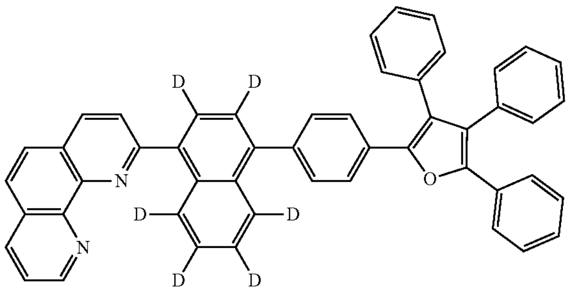

D208
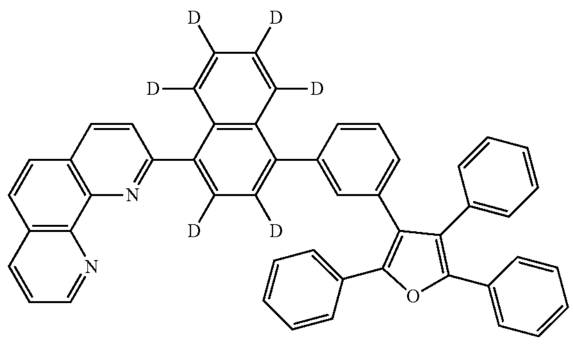
D209
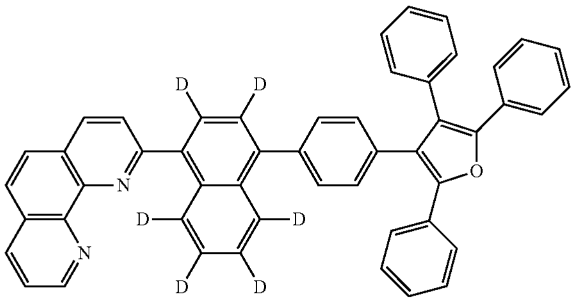
D214
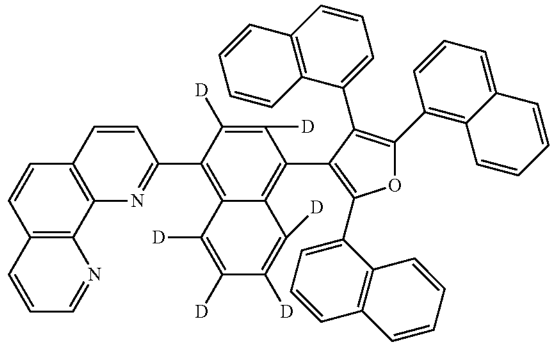
D215
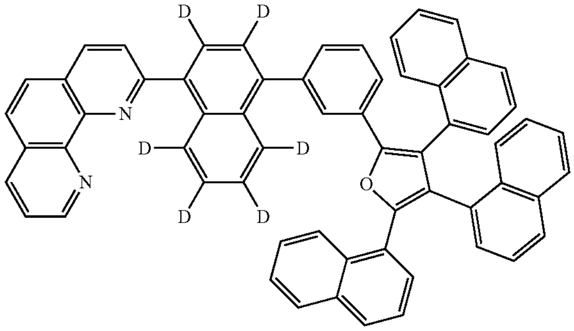
D216
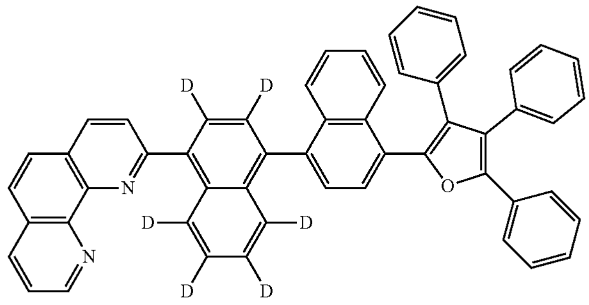
D217
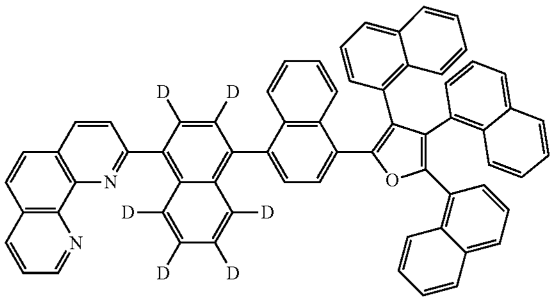
D218
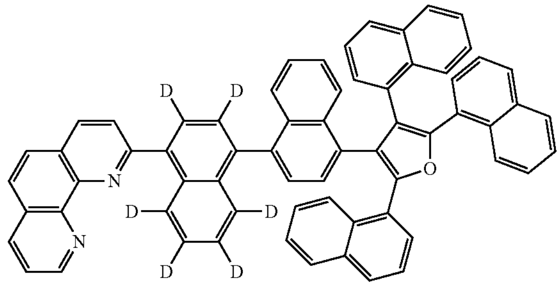
D221
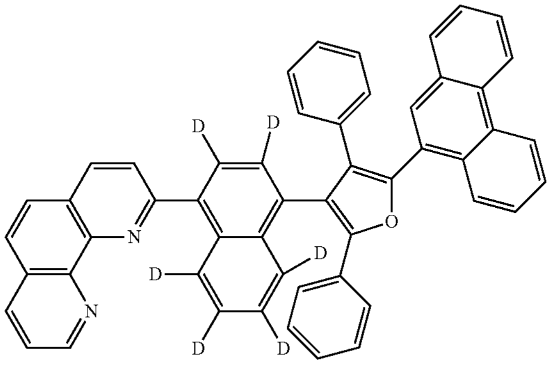

-continued
D222
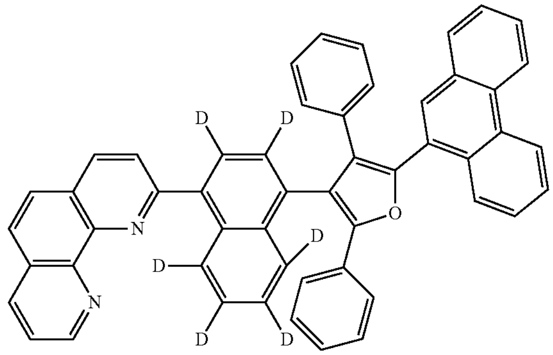
D223
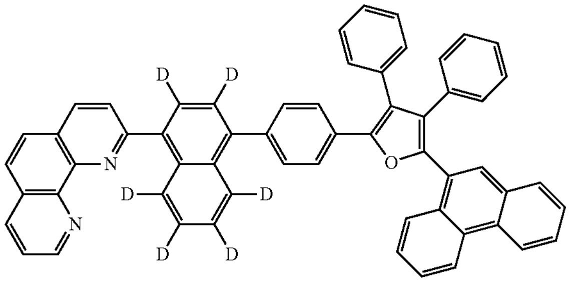
D224
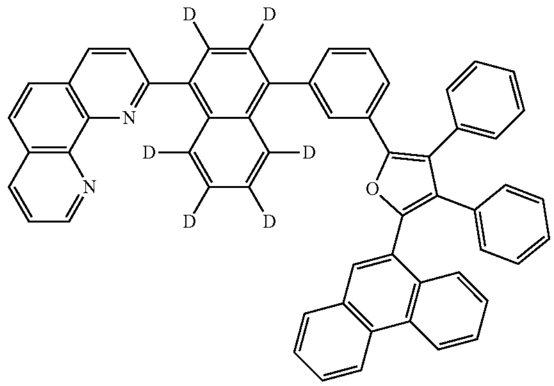
D225
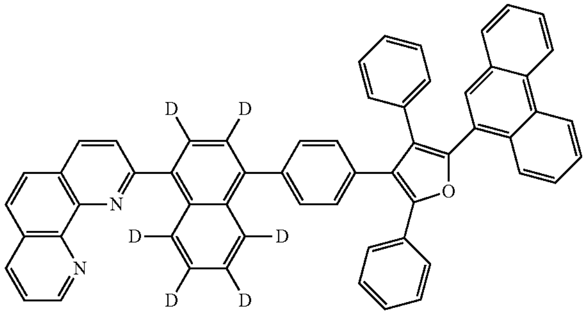
D226
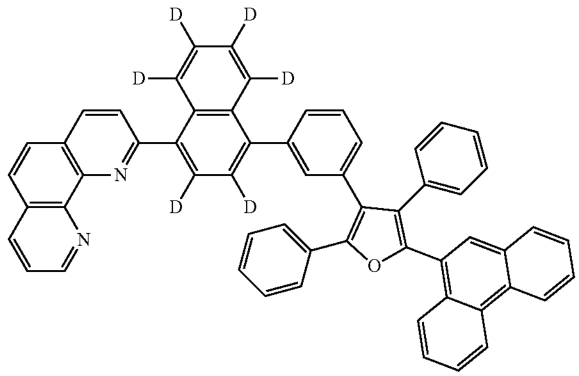
D228
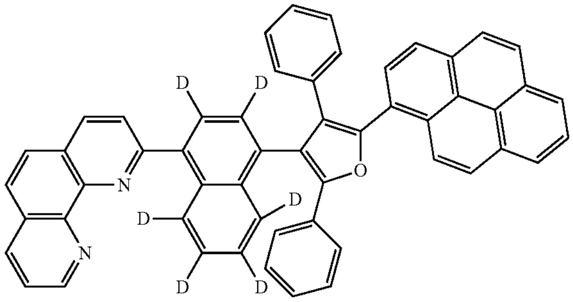
D229
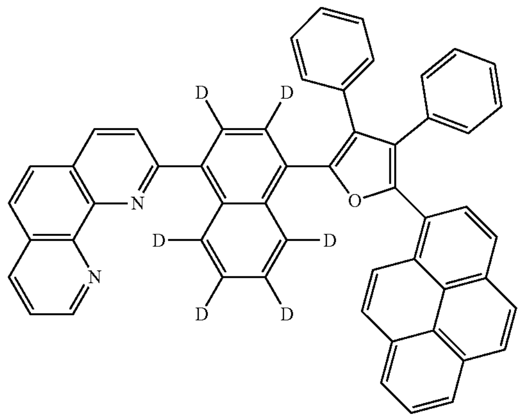
D230
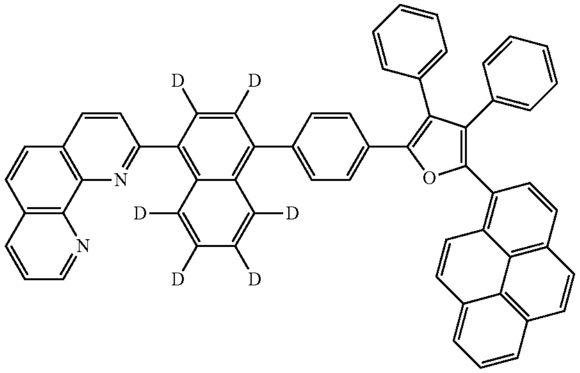

-continued
D231
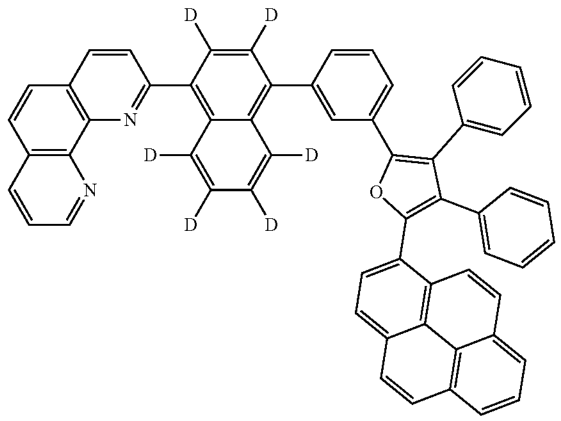
D232
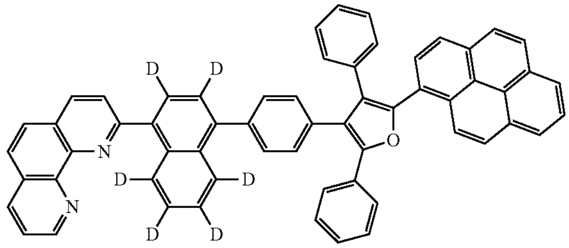
D233
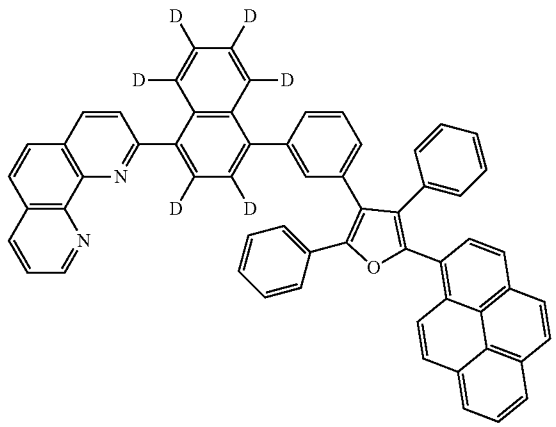
D235
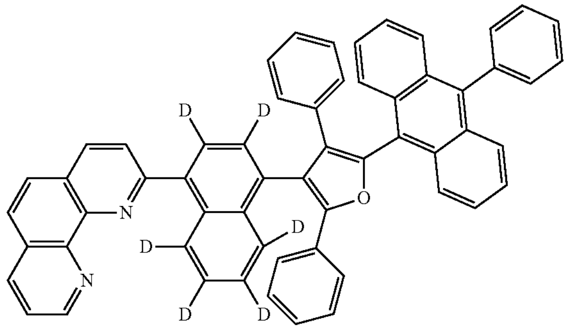
D236
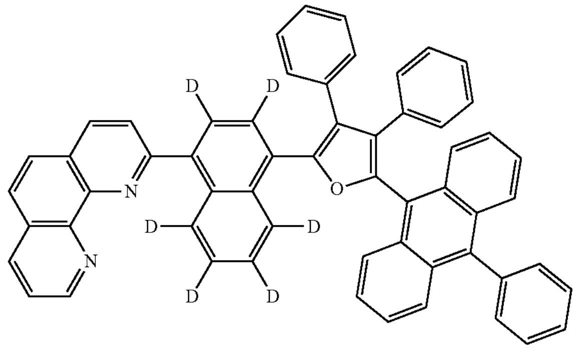
D237
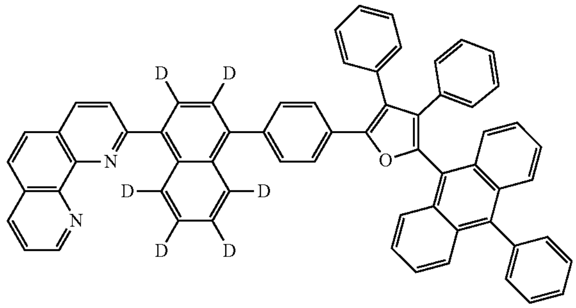

-continued
D238
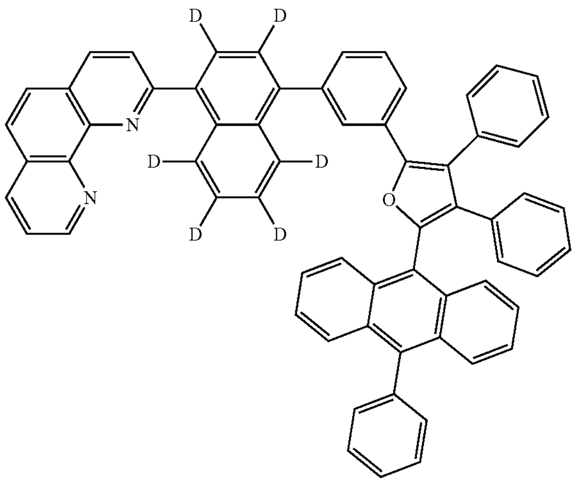
D239
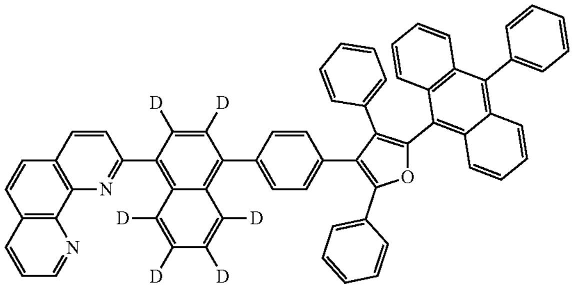
D240
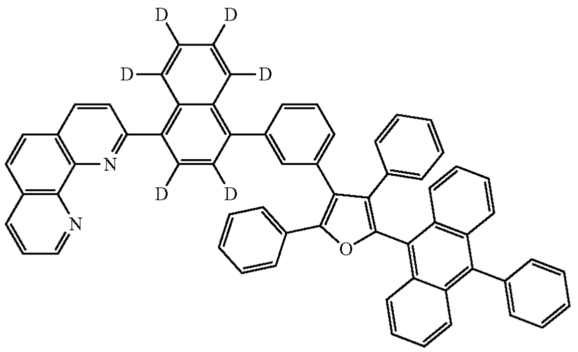
D245
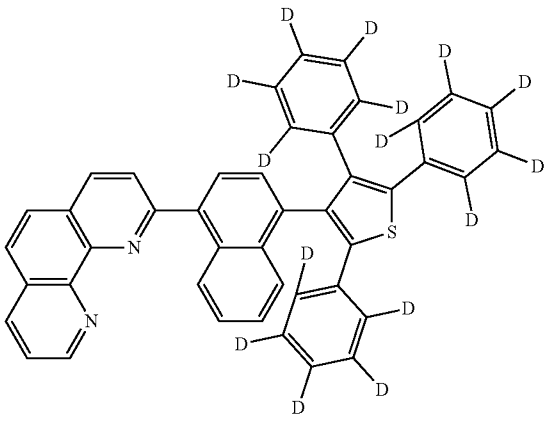
D246
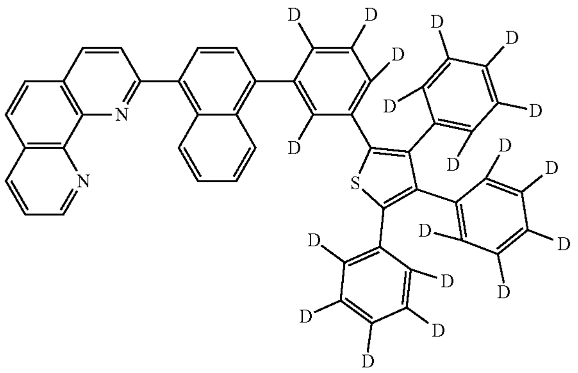
D247
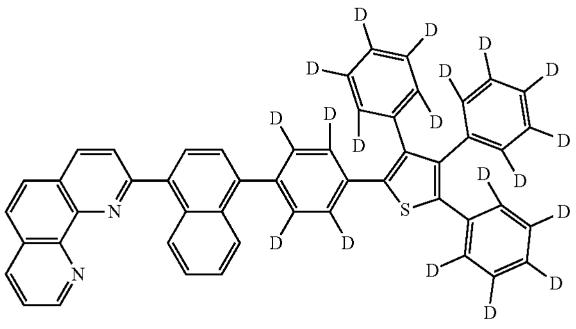

-continued
D248
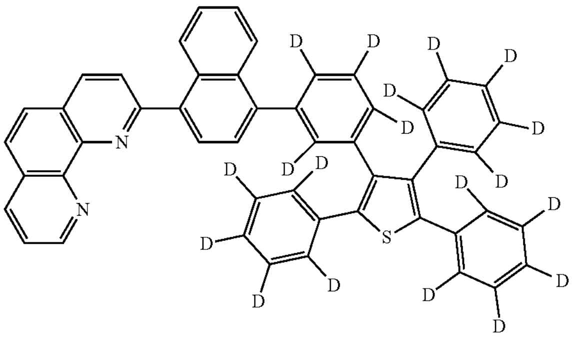
D249
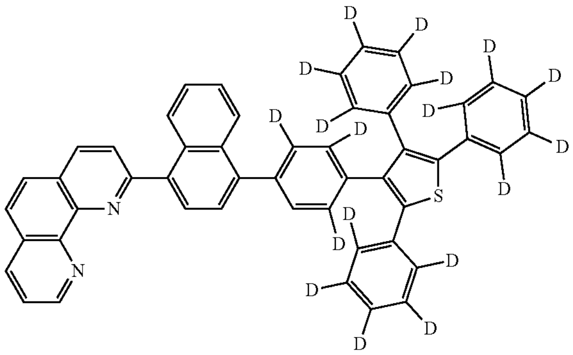
D254
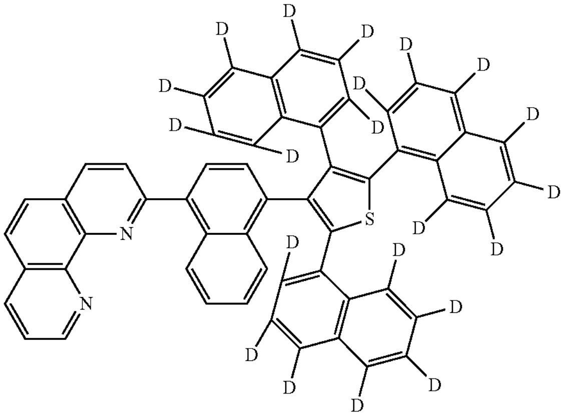
D255
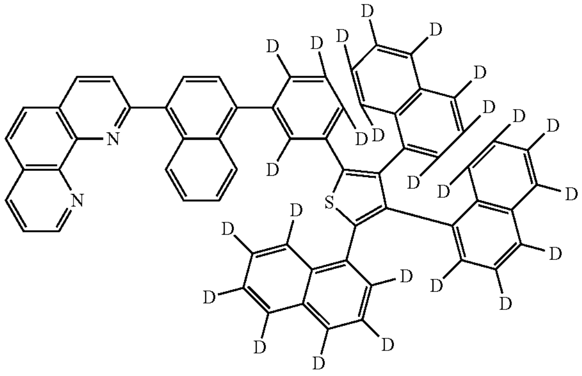
D256
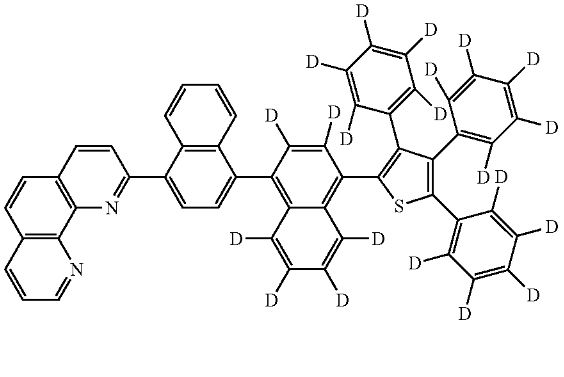
D257
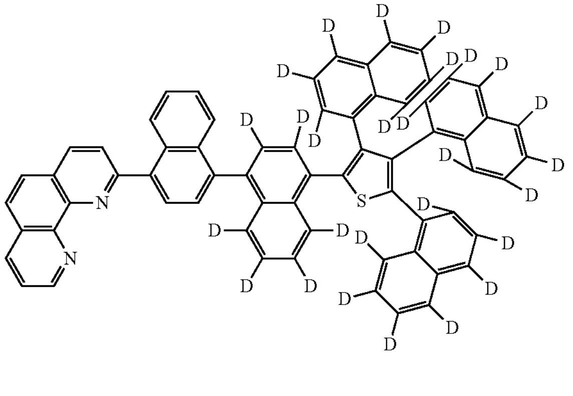

-continued
D258
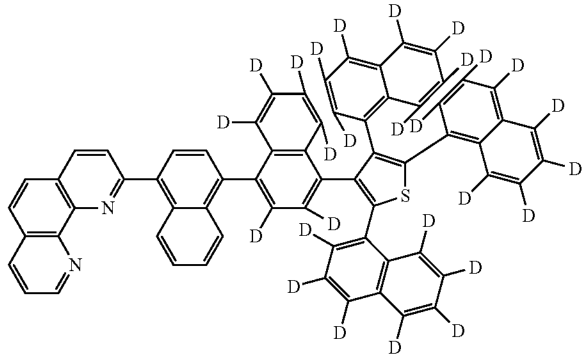
D261
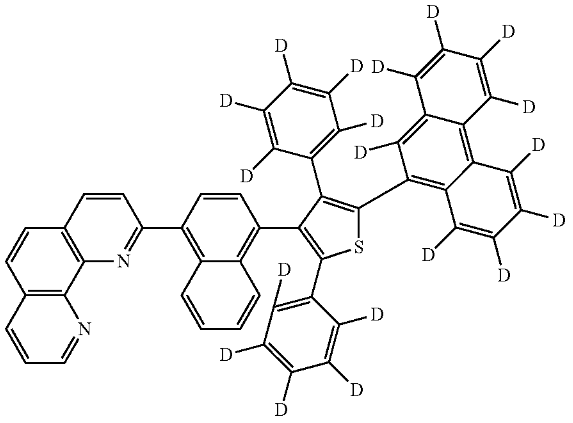
D262
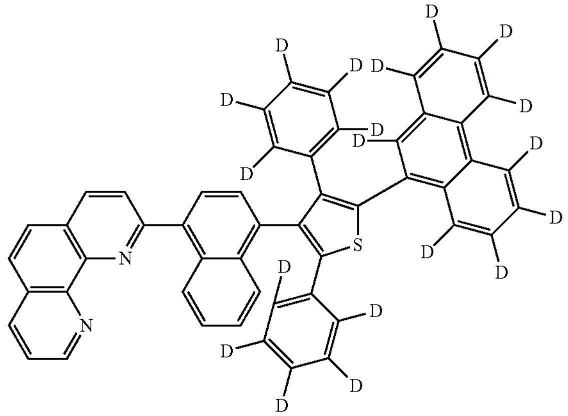
D263
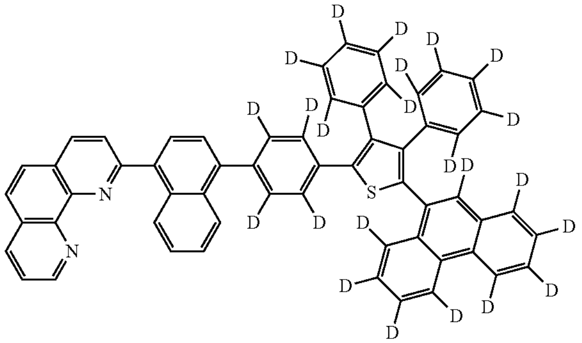
D264
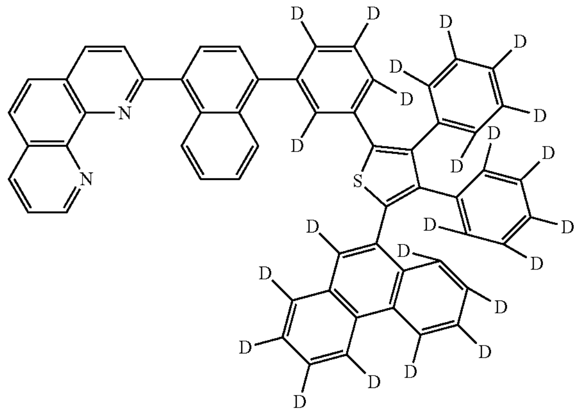
D265
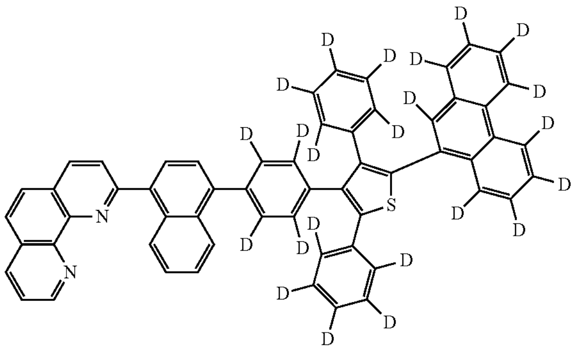

-continued
D266
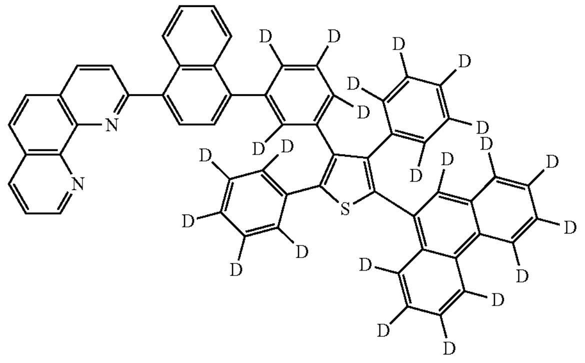
D268
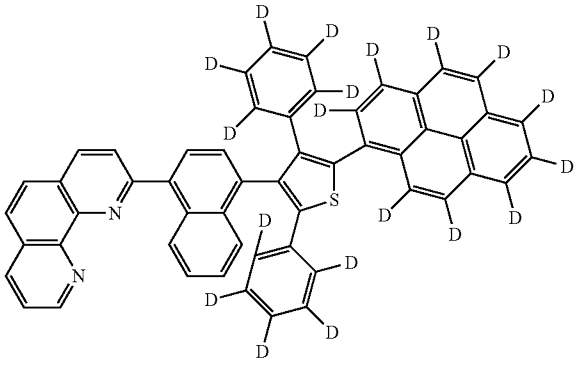
D269
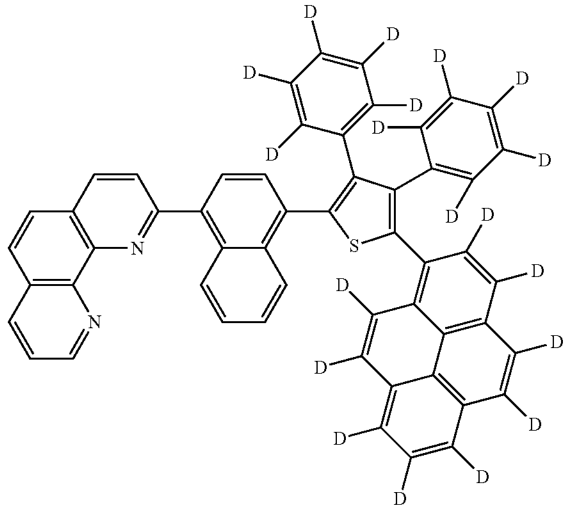
D270
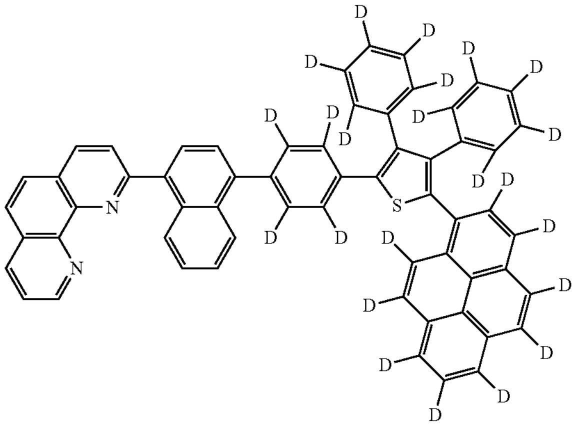
D271
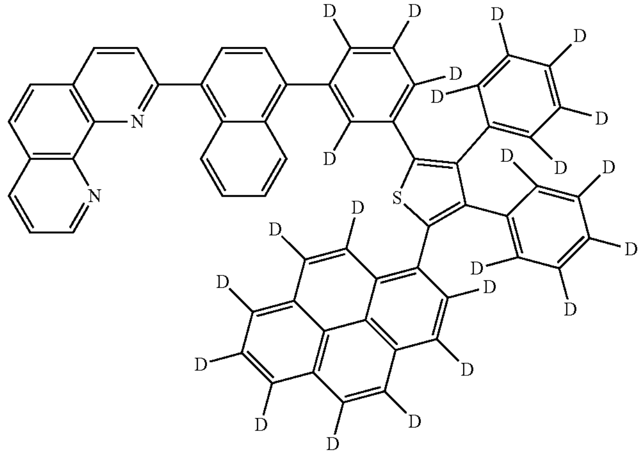

-continued
D272
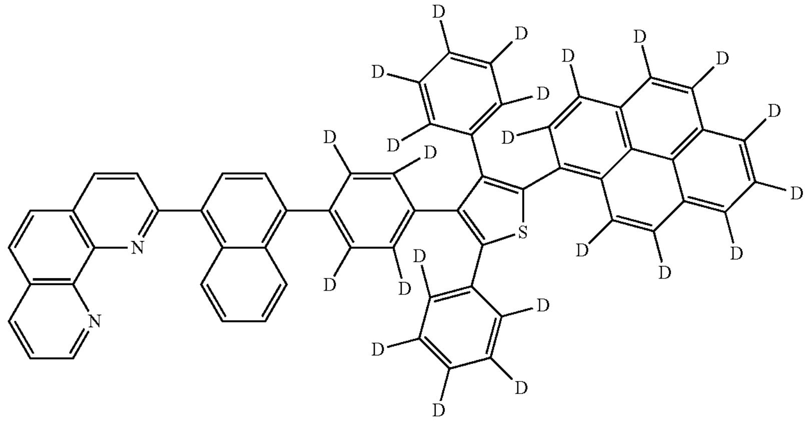
D273
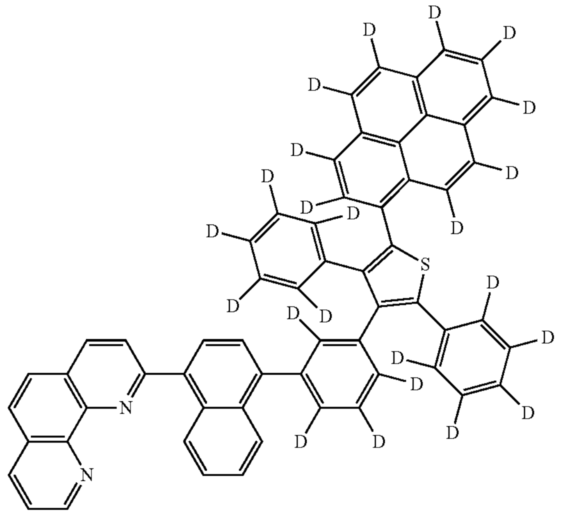
D275
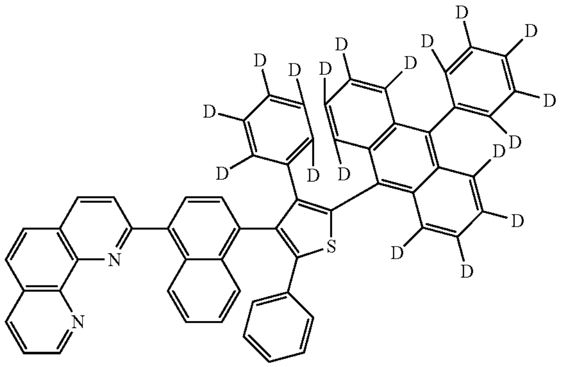
D276
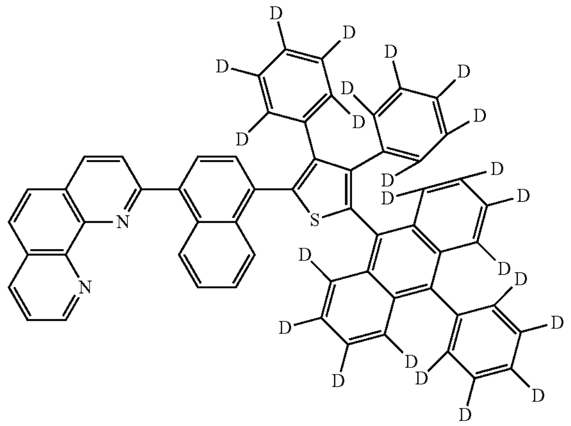
D277
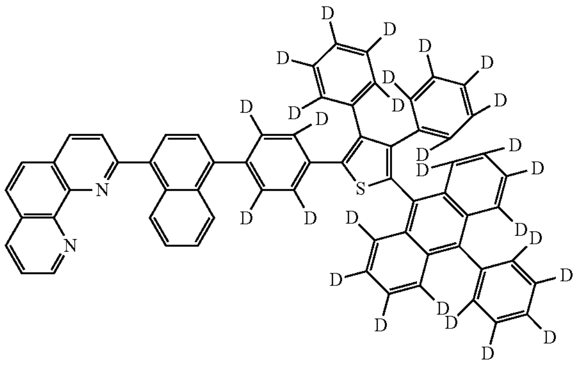

-continued
D278
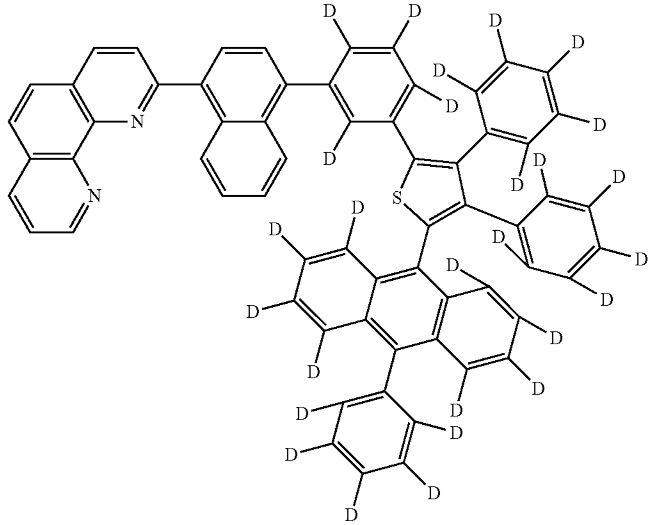
D279
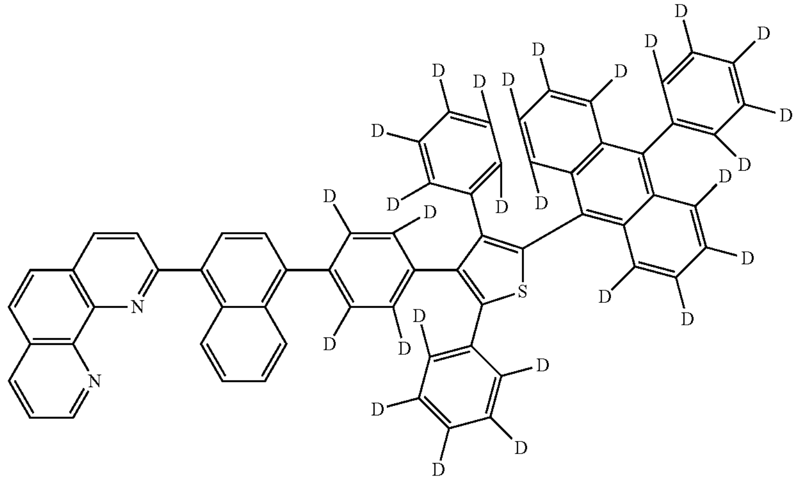
D280
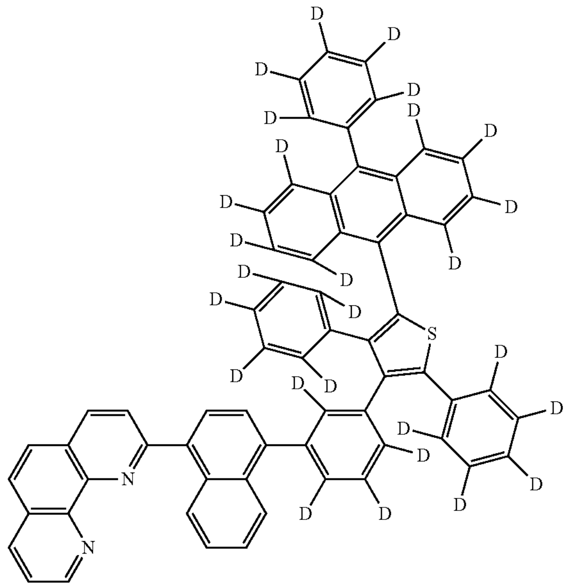
D285
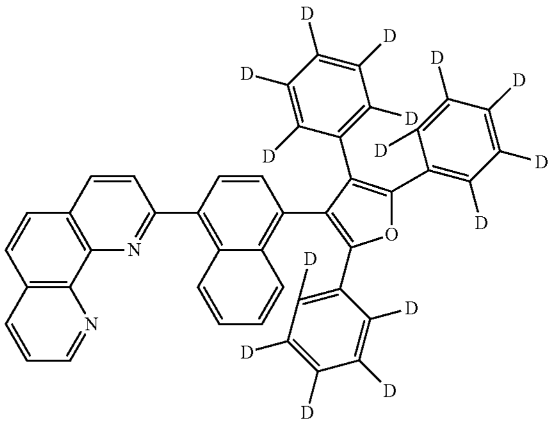

-continued
D286
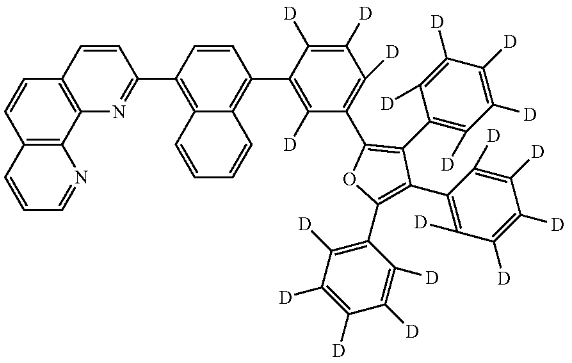
D287
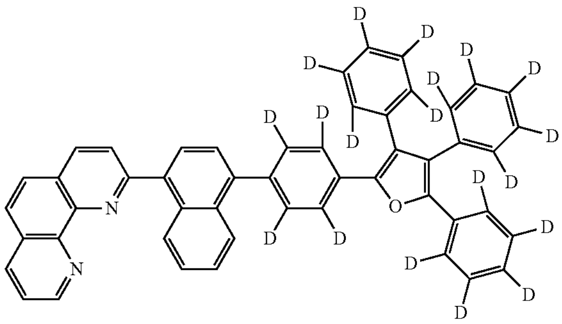
D288
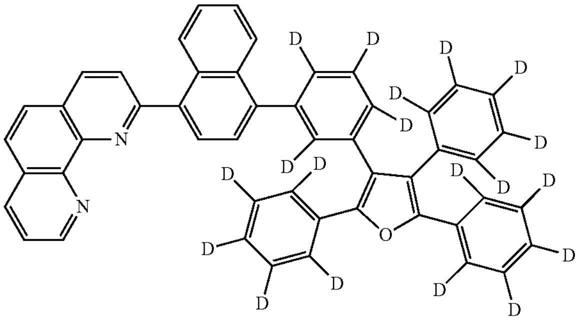
D289
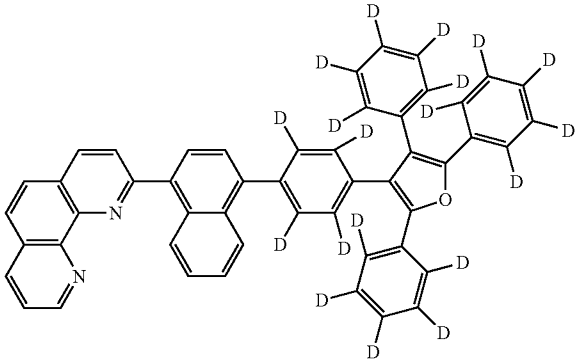
D294
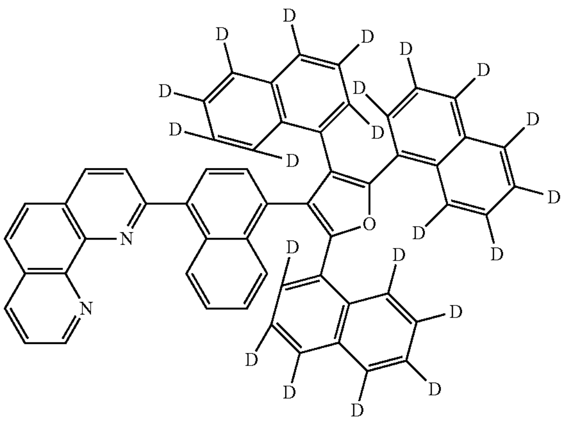
D295
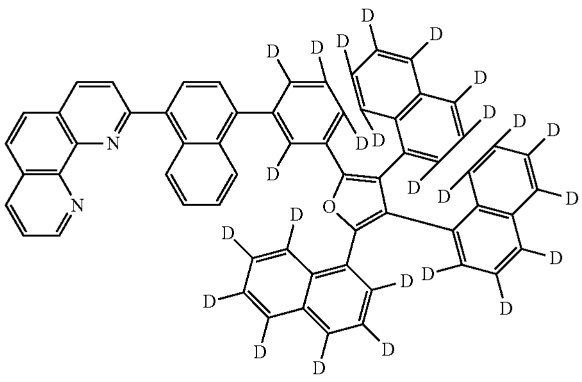
D296
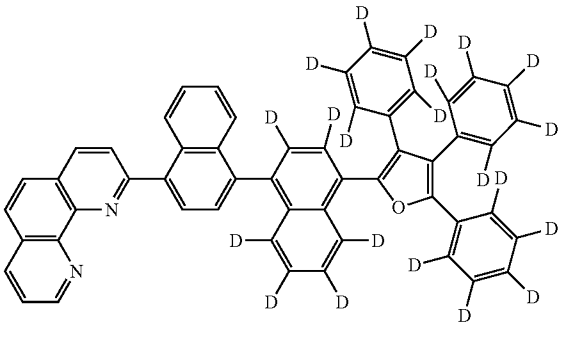
D297
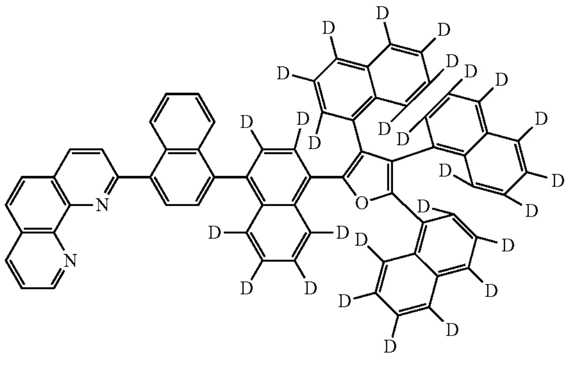

-continued
D298
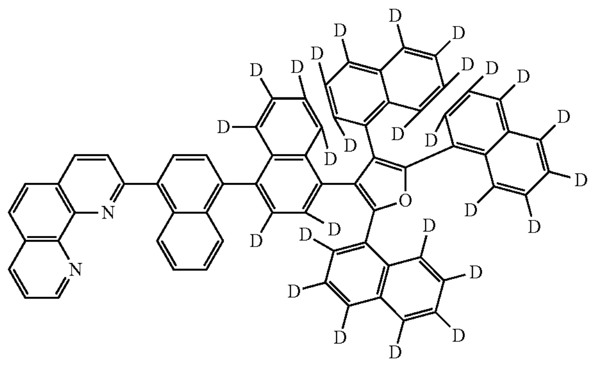
D301
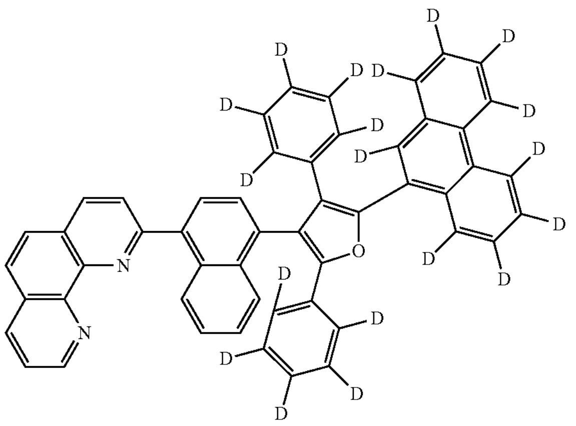
D302
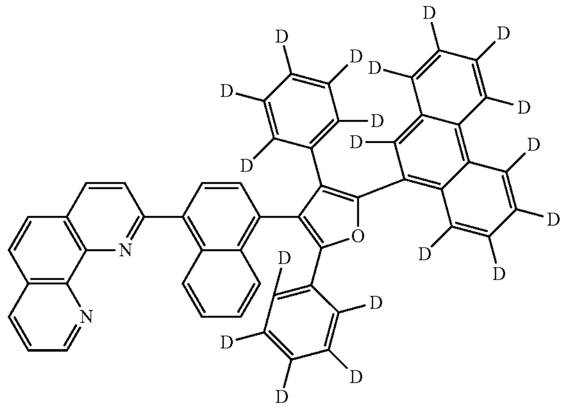
D303
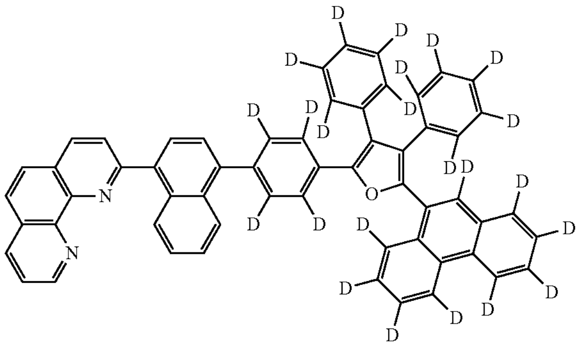
D304
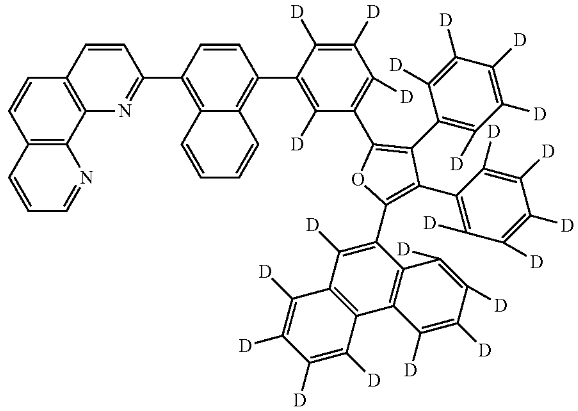
D305
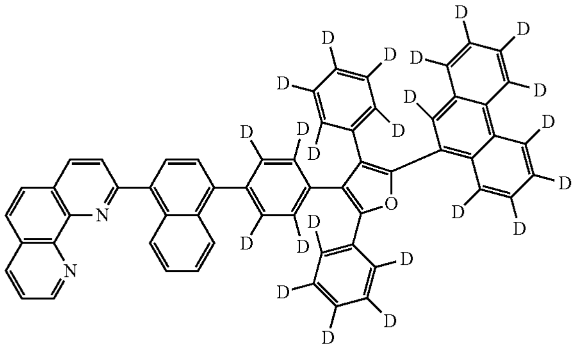

-continued
D306
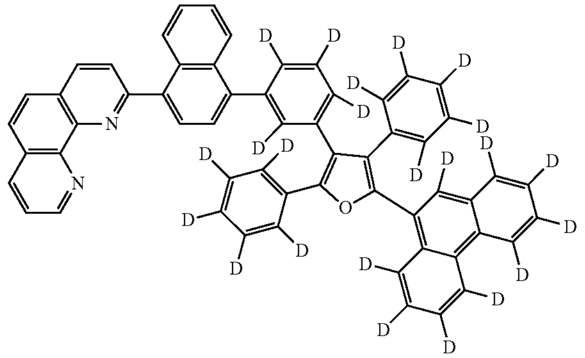
D308
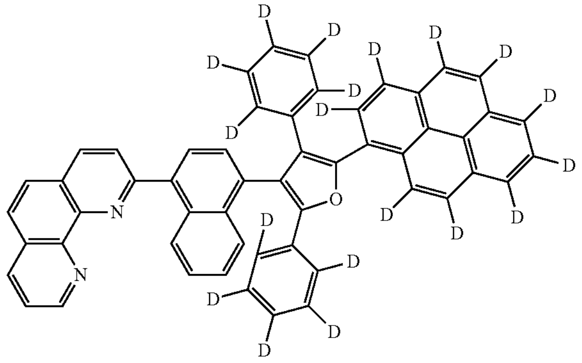
D309
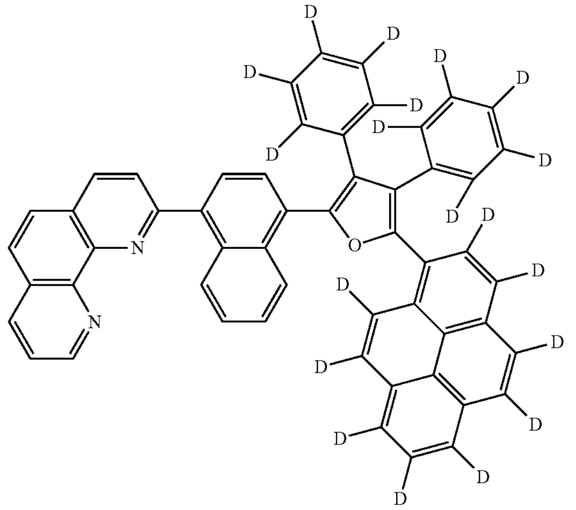
D310
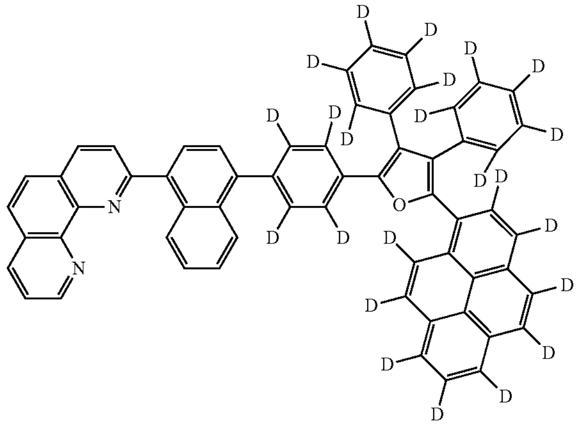
D311
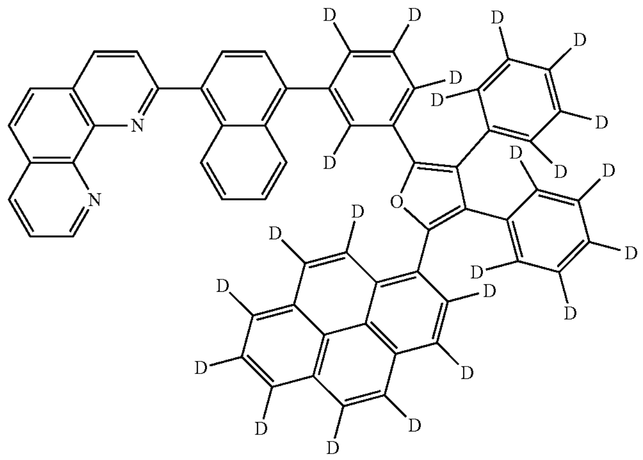

-continued
D312
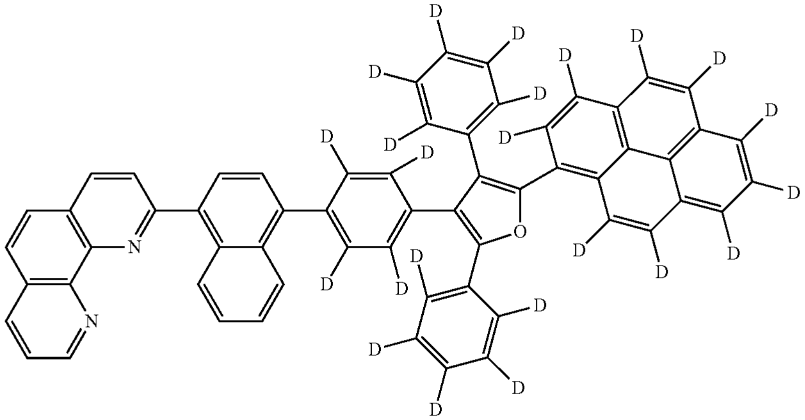
D313
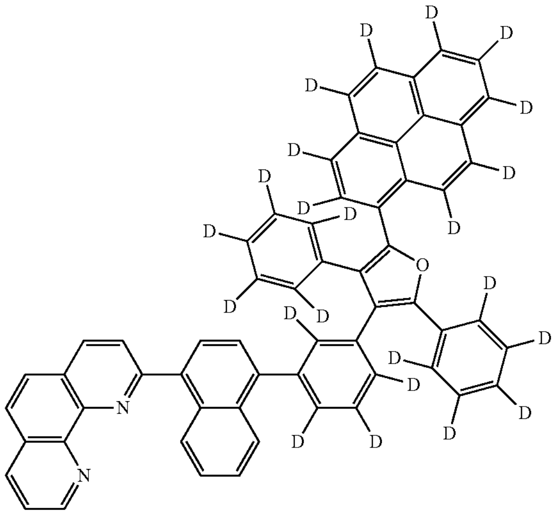
D315
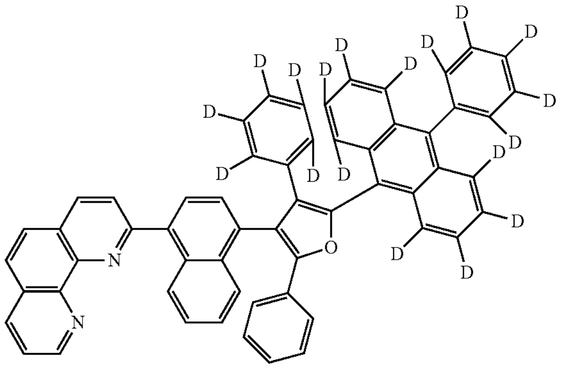
D316
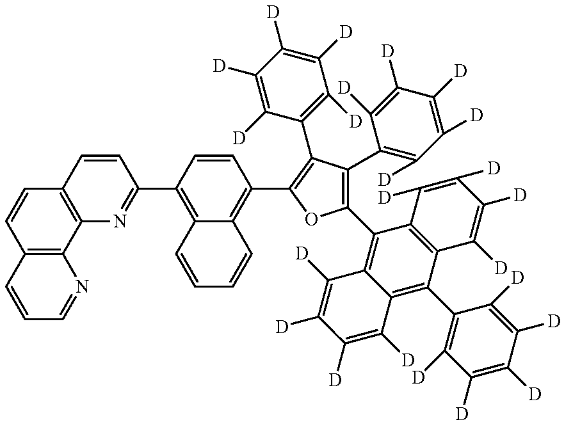
D317
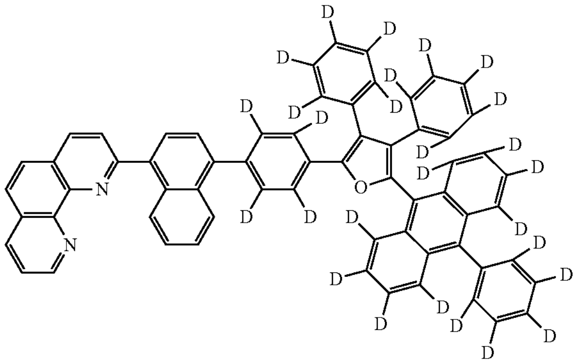

-continued
D318
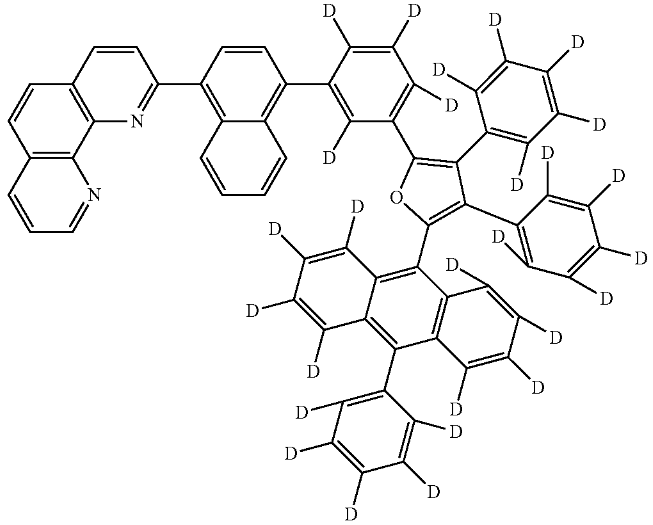
D319
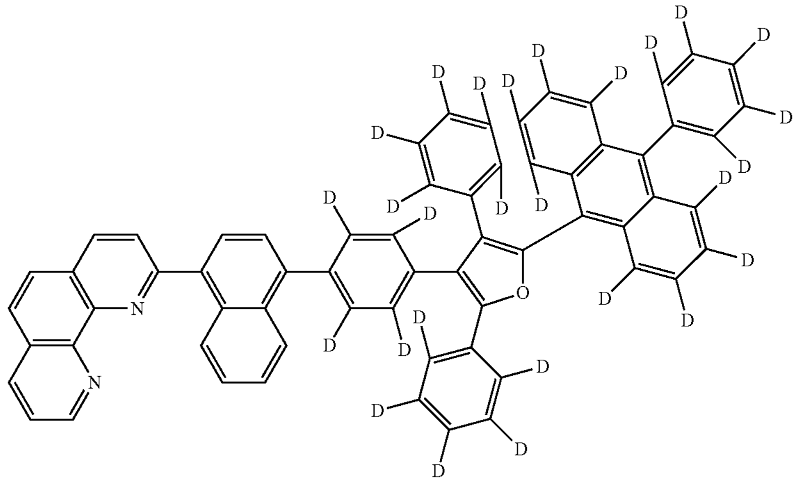
D320
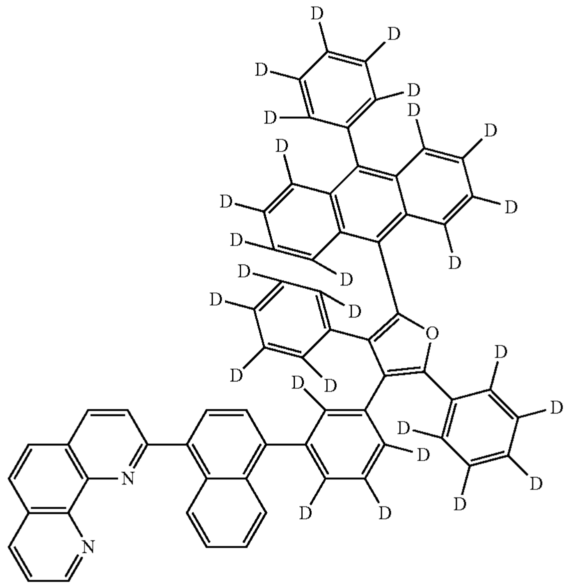
D325
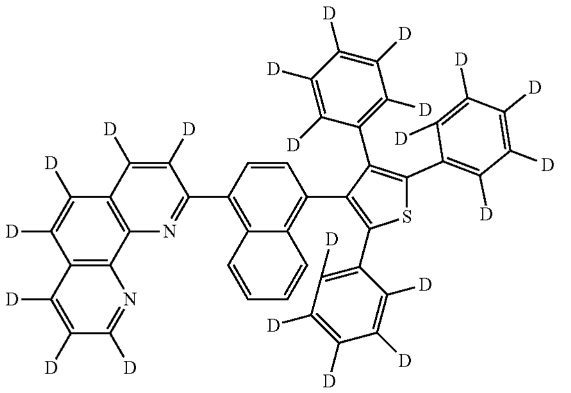

-continued
D326
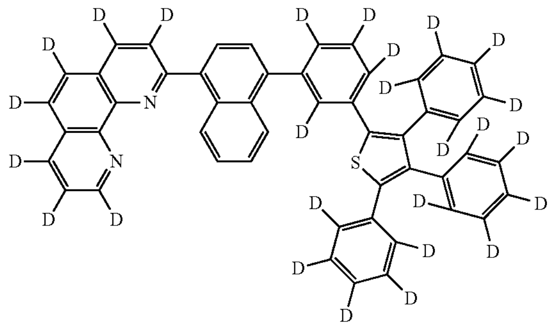
D327
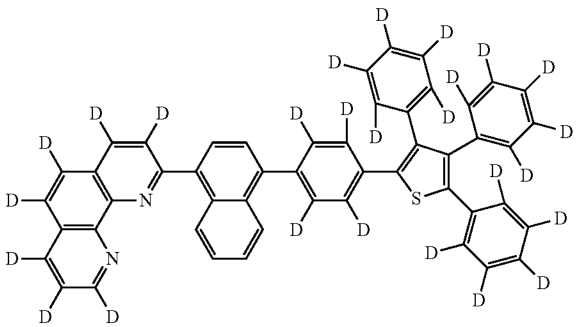
D328
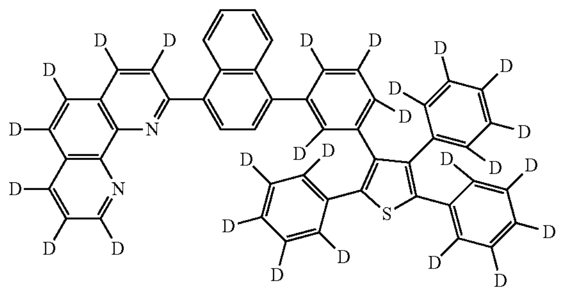
D329
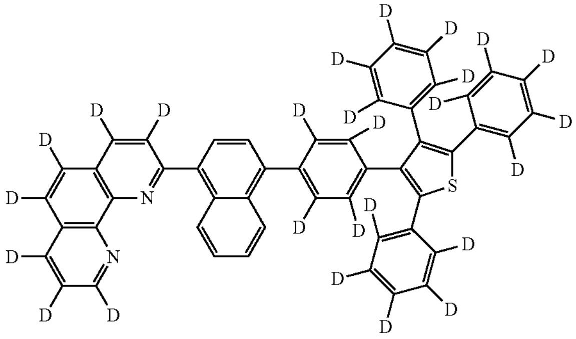
D334
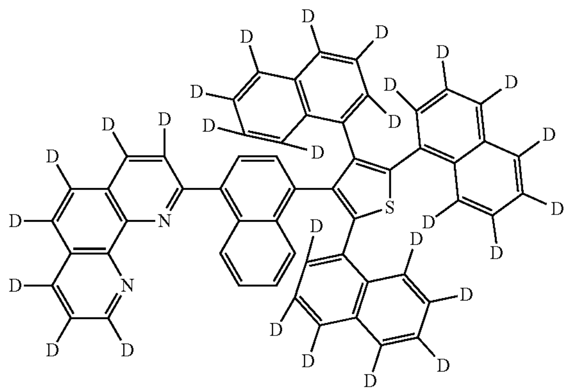
D335
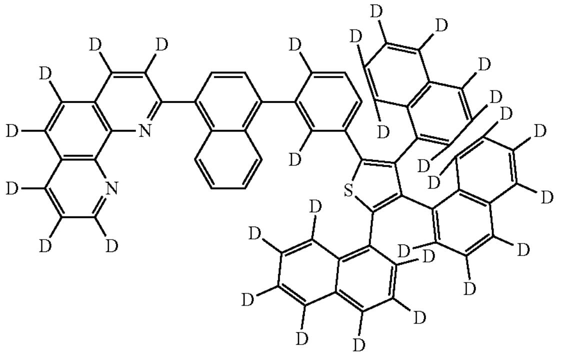
D336
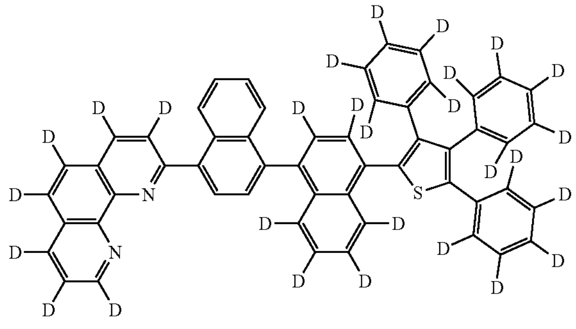
D337
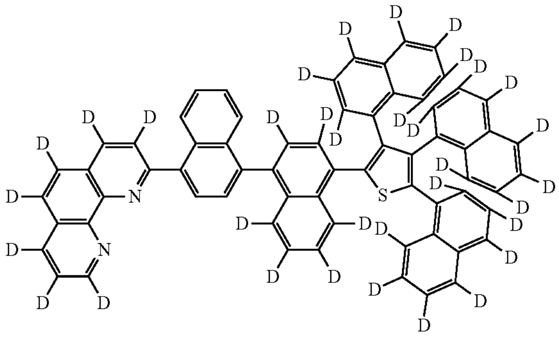

-continued
D338
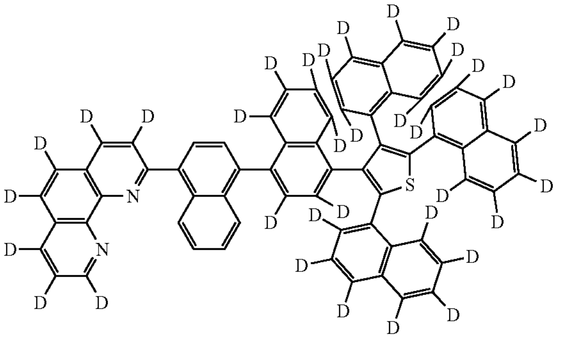
D341
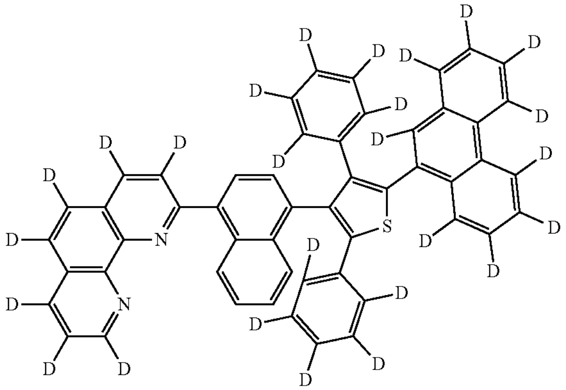
D342
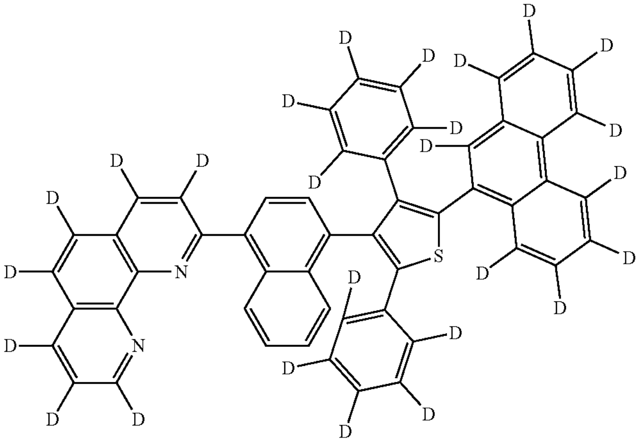
D343
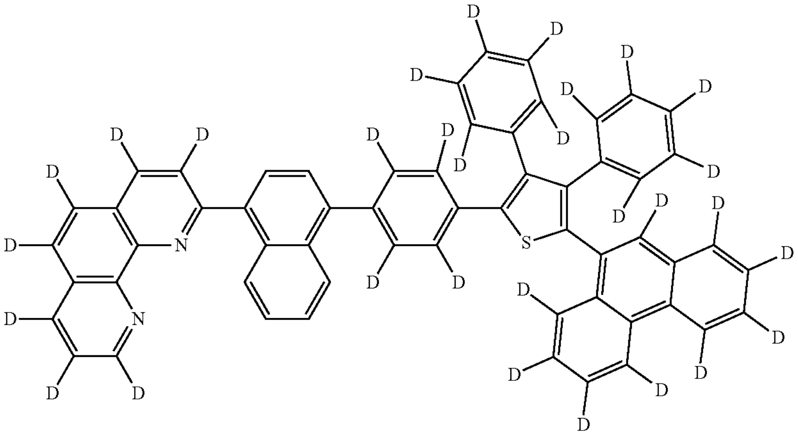

-continued
D344
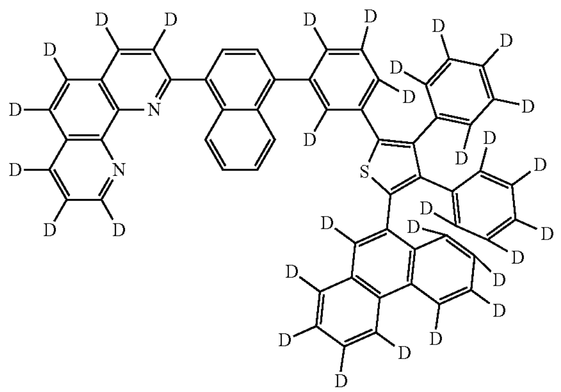
D345
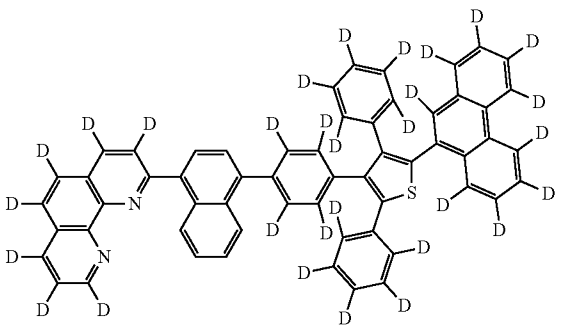
D346
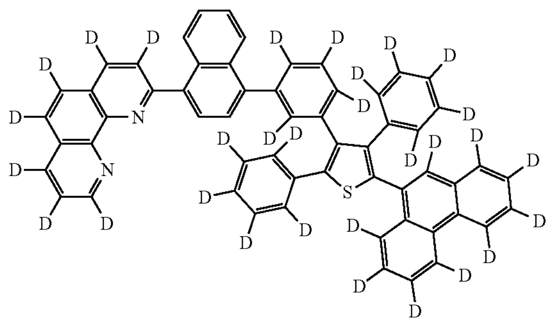
D348
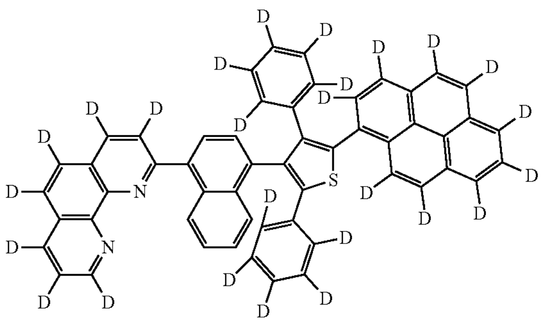
D349
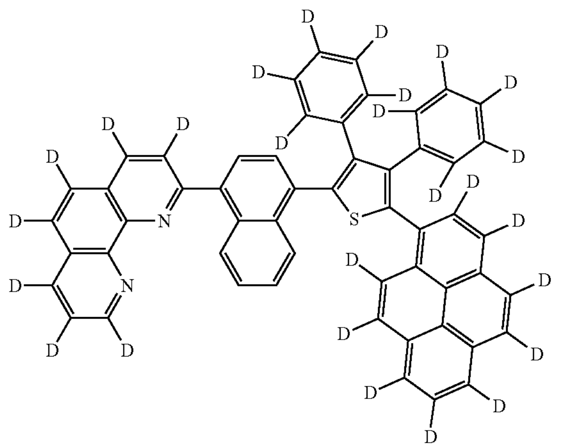
D350
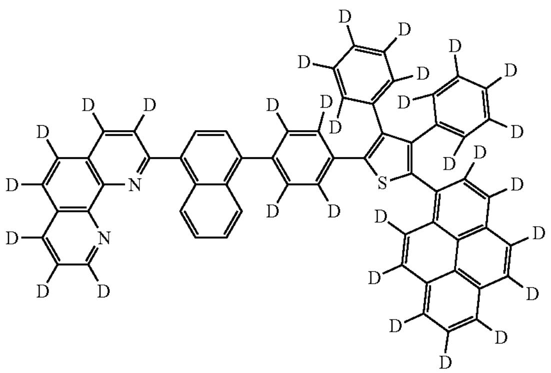

-continued
D351
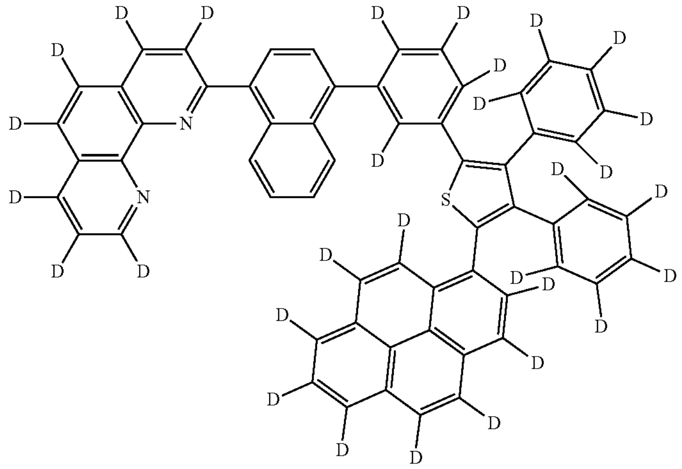
D352
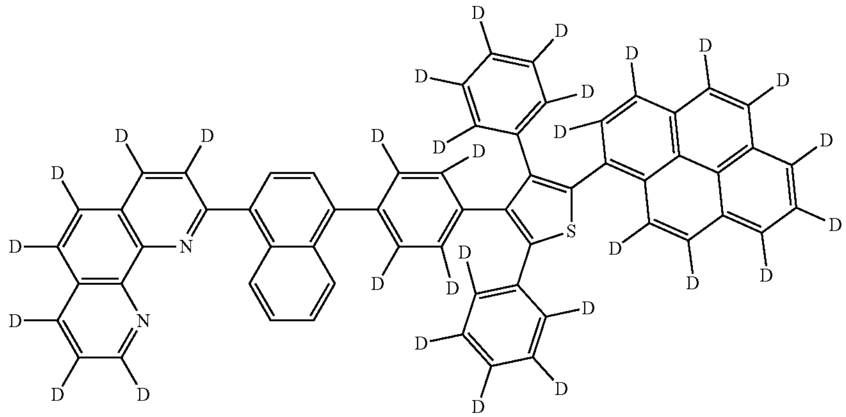
D353
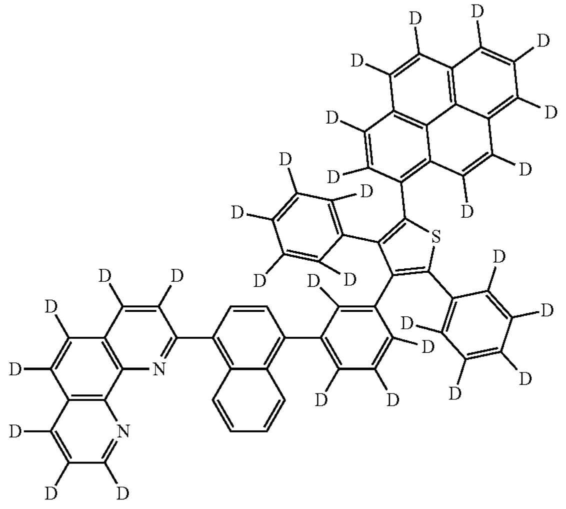
D355
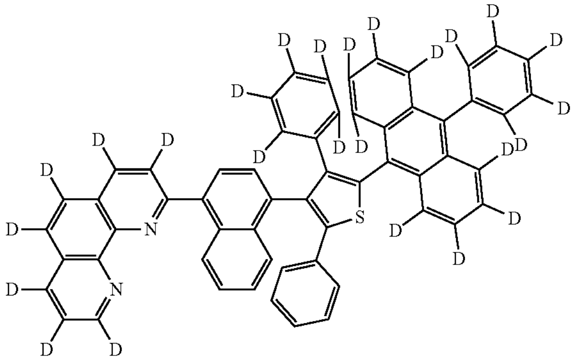

-continued
D356
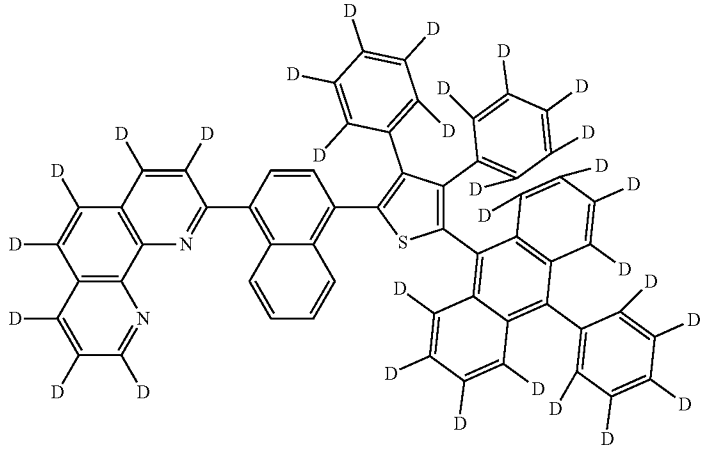
D357
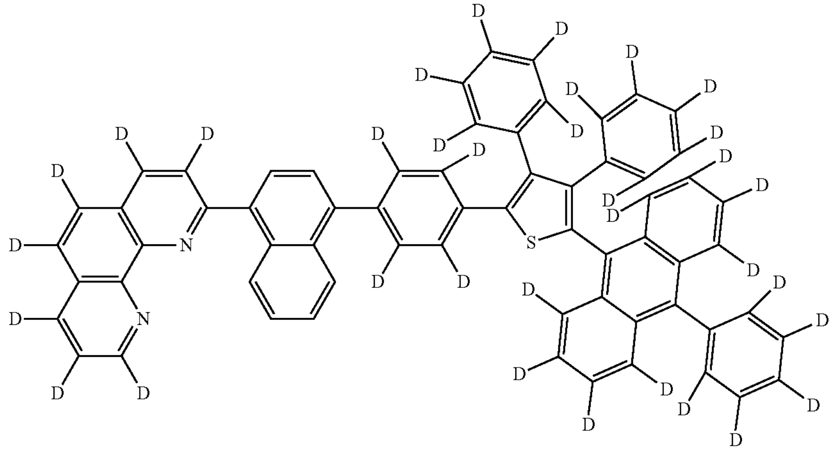
D358
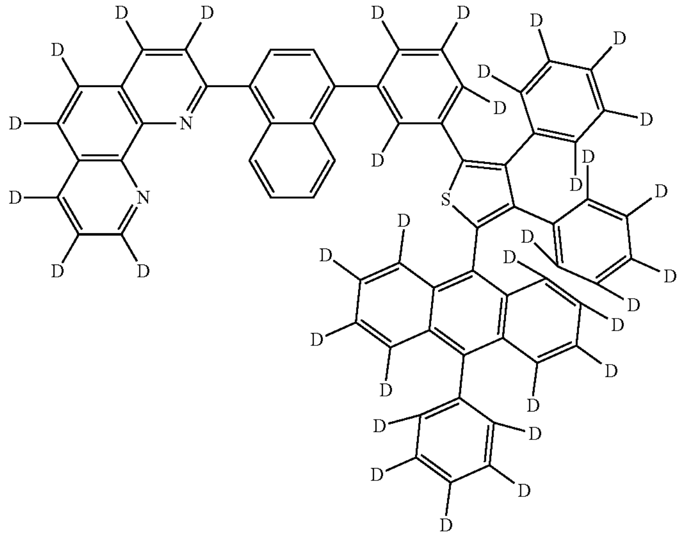

-continued
D359
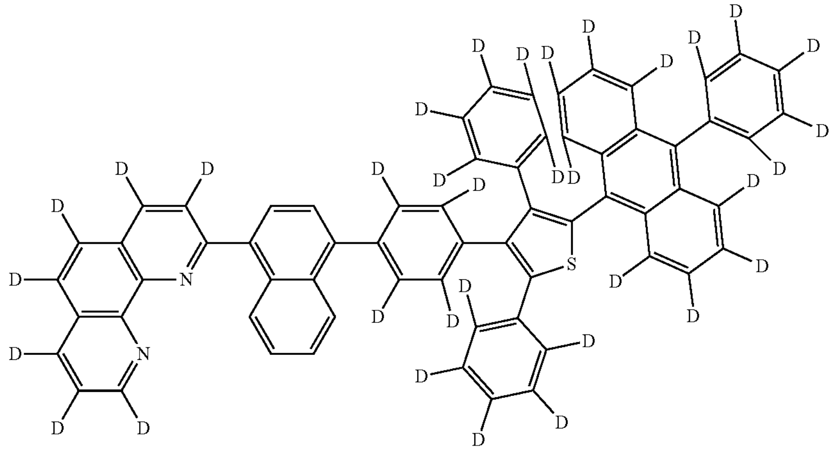
D360
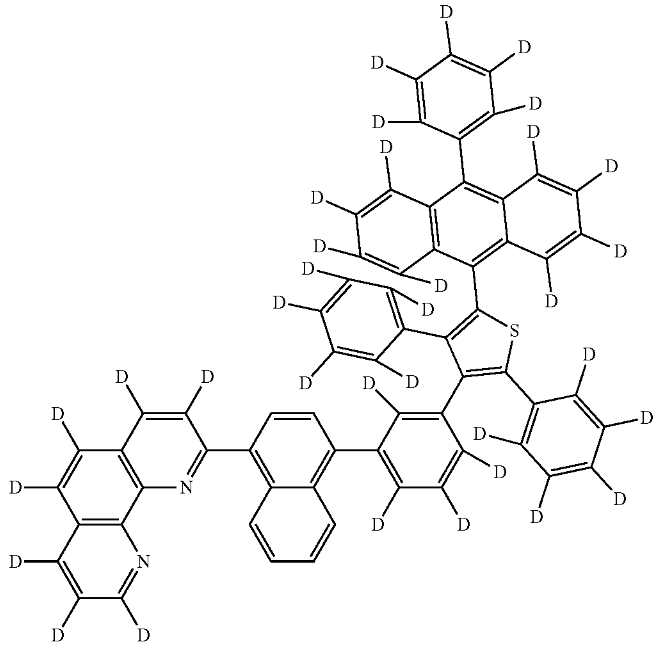
D365
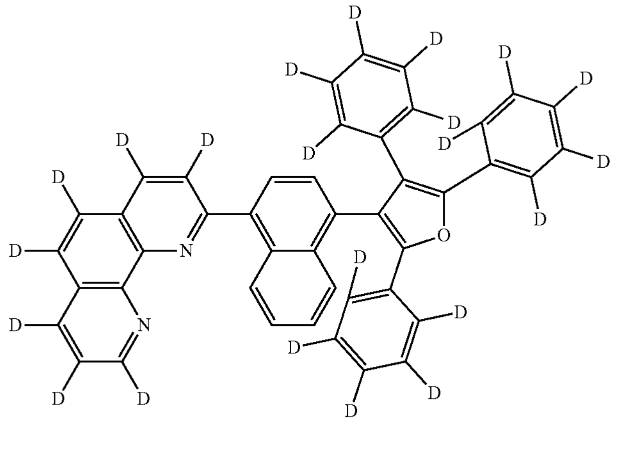

-continued
D366
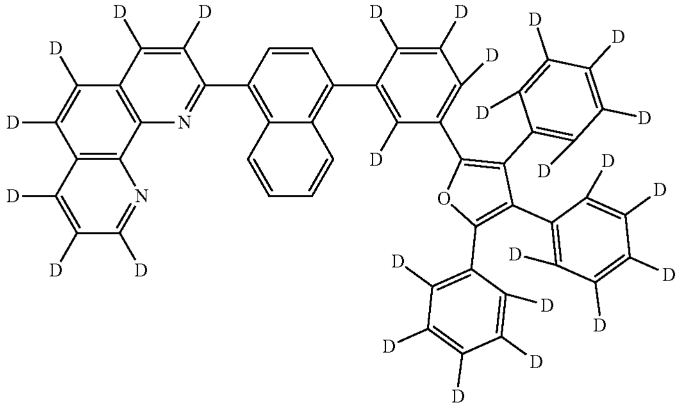
D367
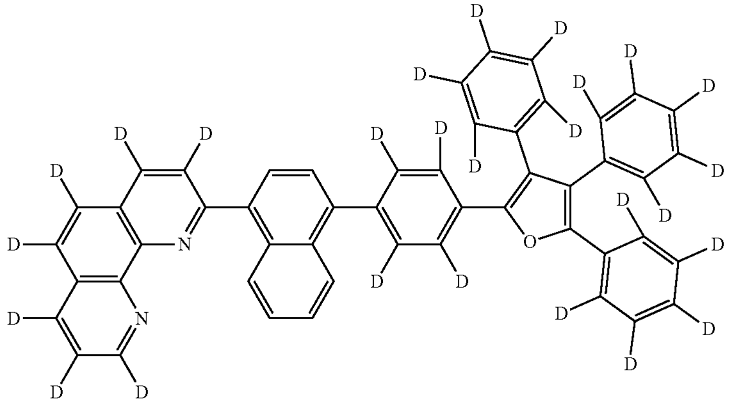
D368
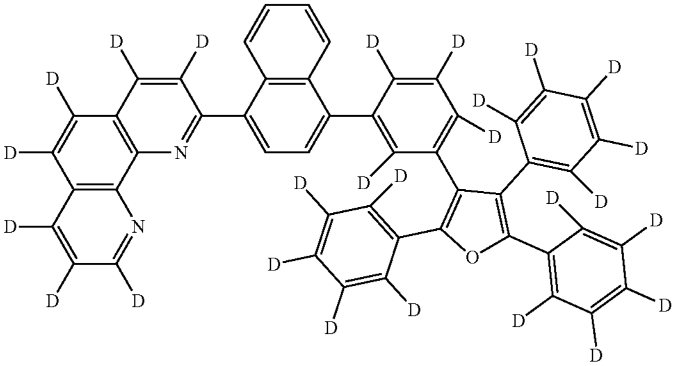
D369
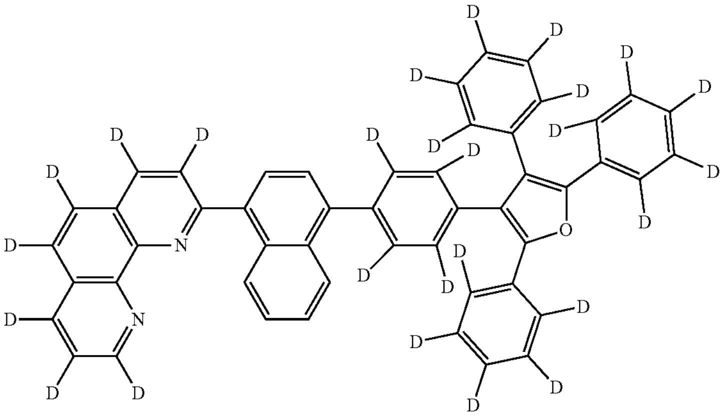

-continued
D374
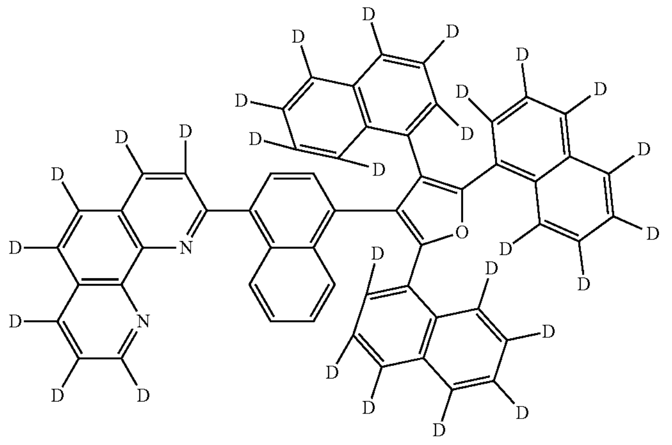
D375
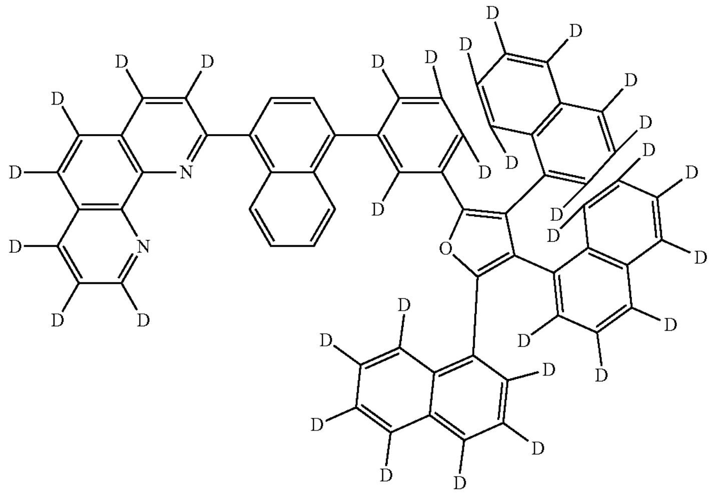
D376
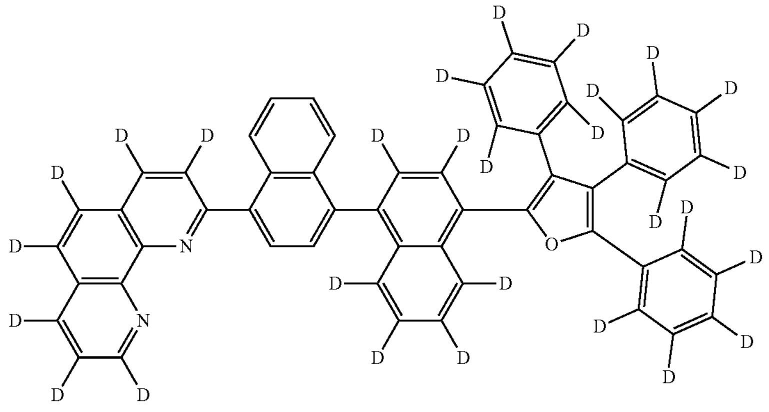

-continued
D377
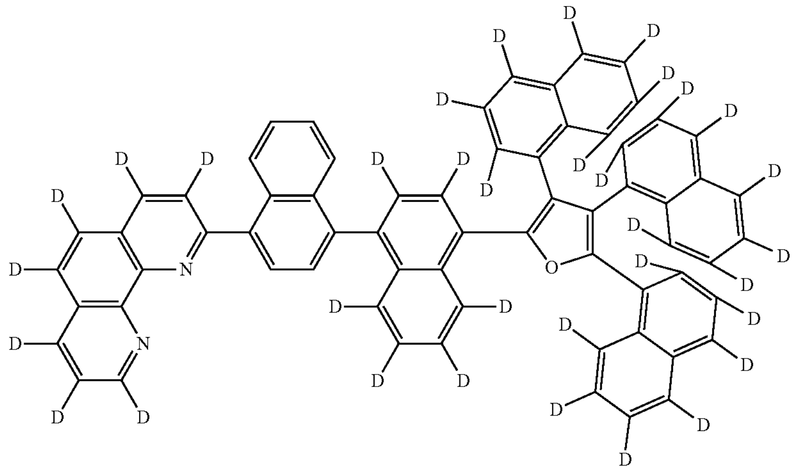
D378
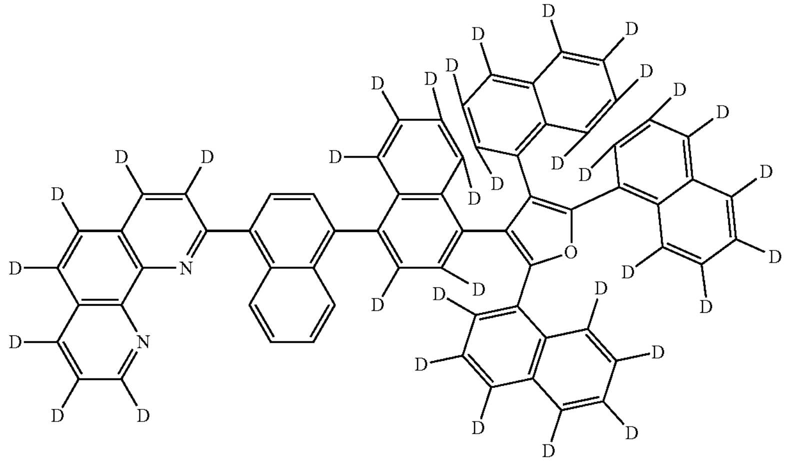
D381
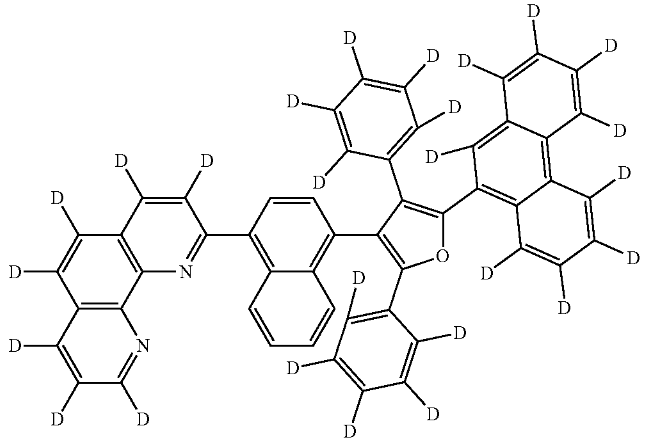

-continued
382
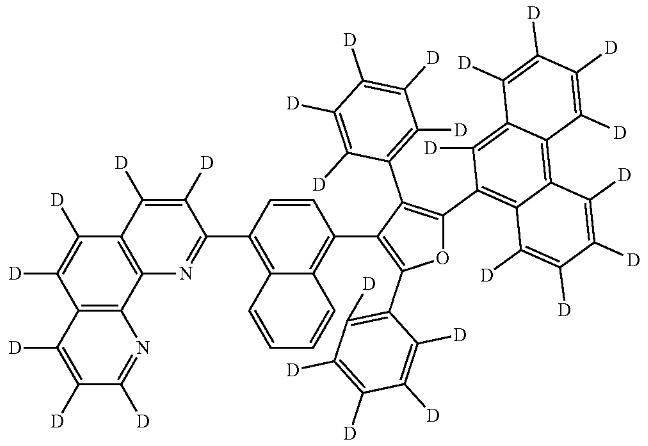
383
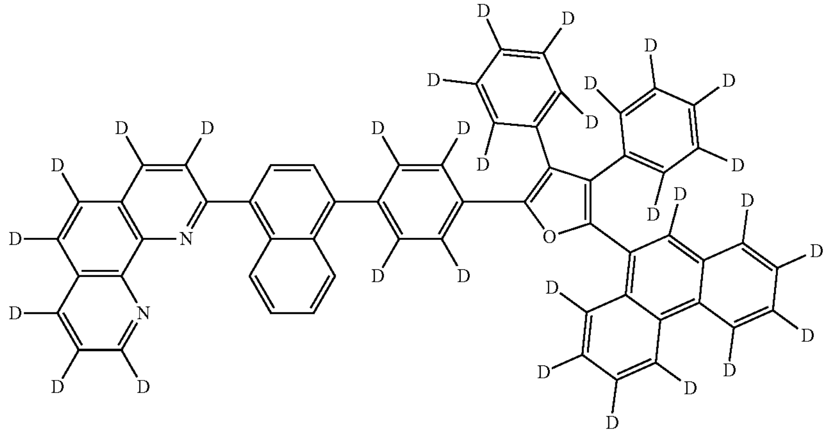
384
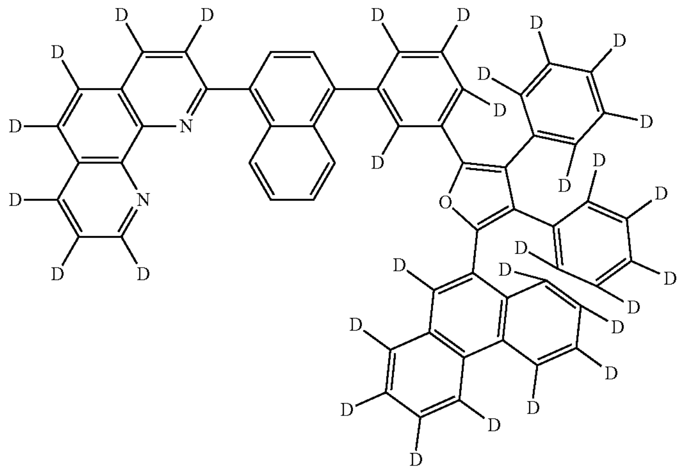

-continued
D385
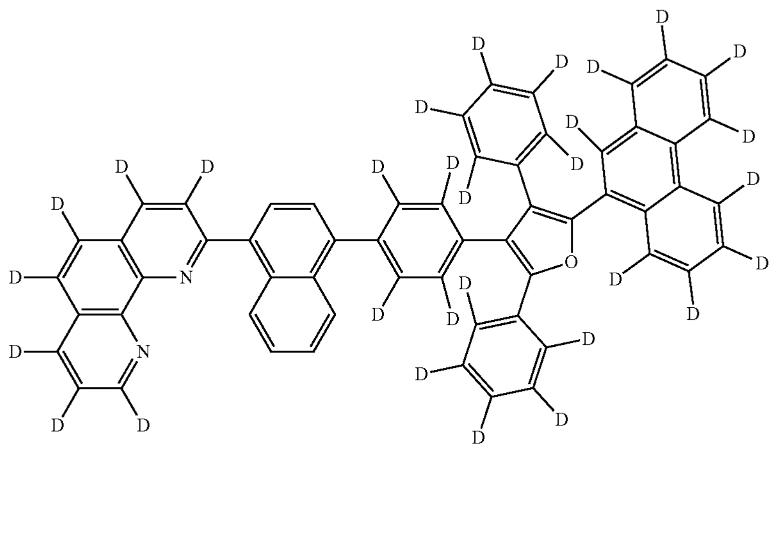
D386
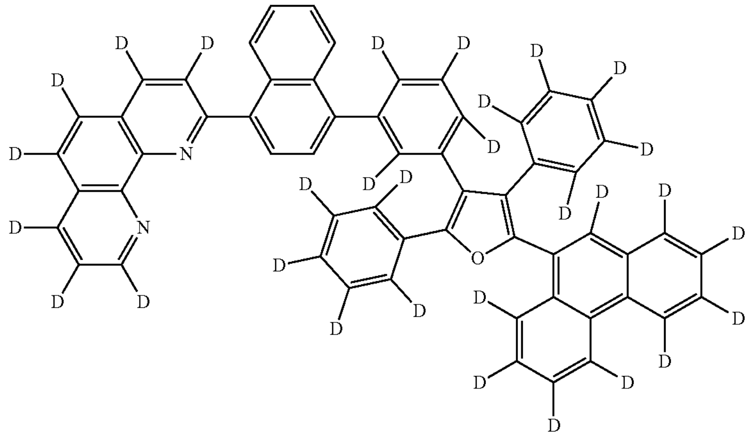
D388
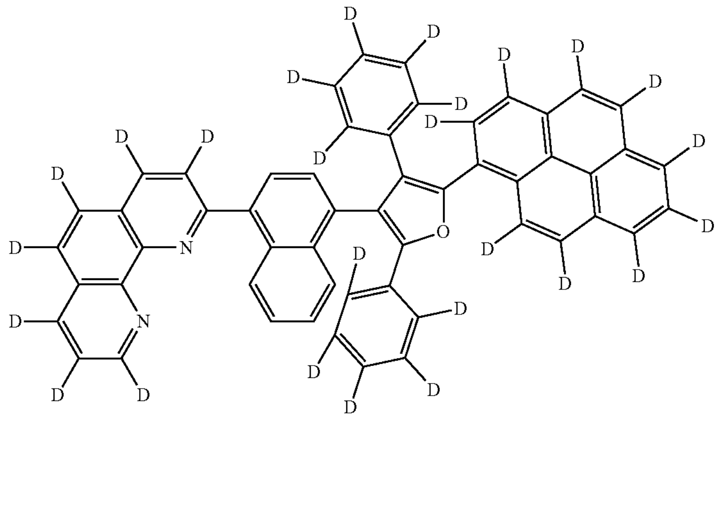

-continued
D389
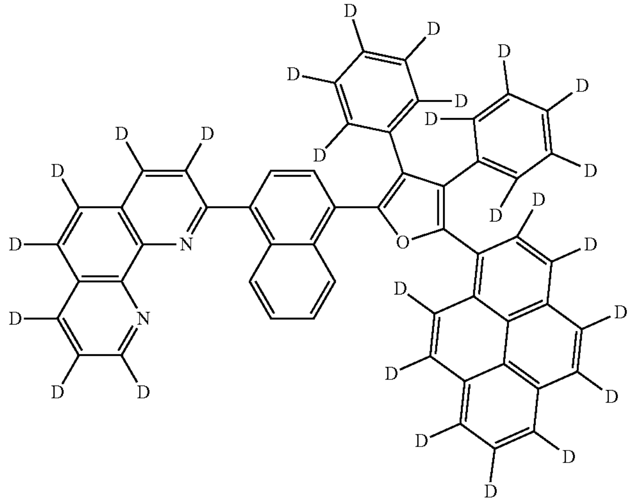
D390
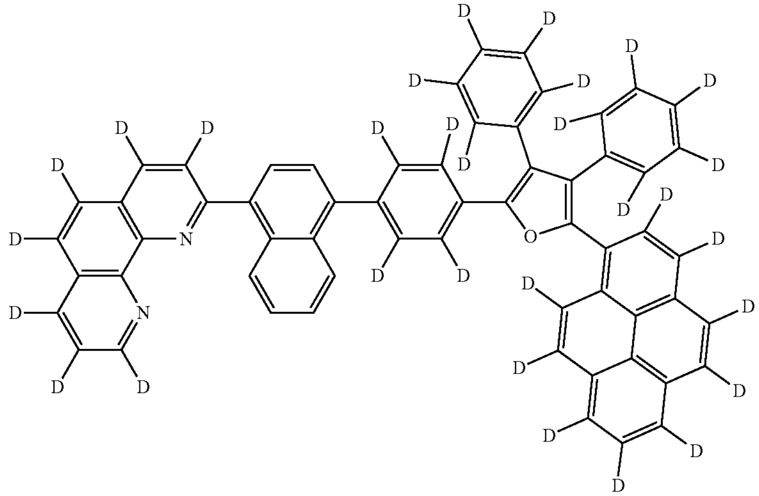
D391
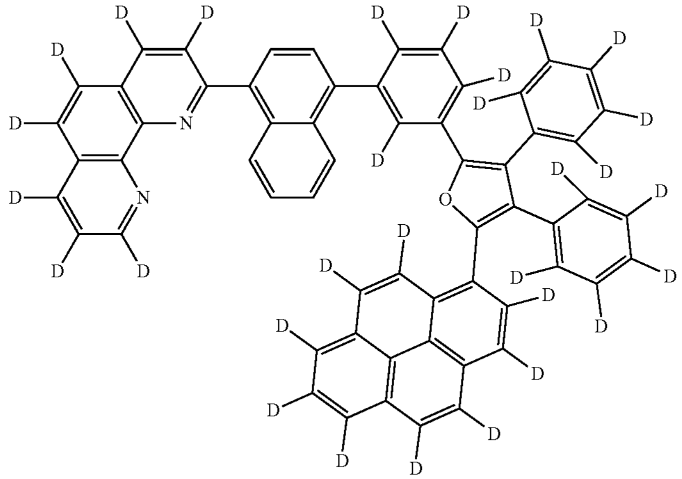

-continued
D392
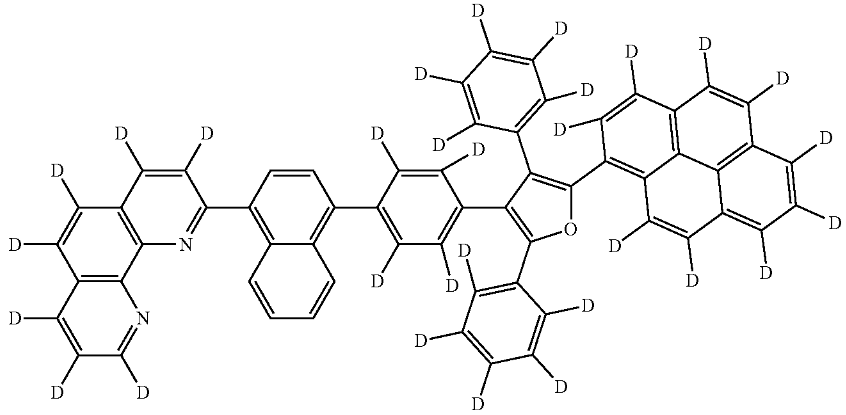
D393
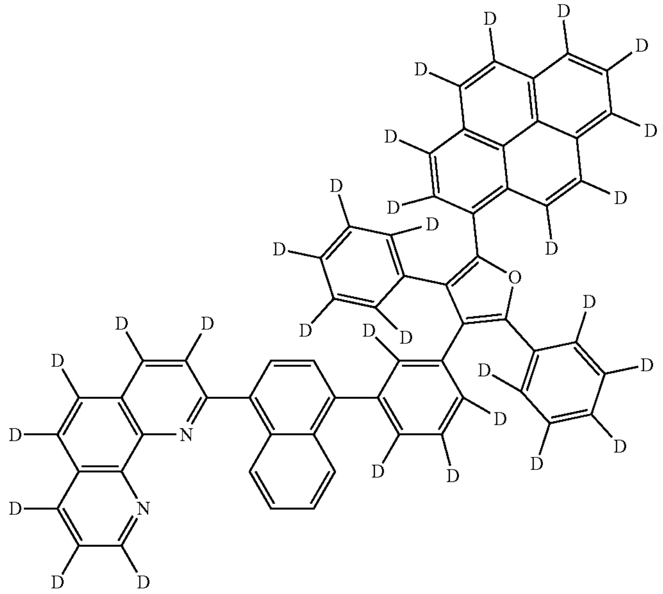
D395
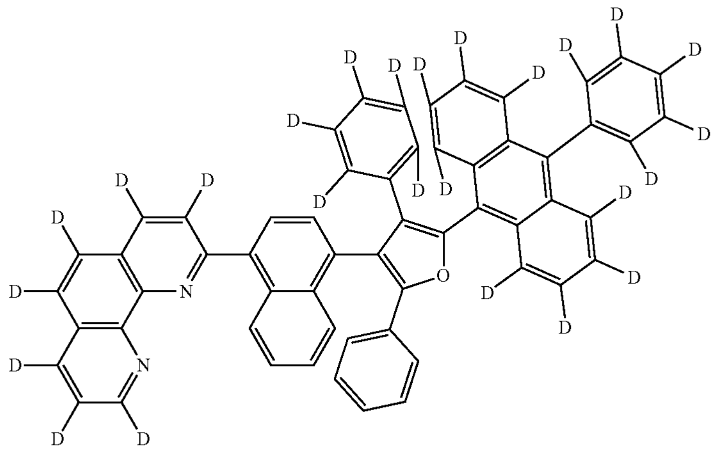

-continued
D396
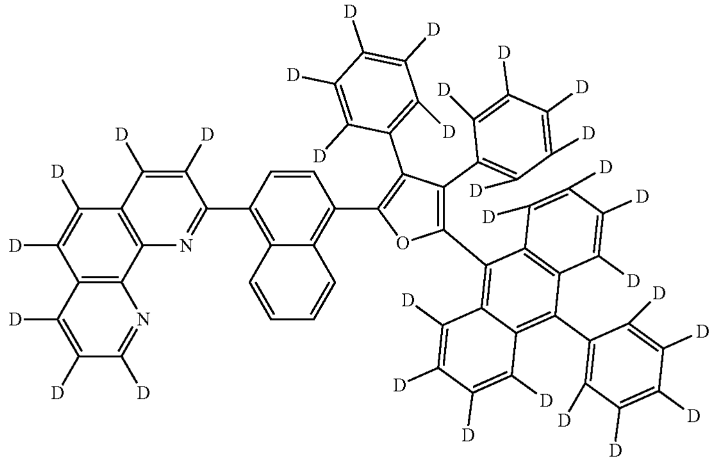
D397
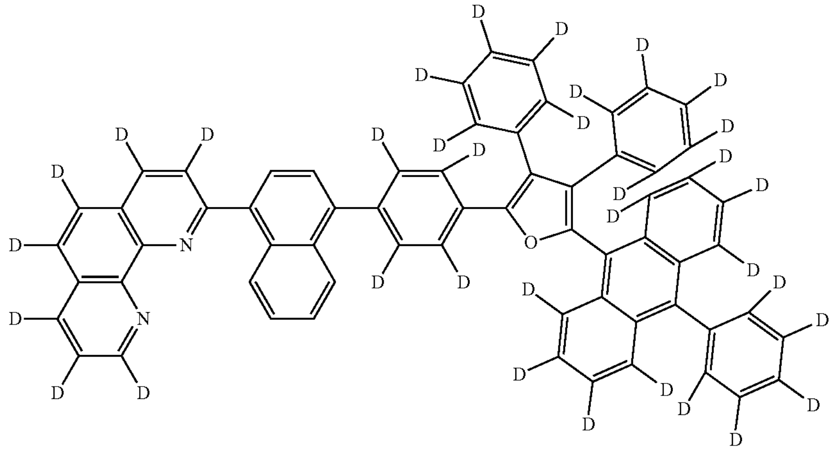
D398
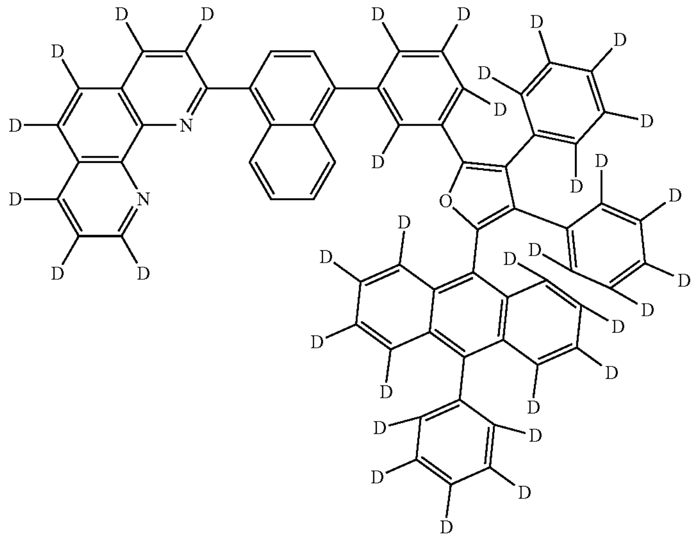

-continued
D399
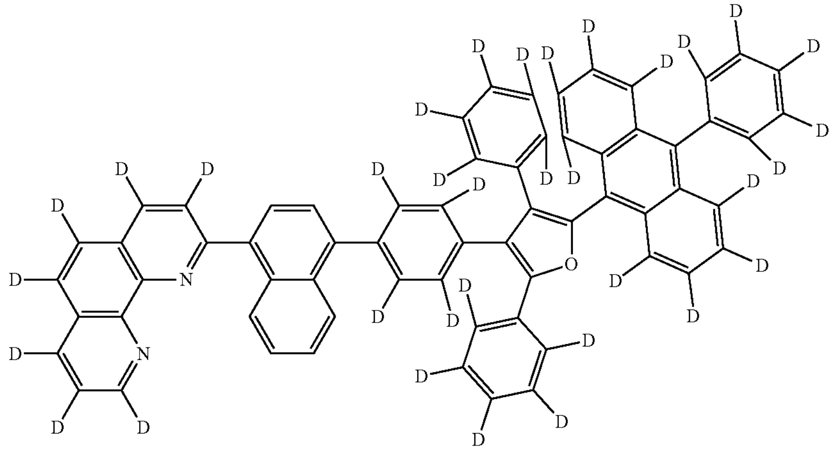
D400
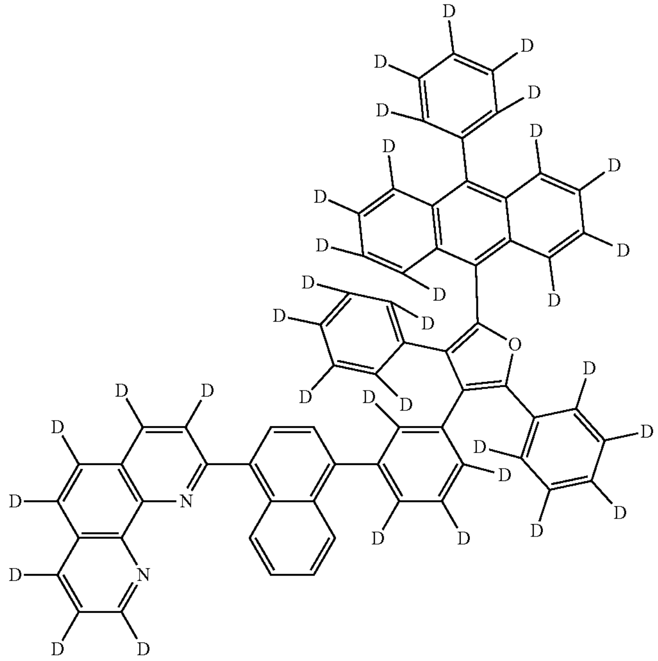
D405
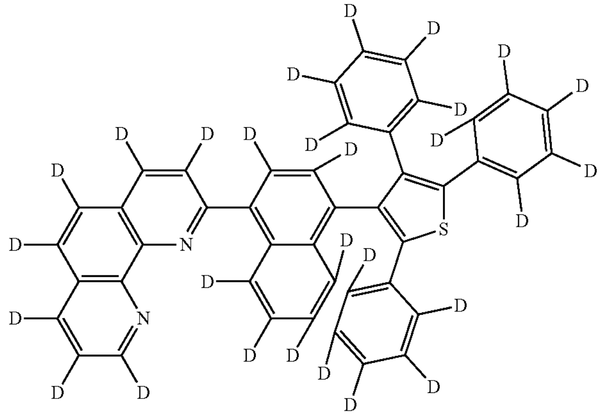

-continued
D406
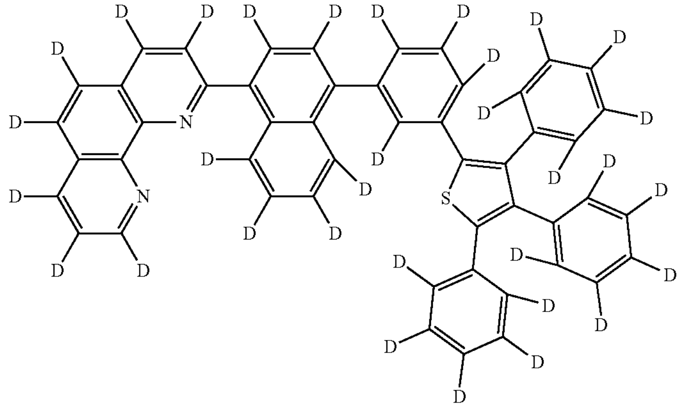
D407
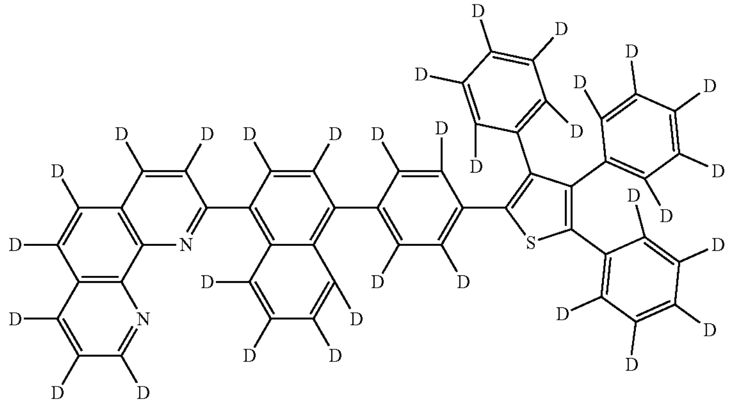
D408
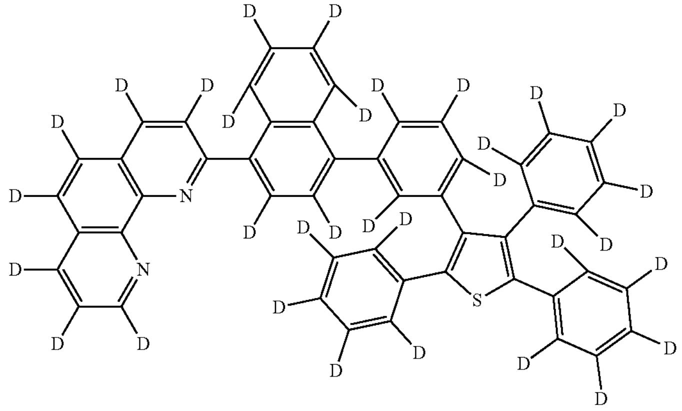
D409
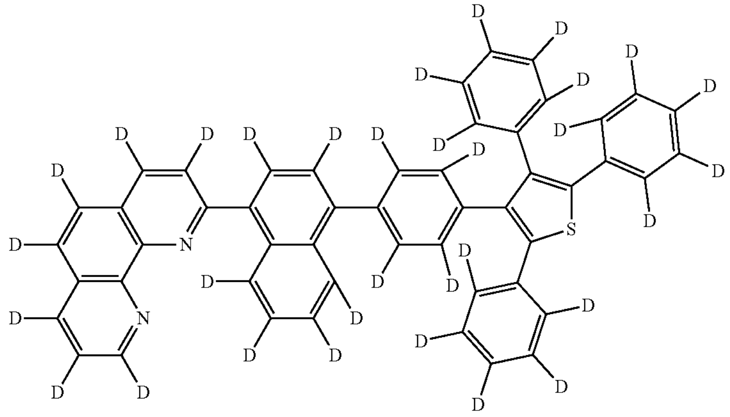

-continued
D414
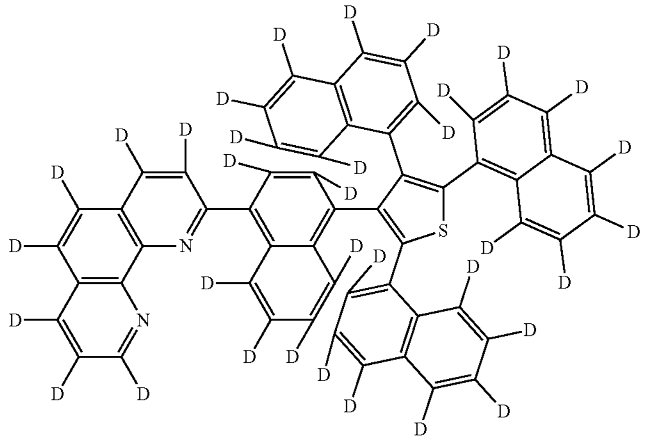
D415
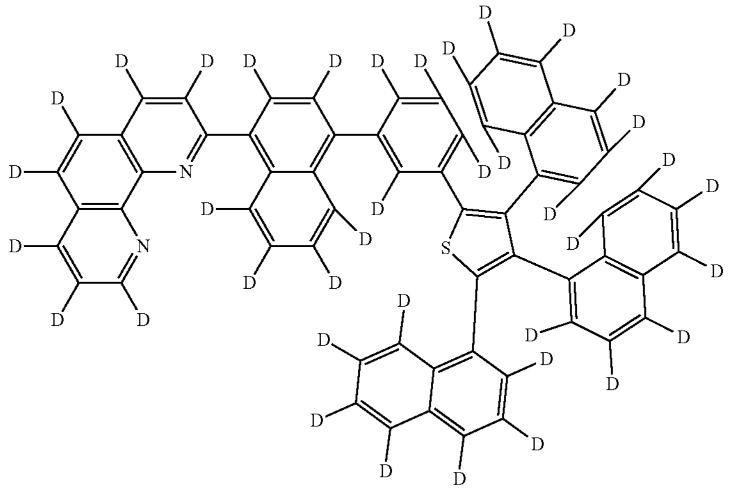
D416
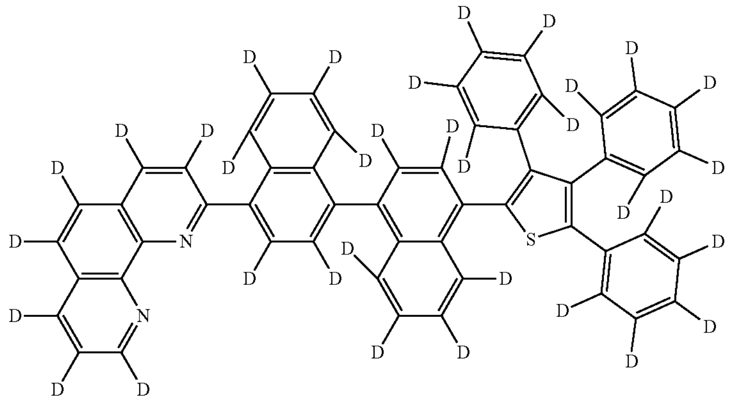

-continued
D417
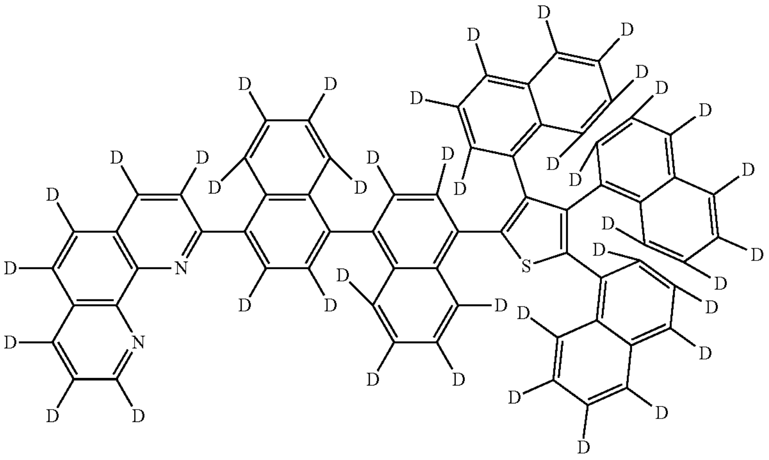
D418
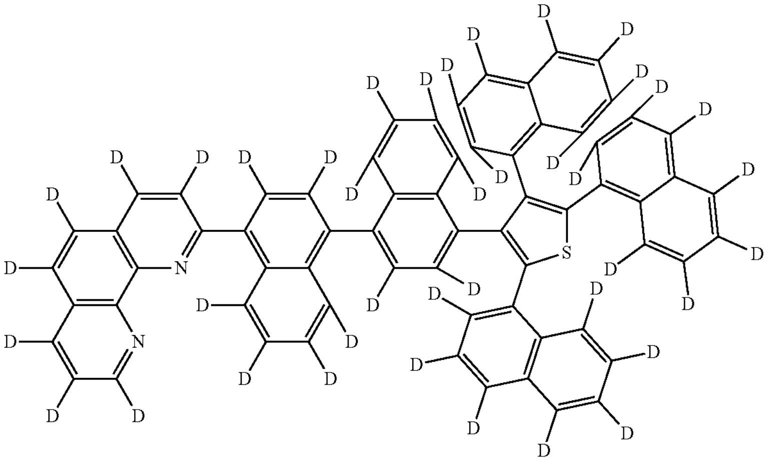
D421
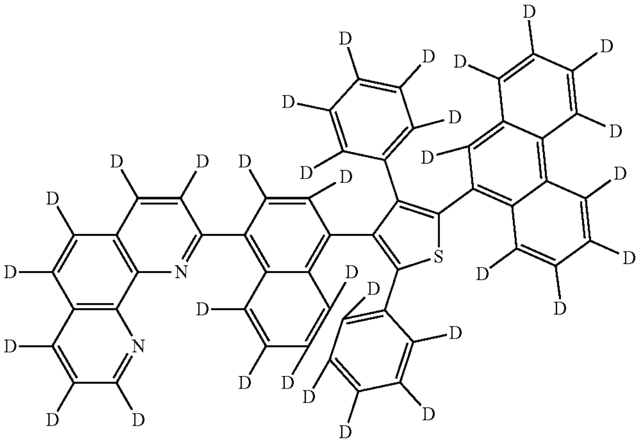

-continued
D422
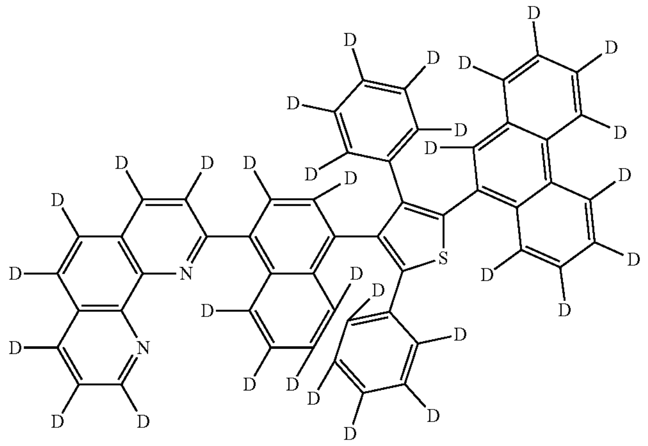
D423
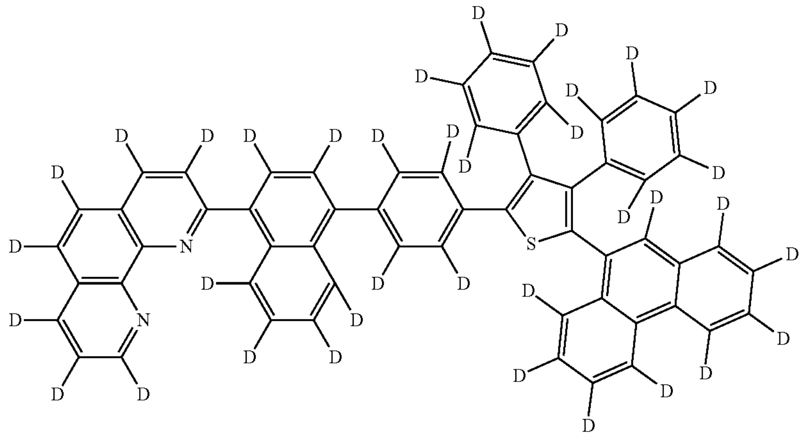
D424
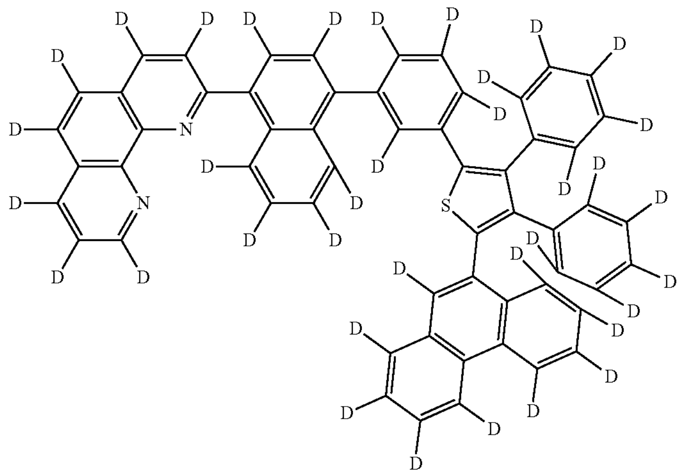

-continued
D425
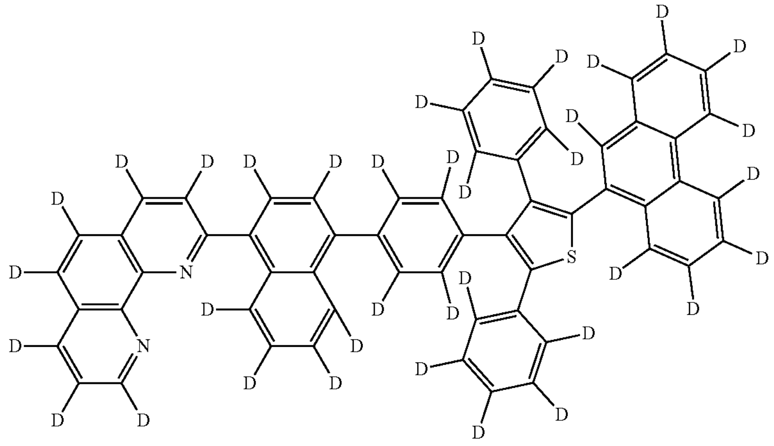
D426
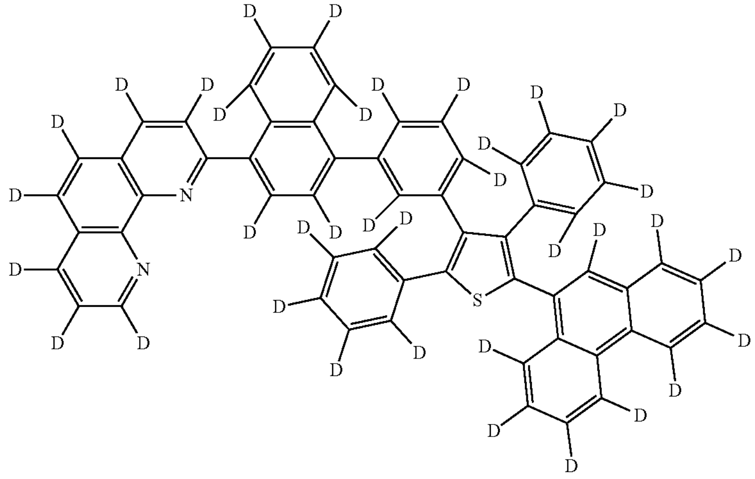
D428
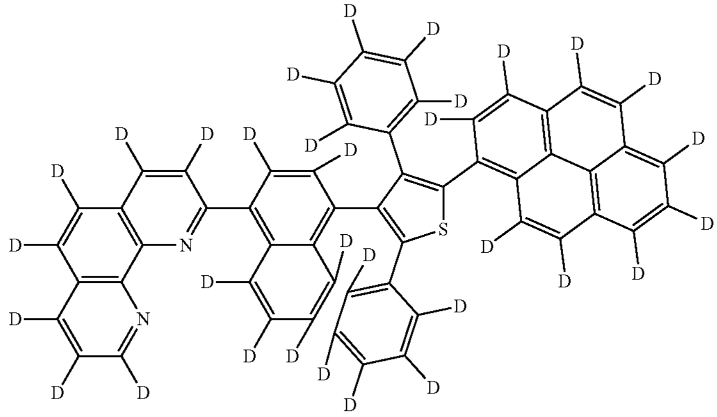

-continued
D429
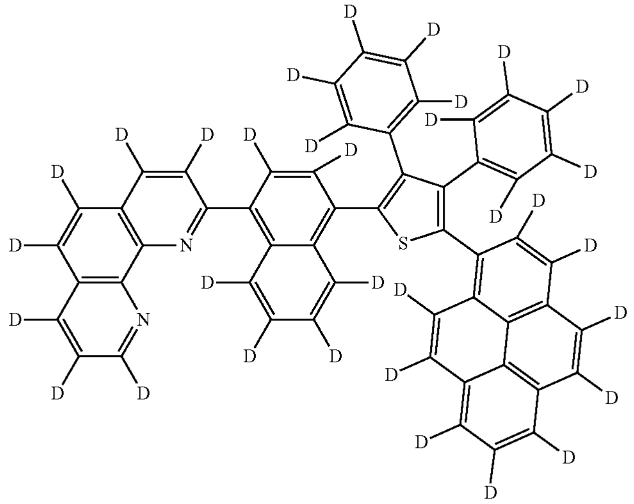
D430
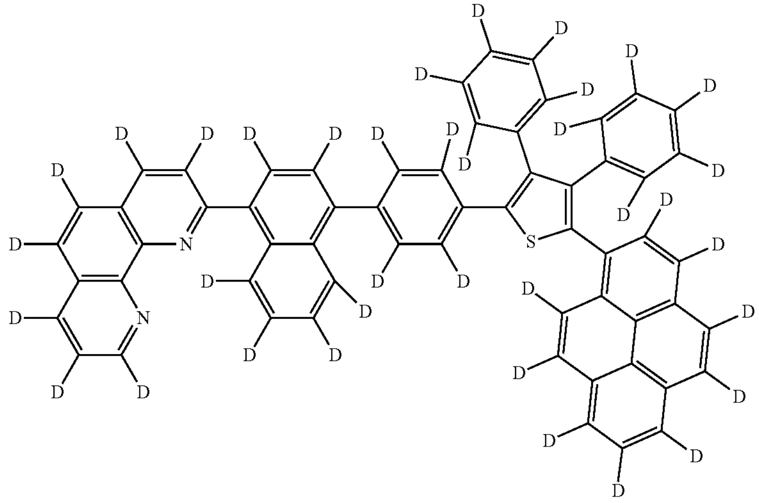
D431
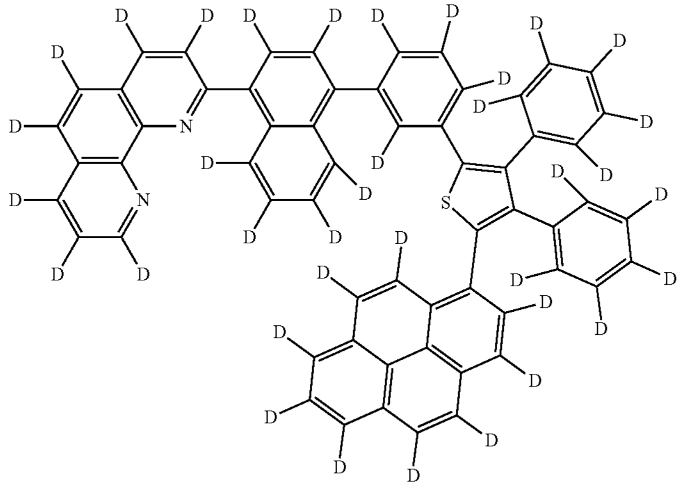

-continued
D432
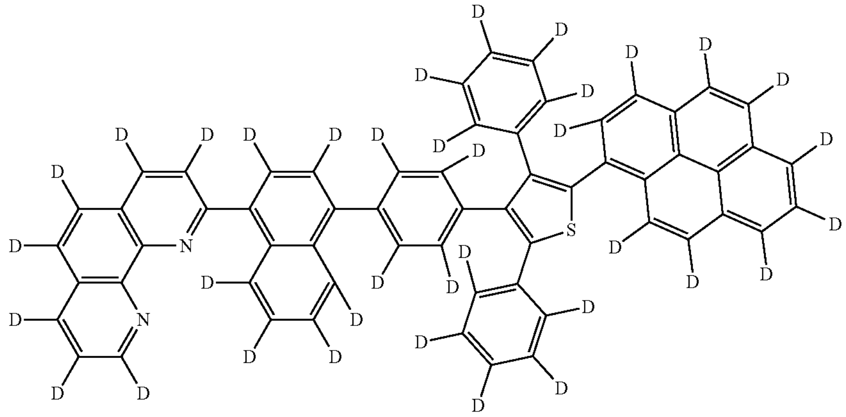
D433
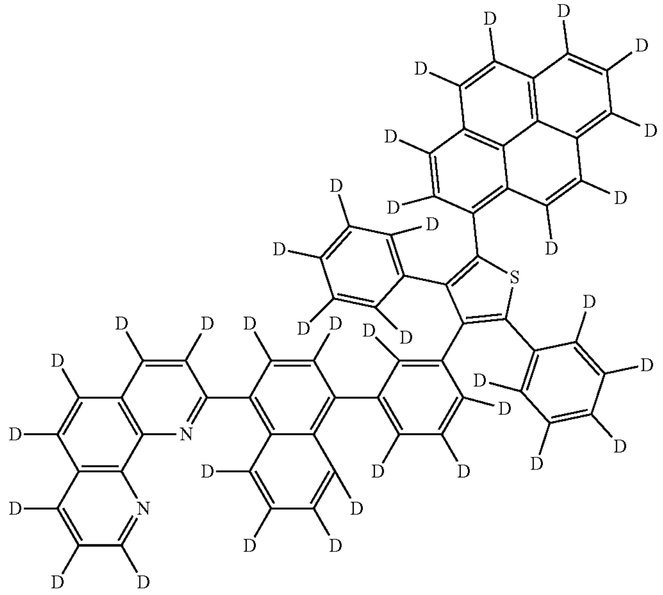
D435
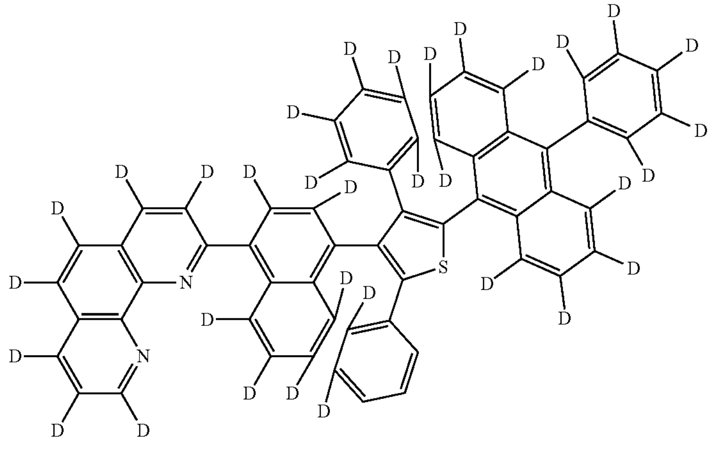

-continued
D436
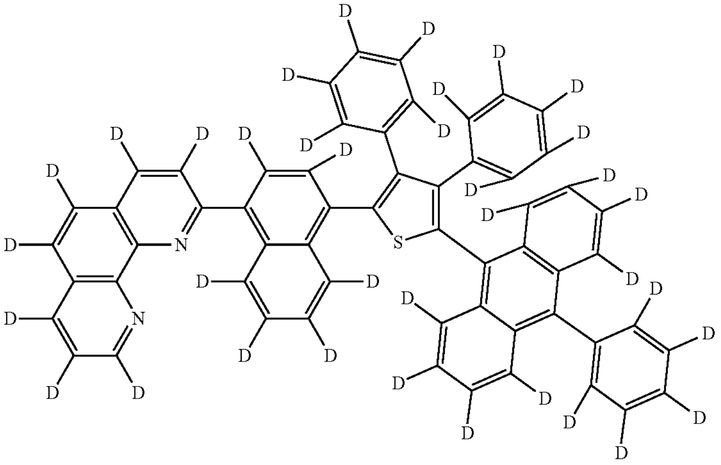
D437
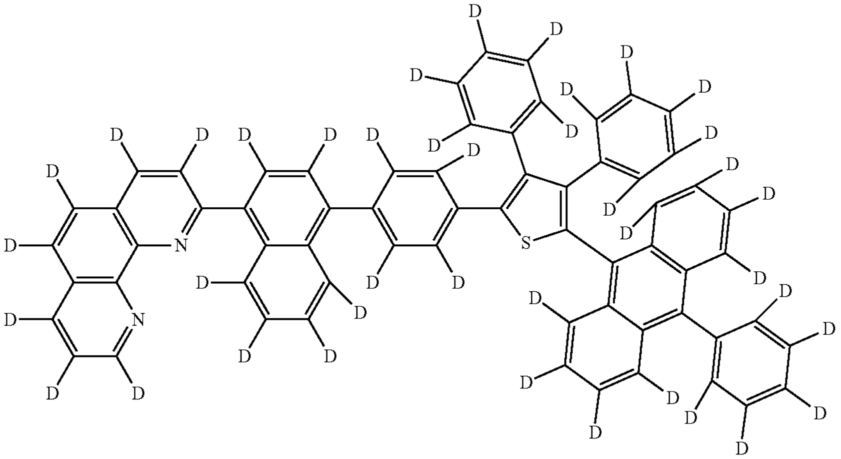
D438
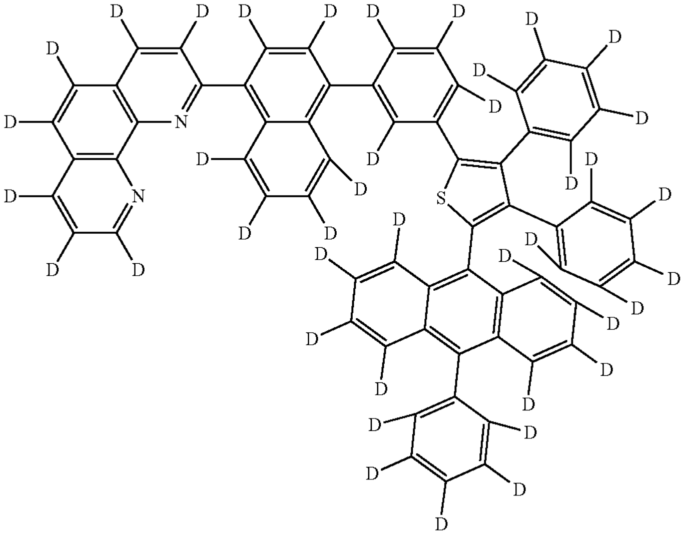

D439
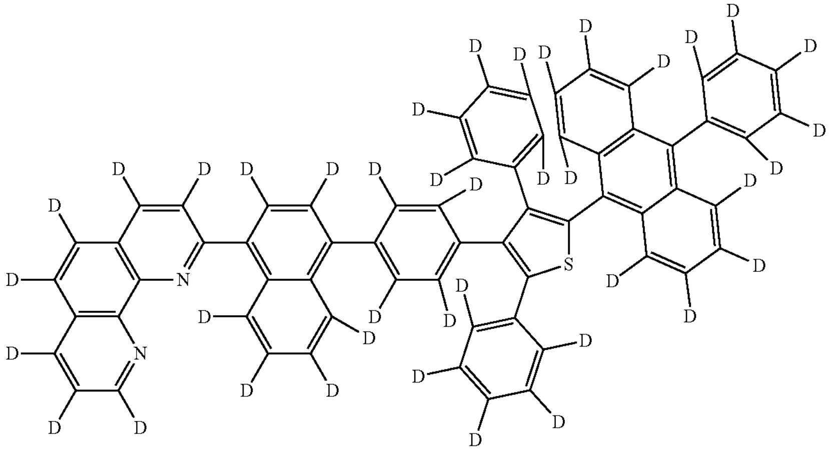
D440
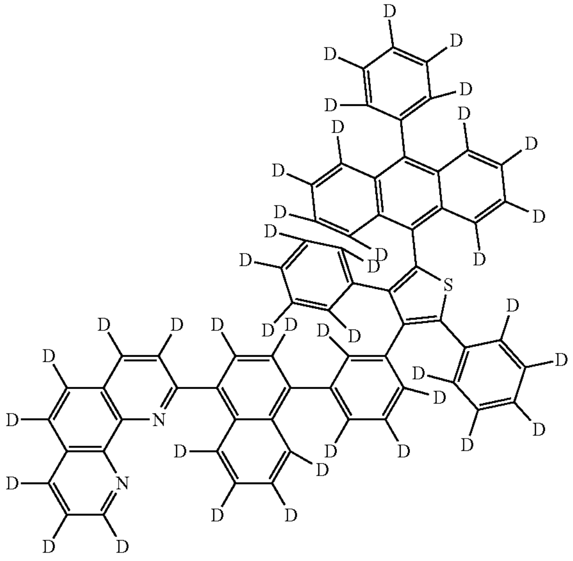
D445
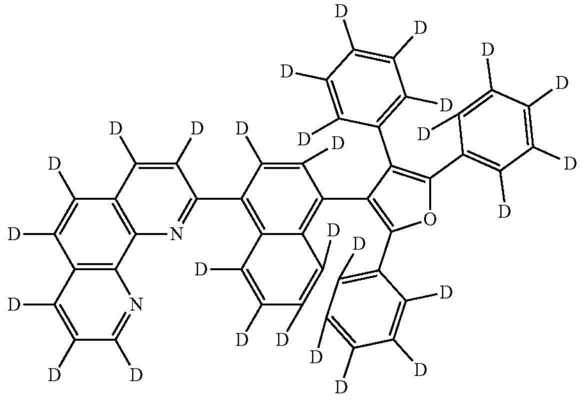
D446
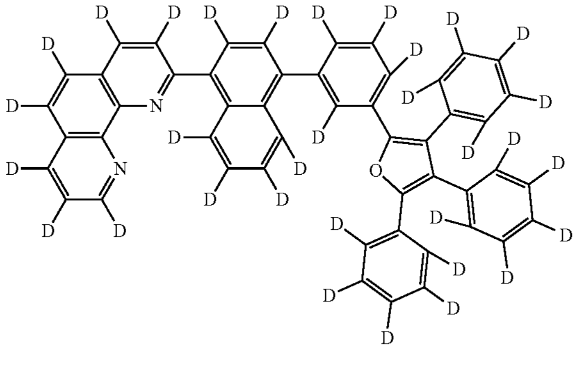
D447
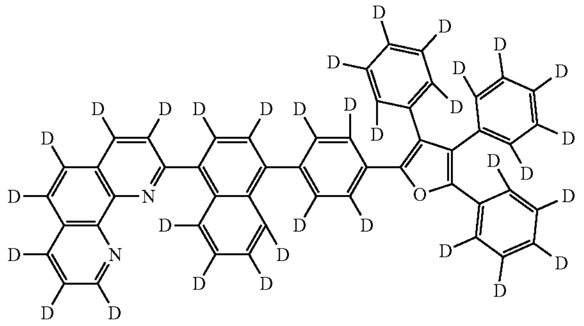

-continued
D448
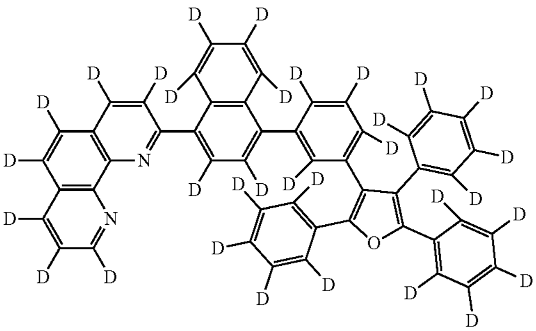
D449
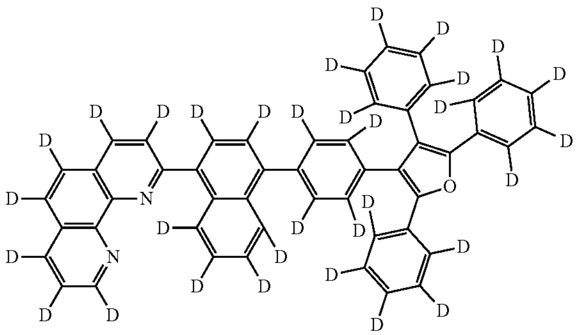
D454
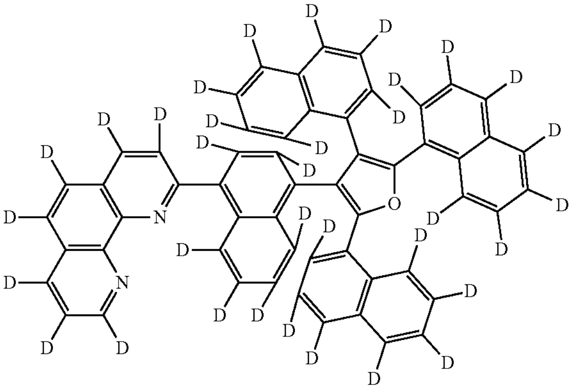
D455
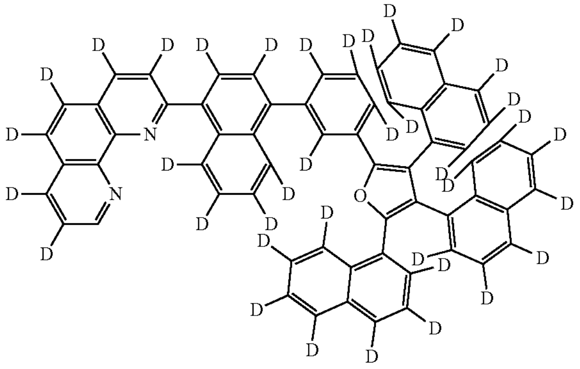
D456
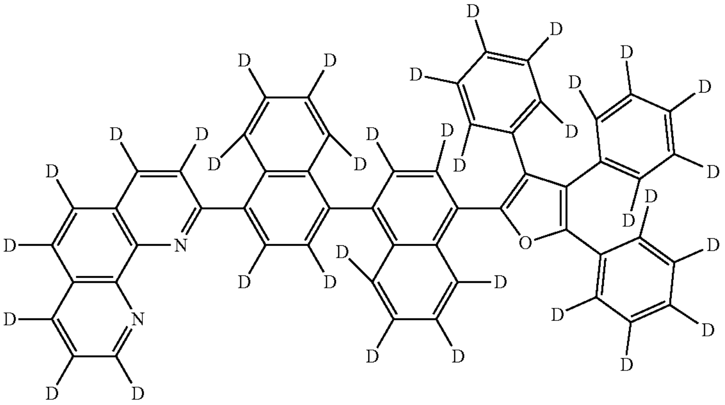
D457
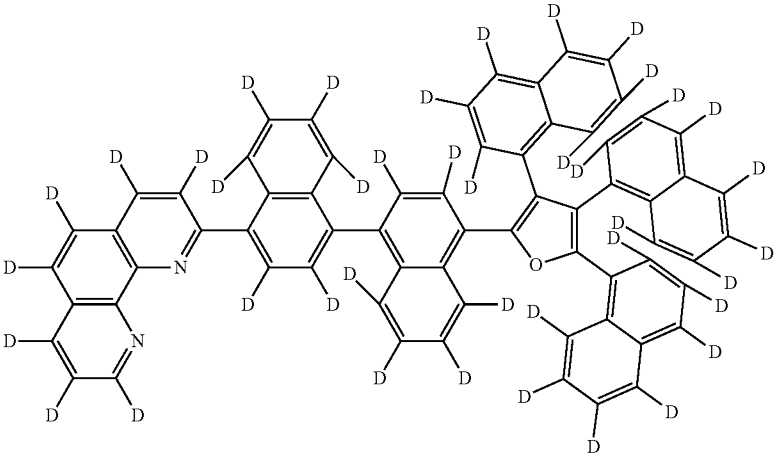

-continued
D458
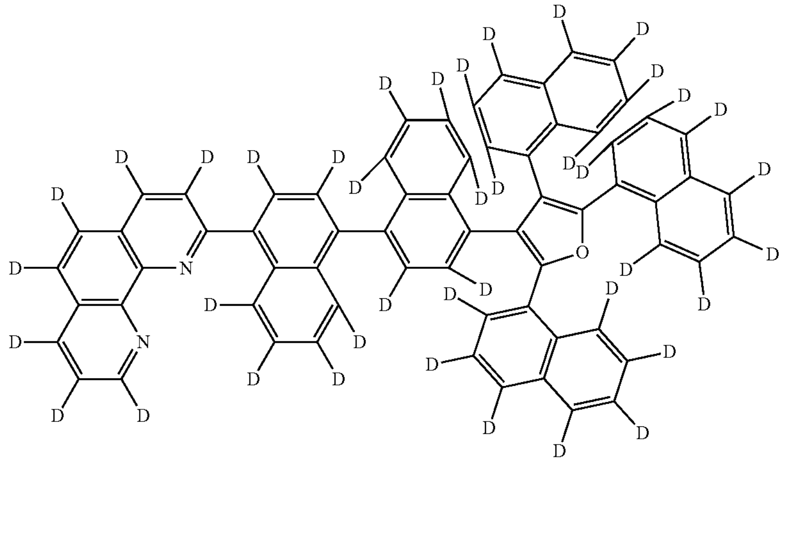
D461
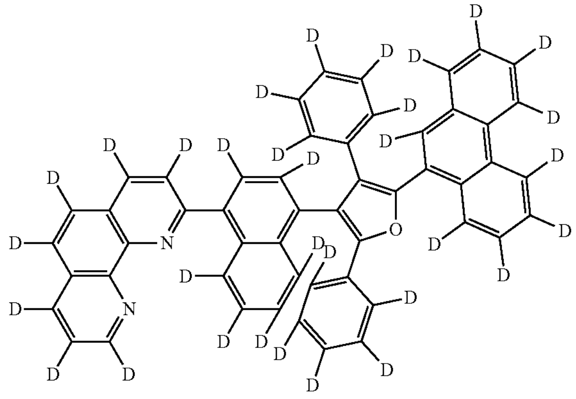
D462
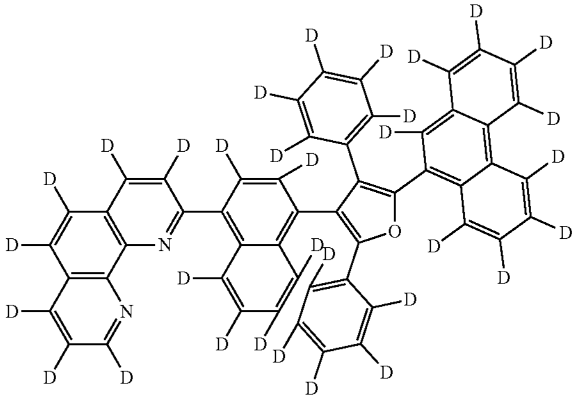
D463
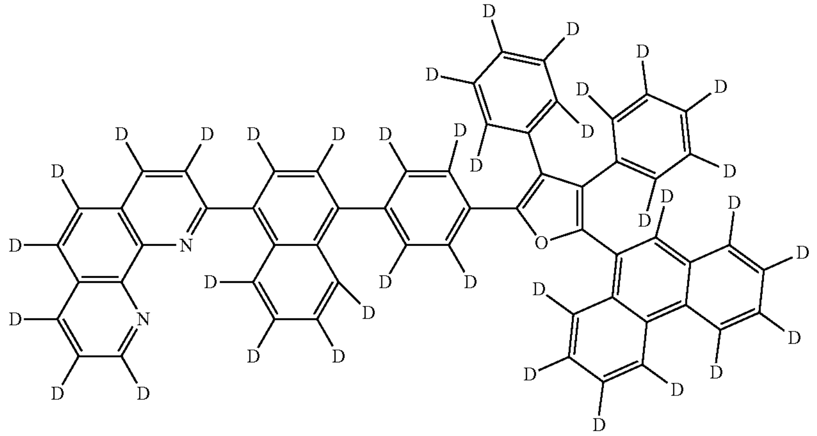

-continued
D464
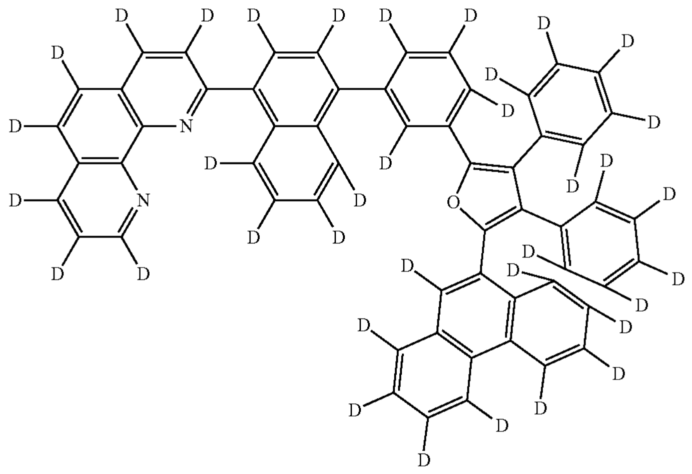
D465
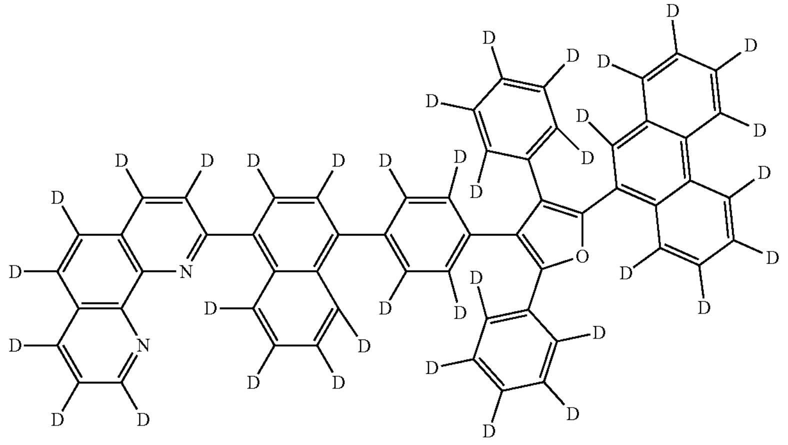
D466
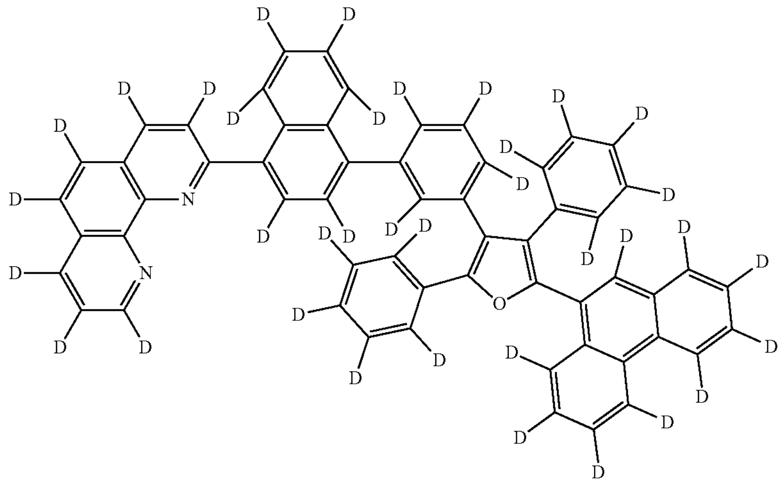

-continued
D468
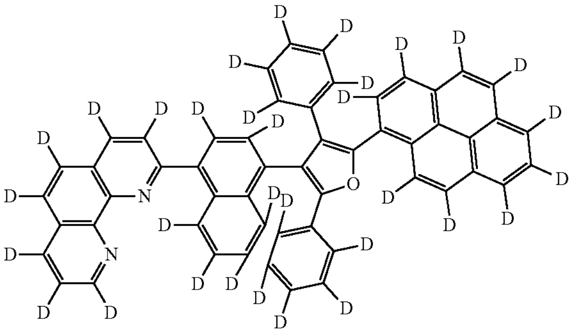
D469
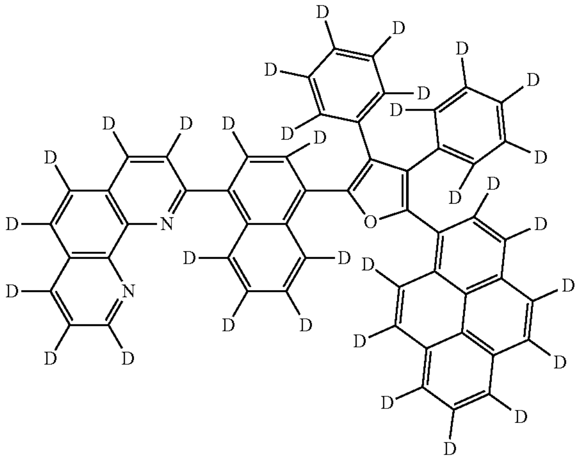
D470
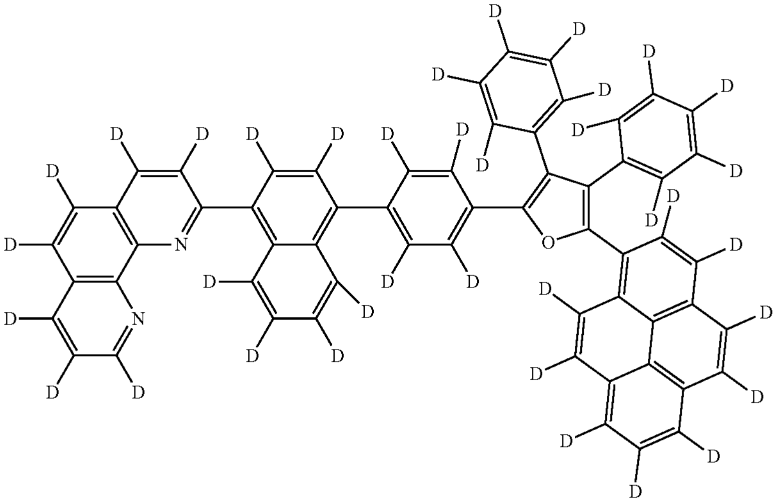
D471
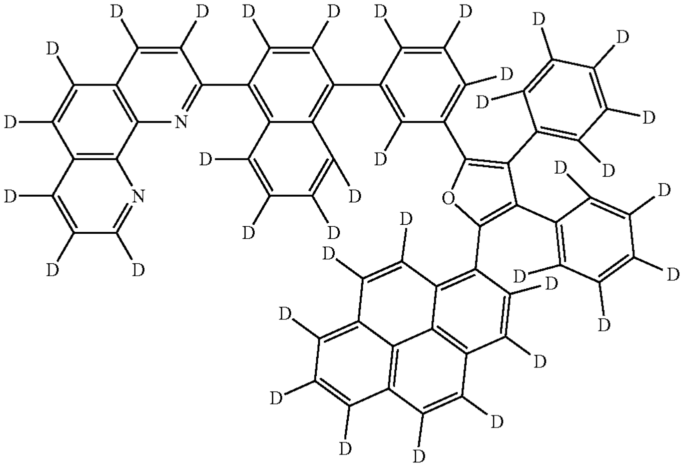

-continued
D472
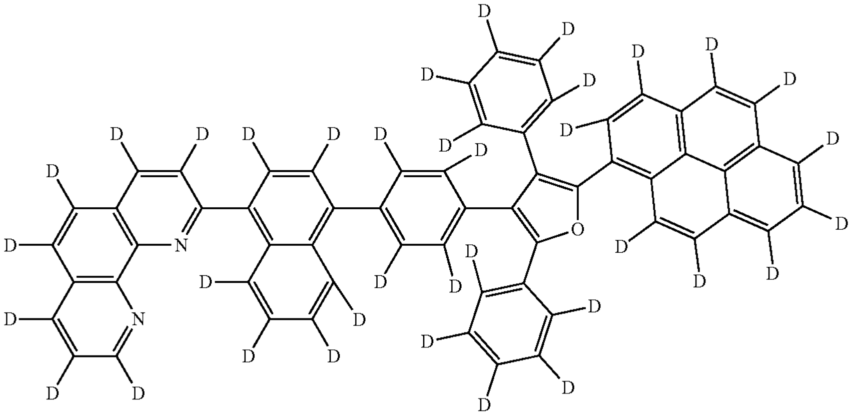
D473
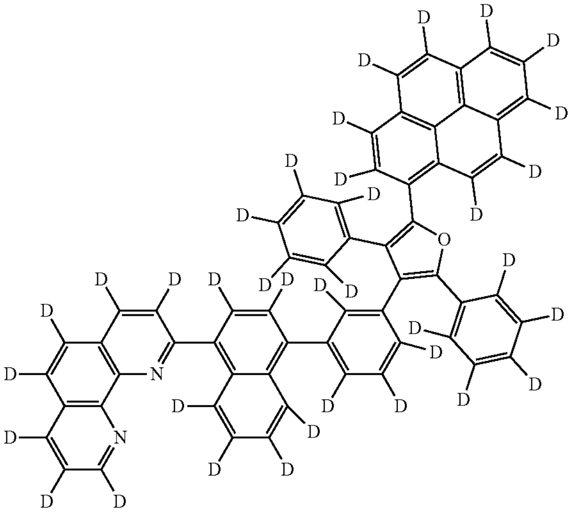
D475
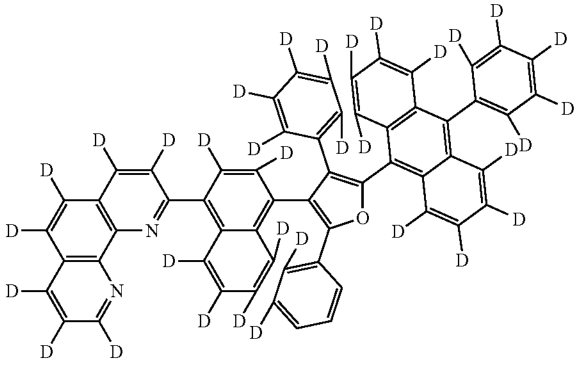
D476
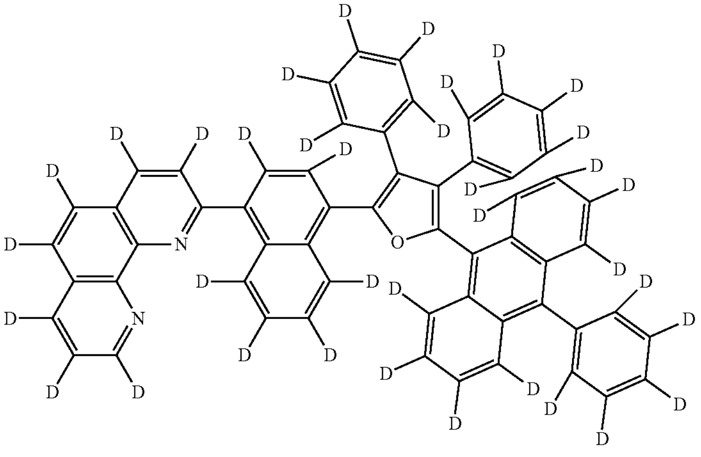

-continued
D477
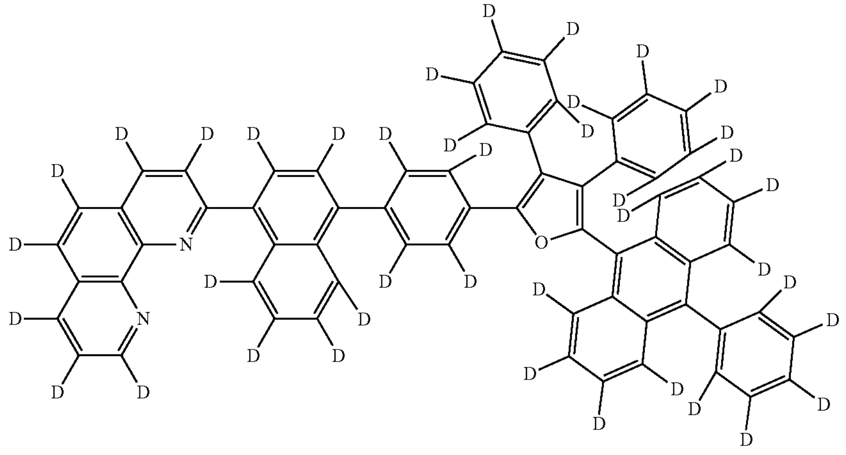
D478
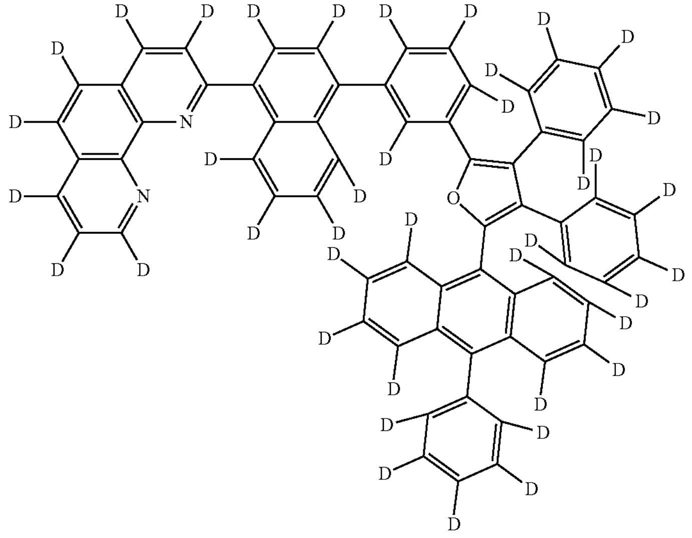
D479
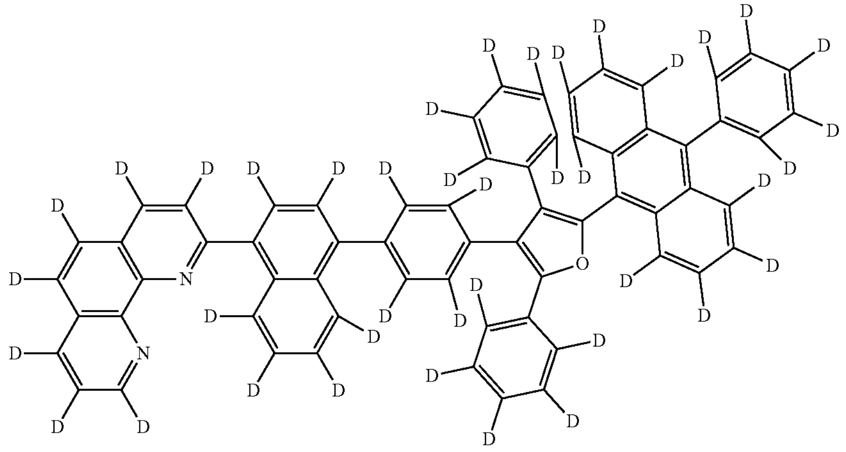

-continued
D480
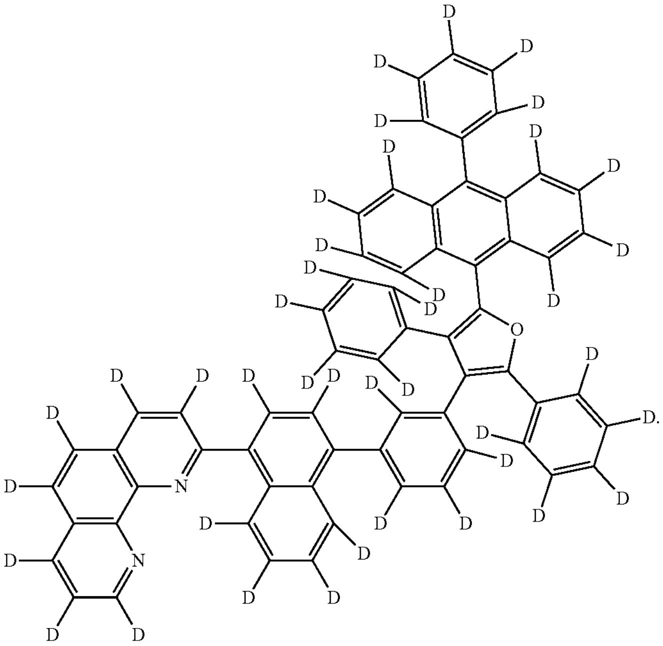
* * * * *